US010918713B2

(12) United States Patent
Sette et al.

(10) Patent No.: US 10,918,713 B2
(45) Date of Patent: Feb. 16, 2021

(54) EPITOPES FROM ALLERGEN PROTEINS AND METHODS AND USES FOR IMMUNE RESPONSE MODULATION

(71) Applicant: LA JOLLA INSTITUTE FOR ALLERGY AND IMMUNOLOGY, San Diego, CA (US)

(72) Inventors: Alessandro Sette, La Jolla, CA (US); Carla Oseroff, San Diego, CA (US); Howard Grey, La Jolla, CA (US); Bjoern Peters, San Diego, CA (US)

(73) Assignee: La Jolla Institute For Allergy And Immunology, La Jolla, CA (US)

( * ) Notice: Subject to any disclaimer, the term of this patent is extended or adjusted under 35 U.S.C. 154(b) by 0 days.

(21) Appl. No.: 15/684,067

(22) Filed: Aug. 23, 2017

(65) Prior Publication Data

US 2018/0078637 A1    Mar. 22, 2018

Related U.S. Application Data

(63) Continuation of application No. 14/376,757, filed as application No. PCT/US2013/025201 on Feb. 7, 2013, now abandoned.

(60) Provisional application No. 61/642,372, filed on May 3, 2012, provisional application No. 61/596,166, filed on Feb. 7, 2012.

(51) Int. Cl.
| | |
|---|---|
| *A61K 39/35* | (2006.01) |
| *C07K 7/08* | (2006.01) |
| *G01N 33/50* | (2006.01) |
| *G01N 33/53* | (2006.01) |
| *A61K 39/00* | (2006.01) |
| *C07K 16/24* | (2006.01) |

(52) U.S. Cl.
CPC ............... *A61K 39/35* (2013.01); *C07K 7/08* (2013.01); *C07K 16/244* (2013.01); *G01N 33/5008* (2013.01); *G01N 33/5308* (2013.01); *A61K 2039/58* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 6,719,976 | B1 | 4/2004 | Sone et al. |
| 6,982,326 | B1 | 1/2006 | Griffith et al. |
| 7,025,964 | B1 | 4/2006 | Sone et al. |
| 7,306,923 | B2 | 12/2007 | Brys et al. |
| 8,067,016 | B2 | 11/2011 | Skeiky et al. |
| 2003/0082190 | A1* | 5/2003 | Saxon ............ C07K 16/00 424/178.1 |
| 2003/0185847 | A1 | 10/2003 | Sone et al. |
| 2009/0136470 | A1 | 5/2009 | Cheroutre et al. |
| 2012/0294888 | A1 | 11/2012 | Kishimoto et al. |

FOREIGN PATENT DOCUMENTS

| | | |
|---|---|---|
| EP | 1 219 299 A1 | 7/2002 |
| JP | 1000-7700 A | 10/1998 |
| JP | 2003-002897 A | 1/2003 |
| JP | 2003-116556 A | 4/2003 |
| WO | WO 94/10194 A2 | 5/1994 |
| WO | WO 94/10194 A3 | 5/1994 |
| WO | WO 2008/156704 A3 | 12/2008 |
| WO | WO 2011/098778 A2 | 8/2011 |
| WO | WO 2011/098778 A3 | 8/2011 |
| WO | WO 2011/098778 A8 | 8/2011 |

OTHER PUBLICATIONS

Admyre, C., et al., "B cell-derived exosomes can present allergen peptides and activate allergen-specific T cells to proliferate and produce $T_H2$-like cytokines," *J Allergy Clin Immunol*, 2007, vol. 120(6), pp. 1418-1424.

Assarsson, E., et al., "A Quantitative Analysis of the Variables Affecting the Repertoire of T Cell Specificities Recognized after Vaccinia Virus Infection," *The Journal of Immunology*, 2007, pp. 7890-7901, vol. 178.

Assarsson, E., et al., "Kinetic analysis of a complete poxvirus transcriptome reveals an immediate-early class of genes," *Proceedings of the National Academy of Sciences*, 2008, pp. 2140-2145, vol. 105.

Assarsson, E., et al., "Immunomic Analysis of the Repertoire of T-Cell Specificities for Influenza A Virus in Humans," *Journal of Virology*, 2008, pp. 12241-12251, vol. 82.

Attwood, et al., "The Babel of Bioinformatics," *Science*, 2000, vol. 290 (5491), pp. 471-473.

Blumenthal, et al., "Definition of Allergen," *Allergens and Allergen Immunotherapy*, Ed. R. Lockey, S. Bukantz and J. Bousquet, New York: Marcel Decker, 2004, pp. 37-50.

Blythe, M., et al., "An analysis of the epitope knowledge related to Mycobacteria," *Immunome Research*, 2007, 3:10.

Botten, J., et al., "Identification of protective Lassa virus epitopes that are restricted by HLAA2," *Journal of Virology*, 2006, pp. 8351-8361, vol. 80.

Bui, H. H., et al., "Ab and T cell epitopes of influenza A virus, knowledge and opportunities," *Proceedings of the National Academy of Sciences*, 2007, pp. 246-251, vol. 104.

Cheng, Y., and W. H. Prusoff, "Relationship Between the Inhibition Constant ($K_I$) and the Concentration of Inhibitor Which Causes 50 Per Cent Inhibition ($I_{50}$) of an Enzymatic Reaction," *Biochemical Pharmacology*, 1973, pp. 3099-3108, vol. 22.

(Continued)

*Primary Examiner* — Nora M Rooney
(74) *Attorney, Agent, or Firm* — Womble Bond Dickinson (US) LLP

(57) ABSTRACT

The invention relates to common allergen proteins and peptides, subsequences, portions, homologues, variants and derivatives thereof, and methods and uses of common allergen proteins and peptides. Methods include, for example, modulating an immune response; protecting a subject against or treating a subject for an allergic response, allergic disorder or allergic disease; and inducing immunological tolerance to the allergen in a subject.

6 Claims, 6 Drawing Sheets

Specification includes a Sequence Listing.

(56) References Cited

OTHER PUBLICATIONS

Ebner, C., et al., "Identification of Multiple T Cell Epitopes on Bet v 1, the Major Birch Pollen Allergen, Using Specific T Cell Clones and Overlapping Peptides," *The Journal of Immunology*, 1993, vol. 150(3), pp. 1047-1054.
Focke, M., et al., "Non-anaphylactic surface-exposed peptides of the major birch pollen allergen, Bet v 1, for preventative vaccination," *Clin Exp Allergy*, 2004, vol. 34, pp. 1525-1533.
Friedl-Hajek, et al., "Identification of a highly promiscuous and an HLA allele-specific T-cell epitope in the birch major allergen Bet v 1 :HLA resteriction, epitope mapping and TCR sequence comparisons," *Clin. Exp. Allergy*, 1999, vol. 29, pp. 478-487.
Greenbaum, J., et al., "Functional classification of class II human leukocyte antigen (HLA) molecules reveals seven different supertypes and a surprising degree of repertoire sharing across supertypes," *Immunogenetics*, 2011, pp. 325-335, vol. 63.
Greiner, A. N., et al., "Allergic Rhinitis," *The Lancet*, 2011, 378:2112-2122.
Gulukota, K., et al., "Two Complementary Methods for Predicting Peptides Binding Major Histocompatibility Complex Molecules," *J. Mol. Biol.*, 1997, pp. 1258-1267, vol. 267.
GSP:AZM48919, "Alder pollen major allergen antigen Aln g 1 SEQ:15," 2011, 1 page.
International Search Report for International Patent Application No. PCT/US2013/025201 dated Apr. 18, 2013.
Kinnunen, et al., "Potential of an altered peptide ligand of lipocalin allergen Bos d 2 for peptide immunotherapy," *J. Allerg. Clin. Immunol.*, 2007, vol. 119(4), pp. 965-972.
Kotturi, M. F., et al., "A Multivalent and Cross-Protective Vaccine Strategy against Arenaviruses Associated with Human Disease," *PLoS Pathogens*, 2009, 5:e1000695.
Kurucz, et al., "Current Animal Models of Bronchial Asthma," *Curr. Pharm. Des.*, 2006, vol. 12, pp. 3175-3194.
Larché, Mark, "Update on the current status of peptide immunotherapy," *J Allergy Clin Immunol*, 2007, vol. 110(4), pp. 906-909.
Locksley, R. M., "Asthma and Allergic Inflammation," *Cell*, 2010, pp. 777-783, vol. 140.
Meyer, D., et al., "Single Locus Polymorphism of Classical HLA Genes," *Proceedings of the 13th International Histocompatibility Workshop and Conference*, 2007, pp. 653-704.
Middleton, D., et al., "New Allele Freuency Database: http://www.allelefrequencies.net," *Tissue Antigens*, 2003, pp. 403-407, vol. 61.
Mothe, B. R., et al., "Chronic Lymphocytic Choriomeningitis Virus Infection Actively Down-Regulates CD4+ T Cell Responses Directed Against a Broad Range of Epitopes," *The Journal of Immunology*, 2007, pp. 1058-1067, vol. 179.
Moutaftsi, M., et al., "A consensus epitope prediction approach identifies the breadth of murine $T_{CD8+}$-cell responses to vaccinia virus," *Nature Biotechnology*, 2006, pp. 817-819, vol. 24.
Moutaftsi, M., et al., "Vaccinia Virus-Specific CD4+ T Cell Responses Target a Set of Antigens Largely Distinct from Those Targeted by CD8+ T Cell Responses," *The Journal of Immunology*, 2007, 178:6814-6820.
Mukherjee, et al., "Allergic Asthma: Influence of Genetic and Environmental Factors," *J. Biol. Chem.*, 2011, vol. 286(38), pp. 32883-32889.
Ngo, et al., "Computational Complexity, Protein Structure Prediction, and the Lveinthal Paradox,"*The Protein Folding Problem and Tertiary Sruction Prediction*, Ed. K. Merz and S. Le Grand, Boston: Birkhauser, 1994, pp. 491-495.
Oseroff, C., et al., "Molecular Determinants of T Cell Epitope Recognition to the Common Timothy Grass Allergen," *The Journal of Immunology*, 2010, 185:943-955.
Oseroff, C., et al., "HLA class I-restricted responses to vaccinia recognize a broad array of proteins mainly involved in virulence and viral gene regulation," *Proceedings of the National Academy of Sciences*, 2005, pp. 13980-13985, vol. 102.
Oseroff, C., et al., "Dissociation Between Epitope Hierarchy and Immunoprevalence CD8 Responses to Vaccinia Virus Western Reserve," *The Journal of Immunology*, 180:7193-7202.
Schein, et al., "Bioinformatics approaches to classifying allergens and predicting cross-reactivity," *Immunol. Allergy Clin. North Am.*, 2007, vol. 27(1), pp. 1-27.
Sidney, J., et al., 1998. "Measurement of MHC/Peptide Interactions by Gel Filtration," *Current Protocols in Immunology*, 1998, pp. 18.3.1-18.3.19.
Sidney, J., et al., "Divergent Motifs but Overlapping Binding Repertoires of Six HLA-DQ Molecules Frequently Expressed in the Worldwide Human Population," *The Journal of Immunology*, 2010, 185:4189-4198.
Sidney, J., et al., "Five HLA-DP Molecules Frequently Expressed in the Worldwide Human Population Share a Common HLA Supertypic Binding Specificity," *The Journal of Immunology*, 2010, 184:2492-2503.
Skolnick, et al., "From genes to protein structure and function: novel applications of computational approaches in the genomic era," *Trends in Biotech.*, 2000, vol. 18, pp. 34-39.
Sparholt, S., et al., "Crossreactivity and T-cell epitope specificity of Bet v 1-specific T cells suggest the involvement of multiple isoallergens in sensitization to birch pollen," *Clinical and Experimental Allergy*, 1997, vol. 27, pp. 932-941.
Stranford, S., et al., "Chapter 18, Vaccines," *Kuby Immunology*, 4th Edition, 2001, pp. 449-465.
Vaughan, K., et al., "Meta-Analysis of Immune Epitope Data for All Plasmodia: Overview and Applications for Malarial Immunobiology and Vaccine-Related Issues," *Parasite Immunology*, 2009, 31:78-97.
Vaughan, K., et al., "Meta-Analysis of All Immune Epitope Data in the *Flavivirus* Genus: Inventory of Current Immune Epitope Data Status in the Context of Virus Immunity and Immunopathology," *Viral Immunology*, 2010, pp. 259-284, vol. 23.
Vaughan, K., et al., "Towards Defining Molecular Determinants Recognized by Adaptive Immunity in Allergic Disease: An Inventory of the Available Data," *Journal of Allergy*, 2010, Article ID 628026, vol. 2010.
Vita, R., et al., "The Immune Epitope Database 2.0," *Nucleic Acids Research*, 2009, pp. D854-D862, vol. 38.
Wang, P., et al., "Peptide binding predictions for HlA DR, DP and DQ molecules," BMC Bioinformatics, 2010, 11:568.
Zarebski, L. M., et al., "Analysis of Epitope Information Related to *Bacillus Anthracis* and *Clostridium Botulinum*," *Expert Review Vaccines*, 2008, vol. 7, pp. 55-74.

\* cited by examiner

SEQUENCE LISTING

```
<160> NUMBER OF SEQ ID NOS: 2008

<210> SEQ ID NO 1
<211> LENGTH: 15
<212> TYPE: PRT
<213> ORGANISM: Alnus glutinosa

<400> SEQUENCE: 1

Met Gly Val Phe Asn Tyr Glu Ala Glu Thr Pro Ser Val Ile Pro
1               5                   10                  15

<210> SEQ ID NO 2
<211> LENGTH: 15
<212> TYPE: PRT
<213> ORGANISM: Alnus glutinosa

<400> SEQUENCE: 2

Pro Ser Val Ile Pro Ala Ala Arg Leu Phe Lys Ala Phe Ile Leu
1               5                   10                  15

<210> SEQ ID NO 3
<211> LENGTH: 15
<212> TYPE: PRT
<213> ORGANISM: Alnus glutinosa

<400> SEQUENCE: 3

Ala Ala Arg Leu Phe Lys Ala Phe Ile Leu Asp Gly Asp Lys Leu
1               5                   10                  15

<210> SEQ ID NO 4
<211> LENGTH: 15
<212> TYPE: PRT
<213> ORGANISM: Alnus glutinosa

<400> SEQUENCE: 4

Asp Arg Val Asn Phe Lys Tyr Ser Phe Ser Val Ile Glu Gly Gly
1               5                   10                  15

<210> SEQ ID NO 5
<211> LENGTH: 15
<212> TYPE: PRT
<213> ORGANISM: Alnus glutinosa

<400> SEQUENCE: 5

Gly Gly Ser Ile Leu Lys Ile Ser Asn Lys Phe His Thr Lys Gly
1               5                   10                  15

<210> SEQ ID NO 6
<211> LENGTH: 15
<212> TYPE: PRT
<213> ORGANISM: Alnus glutinosa

<400> SEQUENCE: 6

Ile Glu Lys Glu Lys Ala Val Gly Leu Leu Lys Ala Val Glu Ser
1               5                   10                  15
```

```
<210> SEQ ID NO 7
<211> LENGTH: 15
<212> TYPE: PRT
<213> ORGANISM: Alnus glutinosa

<400> SEQUENCE: 7

Ala Val Gly Leu Leu Lys Ala Val Glu Ser Tyr Leu Leu Ala His
1               5                   10                  15

<210> SEQ ID NO 8
<211> LENGTH: 15
<212> TYPE: PRT
<213> ORGANISM: Alnus glutinosa

<400> SEQUENCE: 8

Lys Ala Val Glu Ser Tyr Leu Leu Ala His Ser Asp Ala Tyr Asn
1               5                   10                  15

<210> SEQ ID NO 9
<211> LENGTH: 15
<212> TYPE: PRT
<213> ORGANISM: Alnus glutinosa

<400> SEQUENCE: 9

Thr Asp Gly Asp Gly Phe Ile Ser Phe Gln Glu Phe Thr Asn Phe
1               5                   10                  15

<210> SEQ ID NO 10
<211> LENGTH: 15
<212> TYPE: PRT
<213> ORGANISM: Alnus glutinosa

<400> SEQUENCE: 10

Phe Ile Ser Phe Gln Glu Phe Thr Asn Phe Ala Arg Ala Asn Arg
1               5                   10                  15

<210> SEQ ID NO 11
<211> LENGTH: 15
<212> TYPE: PRT
<213> ORGANISM: Alnus glutinosa

<400> SEQUENCE: 11

Ala Arg Ala Asn Arg Gly Leu Val Lys Asp Val Ala Lys Ile Phe
1               5                   10                  15

<210> SEQ ID NO 12
<211> LENGTH: 15
<212> TYPE: PRT
<213> ORGANISM: Alternaria alternata

<400> SEQUENCE: 12

Met Gln Phe Thr Thr Ile Ala Ser Leu Phe Ala Ala Ala Gly Leu
1               5                   10                  15

<210> SEQ ID NO 13
<211> LENGTH: 15
<212> TYPE: PRT
<213> ORGANISM: Alternaria alternata

<400> SEQUENCE: 13

Ile Ala Ser Leu Phe Ala Ala Ala Gly Leu Ala Ala Ala Ala Pro
1               5                   10                  15

<210> SEQ ID NO 14
<211> LENGTH: 15
```

-continued

<212> TYPE: PRT
<213> ORGANISM: Alternaria alternata

<400> SEQUENCE: 14

Ala Ala Ala Gly Leu Ala Ala Ala Pro Leu Glu Ser Arg Gln
1               5                   10                  15

<210> SEQ ID NO 15
<211> LENGTH: 15
<212> TYPE: PRT
<213> ORGANISM: Alternaria alternata

<400> SEQUENCE: 15

Lys Val Ser Asp Asp Ile Thr Tyr Val Ala Thr Ala Thr Leu Pro
1               5                   10                  15

<210> SEQ ID NO 16
<211> LENGTH: 15
<212> TYPE: PRT
<213> ORGANISM: Alternaria alternata

<400> SEQUENCE: 16

Ile Thr Tyr Val Ala Thr Ala Thr Leu Pro Asn Tyr Cys Arg Ala
1               5                   10                  15

<210> SEQ ID NO 17
<211> LENGTH: 15
<212> TYPE: PRT
<213> ORGANISM: Alternaria alternata

<400> SEQUENCE: 17

Gln Gly Val Ala Asp Ala Tyr Ile Thr Leu Val Thr Leu Pro Lys
1               5                   10                  15

<210> SEQ ID NO 18
<211> LENGTH: 15
<212> TYPE: PRT
<213> ORGANISM: Alternaria alternata

<400> SEQUENCE: 18

Val Ala Asp Ala Tyr Ile Thr Leu Val Thr Leu Pro Lys Ser Ser
1               5                   10                  15

<210> SEQ ID NO 19
<211> LENGTH: 15
<212> TYPE: PRT
<213> ORGANISM: Alternaria alternata

<400> SEQUENCE: 19

Gln Pro Thr Gly Leu Phe Ile Asn Asn Glu Phe Val Lys Ala Val
1               5                   10                  15

<210> SEQ ID NO 20
<211> LENGTH: 15
<212> TYPE: PRT
<213> ORGANISM: Alternaria alternata

<400> SEQUENCE: 20

Asp Val Asp Ile Ala Val Ala Ala Ala Arg Lys Ala Phe Asn Gly
1               5                   10                  15

<210> SEQ ID NO 21
<211> LENGTH: 15
<212> TYPE: PRT
<213> ORGANISM: Alternaria alternata

<400> SEQUENCE: 21

Gly Lys Leu Leu Asn Lys Leu Ala Asp Leu Phe Glu Lys Asn Ala
1               5                   10                  15

<210> SEQ ID NO 22
<211> LENGTH: 15
<212> TYPE: PRT
<213> ORGANISM: Alternaria alternata

<400> SEQUENCE: 22

Asp Thr Ala Pro Asp Ser Phe Asn Tyr Ile Arg Lys Glu Pro Ile
1               5                   10                  15

<210> SEQ ID NO 23
<211> LENGTH: 15
<212> TYPE: PRT
<213> ORGANISM: Alternaria alternata

<400> SEQUENCE: 23

Ser Phe Asn Tyr Ile Arg Lys Glu Pro Ile Gly Val Cys Gly Gln
1               5                   10                  15

<210> SEQ ID NO 24
<211> LENGTH: 15
<212> TYPE: PRT
<213> ORGANISM: Alternaria alternata

<400> SEQUENCE: 24

Ile Ile Pro Trp Asn Phe Pro Ile Leu Met Trp Ser Trp Lys Ile
1               5                   10                  15

<210> SEQ ID NO 25
<211> LENGTH: 15
<212> TYPE: PRT
<213> ORGANISM: Alternaria alternata

<400> SEQUENCE: 25

Gly Ser Arg Ile Tyr Val Gln Glu Glu Ile Tyr Asp Lys Phe Ile
1               5                   10                  15

<210> SEQ ID NO 26
<211> LENGTH: 15
<212> TYPE: PRT
<213> ORGANISM: Alternaria alternata

<400> SEQUENCE: 26

Val Gln Glu Glu Ile Tyr Asp Lys Phe Ile Gln Arg Phe Lys Glu
1               5                   10                  15

<210> SEQ ID NO 27
<211> LENGTH: 15
<212> TYPE: PRT
<213> ORGANISM: Alternaria alternata

<400> SEQUENCE: 27

Tyr Asp Lys Phe Ile Gln Arg Phe Lys Glu Arg Ala Ala Gln Asn
1               5                   10                  15

<210> SEQ ID NO 28
<211> LENGTH: 15
<212> TYPE: PRT
<213> ORGANISM: Alternaria alternata

<400> SEQUENCE: 28

-continued

Val Ser Gln Leu Gln Phe Asp Arg Ile Met Gly Tyr Ile Glu Glu
1               5                   10                  15

<210> SEQ ID NO 29
<211> LENGTH: 15
<212> TYPE: PRT
<213> ORGANISM: Alternaria alternata

<400> SEQUENCE: 29

Gly Asp Lys Gly Tyr Phe Ile Glu Pro Thr Ile Phe Ser Asn Val
1               5                   10                  15

<210> SEQ ID NO 30
<211> LENGTH: 15
<212> TYPE: PRT
<213> ORGANISM: Alternaria alternata

<400> SEQUENCE: 30

Tyr Gly Leu Ala Ala Val His Thr Ser Asn Leu Thr Thr Ala
1               5                   10                  15

<210> SEQ ID NO 31
<211> LENGTH: 15
<212> TYPE: PRT
<213> ORGANISM: Alternaria alternata

<400> SEQUENCE: 31

Asn Leu Thr Thr Ala Ile Glu Val Ala Asn Ala Leu Arg Ala Gly
1               5                   10                  15

<210> SEQ ID NO 32
<211> LENGTH: 15
<212> TYPE: PRT
<213> ORGANISM: Alternaria alternata

<400> SEQUENCE: 32

Ile Glu Val Ala Asn Ala Leu Arg Ala Gly Thr Val Trp Val Asn
1               5                   10                  15

<210> SEQ ID NO 33
<211> LENGTH: 15
<212> TYPE: PRT
<213> ORGANISM: Alternaria alternata

<400> SEQUENCE: 33

Thr Val Trp Val Asn Ser Tyr Asn Thr Leu His Trp Gln Leu Pro
1               5                   10                  15

<210> SEQ ID NO 34
<211> LENGTH: 15
<212> TYPE: PRT
<213> ORGANISM: Alternaria alternata

<400> SEQUENCE: 34

Ala Ala Leu Asp Asn Tyr Ile Gln Thr Lys Thr Val Ser Ile Arg
1               5                   10                  15

<210> SEQ ID NO 35
<211> LENGTH: 15
<212> TYPE: PRT
<213> ORGANISM: Alternaria alternata

<400> SEQUENCE: 35

Tyr Ile Gln Thr Lys Thr Val Ser Ile Arg Leu Gly Asp Val Leu

```
1               5               10              15
```

<210> SEQ ID NO 36
<211> LENGTH: 15
<212> TYPE: PRT
<213> ORGANISM: Alternaria alternata

<400> SEQUENCE: 36

```
Met Ser Thr Ser Glu Leu Ala Thr Ser Tyr Ala Ala Leu Ile Leu
1               5                   10                  15
```

<210> SEQ ID NO 37
<211> LENGTH: 15
<212> TYPE: PRT
<213> ORGANISM: Alternaria alternata

<400> SEQUENCE: 37

```
Leu Ala Thr Ser Tyr Ala Ala Leu Ile Leu Ala Asp Asp Gly Val
1               5                   10                  15
```

<210> SEQ ID NO 38
<211> LENGTH: 15
<212> TYPE: PRT
<213> ORGANISM: Alternaria alternata

<400> SEQUENCE: 38

```
Lys Leu Gln Ser Leu Ile Lys Ala Ala Lys Ile Glu Glu Val Glu
1               5                   10                  15
```

<210> SEQ ID NO 39
<211> LENGTH: 15
<212> TYPE: PRT
<213> ORGANISM: Alternaria alternata

<400> SEQUENCE: 39

```
Pro Ile Trp Thr Thr Leu Phe Ala Lys Ala Leu Glu Gly Lys Asp
1               5                   10                  15
```

<210> SEQ ID NO 40
<211> LENGTH: 15
<212> TYPE: PRT
<213> ORGANISM: Alternaria alternata

<400> SEQUENCE: 40

```
Leu Leu Leu Arg Trp Arg Ala Ala Asp Ala Ala Pro Ala Ala Glu
1               5                   10                  15
```

<210> SEQ ID NO 41
<211> LENGTH: 15
<212> TYPE: PRT
<213> ORGANISM: Alternaria alternata

<400> SEQUENCE: 41

```
Ser Glu Leu Ala Val Gln Lys Leu Val Leu Phe Ala Val Lys Gly
1               5                   10                  15
```

<210> SEQ ID NO 42
<211> LENGTH: 15
<212> TYPE: PRT
<213> ORGANISM: Alternaria alternata

<400> SEQUENCE: 42

```
Gln Lys Leu Val Leu Phe Ala Val Lys Gly Thr Ala Thr Ser Thr
1               5                   10                  15
```

<210> SEQ ID NO 43
<211> LENGTH: 15
<212> TYPE: PRT
<213> ORGANISM: Alternaria alternata

<400> SEQUENCE: 43

```
His Asn Thr Val Arg Pro Leu Ile Leu Leu Asp Glu Leu Gly Val
1               5                   10                  15
```

<210> SEQ ID NO 44
<211> LENGTH: 15
<212> TYPE: PRT
<213> ORGANISM: Alternaria alternata

<400> SEQUENCE: 44

```
Asp Thr Leu Arg Ala Trp Glu Ser Thr Ser Thr Leu Met Tyr Ile
1               5                   10                  15
```

<210> SEQ ID NO 45
<211> LENGTH: 15
<212> TYPE: PRT
<213> ORGANISM: Alternaria alternata

<400> SEQUENCE: 45

```
Ile Asn Asn Trp Leu Thr Leu His Thr Ala Ala Leu Gly Pro Thr
1               5                   10                  15
```

<210> SEQ ID NO 46
<211> LENGTH: 15
<212> TYPE: PRT
<213> ORGANISM: Alternaria alternata

<400> SEQUENCE: 46

```
Ala Lys Tyr Trp Leu Tyr Phe Tyr Lys Leu His Pro Glu Lys Leu
1               5                   10                  15
```

<210> SEQ ID NO 47
<211> LENGTH: 15
<212> TYPE: PRT
<213> ORGANISM: Alternaria alternata

<400> SEQUENCE: 47

```
Pro Lys Thr Ile Glu Lys Leu Arg Ser Asn Ile Thr Val Gln Tyr
1               5                   10                  15
```

<210> SEQ ID NO 48
<211> LENGTH: 15
<212> TYPE: PRT
<213> ORGANISM: Alternaria alternata

<400> SEQUENCE: 48

```
Lys Leu Arg Ser Asn Ile Thr Val Gln Tyr Asp Ile Leu Glu Arg
1               5                   10                  15
```

<210> SEQ ID NO 49
<211> LENGTH: 15
<212> TYPE: PRT
<213> ORGANISM: Alternaria alternata

<400> SEQUENCE: 49

```
Gly Gln Gln Tyr Leu Ala Trp Leu Asn Glu Lys Phe Lys Arg Ser
1               5                   10                  15
```

<210> SEQ ID NO 50

```
<211> LENGTH: 15
<212> TYPE: PRT
<213> ORGANISM: Alternaria alternata

<400> SEQUENCE: 50

Ala Trp Leu Asn Glu Lys Phe Lys Arg Ser Ser Tyr Asn Arg Arg
1               5                   10                  15

<210> SEQ ID NO 51
<211> LENGTH: 15
<212> TYPE: PRT
<213> ORGANISM: Alternaria alternata

<400> SEQUENCE: 51

Leu Cys Tyr Glu Lys Tyr Arg Arg Val Val Arg Ala Gly Val Lys
1               5                   10                  15

<210> SEQ ID NO 52
<211> LENGTH: 15
<212> TYPE: PRT
<213> ORGANISM: Alternaria alternata

<400> SEQUENCE: 52

Arg Ala Gly Val Lys Val Ala Gln Thr Ala Arg Val Val Cys Pro
1               5                   10                  15

<210> SEQ ID NO 53
<211> LENGTH: 15
<212> TYPE: PRT
<213> ORGANISM: Alternaria alternata

<400> SEQUENCE: 53

Ser Ala Lys Asn Ala Leu Glu Ser Tyr Ala Tyr Ser Leu Arg Asn
1               5                   10                  15

<210> SEQ ID NO 54
<211> LENGTH: 15
<212> TYPE: PRT
<213> ORGANISM: Alternaria alternata

<400> SEQUENCE: 54

Leu Glu Ser Tyr Ala Tyr Ser Leu Arg Asn Thr Leu Ser Asp Ser
1               5                   10                  15

<210> SEQ ID NO 55
<211> LENGTH: 15
<212> TYPE: PRT
<213> ORGANISM: Alternaria alternata

<400> SEQUENCE: 55

Ala Thr Lys Asp Glu Tyr Glu Ser Gln Gln Lys Glu Leu Glu Gly
1               5                   10                  15

<210> SEQ ID NO 56
<211> LENGTH: 15
<212> TYPE: PRT
<213> ORGANISM: Alternaria alternata

<400> SEQUENCE: 56

Ala Asp Lys Val Val Leu Val Ala Tyr Phe Ala Ala Asp Asp Lys
1               5                   10                  15

<210> SEQ ID NO 57
<211> LENGTH: 15
<212> TYPE: PRT
```

-continued

<213> ORGANISM: Alternaria alternata

<400> SEQUENCE: 57

Asn Phe Leu Phe Gly Ala Thr Asn Asp Ala Ala Leu Ala Lys Ala
1               5                   10                  15

<210> SEQ ID NO 58
<211> LENGTH: 15
<212> TYPE: PRT
<213> ORGANISM: Alternaria alternata

<400> SEQUENCE: 58

Met Arg Thr Tyr Pro Arg Leu Arg Lys Val Ala Ser Thr Pro Leu
1               5                   10                  15

<210> SEQ ID NO 59
<211> LENGTH: 15
<212> TYPE: PRT
<213> ORGANISM: Alternaria alternata

<400> SEQUENCE: 59

Arg Leu Arg Lys Val Ala Ser Thr Pro Leu Ile Gly Glu Val Gly
1               5                   10                  15

<210> SEQ ID NO 60
<211> LENGTH: 15
<212> TYPE: PRT
<213> ORGANISM: Alternaria alternata

<400> SEQUENCE: 60

Pro Glu Thr Tyr Ala Gly Tyr Met Ala Ala Gly Ile Pro Leu Ala
1               5                   10                  15

<210> SEQ ID NO 61
<211> LENGTH: 15
<212> TYPE: PRT
<213> ORGANISM: Alternaria alternata

<400> SEQUENCE: 61

Gly Tyr Met Ala Ala Gly Ile Pro Leu Ala Tyr Ile Phe Ala Glu
1               5                   10                  15

<210> SEQ ID NO 62
<211> LENGTH: 15
<212> TYPE: PRT
<213> ORGANISM: Alternaria alternata

<400> SEQUENCE: 62

Gly Ile Pro Leu Ala Tyr Ile Phe Ala Glu Thr Pro Glu Glu Arg
1               5                   10                  15

<210> SEQ ID NO 63
<211> LENGTH: 15
<212> TYPE: PRT
<213> ORGANISM: Alternaria alternata

<400> SEQUENCE: 63

Gly Glu Ile Asn Phe Ala Thr Ile Asp Ala Lys Ser Phe Gly Gln
1               5                   10                  15

<210> SEQ ID NO 64
<211> LENGTH: 15
<212> TYPE: PRT
<213> ORGANISM: Alternaria alternata

```
<400> SEQUENCE: 64

Asp Glu Leu Ser Lys Leu Val Thr Ile Ala Lys Val Asp Ala Thr
1               5                   10                  15

<210> SEQ ID NO 65
<211> LENGTH: 15
<212> TYPE: PRT
<213> ORGANISM: Alternaria alternata

<400> SEQUENCE: 65

Asp Glu Ile Gln Gly Phe Leu Pro Ser Ser Leu Phe Pro Leu Ala
1               5                   10                  15

<210> SEQ ID NO 66
<211> LENGTH: 15
<212> TYPE: PRT
<213> ORGANISM: Alternaria alternata

<400> SEQUENCE: 66

Met Lys His Leu Ala Ala Tyr Leu Leu Leu Gly Leu Gly Gly Asn
1               5                   10                  15

<210> SEQ ID NO 67
<211> LENGTH: 15
<212> TYPE: PRT
<213> ORGANISM: Alternaria alternata

<400> SEQUENCE: 67

Ala Asp Val Lys Ala Val Leu Glu Ser Val Gly Ile Glu Ala Asp
1               5                   10                  15

<210> SEQ ID NO 68
<211> LENGTH: 15
<212> TYPE: PRT
<213> ORGANISM: Alternaria alternata

<400> SEQUENCE: 68

Ile Asn Glu Leu Ile Ala Ser Gly Ser Glu Lys Leu Ala Ser Val
1               5                   10                  15

<210> SEQ ID NO 69
<211> LENGTH: 15
<212> TYPE: PRT
<213> ORGANISM: Alternaria alternata

<400> SEQUENCE: 69

Met Thr Ile Thr Lys Ile His Ala Arg Ser Val Tyr Asp Ser Arg
1               5                   10                  15

<210> SEQ ID NO 70
<211> LENGTH: 15
<212> TYPE: PRT
<213> ORGANISM: Alternaria alternata

<400> SEQUENCE: 70

Leu Gly Ala Asn Ala Ile Leu Gly Val Ser Met Ala Ile Ala Lys
1               5                   10                  15

<210> SEQ ID NO 71
<211> LENGTH: 15
<212> TYPE: PRT
<213> ORGANISM: Alternaria alternata

<400> SEQUENCE: 71
```

```
Ile Leu Gly Val Ser Met Ala Ile Ala Lys Ala Ala Ala Glu
1               5                   10                  15
```

<210> SEQ ID NO 72
<211> LENGTH: 15
<212> TYPE: PRT
<213> ORGANISM: Alternaria alternata

<400> SEQUENCE: 72

```
Met Ala Ile Ala Lys Ala Ala Ala Glu Lys Gly Val Pro Leu
1               5                   10                  15
```

<210> SEQ ID NO 73
<211> LENGTH: 15
<212> TYPE: PRT
<213> ORGANISM: Alternaria alternata

<400> SEQUENCE: 73

```
Gly Gly Arg Leu Ala Phe Gln Glu Phe Met Ile Val Pro Cys Glu
1               5                   10                  15
```

<210> SEQ ID NO 74
<211> LENGTH: 15
<212> TYPE: PRT
<213> ORGANISM: Alternaria alternata

<400> SEQUENCE: 74

```
Gly Ala Glu Val Tyr Gln Lys Leu Lys Ala Leu Ala Lys Lys Thr
1               5                   10                  15
```

<210> SEQ ID NO 75
<211> LENGTH: 15
<212> TYPE: PRT
<213> ORGANISM: Alternaria alternata

<400> SEQUENCE: 75

```
Ile Lys Ile Ala Met Asp Val Ala Ser Ser Glu Phe Tyr Lys Ala
1               5                   10                  15
```

<210> SEQ ID NO 76
<211> LENGTH: 15
<212> TYPE: PRT
<213> ORGANISM: Alternaria alternata

<400> SEQUENCE: 76

```
Lys Ser Lys Trp Leu Thr Tyr Glu Gln Leu Ala Glu Met Tyr Lys
1               5                   10                  15
```

<210> SEQ ID NO 77
<211> LENGTH: 15
<212> TYPE: PRT
<213> ORGANISM: Alternaria alternata

<400> SEQUENCE: 77

```
Glu Ala Trp Ser Tyr Phe Phe Lys Thr Tyr Asp Gly Gln Ile Val
1               5                   10                  15
```

<210> SEQ ID NO 78
<211> LENGTH: 15
<212> TYPE: PRT
<213> ORGANISM: Alternaria alternata

<400> SEQUENCE: 78

```
Ile Glu Leu Lys Ser Cys Asn Ala Leu Leu Leu Lys Val Asn Gln
1               5                   10                  15
```

```
<210> SEQ ID NO 79
<211> LENGTH: 15
<212> TYPE: PRT
<213> ORGANISM: Alternaria alternata

<400> SEQUENCE: 79

Cys Asn Ala Leu Leu Lys Val Asn Gln Ile Gly Thr Ile Thr
1               5                   10                  15

<210> SEQ ID NO 80
<211> LENGTH: 15
<212> TYPE: PRT
<213> ORGANISM: Alternaria alternata

<400> SEQUENCE: 80

Gly Ala Gly Trp Gly Val Met Val Ser His Arg Ser Gly Glu Thr
1               5                   10                  15

<210> SEQ ID NO 81
<211> LENGTH: 15
<212> TYPE: PRT
<213> ORGANISM: Alternaria alternata

<400> SEQUENCE: 81

Glu Arg Leu Ala Lys Leu Asn Gln Ile Leu Arg Ile Glu Glu Glu
1               5                   10                  15

<210> SEQ ID NO 82
<211> LENGTH: 15
<212> TYPE: PRT
<213> ORGANISM: Alternaria alternata

<400> SEQUENCE: 82

Ala Ile Val Tyr Tyr Ser Met Tyr Gly His Ile Lys Lys Met Ala
1               5                   10                  15

<210> SEQ ID NO 83
<211> LENGTH: 15
<212> TYPE: PRT
<213> ORGANISM: Alternaria alternata

<400> SEQUENCE: 83

Gly Gly Asp Ala Lys Leu Phe Gln Val Ala Glu Thr Leu Pro Gln
1               5                   10                  15

<210> SEQ ID NO 84
<211> LENGTH: 15
<212> TYPE: PRT
<213> ORGANISM: Alternaria alternata

<400> SEQUENCE: 84

Leu Phe Gln Val Ala Glu Thr Leu Pro Gln Glu Val Leu Asp Lys
1               5                   10                  15

<210> SEQ ID NO 85
<211> LENGTH: 15
<212> TYPE: PRT
<213> ORGANISM: Alternaria alternata

<400> SEQUENCE: 85

Pro Ala Val Leu Glu Glu Phe Asp Gly Ile Leu Phe Gly Ile Pro
1               5                   10                  15
```

```
<210> SEQ ID NO 86
<211> LENGTH: 15
<212> TYPE: PRT
<213> ORGANISM: Alternaria alternata

<400> SEQUENCE: 86

Phe Trp Gly Lys Tyr Ala Gly Val Phe Val Ser Thr Gly Thr Leu
1               5                   10                  15

<210> SEQ ID NO 87
<211> LENGTH: 15
<212> TYPE: PRT
<213> ORGANISM: Alternaria alternata

<400> SEQUENCE: 87

Ile Tyr Val Pro Leu Gly Tyr Lys Thr Ala Phe Ser Met Leu Ala
1               5                   10                  15

<210> SEQ ID NO 88
<211> LENGTH: 15
<212> TYPE: PRT
<213> ORGANISM: Alternaria alternata

<400> SEQUENCE: 88

Gly Tyr Lys Thr Ala Phe Ser Met Leu Ala Asn Leu Asp Glu Val
1               5                   10                  15

<210> SEQ ID NO 89
<211> LENGTH: 15
<212> TYPE: PRT
<213> ORGANISM: Alternaria alternata

<400> SEQUENCE: 89

Ser Glu Leu Glu Leu Asn Ile Ala Gln Ala Gln Gly Lys Ala Phe
1               5                   10                  15

<210> SEQ ID NO 90
<211> LENGTH: 15
<212> TYPE: PRT
<213> ORGANISM: Alternaria alternata

<400> SEQUENCE: 90

Ala Gln Gly Lys Ala Phe Tyr Glu Ala Val Ala Lys Ala His Gln
1               5                   10                  15

<210> SEQ ID NO 91
<211> LENGTH: 15
<212> TYPE: PRT
<213> ORGANISM: Alternaria alternata

<400> SEQUENCE: 91

Pro Gln Ala Thr Glu Leu Lys Asp Leu Phe Ser Leu Lys Gly Lys
1               5                   10                  15

<210> SEQ ID NO 92
<211> LENGTH: 15
<212> TYPE: PRT
<213> ORGANISM: Alternaria alternata

<400> SEQUENCE: 92

Leu Lys Asp Leu Phe Ser Leu Lys Gly Lys Val Val Ile Val Thr
1               5                   10                  15

<210> SEQ ID NO 93
<211> LENGTH: 15
```

```
<212> TYPE: PRT
<213> ORGANISM: Alternaria alternata

<400> SEQUENCE: 93

Ala Asp Leu Ala Ile Thr Tyr Asn Ser Arg Ala Glu Gly Ala Glu
1               5                   10                  15

<210> SEQ ID NO 94
<211> LENGTH: 15
<212> TYPE: PRT
<213> ORGANISM: Alternaria alternata

<400> SEQUENCE: 94

Thr Gly Ser Leu Val Ile Thr Ser Ser Met Ser Gly His Ile Ala
1               5                   10                  15

<210> SEQ ID NO 95
<211> LENGTH: 15
<212> TYPE: PRT
<213> ORGANISM: Alternaria alternata

<400> SEQUENCE: 95

Val Ala Lys Ala Gly Cys Ile His Leu Ala Lys Ser Leu Ala Asn
1               5                   10                  15

<210> SEQ ID NO 96
<211> LENGTH: 15
<212> TYPE: PRT
<213> ORGANISM: Alternaria alternata

<400> SEQUENCE: 96

Cys Ile His Leu Ala Lys Ser Leu Ala Asn Glu Trp Arg Asp Phe
1               5                   10                  15

<210> SEQ ID NO 97
<211> LENGTH: 15
<212> TYPE: PRT
<213> ORGANISM: Alternaria alternata

<400> SEQUENCE: 97

Gln Asp Ile Gln Lys Leu Trp His Ser Met Ile Pro Met Gly Arg
1               5                   10                  15

<210> SEQ ID NO 98
<211> LENGTH: 15
<212> TYPE: PRT
<213> ORGANISM: Alternaria alternata

<400> SEQUENCE: 98

Glu Leu Lys Gly Ala Tyr Val Tyr Phe Ala Ser Asp Ala Ser Ser
1               5                   10                  15

<210> SEQ ID NO 99
<211> LENGTH: 15
<212> TYPE: PRT
<213> ORGANISM: Alternaria alternata

<400> SEQUENCE: 99

Tyr Val Tyr Phe Ala Ser Asp Ala Ser Ser Tyr Cys Thr Gly Ser
1               5                   10                  15

<210> SEQ ID NO 100
<211> LENGTH: 15
<212> TYPE: PRT
<213> ORGANISM: Periplaneta americana
```

<400> SEQUENCE: 100

Ile Asn Glu Ile His Ser Ile Ile Gly Leu Pro Pro Phe Val Pro
1               5                   10                  15

<210> SEQ ID NO 101
<211> LENGTH: 15
<212> TYPE: PRT
<213> ORGANISM: Periplaneta americana

<400> SEQUENCE: 101

Asp Glu Leu Lys Ala Leu Phe Gln Glu Lys Leu Glu Thr Ser Pro
1               5                   10                  15

<210> SEQ ID NO 102
<211> LENGTH: 15
<212> TYPE: PRT
<213> ORGANISM: Periplaneta americana

<400> SEQUENCE: 102

Leu Glu Thr Ser Pro Asp Phe Lys Ala Leu Tyr Asp Ala Ile Arg
1               5                   10                  15

<210> SEQ ID NO 103
<211> LENGTH: 15
<212> TYPE: PRT
<213> ORGANISM: Periplaneta americana

<400> SEQUENCE: 103

Asp Phe Lys Ala Leu Tyr Asp Ala Ile Arg Ser Pro Glu Phe Gln
1               5                   10                  15

<210> SEQ ID NO 104
<211> LENGTH: 15
<212> TYPE: PRT
<213> ORGANISM: Periplaneta americana

<400> SEQUENCE: 104

Ser Pro Glu Phe Gln Ser Ile Ile Ser Thr Leu Asn Ala Met Gln
1               5                   10                  15

<210> SEQ ID NO 105
<211> LENGTH: 15
<212> TYPE: PRT
<213> ORGANISM: Periplaneta americana

<400> SEQUENCE: 105

Ser Ile Ile Ser Thr Leu Asn Ala Met Gln Arg Ser Glu His His
1               5                   10                  15

<210> SEQ ID NO 106
<211> LENGTH: 15
<212> TYPE: PRT
<213> ORGANISM: Periplaneta americana

<400> SEQUENCE: 106

Lys Gly Val Asp Val Asp His Phe Ile Gln Leu Ile Arg Ala Leu
1               5                   10                  15

<210> SEQ ID NO 107
<211> LENGTH: 15
<212> TYPE: PRT
<213> ORGANISM: Periplaneta americana

<400> SEQUENCE: 107

Asp His Phe Ile Gln Leu Ile Arg Ala Leu Phe Gly Leu Ser Arg
1               5                   10                  15

<210> SEQ ID NO 108
<211> LENGTH: 15
<212> TYPE: PRT
<213> ORGANISM: Periplaneta americana

<400> SEQUENCE: 108

Leu Ile Arg Ala Leu Phe Gly Leu Ser Arg Ala Ala Arg Asn Leu
1               5                   10                  15

<210> SEQ ID NO 109
<211> LENGTH: 15
<212> TYPE: PRT
<213> ORGANISM: Periplaneta americana

<400> SEQUENCE: 109

Phe Gly Leu Ser Arg Ala Ala Arg Asn Leu Gln Asp Asp Leu Asn
1               5                   10                  15

<210> SEQ ID NO 110
<211> LENGTH: 15
<212> TYPE: PRT
<213> ORGANISM: Periplaneta americana

<400> SEQUENCE: 110

Gln Asp Asp Leu Asn Asp Phe Leu His Ser Leu Glu Pro Ile Ser
1               5                   10                  15

<210> SEQ ID NO 111
<211> LENGTH: 15
<212> TYPE: PRT
<213> ORGANISM: Periplaneta americana

<400> SEQUENCE: 111

Leu His Ala Asp Asp Phe His Lys Ile Ile Thr Thr Ile Glu Ala
1               5                   10                  15

<210> SEQ ID NO 112
<211> LENGTH: 15
<212> TYPE: PRT
<213> ORGANISM: Periplaneta americana

<400> SEQUENCE: 112

Phe His Lys Ile Ile Thr Thr Ile Glu Ala Leu Pro Glu Phe Ala
1               5                   10                  15

<210> SEQ ID NO 113
<211> LENGTH: 15
<212> TYPE: PRT
<213> ORGANISM: Periplaneta americana

<400> SEQUENCE: 113

Leu Pro Glu Phe Ala Asn Phe Tyr Asn Phe Leu Lys Glu His Gly
1               5                   10                  15

<210> SEQ ID NO 114
<211> LENGTH: 15
<212> TYPE: PRT
<213> ORGANISM: Periplaneta americana

<400> SEQUENCE: 114

Asn Phe Tyr Asn Phe Leu Lys Glu His Gly Leu Asp Val Val Asp

<210> SEQ ID NO 115
<211> LENGTH: 15
<212> TYPE: PRT
<213> ORGANISM: Periplaneta americana

<400> SEQUENCE: 115

Leu Asp Val Val Asp Tyr Ile Asn Glu Ile His Ser Ile Ile Gly
1               5                   10                  15

<210> SEQ ID NO 116
<211> LENGTH: 15
<212> TYPE: PRT
<213> ORGANISM: Periplaneta americana

<400> SEQUENCE: 116

Tyr Ile Asn Glu Ile His Ser Ile Ile Gly Leu Pro Pro Phe Val
1               5                   10                  15

<210> SEQ ID NO 117
<211> LENGTH: 15
<212> TYPE: PRT
<213> ORGANISM: Periplaneta americana

<400> SEQUENCE: 117

Val Gly Ile Asn Gly Leu Ile Asp Asp Val Ile Ala Ile Leu Pro
1               5                   10                  15

<210> SEQ ID NO 118
<211> LENGTH: 15
<212> TYPE: PRT
<213> ORGANISM: Periplaneta americana

<400> SEQUENCE: 118

Leu Ile Asp Asp Val Ile Ala Ile Leu Pro Val Asp Glu Leu Lys
1               5                   10                  15

<210> SEQ ID NO 119
<211> LENGTH: 15
<212> TYPE: PRT
<213> ORGANISM: Periplaneta americana

<400> SEQUENCE: 119

Ile Ala Ile Leu Pro Val Asp Glu Leu Lys Ala Leu Phe Gln Glu
1               5                   10                  15

<210> SEQ ID NO 120
<211> LENGTH: 15
<212> TYPE: PRT
<213> ORGANISM: Periplaneta americana

<400> SEQUENCE: 120

Val Asp Glu Leu Lys Ala Leu Phe Gln Glu Lys Leu Glu Thr Ser
1               5                   10                  15

<210> SEQ ID NO 121
<211> LENGTH: 15
<212> TYPE: PRT
<213> ORGANISM: Periplaneta americana

<400> SEQUENCE: 121

Pro Asp Phe Lys Ala Leu Tyr Asp Ala Ile Arg Ser Pro Glu Phe
1               5                   10                  15

<210> SEQ ID NO 122
<211> LENGTH: 15
<212> TYPE: PRT
<213> ORGANISM: Periplaneta americana

<400> SEQUENCE: 122

Arg Ser Pro Glu Phe Gln Ser Ile Ile Ser Thr Leu Asn Ala Met
1               5                   10                  15

<210> SEQ ID NO 123
<211> LENGTH: 15
<212> TYPE: PRT
<213> ORGANISM: Periplaneta americana

<400> SEQUENCE: 123

Asp Leu Asn Asp Phe Leu Ala Leu Ile Pro Thr Asp Gln Ile Leu
1               5                   10                  15

<210> SEQ ID NO 124
<211> LENGTH: 15
<212> TYPE: PRT
<213> ORGANISM: Periplaneta americana

<400> SEQUENCE: 124

Leu Ala Leu Ile Pro Thr Asp Gln Ile Leu Ala Ile Ala Met Asp
1               5                   10                  15

<210> SEQ ID NO 125
<211> LENGTH: 15
<212> TYPE: PRT
<213> ORGANISM: Periplaneta americana

<400> SEQUENCE: 125

Thr Asp Gln Ile Leu Ala Ile Ala Met Asp Tyr Leu Ala Asn Asp
1               5                   10                  15

<210> SEQ ID NO 126
<211> LENGTH: 15
<212> TYPE: PRT
<213> ORGANISM: Periplaneta americana

<400> SEQUENCE: 126

Ala Ile Ala Met Asp Tyr Leu Ala Asn Asp Ala Glu Val Gln Glu
1               5                   10                  15

<210> SEQ ID NO 127
<211> LENGTH: 15
<212> TYPE: PRT
<213> ORGANISM: Periplaneta americana

<400> SEQUENCE: 127

Ala Glu Val Gln Glu Leu Val Ala Tyr Leu Gln Ser Asp Asp Phe
1               5                   10                  15

<210> SEQ ID NO 128
<211> LENGTH: 15
<212> TYPE: PRT
<213> ORGANISM: Periplaneta americana

<400> SEQUENCE: 128

Gln Ser Asp Asp Phe His Lys Ile Ile Thr Thr Ile Glu Ala Leu
1               5                   10                  15

<210> SEQ ID NO 129

```
<211> LENGTH: 15
<212> TYPE: PRT
<213> ORGANISM: Periplaneta americana

<400> SEQUENCE: 129

His Lys Ile Ile Thr Thr Ile Glu Ala Leu Pro Glu Phe Ala Asn
1               5                   10                  15

<210> SEQ ID NO 130
<211> LENGTH: 15
<212> TYPE: PRT
<213> ORGANISM: Periplaneta americana

<400> SEQUENCE: 130

Pro Glu Phe Ala Asn Phe Tyr Asn Phe Leu Lys Glu His Gly Leu
1               5                   10                  15

<210> SEQ ID NO 131
<211> LENGTH: 15
<212> TYPE: PRT
<213> ORGANISM: Periplaneta americana

<400> SEQUENCE: 131

Phe Tyr Asn Phe Leu Lys Glu His Gly Leu Asp Val Val Asp Tyr
1               5                   10                  15

<210> SEQ ID NO 132
<211> LENGTH: 15
<212> TYPE: PRT
<213> ORGANISM: Periplaneta americana

<400> SEQUENCE: 132

Asp Val Val Asp Tyr Ile Asn Glu Ile His Ser Ile Ile Gly Leu
1               5                   10                  15

<210> SEQ ID NO 133
<211> LENGTH: 15
<212> TYPE: PRT
<213> ORGANISM: Periplaneta americana

<400> SEQUENCE: 133

Asp Phe Lys Ala Leu Tyr Asp Ala Ile Asp Leu Arg Ser Ser Arg
1               5                   10                  15

<210> SEQ ID NO 134
<211> LENGTH: 15
<212> TYPE: PRT
<213> ORGANISM: Periplaneta americana

<400> SEQUENCE: 134

Phe Lys Ala Leu Tyr Asp Ala Ile Asp Leu Arg Ser Ser Arg Ala
1               5                   10                  15

<210> SEQ ID NO 135
<211> LENGTH: 15
<212> TYPE: PRT
<213> ORGANISM: Periplaneta americana

<400> SEQUENCE: 135

Met Leu Arg Tyr Leu Val Leu Ala Ser Leu Ile Ala Cys Ser Leu
1               5                   10                  15

<210> SEQ ID NO 136
<211> LENGTH: 15
<212> TYPE: PRT
```

<213> ORGANISM: Periplaneta americana

<400> SEQUENCE: 136

Val Leu Ala Ser Leu Ile Ala Cys Ser Leu Ser Ala Val Pro Lys
1               5                   10                  15

<210> SEQ ID NO 137
<211> LENGTH: 15
<212> TYPE: PRT
<213> ORGANISM: Periplaneta americana

<400> SEQUENCE: 137

Tyr Pro Tyr Gln Leu Ser Phe Glu Tyr Tyr Gly Ser His Met Cys
1               5                   10                  15

<210> SEQ ID NO 138
<211> LENGTH: 15
<212> TYPE: PRT
<213> ORGANISM: Periplaneta americana

<400> SEQUENCE: 138

His Gln Ala Thr Gln Leu Ile Ala Asn Pro Asn Tyr Asp Tyr Tyr
1               5                   10                  15

<210> SEQ ID NO 139
<211> LENGTH: 15
<212> TYPE: PRT
<213> ORGANISM: Periplaneta americana

<400> SEQUENCE: 139

Asn Tyr Asp Tyr Tyr Thr Ile Asp Phe Asp Val Ala Val Ala Arg
1               5                   10                  15

<210> SEQ ID NO 140
<211> LENGTH: 15
<212> TYPE: PRT
<213> ORGANISM: Periplaneta americana

<400> SEQUENCE: 140

Thr Ile Asp Phe Asp Val Ala Val Ala Arg Val Ser Pro Ala Phe
1               5                   10                  15

<210> SEQ ID NO 141
<211> LENGTH: 15
<212> TYPE: PRT
<213> ORGANISM: Periplaneta americana

<400> SEQUENCE: 141

Val Ala Val Ala Arg Val Ser Pro Ala Phe Ser Tyr Gly Thr Gly
1               5                   10                  15

<210> SEQ ID NO 142
<211> LENGTH: 15
<212> TYPE: PRT
<213> ORGANISM: Periplaneta americana

<400> SEQUENCE: 142

Thr Leu Pro Ser Gln Leu Gln Val Val Ser Val Pro Ile Val Ser
1               5                   10                  15

<210> SEQ ID NO 143
<211> LENGTH: 15
<212> TYPE: PRT
<213> ORGANISM: Periplaneta americana

<400> SEQUENCE: 143

Leu Gln Val Val Ser Val Pro Ile Val Ser Arg Ser Glu Cys Asn
1               5                   10                  15

<210> SEQ ID NO 144
<211> LENGTH: 15
<212> TYPE: PRT
<213> ORGANISM: Periplaneta americana

<400> SEQUENCE: 144

Pro Gly Val Tyr Ser Asn Val Ala Ser Leu Lys Gly Phe Ile Thr
1               5                   10                  15

<210> SEQ ID NO 145
<211> LENGTH: 15
<212> TYPE: PRT
<213> ORGANISM: Periplaneta americana

<400> SEQUENCE: 145

Asn Val Ala Ser Leu Lys Gly Phe Ile Thr Glu Gln Thr Gly Val
1               5                   10                  15

<210> SEQ ID NO 146
<211> LENGTH: 15
<212> TYPE: PRT
<213> ORGANISM: Periplaneta americana

<400> SEQUENCE: 146

Val Ala Ser Leu Lys Gly Phe Ile Thr Glu Gln Thr Gly Val Asn
1               5                   10                  15

<210> SEQ ID NO 147
<211> LENGTH: 15
<212> TYPE: PRT
<213> ORGANISM: Periplaneta americana

<400> SEQUENCE: 147

Leu Asn Ala Phe Asn Met Tyr Phe Arg Tyr Ile Tyr Pro Thr Trp
1               5                   10                  15

<210> SEQ ID NO 148
<211> LENGTH: 15
<212> TYPE: PRT
<213> ORGANISM: Periplaneta americana

<400> SEQUENCE: 148

Met Tyr Phe Arg Tyr Ile Tyr Pro Thr Trp Phe Asn Thr Thr Leu
1               5                   10                  15

<210> SEQ ID NO 149
<211> LENGTH: 15
<212> TYPE: PRT
<213> ORGANISM: Periplaneta americana

<400> SEQUENCE: 149

Gln Phe Tyr Tyr Thr Tyr His Gln Ile Tyr Ala Arg Tyr Phe Leu
1               5                   10                  15

<210> SEQ ID NO 150
<211> LENGTH: 15
<212> TYPE: PRT
<213> ORGANISM: Periplaneta americana

<400> SEQUENCE: 150

```
Tyr His Gln Ile Tyr Ala Arg Tyr Phe Leu Glu Arg Leu Ser Asn
1               5                   10                  15

<210> SEQ ID NO 151
<211> LENGTH: 15
<212> TYPE: PRT
<213> ORGANISM: Periplaneta americana

<400> SEQUENCE: 151

Ala Arg Tyr Phe Leu Glu Arg Leu Ser Asn Ser Leu Pro Asp Val
1               5                   10                  15

<210> SEQ ID NO 152
<211> LENGTH: 15
<212> TYPE: PRT
<213> ORGANISM: Periplaneta americana

<400> SEQUENCE: 152

Lys Pro Phe Gln Tyr Ser Lys Pro Leu Lys Thr Gly Tyr Asn Pro
1               5                   10                  15

<210> SEQ ID NO 153
<211> LENGTH: 15
<212> TYPE: PRT
<213> ORGANISM: Periplaneta americana

<400> SEQUENCE: 153

Asn Ile Asp Leu Phe Tyr Val Ser Asp Ile Lys Asn Tyr Glu Ser
1               5                   10                  15

<210> SEQ ID NO 154
<211> LENGTH: 15
<212> TYPE: PRT
<213> ORGANISM: Periplaneta americana

<400> SEQUENCE: 154

Gly Thr Ser Asn Ser Pro Tyr Gln Tyr Phe Tyr Gly Ser Ile Phe
1               5                   10                  15

<210> SEQ ID NO 155
<211> LENGTH: 15
<212> TYPE: PRT
<213> ORGANISM: Periplaneta americana

<400> SEQUENCE: 155

Pro Tyr Gln Tyr Phe Tyr Gly Ser Ile Phe His Phe Tyr Arg Leu
1               5                   10                  15

<210> SEQ ID NO 156
<211> LENGTH: 15
<212> TYPE: PRT
<213> ORGANISM: Periplaneta americana

<400> SEQUENCE: 156

Tyr Gly Ser Ile Phe His Phe Tyr Arg Leu Leu Val Gly His Val
1               5                   10                  15

<210> SEQ ID NO 157
<211> LENGTH: 15
<212> TYPE: PRT
<213> ORGANISM: Periplaneta americana

<400> SEQUENCE: 157

His Phe Tyr Arg Leu Leu Val Gly His Val Val Asp Pro Tyr His
1               5                   10                  15
```

<210> SEQ ID NO 158
<211> LENGTH: 15
<212> TYPE: PRT
<213> ORGANISM: Periplaneta americana

<400> SEQUENCE: 158

Phe Tyr Gln Leu Trp Lys Arg Ile Asp His Ile Val Gln Lys Tyr
1               5                   10                  15

<210> SEQ ID NO 159
<211> LENGTH: 15
<212> TYPE: PRT
<213> ORGANISM: Periplaneta americana

<400> SEQUENCE: 159

Lys Arg Ile Asp His Ile Val Gln Lys Tyr Lys Asn Arg Leu Pro
1               5                   10                  15

<210> SEQ ID NO 160
<211> LENGTH: 15
<212> TYPE: PRT
<213> ORGANISM: Periplaneta americana

<400> SEQUENCE: 160

Lys Leu Tyr Thr Tyr Phe Glu His Phe Glu His Ser Leu Gly Asn
1               5                   10                  15

<210> SEQ ID NO 161
<211> LENGTH: 15
<212> TYPE: PRT
<213> ORGANISM: Periplaneta americana

<400> SEQUENCE: 161

Phe Glu His Phe Glu His Ser Leu Gly Asn Ala Met Tyr Leu Gly
1               5                   10                  15

<210> SEQ ID NO 162
<211> LENGTH: 15
<212> TYPE: PRT
<213> ORGANISM: Periplaneta americana

<400> SEQUENCE: 162

Pro Phe Thr Tyr Asn Ile Glu Val Ser Ser Asp Lys Ala Gln Asp
1               5                   10                  15

<210> SEQ ID NO 163
<211> LENGTH: 15
<212> TYPE: PRT
<213> ORGANISM: Periplaneta americana

<400> SEQUENCE: 163

Asp Lys Ala Gln Asp Val Tyr Val Arg Ile Phe Leu Gly Pro Lys
1               5                   10                  15

<210> SEQ ID NO 164
<211> LENGTH: 15
<212> TYPE: PRT
<213> ORGANISM: Periplaneta americana

<400> SEQUENCE: 164

Tyr Arg Asn Leu Phe Lys Lys Val Ser Asp Ala Leu Glu Gly Lys
1               5                   10                  15

-continued

```
<210> SEQ ID NO 165
<211> LENGTH: 15
<212> TYPE: PRT
<213> ORGANISM: Periplaneta americana

<400> SEQUENCE: 165

Gly Gly Gln Thr Phe Thr Phe Tyr Val Ile Val Thr Pro Tyr Val
1               5                   10                  15

<210> SEQ ID NO 166
<211> LENGTH: 15
<212> TYPE: PRT
<213> ORGANISM: Periplaneta americana

<400> SEQUENCE: 166

Thr Phe Tyr Val Ile Val Thr Pro Tyr Val Lys Gln Asp Glu His
1               5                   10                  15

<210> SEQ ID NO 167
<211> LENGTH: 15
<212> TYPE: PRT
<213> ORGANISM: Periplaneta americana

<400> SEQUENCE: 167

Tyr Thr Pro Asn Met Tyr Phe Lys Asp Val Val Ile Phe His Lys
1               5                   10                  15

<210> SEQ ID NO 168
<211> LENGTH: 15
<212> TYPE: PRT
<213> ORGANISM: Periplaneta americana

<400> SEQUENCE: 168

Tyr Phe Lys Asp Val Val Ile Phe His Lys Lys Tyr Asp Glu Val
1               5                   10                  15

<210> SEQ ID NO 169
<211> LENGTH: 15
<212> TYPE: PRT
<213> ORGANISM: Periplaneta americana

<400> SEQUENCE: 169

Asp Glu Gln Ile Gln Leu Leu Lys Lys Ala Phe Asp Ala Phe Asp
1               5                   10                  15

<210> SEQ ID NO 170
<211> LENGTH: 15
<212> TYPE: PRT
<213> ORGANISM: Periplaneta americana

<400> SEQUENCE: 170

Met Val Gly Thr Ile Leu Glu Met Leu Gly His Pro Leu Asp Asp
1               5                   10                  15

<210> SEQ ID NO 171
<211> LENGTH: 15
<212> TYPE: PRT
<213> ORGANISM: Periplaneta americana

<400> SEQUENCE: 171

Gly Glu Leu Glu Phe Gln Glu Phe Val Thr Leu Ala Ala Arg Phe
1               5                   10                  15

<210> SEQ ID NO 172
<211> LENGTH: 15
```

-continued

```
<212> TYPE: PRT
<213> ORGANISM: Periplaneta americana

<400> SEQUENCE: 172

Gln Glu Phe Val Thr Leu Ala Ala Arg Phe Leu Val Glu Glu Asp
1               5                   10                  15

<210> SEQ ID NO 173
<211> LENGTH: 15
<212> TYPE: PRT
<213> ORGANISM: Periplaneta americana

<400> SEQUENCE: 173

Gly Tyr Ile Thr Thr Thr Val Leu Arg Glu Ile Leu Lys Glu Leu
1               5                   10                  15

<210> SEQ ID NO 174
<211> LENGTH: 15
<212> TYPE: PRT
<213> ORGANISM: Periplaneta americana

<400> SEQUENCE: 174

Thr Val Leu Arg Glu Ile Leu Lys Glu Leu Asp Asp Lys Leu Thr
1               5                   10                  15

<210> SEQ ID NO 175
<211> LENGTH: 15
<212> TYPE: PRT
<213> ORGANISM: Periplaneta americana

<400> SEQUENCE: 175

Arg Ser Glu Glu Arg Leu Ala Thr Ala Thr Ala Lys Leu Ala Glu
1               5                   10                  15

<210> SEQ ID NO 176
<211> LENGTH: 15
<212> TYPE: PRT
<213> ORGANISM: Periplaneta americana

<400> SEQUENCE: 176

Val Glu Leu Glu Glu Glu Leu Arg Val Val Gly Asn Asn Leu Lys
1               5                   10                  15

<210> SEQ ID NO 177
<211> LENGTH: 15
<212> TYPE: PRT
<213> ORGANISM: Periplaneta americana

<400> SEQUENCE: 177

Leu Arg Glu Glu Glu Tyr Lys Gln Gln Ile Lys Thr Leu Thr Thr
1               5                   10                  15

<210> SEQ ID NO 178
<211> LENGTH: 15
<212> TYPE: PRT
<213> ORGANISM: Periplaneta americana

<400> SEQUENCE: 178

Tyr Lys Gln Gln Ile Lys Thr Leu Thr Thr Arg Leu Lys Glu Ala
1               5                   10                  15

<210> SEQ ID NO 179
<211> LENGTH: 15
<212> TYPE: PRT
<213> ORGANISM: Fraxinus excelsior
```

<400> SEQUENCE: 179

Asp Thr Cys Arg Ala Arg Phe Ile Thr Lys Leu Ser Glu Phe Ile
1               5                   10                  15

<210> SEQ ID NO 180
<211> LENGTH: 15
<212> TYPE: PRT
<213> ORGANISM: Fraxinus excelsior

<400> SEQUENCE: 180

Arg Phe Ile Thr Lys Leu Ser Glu Phe Ile Thr Gly Ala Ser Val
1               5                   10                  15

<210> SEQ ID NO 181
<211> LENGTH: 15
<212> TYPE: PRT
<213> ORGANISM: Fraxinus excelsior

<400> SEQUENCE: 181

Leu Ser Glu Phe Ile Thr Gly Ala Ser Val Arg Leu Gln Cys Arg
1               5                   10                  15

<210> SEQ ID NO 182
<211> LENGTH: 15
<212> TYPE: PRT
<213> ORGANISM: Fraxinus excelsior

<400> SEQUENCE: 182

Asn Glu Phe Cys Glu Ile Thr Leu Leu Ser Ser Gly Arg Lys Asp
1               5                   10                  15

<210> SEQ ID NO 183
<211> LENGTH: 15
<212> TYPE: PRT
<213> ORGANISM: Fraxinus excelsior

<400> SEQUENCE: 183

Lys Pro Ser Leu Lys Phe Ile Leu Asn Thr Val Asn Gly Thr Thr
1               5                   10                  15

<210> SEQ ID NO 184
<211> LENGTH: 15
<212> TYPE: PRT
<213> ORGANISM: Fraxinus excelsior

<400> SEQUENCE: 184

Leu Gly Phe Phe Lys Lys Glu Ala Leu Pro Gln Cys Ala Gln Val
1               5                   10                  15

<210> SEQ ID NO 185
<211> LENGTH: 15
<212> TYPE: PRT
<213> ORGANISM: Aspergillus fumigatus

<400> SEQUENCE: 185

Met Val Ala Ile Lys Asn Leu Phe Leu Leu Ala Ala Thr Ala Val
1               5                   10                  15

<210> SEQ ID NO 186
<211> LENGTH: 15
<212> TYPE: PRT
<213> ORGANISM: Aspergillus fumigatus

<400> SEQUENCE: 186

Asn Leu Phe Leu Leu Ala Ala Thr Ala Val Ser Val Leu Ala Ala
1               5                   10                  15

<210> SEQ ID NO 187
<211> LENGTH: 15
<212> TYPE: PRT
<213> ORGANISM: Aspergillus fumigatus

<400> SEQUENCE: 187

Asp Lys Arg Leu Leu Tyr Ser Gln Ala Lys Ala Glu Ser Asn Ser
1               5                   10                  15

<210> SEQ ID NO 188
<211> LENGTH: 15
<212> TYPE: PRT
<213> ORGANISM: Aspergillus fumigatus

<400> SEQUENCE: 188

Asp Asp His Tyr Leu Leu Glu Phe Pro Thr Phe Pro Asp Gly His
1               5                   10                  15

<210> SEQ ID NO 189
<211> LENGTH: 15
<212> TYPE: PRT
<213> ORGANISM: Aspergillus fumigatus

<400> SEQUENCE: 189

Ala Arg Val Ile Tyr Thr Tyr Pro Asn Lys Val Phe Cys Gly Ile
1               5                   10                  15

<210> SEQ ID NO 190
<211> LENGTH: 15
<212> TYPE: PRT
<213> ORGANISM: Aspergillus fumigatus

<400> SEQUENCE: 190

Met Val Val Phe Ser Lys Val Thr Ala Val Val Gly Leu Ser
1               5                   10                  15

<210> SEQ ID NO 191
<211> LENGTH: 15
<212> TYPE: PRT
<213> ORGANISM: Aspergillus fumigatus

<400> SEQUENCE: 191

Lys Val Thr Ala Val Val Gly Leu Ser Thr Ile Val Ser Ala
1               5                   10                  15

<210> SEQ ID NO 192
<211> LENGTH: 15
<212> TYPE: PRT
<213> ORGANISM: Aspergillus fumigatus

<400> SEQUENCE: 192

Val Val Gly Leu Ser Thr Ile Val Ser Ala Val Pro Val Val Gln
1               5                   10                  15

<210> SEQ ID NO 193
<211> LENGTH: 15
<212> TYPE: PRT
<213> ORGANISM: Aspergillus fumigatus

<400> SEQUENCE: 193

Thr Ile Val Ser Ala Val Pro Val Val Gln Pro Arg Lys Gly Phe

```
1               5                   10                  15

<210> SEQ ID NO 194
<211> LENGTH: 15
<212> TYPE: PRT
<213> ORGANISM: Aspergillus fumigatus

<400> SEQUENCE: 194

Pro Arg Lys Gly Phe Thr Ile Asn Gln Val Ala Arg Pro Val Thr
1               5                   10                  15

<210> SEQ ID NO 195
<211> LENGTH: 15
<212> TYPE: PRT
<213> ORGANISM: Aspergillus fumigatus

<400> SEQUENCE: 195

Asn Lys Lys Thr Val Asn Leu Pro Ala Val Tyr Ala Asn Ala Leu
1               5                   10                  15

<210> SEQ ID NO 196
<211> LENGTH: 15
<212> TYPE: PRT
<213> ORGANISM: Aspergillus fumigatus

<400> SEQUENCE: 196

Asn Leu Pro Ala Val Tyr Ala Asn Ala Leu Thr Lys Tyr Gly Gly
1               5                   10                  15

<210> SEQ ID NO 197
<211> LENGTH: 15
<212> TYPE: PRT
<213> ORGANISM: Aspergillus fumigatus

<400> SEQUENCE: 197

Thr Val Pro Asp Ser Val Lys Ala Ala Ala Ser Ser Gly Ser Ala
1               5                   10                  15

<210> SEQ ID NO 198
<211> LENGTH: 15
<212> TYPE: PRT
<213> ORGANISM: Aspergillus fumigatus

<400> SEQUENCE: 198

Ala Asp Leu Trp Val Phe Ser Ser Glu Leu Ser Ala Ser Gln Ser
1               5                   10                  15

<210> SEQ ID NO 199
<211> LENGTH: 15
<212> TYPE: PRT
<213> ORGANISM: Aspergillus fumigatus

<400> SEQUENCE: 199

Val Glu Ala Ala Ser His Ile Ser Ser Gln Phe Val Gln Asp Lys
1               5                   10                  15

<210> SEQ ID NO 200
<211> LENGTH: 15
<212> TYPE: PRT
<213> ORGANISM: Aspergillus fumigatus

<400> SEQUENCE: 200

Asp Asn Asp Gly Leu Leu Gly Leu Ala Phe Ser Ser Ile Asn Thr
1               5                   10                  15
```

```
<210> SEQ ID NO 201
<211> LENGTH: 15
<212> TYPE: PRT
<213> ORGANISM: Aspergillus fumigatus

<400> SEQUENCE: 201

Leu Gly Leu Ala Phe Ser Ser Ile Asn Thr Val Ser Pro Arg Pro
1               5                   10                  15

<210> SEQ ID NO 202
<211> LENGTH: 15
<212> TYPE: PRT
<213> ORGANISM: Aspergillus fumigatus

<400> SEQUENCE: 202

Leu Phe Ala Val Thr Leu Lys Tyr His Ala Pro Gly Thr Tyr Asp
1               5                   10                  15

<210> SEQ ID NO 203
<211> LENGTH: 15
<212> TYPE: PRT
<213> ORGANISM: Aspergillus fumigatus

<400> SEQUENCE: 203

Val Phe Phe Asp Val Glu Tyr Ala Pro Val Gly Thr Ala Glu Thr
1               5                   10                  15

<210> SEQ ID NO 204
<211> LENGTH: 15
<212> TYPE: PRT
<213> ORGANISM: Aspergillus fumigatus

<400> SEQUENCE: 204

Lys Val Gly Arg Ile Val Phe Asn Leu Phe Asp Lys Asp Val Pro
1               5                   10                  15

<210> SEQ ID NO 205
<211> LENGTH: 15
<212> TYPE: PRT
<213> ORGANISM: Aspergillus fumigatus

<400> SEQUENCE: 205

Ser Thr Phe His Arg Ile Ile Pro Asn Phe Met Ile Gln Gly Gly
1               5                   10                  15

<210> SEQ ID NO 206
<211> LENGTH: 15
<212> TYPE: PRT
<213> ORGANISM: Aspergillus fumigatus

<400> SEQUENCE: 206

Lys His Asp Lys Lys Gly Ile Leu Ser Met Ala Asn Ala Gly Pro
1               5                   10                  15

<210> SEQ ID NO 207
<211> LENGTH: 15
<212> TYPE: PRT
<213> ORGANISM: Aspergillus fumigatus

<400> SEQUENCE: 207

Asn Thr Asn Gly Ser Gln Phe Phe Ile Thr Thr Ala Val Thr Ser
1               5                   10                  15

<210> SEQ ID NO 208
```

```
<211> LENGTH: 15
<212> TYPE: PRT
<213> ORGANISM: Aspergillus fumigatus

<400> SEQUENCE: 208

Gln Phe Phe Ile Thr Thr Ala Val Thr Ser Trp Leu Asp Gly Lys
1               5                   10                  15

<210> SEQ ID NO 209
<211> LENGTH: 15
<212> TYPE: PRT
<213> ORGANISM: Aspergillus fumigatus

<400> SEQUENCE: 209

Lys Ser Tyr Ser Val Val Lys Glu Ile Glu Ala Leu Gly Ser Ser
1               5                   10                  15

<210> SEQ ID NO 210
<211> LENGTH: 15
<212> TYPE: PRT
<213> ORGANISM: Aspergillus fumigatus

<400> SEQUENCE: 210

Met Ser Ser Glu Thr Phe Glu Phe Gln Ala Glu Ile Ser Gln Leu
1               5                   10                  15

<210> SEQ ID NO 211
<211> LENGTH: 15
<212> TYPE: PRT
<213> ORGANISM: Aspergillus fumigatus

<400> SEQUENCE: 211

Phe Glu Phe Gln Ala Glu Ile Ser Gln Leu Leu Ser Leu Ile Ile
1               5                   10                  15

<210> SEQ ID NO 212
<211> LENGTH: 15
<212> TYPE: PRT
<213> ORGANISM: Aspergillus fumigatus

<400> SEQUENCE: 212

Glu Ile Ser Gln Leu Leu Ser Leu Ile Ile Asn Thr Val Tyr Ser
1               5                   10                  15

<210> SEQ ID NO 213
<211> LENGTH: 15
<212> TYPE: PRT
<213> ORGANISM: Aspergillus fumigatus

<400> SEQUENCE: 213

Leu Ser Leu Ile Ile Asn Thr Val Tyr Ser Asn Lys Glu Ile Phe
1               5                   10                  15

<210> SEQ ID NO 214
<211> LENGTH: 15
<212> TYPE: PRT
<213> ORGANISM: Aspergillus fumigatus

<400> SEQUENCE: 214

Asn Lys Glu Ile Phe Leu Arg Glu Leu Ile Ser Asn Ala Ser Asp
1               5                   10                  15

<210> SEQ ID NO 215
<211> LENGTH: 15
<212> TYPE: PRT
```

<213> ORGANISM: Aspergillus fumigatus

<400> SEQUENCE: 215

Leu Arg Glu Leu Ile Ser Asn Ala Ser Asp Ala Leu Asp Lys Ile
1               5                   10                  15

<210> SEQ ID NO 216
<211> LENGTH: 15
<212> TYPE: PRT
<213> ORGANISM: Aspergillus fumigatus

<400> SEQUENCE: 216

Ala Leu Asp Lys Ile Arg Tyr Gln Ser Leu Ser Asp Pro Thr Lys
1               5                   10                  15

<210> SEQ ID NO 217
<211> LENGTH: 15
<212> TYPE: PRT
<213> ORGANISM: Aspergillus fumigatus

<400> SEQUENCE: 217

Ile Ala Arg Ser Gly Thr Lys Gln Phe Met Glu Ala Leu Ser Ala
1               5                   10                  15

<210> SEQ ID NO 218
<211> LENGTH: 15
<212> TYPE: PRT
<213> ORGANISM: Aspergillus fumigatus

<400> SEQUENCE: 218

Thr Lys Gln Phe Met Glu Ala Leu Ser Ala Gly Ala Asp Ile Ser
1               5                   10                  15

<210> SEQ ID NO 219
<211> LENGTH: 15
<212> TYPE: PRT
<213> ORGANISM: Aspergillus fumigatus

<400> SEQUENCE: 219

Met Ile Gly Gln Phe Gly Val Gly Phe Tyr Ser Ala Tyr Leu Val
1               5                   10                  15

<210> SEQ ID NO 220
<211> LENGTH: 15
<212> TYPE: PRT
<213> ORGANISM: Aspergillus fumigatus

<400> SEQUENCE: 220

Gly Val Gly Phe Tyr Ser Ala Tyr Leu Val Ala Asp Arg Val Thr
1               5                   10                  15

<210> SEQ ID NO 221
<211> LENGTH: 15
<212> TYPE: PRT
<213> ORGANISM: Aspergillus fumigatus

<400> SEQUENCE: 221

Ser Ala Tyr Leu Val Ala Asp Arg Val Thr Val Ser Lys Asn
1               5                   10                  15

<210> SEQ ID NO 222
<211> LENGTH: 15
<212> TYPE: PRT
<213> ORGANISM: Aspergillus fumigatus

<400> SEQUENCE: 222

Thr Lys Ile Ile Leu His Leu Lys Asp Glu Gln Thr Asp Tyr Leu
1               5                   10                  15

<210> SEQ ID NO 223
<211> LENGTH: 15
<212> TYPE: PRT
<213> ORGANISM: Aspergillus fumigatus

<400> SEQUENCE: 223

Lys Glu Val Val Arg Lys His Ser Glu Phe Ile Ser Tyr Pro Ile
1               5                   10                  15

<210> SEQ ID NO 224
<211> LENGTH: 15
<212> TYPE: PRT
<213> ORGANISM: Aspergillus fumigatus

<400> SEQUENCE: 224

Lys His Ser Glu Phe Ile Ser Tyr Pro Ile Tyr Leu His Val Leu
1               5                   10                  15

<210> SEQ ID NO 225
<211> LENGTH: 15
<212> TYPE: PRT
<213> ORGANISM: Aspergillus fumigatus

<400> SEQUENCE: 225

Ile Thr Gln Glu Glu Tyr Ala Ser Phe Tyr Lys Ser Leu Ser Asn
1               5                   10                  15

<210> SEQ ID NO 226
<211> LENGTH: 15
<212> TYPE: PRT
<213> ORGANISM: Aspergillus fumigatus

<400> SEQUENCE: 226

Leu Ala Val Lys His Phe Ser Val Glu Gly Gln Leu Glu Phe Arg
1               5                   10                  15

<210> SEQ ID NO 227
<211> LENGTH: 15
<212> TYPE: PRT
<213> ORGANISM: Aspergillus fumigatus

<400> SEQUENCE: 227

Gln Leu Glu Phe Arg Ala Ile Leu Tyr Val Pro Lys Arg Ala Pro
1               5                   10                  15

<210> SEQ ID NO 228
<211> LENGTH: 15
<212> TYPE: PRT
<213> ORGANISM: Aspergillus fumigatus

<400> SEQUENCE: 228

Asn Asn Ile Lys Leu Tyr Val Arg Arg Val Phe Ile Thr Asp Asp
1               5                   10                  15

<210> SEQ ID NO 229
<211> LENGTH: 15
<212> TYPE: PRT
<213> ORGANISM: Aspergillus fumigatus

<400> SEQUENCE: 229

```
Tyr Val Arg Arg Val Phe Ile Thr Asp Asp Ala Thr Asp Leu Ile
1               5                   10                  15
```

<210> SEQ ID NO 230
<211> LENGTH: 15
<212> TYPE: PRT
<213> ORGANISM: Aspergillus fumigatus

<400> SEQUENCE: 230

```
Lys Asn Ile Val Lys Lys Thr Leu Glu Leu Phe Asn Glu Ile Ala
1               5                   10                  15
```

<210> SEQ ID NO 231
<211> LENGTH: 15
<212> TYPE: PRT
<213> ORGANISM: Aspergillus fumigatus

<400> SEQUENCE: 231

```
Glu Asp Arg Glu Gln Phe Asp Lys Phe Tyr Ser Ala Phe Ser Lys
1               5                   10                  15
```

<210> SEQ ID NO 232
<211> LENGTH: 15
<212> TYPE: PRT
<213> ORGANISM: Aspergillus fumigatus

<400> SEQUENCE: 232

```
Phe Asp Lys Phe Tyr Ser Ala Phe Ser Lys Asn Ile Lys Leu Gly
1               5                   10                  15
```

<210> SEQ ID NO 233
<211> LENGTH: 15
<212> TYPE: PRT
<213> ORGANISM: Aspergillus fumigatus

<400> SEQUENCE: 233

```
Leu Ala Lys Leu Leu Arg Tyr Gln Ser Thr Lys Ser Gly Asp Glu
1               5                   10                  15
```

<210> SEQ ID NO 234
<211> LENGTH: 15
<212> TYPE: PRT
<213> ORGANISM: Aspergillus fumigatus

<400> SEQUENCE: 234

```
Lys Gln Ile Tyr Tyr Ile Thr Gly Glu Ser Ile Lys Ala Val Ala
1               5                   10                  15
```

<210> SEQ ID NO 235
<211> LENGTH: 15
<212> TYPE: PRT
<213> ORGANISM: Aspergillus fumigatus

<400> SEQUENCE: 235

```
Ile Lys Ala Val Ala Lys Ser Pro Phe Leu Asp Ser Leu Lys Gln
1               5                   10                  15
```

<210> SEQ ID NO 236
<211> LENGTH: 15
<212> TYPE: PRT
<213> ORGANISM: Aspergillus fumigatus

<400> SEQUENCE: 236

```
Lys Asn Phe Glu Val Leu Phe Leu Val Asp Pro Ile Asp Glu Tyr
1               5                   10                  15
```

-continued

```
<210> SEQ ID NO 237
<211> LENGTH: 15
<212> TYPE: PRT
<213> ORGANISM: Aspergillus fumigatus

<400> SEQUENCE: 237

Glu Lys Glu Tyr Glu Asn Leu Ala Lys Ser Leu Lys Asn Ile Leu
1               5                   10                  15

<210> SEQ ID NO 238
<211> LENGTH: 15
<212> TYPE: PRT
<213> ORGANISM: Aspergillus fumigatus

<400> SEQUENCE: 238

Asn Leu Ala Lys Ser Leu Lys Asn Ile Leu Gly Asp Lys Val Glu
1               5                   10                  15

<210> SEQ ID NO 239
<211> LENGTH: 15
<212> TYPE: PRT
<213> ORGANISM: Aspergillus fumigatus

<400> SEQUENCE: 239

Gly Trp Ser Ala Asn Met Glu Arg Ile Met Lys Ala Gln Ala Leu
1               5                   10                  15

<210> SEQ ID NO 240
<211> LENGTH: 15
<212> TYPE: PRT
<213> ORGANISM: Aspergillus fumigatus

<400> SEQUENCE: 240

Met Glu Arg Ile Met Lys Ala Gln Ala Leu Arg Asp Thr Ser Met
1               5                   10                  15

<210> SEQ ID NO 241
<211> LENGTH: 15
<212> TYPE: PRT
<213> ORGANISM: Aspergillus fumigatus

<400> SEQUENCE: 241

Glu Asn Asp Arg Thr Val Lys Ser Ile Thr Gln Leu Leu Phe Glu
1               5                   10                  15

<210> SEQ ID NO 242
<211> LENGTH: 15
<212> TYPE: PRT
<213> ORGANISM: Aspergillus fumigatus

<400> SEQUENCE: 242

Val Lys Ser Ile Thr Gln Leu Leu Phe Glu Thr Ser Leu Leu Val
1               5                   10                  15

<210> SEQ ID NO 243
<211> LENGTH: 15
<212> TYPE: PRT
<213> ORGANISM: Aspergillus fumigatus

<400> SEQUENCE: 243

Gln Leu Leu Phe Glu Thr Ser Leu Leu Val Ser Gly Phe Thr Ile
1               5                   10                  15
```

```
<210> SEQ ID NO 244
<211> LENGTH: 15
<212> TYPE: PRT
<213> ORGANISM: Aspergillus fumigatus

<400> SEQUENCE: 244

Phe Ala Glu Arg Ile His Lys Leu Val Ser Leu Gly Leu Asn Ile
1               5                   10                  15

<210> SEQ ID NO 245
<211> LENGTH: 15
<212> TYPE: PRT
<213> ORGANISM: Aspergillus fumigatus

<400> SEQUENCE: 245

His Lys Leu Val Ser Leu Gly Leu Asn Ile Asp Glu Glu Ala Glu
1               5                   10                  15

<210> SEQ ID NO 246
<211> LENGTH: 15
<212> TYPE: PRT
<213> ORGANISM: Aspergillus fumigatus

<400> SEQUENCE: 246

Met Leu Ser Ile Lys Arg Thr Leu Leu Leu Gly Ala Val Leu
1               5                   10                  15

<210> SEQ ID NO 247
<211> LENGTH: 15
<212> TYPE: PRT
<213> ORGANISM: Aspergillus fumigatus

<400> SEQUENCE: 247

Arg Thr Leu Leu Leu Leu Gly Ala Val Leu Pro Ala Val Phe Gly
1               5                   10                  15

<210> SEQ ID NO 248
<211> LENGTH: 15
<212> TYPE: PRT
<213> ORGANISM: Aspergillus fumigatus

<400> SEQUENCE: 248

Lys Ser Tyr Lys Ile Lys Asp Phe Ala Ala Tyr Ala Gly Ser Phe
1               5                   10                  15

<210> SEQ ID NO 249
<211> LENGTH: 15
<212> TYPE: PRT
<213> ORGANISM: Aspergillus fumigatus

<400> SEQUENCE: 249

His Val Glu Glu Asp Gln Ile Trp Tyr Leu Asp Ala Leu Thr Thr
1               5                   10                  15

<210> SEQ ID NO 250
<211> LENGTH: 15
<212> TYPE: PRT
<213> ORGANISM: Aspergillus fumigatus

<400> SEQUENCE: 250

Gln Ile Trp Tyr Leu Asp Ala Leu Thr Thr Gln Lys Gly Ala Pro
1               5                   10                  15

<210> SEQ ID NO 251
<211> LENGTH: 15
```

```
<212> TYPE: PRT
<213> ORGANISM: Aspergillus fumigatus

<400> SEQUENCE: 251

Gln Ala Ser Thr Asp Tyr Ile Tyr Asp Thr Ser Ala Gly Ala Gly
1               5                   10                  15

<210> SEQ ID NO 252
<211> LENGTH: 15
<212> TYPE: PRT
<213> ORGANISM: Aspergillus fumigatus

<400> SEQUENCE: 252

Tyr Ile Tyr Asp Thr Ser Ala Gly Ala Gly Thr Tyr Ala Tyr Val
1               5                   10                  15

<210> SEQ ID NO 253
<211> LENGTH: 15
<212> TYPE: PRT
<213> ORGANISM: Aspergillus fumigatus

<400> SEQUENCE: 253

Lys Thr Asn Leu Leu Ser Val Lys Val Phe Gln Gly Glu Ser Ser
1               5                   10                  15

<210> SEQ ID NO 254
<211> LENGTH: 15
<212> TYPE: PRT
<213> ORGANISM: Aspergillus fumigatus

<400> SEQUENCE: 254

Ser Val Lys Val Phe Gln Gly Glu Ser Ser Ser Thr Ser Ile Ile
1               5                   10                  15

<210> SEQ ID NO 255
<211> LENGTH: 15
<212> TYPE: PRT
<213> ORGANISM: Aspergillus fumigatus

<400> SEQUENCE: 255

Leu Asp Gly Phe Asn Trp Ala Val Asn Asp Ile Val Ser Lys Gly
1               5                   10                  15

<210> SEQ ID NO 256
<211> LENGTH: 15
<212> TYPE: PRT
<213> ORGANISM: Aspergillus fumigatus

<400> SEQUENCE: 256

Leu Gly Gly Gly Tyr Ser Tyr Ala Phe Asn Asn Ala Val Glu Asn
1               5                   10                  15

<210> SEQ ID NO 257
<211> LENGTH: 15
<212> TYPE: PRT
<213> ORGANISM: Aspergillus fumigatus

<400> SEQUENCE: 257

Ser Ala Pro Asn Ala Leu Thr Val Ala Ala Ile Asn Lys Ser Asn
1               5                   10                  15

<210> SEQ ID NO 258
<211> LENGTH: 15
<212> TYPE: PRT
<213> ORGANISM: Aspergillus fumigatus
```

<400> SEQUENCE: 258

Ala Thr Pro His Ile Val Gly Leu Ser Val Tyr Leu Met Gly Leu
1               5                   10                  15

<210> SEQ ID NO 259
<211> LENGTH: 15
<212> TYPE: PRT
<213> ORGANISM: Aspergillus fumigatus

<400> SEQUENCE: 259

Val Gly Leu Ser Val Tyr Leu Met Gly Leu Glu Asn Leu Ser Gly
1               5                   10                  15

<210> SEQ ID NO 260
<211> LENGTH: 15
<212> TYPE: PRT
<213> ORGANISM: Aspergillus fumigatus

<400> SEQUENCE: 260

Tyr Leu Met Gly Leu Glu Asn Leu Ser Gly Pro Ala Ala Val Thr
1               5                   10                  15

<210> SEQ ID NO 261
<211> LENGTH: 15
<212> TYPE: PRT
<213> ORGANISM: Aspergillus fumigatus

<400> SEQUENCE: 261

Met Lys Phe Thr Thr Pro Ile Ser Leu Ile Ser Leu Phe Val Ser
1               5                   10                  15

<210> SEQ ID NO 262
<211> LENGTH: 15
<212> TYPE: PRT
<213> ORGANISM: Aspergillus fumigatus

<400> SEQUENCE: 262

Pro Ile Ser Leu Ile Ser Leu Phe Val Ser Ser Ala Leu Ala Ala
1               5                   10                  15

<210> SEQ ID NO 263
<211> LENGTH: 15
<212> TYPE: PRT
<213> ORGANISM: Aspergillus fumigatus

<400> SEQUENCE: 263

Ser Leu Phe Val Ser Ser Ala Leu Ala Ala Pro Thr Pro Glu Asn
1               5                   10                  15

<210> SEQ ID NO 264
<211> LENGTH: 15
<212> TYPE: PRT
<213> ORGANISM: Aspergillus fumigatus

<400> SEQUENCE: 264

Gly Lys Cys Tyr Lys Leu Gln Tyr Glu Gln Asn Thr Ile Tyr Val
1               5                   10                  15

<210> SEQ ID NO 265
<211> LENGTH: 15
<212> TYPE: PRT
<213> ORGANISM: Aspergillus fumigatus

<400> SEQUENCE: 265

Leu Gln Tyr Glu Gln Asn Thr Ile Tyr Val Thr Ala Ile Asp Ala
1               5                   10                  15

<210> SEQ ID NO 266
<211> LENGTH: 15
<212> TYPE: PRT
<213> ORGANISM: Aspergillus fumigatus

<400> SEQUENCE: 266

Asn Thr Ile Tyr Val Thr Ala Ile Asp Ala Ala Pro Gly Gly Phe
1               5                   10                  15

<210> SEQ ID NO 267
<211> LENGTH: 15
<212> TYPE: PRT
<213> ORGANISM: Aspergillus fumigatus

<400> SEQUENCE: 267

Ala Pro Gly Gly Phe Asn Ile Ala Thr Ser Ala Met Asp Gln Leu
1               5                   10                  15

<210> SEQ ID NO 268
<211> LENGTH: 15
<212> TYPE: PRT
<213> ORGANISM: Aspergillus fumigatus

<400> SEQUENCE: 268

Met Tyr Phe Lys Tyr Thr Ala Ala Ala Leu Ala Ala Val Leu Pro
1               5                   10                  15

<210> SEQ ID NO 269
<211> LENGTH: 15
<212> TYPE: PRT
<213> ORGANISM: Aspergillus fumigatus

<400> SEQUENCE: 269

Thr Ala Ala Ala Leu Ala Ala Val Leu Pro Leu Cys Ser Ala Gln
1               5                   10                  15

<210> SEQ ID NO 270
<211> LENGTH: 15
<212> TYPE: PRT
<213> ORGANISM: Aspergillus fumigatus

<400> SEQUENCE: 270

Pro Thr Ile Asp Thr Asp Phe Tyr Phe Phe Gly Lys Ala Glu
1               5                   10                  15

<210> SEQ ID NO 271
<211> LENGTH: 15
<212> TYPE: PRT
<213> ORGANISM: Aspergillus fumigatus

<400> SEQUENCE: 271

Asp Phe Tyr Phe Phe Phe Gly Lys Ala Glu Val Val Met Lys Ala
1               5                   10                  15

<210> SEQ ID NO 272
<211> LENGTH: 15
<212> TYPE: PRT
<213> ORGANISM: Aspergillus fumigatus

<400> SEQUENCE: 272

Pro Gln Thr Pro Met Arg Leu Arg Leu Ala Ala Gly Pro Ala Ala
1               5                   10                  15

```
1               5                   10                  15
```

<210> SEQ ID NO 273
<211> LENGTH: 15
<212> TYPE: PRT
<213> ORGANISM: Aspergillus fumigatus

<400> SEQUENCE: 273

```
Val Gly Val Ile Ser Asp Ile Ser Ala Gln Thr Ser Ala Leu Ala
1               5                   10                  15
```

<210> SEQ ID NO 274
<211> LENGTH: 15
<212> TYPE: PRT
<213> ORGANISM: Aspergillus fumigatus

<400> SEQUENCE: 274

```
Ser Lys Lys Asp Lys Phe Val Ala Ala Asn Ala Gly Gly Thr Val
1               5                   10                  15
```

<210> SEQ ID NO 275
<211> LENGTH: 15
<212> TYPE: PRT
<213> ORGANISM: Aspergillus fumigatus

<400> SEQUENCE: 275

```
Ala Gly Gly Thr Val Tyr Glu Asp Leu Lys Ala Gln Tyr Thr Ala
1               5                   10                  15
```

<210> SEQ ID NO 276
<211> LENGTH: 15
<212> TYPE: PRT
<213> ORGANISM: Aspergillus fumigatus

<400> SEQUENCE: 276

```
Ala Gln Tyr Thr Ala Ala Asp Ser Leu Ala Lys Ala Ile Ser Ala
1               5                   10                  15
```

<210> SEQ ID NO 277
<211> LENGTH: 15
<212> TYPE: PRT
<213> ORGANISM: Aspergillus fumigatus

<400> SEQUENCE: 277

```
Ala Asp Ser Leu Ala Lys Ala Ile Ser Ala Lys Val Pro Glu Ser
1               5                   10                  15
```

<210> SEQ ID NO 278
<211> LENGTH: 15
<212> TYPE: PRT
<213> ORGANISM: Aspergillus fumigatus

<400> SEQUENCE: 278

```
Leu Ser Asp Ile Ala Ala Gln Leu Ser Ala Gly Ile Thr Ala Ala
1               5                   10                  15
```

<210> SEQ ID NO 279
<211> LENGTH: 15
<212> TYPE: PRT
<213> ORGANISM: Aspergillus fumigatus

<400> SEQUENCE: 279

```
Ala Gln Leu Ser Ala Gly Ile Thr Ala Ala Ile Gln Lys Gly Ile
1               5                   10                  15
```

```
<210> SEQ ID NO 280
<211> LENGTH: 15
<212> TYPE: PRT
<213> ORGANISM: Aspergillus fumigatus

<400> SEQUENCE: 280

Met Lys Gly Tyr Leu Ser Leu Ser Ile Leu Pro Leu Leu Val Ala
1               5                   10                  15

<210> SEQ ID NO 281
<211> LENGTH: 15
<212> TYPE: PRT
<213> ORGANISM: Aspergillus fumigatus

<400> SEQUENCE: 281

Ser Leu Ser Ile Leu Pro Leu Leu Val Ala Ala Ser Pro Val Val
1               5                   10                  15

<210> SEQ ID NO 282
<211> LENGTH: 15
<212> TYPE: PRT
<213> ORGANISM: Aspergillus fumigatus

<400> SEQUENCE: 282

Pro Leu Leu Val Ala Ala Ser Pro Val Val Val Asp Ser Ile His
1               5                   10                  15

<210> SEQ ID NO 283
<211> LENGTH: 15
<212> TYPE: PRT
<213> ORGANISM: Aspergillus fumigatus

<400> SEQUENCE: 283

Asn Gly Ala Ala Pro Ile Leu Ser Ser Met Asn Ala Lys Glu Val
1               5                   10                  15

<210> SEQ ID NO 284
<211> LENGTH: 15
<212> TYPE: PRT
<213> ORGANISM: Aspergillus fumigatus

<400> SEQUENCE: 284

Val Val Phe Lys Lys His Val Asn Ala Glu Ser Ala Ala Ala His
1               5                   10                  15

<210> SEQ ID NO 285
<211> LENGTH: 15
<212> TYPE: PRT
<213> ORGANISM: Aspergillus fumigatus

<400> SEQUENCE: 285

His Ser Trp Val Gln Asp Ile His Ser Ala Gln Asn Glu Arg Val
1               5                   10                  15

<210> SEQ ID NO 286
<211> LENGTH: 15
<212> TYPE: PRT
<213> ORGANISM: Aspergillus fumigatus

<400> SEQUENCE: 286

Leu Gly Leu Lys Asn Thr Phe Asp Ile Ala Gly Ser Leu Val Gly
1               5                   10                  15

<210> SEQ ID NO 287
```

```
<211> LENGTH: 15
<212> TYPE: PRT
<213> ORGANISM: Aspergillus fumigatus

<400> SEQUENCE: 287

Thr Phe Asp Ile Ala Gly Ser Leu Val Gly Tyr Ser Gly His Phe
1               5                   10                  15

<210> SEQ ID NO 288
<211> LENGTH: 15
<212> TYPE: PRT
<213> ORGANISM: Aspergillus fumigatus

<400> SEQUENCE: 288

Tyr Ala Val Lys Val Leu Arg Ser Ser Gly Ser Gly Thr Met Ser
1               5                   10                  15

<210> SEQ ID NO 289
<211> LENGTH: 15
<212> TYPE: PRT
<213> ORGANISM: Aspergillus fumigatus

<400> SEQUENCE: 289

Lys Gly Phe Lys Gly Ser Val Ala Asn Met Ser Leu Gly Gly Gly
1               5                   10                  15

<210> SEQ ID NO 290
<211> LENGTH: 15
<212> TYPE: PRT
<213> ORGANISM: Aspergillus fumigatus

<400> SEQUENCE: 290

Lys Ser Arg Thr Leu Glu Ala Ala Val Asn Ala Gly Val Glu Ala
1               5                   10                  15

<210> SEQ ID NO 291
<211> LENGTH: 15
<212> TYPE: PRT
<213> ORGANISM: Aspergillus fumigatus

<400> SEQUENCE: 291

Ala Gly Val Glu Ala Gly Leu His Phe Ala Val Ala Ala Gly Asn
1               5                   10                  15

<210> SEQ ID NO 292
<211> LENGTH: 15
<212> TYPE: PRT
<213> ORGANISM: Aspergillus fumigatus

<400> SEQUENCE: 292

Met Ala Ser Pro His Ile Ala Gly Leu Leu Ala Tyr Phe Val Ser
1               5                   10                  15

<210> SEQ ID NO 293
<211> LENGTH: 15
<212> TYPE: PRT
<213> ORGANISM: Aspergillus fumigatus

<400> SEQUENCE: 293

Ile Ala Gly Leu Leu Ala Tyr Phe Val Ser Leu Gln Pro Ser Lys
1               5                   10                  15

<210> SEQ ID NO 294
<211> LENGTH: 15
<212> TYPE: PRT
```

<213> ORGANISM: Aspergillus fumigatus

<400> SEQUENCE: 294

Pro Lys Lys Leu Lys Lys Asp Ile Ile Ala Ile Ala Thr Gln Gly
1               5                   10                  15

<210> SEQ ID NO 295
<211> LENGTH: 15
<212> TYPE: PRT
<213> ORGANISM: Aspergillus fumigatus

<400> SEQUENCE: 295

Lys Asp Ile Ile Ala Ile Ala Thr Gln Gly Ala Leu Thr Asp Ile
1               5                   10                  15

<210> SEQ ID NO 296
<211> LENGTH: 15
<212> TYPE: PRT
<213> ORGANISM: Aspergillus fumigatus

<400> SEQUENCE: 296

Ile Ile Ala Ser Gly Gly Tyr Lys Val Asn Ala Ser Val Lys Asp
1               5                   10                  15

<210> SEQ ID NO 297
<211> LENGTH: 15
<212> TYPE: PRT
<213> ORGANISM: Aspergillus fumigatus

<400> SEQUENCE: 297

Lys Leu Leu Thr Glu Glu Leu Gly Ala Ile Tyr Ser Glu Ile His
1               5                   10                  15

<210> SEQ ID NO 298
<211> LENGTH: 15
<212> TYPE: PRT
<213> ORGANISM: Aspergillus fumigatus

<400> SEQUENCE: 298

Glu Leu Gly Ala Ile Tyr Ser Glu Ile His Asp Ala Ala Val Ala
1               5                   10                  15

<210> SEQ ID NO 299
<211> LENGTH: 15
<212> TYPE: PRT
<213> ORGANISM: Aspergillus fumigatus

<400> SEQUENCE: 299

Met Ala Ala Leu Leu Arg Leu Ala Val Leu Leu Pro Leu Ala Ala
1               5                   10                  15

<210> SEQ ID NO 300
<211> LENGTH: 15
<212> TYPE: PRT
<213> ORGANISM: Aspergillus fumigatus

<400> SEQUENCE: 300

Arg Leu Ala Val Leu Leu Pro Leu Ala Ala Pro Leu Val Ala Thr
1               5                   10                  15

<210> SEQ ID NO 301
<211> LENGTH: 15
<212> TYPE: PRT
<213> ORGANISM: Aspergillus fumigatus

```
<400> SEQUENCE: 301

Pro Leu Val Ala Thr Leu Pro Thr Ser Pro Val Pro Ile Ala Ala
1               5                   10                  15

<210> SEQ ID NO 302
<211> LENGTH: 15
<212> TYPE: PRT
<213> ORGANISM: Aspergillus fumigatus

<400> SEQUENCE: 302

Glu Pro Val Phe Phe Ser Trp Asp Ala Gly Ala Val Thr Ser Phe
1               5                   10                  15

<210> SEQ ID NO 303
<211> LENGTH: 15
<212> TYPE: PRT
<213> ORGANISM: Aspergillus fumigatus

<400> SEQUENCE: 303

Ser Trp Asp Ala Gly Ala Val Thr Ser Phe Pro Ile His Ser Ser
1               5                   10                  15

<210> SEQ ID NO 304
<211> LENGTH: 15
<212> TYPE: PRT
<213> ORGANISM: Aspergillus fumigatus

<400> SEQUENCE: 304

Thr Thr Arg Arg Trp Leu Val Ser Met Cys Ser Gln Gly Tyr Thr
1               5                   10                  15

<210> SEQ ID NO 305
<211> LENGTH: 15
<212> TYPE: PRT
<213> ORGANISM: Aspergillus fumigatus

<400> SEQUENCE: 305

Tyr Asp Glu Val Ile Ala Leu Ala Lys Ser Asn Gly Thr Glu Ser
1               5                   10                  15

<210> SEQ ID NO 306
<211> LENGTH: 15
<212> TYPE: PRT
<213> ORGANISM: Aspergillus fumigatus

<400> SEQUENCE: 306

Thr His Asp Ser Glu Ala Leu Gln Tyr Phe Ala Leu Glu Ala Tyr
1               5                   10                  15

<210> SEQ ID NO 307
<211> LENGTH: 15
<212> TYPE: PRT
<213> ORGANISM: Aspergillus fumigatus

<400> SEQUENCE: 307

Ala Leu Gln Tyr Phe Ala Leu Glu Ala Tyr Ala Phe Asp Ile Ala
1               5                   10                  15

<210> SEQ ID NO 308
<211> LENGTH: 15
<212> TYPE: PRT
<213> ORGANISM: Aspergillus fumigatus

<400> SEQUENCE: 308
```

```
Ala Leu Glu Ala Tyr Ala Phe Asp Ile Ala Ala Pro Gly Val Gly
1               5                   10                  15

<210> SEQ ID NO 309
<211> LENGTH: 15
<212> TYPE: PRT
<213> ORGANISM: Aspergillus fumigatus

<400> SEQUENCE: 309

Met Pro Ile Ser Lys Ile His Ala Arg Ser Val Tyr Asp Ser Arg
1               5                   10                  15

<210> SEQ ID NO 310
<211> LENGTH: 15
<212> TYPE: PRT
<213> ORGANISM: Aspergillus fumigatus

<400> SEQUENCE: 310

Leu Gly Ala Asn Ala Ile Leu Gly Val Ser Leu Ala Val Ala Lys
1               5                   10                  15

<210> SEQ ID NO 311
<211> LENGTH: 15
<212> TYPE: PRT
<213> ORGANISM: Aspergillus fumigatus

<400> SEQUENCE: 311

Ile Leu Gly Val Ser Leu Ala Val Ala Lys Ala Gly Ala Ala Glu
1               5                   10                  15

<210> SEQ ID NO 312
<211> LENGTH: 15
<212> TYPE: PRT
<213> ORGANISM: Aspergillus fumigatus

<400> SEQUENCE: 312

Gly Gly Arg Leu Ala Phe Gln Glu Phe Met Ile Val Pro Asp Ser
1               5                   10                  15

<210> SEQ ID NO 313
<211> LENGTH: 15
<212> TYPE: PRT
<213> ORGANISM: Aspergillus fumigatus

<400> SEQUENCE: 313

Phe Gln Glu Phe Met Ile Val Pro Asp Ser Ala Pro Ser Phe Ser
1               5                   10                  15

<210> SEQ ID NO 314
<211> LENGTH: 15
<212> TYPE: PRT
<213> ORGANISM: Aspergillus fumigatus

<400> SEQUENCE: 314

Gly Ala Glu Val Tyr Gln Lys Leu Lys Ala Leu Ala Lys Lys Lys
1               5                   10                  15

<210> SEQ ID NO 315
<211> LENGTH: 15
<212> TYPE: PRT
<213> ORGANISM: Aspergillus fumigatus

<400> SEQUENCE: 315

Ile Lys Ile Ala Met Asp Val Ala Ser Ser Glu Phe Tyr Lys Ala
1               5                   10                  15
```

<210> SEQ ID NO 316
<211> LENGTH: 15
<212> TYPE: PRT
<213> ORGANISM: Aspergillus fumigatus

<400> SEQUENCE: 316

Pro Ser Lys Trp Leu Thr Tyr Glu Gln Leu Ala Asp Leu Tyr Lys
1               5                   10                  15

<210> SEQ ID NO 317
<211> LENGTH: 15
<212> TYPE: PRT
<213> ORGANISM: Aspergillus fumigatus

<400> SEQUENCE: 317

Ala Asp Leu Tyr Lys Ser Leu Ala Ala Lys Tyr Pro Ile Val Ser
1               5                   10                  15

<210> SEQ ID NO 318
<211> LENGTH: 15
<212> TYPE: PRT
<213> ORGANISM: Aspergillus fumigatus

<400> SEQUENCE: 318

Glu Ala Trp Ser Tyr Phe Tyr Lys Thr Ser Asp Phe Gln Ile Val
1               5                   10                  15

<210> SEQ ID NO 319
<211> LENGTH: 15
<212> TYPE: PRT
<213> ORGANISM: Aspergillus fumigatus

<400> SEQUENCE: 319

Ile Glu Leu Lys Ser Cys Asn Ala Leu Leu Leu Lys Val Asn Gln
1               5                   10                  15

<210> SEQ ID NO 320
<211> LENGTH: 15
<212> TYPE: PRT
<213> ORGANISM: Aspergillus fumigatus

<400> SEQUENCE: 320

Cys Asn Ala Leu Leu Leu Lys Val Asn Gln Ile Gly Thr Leu Thr
1               5                   10                  15

<210> SEQ ID NO 321
<211> LENGTH: 15
<212> TYPE: PRT
<213> ORGANISM: Aspergillus fumigatus

<400> SEQUENCE: 321

Glu Arg Leu Ala Lys Leu Asn Gln Ile Leu Arg Ile Glu Glu Glu
1               5                   10                  15

<210> SEQ ID NO 322
<211> LENGTH: 15
<212> TYPE: PRT
<213> ORGANISM: Aspergillus fumigatus

<400> SEQUENCE: 322

Glu Ile Val Glu Ala Val Thr Ile Ile Glu Thr Pro Pro Leu Val
1               5                   10                  15

-continued

```
<210> SEQ ID NO 323
<211> LENGTH: 15
<212> TYPE: PRT
<213> ORGANISM: Aspergillus fumigatus

<400> SEQUENCE: 323

Pro Arg Gly Leu Arg Ser Leu Thr Thr Val Trp Ala Glu His Leu
1               5                   10                  15

<210> SEQ ID NO 324
<211> LENGTH: 15
<212> TYPE: PRT
<213> ORGANISM: Aspergillus fumigatus

<400> SEQUENCE: 324

Arg Ile Lys Lys Tyr Cys Thr Val Val Arg Val Leu Ala His Thr
1               5                   10                  15

<210> SEQ ID NO 325
<211> LENGTH: 15
<212> TYPE: PRT
<213> ORGANISM: Aspergillus fumigatus

<400> SEQUENCE: 325

Cys Thr Val Val Arg Val Leu Ala His Thr Gln Ile Arg Lys Thr
1               5                   10                  15

<210> SEQ ID NO 326
<211> LENGTH: 15
<212> TYPE: PRT
<213> ORGANISM: Aspergillus fumigatus

<400> SEQUENCE: 326

Met Val Val Lys Thr Phe Phe Asp Ile Thr Ile Asp Gly Gln Pro
1               5                   10                  15

<210> SEQ ID NO 327
<211> LENGTH: 15
<212> TYPE: PRT
<213> ORGANISM: Aspergillus fumigatus

<400> SEQUENCE: 327

Phe Lys Leu Phe Asp Glu Val Val Pro Lys Thr Val Glu Asn Phe
1               5                   10                  15

<210> SEQ ID NO 328
<211> LENGTH: 15
<212> TYPE: PRT
<213> ORGANISM: Aspergillus fumigatus

<400> SEQUENCE: 328

Gly Tyr Lys Gly Ser Ser Phe His Arg Ile Ile Pro Gln Phe Met
1               5                   10                  15

<210> SEQ ID NO 329
<211> LENGTH: 15
<212> TYPE: PRT
<213> ORGANISM: Aspergillus fumigatus

<400> SEQUENCE: 329

Ser Phe His Arg Ile Ile Pro Gln Phe Met Leu Gln Gly Gly Asp
1               5                   10                  15

<210> SEQ ID NO 330
<211> LENGTH: 15
```

```
<212> TYPE: PRT
<213> ORGANISM: Aspergillus fumigatus

<400> SEQUENCE: 330

His Asp Lys Pro Gly Leu Leu Ser Met Ala Asn Ala Gly Lys Asn
1               5                   10                  15

<210> SEQ ID NO 331
<211> LENGTH: 15
<212> TYPE: PRT
<213> ORGANISM: Aspergillus fumigatus

<400> SEQUENCE: 331

Thr Asn Gly Ser Gln Phe Phe Ile Thr Thr Val Val Thr Ser Trp
1               5                   10                  15

<210> SEQ ID NO 332
<211> LENGTH: 15
<212> TYPE: PRT
<213> ORGANISM: Aspergillus fumigatus

<400> SEQUENCE: 332

Phe Phe Ile Thr Thr Val Val Thr Ser Trp Leu Asp Gly Ala His
1               5                   10                  15

<210> SEQ ID NO 333
<211> LENGTH: 15
<212> TYPE: PRT
<213> ORGANISM: Aspergillus fumigatus

<400> SEQUENCE: 333

Asn Pro Ile Ile Tyr Lys Ala Leu Thr Ser Ser Gly Pro Val Val
1               5                   10                  15

<210> SEQ ID NO 334
<211> LENGTH: 15
<212> TYPE: PRT
<213> ORGANISM: Aspergillus fumigatus

<400> SEQUENCE: 334

Leu Ser Glu Lys Tyr Ser Asn Val Arg Phe Ile Gln Val Asp Val
1               5                   10                  15

<210> SEQ ID NO 335
<211> LENGTH: 15
<212> TYPE: PRT
<213> ORGANISM: Aspergillus fumigatus

<400> SEQUENCE: 335

Val Ala His Glu Met Asn Ile Arg Ala Met Pro Thr Phe Val Leu
1               5                   10                  15

<210> SEQ ID NO 336
<211> LENGTH: 15
<212> TYPE: PRT
<213> ORGANISM: Aspergillus fumigatus

<400> SEQUENCE: 336

Asn Ile Arg Ala Met Pro Thr Phe Val Leu Tyr Lys Asp Gly Gln
1               5                   10                  15

<210> SEQ ID NO 337
<211> LENGTH: 15
<212> TYPE: PRT
<213> ORGANISM: Aspergillus fumigatus
```

<400> SEQUENCE: 337

Ser Pro Val Phe Gln Arg Leu Ser Thr Ser Glu Glu Phe Lys Asn
1               5                   10                  15

<210> SEQ ID NO 338
<211> LENGTH: 15
<212> TYPE: PRT
<213> ORGANISM: Aspergillus fumigatus

<400> SEQUENCE: 338

Ala Lys Phe Tyr Glu Ile Asp Val Asp Glu Leu Ser Glu Val Ala
1               5                   10                  15

<210> SEQ ID NO 339
<211> LENGTH: 15
<212> TYPE: PRT
<213> ORGANISM: Aspergillus fumigatus

<400> SEQUENCE: 339

Ala Asn Pro Pro Ala Leu Glu Ala Ala Ile Lys Ala His Val Ala
1               5                   10                  15

<210> SEQ ID NO 340
<211> LENGTH: 15
<212> TYPE: PRT
<213> ORGANISM: Aspergillus fumigatus

<400> SEQUENCE: 340

Lys Lys Val Ile Leu Phe Ala Leu Pro Gly Ala Phe Thr Pro Val
1               5                   10                  15

<210> SEQ ID NO 341
<211> LENGTH: 15
<212> TYPE: PRT
<213> ORGANISM: Aspergillus fumigatus

<400> SEQUENCE: 341

Val Asp Val Val Ala Val Leu Ala Tyr Asn Asp Ala Tyr Val Met
1               5                   10                  15

<210> SEQ ID NO 342
<211> LENGTH: 15
<212> TYPE: PRT
<213> ORGANISM: Aspergillus fumigatus

<400> SEQUENCE: 342

Val Leu Ala Tyr Asn Asp Ala Tyr Val Met Ser Ala Trp Gly Lys
1               5                   10                  15

<210> SEQ ID NO 343
<211> LENGTH: 15
<212> TYPE: PRT
<213> ORGANISM: Aspergillus fumigatus

<400> SEQUENCE: 343

Gly Asp Asp Ile Leu Phe Leu Ser Asp Pro Asp Ala Arg Phe Ser
1               5                   10                  15

<210> SEQ ID NO 344
<211> LENGTH: 15
<212> TYPE: PRT
<213> ORGANISM: Aspergillus fumigatus

<400> SEQUENCE: 344

His Gly Lys Ile Thr Tyr Ala Ala Leu Glu Pro Ala Lys Asn His
1               5                   10                  15

<210> SEQ ID NO 345
<211> LENGTH: 15
<212> TYPE: PRT
<213> ORGANISM: Aspergillus fumigatus

<400> SEQUENCE: 345

Asn His Leu Glu Phe Ser Ser Ala Glu Thr Val Leu Lys His Leu
1               5                   10                  15

<210> SEQ ID NO 346
<211> LENGTH: 15
<212> TYPE: PRT
<213> ORGANISM: Aspergillus fumigatus

<400> SEQUENCE: 346

Met Gln Ile Lys Ser Phe Val Leu Ala Ala Ser Ala Ala Ala Thr
1               5                   10                  15

<210> SEQ ID NO 347
<211> LENGTH: 15
<212> TYPE: PRT
<213> ORGANISM: Aspergillus fumigatus

<400> SEQUENCE: 347

Phe Val Leu Ala Ala Ser Ala Ala Ala Thr Ala Ser Ala Ala Ala
1               5                   10                  15

<210> SEQ ID NO 348
<211> LENGTH: 15
<212> TYPE: PRT
<213> ORGANISM: Aspergillus fumigatus

<400> SEQUENCE: 348

Asn Lys Tyr Phe Gly Ile Val Ala Ile His Ser Gly Ser Ala Val
1               5                   10                  15

<210> SEQ ID NO 349
<211> LENGTH: 15
<212> TYPE: PRT
<213> ORGANISM: Aspergillus fumigatus

<400> SEQUENCE: 349

Ile Val Ala Ile His Ser Gly Ser Ala Val Gln Tyr Gln Pro Phe
1               5                   10                  15

<210> SEQ ID NO 350
<211> LENGTH: 15
<212> TYPE: PRT
<213> ORGANISM: Aspergillus fumigatus

<400> SEQUENCE: 350

Ser Gly Ser Ala Val Gln Tyr Gln Pro Phe Ser Ala Ala Lys Ser
1               5                   10                  15

<210> SEQ ID NO 351
<211> LENGTH: 15
<212> TYPE: PRT
<213> ORGANISM: Aspergillus fumigatus

<400> SEQUENCE: 351

Gln Tyr Gln Pro Phe Ser Ala Ala Lys Ser Ser Ile Phe Ala Gly

<210> SEQ ID NO 352
<211> LENGTH: 15
<212> TYPE: PRT
<213> ORGANISM: Aspergillus fumigatus

<400> SEQUENCE: 352

Ala Thr Phe Tyr Ile Gln Asp Gly Ser Leu Tyr Leu Tyr Ala Ala
1               5                   10                  15

<210> SEQ ID NO 353
<211> LENGTH: 15
<212> TYPE: PRT
<213> ORGANISM: Aspergillus fumigatus

<400> SEQUENCE: 353

Gln Asp Gly Ser Leu Tyr Leu Tyr Ala Ala Ser Ala Thr Pro Gln
1               5                   10                  15

<210> SEQ ID NO 354
<211> LENGTH: 15
<212> TYPE: PRT
<213> ORGANISM: Aspergillus fumigatus

<400> SEQUENCE: 354

Met Gln Leu Lys Asn Ser Met Leu Leu Leu Thr Ala Leu Ala Ala
1               5                   10                  15

<210> SEQ ID NO 355
<211> LENGTH: 15
<212> TYPE: PRT
<213> ORGANISM: Aspergillus fumigatus

<400> SEQUENCE: 355

Ser Met Leu Leu Leu Thr Ala Leu Ala Ala Gly Ser Ser Val Ala
1               5                   10                  15

<210> SEQ ID NO 356
<211> LENGTH: 15
<212> TYPE: PRT
<213> ORGANISM: Aspergillus fumigatus

<400> SEQUENCE: 356

Asp Thr Val Tyr Ala Thr Ile Asn Gly Val Leu Val Ser Trp Ile
1               5                   10                  15

<210> SEQ ID NO 357
<211> LENGTH: 15
<212> TYPE: PRT
<213> ORGANISM: Aspergillus fumigatus

<400> SEQUENCE: 357

Thr Gly Trp Tyr Gly Asn Ser Ala Leu Thr Leu His Leu Glu Ala
1               5                   10                  15

<210> SEQ ID NO 358
<211> LENGTH: 15
<212> TYPE: PRT
<213> ORGANISM: Aspergillus fumigatus

<400> SEQUENCE: 358

Gly Glu Leu Cys Ser Ile Ile Ser His Gly Leu Ser Lys Val Ile
1               5                   10                  15

<210> SEQ ID NO 359
<211> LENGTH: 15
<212> TYPE: PRT
<213> ORGANISM: Aspergillus fumigatus

<400> SEQUENCE: 359

Leu Ser Lys Val Ile Asp Ala Tyr Thr Ala Asp Leu Ala Gly Val
1               5                   10                  15

<210> SEQ ID NO 360
<211> LENGTH: 15
<212> TYPE: PRT
<213> ORGANISM: Aspergillus fumigatus

<400> SEQUENCE: 360

Met Arg Gly Leu Leu Ala Gly Ala Leu Ala Leu Pro Ala Ser
1               5                   10                  15

<210> SEQ ID NO 361
<211> LENGTH: 15
<212> TYPE: PRT
<213> ORGANISM: Aspergillus fumigatus

<400> SEQUENCE: 361

Leu Ala Gly Ala Leu Ala Leu Pro Ala Ser Val Phe Ala His Pro
1               5                   10                  15

<210> SEQ ID NO 362
<211> LENGTH: 15
<212> TYPE: PRT
<213> ORGANISM: Aspergillus fumigatus

<400> SEQUENCE: 362

Thr Val Asp Leu Asn Ala Phe Arg Leu Lys Ser Leu Ala Lys Tyr
1               5                   10                  15

<210> SEQ ID NO 363
<211> LENGTH: 15
<212> TYPE: PRT
<213> ORGANISM: Aspergillus fumigatus

<400> SEQUENCE: 363

Ala Phe Arg Leu Lys Ser Leu Ala Lys Tyr Val Asn Ala Thr Glu
1               5                   10                  15

<210> SEQ ID NO 364
<211> LENGTH: 15
<212> TYPE: PRT
<213> ORGANISM: Aspergillus fumigatus

<400> SEQUENCE: 364

Ser Leu Ala Lys Tyr Val Asn Ala Thr Glu Thr Val Ile Glu Ala
1               5                   10                  15

<210> SEQ ID NO 365
<211> LENGTH: 15
<212> TYPE: PRT
<213> ORGANISM: Aspergillus fumigatus

<400> SEQUENCE: 365

Pro Phe Lys Pro Gln Ser Tyr Val Glu Val Ala Thr Gln His Val
1               5                   10                  15

<210> SEQ ID NO 366

-continued

```
<211> LENGTH: 15
<212> TYPE: PRT
<213> ORGANISM: Aspergillus fumigatus

<400> SEQUENCE: 366

Gly Lys Asp Gly Lys Val Phe Ser Tyr Gly Asn Ser Phe Tyr Thr
1               5                   10                  15

<210> SEQ ID NO 367
<211> LENGTH: 15
<212> TYPE: PRT
<213> ORGANISM: Aspergillus fumigatus

<400> SEQUENCE: 367

Glu Ser Tyr Val Phe Lys Gly Val Ser Gly Thr Val Ser Asp Pro
1               5                   10                  15

<210> SEQ ID NO 368
<211> LENGTH: 15
<212> TYPE: PRT
<213> ORGANISM: Aspergillus fumigatus

<400> SEQUENCE: 368

Lys Ala Lys Leu Val Tyr Phe Val Lys Asp Asp Gly Thr Leu Ala
1               5                   10                  15

<210> SEQ ID NO 369
<211> LENGTH: 15
<212> TYPE: PRT
<213> ORGANISM: Aspergillus fumigatus

<400> SEQUENCE: 369

Ser Asn Trp Leu Leu Thr Tyr Ile Asp Ala Lys Ser Gly Glu Glu
1               5                   10                  15

<210> SEQ ID NO 370
<211> LENGTH: 15
<212> TYPE: PRT
<213> ORGANISM: Aspergillus fumigatus

<400> SEQUENCE: 370

Ser Tyr Leu Asn Asn Tyr Arg Pro Ser Ser Ser Leu Ser Phe
1               5                   10                  15

<210> SEQ ID NO 371
<211> LENGTH: 15
<212> TYPE: PRT
<213> ORGANISM: Aspergillus fumigatus

<400> SEQUENCE: 371

Ser Ser Leu Ser Phe Lys Tyr Pro Tyr Ser Val Ser Ser Ser Pro
1               5                   10                  15

<210> SEQ ID NO 372
<211> LENGTH: 15
<212> TYPE: PRT
<213> ORGANISM: Aspergillus fumigatus

<400> SEQUENCE: 372

Pro Ser Ser Tyr Ile Asp Ala Ser Ile Ile Gln Leu Phe Tyr Thr
1               5                   10                  15

<210> SEQ ID NO 373
<211> LENGTH: 15
<212> TYPE: PRT
```

<213> ORGANISM: Aspergillus fumigatus

<400> SEQUENCE: 373

Asp Ala Ser Ile Ile Gln Leu Phe Tyr Thr Ala Asn Ile Tyr His
1               5                   10                  15

<210> SEQ ID NO 374
<211> LENGTH: 15
<212> TYPE: PRT
<213> ORGANISM: Aspergillus fumigatus

<400> SEQUENCE: 374

Gln Leu Phe Tyr Thr Ala Asn Ile Tyr His Asp Leu Leu Tyr Thr
1               5                   10                  15

<210> SEQ ID NO 375
<211> LENGTH: 15
<212> TYPE: PRT
<213> ORGANISM: Aspergillus fumigatus

<400> SEQUENCE: 375

Ala Asn Ile Tyr His Asp Leu Leu Tyr Thr Leu Gly Phe Thr Glu
1               5                   10                  15

<210> SEQ ID NO 376
<211> LENGTH: 15
<212> TYPE: PRT
<213> ORGANISM: Aspergillus fumigatus

<400> SEQUENCE: 376

Gly Asn Asp Tyr Val Ile Leu Asn Ala Gln Asp Gly Ser Gly Thr
1               5                   10                  15

<210> SEQ ID NO 377
<211> LENGTH: 15
<212> TYPE: PRT
<213> ORGANISM: Aspergillus fumigatus

<400> SEQUENCE: 377

Ile Val Ile His Glu Tyr Thr His Gly Leu Ser Asn Arg Leu Thr
1               5                   10                  15

<210> SEQ ID NO 378
<211> LENGTH: 15
<212> TYPE: PRT
<213> ORGANISM: Aspergillus fumigatus

<400> SEQUENCE: 378

Trp Ser Asp Phe Met Ala Thr Ala Ile Arg Leu Lys Pro Gly Asp
1               5                   10                  15

<210> SEQ ID NO 379
<211> LENGTH: 15
<212> TYPE: PRT
<213> ORGANISM: Aspergillus fumigatus

<400> SEQUENCE: 379

Ala Gly Gly Ile Arg Gln Tyr Pro Tyr Ser Thr Ser Leu Ser Thr
1               5                   10                  15

<210> SEQ ID NO 380
<211> LENGTH: 15
<212> TYPE: PRT
<213> ORGANISM: Aspergillus fumigatus -continued

<400> SEQUENCE: 380

Asn Pro Leu Thr Tyr Thr Ser Val Asn Ser Leu Asn Ala Val His
1               5                   10                  15

<210> SEQ ID NO 381
<211> LENGTH: 15
<212> TYPE: PRT
<213> ORGANISM: Aspergillus fumigatus

<400> SEQUENCE: 381

Leu Asn Ala Val His Ala Ile Gly Thr Val Trp Ala Ser Met Leu
1               5                   10                  15

<210> SEQ ID NO 382
<211> LENGTH: 15
<212> TYPE: PRT
<213> ORGANISM: Aspergillus fumigatus

<400> SEQUENCE: 382

Ala Ile Gly Thr Val Trp Ala Ser Met Leu Tyr Glu Val Leu Trp
1               5                   10                  15

<210> SEQ ID NO 383
<211> LENGTH: 15
<212> TYPE: PRT
<213> ORGANISM: Aspergillus fumigatus

<400> SEQUENCE: 383

Trp Ala Ser Met Leu Tyr Glu Val Leu Trp Asn Leu Ile Asp Lys
1               5                   10                  15

<210> SEQ ID NO 384
<211> LENGTH: 15
<212> TYPE: PRT
<213> ORGANISM: Aspergillus fumigatus

<400> SEQUENCE: 384

Pro Thr Asp Gly Lys Tyr Leu Ala Met Lys Leu Val Met Asp Gly
1               5                   10                  15

<210> SEQ ID NO 385
<211> LENGTH: 15
<212> TYPE: PRT
<213> ORGANISM: Aspergillus fumigatus

<400> SEQUENCE: 385

Cys Asn Pro Asn Phe Val Gln Ala Arg Asp Ala Ile Leu Asp Ala
1               5                   10                  15

<210> SEQ ID NO 386
<211> LENGTH: 15
<212> TYPE: PRT
<213> ORGANISM: Aspergillus fumigatus

<400> SEQUENCE: 386

Pro Tyr Pro Tyr Asp Ala Leu Gln Pro Tyr Ile Ser Gln Gln Ile
1               5                   10                  15

<210> SEQ ID NO 387
<211> LENGTH: 15
<212> TYPE: PRT
<213> ORGANISM: Aspergillus fumigatus

<400> SEQUENCE: 387

Ala Leu Gln Pro Tyr Ile Ser Gln Gln Ile Met Glu Leu His His
1               5                   10                  15

<210> SEQ ID NO 388
<211> LENGTH: 15
<212> TYPE: PRT
<213> ORGANISM: Aspergillus fumigatus

<400> SEQUENCE: 388

Lys Lys His His Gln Thr Tyr Val Asn Gly Leu Asn Ala Ala Leu
1               5                   10                  15

<210> SEQ ID NO 389
<211> LENGTH: 15
<212> TYPE: PRT
<213> ORGANISM: Aspergillus fumigatus

<400> SEQUENCE: 389

Thr Tyr Val Asn Gly Leu Asn Ala Ala Leu Glu Ala Gln Lys Lys
1               5                   10                  15

<210> SEQ ID NO 390
<211> LENGTH: 15
<212> TYPE: PRT
<213> ORGANISM: Aspergillus fumigatus

<400> SEQUENCE: 390

Asp Val Pro Lys Leu Val Ser Val Gln Gln Ala Ile Lys Phe Asn
1               5                   10                  15

<210> SEQ ID NO 391
<211> LENGTH: 15
<212> TYPE: PRT
<213> ORGANISM: Aspergillus fumigatus

<400> SEQUENCE: 391

Val Ser Val Gln Gln Ala Ile Lys Phe Asn Gly Gly Gly His Ile
1               5                   10                  15

<210> SEQ ID NO 392
<211> LENGTH: 15
<212> TYPE: PRT
<213> ORGANISM: Aspergillus fumigatus

<400> SEQUENCE: 392

Phe Asp Lys Phe Lys Asp Ala Phe Asn Thr Thr Leu Leu Gly Ile
1               5                   10                  15

<210> SEQ ID NO 393
<211> LENGTH: 15
<212> TYPE: PRT
<213> ORGANISM: Aspergillus fumigatus

<400> SEQUENCE: 393

Glu His Ala Tyr Tyr Leu Gln Tyr Leu Asn Asp Lys Ala Ser Tyr
1               5                   10                  15

<210> SEQ ID NO 394
<211> LENGTH: 15
<212> TYPE: PRT
<213> ORGANISM: Aspergillus fumigatus

<400> SEQUENCE: 394

Leu Gln Tyr Leu Asn Asp Lys Ala Ser Tyr Ala Lys Gly Ile Trp
1               5                   10                  15

<210> SEQ ID NO 395
<211> LENGTH: 15
<212> TYPE: PRT
<213> ORGANISM: Aspergillus fumigatus

<400> SEQUENCE: 395

Met Ala Pro Ile Phe Lys Ser Leu Ala Leu Val Ser Ala Leu Phe
1               5                   10                  15

<210> SEQ ID NO 396
<211> LENGTH: 15
<212> TYPE: PRT
<213> ORGANISM: Aspergillus fumigatus

<400> SEQUENCE: 396

Lys Ser Leu Ala Leu Val Ser Ala Leu Phe Ala Ala Ile Ser Ser
1               5                   10                  15

<210> SEQ ID NO 397
<211> LENGTH: 15
<212> TYPE: PRT
<213> ORGANISM: Aspergillus fumigatus

<400> SEQUENCE: 397

Val Ser Ala Leu Phe Ala Ala Ile Ser Ser Ala Ala Pro Val Asn
1               5                   10                  15

<210> SEQ ID NO 398
<211> LENGTH: 15
<212> TYPE: PRT
<213> ORGANISM: Aspergillus fumigatus

<400> SEQUENCE: 398

Thr Gln Pro Ser Val Ala Thr Phe Ile Pro Val Ala Ala Ala Ala
1               5                   10                  15

<210> SEQ ID NO 399
<211> LENGTH: 15
<212> TYPE: PRT
<213> ORGANISM: Aspergillus fumigatus

<400> SEQUENCE: 399

Ala Thr Phe Ile Pro Val Ala Ala Ala Ala Ala Ala Ala Asp Ser
1               5                   10                  15

<210> SEQ ID NO 400
<211> LENGTH: 15
<212> TYPE: PRT
<213> ORGANISM: Aspergillus fumigatus

<400> SEQUENCE: 400

Leu Thr Tyr Tyr Asp Thr Ala Thr Ser Ala Ser Ala Pro Ser Ser
1               5                   10                  15

<210> SEQ ID NO 401
<211> LENGTH: 15
<212> TYPE: PRT
<213> ORGANISM: Aspergillus fumigatus

<400> SEQUENCE: 401

Asp Gly Phe Ser Glu Asn Val Val Ala Leu Pro Val Gly Ile Met
1               5                   10                  15

```
<210> SEQ ID NO 402
<211> LENGTH: 15
<212> TYPE: PRT
<213> ORGANISM: Aspergillus fumigatus

<400> SEQUENCE: 402

Met Lys His Leu Ala Ala Tyr Leu Leu Leu Ala Leu Ala Gly Asn
1               5                   10                  15

<210> SEQ ID NO 403
<211> LENGTH: 15
<212> TYPE: PRT
<213> ORGANISM: Aspergillus fumigatus

<400> SEQUENCE: 403

Ala Tyr Leu Leu Leu Ala Leu Ala Gly Asn Thr Ser Pro Ser Ser
1               5                   10                  15

<210> SEQ ID NO 404
<211> LENGTH: 15
<212> TYPE: PRT
<213> ORGANISM: Aspergillus fumigatus

<400> SEQUENCE: 404

Glu Asp Val Lys Ala Val Leu Ser Ser Val Gly Ile Asp Ala Asp
1               5                   10                  15

<210> SEQ ID NO 405
<211> LENGTH: 15
<212> TYPE: PRT
<213> ORGANISM: Aspergillus fumigatus

<400> SEQUENCE: 405

Glu Glu Arg Leu Asn Lys Leu Ile Ala Glu Leu Glu Gly Lys Asp
1               5                   10                  15

<210> SEQ ID NO 406
<211> LENGTH: 15
<212> TYPE: PRT
<213> ORGANISM: Aspergillus fumigatus

<400> SEQUENCE: 406

Leu Gln Glu Leu Ile Ala Glu Gly Ser Thr Lys Leu Ala Ser Val
1               5                   10                  15

<210> SEQ ID NO 407
<211> LENGTH: 15
<212> TYPE: PRT
<213> ORGANISM: Aspergillus fumigatus

<400> SEQUENCE: 407

Lys Arg Ser Phe Ile Leu Arg Ser Ala Asp Met Tyr Phe Lys Tyr
1               5                   10                  15

<210> SEQ ID NO 408
<211> LENGTH: 15
<212> TYPE: PRT
<213> ORGANISM: Aspergillus fumigatus

<400> SEQUENCE: 408

Leu Arg Ser Ala Asp Met Tyr Phe Lys Tyr Thr Ala Ala Ala Leu
1               5                   10                  15

<210> SEQ ID NO 409
<211> LENGTH: 15
```

```
<212> TYPE: PRT
<213> ORGANISM: Aspergillus fumigatus

<400> SEQUENCE: 409

Met Tyr Phe Lys Tyr Thr Ala Ala Ala Leu Ala Ala Val Leu Pro
1               5                   10                  15

<210> SEQ ID NO 410
<211> LENGTH: 15
<212> TYPE: PRT
<213> ORGANISM: Aspergillus fumigatus

<400> SEQUENCE: 410

Thr Ala Ala Ala Leu Ala Ala Val Leu Pro Leu Cys Ser Ala Gln
1               5                   10                  15

<210> SEQ ID NO 411
<211> LENGTH: 15
<212> TYPE: PRT
<213> ORGANISM: Aspergillus fumigatus

<400> SEQUENCE: 411

Ser Thr Tyr Thr Ala Asp Phe Thr Ser Ala Ser Ala Leu Asp Gln
1               5                   10                  15

<210> SEQ ID NO 412
<211> LENGTH: 15
<212> TYPE: PRT
<213> ORGANISM: Aspergillus fumigatus

<400> SEQUENCE: 412

Pro Thr Ile Asp Thr Asp Phe Tyr Phe Phe Phe Gly Lys Ala Glu
1               5                   10                  15

<210> SEQ ID NO 413
<211> LENGTH: 15
<212> TYPE: PRT
<213> ORGANISM: Aspergillus fumigatus

<400> SEQUENCE: 413

Asp Phe Tyr Phe Phe Phe Gly Lys Ala Glu Val Val Met Lys Ala
1               5                   10                  15

<210> SEQ ID NO 414
<211> LENGTH: 15
<212> TYPE: PRT
<213> ORGANISM: Cynodon dactylon

<400> SEQUENCE: 414

Met Leu Ala Val Val Ala Val Val Leu Ala Ser Met Val Gly Gly
1               5                   10                  15

<210> SEQ ID NO 415
<211> LENGTH: 15
<212> TYPE: PRT
<213> ORGANISM: Cynodon dactylon

<400> SEQUENCE: 415

Ile Thr Asp Lys Asn Tyr Glu His Ile Ala Ala Tyr His Phe Asp
1               5                   10                  15

<210> SEQ ID NO 416
<211> LENGTH: 15
<212> TYPE: PRT
<213> ORGANISM: Cynodon dactylon
```

-continued

```
<400> SEQUENCE: 416

Tyr Glu His Ile Ala Ala Tyr His Phe Asp Leu Ser Gly Lys Ala
1               5                   10                  15

<210> SEQ ID NO 417
<211> LENGTH: 15
<212> TYPE: PRT
<213> ORGANISM: Cynodon dactylon

<400> SEQUENCE: 417

Asp Lys Leu Arg Lys Ala Gly Glu Leu Met Leu Gln Phe Arg Arg
1               5                   10                  15

<210> SEQ ID NO 418
<211> LENGTH: 15
<212> TYPE: PRT
<213> ORGANISM: Cynodon dactylon

<400> SEQUENCE: 418

Pro Asn Tyr Leu Ala Leu Leu Val Lys Tyr Ala Ala Gly Asp Gly
1               5                   10                  15

<210> SEQ ID NO 419
<211> LENGTH: 15
<212> TYPE: PRT
<213> ORGANISM: Cynodon dactylon

<400> SEQUENCE: 419

Thr Val Trp Ala Gln Ser Ala Ala Phe Pro Ala Phe Lys Pro Glu
1               5                   10                  15

<210> SEQ ID NO 420
<211> LENGTH: 15
<212> TYPE: PRT
<213> ORGANISM: Cynodon dactylon

<400> SEQUENCE: 420

Phe Leu Gly Pro Thr Lys Tyr Met Val Ile Gln Gly Glu Pro Gly
1               5                   10                  15

<210> SEQ ID NO 421
<211> LENGTH: 15
<212> TYPE: PRT
<213> ORGANISM: Cynodon dactylon

<400> SEQUENCE: 421

Lys Tyr Met Val Ile Gln Gly Glu Pro Gly Ala Val Ile Arg Gly
1               5                   10                  15

<210> SEQ ID NO 422
<211> LENGTH: 15
<212> TYPE: PRT
<213> ORGANISM: Cynodon dactylon

<400> SEQUENCE: 422

Met Ala Thr Leu Thr Phe Pro Val Leu Leu Ala Thr Met Val Gly
1               5                   10                  15

<210> SEQ ID NO 423
<211> LENGTH: 15
<212> TYPE: PRT
<213> ORGANISM: Cynodon dactylon

<400> SEQUENCE: 423
```

```
Phe Pro Val Leu Leu Ala Thr Met Val Gly His Ala Trp Cys Val
1               5                   10                  15

<210> SEQ ID NO 424
<211> LENGTH: 15
<212> TYPE: PRT
<213> ORGANISM: Cynodon dactylon

<400> SEQUENCE: 424

Asn Ile Ile Phe His Val Glu Glu Ser Ser Pro Lys Phe Ala Leu
1               5                   10                  15

<210> SEQ ID NO 425
<211> LENGTH: 15
<212> TYPE: PRT
<213> ORGANISM: Cynodon dactylon

<400> SEQUENCE: 425

Lys Pro Leu Lys Gly Pro Leu Asn Ile Arg Leu Arg Ala Glu Gly
1               5                   10                  15

<210> SEQ ID NO 426
<211> LENGTH: 15
<212> TYPE: PRT
<213> ORGANISM: Cynodon dactylon

<400> SEQUENCE: 426

Met Ala Lys Val Ile Ala Ile Ile Leu Val Ala Thr Met Val Thr
1               5                   10                  15

<210> SEQ ID NO 427
<211> LENGTH: 15
<212> TYPE: PRT
<213> ORGANISM: Cynodon dactylon

<400> SEQUENCE: 427

Ala Ile Ile Leu Val Ala Thr Met Val Thr Ala Ala Leu Val Pro
1               5                   10                  15

<210> SEQ ID NO 428
<211> LENGTH: 15
<212> TYPE: PRT
<213> ORGANISM: Cynodon dactylon

<400> SEQUENCE: 428

Ala Thr Met Val Thr Ala Ala Leu Val Pro Ile Glu Cys Ala Thr
1               5                   10                  15

<210> SEQ ID NO 429
<211> LENGTH: 15
<212> TYPE: PRT
<213> ORGANISM: Cynodon dactylon

<400> SEQUENCE: 429

Asp Ala Ala Val Asn Leu Met Ala Met Ser Phe Ile Cys Ile Gly
1               5                   10                  15

<210> SEQ ID NO 430
<211> LENGTH: 15
<212> TYPE: PRT
<213> ORGANISM: Cynodon dactylon

<400> SEQUENCE: 430

Leu Met Ala Met Ser Phe Ile Cys Ile Gly Trp Ala Lys Lys Ala
```

```
                1               5                   10                  15

<210> SEQ ID NO 431
<211> LENGTH: 15
<212> TYPE: PRT
<213> ORGANISM: Cynodon dactylon

<400> SEQUENCE: 431

Ala Ala Asp Gln Val Leu Ala Ala Ala Pro Ala His Lys Tyr Lys
1               5                   10                  15

<210> SEQ ID NO 432
<211> LENGTH: 15
<212> TYPE: PRT
<213> ORGANISM: Cynodon dactylon

<400> SEQUENCE: 432

Glu Leu Thr Asp Ala Leu Arg Thr Leu Gly Ser Thr Ser Ala Asp
1               5                   10                  15

<210> SEQ ID NO 433
<211> LENGTH: 15
<212> TYPE: PRT
<213> ORGANISM: Cynodon dactylon

<400> SEQUENCE: 433

Leu Arg Thr Leu Gly Ser Thr Ser Ala Asp Glu Val Gln Arg Met
1               5                   10                  15

<210> SEQ ID NO 434
<211> LENGTH: 15
<212> TYPE: PRT
<213> ORGANISM: Cynodon dactylon

<400> SEQUENCE: 434

Phe Ile Asp Phe Asp Glu Phe Ile Ser Phe Cys Asn Ala Asn Pro
1               5                   10                  15

<210> SEQ ID NO 435
<211> LENGTH: 15
<212> TYPE: PRT
<213> ORGANISM: Betula pendula

<400> SEQUENCE: 435

Tyr Glu Thr Glu Thr Thr Ser Val Ile Pro Ala Ala Arg Leu Phe
1               5                   10                  15

<210> SEQ ID NO 436
<211> LENGTH: 15
<212> TYPE: PRT
<213> ORGANISM: Betula pendula

<400> SEQUENCE: 436

Thr Ser Val Ile Pro Ala Ala Arg Leu Phe Lys Ala Phe Phe Leu
1               5                   10                  15

<210> SEQ ID NO 437
<211> LENGTH: 15
<212> TYPE: PRT
<213> ORGANISM: Betula pendula

<400> SEQUENCE: 437

Asp His Thr Asn Phe Lys Tyr Ser Tyr Ser Val Ile Glu Gly Gly
1               5                   10                  15
```

<210> SEQ ID NO 438
<211> LENGTH: 15
<212> TYPE: PRT
<213> ORGANISM: Betula pendula

<400> SEQUENCE: 438

Leu Glu Lys Ile Ser Asn Glu Ile Lys Ile Val Ala Thr Pro Asp
1               5                   10                  15

<210> SEQ ID NO 439
<211> LENGTH: 15
<212> TYPE: PRT
<213> ORGANISM: Betula pendula

<400> SEQUENCE: 439

Gly Gly Ser Ile Leu Lys Ile Ser Asn Lys Tyr His Thr Lys Gly
1               5                   10                  15

<210> SEQ ID NO 440
<211> LENGTH: 15
<212> TYPE: PRT
<213> ORGANISM: Betula pendula

<400> SEQUENCE: 440

Gly Glu Thr Leu Leu Arg Ala Val Glu Ser Tyr Leu Leu Ala His
1               5                   10                  15

<210> SEQ ID NO 441
<211> LENGTH: 15
<212> TYPE: PRT
<213> ORGANISM: Betula pendula

<400> SEQUENCE: 441

Arg Ala Val Glu Ser Tyr Leu Leu Ala His Ser Asp Ala Tyr Asn
1               5                   10                  15

<210> SEQ ID NO 442
<211> LENGTH: 15
<212> TYPE: PRT
<213> ORGANISM: Betula pendula

<400> SEQUENCE: 442

Asp Gly Ser Val Trp Ala Gln Ser Ser Ser Phe Pro Gln Phe Lys
1 5 10 15

<210> SEQ ID NO 443
<211> LENGTH: 15
<212> TYPE: PRT
<213> ORGANISM: Betula pendula

<400> SEQUENCE: 443

Gly Leu His Leu Gly Gly Ile Lys Tyr Met Val Ile Gln Gly Glu
1 5 10 15

<210> SEQ ID NO 444
<211> LENGTH: 15
<212> TYPE: PRT
<213> ORGANISM: Betula pendula

<400> SEQUENCE: 444

Gly Ile Lys Tyr Met Val Ile Gln Gly Glu Ala Gly Ala Val Ile
1 5 10 15

<210> SEQ ID NO 445

-continued

```
<211> LENGTH: 15
<212> TYPE: PRT
<213> ORGANISM: Betula pendula

<400> SEQUENCE: 445

Asn Ser Ser Phe Arg Leu Arg Ser Glu Ser Leu Asn Thr Leu Arg
1               5                   10                  15

<210> SEQ ID NO 446
<211> LENGTH: 15
<212> TYPE: PRT
<213> ORGANISM: Betula pendula

<400> SEQUENCE: 446

Leu Arg Ser Glu Ser Leu Asn Thr Leu Arg Leu Arg Arg Ile Phe
1               5                   10                  15

<210> SEQ ID NO 447
<211> LENGTH: 15
<212> TYPE: PRT
<213> ORGANISM: Betula pendula

<400> SEQUENCE: 447

Leu Asn Thr Leu Arg Leu Arg Arg Ile Phe Asp Leu Phe Asp Lys
1               5                   10                  15

<210> SEQ ID NO 448
<211> LENGTH: 15
<212> TYPE: PRT
<213> ORGANISM: Betula pendula

<400> SEQUENCE: 448

Ile Thr Val Asp Glu Leu Ser Arg Ala Leu Asn Leu Leu Gly Leu
1               5                   10                  15

<210> SEQ ID NO 449
<211> LENGTH: 15
<212> TYPE: PRT
<213> ORGANISM: Betula pendula

<400> SEQUENCE: 449

Leu Ser Arg Ala Leu Asn Leu Leu Gly Leu Glu Thr Asp Leu Ser
1               5                   10                  15

<210> SEQ ID NO 450
<211> LENGTH: 15
<212> TYPE: PRT
<213> ORGANISM: Betula pendula

<400> SEQUENCE: 450

Gly Leu Gln Phe Glu Asp Phe Ile Ser Leu His Gln Ser Leu Asn
1               5                   10                  15

<210> SEQ ID NO 451
<211> LENGTH: 15
<212> TYPE: PRT
<213> ORGANISM: Betula pendula

<400> SEQUENCE: 451

Asp Phe Ile Ser Leu His Gln Ser Leu Asn Asp Ser Tyr Phe Ala
1               5                   10                  15

<210> SEQ ID NO 452
<211> LENGTH: 15
<212> TYPE: PRT
```

<213> ORGANISM: Betula pendula

<400> SEQUENCE: 452

Gly Asp Gly Tyr Ile Ser Ala Arg Glu Leu Gln Met Val Leu Gly
1               5                   10                  15

<210> SEQ ID NO 453
<211> LENGTH: 15
<212> TYPE: PRT
<213> ORGANISM: Betula pendula

<400> SEQUENCE: 453

Asp Arg Val Glu Lys Met Ile Val Ser Val Asp Ser Asn Arg Asp
1               5                   10                  15

<210> SEQ ID NO 454
<211> LENGTH: 15
<212> TYPE: PRT
<213> ORGANISM: Betula pendula

<400> SEQUENCE: 454

Phe Glu Phe Lys Asp Met Met Arg Ser Val Leu Val Arg Ser Ser
1               5                   10                  15

<210> SEQ ID NO 455
<211> LENGTH: 15
<212> TYPE: PRT
<213> ORGANISM: Betula pendula

<400> SEQUENCE: 455

Glu Leu Gly Glu Ala Leu Lys Thr Leu Gly Ser Ile Thr Pro Asp
1               5                   10                  15

<210> SEQ ID NO 456
<211> LENGTH: 15
<212> TYPE: PRT
<213> ORGANISM: Betula pendula

<400> SEQUENCE: 456

Phe Ile Ser Phe Gln Glu Phe Thr Asp Phe Gly Arg Ala Asn Arg
1               5                   10                  15

<210> SEQ ID NO 457
<211> LENGTH: 15
<212> TYPE: PRT
<213> ORGANISM: Betula pendula

<400> SEQUENCE: 457

Gly Arg Ala Asn Arg Gly Leu Leu Lys Asp Val Ala Lys Ile Phe
1               5                   10                  15

<210> SEQ ID NO 458
<211> LENGTH: 15
<212> TYPE: PRT
<213> ORGANISM: Betula pendula

<400> SEQUENCE: 458

Ile Gly Lys Phe Ile Val Glu Ala Ser Ala Lys Ser Gly His Pro
1               5                   10                  15

<210> SEQ ID NO 459
<211> LENGTH: 15
<212> TYPE: PRT
<213> ORGANISM: Betula pendula

<400> SEQUENCE: 459

Gly Lys Leu Val Glu Lys Phe Lys Gly Leu Gly Val Thr Leu Leu
1               5                   10                  15

<210> SEQ ID NO 460
<211> LENGTH: 15
<212> TYPE: PRT
<213> ORGANISM: Betula pendula

<400> SEQUENCE: 460

Lys Phe Lys Gly Leu Gly Val Thr Leu Leu His Gly Asp Leu Tyr
1               5                   10                  15

<210> SEQ ID NO 461
<211> LENGTH: 15
<212> TYPE: PRT
<213> ORGANISM: Betula pendula

<400> SEQUENCE: 461

Val Lys Ala Phe Lys Gln Val Asp Val Val Ile Ser Thr Val Gly
1               5                   10                  15

<210> SEQ ID NO 462
<211> LENGTH: 15
<212> TYPE: PRT
<213> ORGANISM: Betula pendula

<400> SEQUENCE: 462

Gln Val Asp Val Val Ile Ser Thr Val Gly His Leu Gln Leu Ala
1               5                   10                  15

<210> SEQ ID NO 463
<211> LENGTH: 15
<212> TYPE: PRT
<213> ORGANISM: Betula pendula

<400> SEQUENCE: 463

His Leu Gln Leu Ala Asp Gln Val Lys Ile Ile Ala Ala Ile Lys
1               5                   10                  15

<210> SEQ ID NO 464
<211> LENGTH: 15
<212> TYPE: PRT
<213> ORGANISM: Betula pendula

<400> SEQUENCE: 464

Asp Gln Val Lys Ile Ile Ala Ala Ile Lys Glu Ala Gly Asn Ile
1               5                   10                  15

<210> SEQ ID NO 465
<211> LENGTH: 15
<212> TYPE: PRT
<213> ORGANISM: Betula pendula

<400> SEQUENCE: 465

Glu Ala Gly Asn Ile Lys Arg Phe Phe Pro Ser Glu Phe Gly Asn
1               5                   10                  15

<210> SEQ ID NO 466
<211> LENGTH: 15
<212> TYPE: PRT
<213> ORGANISM: Betula pendula

<400> SEQUENCE: 466

-continued

Glu Ala Glu Gly Ile Pro Tyr Thr Tyr Val Ser Ser Asn Phe Phe
1               5                   10                  15

<210> SEQ ID NO 467
<211> LENGTH: 15
<212> TYPE: PRT
<213> ORGANISM: Betula pendula

<400> SEQUENCE: 467

Pro Tyr Thr Tyr Val Ser Ser Asn Phe Phe Ala Gly Tyr Phe Leu
1               5                   10                  15

<210> SEQ ID NO 468
<211> LENGTH: 15
<212> TYPE: PRT
<213> ORGANISM: Betula pendula

<400> SEQUENCE: 468

Ser Ser Asn Phe Phe Ala Gly Tyr Phe Leu Pro Thr Leu Ala Gln
1               5                   10                  15

<210> SEQ ID NO 469
<211> LENGTH: 15
<212> TYPE: PRT
<213> ORGANISM: Betula pendula

<400> SEQUENCE: 469

Ala Gly Tyr Phe Leu Pro Thr Leu Ala Gln Pro Gly Leu Thr Ser
1               5                   10                  15

<210> SEQ ID NO 470
<211> LENGTH: 15
<212> TYPE: PRT
<213> ORGANISM: Betula pendula

<400> SEQUENCE: 470

Arg Thr Leu Asn Lys Ile Val Tyr Ile Lys Pro Ala Lys Asn Ile
1               5                   10                  15

<210> SEQ ID NO 471
<211> LENGTH: 15
<212> TYPE: PRT
<213> ORGANISM: Betula pendula

<400> SEQUENCE: 471

Ile Val Tyr Ile Lys Pro Ala Lys Asn Ile Tyr Ser Phe Asn Glu
1               5                   10                  15

<210> SEQ ID NO 472
<211> LENGTH: 15
<212> TYPE: PRT
<213> ORGANISM: Betula pendula

<400> SEQUENCE: 472

Pro Ala Lys Asn Ile Tyr Ser Phe Asn Glu Ile Val Ala Leu Trp
1               5                   10                  15

<210> SEQ ID NO 473
<211> LENGTH: 15
<212> TYPE: PRT
<213> ORGANISM: Betula pendula

<400> SEQUENCE: 473

Tyr Ser Phe Asn Glu Ile Val Ala Leu Trp Glu Lys Lys Ile Gly
1               5                   10                  15

<210> SEQ ID NO 474
<211> LENGTH: 15
<212> TYPE: PRT
<213> ORGANISM: Betula pendula

<400> SEQUENCE: 474

Pro Ile Pro Ile Asn Val Ile Leu Ala Ile Asn His Ser Val Phe
1               5                   10                  15

<210> SEQ ID NO 475
<211> LENGTH: 15
<212> TYPE: PRT
<213> ORGANISM: Betula pendula

<400> SEQUENCE: 475

Val Ile Leu Ala Ile Asn His Ser Val Phe Val Lys Gly Asp His
1               5                   10                  15

<210> SEQ ID NO 476
<211> LENGTH: 15
<212> TYPE: PRT
<213> ORGANISM: Betula pendula

<400> SEQUENCE: 476

Thr Asn Phe Glu Ile Glu Ala Ser Phe Gly Val Glu Ala Ser Glu
1               5                   10                  15

<210> SEQ ID NO 477
<211> LENGTH: 15
<212> TYPE: PRT
<213> ORGANISM: Betula pendula

<400> SEQUENCE: 477

Leu Tyr Pro Asp Val Lys Tyr Thr Thr Val Glu Glu Tyr Leu Gln
1               5                   10                  15

<210> SEQ ID NO 478
<211> LENGTH: 15
<212> TYPE: PRT
<213> ORGANISM: Betula pendula

<400> SEQUENCE: 478

Asp Val Lys Tyr Thr Thr Val Glu Glu Tyr Leu Gln Gln Phe Val
1               5                   10                  15

<210> SEQ ID NO 479
<211> LENGTH: 15
<212> TYPE: PRT
<213> ORGANISM: Betula pendula

<400> SEQUENCE: 479

Gly Lys Pro Leu His Tyr Lys Lys Ser Ser Phe His Arg Val Ile
1               5                   10                  15

<210> SEQ ID NO 480
<211> LENGTH: 15
<212> TYPE: PRT
<213> ORGANISM: Betula pendula

<400> SEQUENCE: 480

Thr Gly Pro Gly Ile Leu Ser Met Ala Asn Ala Gly Pro Gly Thr
1               5                   10                  15

```
<210> SEQ ID NO 481
<211> LENGTH: 15
<212> TYPE: PRT
<213> ORGANISM: Betula pendula

<400> SEQUENCE: 481

Asn Gly Ser Gln Phe Phe Ile Cys Thr Ala Lys Thr Glu Trp Leu
1               5                   10                  15

<210> SEQ ID NO 482
<211> LENGTH: 15
<212> TYPE: PRT
<213> ORGANISM: Juglans nigra

<400> SEQUENCE: 482

Lys Cys Ile Phe His Thr Phe Ser Leu Thr Met Ala Arg Leu Ala
1               5                   10                  15

<210> SEQ ID NO 483
<211> LENGTH: 15
<212> TYPE: PRT
<213> ORGANISM: Juglans nigra

<400> SEQUENCE: 483

Thr Phe Ser Leu Thr Met Ala Arg Leu Ala Thr Leu Ala Ala Leu
1               5                   10                  15

<210> SEQ ID NO 484
<211> LENGTH: 15
<212> TYPE: PRT
<213> ORGANISM: Juglans nigra

<400> SEQUENCE: 484

Met Ala Arg Leu Ala Thr Leu Ala Ala Leu Leu Val Ala Leu Leu
1               5                   10                  15

<210> SEQ ID NO 485
<211> LENGTH: 15
<212> TYPE: PRT
<213> ORGANISM: Juglans nigra

<400> SEQUENCE: 485

Thr Leu Ala Ala Leu Leu Val Ala Leu Leu Phe Val Ala Asn Ala
1               5                   10                  15

<210> SEQ ID NO 486
<211> LENGTH: 15
<212> TYPE: PRT
<213> ORGANISM: Juglans nigra

<400> SEQUENCE: 486

Leu Val Ala Leu Leu Phe Val Ala Asn Ala Ala Ala Phe Arg Thr
1               5                   10                  15

<210> SEQ ID NO 487
<211> LENGTH: 15
<212> TYPE: PRT
<213> ORGANISM: Juglans nigra

<400> SEQUENCE: 487

Phe Val Ala Asn Ala Ala Ala Phe Arg Thr Thr Ile Thr Thr Met
1               5                   10                  15

<210> SEQ ID NO 488
<211> LENGTH: 15
```

```
<212> TYPE: PRT
<213> ORGANISM: Juglans nigra

<400> SEQUENCE: 488

Ala Ala Phe Arg Thr Thr Ile Thr Thr Met Glu Ile Asp Glu Asp
1               5                   10                  15

<210> SEQ ID NO 489
<211> LENGTH: 15
<212> TYPE: PRT
<213> ORGANISM: Juglans nigra

<400> SEQUENCE: 489

Leu Asn His Cys Gln Tyr Tyr Leu Arg Gln Gln Ser Arg Ser Gly
1               5                   10                  15

<210> SEQ ID NO 490
<211> LENGTH: 15
<212> TYPE: PRT
<213> ORGANISM: Juglans nigra

<400> SEQUENCE: 490

Arg His Asn Pro Tyr Tyr Phe His Ser Gln Ser Ile Arg Ser Arg
1               5                   10                  15

<210> SEQ ID NO 491
<211> LENGTH: 15
<212> TYPE: PRT
<213> ORGANISM: Juglans nigra

<400> SEQUENCE: 491

Gly Glu Val Lys Tyr Leu Glu Arg Phe Ala Glu Arg Thr Glu Leu
1               5                   10                  15

<210> SEQ ID NO 492
<211> LENGTH: 15
<212> TYPE: PRT
<213> ORGANISM: Juglans nigra

<400> SEQUENCE: 492

Glu Arg Thr Glu Leu Leu Arg Gly Ile Glu Asn Tyr Arg Val Val
1               5                   10                  15

<210> SEQ ID NO 493
<211> LENGTH: 15
<212> TYPE: PRT
<213> ORGANISM: Juglans nigra

<400> SEQUENCE: 493

Leu Arg Gly Ile Glu Asn Tyr Arg Val Val Ile Leu Asp Ala Asn
1               5                   10                  15

<210> SEQ ID NO 494
<211> LENGTH: 15
<212> TYPE: PRT
<213> ORGANISM: Juglans nigra

<400> SEQUENCE: 494

Asn Tyr Arg Val Val Ile Leu Asp Ala Asn Pro Asn Thr Phe Met
1               5                   10                  15

<210> SEQ ID NO 495
<211> LENGTH: 15
<212> TYPE: PRT
<213> ORGANISM: Juglans nigra
```

<400> SEQUENCE: 495

Gly Gln Val Arg Glu Tyr Tyr Ala Ala Gly Ala Lys Ser Pro Asp
1               5                   10                  15

<210> SEQ ID NO 496
<211> LENGTH: 15
<212> TYPE: PRT
<213> ORGANISM: Juglans nigra

<400> SEQUENCE: 496

Gln Ser Tyr Leu Arg Val Phe Ser Asn Asp Ile Leu Val Ala Ala
1               5                   10                  15

<210> SEQ ID NO 497
<211> LENGTH: 15
<212> TYPE: PRT
<213> ORGANISM: Juglans nigra

<400> SEQUENCE: 497

Val Phe Ser Asn Asp Ile Leu Val Ala Ala Leu Asn Thr Pro Arg
1               5                   10                  15

<210> SEQ ID NO 498
<211> LENGTH: 15
<212> TYPE: PRT
<213> ORGANISM: Juglans nigra

<400> SEQUENCE: 498

Leu Gln Glu Met Asp Val Leu Val Asn Tyr Ala Glu Ile Lys Arg
1               5                   10                  15

<210> SEQ ID NO 499
<211> LENGTH: 15
<212> TYPE: PRT
<213> ORGANISM: Juglans nigra

<400> SEQUENCE: 499

Thr Gly Arg Phe Gln Lys Val Thr Ala Arg Leu Ala Arg Gly Asp
1               5                   10                  15

<210> SEQ ID NO 500
<211> LENGTH: 15
<212> TYPE: PRT
<213> ORGANISM: Juglans nigra

<400> SEQUENCE: 500

Ile Phe Val Ile Pro Ala Gly His Pro Ile Ala Ile Thr Ala Ser
1               5                   10                  15

<210> SEQ ID NO 501
<211> LENGTH: 15
<212> TYPE: PRT
<213> ORGANISM: Juglans nigra

<400> SEQUENCE: 501

Asn Asn Gln Arg Asn Phe Leu Ala Gly Gln Asn Ser Ile Ile Asn
1               5                   10                  15

<210> SEQ ID NO 502
<211> LENGTH: 15
<212> TYPE: PRT
<213> ORGANISM: Juglans nigra

<400> SEQUENCE: 502

```
Phe Leu Ala Gly Gln Asn Ser Ile Ile Asn Gln Leu Glu Arg Glu
1               5                   10                  15

<210> SEQ ID NO 503
<211> LENGTH: 15
<212> TYPE: PRT
<213> ORGANISM: Juglans nigra

<400> SEQUENCE: 503

Ile Phe Glu Ser Gln Met Glu Ser Tyr Phe Val Pro Thr Glu Arg
1               5                   10                  15

<210> SEQ ID NO 504
<211> LENGTH: 15
<212> TYPE: PRT
<213> ORGANISM: Phalaris aquatica

<400> SEQUENCE: 504

Met Met Lys Met Val Cys Ser Ser Ser Ser Ser Leu Leu Val
1               5                   10                  15

<210> SEQ ID NO 505
<211> LENGTH: 15
<212> TYPE: PRT
<213> ORGANISM: Phalaris aquatica

<400> SEQUENCE: 505

Ser Ser Leu Leu Val Val Ala Ala Leu Leu Ala Val Phe Val Gly
1               5                   10                  15

<210> SEQ ID NO 506
<211> LENGTH: 15
<212> TYPE: PRT
<213> ORGANISM: Phalaris aquatica

<400> SEQUENCE: 506

Val Ala Ala Leu Leu Ala Val Phe Val Gly Ser Ala Gln Gly Ile
1               5                   10                  15

<210> SEQ ID NO 507
<211> LENGTH: 15
<212> TYPE: PRT
<213> ORGANISM: Phalaris aquatica

<400> SEQUENCE: 507

Glu Glu Pro Ile Ala Pro Tyr His Phe Asp Leu Ser Gly His Ala
1               5                   10                  15

<210> SEQ ID NO 508
<211> LENGTH: 15
<212> TYPE: PRT
<213> ORGANISM: Phalaris aquatica

<400> SEQUENCE: 508

Pro Asn Tyr Leu Ala Leu Leu Val Lys Tyr Val Asp Gly Asp Gly
1               5                   10                  15

<210> SEQ ID NO 509
<211> LENGTH: 15
<212> TYPE: PRT
<213> ORGANISM: Phalaris aquatica

<400> SEQUENCE: 509

Ser Trp Gly Ala Ile Trp Arg Ile Asp Thr Pro Asp Lys Leu Thr
```

<210> SEQ ID NO 510
<211> LENGTH: 15
<212> TYPE: PRT
<213> ORGANISM: Phalaris aquatica

<400> SEQUENCE: 510

Met Ala Val Gln Lys Tyr Thr Met Ala Leu Phe Leu Ala Val Ala
1               5                   10                  15

<210> SEQ ID NO 511
<211> LENGTH: 15
<212> TYPE: PRT
<213> ORGANISM: Phalaris aquatica

<400> SEQUENCE: 511

Tyr Thr Met Ala Leu Phe Leu Ala Val Ala Leu Val Ala Gly Pro
1               5                   10                  15

<210> SEQ ID NO 512
<211> LENGTH: 15
<212> TYPE: PRT
<213> ORGANISM: Phalaris aquatica

<400> SEQUENCE: 512

Phe Leu Ala Val Ala Leu Val Ala Gly Pro Ala Ala Pro Thr Pro
1               5                   10                  15

<210> SEQ ID NO 513
<211> LENGTH: 15
<212> TYPE: PRT
<213> ORGANISM: Phalaris aquatica

<400> SEQUENCE: 513

Asp Ala Ala Tyr Arg Val Ala Tyr Glu Ala Ala Glu Gly Ser Thr
1               5                   10                  15

<210> SEQ ID NO 514
<211> LENGTH: 15
<212> TYPE: PRT
<213> ORGANISM: Phalaris aquatica

<400> SEQUENCE: 514

Pro Glu Ala Lys Tyr Asp Ala Phe Ile Ala Ala Leu Thr Glu Ala
1               5                   10                  15

<210> SEQ ID NO 515
<211> LENGTH: 15
<212> TYPE: PRT
<213> ORGANISM: Phalaris aquatica

<400> SEQUENCE: 515

Asp Ala Phe Ile Ala Ala Leu Thr Glu Ala Leu Arg Val Ile Ala
1               5                   10                  15

<210> SEQ ID NO 516
<211> LENGTH: 15
<212> TYPE: PRT
<213> ORGANISM: Phalaris aquatica

<400> SEQUENCE: 516

Ala Leu Thr Glu Ala Leu Arg Val Ile Ala Gly Ala Phe Glu Val
1               5                   10                  15

<210> SEQ ID NO 517
<211> LENGTH: 15
<212> TYPE: PRT
<213> ORGANISM: Phalaris aquatica

<400> SEQUENCE: 517

Val Asp Lys Ile Asp Ala Ala Phe Lys Ile Ala Ala Thr Ala Ala
1               5                   10                  15

<210> SEQ ID NO 518
<211> LENGTH: 15
<212> TYPE: PRT
<213> ORGANISM: Phalaris aquatica

<400> SEQUENCE: 518

Ala Ala Phe Lys Ile Ala Ala Thr Ala Ala Asn Ser Ala Pro Ala
1               5                   10                  15

<210> SEQ ID NO 519
<211> LENGTH: 15
<212> TYPE: PRT
<213> ORGANISM: Phalaris aquatica

<400> SEQUENCE: 519

Asn Asp Lys Phe Thr Val Phe Glu Gly Ala Phe Asn Lys Ala Ile
1               5                   10                  15

<210> SEQ ID NO 520
<211> LENGTH: 15
<212> TYPE: PRT
<213> ORGANISM: Phalaris aquatica

<400> SEQUENCE: 520

Gly Ala Tyr Glu Thr Tyr Lys Phe Ile Pro Ser Leu Glu Ala Ala
1               5                   10                  15

<210> SEQ ID NO 521
<211> LENGTH: 15
<212> TYPE: PRT
<213> ORGANISM: Phalaris aquatica

<400> SEQUENCE: 521

Tyr Lys Phe Ile Pro Ser Leu Glu Ala Ala Val Lys Gln Ala Tyr
1               5                   10                  15

<210> SEQ ID NO 522
<211> LENGTH: 15
<212> TYPE: PRT
<213> ORGANISM: Phalaris aquatica

<400> SEQUENCE: 522

Val Lys Gln Ala Tyr Gly Ala Thr Val Ala Arg Ala Pro Glu Val
1               5                   10                  15

<210> SEQ ID NO 523
<211> LENGTH: 15
<212> TYPE: PRT
<213> ORGANISM: Phalaris aquatica

<400> SEQUENCE: 523

Arg Ala Pro Glu Val Lys Tyr Ala Val Phe Glu Ala Gly Leu Thr
1               5                   10                  15

<210> SEQ ID NO 524

```
<211> LENGTH: 15
<212> TYPE: PRT
<213> ORGANISM: Felis catus

<400> SEQUENCE: 524

Met Lys Gly Ala Cys Val Leu Val Leu Leu Trp Ala Ala Leu Leu
1               5                   10                  15

<210> SEQ ID NO 525
<211> LENGTH: 15
<212> TYPE: PRT
<213> ORGANISM: Felis catus

<400> SEQUENCE: 525

Val Leu Val Leu Leu Trp Ala Ala Leu Leu Leu Ile Ser Gly Gly
1               5                   10                  15

<210> SEQ ID NO 526
<211> LENGTH: 15
<212> TYPE: PRT
<213> ORGANISM: Felis catus

<400> SEQUENCE: 526

Asp Glu Tyr Val Glu Gln Val Ala Gln Tyr Lys Ala Leu Pro Val
1               5                   10                  15

<210> SEQ ID NO 527
<211> LENGTH: 15
<212> TYPE: PRT
<213> ORGANISM: Felis catus

<400> SEQUENCE: 527

Gln Val Ala Gln Tyr Lys Ala Leu Pro Val Val Leu Glu Asn Ala
1               5                   10                  15

<210> SEQ ID NO 528
<211> LENGTH: 15
<212> TYPE: PRT
<213> ORGANISM: Felis catus

<400> SEQUENCE: 528

Lys Ala Leu Pro Val Val Leu Glu Asn Ala Arg Ile Leu Lys Asn
1               5                   10                  15

<210> SEQ ID NO 529
<211> LENGTH: 15
<212> TYPE: PRT
<213> ORGANISM: Felis catus

<400> SEQUENCE: 529

Asn Ala Leu Ser Val Leu Asp Lys Ile Tyr Thr Ser Pro Leu Cys
1               5                   10                  15

<210> SEQ ID NO 530
<211> LENGTH: 15
<212> TYPE: PRT
<213> ORGANISM: Felis catus

<400> SEQUENCE: 530

Met Arg Gly Ala Leu Leu Val Leu Ala Leu Leu Val Thr Gln Ala
1               5                   10                  15

<210> SEQ ID NO 531
<211> LENGTH: 15
<212> TYPE: PRT
```

<213> ORGANISM: Felis catus

<400> SEQUENCE: 531

Leu Val Leu Ala Leu Leu Val Thr Gln Ala Leu Gly Val Lys Met
1               5                   10                  15

<210> SEQ ID NO 532
<211> LENGTH: 15
<212> TYPE: PRT
<213> ORGANISM: Felis catus

<400> SEQUENCE: 532

Ala Glu Thr Cys Pro Ile Phe Tyr Asp Val Phe Phe Ala Val Ala
1               5                   10                  15

<210> SEQ ID NO 533
<211> LENGTH: 15
<212> TYPE: PRT
<213> ORGANISM: Felis catus

<400> SEQUENCE: 533

Ile Phe Tyr Asp Val Phe Phe Ala Val Ala Asn Gly Asn Glu Leu
1               5                   10                  15

<210> SEQ ID NO 534
<211> LENGTH: 15
<212> TYPE: PRT
<213> ORGANISM: Felis catus

<400> SEQUENCE: 534

Asn Gly Asn Glu Leu Leu Leu Asp Leu Ser Leu Thr Lys Val Asn
1               5                   10                  15

<210> SEQ ID NO 535
<211> LENGTH: 15
<212> TYPE: PRT
<213> ORGANISM: Felis catus

<400> SEQUENCE: 535

Tyr Val Glu Asn Gly Leu Ile Ser Arg Val Leu Asp Gly Leu Val
1               5                   10                  15

<210> SEQ ID NO 536
<211> LENGTH: 15
<212> TYPE: PRT
<213> ORGANISM: Felis catus

<400> SEQUENCE: 536

Met Lys Trp Val Thr Phe Ile Ser Leu Leu Leu Leu Phe Ser Ser
1               5                   10                  15

<210> SEQ ID NO 537
<211> LENGTH: 15
<212> TYPE: PRT
<213> ORGANISM: Felis catus

<400> SEQUENCE: 537

Phe Ile Ser Leu Leu Leu Leu Phe Ser Ser Ala Tyr Ser Arg Gly
1               5                   10                  15

<210> SEQ ID NO 538
<211> LENGTH: 15
<212> TYPE: PRT
<213> ORGANISM: Felis catus

```
<400> SEQUENCE: 538

Glu His Phe Arg Gly Leu Val Leu Val Ala Phe Ser Gln Tyr Leu
1               5                   10                  15

<210> SEQ ID NO 539
<211> LENGTH: 15
<212> TYPE: PRT
<213> ORGANISM: Felis catus

<400> SEQUENCE: 539

Leu Val Leu Val Ala Phe Ser Gln Tyr Leu Gln Gln Cys Pro Phe
1               5                   10                  15

<210> SEQ ID NO 540
<211> LENGTH: 15
<212> TYPE: PRT
<213> ORGANISM: Felis catus

<400> SEQUENCE: 540

Glu Asp His Val Lys Leu Val Asn Glu Val Thr Glu Phe Ala Lys
1               5                   10                  15

<210> SEQ ID NO 541
<211> LENGTH: 15
<212> TYPE: PRT
<213> ORGANISM: Felis catus

<400> SEQUENCE: 541

Gln Arg Phe Leu Gly Lys Tyr Leu Tyr Glu Ile Ala Arg Arg His
1               5                   10                  15

<210> SEQ ID NO 542
<211> LENGTH: 15
<212> TYPE: PRT
<213> ORGANISM: Felis catus

<400> SEQUENCE: 542

Lys Tyr Leu Tyr Glu Ile Ala Arg Arg His Pro Tyr Phe Tyr Ala
1               5                   10                  15

<210> SEQ ID NO 543
<211> LENGTH: 15
<212> TYPE: PRT
<213> ORGANISM: Felis catus

<400> SEQUENCE: 543

Ile Ala Arg Arg His Pro Tyr Phe Tyr Ala Pro Glu Leu Leu Tyr
1               5                   10                  15

<210> SEQ ID NO 544
<211> LENGTH: 15
<212> TYPE: PRT
<213> ORGANISM: Felis catus

<400> SEQUENCE: 544

Pro Tyr Phe Tyr Ala Pro Glu Leu Leu Tyr Tyr Ala Glu Glu Tyr
1               5                   10                  15

<210> SEQ ID NO 545
<211> LENGTH: 15
<212> TYPE: PRT
<213> ORGANISM: Felis catus

<400> SEQUENCE: 545
```

Gly Glu Arg Ala Phe Lys Ala Trp Ser Val Ala Arg Leu Ser Gln
1               5                   10                  15

<210> SEQ ID NO 546
<211> LENGTH: 15
<212> TYPE: PRT
<213> ORGANISM: Felis catus

<400> SEQUENCE: 546

Lys Phe Pro Lys Ala Glu Phe Ala Glu Ile Ser Lys Leu Val Thr
1               5                   10                  15

<210> SEQ ID NO 547
<211> LENGTH: 15
<212> TYPE: PRT
<213> ORGANISM: Felis catus

<400> SEQUENCE: 547

Ala Lys Asp Val Phe Leu Gly Thr Phe Leu Tyr Glu Tyr Ser Arg
1               5                   10                  15

<210> SEQ ID NO 548
<211> LENGTH: 15
<212> TYPE: PRT
<213> ORGANISM: Felis catus

<400> SEQUENCE: 548

Leu Gly Thr Phe Leu Tyr Glu Tyr Ser Arg Arg His Pro Glu Tyr
1               5                   10                  15

<210> SEQ ID NO 549
<211> LENGTH: 15
<212> TYPE: PRT
<213> ORGANISM: Felis catus

<400> SEQUENCE: 549

Arg His Pro Glu Tyr Ser Val Ser Leu Leu Arg Leu Ala Lys
1               5                   10                  15

<210> SEQ ID NO 550
<211> LENGTH: 15
<212> TYPE: PRT
<213> ORGANISM: Felis catus

<400> SEQUENCE: 550

Ser Val Ser Leu Leu Leu Arg Leu Ala Lys Glu Tyr Glu Ala Thr
1               5                   10                  15

<210> SEQ ID NO 551
<211> LENGTH: 15
<212> TYPE: PRT
<213> ORGANISM: Felis catus

<400> SEQUENCE: 551

His Val Phe Asp Glu Phe Lys Pro Leu Val Glu Glu Pro His Asn
1               5                   10                  15

<210> SEQ ID NO 552
<211> LENGTH: 15
<212> TYPE: PRT
<213> ORGANISM: Felis catus

<400> SEQUENCE: 552

Lys Leu Gly Glu Tyr Gly Phe Gln Asn Ala Leu Leu Val Arg Tyr
1               5                   10                  15

```
<210> SEQ ID NO 553
<211> LENGTH: 15
<212> TYPE: PRT
<213> ORGANISM: Felis catus

<400> SEQUENCE: 553

Gly Phe Gln Asn Ala Leu Leu Val Arg Tyr Thr Lys Lys Val Pro
1               5                   10                  15

<210> SEQ ID NO 554
<211> LENGTH: 15
<212> TYPE: PRT
<213> ORGANISM: Felis catus

<400> SEQUENCE: 554

Ser Cys Ala Glu Asp Tyr Leu Ser Val Val Leu Asn Arg Leu Cys
1               5                   10                  15

<210> SEQ ID NO 555
<211> LENGTH: 15
<212> TYPE: PRT
<213> ORGANISM: Felis catus

<400> SEQUENCE: 555

Tyr Leu Ser Val Val Leu Asn Arg Leu Cys Val Leu His Glu Lys
1               5                   10                  15

<210> SEQ ID NO 556
<211> LENGTH: 15
<212> TYPE: PRT
<213> ORGANISM: Felis catus

<400> SEQUENCE: 556

Val Asn Arg Arg Pro Cys Phe Ser Ala Leu Gln Val Asp Glu Thr
1               5                   10                  15

<210> SEQ ID NO 557
<211> LENGTH: 15
<212> TYPE: PRT
<213> ORGANISM: Felis catus

<400> SEQUENCE: 557

Phe Thr Phe His Ala Asp Leu Cys Thr Leu Pro Glu Ala Glu Lys
1               5                   10                  15

<210> SEQ ID NO 558
<211> LENGTH: 15
<212> TYPE: PRT
<213> ORGANISM: Felis catus

<400> SEQUENCE: 558

Gln Ile Lys Lys Gln Ser Ala Leu Val Glu Leu Leu Lys His Lys
1               5                   10                  15

<210> SEQ ID NO 559
<211> LENGTH: 15
<212> TYPE: PRT
<213> ORGANISM: Felis catus

<400> SEQUENCE: 559

Glu Glu Gly Pro Lys Leu Val Ala Ala Ala Gln Ala Ala Leu Ala
1               5                   10                  15
```

<210> SEQ ID NO 560
<211> LENGTH: 15
<212> TYPE: PRT
<213> ORGANISM: Felis catus

<400> SEQUENCE: 560

Thr Asn Glu Thr Tyr Gln Lys Phe Glu Ala Ile Glu Tyr Lys Thr
1               5                   10                  15

<210> SEQ ID NO 561
<211> LENGTH: 15
<212> TYPE: PRT
<213> ORGANISM: Felis catus

<400> SEQUENCE: 561

Ile Glu Tyr Lys Thr Gln Val Val Ala Gly Ile Asn Tyr Tyr Ile
1               5                   10                  15

<210> SEQ ID NO 562
<211> LENGTH: 15
<212> TYPE: PRT
<213> ORGANISM: Felis catus

<400> SEQUENCE: 562

Gln Val Val Ala Gly Ile Asn Tyr Tyr Ile Lys Val Gln Val Asp
1               5                   10                  15

<210> SEQ ID NO 563
<211> LENGTH: 15
<212> TYPE: PRT
<213> ORGANISM: Felis catus

<400> SEQUENCE: 563

Ile Asn Tyr Tyr Ile Lys Val Gln Val Asp Asp Asn Arg Tyr Ile
1               5                   10                  15

<210> SEQ ID NO 564
<211> LENGTH: 15
<212> TYPE: PRT
<213> ORGANISM: Felis catus

<400> SEQUENCE: 564

Asp Asn Arg Tyr Ile His Ile Lys Val Phe Lys Gly Leu Pro Val
1               5                   10                  15

<210> SEQ ID NO 565
<211> LENGTH: 15
<212> TYPE: PRT
<213> ORGANISM: Felis catus

<400> SEQUENCE: 565

His Ile Lys Val Phe Lys Gly Leu Pro Val Gln Asp Ser Ser Leu
1               5                   10                  15

<210> SEQ ID NO 566
<211> LENGTH: 15
<212> TYPE: PRT
<213> ORGANISM: Felis catus

<400> SEQUENCE: 566

Met Lys Leu Leu Leu Leu Cys Leu Gly Leu Ile Leu Val Cys Ala
1               5                   10                  15

<210> SEQ ID NO 567
<211> LENGTH: 15

<212> TYPE: PRT
<213> ORGANISM: Felis catus

<400> SEQUENCE: 567

Ile Ser Gly Glu Trp Tyr Ser Ile Leu Leu Ala Ser Asp Val Lys
1               5                   10                  15

<210> SEQ ID NO 568
<211> LENGTH: 15
<212> TYPE: PRT
<213> ORGANISM: Felis catus

<400> SEQUENCE: 568

Tyr Ser Ile Leu Leu Ala Ser Asp Val Lys Glu Lys Ile Glu Glu
1               5                   10                  15

<210> SEQ ID NO 569
<211> LENGTH: 15
<212> TYPE: PRT
<213> ORGANISM: Felis catus

<400> SEQUENCE: 569

Asn Gly Ser Met Arg Val Phe Val Glu His Ile Lys Ala Leu Asp
1               5                   10                  15

<210> SEQ ID NO 570
<211> LENGTH: 15
<212> TYPE: PRT
<213> ORGANISM: Felis catus

<400> SEQUENCE: 570

Val Phe Val Glu His Ile Lys Ala Leu Asp Asn Ser Ser Leu Ser
1               5                   10                  15

<210> SEQ ID NO 571
<211> LENGTH: 15
<212> TYPE: PRT
<213> ORGANISM: Felis catus

<400> SEQUENCE: 571

Ile Lys Ala Leu Asp Asn Ser Ser Leu Ser Phe Val Phe His Thr
1               5                   10                  15

<210> SEQ ID NO 572
<211> LENGTH: 15
<212> TYPE: PRT
<213> ORGANISM: Felis catus

<400> SEQUENCE: 572

Tyr Thr Val Val Tyr Asp Gly Tyr Asn Val Phe Ser Ile Val Glu
1               5                   10                  15

<210> SEQ ID NO 573
<211> LENGTH: 15
<212> TYPE: PRT
<213> ORGANISM: Felis catus

<400> SEQUENCE: 573

Asp Gly Tyr Asn Val Phe Ser Ile Val Glu Thr Val Tyr Asp Glu
1               5                   10                  15

<210> SEQ ID NO 574
<211> LENGTH: 15
<212> TYPE: PRT
<213> ORGANISM: Felis catus

<400> SEQUENCE: 574

Phe Ser Ile Val Glu Thr Val Tyr Asp Glu Tyr Ile Leu Leu His
1               5                   10                  15

<210> SEQ ID NO 575
<211> LENGTH: 15
<212> TYPE: PRT
<213> ORGANISM: Felis catus

<400> SEQUENCE: 575

Thr Val Tyr Asp Glu Tyr Ile Leu Leu His Leu Leu Asn Phe Asp
1               5                   10                  15

<210> SEQ ID NO 576
<211> LENGTH: 15
<212> TYPE: PRT
<213> ORGANISM: Felis catus

<400> SEQUENCE: 576

Tyr Ile Leu Leu His Leu Leu Asn Phe Asp Lys Thr Arg Pro Phe
1               5                   10                  15

<210> SEQ ID NO 577
<211> LENGTH: 15
<212> TYPE: PRT
<213> ORGANISM: Felis catus

<400> SEQUENCE: 577

Leu Leu Asn Phe Asp Lys Thr Arg Pro Phe Gln Leu Val Glu Phe
1               5                   10                  15

<210> SEQ ID NO 578
<211> LENGTH: 15
<212> TYPE: PRT
<213> ORGANISM: Felis catus

<400> SEQUENCE: 578

Lys Thr Arg Pro Phe Gln Leu Val Glu Phe Tyr Ala Arg Glu Pro
1               5                   10                  15

<210> SEQ ID NO 579
<211> LENGTH: 15
<212> TYPE: PRT
<213> ORGANISM: Cladosporium herbarum

<400> SEQUENCE: 579

Gln Pro Thr Gly Leu Phe Ile Asn Asn Glu Phe Val Lys Gly Gln
1               5                   10                  15

<210> SEQ ID NO 580
<211> LENGTH: 15
<212> TYPE: PRT
<213> ORGANISM: Cladosporium herbarum

<400> SEQUENCE: 580

Asp Val Asp Ile Ala Val Ala Ala Ala Arg Lys Ala Phe Glu Gly
1               5                   10                  15

<210> SEQ ID NO 581
<211> LENGTH: 15
<212> TYPE: PRT
<213> ORGANISM: Cladosporium herbarum

<400> SEQUENCE: 581

Gly Lys Leu Leu Asn Asn Leu Ala Asn Leu Phe Glu Lys Asn Ile
1               5                   10                  15

<210> SEQ ID NO 582
<211> LENGTH: 15
<212> TYPE: PRT
<213> ORGANISM: Cladosporium herbarum

<400> SEQUENCE: 582

Asn Leu Ala Asn Leu Phe Glu Lys Asn Ile Asp Leu Leu Ala Ala
1               5                   10                  15

<210> SEQ ID NO 583
<211> LENGTH: 15
<212> TYPE: PRT
<213> ORGANISM: Cladosporium herbarum

<400> SEQUENCE: 583

Phe Glu Lys Asn Ile Asp Leu Leu Ala Ala Val Glu Ser Leu Asp
1               5                   10                  15

<210> SEQ ID NO 584
<211> LENGTH: 15
<212> TYPE: PRT
<213> ORGANISM: Cladosporium herbarum

<400> SEQUENCE: 584

Pro Leu Leu Met Trp Ala Trp Lys Ile Gly Pro Ala Ile Ala Cys
1               5                   10                  15

<210> SEQ ID NO 585
<211> LENGTH: 15
<212> TYPE: PRT
<213> ORGANISM: Cladosporium herbarum

<400> SEQUENCE: 585

Gln Thr Pro Leu Gly Gly Leu Val Ala Ala Ser Leu Val Lys Glu
1               5                   10                  15

<210> SEQ ID NO 586
<211> LENGTH: 15
<212> TYPE: PRT
<213> ORGANISM: Cladosporium herbarum

<400> SEQUENCE: 586

Arg Thr Ile Leu Lys Ala Ala Ala Ser Ser Asn Leu Lys Lys Val
1               5                   10                  15

<210> SEQ ID NO 587
<211> LENGTH: 15
<212> TYPE: PRT
<213> ORGANISM: Cladosporium herbarum

<400> SEQUENCE: 587

Ala Ile Ser Trp Val Asn Phe Gly Ile Phe Phe Asn His Gly Gln
1               5                   10                  15

<210> SEQ ID NO 588
<211> LENGTH: 15
<212> TYPE: PRT
<213> ORGANISM: Cladosporium herbarum

<400> SEQUENCE: 588

Ser Lys Val Gln Phe Asp Arg Ile Met Glu Tyr Ile Gln Ala Gly

```
1               5                  10                  15
```

<210> SEQ ID NO 589
<211> LENGTH: 15
<212> TYPE: PRT
<213> ORGANISM: Cladosporium herbarum

<400> SEQUENCE: 589

```
Asp Lys Gly Tyr Phe Ile Glu Pro Thr Ile Phe Ser Asn Val Thr
1               5                  10                  15
```

<210> SEQ ID NO 590
<211> LENGTH: 15
<212> TYPE: PRT
<213> ORGANISM: Cladosporium herbarum

<400> SEQUENCE: 590

```
Glu Asp Met Lys Ile Val Lys Glu Glu Ile Phe Gly Pro Val Cys
1               5                  10                  15
```

<210> SEQ ID NO 591
<211> LENGTH: 15
<212> TYPE: PRT
<213> ORGANISM: Cladosporium herbarum

<400> SEQUENCE: 591

```
Asn Ala Ser Thr Tyr Gly Leu Ala Ala Ala Val His Thr Lys Asn
1               5                  10                  15
```

<210> SEQ ID NO 592
<211> LENGTH: 15
<212> TYPE: PRT
<213> ORGANISM: Cladosporium herbarum

<400> SEQUENCE: 592

```
Leu Asn Thr Ala Ile Glu Val Ser Asn Ala Leu Lys Ala Gly Thr
1               5                  10                  15
```

<210> SEQ ID NO 593
<211> LENGTH: 15
<212> TYPE: PRT
<213> ORGANISM: Cladosporium herbarum

<400> SEQUENCE: 593

```
Leu Lys Ala Gly Thr Val Trp Val Asn Thr Tyr Asn Thr Leu His
1               5                  10                  15
```

<210> SEQ ID NO 594
<211> LENGTH: 15
<212> TYPE: PRT
<213> ORGANISM: Cladosporium herbarum

<400> SEQUENCE: 594

```
Met Ser Ala Ala Glu Leu Ala Ser Ser Tyr Ala Ala Leu Ile Leu
1               5                  10                  15
```

<210> SEQ ID NO 595
<211> LENGTH: 15
<212> TYPE: PRT
<213> ORGANISM: Cladosporium herbarum

<400> SEQUENCE: 595

```
Leu Ala Ser Ser Tyr Ala Ala Leu Ile Leu Ala Asp Glu Gly Leu
1               5                  10                  15
```

<210> SEQ ID NO 596
<211> LENGTH: 15
<212> TYPE: PRT
<213> ORGANISM: Cladosporium herbarum

<400> SEQUENCE: 596

Glu Ile Thr Ala Asp Lys Leu Gln Ala Leu Ile Ser Ala Ala Lys
1               5                   10                  15

<210> SEQ ID NO 597
<211> LENGTH: 15
<212> TYPE: PRT
<213> ORGANISM: Cladosporium herbarum

<400> SEQUENCE: 597

Lys Leu Gln Ala Leu Ile Ser Ala Ala Lys Val Pro Glu Ile Glu
1               5                   10                  15

<210> SEQ ID NO 598
<211> LENGTH: 15
<212> TYPE: PRT
<213> ORGANISM: Cladosporium herbarum

<400> SEQUENCE: 598

Val Pro Glu Ile Glu Pro Ile Trp Thr Ser Leu Phe Ala Lys Ala
1               5                   10                  15

<210> SEQ ID NO 599
<211> LENGTH: 15
<212> TYPE: PRT
<213> ORGANISM: Cladosporium herbarum

<400> SEQUENCE: 599

Pro Ile Trp Thr Ser Leu Phe Ala Lys Ala Leu Glu Gly Lys Asp
1               5                   10                  15

<210> SEQ ID NO 600
<211> LENGTH: 15
<212> TYPE: PRT
<213> ORGANISM: Cladosporium herbarum

<400> SEQUENCE: 600

Met Lys Tyr Leu Ala Ala Phe Leu Leu Leu Gly Leu Ala Gly Asn
1               5                   10                  15

<210> SEQ ID NO 601
<211> LENGTH: 15
<212> TYPE: PRT
<213> ORGANISM: Cladosporium herbarum

<400> SEQUENCE: 601

Ala Phe Leu Leu Leu Gly Leu Ala Gly Asn Ser Ser Pro Ser Ala
1               5                   10                  15

<210> SEQ ID NO 602
<211> LENGTH: 15
<212> TYPE: PRT
<213> ORGANISM: Cladosporium herbarum

<400> SEQUENCE: 602

Glu Asp Ile Lys Thr Val Leu Ser Ser Val Gly Ile Asp Ala Asp
1               5                   10                  15

<210> SEQ ID NO 603

```
<211> LENGTH: 15
<212> TYPE: PRT
<213> ORGANISM: Cladosporium herbarum

<400> SEQUENCE: 603

Leu Glu Gly Lys Asp Ile Asn Glu Leu Ile Ser Ser Gly Ser Glu
1               5                   10                  15

<210> SEQ ID NO 604
<211> LENGTH: 15
<212> TYPE: PRT
<213> ORGANISM: Cladosporium herbarum

<400> SEQUENCE: 604

Ile Asn Glu Leu Ile Ser Ser Gly Ser Glu Lys Leu Ala Ser Val
1               5                   10                  15

<210> SEQ ID NO 605
<211> LENGTH: 15
<212> TYPE: PRT
<213> ORGANISM: Cladosporium herbarum

<400> SEQUENCE: 605

Met Pro Ile Ser Lys Ile His Ser Arg Tyr Val Tyr Asp Ser Arg
1               5                   10                  15

<210> SEQ ID NO 606
<211> LENGTH: 15
<212> TYPE: PRT
<213> ORGANISM: Cladosporium herbarum

<400> SEQUENCE: 606

Val Ala Asn Val Asn Glu Ile Ile Ala Pro Ala Leu Ile Lys Glu
1               5                   10                  15

<210> SEQ ID NO 607
<211> LENGTH: 15
<212> TYPE: PRT
<213> ORGANISM: Cladosporium herbarum

<400> SEQUENCE: 607

Ile Gly Ala Asn Ala Ile Leu Gly Val Ser Met Ala Val Ala Lys
1               5                   10                  15

<210> SEQ ID NO 608
<211> LENGTH: 15
<212> TYPE: PRT
<213> ORGANISM: Cladosporium herbarum

<400> SEQUENCE: 608

Ile Leu Gly Val Ser Met Ala Val Ala Lys Ala Ala Ala Ala Glu
1               5                   10                  15

<210> SEQ ID NO 609
<211> LENGTH: 15
<212> TYPE: PRT
<213> ORGANISM: Cladosporium herbarum

<400> SEQUENCE: 609

Lys Arg Val Pro Leu Tyr Ala His Ile Ser Asp Leu Ser Gly Thr
1               5                   10                  15

<210> SEQ ID NO 610
<211> LENGTH: 15
<212> TYPE: PRT
```

-continued

<213> ORGANISM: Cladosporium herbarum

<400> SEQUENCE: 610

Gly Gly Arg Leu Ala Phe Gln Glu Phe Met Ile Val Pro Ser Gly
1               5                   10                  15

<210> SEQ ID NO 611
<211> LENGTH: 15
<212> TYPE: PRT
<213> ORGANISM: Cladosporium herbarum

<400> SEQUENCE: 611

Phe Gln Glu Phe Met Ile Val Pro Ser Gly Ala Pro Ser Phe Thr
1               5                   10                  15

<210> SEQ ID NO 612
<211> LENGTH: 15
<212> TYPE: PRT
<213> ORGANISM: Cladosporium herbarum

<400> SEQUENCE: 612

Gly Ala Glu Val Tyr Gln Lys Leu Lys Ser Leu Thr Lys Lys Arg
1               5                   10                  15

<210> SEQ ID NO 613
<211> LENGTH: 15
<212> TYPE: PRT
<213> ORGANISM: Cladosporium herbarum

<400> SEQUENCE: 613

Ile Lys Ile Ala Met Asp Val Ala Ser Ser Glu Phe Tyr Lys Ala
1               5                   10                  15

<210> SEQ ID NO 614
<211> LENGTH: 15
<212> TYPE: PRT
<213> ORGANISM: Cladosporium herbarum

<400> SEQUENCE: 614

Lys Ser Lys Trp Ile Thr Tyr Glu Gln Leu Ala Asp Gln Tyr Lys
1               5                   10                  15

<210> SEQ ID NO 615
<211> LENGTH: 15
<212> TYPE: PRT
<213> ORGANISM: Cladosporium herbarum

<400> SEQUENCE: 615

Ala Asp Gln Tyr Lys Gln Leu Ala Ala Lys Tyr Pro Ile Val Ser
1               5                   10                  15

<210> SEQ ID NO 616
<211> LENGTH: 15
<212> TYPE: PRT
<213> ORGANISM: Cladosporium herbarum

<400> SEQUENCE: 616

Glu Ala Trp Ser Tyr Phe Tyr Lys Thr Ser Gly Ser Asp Phe Gln
1               5                   10                  15

<210> SEQ ID NO 617
<211> LENGTH: 15
<212> TYPE: PRT
<213> ORGANISM: Cladosporium herbarum

<400> SEQUENCE: 617

Lys Ala Cys Asn Ala Leu Leu Leu Lys Val Asn Gln Ile Gly Thr
1               5                   10                  15

<210> SEQ ID NO 618
<211> LENGTH: 15
<212> TYPE: PRT
<213> ORGANISM: Cladosporium herbarum

<400> SEQUENCE: 618

Leu Leu Leu Lys Val Asn Gln Ile Gly Thr Ile Thr Glu Ala Ile
1               5                   10                  15

<210> SEQ ID NO 619
<211> LENGTH: 15
<212> TYPE: PRT
<213> ORGANISM: Cladosporium herbarum

<400> SEQUENCE: 619

Ser Phe Ala Ala Gly Trp Gly Val Met Val Ser His Arg Ser Gly
1 5 10 15

<210> SEQ ID NO 620
<211> LENGTH: 15
<212> TYPE: PRT
<213> ORGANISM: Cladosporium herbarum

<400> SEQUENCE: 620

Thr Ile Ala Asp Ile Val Val Gly Leu Arg Ala Gly Gln Ile Lys
1 5 10 15

<210> SEQ ID NO 621
<211> LENGTH: 15
<212> TYPE: PRT
<213> ORGANISM: Cladosporium herbarum

<400> SEQUENCE: 621

Ala Lys Leu Asn Gln Ile Leu Arg Ile Glu Glu Glu Leu Gly Asp
1 5 10 15

<210> SEQ ID NO 622
<211> LENGTH: 15
<212> TYPE: PRT
<213> ORGANISM: Cladosporium herbarum

<400> SEQUENCE: 622

Met Ala Pro Lys Ile Ala Ile Ile Phe Tyr Ser Thr Trp Gly His
1 5 10 15

<210> SEQ ID NO 623
<211> LENGTH: 15
<212> TYPE: PRT
<213> ORGANISM: Cladosporium herbarum

<400> SEQUENCE: 623

Ala Met Ser Thr Leu Ser His His Gly Ile Ile Tyr Val Pro Leu
1 5 10 15

<210> SEQ ID NO 624
<211> LENGTH: 15
<212> TYPE: PRT
<213> ORGANISM: Cladosporium herbarum

<400> SEQUENCE: 624

```
Ile Tyr Val Pro Leu Gly Tyr Lys Thr Thr Phe His Leu Leu Gly
 1               5                  10                  15
```

<210> SEQ ID NO 625
<211> LENGTH: 15
<212> TYPE: PRT
<213> ORGANISM: Cladosporium herbarum

<400> SEQUENCE: 625

```
Gln Gly Lys Ala Phe Tyr Glu Ala Val Ala Lys Val Asn Phe Gln
 1               5                  10                  15
```

<210> SEQ ID NO 626
<211> LENGTH: 15
<212> TYPE: PRT
<213> ORGANISM: Cladosporium herbarum

<400> SEQUENCE: 626

```
Gly Ala Ala Val Ala Ile Thr Tyr Ala Ser Arg Ala Gln Gly Ala
 1               5                  10                  15
```

<210> SEQ ID NO 627
<211> LENGTH: 15
<212> TYPE: PRT
<213> ORGANISM: Cladosporium herbarum

<400> SEQUENCE: 627

```
Gln Ile Asp Ala Phe Ile Ala Asn Ala Gly Ala Thr Ala Asp Ser
 1               5                  10                  15
```

<210> SEQ ID NO 628
<211> LENGTH: 15
<212> TYPE: PRT
<213> ORGANISM: Cladosporium herbarum

<400> SEQUENCE: 628

```
Gly Thr Gly Ser Leu Val Ile Thr Ala Ser Met Ser Gly His Ile
 1               5                  10                  15
```

<210> SEQ ID NO 629
<211> LENGTH: 15
<212> TYPE: PRT
<213> ORGANISM: Cladosporium herbarum

<400> SEQUENCE: 629

```
Gly Cys Ile His Met Ala Arg Ser Leu Ala Asn Glu Trp Arg Asp
 1               5                  10                  15
```

<210> SEQ ID NO 630
<211> LENGTH: 15
<212> TYPE: PRT
<213> ORGANISM: Cladosporium herbarum

<400> SEQUENCE: 630

```
Lys Glu Leu Lys Gly Ala Tyr Val Tyr Phe Ala Ser Asp Ala Ser
 1               5                  10                  15
```

<210> SEQ ID NO 631
<211> LENGTH: 15
<212> TYPE: PRT
<213> ORGANISM: Cladosporium herbarum

<400> SEQUENCE: 631

```
Ala Tyr Val Tyr Phe Ala Ser Asp Ala Ser Thr Tyr Thr Thr Gly
 1               5                  10                  15
```

<210> SEQ ID NO 632
<211> LENGTH: 15
<212> TYPE: PRT
<213> ORGANISM: Chamaecyparis obtusa

<400> SEQUENCE: 632

Met Ala Ser Cys Thr Leu Leu Ala Val Leu Val Phe Leu Cys Ala
1               5                   10                  15

<210> SEQ ID NO 633
<211> LENGTH: 15
<212> TYPE: PRT
<213> ORGANISM: Chamaecyparis obtusa

<400> SEQUENCE: 633

Leu Leu Ala Val Leu Val Phe Leu Cys Ala Ile Val Ser Cys Phe
1               5                   10                  15

<210> SEQ ID NO 634
<211> LENGTH: 15
<212> TYPE: PRT
<213> ORGANISM: Chamaecyparis obtusa

<400> SEQUENCE: 634

Glu Arg Ser Leu Trp Ile Ile Phe Ser Lys Asn Leu Asn Ile Lys
1               5                   10                  15

<210> SEQ ID NO 635
<211> LENGTH: 15
<212> TYPE: PRT
<213> ORGANISM: Chamaecyparis obtusa

<400> SEQUENCE: 635

Ile Ile Phe Ser Lys Asn Leu Asn Ile Lys Leu Asn Met Pro Leu
1               5                   10                  15

<210> SEQ ID NO 636
<211> LENGTH: 15
<212> TYPE: PRT
<213> ORGANISM: Chamaecyparis obtusa

<400> SEQUENCE: 636

Asn Leu Asn Ile Lys Leu Asn Met Pro Leu Tyr Ile Ala Gly Asn
1               5                   10                  15

<210> SEQ ID NO 637
<211> LENGTH: 15
<212> TYPE: PRT
<213> ORGANISM: Chamaecyparis obtusa

<400> SEQUENCE: 637

Gly Pro Cys Leu Phe Met Arg Thr Val Ser His Val Ile Leu His
1               5                   10                  15

<210> SEQ ID NO 638
<211> LENGTH: 15
<212> TYPE: PRT
<213> ORGANISM: Chamaecyparis obtusa

<400> SEQUENCE: 638

Met Arg Thr Val Ser His Val Ile Leu His Gly Leu Asn Ile His
1               5                   10                  15

<210> SEQ ID NO 639
<211> LENGTH: 15
<212> TYPE: PRT
<213> ORGANISM: Chamaecyparis obtusa

<400> SEQUENCE: 639

Val Ser Gly Asn Val Leu Ile Ser Glu Ala Ser Gly Val Val Pro
1               5                   10                  15

<210> SEQ ID NO 640
<211> LENGTH: 15
<212> TYPE: PRT
<213> ORGANISM: Chamaecyparis obtusa

<400> SEQUENCE: 640

Leu Val Asp Val Thr Leu Ala Ser Thr Gly Val Thr Ile Ser Asn
1               5                   10                  15

<210> SEQ ID NO 641
<211> LENGTH: 15
<212> TYPE: PRT
<213> ORGANISM: Chamaecyparis obtusa

<400> SEQUENCE: 641

Asn His Phe Phe Asn His His Lys Val Met Leu Leu Gly His Ser
1               5                   10                  15

<210> SEQ ID NO 642
<211> LENGTH: 15
<212> TYPE: PRT
<213> ORGANISM: Chamaecyparis obtusa

<400> SEQUENCE: 642

Asp Lys Ser Met Lys Val Thr Val Ala Phe Asn Gln Phe Gly Pro
1               5                   10                  15

<210> SEQ ID NO 643
<211> LENGTH: 15
<212> TYPE: PRT
<213> ORGANISM: Chamaecyparis obtusa

<400> SEQUENCE: 643

Tyr Gly Leu Ile His Val Ala Asn Asn Asn Tyr Asp Pro Trp Ser
1               5                   10                  15

<210> SEQ ID NO 644
<211> LENGTH: 15
<212> TYPE: PRT
<213> ORGANISM: Chamaecyparis obtusa

<400> SEQUENCE: 644

Met Gly Met Lys Phe Met Ala Ala Val Ala Phe Leu Ala Leu Gln
1               5                   10                  15

<210> SEQ ID NO 645
<211> LENGTH: 15
<212> TYPE: PRT
<213> ORGANISM: Chamaecyparis obtusa

<400> SEQUENCE: 645

Met Ala Ala Val Ala Phe Leu Ala Leu Gln Leu Ile Val Met Ala
1               5                   10                  15

<210> SEQ ID NO 646
<211> LENGTH: 15

-continued

<210> SEQ ID NO 646
<211> LENGTH: 15
<212> TYPE: PRT
<213> ORGANISM: Chamaecyparis obtusa

<400> SEQUENCE: 646

Phe Leu Ala Leu Gln Leu Ile Val Met Ala Ala Ala Glu Asp Gln
1               5                   10                  15

<210> SEQ ID NO 647
<211> LENGTH: 15
<212> TYPE: PRT
<213> ORGANISM: Chamaecyparis obtusa

<400> SEQUENCE: 647

Leu Asp Ser Asp Ile Glu Gln Tyr Leu Arg Ser Asn Arg Ser Leu
1               5                   10                  15

<210> SEQ ID NO 648
<211> LENGTH: 15
<212> TYPE: PRT
<213> ORGANISM: Chamaecyparis obtusa

<400> SEQUENCE: 648

Glu Gln Tyr Leu Arg Ser Asn Arg Ser Leu Lys Lys Leu Val His
1               5                   10                  15

<210> SEQ ID NO 649
<211> LENGTH: 15
<212> TYPE: PRT
<213> ORGANISM: Chamaecyparis obtusa

<400> SEQUENCE: 649

Glu Ala Phe Ala Thr Thr Trp Asn Ala Ala Cys Lys Lys Ala Ser
1               5                   10                  15

<210> SEQ ID NO 650
<211> LENGTH: 15
<212> TYPE: PRT
<213> ORGANISM: Chamaecyparis obtusa

<400> SEQUENCE: 650

Thr Trp Asn Ala Ala Cys Lys Lys Ala Ser Ala Val Leu Leu Val
1               5                   10                  15

<210> SEQ ID NO 651
<211> LENGTH: 15
<212> TYPE: PRT
<213> ORGANISM: Chamaecyparis obtusa

<400> SEQUENCE: 651

Cys Lys Lys Ala Ser Ala Val Leu Leu Val Pro Ala Asn Lys Lys
1               5                   10                  15

<210> SEQ ID NO 652
<211> LENGTH: 15
<212> TYPE: PRT
<213> ORGANISM: Chamaecyparis obtusa

<400> SEQUENCE: 652

Pro Ala Asn Lys Lys Phe Phe Val Asn Asn Leu Val Phe Arg Gly
1               5                   10                  15

<210> SEQ ID NO 653
<211> LENGTH: 15
<212> TYPE: PRT
<213> ORGANISM: Chamaecyparis obtusa

<400> SEQUENCE: 653

Ala Arg Trp Lys Asn Ser Lys Ile Trp Leu Gln Phe Ala Gln Leu
1               5                   10                  15

<210> SEQ ID NO 654
<211> LENGTH: 15
<212> TYPE: PRT
<213> ORGANISM: Chamaecyparis obtusa

<400> SEQUENCE: 654

Ser Lys Ile Trp Leu Gln Phe Ala Gln Leu Thr Asp Phe Asn Leu
1               5                   10                  15

<210> SEQ ID NO 655
<211> LENGTH: 15
<212> TYPE: PRT
<213> ORGANISM: Chamaecyparis obtusa

<400> SEQUENCE: 655

Asn Arg Pro Thr Ala Ile Lys Ile Asp Tyr Ser Lys Ser Val Thr
1               5                   10                  15

<210> SEQ ID NO 656
<211> LENGTH: 15
<212> TYPE: PRT
<213> ORGANISM: Chamaecyparis obtusa

<400> SEQUENCE: 656

Ile Lys Ile Asp Tyr Ser Lys Ser Val Thr Val Lys Glu Leu Thr
1               5                   10                  15

<210> SEQ ID NO 657
<211> LENGTH: 15
<212> TYPE: PRT
<213> ORGANISM: Chamaecyparis obtusa

<400> SEQUENCE: 657

Val Lys Glu Leu Thr Leu Met Asn Ser Pro Glu Phe His Leu Val
1               5                   10                  15

<210> SEQ ID NO 658
<211> LENGTH: 15
<212> TYPE: PRT
<213> ORGANISM: Chamaecyparis obtusa

<400> SEQUENCE: 658

Ile Asp Ile Phe Ala Ser Lys Arg Phe His Ile Glu Lys Cys Val
1               5                   10                  15

<210> SEQ ID NO 659
<211> LENGTH: 15
<212> TYPE: PRT
<213> ORGANISM: Chamaecyparis obtusa

<400> SEQUENCE: 659

His Val His Val Asn Arg Ala Lys Phe Ile Asp Thr Gln Asn Gly
1               5                   10                  15

<210> SEQ ID NO 660
<211> LENGTH: 15
<212> TYPE: PRT
<213> ORGANISM: Chamaecyparis obtusa

<400> SEQUENCE: 660

```
Gly Leu Ala Ser Tyr Ile Thr Tyr Glu Asn Val Glu Met Ile Asn
1               5                   10                  15

<210> SEQ ID NO 661
<211> LENGTH: 15
<212> TYPE: PRT
<213> ORGANISM: Chamaecyparis obtusa

<400> SEQUENCE: 661

Val Glu Met Ile Asn Ser Glu Asn Pro Ile Leu Ile Asn Gln Phe
1               5                   10                  15

<210> SEQ ID NO 662
<211> LENGTH: 15
<212> TYPE: PRT
<213> ORGANISM: Chamaecyparis obtusa

<400> SEQUENCE: 662

Ser Glu Asn Pro Ile Leu Ile Asn Gln Phe Tyr Cys Thr Ser Ala
1               5                   10                  15

<210> SEQ ID NO 663
<211> LENGTH: 15
<212> TYPE: PRT
<213> ORGANISM: Chamaecyparis obtusa

<400> SEQUENCE: 663

Thr Tyr Lys Asn Ile His Gly Thr Ser Ala Thr Ala Ala Ala Ile
1               5                   10                  15

<210> SEQ ID NO 664
<211> LENGTH: 15
<212> TYPE: PRT
<213> ORGANISM: Chamaecyparis obtusa

<400> SEQUENCE: 664

Thr Ala Ala Ala Ile Gln Leu Met Cys Ser Asp Ser Val Pro Cys
1               5                   10                  15

<210> SEQ ID NO 665
<211> LENGTH: 15
<212> TYPE: PRT
<213> ORGANISM: Chamaecyparis obtusa

<400> SEQUENCE: 665

Thr Gly Ile Gln Leu Ser Asn Val Ser Leu Lys Leu Thr Ser Gly
1               5                   10                  15

<210> SEQ ID NO 666
<211> LENGTH: 15
<212> TYPE: PRT
<213> ORGANISM: Chamaecyparis obtusa

<400> SEQUENCE: 666

Gln Pro Cys Lys Pro Lys Leu Ile Ile Val His Pro Asn Lys Pro
1               5                   10                  15

<210> SEQ ID NO 667
<211> LENGTH: 15
<212> TYPE: PRT
<213> ORGANISM: Hesperocyparis arizonica

<400> SEQUENCE: 667

Lys Ala Leu Trp Ile Ile Phe Ser Gln Asn Met Asn Ile Lys Leu
```

-continued

```
1               5                   10                  15

<210> SEQ ID NO 668
<211> LENGTH: 15
<212> TYPE: PRT
<213> ORGANISM: Hesperocyparis arizonica

<400> SEQUENCE: 668

Ile Phe Ser Gln Asn Met Asn Ile Lys Leu Gln Met Pro Leu Tyr
1               5                   10                  15

<210> SEQ ID NO 669
<211> LENGTH: 15
<212> TYPE: PRT
<213> ORGANISM: Hesperocyparis arizonica

<400> SEQUENCE: 669

Met Asn Ile Lys Leu Gln Met Pro Leu Tyr Val Ala Gly Tyr Lys
1               5                   10                  15

<210> SEQ ID NO 670
<211> LENGTH: 15
<212> TYPE: PRT
<213> ORGANISM: Hesperocyparis arizonica

<400> SEQUENCE: 670

Pro Cys Leu Phe Met Arg Lys Ala Ser His Val Ile Leu His Gly
1               5                   10                  15

<210> SEQ ID NO 671
<211> LENGTH: 15
<212> TYPE: PRT
<213> ORGANISM: Hesperocyparis arizonica

<400> SEQUENCE: 671

Leu Gly Asp Val Leu Val Ser Glu Ser Ile Gly Val Glu Pro Val
1               5                   10                  15

<210> SEQ ID NO 672
<211> LENGTH: 15
<212> TYPE: PRT
<213> ORGANISM: Hesperocyparis arizonica

<400> SEQUENCE: 672

Thr Ile Ser Asn Asn His Phe Phe Asn His His Lys Val Met Leu
1               5                   10                  15

<210> SEQ ID NO 673
<211> LENGTH: 15
<212> TYPE: PRT
<213> ORGANISM: Hesperocyparis arizonica

<400> SEQUENCE: 673

His Phe Phe Asn His His Lys Val Met Leu Leu Gly His Asp Asp
1               5                   10                  15

<210> SEQ ID NO 674
<211> LENGTH: 15
<212> TYPE: PRT
<213> ORGANISM: Hesperocyparis arizonica

<400> SEQUENCE: 674

Lys Ser Met Lys Val Thr Val Ala Phe Asn Gln Phe Gly Pro Asn
1               5                   10                  15
```

<210> SEQ ID NO 675
<211> LENGTH: 15
<212> TYPE: PRT
<213> ORGANISM: Hesperocyparis arizonica

<400> SEQUENCE: 675

Pro Arg Ala Arg Tyr Gly Leu Val His Val Ala Asn Asn Asn Tyr
1               5                   10                  15

<210> SEQ ID NO 676
<211> LENGTH: 15
<212> TYPE: PRT
<213> ORGANISM: Hesperocyparis arizonica

<400> SEQUENCE: 676

Glu Asp Thr Asn Ile Tyr Asn Ser Asn Glu Ala Phe Lys Val Glu
1               5                   10                  15

<210> SEQ ID NO 677
<211> LENGTH: 15
<212> TYPE: PRT
<213> ORGANISM: Cupressus sempervirens

<400> SEQUENCE: 677

Met Asp Ser Pro Cys Leu Ile Ala Val Leu Val Phe Leu Cys Ala
1               5                   10                  15

<210> SEQ ID NO 678
<211> LENGTH: 15
<212> TYPE: PRT
<213> ORGANISM: Cupressus sempervirens

<400> SEQUENCE: 678

Leu Ile Ala Val Leu Val Phe Leu Cys Ala Ile Val Ser Cys Tyr
1               5                   10                  15

<210> SEQ ID NO 679
<211> LENGTH: 15
<212> TYPE: PRT
<213> ORGANISM: Cupressus sempervirens

<400> SEQUENCE: 679

Val Phe Leu Cys Ala Ile Val Ser Cys Tyr Ser Asp Asn Pro Ile
1               5                   10                  15

<210> SEQ ID NO 680
<211> LENGTH: 15
<212> TYPE: PRT
<213> ORGANISM: Cupressus sempervirens

<400> SEQUENCE: 680

Glu Lys Ala Leu Trp Ile Ile Phe Ser Gln Asn Met Asn Ile Lys
1               5                   10                  15

<210> SEQ ID NO 681
<211> LENGTH: 15
<212> TYPE: PRT
<213> ORGANISM: Cupressus sempervirens

<400> SEQUENCE: 681

Ile Ile Phe Ser Gln Asn Met Asn Ile Lys Leu Lys Met Pro Leu
1               5                   10                  15

<210> SEQ ID NO 682

```
<211> LENGTH: 15
<212> TYPE: PRT
<213> ORGANISM: Cupressus sempervirens

<400> SEQUENCE: 682

Asn Met Asn Ile Lys Leu Lys Met Pro Leu Tyr Val Ala Gly His
1               5                   10                  15

<210> SEQ ID NO 683
<211> LENGTH: 15
<212> TYPE: PRT
<213> ORGANISM: Cupressus sempervirens

<400> SEQUENCE: 683

Gly Pro Cys Leu Phe Met Arg Lys Val Ser His Val Ile Leu His
1               5                   10                  15

<210> SEQ ID NO 684
<211> LENGTH: 15
<212> TYPE: PRT
<213> ORGANISM: Cupressus sempervirens

<400> SEQUENCE: 684

Met Arg Lys Val Ser His Val Ile Leu His Gly Leu His Ile His
1               5                   10                  15

<210> SEQ ID NO 685
<211> LENGTH: 15
<212> TYPE: PRT
<213> ORGANISM: Cupressus sempervirens

<400> SEQUENCE: 685

Val Leu Gly Asn Val Leu Val Ser Glu Ser Ile Gly Val Glu Pro
1               5                   10                  15

<210> SEQ ID NO 686
<211> LENGTH: 15
<212> TYPE: PRT
<213> ORGANISM: Cupressus sempervirens

<400> SEQUENCE: 686

Asn His Phe Phe Asn His His Lys Val Met Leu Leu Gly His Asp
1               5                   10                  15

<210> SEQ ID NO 687
<211> LENGTH: 15
<212> TYPE: PRT
<213> ORGANISM: Cupressus sempervirens

<400> SEQUENCE: 687

Asp Lys Ser Met Lys Val Thr Val Ala Phe Asn Gln Phe Gly Pro
1               5                   10                  15

<210> SEQ ID NO 688
<211> LENGTH: 15
<212> TYPE: PRT
<213> ORGANISM: Cupressus sempervirens

<400> SEQUENCE: 688

Tyr Gly Leu Val His Val Ala Asn Asn Asn Tyr Asp Gln Trp Asn
1               5                   10                  15

<210> SEQ ID NO 689
<211> LENGTH: 15
<212> TYPE: PRT
```

-continued

<213> ORGANISM: Cupressus sempervirens

<400> SEQUENCE: 689

Thr Glu Glu Thr Asn Ile Tyr Thr Ser Asn Glu Ala Phe Lys Val
1               5                   10                  15

<210> SEQ ID NO 690
<211> LENGTH: 15
<212> TYPE: PRT
<213> ORGANISM: Cupressus sempervirens

<400> SEQUENCE: 690

Glu Ala Phe Lys Val Glu Asn Gly Asn Leu Ala Pro Gln Leu Thr
1               5                   10                  15

<210> SEQ ID NO 691
<211> LENGTH: 15
<212> TYPE: PRT
<213> ORGANISM: Cupressus sempervirens

<400> SEQUENCE: 691

Met Ala Arg Val Ser Glu Leu Ala Leu Leu Val Ala Thr Ser
1               5                   10                  15

<210> SEQ ID NO 692
<211> LENGTH: 15
<212> TYPE: PRT
<213> ORGANISM: Cupressus sempervirens

<400> SEQUENCE: 692

Glu Leu Ala Leu Leu Leu Val Ala Thr Ser Ala Ile Ser Leu His
1               5                   10                  15

<210> SEQ ID NO 693
<211> LENGTH: 15
<212> TYPE: PRT
<213> ORGANISM: Cupressus sempervirens

<400> SEQUENCE: 693

Leu Val Ala Thr Ser Ala Ile Ser Leu His Met Gln Glu Ala Gly
1               5                   10                  15

<210> SEQ ID NO 694
<211> LENGTH: 15
<212> TYPE: PRT
<213> ORGANISM: Cupressus sempervirens

<400> SEQUENCE: 694

Thr Trp Thr Val Asn Leu Ala Ala Gly Thr Ala Ser Ala Arg Phe
1               5                   10                  15

<210> SEQ ID NO 695
<211> LENGTH: 15
<212> TYPE: PRT
<213> ORGANISM: Cupressus sempervirens

<400> SEQUENCE: 695

Asp Tyr Tyr Asp Val Ser Leu Val Asp Gly Phe Asn Ile Pro Leu
1               5                   10                  15

<210> SEQ ID NO 696
<211> LENGTH: 15
<212> TYPE: PRT
<213> ORGANISM: Cupressus sempervirens

<400> SEQUENCE: 696

Ser Leu Val Asp Gly Phe Asn Ile Pro Leu Ala Ile Asn Pro Thr
1               5                   10                  15

<210> SEQ ID NO 697
<211> LENGTH: 15
<212> TYPE: PRT
<213> ORGANISM: Phoenix dactylifera

<400> SEQUENCE: 697

Ser Ser Ser Phe Pro Gln Phe Lys Ser Glu Glu Ile Thr Asn Ile
1               5                   10                  15

<210> SEQ ID NO 698
<211> LENGTH: 15
<212> TYPE: PRT
<213> ORGANISM: Phoenix dactylifera

<400> SEQUENCE: 698

Ala Pro Thr Gly Leu Tyr Leu Gly Ser Thr Lys Tyr Met Val Ile
1               5                   10                  15

<210> SEQ ID NO 699
<211> LENGTH: 15
<212> TYPE: PRT
<213> ORGANISM: Phoenix dactylifera

<400> SEQUENCE: 699

Tyr Leu Gly Ser Thr Lys Tyr Met Val Ile Gln Gly Glu Pro Gly
1               5                   10                  15

<210> SEQ ID NO 700
<211> LENGTH: 15
<212> TYPE: PRT
<213> ORGANISM: Phoenix dactylifera

<400> SEQUENCE: 700

Lys Tyr Met Val Ile Gln Gly Glu Pro Gly Ala Val Ile Arg Gly
1               5                   10                  15

<210> SEQ ID NO 701
<211> LENGTH: 15
<212> TYPE: PRT
<213> ORGANISM: Phoenix dactylifera

<400> SEQUENCE: 701

Gly Val Thr Val Lys Lys Thr Asn Gln Ala Leu Ile Phe Gly Ile
1               5                   10                  15

<210> SEQ ID NO 702
<211> LENGTH: 15
<212> TYPE: PRT
<213> ORGANISM: Dermatophagoides farinae

<400> SEQUENCE: 702

Met Lys Phe Val Leu Ala Ile Ala Ser Leu Leu Val Leu Ser Thr
1               5                   10                  15

<210> SEQ ID NO 703
<211> LENGTH: 15
<212> TYPE: PRT
<213> ORGANISM: Dermatophagoides farinae

<400> SEQUENCE: 703

Ala Ile Ala Ser Leu Leu Val Leu Ser Thr Val Tyr Ala Arg Pro
1               5                   10                  15

<210> SEQ ID NO 704
<211> LENGTH: 15
<212> TYPE: PRT
<213> ORGANISM: Dermatophagoides farinae

<400> SEQUENCE: 704

Leu Val Leu Ser Thr Val Tyr Ala Arg Pro Ala Ser Ile Lys Thr
1               5                   10                  15

<210> SEQ ID NO 705
<211> LENGTH: 15
<212> TYPE: PRT
<213> ORGANISM: Dermatophagoides farinae

<400> SEQUENCE: 705

Phe Glu Glu Phe Lys Lys Ala Phe Asn Lys Asn Tyr Ala Thr Val
1               5                   10                  15

<210> SEQ ID NO 706
<211> LENGTH: 15
<212> TYPE: PRT
<213> ORGANISM: Dermatophagoides farinae

<400> SEQUENCE: 706

Ala Arg Lys Asn Phe Leu Glu Ser Leu Lys Tyr Val Glu Ala Asn
1               5                   10                  15

<210> SEQ ID NO 707
<211> LENGTH: 15
<212> TYPE: PRT
<213> ORGANISM: Dermatophagoides farinae

<400> SEQUENCE: 707

Lys Gly Ala Ile Asn His Leu Ser Asp Leu Ser Leu Asp Glu Phe
1               5                   10                  15

<210> SEQ ID NO 708
<211> LENGTH: 15
<212> TYPE: PRT
<213> ORGANISM: Dermatophagoides farinae

<400> SEQUENCE: 708

Ser Leu Asp Glu Phe Lys Asn Arg Tyr Leu Met Ser Ala Glu Ala
1               5                   10                  15

<210> SEQ ID NO 709
<211> LENGTH: 15
<212> TYPE: PRT
<213> ORGANISM: Dermatophagoides farinae

<400> SEQUENCE: 709

Lys Asn Arg Tyr Leu Met Ser Ala Glu Ala Phe Glu Gln Leu Lys
1               5                   10                  15

<210> SEQ ID NO 710
<211> LENGTH: 15
<212> TYPE: PRT
<213> ORGANISM: Dermatophagoides farinae

<400> SEQUENCE: 710

Met Ser Ala Glu Ala Phe Glu Gln Leu Lys Thr Gln Phe Asp Leu
1               5                   10                  15

```
<210> SEQ ID NO 711
<211> LENGTH: 15
<212> TYPE: PRT
<213> ORGANISM: Dermatophagoides farinae

<400> SEQUENCE: 711

Phe Glu Gln Leu Lys Thr Gln Phe Asp Leu Asn Ala Glu Thr Ser
1               5                   10                  15

<210> SEQ ID NO 712
<211> LENGTH: 15
<212> TYPE: PRT
<213> ORGANISM: Dermatophagoides farinae

<400> SEQUENCE: 712

Gly Ser Cys Trp Ala Phe Ser Gly Val Ala Ala Thr Glu Ser Ala
1               5                   10                  15

<210> SEQ ID NO 713
<211> LENGTH: 15
<212> TYPE: PRT
<213> ORGANISM: Dermatophagoides farinae

<400> SEQUENCE: 713

Phe Ser Gly Val Ala Ala Thr Glu Ser Ala Tyr Leu Ala Tyr Arg
1               5                   10                  15

<210> SEQ ID NO 714
<211> LENGTH: 15
<212> TYPE: PRT
<213> ORGANISM: Dermatophagoides farinae

<400> SEQUENCE: 714

Ala Thr Glu Ser Ala Tyr Leu Ala Tyr Arg Asn Thr Ser Leu Asp
1               5                   10                  15

<210> SEQ ID NO 715
<211> LENGTH: 15
<212> TYPE: PRT
<213> ORGANISM: Dermatophagoides farinae

<400> SEQUENCE: 715

Tyr Leu Ala Tyr Arg Asn Thr Ser Leu Asp Leu Ser Glu Gln Glu
1               5                   10                  15

<210> SEQ ID NO 716
<211> LENGTH: 15
<212> TYPE: PRT
<213> ORGANISM: Dermatophagoides farinae

<400> SEQUENCE: 716

Pro Arg Gly Ile Glu Tyr Ile Gln Gln Asn Gly Val Val Glu Glu
1               5                   10                  15

<210> SEQ ID NO 717
<211> LENGTH: 15
<212> TYPE: PRT
<213> ORGANISM: Dermatophagoides farinae

<400> SEQUENCE: 717

Pro Asp Val Lys Gln Ile Arg Glu Ala Leu Thr Gln Thr His Thr
1               5                   10                  15
```

```
<210> SEQ ID NO 718
<211> LENGTH: 15
<212> TYPE: PRT
<213> ORGANISM: Dermatophagoides farinae

<400> SEQUENCE: 718

Thr Gln Thr His Thr Ala Ile Ala Val Ile Ile Gly Ile Lys Asp
 1               5                  10                  15

<210> SEQ ID NO 719
<211> LENGTH: 15
<212> TYPE: PRT
<213> ORGANISM: Dermatophagoides farinae

<400> SEQUENCE: 719

Ile Gly Ile Lys Asp Leu Arg Ala Phe Gln His Tyr Asp Gly Arg
 1               5                  10                  15

<210> SEQ ID NO 720
<211> LENGTH: 15
<212> TYPE: PRT
<213> ORGANISM: Dermatophagoides farinae

<400> SEQUENCE: 720

Gly Asp Ser Gly Tyr Gly Tyr Phe Gln Ala Gly Asn Asn Leu Met
 1               5                  10                  15

<210> SEQ ID NO 721
<211> LENGTH: 15
<212> TYPE: PRT
<213> ORGANISM: Dermatophagoides farinae

<400> SEQUENCE: 721

Gly Tyr Phe Gln Ala Gly Asn Asn Leu Met Met Ile Glu Gln Tyr
 1               5                  10                  15

<210> SEQ ID NO 722
<211> LENGTH: 15
<212> TYPE: PRT
<213> ORGANISM: Dermatophagoides farinae

<400> SEQUENCE: 722

Gly Asn Asn Leu Met Met Ile Glu Gln Tyr Pro Tyr Val Val Ile
 1               5                  10                  15

<210> SEQ ID NO 723
<211> LENGTH: 15
<212> TYPE: PRT
<213> ORGANISM: Dermatophagoides farinae

<400> SEQUENCE: 723

Asn Asn Leu Met Met Ile Glu Gln Tyr Pro Tyr Val Val Ile Met
 1               5                  10                  15

<210> SEQ ID NO 724
<211> LENGTH: 15
<212> TYPE: PRT
<213> ORGANISM: Dermatophagoides farinae

<400> SEQUENCE: 724

Arg Ser Glu Glu Arg Leu Lys Ile Ala Thr Ala Lys Leu Glu Glu
 1               5                  10                  15

<210> SEQ ID NO 725
<211> LENGTH: 15
```

<212> TYPE: PRT
<213> ORGANISM: Dermatophagoides farinae

<400> SEQUENCE: 725

Leu Lys Ile Ala Thr Ala Lys Leu Glu Glu Ala Ser Gln Ser Ala
1               5                   10                  15

<210> SEQ ID NO 726
<211> LENGTH: 15
<212> TYPE: PRT
<213> ORGANISM: Dermatophagoides farinae

<400> SEQUENCE: 726

Val Glu Leu Glu Glu Glu Leu Arg Val Val Gly Asn Asn Leu Lys
1               5                   10                  15

<210> SEQ ID NO 727
<211> LENGTH: 15
<212> TYPE: PRT
<213> ORGANISM: Dermatophagoides farinae

<400> SEQUENCE: 727

Gln Arg Glu Glu Ala Tyr Glu Gln Gln Ile Arg Ile Met Thr Ala
1               5                   10                  15

<210> SEQ ID NO 728
<211> LENGTH: 15
<212> TYPE: PRT
<213> ORGANISM: Dermatophagoides farinae

<400> SEQUENCE: 728

Tyr Glu Gln Gln Ile Arg Ile Met Thr Ala Lys Leu Lys Glu Ala
1               5                   10                  15

<210> SEQ ID NO 729
<211> LENGTH: 15
<212> TYPE: PRT
<213> ORGANISM: Dermatophagoides farinae

<400> SEQUENCE: 729

Lys Leu Arg Lys Leu Leu Glu Asp Val His Ile Glu Ser Glu Glu
1               5                   10                  15

<210> SEQ ID NO 730
<211> LENGTH: 15
<212> TYPE: PRT
<213> ORGANISM: Dermatophagoides farinae

<400> SEQUENCE: 730

Lys Phe Gln Ala Glu Val Phe Glu Leu Leu Ala Gln Leu Glu Thr
1               5                   10                  15

<210> SEQ ID NO 731
<211> LENGTH: 15
<212> TYPE: PRT
<213> ORGANISM: Dermatophagoides farinae

<400> SEQUENCE: 731

Val Phe Glu Leu Leu Ala Gln Leu Glu Thr Ala Asn Lys Glu Lys
1               5                   10                  15

<210> SEQ ID NO 732
<211> LENGTH: 15
<212> TYPE: PRT
<213> ORGANISM: Dermatophagoides farinae -continued

<400> SEQUENCE: 732

Glu Leu Asn Ile Lys Ile Glu Glu Ile Asn Arg Thr Val Ile Glu
1               5                   10                  15

<210> SEQ ID NO 733
<211> LENGTH: 15
<212> TYPE: PRT
<213> ORGANISM: Dermatophagoides farinae

<400> SEQUENCE: 733

Ile Glu Glu Ile Asn Arg Thr Val Ile Glu Leu Thr Ser His Lys
1               5                   10                  15

<210> SEQ ID NO 734
<211> LENGTH: 15
<212> TYPE: PRT
<213> ORGANISM: Dermatophagoides farinae

<400> SEQUENCE: 734

Glu Val Lys Leu Gln Leu Asp Asn Ala Asn His Leu Lys Thr Gln
1               5                   10                  15

<210> SEQ ID NO 735
<211> LENGTH: 15
<212> TYPE: PRT
<213> ORGANISM: Dermatophagoides farinae

<400> SEQUENCE: 735

Leu Asp Asn Ala Asn His Leu Lys Thr Gln Ile Ala Gln Gln Leu
1               5                   10                  15

<210> SEQ ID NO 736
<211> LENGTH: 15
<212> TYPE: PRT
<213> ORGANISM: Dermatophagoides farinae

<400> SEQUENCE: 736

His Leu Lys Thr Gln Ile Ala Gln Gln Leu Glu Asp Thr Arg His
1               5                   10                  15

<210> SEQ ID NO 737
<211> LENGTH: 15
<212> TYPE: PRT
<213> ORGANISM: Dermatophagoides farinae

<400> SEQUENCE: 737

Ala His Thr Leu Glu Val Glu Leu Glu Ser Leu Lys Val Gln Leu
1               5                   10                  15

<210> SEQ ID NO 738
<211> LENGTH: 15
<212> TYPE: PRT
<213> ORGANISM: Dermatophagoides farinae

<400> SEQUENCE: 738

Ala Arg Leu Glu Leu Glu Arg Gln Leu Thr Lys Ala Asn Gly Asp
1               5                   10                  15

<210> SEQ ID NO 739
<211> LENGTH: 15
<212> TYPE: PRT
<213> ORGANISM: Dermatophagoides farinae

<400> SEQUENCE: 739

Glu Leu Arg Arg Lys Met Ala Gln Lys Ile Ser Glu Tyr Glu Glu
1               5                   10                  15

<210> SEQ ID NO 740
<211> LENGTH: 15
<212> TYPE: PRT
<213> ORGANISM: Dermatophagoides farinae

<400> SEQUENCE: 740

Ser Glu Tyr Glu Glu Gln Leu Glu Ala Leu Leu Asn Lys Cys Ser
1               5                   10                  15

<210> SEQ ID NO 741
<211> LENGTH: 15
<212> TYPE: PRT
<213> ORGANISM: Dermatophagoides farinae

<400> SEQUENCE: 741

Lys Ser Arg Leu Gln Ser Glu Val Glu Val Leu Ile Met Asp Leu
1               5                   10                  15

<210> SEQ ID NO 742
<211> LENGTH: 15
<212> TYPE: PRT
<213> ORGANISM: Dermatophagoides farinae

<400> SEQUENCE: 742

Ser Glu Val Glu Val Leu Ile Met Asp Leu Glu Lys Ala Thr Arg
1               5                   10                  15

<210> SEQ ID NO 743
<211> LENGTH: 15
<212> TYPE: PRT
<213> ORGANISM: Dermatophagoides farinae

<400> SEQUENCE: 743

Glu Lys Arg Val Ala Gln Leu Glu Lys Ile Asn Leu Asp Leu Lys
1               5                   10                  15

<210> SEQ ID NO 744
<211> LENGTH: 15
<212> TYPE: PRT
<213> ORGANISM: Dermatophagoides farinae

<400> SEQUENCE: 744

Glu Leu Arg Val Lys Ile Ala Glu Leu Gln Lys Leu Gln His Glu
1               5                   10                  15

<210> SEQ ID NO 745
<211> LENGTH: 15
<212> TYPE: PRT
<213> ORGANISM: Dermatophagoides farinae

<400> SEQUENCE: 745

Ile Ala Glu Leu Gln Lys Leu Gln His Glu Tyr Glu Lys Leu Arg
1               5                   10                  15

<210> SEQ ID NO 746
<211> LENGTH: 15
<212> TYPE: PRT
<213> ORGANISM: Dermatophagoides farinae

<400> SEQUENCE: 746

Asp Glu Leu Ser Ala Ala Tyr Lys Glu Ala Glu Thr Leu Arg Lys

```
1               5                  10                 15
```

<210> SEQ ID NO 747
<211> LENGTH: 15
<212> TYPE: PRT
<213> ORGANISM: Dermatophagoides farinae

<400> SEQUENCE: 747

```
Asn Gln Arg Leu Ile Ala Glu Leu Ala Gln Val Arg His Asp Tyr
1               5                  10                 15
```

<210> SEQ ID NO 748
<211> LENGTH: 15
<212> TYPE: PRT
<213> ORGANISM: Dermatophagoides farinae

<400> SEQUENCE: 748

```
Ile Glu Ala Leu Arg Lys Gln Tyr Gln Ile Glu Ile Glu Gln Leu
1               5                  10                 15
```

<210> SEQ ID NO 749
<211> LENGTH: 15
<212> TYPE: PRT
<213> ORGANISM: Dermatophagoides farinae

<400> SEQUENCE: 749

```
Lys Gln Tyr Gln Ile Glu Ile Glu Gln Leu Asn Met Arg Leu Ala
1               5                  10                 15
```

<210> SEQ ID NO 750
<211> LENGTH: 15
<212> TYPE: PRT
<213> ORGANISM: Dermatophagoides farinae

<400> SEQUENCE: 750

```
Glu Ile Glu Gln Leu Asn Met Arg Leu Ala Glu Ala Glu Ala Lys
1               5                  10                 15
```

<210> SEQ ID NO 751
<211> LENGTH: 15
<212> TYPE: PRT
<213> ORGANISM: Dermatophagoides farinae

<400> SEQUENCE: 751

```
Ala Arg Leu Lys Lys Lys Tyr Gln Ala Gln Ile Thr Glu Leu Glu
1               5                  10                 15
```

<210> SEQ ID NO 752
<211> LENGTH: 15
<212> TYPE: PRT
<213> ORGANISM: Dermatophagoides farinae

<400> SEQUENCE: 752

```
Lys Tyr Gln Ala Gln Ile Thr Glu Leu Glu Leu Ser Leu Asp Ala
1               5                  10                 15
```

<210> SEQ ID NO 753
<211> LENGTH: 15
<212> TYPE: PRT
<213> ORGANISM: Dermatophagoides farinae

<400> SEQUENCE: 753

```
Thr Ile Lys Lys Gln Ala Leu Gln Ile Thr Glu Leu Gln Ala His
1               5                  10                 15
```

<210> SEQ ID NO 754
<211> LENGTH: 15
<212> TYPE: PRT
<213> ORGANISM: Dermatophagoides farinae

<400> SEQUENCE: 754

Gln Ala Glu Leu Glu Glu Met Arg Ile Ala Leu Glu Gln Ala Asn
1               5                   10                  15

<210> SEQ ID NO 755
<211> LENGTH: 15
<212> TYPE: PRT
<213> ORGANISM: Dermatophagoides farinae

<400> SEQUENCE: 755

Leu Glu Gln Ala Asn Arg Ala Lys Arg Gln Ala Glu Gln Leu His
1               5                   10                  15

<210> SEQ ID NO 756
<211> LENGTH: 15
<212> TYPE: PRT
<213> ORGANISM: Dermatophagoides farinae

<400> SEQUENCE: 756

Thr Thr Ile Asn Val Asn Leu Ala Ser Ala Lys Ser Lys Leu Glu
1               5                   10                  15

<210> SEQ ID NO 757
<211> LENGTH: 15
<212> TYPE: PRT
<213> ORGANISM: Dermatophagoides farinae

<400> SEQUENCE: 757

Lys Ser Lys Leu Glu Ser Glu Phe Ser Ala Leu Gln Ala Asp Tyr
1               5                   10                  15

<210> SEQ ID NO 758
<211> LENGTH: 15
<212> TYPE: PRT
<213> ORGANISM: Dermatophagoides farinae

<400> SEQUENCE: 758

Lys Leu Thr Ile Glu Leu Lys Ser Thr Lys Asp Leu Leu Ile Glu
1               5                   10                  15

<210> SEQ ID NO 759
<211> LENGTH: 15
<212> TYPE: PRT
<213> ORGANISM: Dermatophagoides farinae

<400> SEQUENCE: 759

Leu Lys Ser Thr Lys Asp Leu Leu Ile Glu Glu Gln Glu Arg Leu
1               5                   10                  15

<210> SEQ ID NO 760
<211> LENGTH: 15
<212> TYPE: PRT
<213> ORGANISM: Dermatophagoides farinae

<400> SEQUENCE: 760

Val Lys Leu Glu Thr Val Lys Lys Ser Leu Glu Gln Glu Val Arg
1               5                   10                  15

<210> SEQ ID NO 761

-continued

<210> SEQ ID NO 761
<211> LENGTH: 15
<212> TYPE: PRT
<213> ORGANISM: Dermatophagoides farinae

<400> SEQUENCE: 761

Thr Leu His Val Arg Ile Glu Glu Val Glu Ala Asn Ala Leu Ala
1               5                   10                  15

<210> SEQ ID NO 762
<211> LENGTH: 15
<212> TYPE: PRT
<213> ORGANISM: Dermatophagoides farinae

<400> SEQUENCE: 762

Gly Lys Tyr Lys Leu Glu Lys Ser Glu Lys Phe Asp Glu Phe Leu
1               5                   10                  15

<210> SEQ ID NO 763
<211> LENGTH: 15
<212> TYPE: PRT
<213> ORGANISM: Dermatophagoides farinae

<400> SEQUENCE: 763

Gly Phe Met Val Lys Thr Ala Ala Lys Thr Leu Lys Pro Thr Phe
1               5                   10                  15

<210> SEQ ID NO 764
<211> LENGTH: 15
<212> TYPE: PRT
<213> ORGANISM: Dermatophagoides farinae

<400> SEQUENCE: 764

Asn Asp Gln Tyr Ile Phe Arg Ser Leu Ser Thr Phe Lys Asn Thr
1               5                   10                  15

<210> SEQ ID NO 765
<211> LENGTH: 15
<212> TYPE: PRT
<213> ORGANISM: Dermatophagoides farinae

<400> SEQUENCE: 765

Phe Arg Ser Leu Ser Thr Phe Lys Asn Thr Glu Ala Lys Phe Lys
1               5                   10                  15

<210> SEQ ID NO 766
<211> LENGTH: 15
<212> TYPE: PRT
<213> ORGANISM: Dermatophagoides farinae

<400> SEQUENCE: 766

Thr Arg Arg Tyr Val Ala Glu Leu Thr Ala Val Gly Ser Pro Ser
1               5                   10                  15

<210> SEQ ID NO 767
<211> LENGTH: 15
<212> TYPE: PRT
<213> ORGANISM: Dermatophagoides farinae

<400> SEQUENCE: 767

Lys Ser Pro Glu His Glu Phe Asn Thr Glu Phe Thr Ile His Ala
1               5                   10                  15

<210> SEQ ID NO 768
<211> LENGTH: 15
<212> TYPE: PRT

<213> ORGANISM: Dermatophagoides farinae

<400> SEQUENCE: 768

Asp Lys Glu Asn Asn Val Arg Lys Asn Gln Leu Asn Leu Gln Tyr
1               5                   10                  15

<210> SEQ ID NO 769
<211> LENGTH: 15
<212> TYPE: PRT
<213> ORGANISM: Dermatophagoides farinae

<400> SEQUENCE: 769

Val Arg Lys Asn Gln Leu Asn Leu Gln Tyr Lys Phe Ala Gly Asp
1               5                   10                  15

<210> SEQ ID NO 770
<211> LENGTH: 15
<212> TYPE: PRT
<213> ORGANISM: Dermatophagoides farinae

<400> SEQUENCE: 770

Val Asp Tyr Glu Asn Glu Phe Ser Phe Asn Leu Lys Arg Ser Ser
1               5                   10                  15

<210> SEQ ID NO 771
<211> LENGTH: 15
<212> TYPE: PRT
<213> ORGANISM: Dermatophagoides farinae

<400> SEQUENCE: 771

Ala Lys Tyr Met Ser Ser His Phe Pro Ile Leu Asn His Lys Val
1               5                   10                  15

<210> SEQ ID NO 772
<211> LENGTH: 15
<212> TYPE: PRT
<213> ORGANISM: Dermatophagoides farinae

<400> SEQUENCE: 772

Ser His Phe Pro Ile Leu Asn His Lys Val Asn Ile Gln Phe Lys
1               5                   10                  15

<210> SEQ ID NO 773
<211> LENGTH: 15
<212> TYPE: PRT
<213> ORGANISM: Dermatophagoides farinae

<400> SEQUENCE: 773

Leu Asn His Lys Val Asn Ile Gln Phe Lys Tyr Arg Pro Phe Lys
1               5                   10                  15

<210> SEQ ID NO 774
<211> LENGTH: 15
<212> TYPE: PRT
<213> ORGANISM: Dermatophagoides farinae

<400> SEQUENCE: 774

Asn Ile Gln Phe Lys Tyr Arg Pro Phe Lys Val Asn Glu Leu Asn
1               5                   10                  15

<210> SEQ ID NO 775
<211> LENGTH: 15
<212> TYPE: PRT
<213> ORGANISM: Dermatophagoides farinae

<400> SEQUENCE: 775

His Lys Phe Gln Leu Met Arg Asn Ser Gln Ile Glu Val Glu Glu
1               5                   10                  15

<210> SEQ ID NO 776
<211> LENGTH: 15
<212> TYPE: PRT
<213> ORGANISM: Dermatophagoides farinae

<400> SEQUENCE: 776

Val Arg Pro Phe Lys Met His Gly Asn Ser Asp Ile Lys Leu Met
1               5                   10                  15

<210> SEQ ID NO 777
<211> LENGTH: 15
<212> TYPE: PRT
<213> ORGANISM: Dermatophagoides farinae

<400> SEQUENCE: 777

Lys Ile Phe Ile Asn His Lys Ser Glu Met Thr Lys Pro Thr Asn
1               5                   10                  15

<210> SEQ ID NO 778
<211> LENGTH: 15
<212> TYPE: PRT
<213> ORGANISM: Dermatophagoides farinae

<400> SEQUENCE: 778

Met Lys Thr Ile Tyr Ala Ile Leu Ser Ile Met Ala Cys Ile Gly
1               5                   10                  15

<210> SEQ ID NO 779
<211> LENGTH: 15
<212> TYPE: PRT
<213> ORGANISM: Dermatophagoides farinae

<400> SEQUENCE: 779

Ala Ile Leu Ser Ile Met Ala Cys Ile Gly Leu Met Asn Ala Ser
1               5                   10                  15

<210> SEQ ID NO 780
<211> LENGTH: 15
<212> TYPE: PRT
<213> ORGANISM: Dermatophagoides farinae

<400> SEQUENCE: 780

Met Ala Cys Ile Gly Leu Met Asn Ala Ser Ile Lys Arg Asp His
1               5                   10                  15

<210> SEQ ID NO 781
<211> LENGTH: 15
<212> TYPE: PRT
<213> ORGANISM: Dermatophagoides farinae

<400> SEQUENCE: 781

Ser Trp Glu Lys Arg Gly Tyr Glu Arg Phe Asn Asn Leu Arg Leu
1               5                   10                  15

<210> SEQ ID NO 782
<211> LENGTH: 15
<212> TYPE: PRT
<213> ORGANISM: Dermatophagoides farinae

<400> SEQUENCE: 782

```
Gly Tyr Glu Arg Phe Asn Asn Leu Arg Leu Lys Asn Pro Glu Leu
1               5                   10                  15
```

<210> SEQ ID NO 783
<211> LENGTH: 15
<212> TYPE: PRT
<213> ORGANISM: Dermatophagoides farinae

<400> SEQUENCE: 783

```
Lys Asn Pro Glu Leu Thr Thr Met Ile Ser Leu Gly Gly Trp Tyr
1               5                   10                  15
```

<210> SEQ ID NO 784
<211> LENGTH: 15
<212> TYPE: PRT
<213> ORGANISM: Dermatophagoides farinae

<400> SEQUENCE: 784

```
Ala Asn Pro Thr Tyr Arg Gln Gln Phe Ile Gln Ser Val Leu Asp
1               5                   10                  15
```

<210> SEQ ID NO 785
<211> LENGTH: 15
<212> TYPE: PRT
<213> ORGANISM: Dermatophagoides farinae

<400> SEQUENCE: 785

```
Arg Gln Gln Phe Ile Gln Ser Val Leu Asp Phe Leu Gln Glu Tyr
1               5                   10                  15
```

<210> SEQ ID NO 786
<211> LENGTH: 15
<212> TYPE: PRT
<213> ORGANISM: Dermatophagoides farinae

<400> SEQUENCE: 786

```
Ile Asp Lys Gln Asn Tyr Leu Ala Leu Val Arg Glu Leu Lys Asp
1               5                   10                  15
```

<210> SEQ ID NO 787
<211> LENGTH: 15
<212> TYPE: PRT
<213> ORGANISM: Dermatophagoides farinae

<400> SEQUENCE: 787

```
Tyr Leu Ala Leu Val Arg Glu Leu Lys Asp Ala Phe Glu Pro His
1               5                   10                  15
```

<210> SEQ ID NO 788
<211> LENGTH: 15
<212> TYPE: PRT
<213> ORGANISM: Dermatophagoides farinae

<400> SEQUENCE: 788

```
Ala Phe Glu Pro His Gly Tyr Leu Leu Thr Ala Ala Val Ser Pro
1               5                   10                  15
```

<210> SEQ ID NO 789
<211> LENGTH: 15
<212> TYPE: PRT
<213> ORGANISM: Dermatophagoides farinae

<400> SEQUENCE: 789

```
Gly Trp Glu Asn Phe Tyr Gly His Asn Ala Pro Leu Tyr Lys Arg
1               5                   10                  15
```

<210> SEQ ID NO 790
<211> LENGTH: 15
<212> TYPE: PRT
<213> ORGANISM: Dermatophagoides farinae

<400> SEQUENCE: 790

Glu Leu His Thr Tyr Phe Asn Val Asn Tyr Thr Met His Tyr Tyr
1               5                   10                  15

<210> SEQ ID NO 791
<211> LENGTH: 15
<212> TYPE: PRT
<213> ORGANISM: Dermatophagoides farinae

<400> SEQUENCE: 791

Phe Asn Val Asn Tyr Thr Met His Tyr Tyr Leu Asn Asn Gly Ala
1               5                   10                  15

<210> SEQ ID NO 792
<211> LENGTH: 15
<212> TYPE: PRT
<213> ORGANISM: Dermatophagoides farinae

<400> SEQUENCE: 792

Leu Ser Tyr Ile Glu Leu Cys Gln Leu Phe Gln Lys Glu Glu Trp
1               5                   10                  15

<210> SEQ ID NO 793
<211> LENGTH: 15
<212> TYPE: PRT
<213> ORGANISM: Dermatophagoides farinae

<400> SEQUENCE: 793

Lys Leu Ala Phe Leu Lys Glu Leu Gly Val Ser Gly Val Met Val
1               5                   10                  15

<210> SEQ ID NO 794
<211> LENGTH: 15
<212> TYPE: PRT
<213> ORGANISM: Dermatophagoides farinae

<400> SEQUENCE: 794

Asn Pro Leu Leu Asn Lys Val His Asn Met Ile Asn Gly Asp Glu
1               5                   10                  15

<210> SEQ ID NO 795
<211> LENGTH: 15
<212> TYPE: PRT
<213> ORGANISM: Dermatophagoides farinae

<400> SEQUENCE: 795

Lys Asn Phe Asp Val Ile Pro Ile Gly His Thr Phe Phe Phe Ile
1               5                   10                  15

<210> SEQ ID NO 796
<211> LENGTH: 15
<212> TYPE: PRT
<213> ORGANISM: Dermatophagoides farinae

<400> SEQUENCE: 796

Ile Pro Ile Gly His Thr Phe Phe Phe Ile Trp Arg Ile Lys Gln
1               5                   10                  15

-continued

```
<210> SEQ ID NO 797
<211> LENGTH: 15
<212> TYPE: PRT
<213> ORGANISM: Dermatophagoides farinae

<400> SEQUENCE: 797

Thr Phe Phe Phe Ile Trp Arg Ile Lys Gln Phe Glu Leu Val Pro
1               5                   10                  15

<210> SEQ ID NO 798
<211> LENGTH: 15
<212> TYPE: PRT
<213> ORGANISM: Dermatophagoides farinae

<400> SEQUENCE: 798

Trp Arg Ile Lys Gln Phe Glu Leu Val Pro Val Pro Lys Glu Asp
1               5                   10                  15

<210> SEQ ID NO 799
<211> LENGTH: 15
<212> TYPE: PRT
<213> ORGANISM: Dermatophagoides farinae

<400> SEQUENCE: 799

Glu Ile Glu Glu Phe Glu Ser Arg Gln Phe Ser Ser Tyr Phe Lys
1               5                   10                  15

<210> SEQ ID NO 800
<211> LENGTH: 15
<212> TYPE: PRT
<213> ORGANISM: Dermatophagoides farinae

<400> SEQUENCE: 800

Ser Ser Tyr Phe Lys Asn Gly Ile Ile Tyr Leu Lys Gly Gly Tyr
1               5                   10                  15

<210> SEQ ID NO 801
<211> LENGTH: 15
<212> TYPE: PRT
<213> ORGANISM: Dermatophagoides farinae

<400> SEQUENCE: 801

Val Met Asn Asn Gly Asp Val Phe Ile Leu Leu Val Pro Asn Phe
1               5                   10                  15

<210> SEQ ID NO 802
<211> LENGTH: 15
<212> TYPE: PRT
<213> ORGANISM: Dermatophagoides farinae

<400> SEQUENCE: 802

Asp Val Phe Ile Leu Leu Val Pro Asn Phe Val Phe Val Trp Thr
1               5                   10                  15

<210> SEQ ID NO 803
<211> LENGTH: 15
<212> TYPE: PRT
<213> ORGANISM: Dermatophagoides farinae

<400> SEQUENCE: 803

Leu Val Pro Asn Phe Val Phe Val Trp Thr Gly Lys His Ser Asn
1               5                   10                  15

<210> SEQ ID NO 804
<211> LENGTH: 15
```

<212> TYPE: PRT
<213> ORGANISM: Dermatophagoides farinae

<400> SEQUENCE: 804

Ser Glu Leu Asn Arg Phe Lys Leu Ser Ser Val Ile Leu Glu Asp
1               5                   10                  15

<210> SEQ ID NO 805
<211> LENGTH: 15
<212> TYPE: PRT
<213> ORGANISM: Dermatophagoides farinae

<400> SEQUENCE: 805

Phe Lys Leu Ser Ser Val Ile Leu Glu Asp Gly Lys Glu Val Glu
1               5                   10                  15

<210> SEQ ID NO 806
<211> LENGTH: 15
<212> TYPE: PRT
<213> ORGANISM: Dermatophagoides farinae

<400> SEQUENCE: 806

Glu Tyr Asp Ala Phe Asn Lys Ala Leu Ser Leu Asp Lys Lys Asp
1               5                   10                  15

<210> SEQ ID NO 807
<211> LENGTH: 15
<212> TYPE: PRT
<213> ORGANISM: Dermatophagoides farinae

<400> SEQUENCE: 807

Ile Ser Phe Val Lys Asn Gly Pro Leu Ser Arg Ala Asp Leu Asp
1               5                   10                  15

<210> SEQ ID NO 808
<211> LENGTH: 15
<212> TYPE: PRT
<213> ORGANISM: Dermatophagoides farinae

<400> SEQUENCE: 808

Ile Lys Tyr Ala Met Glu Leu Ile Asn Lys Lys Lys Tyr Pro Asn
1               5                   10                  15

<210> SEQ ID NO 809
<211> LENGTH: 15
<212> TYPE: PRT
<213> ORGANISM: Dermatophagoides farinae

<400> SEQUENCE: 809

Asp Glu Ser Val Glu Phe Lys Ser Leu Phe Glu Ser Trp Gln Met
1               5                   10                  15

<210> SEQ ID NO 810
<211> LENGTH: 15
<212> TYPE: PRT
<213> ORGANISM: Dermatophagoides farinae

<400> SEQUENCE: 810

Phe Lys Ser Leu Phe Glu Ser Trp Gln Met Ser Glu Gln Glu Lys
1               5                   10                  15

<210> SEQ ID NO 811
<211> LENGTH: 15
<212> TYPE: PRT
<213> ORGANISM: Dermatophagoides farinae

<400> SEQUENCE: 811

Ser Glu Gln Glu Lys Ile Thr Ser Ala Arg Leu Phe Arg Val Ser
1               5                   10                  15

<210> SEQ ID NO 812
<211> LENGTH: 15
<212> TYPE: PRT
<213> ORGANISM: Dermatophagoides farinae

<400> SEQUENCE: 812

Ile Thr Ser Ala Arg Leu Phe Arg Val Ser Arg Asn Gly Ile Phe
1               5                   10                  15

<210> SEQ ID NO 813
<211> LENGTH: 15
<212> TYPE: PRT
<213> ORGANISM: Dermatophagoides farinae

<400> SEQUENCE: 813

Val Met Asp Lys Ile Tyr Val Trp Ile Gly Asn Gln Phe Ala Glu
1               5                   10                  15

<210> SEQ ID NO 814
<211> LENGTH: 15
<212> TYPE: PRT
<213> ORGANISM: Dermatophagoides farinae

<400> SEQUENCE: 814

Tyr Val Trp Ile Gly Asn Gln Phe Ala Glu Arg Ile Ala Asp Glu
1               5                   10                  15

<210> SEQ ID NO 815
<211> LENGTH: 15
<212> TYPE: PRT
<213> ORGANISM: Dermatophagoides farinae

<400> SEQUENCE: 815

Ser Gly Arg Lys Phe Gln Pro Asn Gln Ile Ile Lys Leu Lys Gln
1               5                   10                  15

<210> SEQ ID NO 816
<211> LENGTH: 15
<212> TYPE: PRT
<213> ORGANISM: Dermatophagoides farinae

<400> SEQUENCE: 816

Met Thr Arg Phe Ser Leu Thr Val Leu Ala Val Leu Ala Ala Cys
1               5                   10                  15

<210> SEQ ID NO 817
<211> LENGTH: 15
<212> TYPE: PRT
<213> ORGANISM: Dermatophagoides farinae

<400> SEQUENCE: 817

Leu Thr Val Leu Ala Val Leu Ala Ala Cys Phe Gly Ser Asn Ile
1               5                   10                  15

<210> SEQ ID NO 818
<211> LENGTH: 15
<212> TYPE: PRT
<213> ORGANISM: Dermatophagoides farinae

<400> SEQUENCE: 818

```
Ser Leu Cys Thr His Ile Val Tyr Ser Tyr Phe Gly Ile Asp Ala
1               5                   10                  15

<210> SEQ ID NO 819
<211> LENGTH: 15
<212> TYPE: PRT
<213> ORGANISM: Dermatophagoides farinae

<400> SEQUENCE: 819

Ile Val Tyr Ser Tyr Phe Gly Ile Asp Ala Ala Thr His Glu Ile
1               5                   10                  15

<210> SEQ ID NO 820
<211> LENGTH: 15
<212> TYPE: PRT
<213> ORGANISM: Dermatophagoides farinae

<400> SEQUENCE: 820

Ala Thr His Glu Ile Lys Leu Leu Asp Glu Tyr Leu Met Lys Asp
1               5                   10                  15

<210> SEQ ID NO 821
<211> LENGTH: 15
<212> TYPE: PRT
<213> ORGANISM: Dermatophagoides farinae

<400> SEQUENCE: 821

Glu His Tyr Arg Glu Thr Phe Val Val Ser Thr Val Asp Leu Met
1               5                   10                  15

<210> SEQ ID NO 822
<211> LENGTH: 15
<212> TYPE: PRT
<213> ORGANISM: Dermatophagoides farinae

<400> SEQUENCE: 822

Thr Phe Val Val Ser Thr Val Asp Leu Met Thr Arg Tyr Gly Phe
1               5                   10                  15

<210> SEQ ID NO 823
<211> LENGTH: 15
<212> TYPE: PRT
<213> ORGANISM: Dermatophagoides farinae

<400> SEQUENCE: 823

His Thr Ser Phe Val Met Gly Val Thr Leu Pro Ala Thr Ile Ala
1               5                   10                  15

<210> SEQ ID NO 824
<211> LENGTH: 15
<212> TYPE: PRT
<213> ORGANISM: Dermatophagoides farinae

<400> SEQUENCE: 824

Ser Asn Tyr Val Asp Phe Met Asn Val Leu Ser Leu Asp Tyr Thr
1               5                   10                  15

<210> SEQ ID NO 825
<211> LENGTH: 15
<212> TYPE: PRT
<213> ORGANISM: Dermatophagoides farinae

<400> SEQUENCE: 825

His Lys Met Val Met Ala Val Pro Phe Tyr Ala Arg Thr Trp Ile
```

```
1               5                   10                  15

<210> SEQ ID NO 826
<211> LENGTH: 15
<212> TYPE: PRT
<213> ORGANISM: Dermatophagoides farinae

<400> SEQUENCE: 826

Ala Val Pro Phe Tyr Ala Arg Thr Trp Ile Leu Glu Lys Met Asn
1               5                   10                  15

<210> SEQ ID NO 827
<211> LENGTH: 15
<212> TYPE: PRT
<213> ORGANISM: Dermatophagoides farinae

<400> SEQUENCE: 827

Asp Gly Phe Leu Ser Tyr Asn Glu Leu Cys Val Gln Ile Gln Ala
1               5                   10                  15

<210> SEQ ID NO 828
<211> LENGTH: 15
<212> TYPE: PRT
<213> ORGANISM: Dermatophagoides farinae

<400> SEQUENCE: 828

His Asp Asn Thr Ala Ile Tyr Ala Val Tyr Val His Ser Asn His
1               5                   10                  15

<210> SEQ ID NO 829
<211> LENGTH: 15
<212> TYPE: PRT
<213> ORGANISM: Dermatophagoides farinae

<400> SEQUENCE: 829

Ile Tyr Ala Val Tyr Val His Ser Asn His Ala Glu Trp Ile Ser
1               5                   10                  15

<210> SEQ ID NO 830
<211> LENGTH: 15
<212> TYPE: PRT
<213> ORGANISM: Dermatophagoides farinae

<400> SEQUENCE: 830

Pro Leu Leu His Ala Ile Gln Ser Asn Tyr Tyr His Gly Val Val
1               5                   10                  15

<210> SEQ ID NO 831
<211> LENGTH: 15
<212> TYPE: PRT
<213> ORGANISM: Dermatophagoides farinae

<400> SEQUENCE: 831

Met Ile Ser Lys Ile Leu Cys Leu Ser Leu Leu Val Ala Ala Val
1               5                   10                  15

<210> SEQ ID NO 832
<211> LENGTH: 15
<212> TYPE: PRT
<213> ORGANISM: Dermatophagoides farinae

<400> SEQUENCE: 832

Leu Cys Leu Ser Leu Leu Val Ala Ala Val Val Ala Asp Gln Val
1               5                   10                  15
```

<210> SEQ ID NO 833
<211> LENGTH: 15
<212> TYPE: PRT
<213> ORGANISM: Dermatophagoides farinae

<400> SEQUENCE: 833

Pro Phe Thr Leu Glu Ala Leu Phe Asp Ala Asn Gln Asn Thr Lys
1               5                   10                  15

<210> SEQ ID NO 834
<211> LENGTH: 15
<212> TYPE: PRT
<213> ORGANISM: Dermatophagoides farinae

<400> SEQUENCE: 834

Gln Gln Tyr Asp Ile Lys Tyr Thr Trp Asn Val Pro Lys Ile Ala
1               5                   10                  15

<210> SEQ ID NO 835
<211> LENGTH: 15
<212> TYPE: PRT
<213> ORGANISM: Dermatophagoides farinae

<400> SEQUENCE: 835

Val Val Val Thr Val Lys Leu Ile Gly Asp Asn Gly Val Leu Ala
1               5                   10                  15

<210> SEQ ID NO 836
<211> LENGTH: 15
<212> TYPE: PRT
<213> ORGANISM: Dermatophagoides farinae

<400> SEQUENCE: 836

Met Met Ile Leu Thr Ile Val Val Leu Leu Ala Ala Asn Ile Leu
1               5                   10                  15

<210> SEQ ID NO 837
<211> LENGTH: 15
<212> TYPE: PRT
<213> ORGANISM: Dermatophagoides farinae

<400> SEQUENCE: 837

Ile Val Val Leu Leu Ala Ala Asn Ile Leu Ala Thr Pro Ile Leu
1               5                   10                  15

<210> SEQ ID NO 838
<211> LENGTH: 15
<212> TYPE: PRT
<213> ORGANISM: Dermatophagoides farinae

<400> SEQUENCE: 838

Ala Ala Asn Ile Leu Ala Thr Pro Ile Leu Pro Ser Ser Pro Asn
1               5                   10                  15

<210> SEQ ID NO 839
<211> LENGTH: 15
<212> TYPE: PRT
<213> ORGANISM: Dermatophagoides farinae

<400> SEQUENCE: 839

Ala Gly Asp Cys Pro Tyr Gln Ile Ser Leu Gln Ser Ser Ser His
1               5                   10                  15

<210> SEQ ID NO 840

```
<210> SEQ ID NO 840
<211> LENGTH: 15
<212> TYPE: PRT
<213> ORGANISM: Dermatophagoides farinae

<400> SEQUENCE: 840

Tyr Gln Ile Ser Leu Gln Ser Ser His Phe Cys Gly Gly Ser
1               5                   10                  15

<210> SEQ ID NO 841
<211> LENGTH: 15
<212> TYPE: PRT
<213> ORGANISM: Dermatophagoides farinae

<400> SEQUENCE: 841

Ile Leu Asp Glu Tyr Trp Ile Leu Thr Ala Ala His Cys Val Asn
1               5                   10                  15

<210> SEQ ID NO 842
<211> LENGTH: 15
<212> TYPE: PRT
<213> ORGANISM: Dermatophagoides farinae

<400> SEQUENCE: 842

Lys Leu Ser Ile Arg Tyr Asn Thr Leu Lys His Ala Ser Gly Gly
1               5                   10                  15

<210> SEQ ID NO 843
<211> LENGTH: 15
<212> TYPE: PRT
<213> ORGANISM: Dermatophagoides farinae

<400> SEQUENCE: 843

Asn Asp Val Ala Leu Ile Lys Leu Lys Thr Pro Met Thr Leu Asp
1               5                   10                  15

<210> SEQ ID NO 844
<211> LENGTH: 15
<212> TYPE: PRT
<213> ORGANISM: Dermatophagoides farinae

<400> SEQUENCE: 844

Met Ile Lys Ile Phe Leu Val Thr Ile Leu Ile Val Ile Thr Val
1               5                   10                  15

<210> SEQ ID NO 845
<211> LENGTH: 15
<212> TYPE: PRT
<213> ORGANISM: Dermatophagoides farinae

<400> SEQUENCE: 845

Leu Val Thr Ile Leu Ile Val Ile Thr Val Thr Val Asp Ala Arg
1               5                   10                  15

<210> SEQ ID NO 846
<211> LENGTH: 15
<212> TYPE: PRT
<213> ORGANISM: Dermatophagoides farinae

<400> SEQUENCE: 846

Gln Pro Lys Trp Ala Tyr Leu Asp Ser Asn Glu Phe Pro Arg Ser
1               5                   10                  15

<210> SEQ ID NO 847
<211> LENGTH: 15
<212> TYPE: PRT
```

<213> ORGANISM: Dermatophagoides farinae

<400> SEQUENCE: 847

Ala Pro Phe Gln Ile Ser Leu Leu Lys Asp Tyr Leu Ile Met Lys
1               5                   10                  15

<210> SEQ ID NO 848
<211> LENGTH: 15
<212> TYPE: PRT
<213> ORGANISM: Dermatophagoides farinae

<400> SEQUENCE: 848

Ser Leu Leu Lys Asp Tyr Leu Ile Met Lys Arg His Met Cys Gly
1               5                   10                  15

<210> SEQ ID NO 849
<211> LENGTH: 15
<212> TYPE: PRT
<213> ORGANISM: Dermatophagoides farinae

<400> SEQUENCE: 849

Lys Thr Ile Ile Ile Leu Pro Asn Pro Val Val Pro Ser Thr Asn
1               5                   10                  15

<210> SEQ ID NO 850
<211> LENGTH: 15
<212> TYPE: PRT
<213> ORGANISM: Dermatophagoides farinae

<400> SEQUENCE: 850

Thr Arg Pro Lys Tyr Tyr Leu Asp Trp Ile Thr Lys Asn Ile Val
1               5                   10                  15

<210> SEQ ID NO 851
<211> LENGTH: 15
<212> TYPE: PRT
<213> ORGANISM: Dermatophagoides farinae

<400> SEQUENCE: 851

Met Met Lys Phe Leu Leu Ile Ala Ala Val Ala Phe Val Ala Val
1               5                   10                  15

<210> SEQ ID NO 852
<211> LENGTH: 15
<212> TYPE: PRT
<213> ORGANISM: Dermatophagoides farinae

<400> SEQUENCE: 852

Leu Ile Ala Ala Val Ala Phe Val Ala Val Ser Ala Asp Pro Ile
1               5                   10                  15

<210> SEQ ID NO 853
<211> LENGTH: 15
<212> TYPE: PRT
<213> ORGANISM: Dermatophagoides farinae

<400> SEQUENCE: 853

Ala Phe Val Ala Val Ser Ala Asp Pro Ile His Tyr Asp Lys Ile
1               5                   10                  15

<210> SEQ ID NO 854
<211> LENGTH: 15
<212> TYPE: PRT
<213> ORGANISM: Dermatophagoides farinae -continued

<400> SEQUENCE: 854

Ile Val Ser Met Glu Tyr Asp Leu Ala Tyr Lys Leu Gly Asp Leu
1               5                   10                  15

<210> SEQ ID NO 855
<211> LENGTH: 15
<212> TYPE: PRT
<213> ORGANISM: Dermatophagoides farinae

<400> SEQUENCE: 855

Val Ile Ser Asp Ile Gln Asp Phe Val Val Ala Leu Ser Leu Glu
1               5                   10                  15

<210> SEQ ID NO 856
<211> LENGTH: 15
<212> TYPE: PRT
<213> ORGANISM: Dermatophagoides farinae

<400> SEQUENCE: 856

Gln Asp Phe Val Val Ala Leu Ser Leu Glu Ile Ser Asp Glu Gly
1               5                   10                  15

<210> SEQ ID NO 857
<211> LENGTH: 15
<212> TYPE: PRT
<213> ORGANISM: Dermatophagoides farinae

<400> SEQUENCE: 857

Ser Phe Glu Val Arg Gln Phe Ala Asn Val Val Asn His Ile Gly
1               5                   10                  15

<210> SEQ ID NO 858
<211> LENGTH: 15
<212> TYPE: PRT
<213> ORGANISM: Dermatophagoides farinae

<400> SEQUENCE: 858

Gln Phe Ala Asn Val Val Asn His Ile Gly Gly Leu Ser Ile Leu
1               5                   10                  15

<210> SEQ ID NO 859
<211> LENGTH: 15
<212> TYPE: PRT
<213> ORGANISM: Dermatophagoides farinae

<400> SEQUENCE: 859

Val Asn His Ile Gly Gly Leu Ser Ile Leu Asp Pro Ile Phe Gly
1               5                   10                  15

<210> SEQ ID NO 860
<211> LENGTH: 15
<212> TYPE: PRT
<213> ORGANISM: Dermatophagoides farinae

<400> SEQUENCE: 860

Gly Leu Ser Ile Leu Asp Pro Ile Phe Gly Val Leu Ser Asp Val
1               5                   10                  15

<210> SEQ ID NO 861
<211> LENGTH: 15
<212> TYPE: PRT
<213> ORGANISM: Dermatophagoides farinae

<400> SEQUENCE: 861

-continued

Asp Pro Ile Phe Gly Val Leu Ser Asp Val Leu Thr Ala Ile Phe
1               5                   10                  15

<210> SEQ ID NO 862
<211> LENGTH: 15
<212> TYPE: PRT
<213> ORGANISM: Dermatophagoides pteronyssinus

<400> SEQUENCE: 862

Met Lys Ile Val Leu Ala Ile Ala Ser Leu Leu Ala Leu Ser Ala
1               5                   10                  15

<210> SEQ ID NO 863
<211> LENGTH: 15
<212> TYPE: PRT
<213> ORGANISM: Dermatophagoides pteronyssinus

<400> SEQUENCE: 863

Ala Ile Ala Ser Leu Leu Ala Leu Ser Ala Val Tyr Ala Arg Pro
1               5                   10                  15

<210> SEQ ID NO 864
<211> LENGTH: 15
<212> TYPE: PRT
<213> ORGANISM: Dermatophagoides pteronyssinus

<400> SEQUENCE: 864

Leu Ala Leu Ser Ala Val Tyr Ala Arg Pro Ser Ser Ile Lys Thr
1               5                   10                  15

<210> SEQ ID NO 865
<211> LENGTH: 15
<212> TYPE: PRT
<213> ORGANISM: Dermatophagoides pteronyssinus

<400> SEQUENCE: 865

Lys Ala Phe Asn Lys Ser Tyr Ala Thr Phe Glu Asp Glu Glu Ala
1               5                   10                  15

<210> SEQ ID NO 866
<211> LENGTH: 15
<212> TYPE: PRT
<213> ORGANISM: Dermatophagoides pteronyssinus

<400> SEQUENCE: 866

Ala Arg Lys Asn Phe Leu Glu Ser Val Lys Tyr Val Gln Ser Asn
1               5                   10                  15

<210> SEQ ID NO 867
<211> LENGTH: 15
<212> TYPE: PRT
<213> ORGANISM: Dermatophagoides pteronyssinus

<400> SEQUENCE: 867

Leu Glu Ser Val Lys Tyr Val Gln Ser Asn Gly Gly Ala Ile Asn
1               5                   10                  15

<210> SEQ ID NO 868
<211> LENGTH: 15
<212> TYPE: PRT
<213> ORGANISM: Dermatophagoides pteronyssinus

<400> SEQUENCE: 868

Gly Gly Ala Ile Asn His Leu Ser Asp Leu Ser Leu Asp Glu Phe
1               5                   10                  15

<210> SEQ ID NO 869
<211> LENGTH: 15
<212> TYPE: PRT
<213> ORGANISM: Dermatophagoides pteronyssinus

<400> SEQUENCE: 869

Ser Leu Asp Glu Phe Lys Asn Arg Phe Leu Met Ser Ala Glu Ala
1               5                   10                  15

<210> SEQ ID NO 870
<211> LENGTH: 15
<212> TYPE: PRT
<213> ORGANISM: Dermatophagoides pteronyssinus

<400> SEQUENCE: 870

Lys Asn Arg Phe Leu Met Ser Ala Glu Ala Phe Glu His Leu Lys
1               5                   10                  15

<210> SEQ ID NO 871
<211> LENGTH: 15
<212> TYPE: PRT
<213> ORGANISM: Dermatophagoides pteronyssinus

<400> SEQUENCE: 871

Met Ser Ala Glu Ala Phe Glu His Leu Lys Thr Gln Phe Asp Leu
1               5                   10                  15

<210> SEQ ID NO 872
<211> LENGTH: 15
<212> TYPE: PRT
<213> ORGANISM: Dermatophagoides pteronyssinus

<400> SEQUENCE: 872

Phe Glu His Leu Lys Thr Gln Phe Asp Leu Asn Ala Glu Thr Asn
1               5                   10                  15

<210> SEQ ID NO 873
<211> LENGTH: 15
<212> TYPE: PRT
<213> ORGANISM: Dermatophagoides pteronyssinus

<400> SEQUENCE: 873

Glu Ile Asp Leu Arg Gln Met Arg Thr Val Thr Pro Ile Arg Met
1               5                   10                  15

<210> SEQ ID NO 874
<211> LENGTH: 15
<212> TYPE: PRT
<213> ORGANISM: Dermatophagoides pteronyssinus

<400> SEQUENCE: 874

Ser Cys Trp Ala Phe Ser Gly Val Ala Ala Thr Glu Ser Ala Tyr
1               5                   10                  15

<210> SEQ ID NO 875
<211> LENGTH: 15
<212> TYPE: PRT
<213> ORGANISM: Dermatophagoides pteronyssinus

<400> SEQUENCE: 875

Ser Gly Val Ala Ala Thr Glu Ser Ala Tyr Leu Ala Tyr Arg Asn
1               5                   10                  15

```
<210> SEQ ID NO 876
<211> LENGTH: 15
<212> TYPE: PRT
<213> ORGANISM: Dermatophagoides pteronyssinus

<400> SEQUENCE: 876

Thr Glu Ser Ala Tyr Leu Ala Tyr Arg Asn Gln Ser Leu Asp Leu
1               5                   10                  15

<210> SEQ ID NO 877
<211> LENGTH: 15
<212> TYPE: PRT
<213> ORGANISM: Dermatophagoides pteronyssinus

<400> SEQUENCE: 877

Arg Gly Ile Glu Tyr Ile Gln His Asn Gly Val Val Gln Glu Ser
1               5                   10                  15

<210> SEQ ID NO 878
<211> LENGTH: 15
<212> TYPE: PRT
<213> ORGANISM: Dermatophagoides pteronyssinus

<400> SEQUENCE: 878

Val Val Gln Glu Ser Tyr Tyr Arg Tyr Val Ala Arg Glu Gln Ser
1               5                   10                  15

<210> SEQ ID NO 879
<211> LENGTH: 15
<212> TYPE: PRT
<213> ORGANISM: Dermatophagoides pteronyssinus

<400> SEQUENCE: 879

Ile Ser Asn Tyr Cys Gln Ile Tyr Pro Pro Asn Val Asn Lys Ile
1               5                   10                  15

<210> SEQ ID NO 880
<211> LENGTH: 15
<212> TYPE: PRT
<213> ORGANISM: Dermatophagoides pteronyssinus

<400> SEQUENCE: 880

Arg Glu Ala Leu Ala Gln Thr His Ser Ala Ile Ala Val Ile Ile
1               5                   10                  15

<210> SEQ ID NO 881
<211> LENGTH: 15
<212> TYPE: PRT
<213> ORGANISM: Dermatophagoides pteronyssinus

<400> SEQUENCE: 881

Gln Thr His Ser Ala Ile Ala Val Ile Ile Gly Ile Lys Asp Leu
1               5                   10                  15

<210> SEQ ID NO 882
<211> LENGTH: 15
<212> TYPE: PRT
<213> ORGANISM: Dermatophagoides pteronyssinus

<400> SEQUENCE: 882

Asp Asn Gly Tyr Gly Tyr Phe Ala Ala Asn Ile Asp Leu Met Met
1               5                   10                  15

<210> SEQ ID NO 883
<211> LENGTH: 15
```

-continued

<212> TYPE: PRT
<213> ORGANISM: Dermatophagoides pteronyssinus

<400> SEQUENCE: 883

Ile Asp Leu Met Met Ile Glu Glu Tyr Pro Tyr Val Val Ile Leu
1               5                   10                  15

<210> SEQ ID NO 884
<211> LENGTH: 15
<212> TYPE: PRT
<213> ORGANISM: Dermatophagoides pteronyssinus

<400> SEQUENCE: 884

Arg Ser Glu Glu Arg Leu Lys Ile Ala Thr Ala Lys Leu Glu Glu
1               5                   10                  15

<210> SEQ ID NO 885
<211> LENGTH: 15
<212> TYPE: PRT
<213> ORGANISM: Dermatophagoides pteronyssinus

<400> SEQUENCE: 885

Leu Lys Ile Ala Thr Ala Lys Leu Glu Glu Ala Ser Gln Ser Ala
1               5                   10                  15

<210> SEQ ID NO 886
<211> LENGTH: 15
<212> TYPE: PRT
<213> ORGANISM: Dermatophagoides pteronyssinus

<400> SEQUENCE: 886

Val Glu Leu Glu Glu Glu Leu Arg Val Val Gly Asn Asn Leu Lys
1               5                   10                  15

<210> SEQ ID NO 887
<211> LENGTH: 15
<212> TYPE: PRT
<213> ORGANISM: Dermatophagoides pteronyssinus

<400> SEQUENCE: 887

His Glu Gln Gln Ile Arg Ile Met Thr Thr Lys Leu Lys Glu Ala
1               5                   10                  15

<210> SEQ ID NO 888
<211> LENGTH: 15
<212> TYPE: PRT
<213> ORGANISM: Dermatophagoides pteronyssinus

<400> SEQUENCE: 888

Ala Glu Leu Gln Ile Gln Val Met Ser Leu Ser Glu Arg Leu Glu
1               5                   10                  15

<210> SEQ ID NO 889
<211> LENGTH: 15
<212> TYPE: PRT
<213> ORGANISM: Dermatophagoides pteronyssinus

<400> SEQUENCE: 889

Gln Lys Phe Gln Ala Glu Val Phe Glu Leu Leu Ser Gln Leu Glu
1               5                   10                  15

<210> SEQ ID NO 890
<211> LENGTH: 15
<212> TYPE: PRT
<213> ORGANISM: Dermatophagoides pteronyssinus -continued

```
<400> SEQUENCE: 890

Glu Val Phe Glu Leu Leu Ser Gln Leu Glu Thr Ala Asn Lys Glu
1               5                   10                  15

<210> SEQ ID NO 891
<211> LENGTH: 15
<212> TYPE: PRT
<213> ORGANISM: Dermatophagoides pteronyssinus

<400> SEQUENCE: 891

Leu Glu Tyr Thr Val His Glu Leu Asn Ile Lys Ile Glu Glu Ile
1               5                   10                  15

<210> SEQ ID NO 892
<211> LENGTH: 15
<212> TYPE: PRT
<213> ORGANISM: Dermatophagoides pteronyssinus

<400> SEQUENCE: 892

His Glu Leu Asn Ile Lys Ile Glu Glu Ile Asn Arg Thr Val Ile
1               5                   10                  15

<210> SEQ ID NO 893
<211> LENGTH: 15
<212> TYPE: PRT
<213> ORGANISM: Dermatophagoides pteronyssinus

<400> SEQUENCE: 893

His Glu Val Lys Leu Gln Leu Asp Asn Ala Asn His Leu Lys Gln
1               5                   10                  15

<210> SEQ ID NO 894
<211> LENGTH: 15
<212> TYPE: PRT
<213> ORGANISM: Dermatophagoides pteronyssinus

<400> SEQUENCE: 894

Asn His Leu Lys Gln Gln Ile Ala Gln Gln Leu Glu Asp Thr Arg
1               5                   10                  15

<210> SEQ ID NO 895
<211> LENGTH: 15
<212> TYPE: PRT
<213> ORGANISM: Dermatophagoides pteronyssinus

<400> SEQUENCE: 895

Glu Ala Arg Leu Glu Leu Glu Arg Gln Leu Thr Lys Ala Asn Gly
1               5                   10                  15

<210> SEQ ID NO 896
<211> LENGTH: 15
<212> TYPE: PRT
<213> ORGANISM: Dermatophagoides pteronyssinus

<400> SEQUENCE: 896

Glu Glu Leu Arg Arg Lys Met Ala Gln Lys Ile Ser Glu Tyr Glu
1               5                   10                  15

<210> SEQ ID NO 897
<211> LENGTH: 15
<212> TYPE: PRT
<213> ORGANISM: Dermatophagoides pteronyssinus

<400> SEQUENCE: 897
```

```
Gln Ser Glu Val Glu Val Leu Ile Met Asp Leu Glu Lys Ala Ala
1               5                   10                  15

<210> SEQ ID NO 898
<211> LENGTH: 15
<212> TYPE: PRT
<213> ORGANISM: Dermatophagoides pteronyssinus

<400> SEQUENCE: 898

Val Leu Ile Met Asp Leu Glu Lys Ala Ala Ala His Ala Gln Gln
1               5                   10                  15

<210> SEQ ID NO 899
<211> LENGTH: 15
<212> TYPE: PRT
<213> ORGANISM: Dermatophagoides pteronyssinus

<400> SEQUENCE: 899

Lys Asn Gln Arg Leu Ile Ala Glu Leu Ala Gln Val Arg His Asp
1               5                   10                  15

<210> SEQ ID NO 900
<211> LENGTH: 15
<212> TYPE: PRT
<213> ORGANISM: Dermatophagoides pteronyssinus

<400> SEQUENCE: 900

Glu Ile Glu Ala Leu Arg Lys Gln Tyr Gln Ile Glu Ile Glu Gln
1               5                   10                  15

<210> SEQ ID NO 901
<211> LENGTH: 15
<212> TYPE: PRT
<213> ORGANISM: Dermatophagoides pteronyssinus

<400> SEQUENCE: 901

Arg Lys Gln Tyr Gln Ile Glu Ile Glu Gln Leu Asn Met Arg Leu
1               5                   10                  15

<210> SEQ ID NO 902
<211> LENGTH: 15
<212> TYPE: PRT
<213> ORGANISM: Dermatophagoides pteronyssinus

<400> SEQUENCE: 902

Ile Glu Ile Glu Gln Leu Asn Met Arg Leu Ala Glu Ala Glu Ala
1               5                   10                  15

<210> SEQ ID NO 903
<211> LENGTH: 15
<212> TYPE: PRT
<213> ORGANISM: Dermatophagoides pteronyssinus

<400> SEQUENCE: 903

Ile Ala Arg Leu Lys Lys Lys Tyr Gln Ala Gln Ile Thr Glu Leu
1               5                   10                  15

<210> SEQ ID NO 904
<211> LENGTH: 15
<212> TYPE: PRT
<213> ORGANISM: Dermatophagoides pteronyssinus

<400> SEQUENCE: 904

Lys Lys Tyr Gln Ala Gln Ile Thr Glu Leu Glu Leu Ser Leu Asp
```

-continued

```
1               5                   10                  15
```

<210> SEQ ID NO 905
<211> LENGTH: 15
<212> TYPE: PRT
<213> ORGANISM: Dermatophagoides pteronyssinus

<400> SEQUENCE: 905

```
Lys Thr Ile Lys Lys Gln Ala Leu Gln Ile Thr Glu Leu Gln Ala
1               5                   10                  15
```

<210> SEQ ID NO 906
<211> LENGTH: 15
<212> TYPE: PRT
<213> ORGANISM: Dermatophagoides pteronyssinus

<400> SEQUENCE: 906

```
Glu Glu Met Arg Ile Ala Leu Glu Gln Ala Ser Arg Ala Lys Arg
1               5                   10                  15
```

<210> SEQ ID NO 907
<211> LENGTH: 15
<212> TYPE: PRT
<213> ORGANISM: Dermatophagoides pteronyssinus

<400> SEQUENCE: 907

```
Val Arg Val Asn Glu Leu Thr Thr Ile Asn Val Asn Leu Ala Ser
1               5                   10                  15
```

<210> SEQ ID NO 908
<211> LENGTH: 15
<212> TYPE: PRT
<213> ORGANISM: Dermatophagoides pteronyssinus

<400> SEQUENCE: 908

```
Leu Thr Thr Ile Asn Val Asn Leu Ala Ser Ala Lys Ser Lys Leu
1               5                   10                  15
```

<210> SEQ ID NO 909
<211> LENGTH: 15
<212> TYPE: PRT
<213> ORGANISM: Dermatophagoides pteronyssinus

<400> SEQUENCE: 909

```
Val Asn Leu Ala Ser Ala Lys Ser Lys Leu Glu Ser Glu Phe Ser
1               5                   10                  15
```

<210> SEQ ID NO 910
<211> LENGTH: 15
<212> TYPE: PRT
<213> ORGANISM: Dermatophagoides pteronyssinus

<400> SEQUENCE: 910

```
Ala Lys Ser Lys Leu Glu Ser Glu Phe Ser Ala Leu Gln Ala Asp
1               5                   10                  15
```

<210> SEQ ID NO 911
<211> LENGTH: 15
<212> TYPE: PRT
<213> ORGANISM: Dermatophagoides pteronyssinus

<400> SEQUENCE: 911

```
Gln Lys Leu Thr Ile Glu Leu Lys Ser Thr Lys Asp Leu Leu Ile
1               5                   10                  15
```

<210> SEQ ID NO 912
<211> LENGTH: 15
<212> TYPE: PRT
<213> ORGANISM: Dermatophagoides pteronyssinus

<400> SEQUENCE: 912

Glu Leu Lys Ser Thr Lys Asp Leu Leu Ile Glu Glu Gln Glu Arg
1               5                   10                  15

<210> SEQ ID NO 913
<211> LENGTH: 15
<212> TYPE: PRT
<213> ORGANISM: Dermatophagoides pteronyssinus

<400> SEQUENCE: 913

Leu Val Lys Leu Glu Thr Val Lys Lys Ser Leu Glu Gln Glu Val
1               5                   10                  15

<210> SEQ ID NO 914
<211> LENGTH: 15
<212> TYPE: PRT
<213> ORGANISM: Dermatophagoides pteronyssinus

<400> SEQUENCE: 914

Arg Thr Leu His Val Arg Ile Glu Glu Val Glu Ala Asn Ala Leu
1               5                   10                  15

<210> SEQ ID NO 915
<211> LENGTH: 15
<212> TYPE: PRT
<213> ORGANISM: Dermatophagoides pteronyssinus

<400> SEQUENCE: 915

Ala Gly Gly Lys Arg Val Ile Ala Lys Leu Glu Ser Arg Ile Arg
1               5                   10                  15

<210> SEQ ID NO 916
<211> LENGTH: 15
<212> TYPE: PRT
<213> ORGANISM: Dermatophagoides pteronyssinus

<400> SEQUENCE: 916

Asp Gln Ala Glu Ser Asn Leu Ser Phe Ile Arg Ala Lys His Arg
1               5                   10                  15

<210> SEQ ID NO 917
<211> LENGTH: 15
<212> TYPE: PRT
<213> ORGANISM: Dermatophagoides pteronyssinus

<400> SEQUENCE: 917

Ala Gln Ser Thr Tyr Val Tyr Ser Leu Asp Ala Lys Thr Val Leu
1               5                   10                  15

<210> SEQ ID NO 918
<211> LENGTH: 15
<212> TYPE: PRT
<213> ORGANISM: Dermatophagoides pteronyssinus

<400> SEQUENCE: 918

Val Tyr Ser Leu Asp Ala Lys Thr Val Leu Thr Pro Arg Asp Ser
1               5                   10                  15

<210> SEQ ID NO 919

-continued

```
<210> SEQ ID NO 919
<211> LENGTH: 15
<212> TYPE: PRT
<213> ORGANISM: Dermatophagoides pteronyssinus

<400> SEQUENCE: 919

Val Ala Phe Val Ser Asp Cys Glu Ala Val Leu Arg Leu Gln Asn
1               5                   10                  15

<210> SEQ ID NO 920
<211> LENGTH: 15
<212> TYPE: PRT
<213> ORGANISM: Dermatophagoides pteronyssinus

<400> SEQUENCE: 920

Asp Cys Glu Ala Val Leu Arg Leu Gln Asn Val Ala Ile Asp Gly
1               5                   10                  15

<210> SEQ ID NO 921
<211> LENGTH: 15
<212> TYPE: PRT
<213> ORGANISM: Dermatophagoides pteronyssinus

<400> SEQUENCE: 921

Phe Ala Phe Gly Tyr Phe Asn Gly Arg Ile Leu Gly Val Cys Pro
1               5                   10                  15

<210> SEQ ID NO 922
<211> LENGTH: 15
<212> TYPE: PRT
<213> ORGANISM: Dermatophagoides pteronyssinus

<400> SEQUENCE: 922

Asp Trp Ser Leu Asn Val Lys Lys Ala Ile Val Ser Ser Leu Gln
1               5                   10                  15

<210> SEQ ID NO 923
<211> LENGTH: 15
<212> TYPE: PRT
<213> ORGANISM: Dermatophagoides pteronyssinus

<400> SEQUENCE: 923

Val Lys Lys Ala Ile Val Ser Ser Leu Gln Ala Leu Ser Asp Gly
1               5                   10                  15

<210> SEQ ID NO 924
<211> LENGTH: 15
<212> TYPE: PRT
<213> ORGANISM: Dermatophagoides pteronyssinus

<400> SEQUENCE: 924

Lys Pro Val His Met Ser Tyr Val Lys Met Met Leu Lys Gln Asn
1               5                   10                  15

<210> SEQ ID NO 925
<211> LENGTH: 15
<212> TYPE: PRT
<213> ORGANISM: Dermatophagoides pteronyssinus

<400> SEQUENCE: 925

Glu Val Leu Lys Lys Leu Cys Ser Glu Ile Thr Glu Pro Gln Ala
1               5                   10                  15

<210> SEQ ID NO 926
<211> LENGTH: 15
<212> TYPE: PRT
```

<213> ORGANISM: Dermatophagoides pteronyssinus

<400> SEQUENCE: 926

Phe Thr Phe Gln Lys Leu Val Asp Lys Leu Arg Tyr Leu Ser Ala
1               5                   10                  15

<210> SEQ ID NO 927
<211> LENGTH: 15
<212> TYPE: PRT
<213> ORGANISM: Dermatophagoides pteronyssinus

<400> SEQUENCE: 927

Leu Val Asp Lys Leu Arg Tyr Leu Ser Ala Glu Glu Thr Ala Ser
1               5                   10                  15

<210> SEQ ID NO 928
<211> LENGTH: 15
<212> TYPE: PRT
<213> ORGANISM: Dermatophagoides pteronyssinus

<400> SEQUENCE: 928

Arg Leu Arg Glu Leu Phe Leu Asp Ala Ser Ala Phe Ala Ala Ser
1               5                   10                  15

<210> SEQ ID NO 929
<211> LENGTH: 15
<212> TYPE: PRT
<213> ORGANISM: Dermatophagoides pteronyssinus

<400> SEQUENCE: 929

Phe Leu Asp Ala Ser Ala Phe Ala Ala Ser Asp Gly Ser Ile Arg
1               5                   10                  15

<210> SEQ ID NO 930
<211> LENGTH: 15
<212> TYPE: PRT
<213> ORGANISM: Dermatophagoides pteronyssinus

<400> SEQUENCE: 930

Leu Ser Ile Thr Arg Ser Thr Ala Leu Phe Thr Val Ala Ala Ile
1               5                   10                  15

<210> SEQ ID NO 931
<211> LENGTH: 15
<212> TYPE: PRT
<213> ORGANISM: Dermatophagoides pteronyssinus

<400> SEQUENCE: 931

Ser Thr Ala Leu Phe Thr Val Ala Ala Ile Lys Ala Ala Pro Asn
1               5                   10                  15

<210> SEQ ID NO 932
<211> LENGTH: 15
<212> TYPE: PRT
<213> ORGANISM: Dermatophagoides pteronyssinus

<400> SEQUENCE: 932

Lys Glu Thr Val Gln Val Leu Leu Pro Val Ile Ala Ser Glu Lys
1               5                   10                  15

<210> SEQ ID NO 933
<211> LENGTH: 15
<212> TYPE: PRT
<213> ORGANISM: Dermatophagoides pteronyssinus -continued

<400> SEQUENCE: 933

Thr Ile Arg Pro Met Leu Leu Gly Phe Ser Val Leu Val Arg Arg
1               5                   10                  15

<210> SEQ ID NO 934
<211> LENGTH: 15
<212> TYPE: PRT
<213> ORGANISM: Dermatophagoides pteronyssinus

<400> SEQUENCE: 934

Asp Ala Arg Asp Ala Tyr Leu Ala Arg Leu Ala Val Ala Arg Asp
1               5                   10                  15

<210> SEQ ID NO 935
<211> LENGTH: 15
<212> TYPE: PRT
<213> ORGANISM: Dermatophagoides pteronyssinus

<400> SEQUENCE: 935

Tyr Leu Ala Arg Leu Ala Val Ala Arg Asp Ala Ser Glu Arg Met
1               5                   10                  15

<210> SEQ ID NO 936
<211> LENGTH: 15
<212> TYPE: PRT
<213> ORGANISM: Dermatophagoides pteronyssinus

<400> SEQUENCE: 936

Ala Ser Glu Arg Met Thr Ile Val Arg Ala Leu Glu Asn Leu Asn
1               5                   10                  15

<210> SEQ ID NO 937
<211> LENGTH: 15
<212> TYPE: PRT
<213> ORGANISM: Dermatophagoides pteronyssinus

<400> SEQUENCE: 937

Thr Ile Val Arg Ala Leu Glu Asn Leu Asn Val Asn Thr Asp Gly
1               5                   10                  15

<210> SEQ ID NO 938
<211> LENGTH: 15
<212> TYPE: PRT
<213> ORGANISM: Dermatophagoides pteronyssinus

<400> SEQUENCE: 938

Asn Ala Met Asp Glu Ile Ile Lys Ser Thr Asp Ala Glu Pro Ala
1               5                   10                  15

<210> SEQ ID NO 939
<211> LENGTH: 15
<212> TYPE: PRT
<213> ORGANISM: Dermatophagoides pteronyssinus

<400> SEQUENCE: 939

Asp Ala Glu Pro Ala Met Arg Ala Ala Ala Val Asn Ala Leu Pro
1               5                   10                  15

<210> SEQ ID NO 940
<211> LENGTH: 15
<212> TYPE: PRT
<213> ORGANISM: Dermatophagoides pteronyssinus

<400> SEQUENCE: 940

```
Met Ser His Ile Lys Asp Leu Phe Ala Val Lys Gly Glu Cys Met
1               5                   10                  15
```

<210> SEQ ID NO 941
<211> LENGTH: 15
<212> TYPE: PRT
<213> ORGANISM: Dermatophagoides pteronyssinus

<400> SEQUENCE: 941

```
Lys Asn Tyr Val Leu Thr Tyr Val Asp Asn Leu Lys Lys Ser Lys
1               5                   10                  15
```

<210> SEQ ID NO 942
<211> LENGTH: 15
<212> TYPE: PRT
<213> ORGANISM: Dermatophagoides pteronyssinus

<400> SEQUENCE: 942

```
Leu Lys Glu Leu Val Glu Phe Gln Val Thr Gln Ser Gly Phe Asp
1               5                   10                  15
```

<210> SEQ ID NO 943
<211> LENGTH: 15
<212> TYPE: PRT
<213> ORGANISM: Dermatophagoides pteronyssinus

<400> SEQUENCE: 943

```
Arg Glu Leu Asn Asn Ala Met Ser Leu Leu Glu Lys Lys Ser Phe
1               5                   10                  15
```

<210> SEQ ID NO 944
<211> LENGTH: 15
<212> TYPE: PRT
<213> ORGANISM: Dermatophagoides pteronyssinus

<400> SEQUENCE: 944

```
Ala Met Ser Leu Leu Glu Lys Lys Ser Phe Gln Ser Val Met Gln
1               5                   10                  15
```

<210> SEQ ID NO 945
<211> LENGTH: 15
<212> TYPE: PRT
<213> ORGANISM: Dermatophagoides pteronyssinus

<400> SEQUENCE: 945

```
Glu Lys Lys Ser Phe Gln Ser Val Met Gln Phe Leu Arg Asp Met
1               5                   10                  15
```

<210> SEQ ID NO 946
<211> LENGTH: 15
<212> TYPE: PRT
<213> ORGANISM: Dermatophagoides pteronyssinus

<400> SEQUENCE: 946

```
Gln Ser Val Met Gln Phe Leu Arg Asp Met Leu Lys Met Leu Ser
1               5                   10                  15
```

<210> SEQ ID NO 947
<211> LENGTH: 15
<212> TYPE: PRT
<213> ORGANISM: Dermatophagoides pteronyssinus

<400> SEQUENCE: 947

```
Phe Leu Arg Asp Met Leu Lys Met Leu Ser Gln Ile Arg Lys Asn
1               5                   10                  15
```

<210> SEQ ID NO 948
<211> LENGTH: 15
<212> TYPE: PRT
<213> ORGANISM: Dermatophagoides pteronyssinus

<400> SEQUENCE: 948

Leu Lys Met Leu Ser Gln Ile Arg Lys Asn Ala Asp Asn His
1               5                   10                  15

<210> SEQ ID NO 949
<211> LENGTH: 15
<212> TYPE: PRT
<213> ORGANISM: Dermatophagoides pteronyssinus

<400> SEQUENCE: 949

Leu Asp Ser Lys Leu Val Leu Pro Thr Ile Thr Gly Leu Pro Leu
1               5                   10                  15

<210> SEQ ID NO 950
<211> LENGTH: 15
<212> TYPE: PRT
<213> ORGANISM: Dermatophagoides pteronyssinus

<400> SEQUENCE: 950

Thr Gly Leu Pro Leu Met Tyr Lys Phe Gly Asp Asn Leu Val Val
1               5                   10                  15

<210> SEQ ID NO 951
<211> LENGTH: 15
<212> TYPE: PRT
<213> ORGANISM: Dermatophagoides pteronyssinus

<400> SEQUENCE: 951

Met Ile Asp Met Asn Val Gln Lys Gln Glu His Ser Leu Leu Val
1               5                   10                  15

<210> SEQ ID NO 952
<211> LENGTH: 15
<212> TYPE: PRT
<213> ORGANISM: Dermatophagoides pteronyssinus

<400> SEQUENCE: 952

Val Gln Lys Gln Glu His Ser Leu Leu Val Arg Phe Asn Met Lys
1               5                   10                  15

<210> SEQ ID NO 953
<211> LENGTH: 15
<212> TYPE: PRT
<213> ORGANISM: Dermatophagoides pteronyssinus

<400> SEQUENCE: 953

Thr Val Met Arg Phe Lys Gln Ser Leu Arg Glu Lys Arg Ala Thr
1               5                   10                  15

<210> SEQ ID NO 954
<211> LENGTH: 15
<212> TYPE: PRT
<213> ORGANISM: Dermatophagoides pteronyssinus

<400> SEQUENCE: 954

Lys Glu Val Thr Ala Leu Glu Leu Met Leu Lys Ser Glu Thr Gln
1               5                   10                  15

```
<210> SEQ ID NO 955
<211> LENGTH: 15
<212> TYPE: PRT
<213> ORGANISM: Dermatophagoides pteronyssinus

<400> SEQUENCE: 955

Asp Lys Thr Arg Arg Tyr Ile Ala Glu Met Thr Ala Val Gly Ser
1               5                   10                  15

<210> SEQ ID NO 956
<211> LENGTH: 15
<212> TYPE: PRT
<213> ORGANISM: Dermatophagoides pteronyssinus

<400> SEQUENCE: 956

Asn Leu Lys Met His Met Asp Leu Pro Asn Val Leu Gln Ala Asp
1               5                   10                  15

<210> SEQ ID NO 957
<211> LENGTH: 15
<212> TYPE: PRT
<213> ORGANISM: Dermatophagoides pteronyssinus

<400> SEQUENCE: 957

Asn Asn Val Arg Lys Asn Arg Leu Asn Leu Gln Tyr Lys Phe Ala
1               5                   10                  15

<210> SEQ ID NO 958
<211> LENGTH: 15
<212> TYPE: PRT
<213> ORGANISM: Dermatophagoides pteronyssinus

<400> SEQUENCE: 958

Glu Asn Glu Phe Leu Phe Asn Leu Lys Arg Ser Ser Lys Glu Lys
1               5                   10                  15

<210> SEQ ID NO 959
<211> LENGTH: 15
<212> TYPE: PRT
<213> ORGANISM: Dermatophagoides pteronyssinus

<400> SEQUENCE: 959

Tyr Arg Ala Lys Tyr Met Ser Ser His Phe Pro Ile Leu Asn His
1               5                   10                  15

<210> SEQ ID NO 960
<211> LENGTH: 15
<212> TYPE: PRT
<213> ORGANISM: Dermatophagoides pteronyssinus

<400> SEQUENCE: 960

Pro Ile Leu Asn His Lys Val Asn Val Gln Phe Lys Tyr Arg Pro
1               5                   10                  15

<210> SEQ ID NO 961
<211> LENGTH: 15
<212> TYPE: PRT
<213> ORGANISM: Dermatophagoides pteronyssinus

<400> SEQUENCE: 961

Phe Lys Tyr Arg Pro Phe Lys Val Asn Glu Leu Asn Leu Glu Gly
1               5                   10                  15

<210> SEQ ID NO 962
<211> LENGTH: 15
```

```
<212> TYPE: PRT
<213> ORGANISM: Dermatophagoides pteronyssinus

<400> SEQUENCE: 962

Leu Gln His Lys Phe Arg Leu Met Arg Asn Ser Gln Met Glu Val
1               5                   10                  15

<210> SEQ ID NO 963
<211> LENGTH: 15
<212> TYPE: PRT
<213> ORGANISM: Dermatophagoides pteronyssinus

<400> SEQUENCE: 963

Asp Lys Lys Ile Phe Ile Thr His Lys Thr Glu Met Thr Lys Pro
1               5                   10                  15

<210> SEQ ID NO 964
<211> LENGTH: 15
<212> TYPE: PRT
<213> ORGANISM: Dermatophagoides pteronyssinus

<400> SEQUENCE: 964

Leu Phe Tyr Glu Asn Tyr Leu Thr Val His Lys Gly Gly Lys Leu
1               5                   10                  15

<210> SEQ ID NO 965
<211> LENGTH: 15
<212> TYPE: PRT
<213> ORGANISM: Dermatophagoides pteronyssinus

<400> SEQUENCE: 965

Arg Asn Asp Arg Lys Ile Leu Leu Asp Leu Asp Asn Ala Leu Ser
1               5                   10                  15

<210> SEQ ID NO 966
<211> LENGTH: 15
<212> TYPE: PRT
<213> ORGANISM: Dermatophagoides pteronyssinus

<400> SEQUENCE: 966

Ile Leu Leu Asp Leu Asp Asn Ala Leu Ser Pro Arg Glu Gly Thr
1               5                   10                  15

<210> SEQ ID NO 967
<211> LENGTH: 15
<212> TYPE: PRT
<213> ORGANISM: Dermatophagoides pteronyssinus

<400> SEQUENCE: 967

Asn Gly Lys Leu His Leu Ser Leu Ile Asp Pro Ser Thr Leu Ser
1               5                   10                  15

<210> SEQ ID NO 968
<211> LENGTH: 15
<212> TYPE: PRT
<213> ORGANISM: Dermatophagoides pteronyssinus

<400> SEQUENCE: 968

Leu Ser Leu Ile Asp Pro Ser Thr Leu Ser Leu Val Thr Lys Ala
1               5                   10                  15

<210> SEQ ID NO 969
<211> LENGTH: 15
<212> TYPE: PRT
<213> ORGANISM: Dermatophagoides pteronyssinus
```

-continued

<400> SEQUENCE: 969

Gly Lys Leu Glu Gly Val Leu Ser Arg Lys Val Pro Ser His Leu
1               5                   10                  15

<210> SEQ ID NO 970
<211> LENGTH: 15
<212> TYPE: PRT
<213> ORGANISM: Dermatophagoides pteronyssinus

<400> SEQUENCE: 970

Val Leu Ser Arg Lys Val Pro Ser His Leu Thr Leu Glu Thr Pro
1               5                   10                  15

<210> SEQ ID NO 971
<211> LENGTH: 15
<212> TYPE: PRT
<213> ORGANISM: Dermatophagoides pteronyssinus

<400> SEQUENCE: 971

Pro Gly Val Gln Tyr Lys Ile Ile Gly Asn Gly Lys Ile Lys Asp
1               5                   10                  15

<210> SEQ ID NO 972
<211> LENGTH: 15
<212> TYPE: PRT
<213> ORGANISM: Dermatophagoides pteronyssinus

<400> SEQUENCE: 972

Phe Asp Pro His Arg Ala Tyr Tyr Ile Asn Trp Ile Ser Ser Ile
1               5                   10                  15

<210> SEQ ID NO 973
<211> LENGTH: 15
<212> TYPE: PRT
<213> ORGANISM: Dermatophagoides pteronyssinus

<400> SEQUENCE: 973

Ala Tyr Tyr Ile Asn Trp Ile Ser Ser Ile Arg Lys Tyr Ile Gln
1               5                   10                  15

<210> SEQ ID NO 974
<211> LENGTH: 15
<212> TYPE: PRT
<213> ORGANISM: Dermatophagoides pteronyssinus

<400> SEQUENCE: 974

Trp Ile Ser Ser Ile Arg Lys Tyr Ile Gln Asn Phe Ile Val Glu
1               5                   10                  15

<210> SEQ ID NO 975
<211> LENGTH: 15
<212> TYPE: PRT
<213> ORGANISM: Dermatophagoides pteronyssinus

<400> SEQUENCE: 975

Ser Ser Ile Arg Lys Tyr Ile Gln Asn Phe Ile Val Glu Asp His
1               5                   10                  15

<210> SEQ ID NO 976
<211> LENGTH: 15
<212> TYPE: PRT
<213> ORGANISM: Dermatophagoides pteronyssinus

<400> SEQUENCE: 976

Met Met Tyr Lys Ile Leu Cys Leu Ser Leu Leu Val Ala Ala Val
1               5                   10                  15

<210> SEQ ID NO 977
<211> LENGTH: 15
<212> TYPE: PRT
<213> ORGANISM: Dermatophagoides pteronyssinus

<400> SEQUENCE: 977

Leu Cys Leu Ser Leu Leu Val Ala Ala Val Ala Arg Asp Gln Val
1               5                   10                  15

<210> SEQ ID NO 978
<211> LENGTH: 15
<212> TYPE: PRT
<213> ORGANISM: Dermatophagoides pteronyssinus

<400> SEQUENCE: 978

Ile His Arg Gly Lys Pro Phe Gln Leu Glu Ala Val Phe Glu Ala
1               5                   10                  15

<210> SEQ ID NO 979
<211> LENGTH: 15
<212> TYPE: PRT
<213> ORGANISM: Dermatophagoides pteronyssinus

<400> SEQUENCE: 979

Pro Phe Gln Leu Glu Ala Val Phe Glu Ala Asn Gln Asn Thr Lys
1               5                   10                  15

<210> SEQ ID NO 980
<211> LENGTH: 15
<212> TYPE: PRT
<213> ORGANISM: Dermatophagoides pteronyssinus

<400> SEQUENCE: 980

Gln Gln Tyr Asp Ile Lys Tyr Thr Trp Asn Val Pro Lys Ile Ala
1               5                   10                  15

<210> SEQ ID NO 981
<211> LENGTH: 15
<212> TYPE: PRT
<213> ORGANISM: Dermatophagoides pteronyssinus

<400> SEQUENCE: 981

Leu Leu Lys Lys Tyr Leu Thr Arg Asp Val Phe Asp Gln Leu Lys
1               5                   10                  15

<210> SEQ ID NO 982
<211> LENGTH: 15
<212> TYPE: PRT
<213> ORGANISM: Dermatophagoides pteronyssinus

<400> SEQUENCE: 982

Leu Thr Arg Asp Val Phe Asp Gln Leu Lys Asn Lys Lys Thr Asp
1               5                   10                  15

<210> SEQ ID NO 983
<211> LENGTH: 15
<212> TYPE: PRT
<213> ORGANISM: Dermatophagoides pteronyssinus

<400> SEQUENCE: 983

Asp Ala Gln Ser Tyr Lys Thr Phe Ala Ala Leu Phe Asp Pro Ile

<210> SEQ ID NO 984
<211> LENGTH: 15
<212> TYPE: PRT
<213> ORGANISM: Dermatophagoides pteronyssinus

<400> SEQUENCE: 984

Lys Thr Phe Ala Ala Leu Phe Asp Pro Ile Ile Asp Asp Tyr His
1               5                   10                  15

<210> SEQ ID NO 985
<211> LENGTH: 15
<212> TYPE: PRT
<213> ORGANISM: Dermatophagoides pteronyssinus

<400> SEQUENCE: 985

Leu Asn Gly Tyr Pro Phe Asn Pro Met Leu Thr Glu Ala Gln Tyr
1               5                   10                  15

<210> SEQ ID NO 986
<211> LENGTH: 15
<212> TYPE: PRT
<213> ORGANISM: Dermatophagoides pteronyssinus

<400> SEQUENCE: 986

Met Lys Phe Ile Ile Thr Leu Phe Ala Ala Ile Val Met Ala Ala
1               5                   10                  15

<210> SEQ ID NO 987
<211> LENGTH: 15
<212> TYPE: PRT
<213> ORGANISM: Dermatophagoides pteronyssinus

<400> SEQUENCE: 987

Thr Leu Phe Ala Ala Ile Val Met Ala Ala Ala Val Ser Gly Phe
1               5                   10                  15

<210> SEQ ID NO 988
<211> LENGTH: 15
<212> TYPE: PRT
<213> ORGANISM: Dermatophagoides pteronyssinus

<400> SEQUENCE: 988

Ile Val Met Ala Ala Ala Val Ser Gly Phe Ile Val Gly Asp Lys
1               5                   10                  15

<210> SEQ ID NO 989
<211> LENGTH: 15
<212> TYPE: PRT
<213> ORGANISM: Dermatophagoides pteronyssinus

<400> SEQUENCE: 989

Lys Glu Asp Glu Trp Arg Met Ala Phe Asp Arg Leu Met Met Glu
1               5                   10                  15

<210> SEQ ID NO 990
<211> LENGTH: 15
<212> TYPE: PRT
<213> ORGANISM: Dermatophagoides pteronyssinus

<400> SEQUENCE: 990

Arg Met Ala Phe Asp Arg Leu Met Met Glu Glu Leu Glu Thr Lys
1               5                   10                  15

```
<210> SEQ ID NO 991
<211> LENGTH: 15
<212> TYPE: PRT
<213> ORGANISM: Dermatophagoides pteronyssinus

<400> SEQUENCE: 991

Lys Gly Leu Leu His Leu Ser Glu Gln Tyr Lys Glu Leu Glu Lys
1               5                   10                  15

<210> SEQ ID NO 992
<211> LENGTH: 15
<212> TYPE: PRT
<213> ORGANISM: Dermatophagoides pteronyssinus

<400> SEQUENCE: 992

Met Lys Gly Ala Leu Lys Phe Phe Glu Met Glu Ala Lys Arg Thr
1               5                   10                  15

<210> SEQ ID NO 993
<211> LENGTH: 15
<212> TYPE: PRT
<213> ORGANISM: Dermatophagoides pteronyssinus

<400> SEQUENCE: 993

Glu Arg Tyr Asn Tyr Glu Phe Ala Leu Glu Ser Ile Lys Leu Leu
1               5                   10                  15

<210> SEQ ID NO 994
<211> LENGTH: 15
<212> TYPE: PRT
<213> ORGANISM: Dermatophagoides pteronyssinus

<400> SEQUENCE: 994

Glu Phe Ala Leu Glu Ser Ile Lys Leu Leu Ile Lys Lys Leu Asp
1               5                   10                  15

<210> SEQ ID NO 995
<211> LENGTH: 15
<212> TYPE: PRT
<213> ORGANISM: Dermatophagoides pteronyssinus

<400> SEQUENCE: 995

Ser Ile Lys Leu Leu Ile Lys Lys Leu Asp Glu Leu Ala Lys Lys
1               5                   10                  15

<210> SEQ ID NO 996
<211> LENGTH: 15
<212> TYPE: PRT
<213> ORGANISM: Dermatophagoides pteronyssinus

<400> SEQUENCE: 996

Met Ile Ile Tyr Asn Ile Leu Ile Val Leu Leu Leu Ala Ile Asn
1               5                   10                  15

<210> SEQ ID NO 997
<211> LENGTH: 15
<212> TYPE: PRT
<213> ORGANISM: Dermatophagoides pteronyssinus

<400> SEQUENCE: 997

Ile Leu Ile Val Leu Leu Leu Ala Ile Asn Thr Leu Ala Asn Pro
1               5                   10                  15

<210> SEQ ID NO 998
```

<211> LENGTH: 15
<212> TYPE: PRT
<213> ORGANISM: Dermatophagoides pteronyssinus

<400> SEQUENCE: 998

Leu Leu Ala Ile Asn Thr Leu Ala Asn Pro Ile Leu Pro Ala Ser
1               5                   10                  15

<210> SEQ ID NO 999
<211> LENGTH: 15
<212> TYPE: PRT
<213> ORGANISM: Dermatophagoides pteronyssinus

<400> SEQUENCE: 999

Thr Leu Ala Asn Pro Ile Leu Pro Ala Ser Pro Asn Ala Thr Ile
1               5                   10                  15

<210> SEQ ID NO 1000
<211> LENGTH: 15
<212> TYPE: PRT
<213> ORGANISM: Dermatophagoides pteronyssinus

<400> SEQUENCE: 1000

Cys Pro Tyr Gln Ile Ser Leu Gln Ser Ser His Phe Cys Gly
1               5                   10                  15

<210> SEQ ID NO 1001
<211> LENGTH: 15
<212> TYPE: PRT
<213> ORGANISM: Dermatophagoides pteronyssinus

<400> SEQUENCE: 1001

Gly Thr Ile Leu Asp Glu Tyr Trp Ile Leu Thr Ala Ala His Cys
1               5                   10                  15

<210> SEQ ID NO 1002
<211> LENGTH: 15
<212> TYPE: PRT
<213> ORGANISM: Dermatophagoides pteronyssinus

<400> SEQUENCE: 1002

Glu Tyr Trp Ile Leu Thr Ala Ala His Cys Val Ala Gly Gln Thr
1               5                   10                  15

<210> SEQ ID NO 1003
<211> LENGTH: 15
<212> TYPE: PRT
<213> ORGANISM: Dermatophagoides pteronyssinus

<400> SEQUENCE: 1003

Ala Ser Lys Leu Ser Ile Arg Tyr Asn Ser Leu Lys His Ser Leu
1               5                   10                  15

<210> SEQ ID NO 1004
<211> LENGTH: 15
<212> TYPE: PRT
<213> ORGANISM: Dermatophagoides pteronyssinus

<400> SEQUENCE: 1004

Ile Arg Tyr Asn Ser Leu Lys His Ser Leu Gly Gly Glu Lys Ile
1               5                   10                  15

<210> SEQ ID NO 1005
<211> LENGTH: 15
<212> TYPE: PRT

<213> ORGANISM: Dermatophagoides pteronyssinus

<400> SEQUENCE: 1005

Gly Gly Glu Lys Ile Ser Val Ala Lys Ile Phe Ala His Glu Lys
1               5                   10                  15

<210> SEQ ID NO 1006
<211> LENGTH: 15
<212> TYPE: PRT
<213> ORGANISM: Dermatophagoides pteronyssinus

<400> SEQUENCE: 1006

Ile Asp Asn Asp Ile Ala Leu Ile Lys Leu Lys Ser Pro Met Lys
1               5                   10                  15

<210> SEQ ID NO 1007
<211> LENGTH: 15
<212> TYPE: PRT
<213> ORGANISM: Dermatophagoides pteronyssinus

<400> SEQUENCE: 1007

Ala Leu Ile Lys Leu Lys Ser Pro Met Lys Leu Asn Gln Lys Asn
1               5                   10                  15

<210> SEQ ID NO 1008
<211> LENGTH: 15
<212> TYPE: PRT
<213> ORGANISM: Dermatophagoides pteronyssinus

<400> SEQUENCE: 1008

Ser Glu Leu Arg Arg Val Asp Ile Ala Val Val Ser Arg Lys Glu
1               5                   10                  15

<210> SEQ ID NO 1009
<211> LENGTH: 15
<212> TYPE: PRT
<213> ORGANISM: Dermatophagoides pteronyssinus

<400> SEQUENCE: 1009

Lys Tyr His Asn Pro His Phe Ile Gly Asn Arg Ser Val Ile Thr
1               5                   10                  15

<210> SEQ ID NO 1010
<211> LENGTH: 15
<212> TYPE: PRT
<213> ORGANISM: Dermatophagoides pteronyssinus

<400> SEQUENCE: 1010

His Phe Ile Gly Asn Arg Ser Val Ile Thr His Leu Met Glu Trp
1               5                   10                  15

<210> SEQ ID NO 1011
<211> LENGTH: 15
<212> TYPE: PRT
<213> ORGANISM: Dermatophagoides pteronyssinus

<400> SEQUENCE: 1011

Asn Lys Ala Gly Val Arg Ile Tyr Val Asp Ile Val Leu Asn His
1               5                   10                  15

<210> SEQ ID NO 1012
<211> LENGTH: 15
<212> TYPE: PRT

<400> SEQUENCE: 1012

Arg Ile Tyr Val Asp Ile Val Leu Asn His Met Thr Gly Ala Gln
1               5                   10                  15

<210> SEQ ID NO 1013
<211> LENGTH: 15
<212> TYPE: PRT
<213> ORGANISM: Dermatophagoides pteronyssinus

<400> SEQUENCE: 1013

Ile Val Leu Asn His Met Thr Gly Ala Gln Ser Gly Lys Gly Thr
1               5                   10                  15

<210> SEQ ID NO 1014
<211> LENGTH: 15
<212> TYPE: PRT
<213> ORGANISM: Dermatophagoides pteronyssinus

<400> SEQUENCE: 1014

Gln Val Asp Phe Leu Asn His Leu Ile Asp Ile Gly Val Ala Gly
1               5                   10                  15

<210> SEQ ID NO 1015
<211> LENGTH: 15
<212> TYPE: PRT
<213> ORGANISM: Dermatophagoides pteronyssinus

<400> SEQUENCE: 1015

Pro Asp Asp Leu Arg Ser Ile Tyr Ser Arg Leu His Asn Leu Asn
1               5                   10                  15

<210> SEQ ID NO 1016
<211> LENGTH: 15
<212> TYPE: PRT
<213> ORGANISM: Dermatophagoides pteronyssinus

<400> SEQUENCE: 1016

Ser Ile Tyr Ser Arg Leu His Asn Leu Asn Lys Glu Phe Phe Pro
1               5                   10                  15

<210> SEQ ID NO 1017
<211> LENGTH: 15
<212> TYPE: PRT
<213> ORGANISM: Dermatophagoides pteronyssinus

<400> SEQUENCE: 1017

Glu Asn Ser Gln Pro Phe Ile Tyr His Glu Thr Ile Tyr Tyr Gly
1               5                   10                  15

<210> SEQ ID NO 1018
<211> LENGTH: 15
<212> TYPE: PRT
<213> ORGANISM: Dermatophagoides pteronyssinus

<400> SEQUENCE: 1018

Ile Glu Phe Arg Phe Tyr Lys Glu Ile Thr Asn Val Phe Arg Gly
1               5                   10                  15

<210> SEQ ID NO 1019
<211> LENGTH: 15
<212> TYPE: PRT
<213> ORGANISM: Dermatophagoides pteronyssinus

<400> SEQUENCE: 1019

```
Asp Ala Leu Val Met Ile Asp Ser His Asp Leu Arg Val Gly His
1               5                   10                  15
```

<210> SEQ ID NO 1020
<211> LENGTH: 15
<212> TYPE: PRT
<213> ORGANISM: Dermatophagoides pteronyssinus

<400> SEQUENCE: 1020

```
Phe Glu Gly Arg Leu Leu Lys Ala Ala Thr Ala Phe Met Leu Ala
1               5                   10                  15
```

<210> SEQ ID NO 1021
<211> LENGTH: 15
<212> TYPE: PRT
<213> ORGANISM: Dermatophagoides pteronyssinus

<400> SEQUENCE: 1021

```
Leu Lys Ala Ala Thr Ala Phe Met Leu Ala Trp Asn Tyr Gly Val
1               5                   10                  15
```

<210> SEQ ID NO 1022
<211> LENGTH: 15
<212> TYPE: PRT
<213> ORGANISM: Dermatophagoides pteronyssinus

<400> SEQUENCE: 1022

```
Ala Phe Met Leu Ala Trp Asn Tyr Gly Val Pro Arg Val Met Ser
1               5                   10                  15
```

<210> SEQ ID NO 1023
<211> LENGTH: 15
<212> TYPE: PRT
<213> ORGANISM: Dermatophagoides pteronyssinus

<400> SEQUENCE: 1023

```
Pro Arg Val Met Ser Ser Tyr Phe Trp Asn Gln Ile Ile Lys Asp
1               5                   10                  15
```

<210> SEQ ID NO 1024
<211> LENGTH: 15
<212> TYPE: PRT
<213> ORGANISM: Dermatophagoides pteronyssinus

<400> SEQUENCE: 1024

```
Glu His Arg Trp Arg Glu Ile Tyr Asn Met Val Lys Phe Arg Met
1               5                   10                  15
```

<210> SEQ ID NO 1025
<211> LENGTH: 15
<212> TYPE: PRT
<213> ORGANISM: Dermatophagoides pteronyssinus

<400> SEQUENCE: 1025

```
Glu Ile Tyr Asn Met Val Lys Phe Arg Met Ile Ala Gly Gln Glu
1               5                   10                  15
```

<210> SEQ ID NO 1026
<211> LENGTH: 15
<212> TYPE: PRT
<213> ORGANISM: Dermatophagoides pteronyssinus

<400> SEQUENCE: 1026

```
Val Lys Phe Arg Met Ile Ala Gly Gln Glu Pro Val His Asn Trp
1               5                   10                  15
```

<210> SEQ ID NO 1027
<211> LENGTH: 15
<212> TYPE: PRT
<213> ORGANISM: Dermatophagoides pteronyssinus

<400> SEQUENCE: 1027

Tyr Gln Ile Ala Phe Ser Arg Gly Asn Arg Ala Phe Ile Ala Ile
1               5                   10                  15

<210> SEQ ID NO 1028
<211> LENGTH: 15
<212> TYPE: PRT
<213> ORGANISM: Dermatophagoides pteronyssinus

<400> SEQUENCE: 1028

Ser Arg Gly Asn Arg Ala Phe Ile Ala Ile Asn Leu Gln Lys Asn
1               5                   10                  15

<210> SEQ ID NO 1029
<211> LENGTH: 15
<212> TYPE: PRT
<213> ORGANISM: Dermatophagoides pteronyssinus

<400> SEQUENCE: 1029

Ala Phe Ile Ala Ile Asn Leu Gln Lys Asn Gln Gln Asn Leu Gln
1               5                   10                  15

<210> SEQ ID NO 1030
<211> LENGTH: 15
<212> TYPE: PRT
<213> ORGANISM: Dermatophagoides pteronyssinus

<400> SEQUENCE: 1030

Tyr Val Gly His Asp Glu Phe Asp Ala Phe Val Ala Tyr His Ile
1               5                   10                  15

<210> SEQ ID NO 1031
<211> LENGTH: 15
<212> TYPE: PRT
<213> ORGANISM: Dermatophagoides pteronyssinus

<400> SEQUENCE: 1031

Glu Phe Asp Ala Phe Val Ala Tyr His Ile Gly Ala Arg Ile Val
1               5                   10                  15

<210> SEQ ID NO 1032
<211> LENGTH: 15
<212> TYPE: PRT
<213> ORGANISM: Dermatophagoides pteronyssinus

<400> SEQUENCE: 1032

Phe Asp Ala Phe Val Ala Tyr His Ile Gly Ala Arg Ile Val Ser
1               5                   10                  15

<210> SEQ ID NO 1033
<211> LENGTH: 15
<212> TYPE: PRT
<213> ORGANISM: Dermatophagoides pteronyssinus

<400> SEQUENCE: 1033

Lys Asp Pro Lys Pro Leu Lys Lys Ile Ser Ile Met Lys Phe Ile
1               5                   10                  15

-continued

<210> SEQ ID NO 1034
<211> LENGTH: 15
<212> TYPE: PRT
<213> ORGANISM: Dermatophagoides pteronyssinus

<400> SEQUENCE: 1034

Leu Lys Lys Ile Ser Ile Met Lys Phe Ile Ile Ala Phe Phe Val
1               5                   10                  15

<210> SEQ ID NO 1035
<211> LENGTH: 15
<212> TYPE: PRT
<213> ORGANISM: Dermatophagoides pteronyssinus

<400> SEQUENCE: 1035

Ile Met Lys Phe Ile Ile Ala Phe Phe Val Ala Thr Leu Ala Val
1               5                   10                  15

<210> SEQ ID NO 1036
<211> LENGTH: 15
<212> TYPE: PRT
<213> ORGANISM: Dermatophagoides pteronyssinus

<400> SEQUENCE: 1036

Ile Ala Phe Phe Val Ala Thr Leu Ala Val Met Thr Val Ser Gly
1               5                   10                  15

<210> SEQ ID NO 1037
<211> LENGTH: 15
<212> TYPE: PRT
<213> ORGANISM: Dermatophagoides pteronyssinus

<400> SEQUENCE: 1037

Phe Asp Phe Leu Leu Met Glu Arg Ile His Glu Gln Ile Lys Lys
1               5                   10                  15

<210> SEQ ID NO 1038
<211> LENGTH: 15
<212> TYPE: PRT
<213> ORGANISM: Dermatophagoides pteronyssinus

<400> SEQUENCE: 1038

Gly Glu Leu Ala Leu Phe Tyr Leu Gln Glu Gln Ile Asn His Phe
1               5                   10                  15

<210> SEQ ID NO 1039
<211> LENGTH: 15
<212> TYPE: PRT
<213> ORGANISM: Dermatophagoides pteronyssinus

<400> SEQUENCE: 1039

Phe Tyr Leu Gln Glu Gln Ile Asn His Phe Glu Glu Lys Pro Thr
1               5                   10                  15

<210> SEQ ID NO 1040
<211> LENGTH: 15
<212> TYPE: PRT
<213> ORGANISM: Dermatophagoides pteronyssinus

<400> SEQUENCE: 1040

Asp Arg Leu Met Gln Arg Lys Asp Leu Asp Ile Phe Glu Gln Tyr
1               5                   10                  15

<210> SEQ ID NO 1041
<211> LENGTH: 15

<212> TYPE: PRT
<213> ORGANISM: Dermatophagoides pteronyssinus

<400> SEQUENCE: 1041

Arg Lys Asp Leu Asp Ile Phe Glu Gln Tyr Asn Leu Glu Met Ala
1               5                   10                  15

<210> SEQ ID NO 1042
<211> LENGTH: 15
<212> TYPE: PRT
<213> ORGANISM: Dermatophagoides pteronyssinus

<400> SEQUENCE: 1042

Met Ile Lys Ile Ile Thr Thr Ile Ile Leu Ile Ile Thr Val Val
1               5                   10                  15

<210> SEQ ID NO 1043
<211> LENGTH: 15
<212> TYPE: PRT
<213> ORGANISM: Dermatophagoides pteronyssinus

<400> SEQUENCE: 1043

Thr Thr Ile Ile Leu Ile Ile Thr Val Val Val Asp Cys Arg Phe
1               5                   10                  15

<210> SEQ ID NO 1044
<211> LENGTH: 15
<212> TYPE: PRT
<213> ORGANISM: Dermatophagoides pteronyssinus

<400> SEQUENCE: 1044

Pro Lys Trp Ser Tyr Leu Asp Ser Leu Pro Ala Ser Ser Ser Met
1               5                   10                  15

<210> SEQ ID NO 1045
<211> LENGTH: 15
<212> TYPE: PRT
<213> ORGANISM: Dermatophagoides pteronyssinus

<400> SEQUENCE: 1045

Ala Ser Ser Ser Met Met Asn Asp Asn Ser Ser Pro Ile Ala Gly
1               5                   10                  15

<210> SEQ ID NO 1046
<211> LENGTH: 15
<212> TYPE: PRT
<213> ORGANISM: Dermatophagoides pteronyssinus

<400> SEQUENCE: 1046

Met Met Lys Leu Leu Leu Ile Ala Ala Ala Ala Phe Val Ala Val
1               5                   10                  15

<210> SEQ ID NO 1047
<211> LENGTH: 15
<212> TYPE: PRT
<213> ORGANISM: Dermatophagoides pteronyssinus

<400> SEQUENCE: 1047

Leu Ile Ala Ala Ala Ala Phe Val Ala Val Ser Ala Asp Pro Ile
1               5                   10                  15

<210> SEQ ID NO 1048
<211> LENGTH: 15
<212> TYPE: PRT
<213> ORGANISM: Dermatophagoides pteronyssinus

<400> SEQUENCE: 1048

Ala Phe Val Ala Val Ser Ala Asp Pro Ile His Tyr Asp Lys Ile
1               5                   10                  15

<210> SEQ ID NO 1049
<211> LENGTH: 15
<212> TYPE: PRT
<213> ORGANISM: Dermatophagoides pteronyssinus

<400> SEQUENCE: 1049

Val Val Ser Met Glu Tyr Asp Leu Ala Tyr Lys Leu Gly Asp Leu
1               5                   10                  15

<210> SEQ ID NO 1050
<211> LENGTH: 15
<212> TYPE: PRT
<213> ORGANISM: Dermatophagoides pteronyssinus

<400> SEQUENCE: 1050

Val Ile Ser Asp Ile Gln Asp Phe Val Val Glu Leu Ser Leu Glu
1               5                   10                  15

<210> SEQ ID NO 1051
<211> LENGTH: 15
<212> TYPE: PRT
<213> ORGANISM: Dermatophagoides pteronyssinus

<400> SEQUENCE: 1051

Gln Asp Phe Val Val Glu Leu Ser Leu Glu Val Ser Glu Glu Gly
1               5                   10                  15

<210> SEQ ID NO 1052
<211> LENGTH: 15
<212> TYPE: PRT
<213> ORGANISM: Dermatophagoides pteronyssinus

<400> SEQUENCE: 1052

Asn Met Thr Leu Thr Ser Phe Glu Val Arg Gln Phe Ala Asn Val
1               5                   10                  15

<210> SEQ ID NO 1053
<211> LENGTH: 15
<212> TYPE: PRT
<213> ORGANISM: Dermatophagoides pteronyssinus

<400> SEQUENCE: 1053

Ser Phe Glu Val Arg Gln Phe Ala Asn Val Val Asn His Ile Gly
1               5                   10                  15

<210> SEQ ID NO 1054
<211> LENGTH: 15
<212> TYPE: PRT
<213> ORGANISM: Dermatophagoides pteronyssinus

<400> SEQUENCE: 1054

Gln Phe Ala Asn Val Val Asn His Ile Gly Gly Leu Ser Ile Leu
1               5                   10                  15

<210> SEQ ID NO 1055
<211> LENGTH: 15
<212> TYPE: PRT
<213> ORGANISM: Dermatophagoides pteronyssinus

<400> SEQUENCE: 1055

Val Asn His Ile Gly Gly Leu Ser Ile Leu Asp Pro Ile Phe Ala
1               5                   10                  15

<210> SEQ ID NO 1056
<211> LENGTH: 15
<212> TYPE: PRT
<213> ORGANISM: Dermatophagoides pteronyssinus

<400> SEQUENCE: 1056

Gly Leu Ser Ile Leu Asp Pro Ile Phe Ala Val Leu Ser Asp Val
1               5                   10                  15

<210> SEQ ID NO 1057
<211> LENGTH: 15
<212> TYPE: PRT
<213> ORGANISM: Dermatophagoides pteronyssinus

<400> SEQUENCE: 1057

Asp Pro Ile Phe Ala Val Leu Ser Asp Val Leu Thr Ala Ile Phe
1               5                   10                  15

<210> SEQ ID NO 1058
<211> LENGTH: 15
<212> TYPE: PRT
<213> ORGANISM: Dermatophagoides pteronyssinus

<400> SEQUENCE: 1058

Leu Thr Ala Ile Phe Gln Asp Thr Val Arg Ala Glu Met Thr Lys
1               5                   10                  15

<210> SEQ ID NO 1059
<211> LENGTH: 15
<212> TYPE: PRT
<213> ORGANISM: Dermatophagoides pteronyssinus

<400> SEQUENCE: 1059

Ala Glu Met Thr Lys Val Leu Ala Pro Ala Phe Lys Lys Glu Leu
1               5                   10                  15

<210> SEQ ID NO 1060
<211> LENGTH: 15
<212> TYPE: PRT
<213> ORGANISM: Dermatophagoides pteronyssinus

<400> SEQUENCE: 1060

Gln Pro Ile Arg Leu Leu Leu Thr Tyr Ser Gly Val Asp Phe Val
1               5                   10                  15

<210> SEQ ID NO 1061
<211> LENGTH: 15
<212> TYPE: PRT
<213> ORGANISM: Dermatophagoides pteronyssinus

<400> SEQUENCE: 1061

Glu Trp Leu Asn Glu Lys Phe Asn Leu Gly Leu Asp Phe Pro Asn
1               5                   10                  15

<210> SEQ ID NO 1062
<211> LENGTH: 15
<212> TYPE: PRT
<213> ORGANISM: Dermatophagoides pteronyssinus

<400> SEQUENCE: 1062

Asp Gly Asp Met Lys Met Thr Gln Thr Phe Ala Ile Leu Arg Tyr

```
1               5                  10                 15

<210> SEQ ID NO 1063
<211> LENGTH: 15
<212> TYPE: PRT
<213> ORGANISM: Dermatophagoides pteronyssinus

<400> SEQUENCE: 1063

Met Thr Gln Thr Phe Ala Ile Leu Arg Tyr Leu Gly Arg Lys Tyr
1               5                  10                 15

<210> SEQ ID NO 1064
<211> LENGTH: 15
<212> TYPE: PRT
<213> ORGANISM: Dermatophagoides pteronyssinus

<400> SEQUENCE: 1064

Leu Lys Leu Met Ser Lys Phe Val Gly Glu His Ala Phe Ile Ala
1               5                  10                 15

<210> SEQ ID NO 1065
<211> LENGTH: 15
<212> TYPE: PRT
<213> ORGANISM: Dermatophagoides pteronyssinus

<400> SEQUENCE: 1065

Lys Phe Val Gly Glu His Ala Phe Ile Ala Gly Ala Asn Ile Ser
1               5                  10                 15

<210> SEQ ID NO 1066
<211> LENGTH: 15
<212> TYPE: PRT
<213> ORGANISM: Dermatophagoides pteronyssinus

<400> SEQUENCE: 1066

His Ala Phe Ile Ala Gly Ala Asn Ile Ser Tyr Val Asp Phe Asn
1               5                  10                 15

<210> SEQ ID NO 1067
<211> LENGTH: 15
<212> TYPE: PRT
<213> ORGANISM: Dermatophagoides pteronyssinus

<400> SEQUENCE: 1067

Tyr Val Asp Phe Asn Leu Tyr Glu Tyr Leu Cys His Val Lys Val
1               5                  10                 15

<210> SEQ ID NO 1068
<211> LENGTH: 15
<212> TYPE: PRT
<213> ORGANISM: Dermatophagoides pteronyssinus

<400> SEQUENCE: 1068

Met Val Pro Glu Val Phe Gly Gln Phe Glu Asn Leu Lys Arg Tyr
1               5                  10                 15

<210> SEQ ID NO 1069
<211> LENGTH: 15
<212> TYPE: PRT
<213> ORGANISM: Dermatophagoides pteronyssinus

<400> SEQUENCE: 1069

Asn Leu Lys Arg Tyr Val Glu Arg Met Glu Ser Leu Pro Arg Val
1               5                  10                 15
```

<210> SEQ ID NO 1070
<211> LENGTH: 15
<212> TYPE: PRT
<213> ORGANISM: Dermatophagoides pteronyssinus

<400> SEQUENCE: 1070

Met Lys Phe Met Ile Leu Phe Ala Leu Ile Ala Ile Gly Thr Ser
1               5                   10                  15

<210> SEQ ID NO 1071
<211> LENGTH: 15
<212> TYPE: PRT
<213> ORGANISM: Dermatophagoides pteronyssinus

<400> SEQUENCE: 1071

Leu Phe Ala Leu Ile Ala Ile Gly Thr Ser Val Ala Ile Gly Glu
1               5                   10                  15

<210> SEQ ID NO 1072
<211> LENGTH: 15
<212> TYPE: PRT
<213> ORGANISM: Dermatophagoides pteronyssinus

<400> SEQUENCE: 1072

Ile Thr Glu Lys Phe Pro Trp Met Ile Asn Glu Pro Leu Asn Asp
1               5                   10                  15

<210> SEQ ID NO 1073
<211> LENGTH: 15
<212> TYPE: PRT
<213> ORGANISM: Dermatophagoides pteronyssinus

<400> SEQUENCE: 1073

Ala Ser Pro Gly Asp Ala Val Tyr Gln Ile Ala Leu Phe Arg Lys
1               5                   10                  15

<210> SEQ ID NO 1074
<211> LENGTH: 15
<212> TYPE: PRT
<213> ORGANISM: Dermatophagoides pteronyssinus

<400> SEQUENCE: 1074

Ala Val Tyr Gln Ile Ala Leu Phe Arg Lys Asp Ser Phe Thr Cys
1               5                   10                  15

<210> SEQ ID NO 1075
<211> LENGTH: 15
<212> TYPE: PRT
<213> ORGANISM: Dermatophagoides pteronyssinus

<400> SEQUENCE: 1075

Gly Gly Ser Leu Ile Ser Ser Arg Thr Val Leu Thr Ala Ala His
1               5                   10                  15

<210> SEQ ID NO 1076
<211> LENGTH: 15
<212> TYPE: PRT
<213> ORGANISM: Dermatophagoides pteronyssinus

<400> SEQUENCE: 1076

Glu Ala Thr Pro Ser Tyr Phe Lys Ile Arg Tyr Asn Thr Leu Asp
1               5                   10                  15

<210> SEQ ID NO 1077

-continued

```
<211> LENGTH: 15
<212> TYPE: PRT
<213> ORGANISM: Dermatophagoides pteronyssinus

<400> SEQUENCE: 1077

Tyr Phe Lys Ile Arg Tyr Asn Thr Leu Asp Arg Thr Asn Gly Pro
1               5                   10                  15

<210> SEQ ID NO 1078
<211> LENGTH: 15
<212> TYPE: PRT
<213> ORGANISM: Dermatophagoides pteronyssinus

<400> SEQUENCE: 1078

Lys Ile Tyr Arg His Asn Leu Tyr Ser Ser Ser Pro Ile Asp Tyr
1               5                   10                  15

<210> SEQ ID NO 1079
<211> LENGTH: 15
<212> TYPE: PRT
<213> ORGANISM: Dermatophagoides pteronyssinus

<400> SEQUENCE: 1079

Ser Pro Ile Asp Tyr Asp Val Ala Thr Leu Ile Leu Ser Gln Pro
1               5                   10                  15

<210> SEQ ID NO 1080
<211> LENGTH: 15
<212> TYPE: PRT
<213> ORGANISM: Dermatophagoides pteronyssinus

<400> SEQUENCE: 1080

Asp Val Ala Thr Leu Ile Leu Ser Gln Pro Phe Thr Pro Ser Ala
1               5                   10                  15

<210> SEQ ID NO 1081
<211> LENGTH: 15
<212> TYPE: PRT
<213> ORGANISM: Dermatophagoides pteronyssinus

<400> SEQUENCE: 1081

Thr Leu Pro Thr Ile Leu Gln Ile Ala Ser Val Thr Lys Met Ser
1               5                   10                  15

<210> SEQ ID NO 1082
<211> LENGTH: 15
<212> TYPE: PRT
<213> ORGANISM: Dermatophagoides pteronyssinus

<400> SEQUENCE: 1082

Ser Thr Trp Gly Ser Val Asn Ala Ile Thr Asn Arg Met Leu Cys
1               5                   10                  15

<210> SEQ ID NO 1083
<211> LENGTH: 15
<212> TYPE: PRT
<213> ORGANISM: Dermatophagoides pteronyssinus

<400> SEQUENCE: 1083

Ser Thr Lys Tyr Pro Thr Ile Tyr Ser Asn Val Ala Asn Leu Arg
1               5                   10                  15

<210> SEQ ID NO 1084
<211> LENGTH: 15
<212> TYPE: PRT
```

<213> ORGANISM: Dermatophagoides pteronyssinus

<400> SEQUENCE: 1084

Thr Ile Tyr Ser Asn Val Ala Asn Leu Arg Asn Trp Ile Ile Ser
1               5                   10                  15

<210> SEQ ID NO 1085
<211> LENGTH: 15
<212> TYPE: PRT
<213> ORGANISM: Dermatophagoides pteronyssinus

<400> SEQUENCE: 1085

Ser Asn Val Ala Asn Leu Arg Asn Trp Ile Ile Ser Asn Thr Val
1               5                   10                  15

<210> SEQ ID NO 1086
<211> LENGTH: 15
<212> TYPE: PRT
<213> ORGANISM: Canis familiaris

<400> SEQUENCE: 1086

Met Lys Thr Leu Leu Leu Thr Ile Gly Phe Ser Leu Ile Ala Ile
1               5                   10                  15

<210> SEQ ID NO 1087
<211> LENGTH: 15
<212> TYPE: PRT
<213> ORGANISM: Canis familiaris

<400> SEQUENCE: 1087

Leu Thr Ile Gly Phe Ser Leu Ile Ala Ile Leu Gln Ala Gln Asp
1               5                   10                  15

<210> SEQ ID NO 1088
<211> LENGTH: 15
<212> TYPE: PRT
<213> ORGANISM: Canis familiaris

<400> SEQUENCE: 1088

Ser Leu Ile Ala Ile Leu Gln Ala Gln Asp Thr Pro Ala Leu Gly
1               5                   10                  15

<210> SEQ ID NO 1089
<211> LENGTH: 15
<212> TYPE: PRT
<213> ORGANISM: Canis familiaris

<400> SEQUENCE: 1089

Val Ser Gly Lys Trp Tyr Leu Lys Ala Met Thr Ala Asp Gln Glu
1               5                   10                  15

<210> SEQ ID NO 1090
<211> LENGTH: 15
<212> TYPE: PRT
<213> ORGANISM: Canis familiaris

<400> SEQUENCE: 1090

Tyr Leu Lys Ala Met Thr Ala Asp Gln Glu Val Pro Glu Lys Pro
1               5                   10                  15

<210> SEQ ID NO 1091
<211> LENGTH: 15
<212> TYPE: PRT
<213> ORGANISM: Canis familiaris

<400> SEQUENCE: 1091

Pro Gly Lys Tyr Thr Ala Tyr Glu Gly Gln Arg Val Val Phe Ile
1               5                   10                  15

<210> SEQ ID NO 1092
<211> LENGTH: 15
<212> TYPE: PRT
<213> ORGANISM: Canis familiaris

<400> SEQUENCE: 1092

Ala Tyr Glu Gly Gln Arg Val Val Phe Ile Gln Pro Ser Pro Val
1               5                   10                  15

<210> SEQ ID NO 1093
<211> LENGTH: 15
<212> TYPE: PRT
<213> ORGANISM: Canis familiaris

<400> SEQUENCE: 1093

Arg Val Val Phe Ile Gln Pro Ser Pro Val Arg Asp His Tyr Ile
1               5                   10                  15

<210> SEQ ID NO 1094
<211> LENGTH: 15
<212> TYPE: PRT
<213> ORGANISM: Canis familiaris

<400> SEQUENCE: 1094

Met Gln Leu Leu Leu Leu Thr Val Gly Leu Ala Leu Ile Cys Gly
1               5                   10                  15

<210> SEQ ID NO 1095
<211> LENGTH: 15
<212> TYPE: PRT
<213> ORGANISM: Canis familiaris

<400> SEQUENCE: 1095

Arg Trp His Ser Val Ala Leu Ala Ser Asn Lys Ser Asp Leu Ile
1               5                   10                  15

<210> SEQ ID NO 1096
<211> LENGTH: 15
<212> TYPE: PRT
<213> ORGANISM: Canis familiaris

<400> SEQUENCE: 1096

Lys Pro Trp Gly His Phe Arg Val Phe Ile His Ser Met Ser Ala
1               5                   10                  15

<210> SEQ ID NO 1097
<211> LENGTH: 15
<212> TYPE: PRT
<213> ORGANISM: Canis familiaris

<400> SEQUENCE: 1097

Phe Arg Val Phe Ile His Ser Met Ser Ala Lys Asp Gly Asn Leu
1               5                   10                  15

<210> SEQ ID NO 1098
<211> LENGTH: 15
<212> TYPE: PRT
<213> ORGANISM: Canis familiaris

<400> SEQUENCE: 1098

```
Gln Cys Glu Lys Val Ser Leu Thr Ala Phe Lys Thr Ala Thr Ser
1               5                   10                  15
```

<210> SEQ ID NO 1099
<211> LENGTH: 15
<212> TYPE: PRT
<213> ORGANISM: Canis familiaris

<400> SEQUENCE: 1099

```
Ser Leu Thr Ala Phe Lys Thr Ala Thr Ser Asn Lys Phe Asp Leu
1               5                   10                  15
```

<210> SEQ ID NO 1100
<211> LENGTH: 15
<212> TYPE: PRT
<213> ORGANISM: Canis familiaris

<400> SEQUENCE: 1100

```
Lys Ser Tyr Leu Ile Leu Tyr Met Ile Asn Gln Tyr Asn Asp Asp
1               5                   10                  15
```

<210> SEQ ID NO 1101
<211> LENGTH: 15
<212> TYPE: PRT
<213> ORGANISM: Canis familiaris

<400> SEQUENCE: 1101

```
Leu Tyr Met Ile Asn Gln Tyr Asn Asp Asp Thr Ser Leu Val Ala
1               5                   10                  15
```

<210> SEQ ID NO 1102
<211> LENGTH: 15
<212> TYPE: PRT
<213> ORGANISM: Canis familiaris

<400> SEQUENCE: 1102

```
Thr Ser Leu Val Ala His Leu Met Val Arg Asp Leu Ser Arg Gln
1               5                   10                  15
```

<210> SEQ ID NO 1103
<211> LENGTH: 15
<212> TYPE: PRT
<213> ORGANISM: Canis familiaris

<400> SEQUENCE: 1103

```
Met Lys Trp Val Thr Phe Ile Ser Leu Phe Phe Leu Phe Ser Ser
1               5                   10                  15
```

<210> SEQ ID NO 1104
<211> LENGTH: 15
<212> TYPE: PRT
<213> ORGANISM: Canis familiaris

<400> SEQUENCE: 1104

```
Phe Ile Ser Leu Phe Phe Leu Phe Ser Ser Ala Tyr Ser Arg Gly
1               5                   10                  15
```

<210> SEQ ID NO 1105
<211> LENGTH: 15
<212> TYPE: PRT
<213> ORGANISM: Canis familiaris

<400> SEQUENCE: 1105

```
Leu Val Arg Arg Glu Ala Tyr Lys Ser Glu Ile Ala His Arg Tyr
1               5                   10                  15
```

<210> SEQ ID NO 1106
<211> LENGTH: 15
<212> TYPE: PRT
<213> ORGANISM: Canis familiaris

<400> SEQUENCE: 1106

Glu His Phe Arg Gly Leu Val Leu Val Ala Phe Ser Gln Tyr Leu
1               5                   10                  15

<210> SEQ ID NO 1107
<211> LENGTH: 15
<212> TYPE: PRT
<213> ORGANISM: Canis familiaris

<400> SEQUENCE: 1107

Leu Val Leu Val Ala Phe Ser Gln Tyr Leu Gln Gln Cys Pro Phe
1               5                   10                  15

<210> SEQ ID NO 1108
<211> LENGTH: 15
<212> TYPE: PRT
<213> ORGANISM: Canis familiaris

<400> SEQUENCE: 1108

Gln Leu Phe Leu Gly Lys Tyr Leu Tyr Glu Ile Ala Arg Arg His
1               5                   10                  15

<210> SEQ ID NO 1109
<211> LENGTH: 15
<212> TYPE: PRT
<213> ORGANISM: Canis familiaris

<400> SEQUENCE: 1109

Lys Tyr Leu Tyr Glu Ile Ala Arg Arg His Pro Tyr Phe Tyr Ala
1               5                   10                  15

<210> SEQ ID NO 1110
<211> LENGTH: 15
<212> TYPE: PRT
<213> ORGANISM: Canis familiaris

<400> SEQUENCE: 1110

Ile Ala Arg Arg His Pro Tyr Phe Tyr Ala Pro Glu Leu Leu Tyr
1               5                   10                  15

<210> SEQ ID NO 1111
<211> LENGTH: 15
<212> TYPE: PRT
<213> ORGANISM: Canis familiaris

<400> SEQUENCE: 1111

Pro Tyr Phe Tyr Ala Pro Glu Leu Leu Tyr Tyr Ala Gln Gln Tyr
1               5                   10                  15

<210> SEQ ID NO 1112
<211> LENGTH: 15
<212> TYPE: PRT
<213> ORGANISM: Canis familiaris

<400> SEQUENCE: 1112

Pro Glu Leu Leu Tyr Tyr Ala Gln Gln Tyr Lys Gly Val Phe Ala
1               5                   10                  15

```
<210> SEQ ID NO 1113
<211> LENGTH: 15
<212> TYPE: PRT
<213> ORGANISM: Canis familiaris

<400> SEQUENCE: 1113

Ile Glu Ala Leu Arg Glu Lys Val Leu Leu Ser Ser Ala Lys Glu
1               5                   10                  15

<210> SEQ ID NO 1114
<211> LENGTH: 15
<212> TYPE: PRT
<213> ORGANISM: Canis familiaris

<400> SEQUENCE: 1114

Gly Asp Arg Ala Phe Lys Ala Trp Ser Val Ala Arg Leu Ser Gln
1               5                   10                  15

<210> SEQ ID NO 1115
<211> LENGTH: 15
<212> TYPE: PRT
<213> ORGANISM: Canis familiaris

<400> SEQUENCE: 1115

Ala Lys Asp Val Phe Leu Gly Thr Phe Leu Tyr Glu Tyr Ala Arg
1               5                   10                  15

<210> SEQ ID NO 1116
<211> LENGTH: 15
<212> TYPE: PRT
<213> ORGANISM: Canis familiaris

<400> SEQUENCE: 1116

Leu Gly Thr Phe Leu Tyr Glu Tyr Ala Arg Arg His Pro Glu Tyr
1               5                   10                  15

<210> SEQ ID NO 1117
<211> LENGTH: 15
<212> TYPE: PRT
<213> ORGANISM: Canis familiaris

<400> SEQUENCE: 1117

Arg His Pro Glu Tyr Ser Val Ser Leu Leu Leu Arg Leu Ala Lys
1               5                   10                  15

<210> SEQ ID NO 1118
<211> LENGTH: 15
<212> TYPE: PRT
<213> ORGANISM: Canis familiaris

<400> SEQUENCE: 1118

Ser Val Ser Leu Leu Leu Arg Leu Ala Lys Glu Tyr Glu Ala Thr
1               5                   10                  15

<210> SEQ ID NO 1119
<211> LENGTH: 15
<212> TYPE: PRT
<213> ORGANISM: Canis familiaris

<400> SEQUENCE: 1119

Lys Val Leu Asp Glu Phe Lys Pro Leu Val Asp Glu Pro Gln Asn
1               5                   10                  15

<210> SEQ ID NO 1120
<211> LENGTH: 15
```

```
<212> TYPE: PRT
<213> ORGANISM: Canis familiaris

<400> SEQUENCE: 1120

Lys Leu Gly Glu Tyr Gly Phe Gln Asn Ala Leu Leu Val Arg Tyr
1               5                   10                  15

<210> SEQ ID NO 1121
<211> LENGTH: 15
<212> TYPE: PRT
<213> ORGANISM: Canis familiaris

<400> SEQUENCE: 1121

Ser Cys Ala Glu Asp Phe Leu Ser Val Val Leu Asn Arg Leu Cys
1               5                   10                  15

<210> SEQ ID NO 1122
<211> LENGTH: 15
<212> TYPE: PRT
<213> ORGANISM: Canis familiaris

<400> SEQUENCE: 1122

Phe Leu Ser Val Val Leu Asn Arg Leu Cys Val Leu His Glu Lys
1               5                   10                  15

<210> SEQ ID NO 1123
<211> LENGTH: 15
<212> TYPE: PRT
<213> ORGANISM: Canis familiaris

<400> SEQUENCE: 1123

Phe Thr Phe His Ala Asp Leu Cys Thr Leu Pro Glu Ala Glu Lys
1               5                   10                  15

<210> SEQ ID NO 1124
<211> LENGTH: 15
<212> TYPE: PRT
<213> ORGANISM: Canis familiaris

<400> SEQUENCE: 1124

Glu Glu Gly Pro Lys Leu Val Ala Ala Ala Gln Ala Ala Leu Val
1               5                   10                  15

<210> SEQ ID NO 1125
<211> LENGTH: 15
<212> TYPE: PRT
<213> ORGANISM: Canis familiaris

<400> SEQUENCE: 1125

Met Trp Phe Leu Ala Leu Cys Leu Ala Met Ser Leu Gly Trp Thr
1               5                   10                  15

<210> SEQ ID NO 1126
<211> LENGTH: 15
<212> TYPE: PRT
<213> ORGANISM: Canis familiaris

<400> SEQUENCE: 1126

Glu Gly Gln Leu Val Gln Val Arg Lys Ser Phe Ile His Pro Leu
1               5                   10                  15

<210> SEQ ID NO 1127
<211> LENGTH: 15
<212> TYPE: PRT
<213> ORGANISM: Canis familiaris
```

<400> SEQUENCE: 1127

Gln Val Arg Lys Ser Phe Ile His Pro Leu Tyr Lys Thr Lys Val
1               5                   10                  15

<210> SEQ ID NO 1128
<211> LENGTH: 15
<212> TYPE: PRT
<213> ORGANISM: Canis familiaris

<400> SEQUENCE: 1128

Arg Ser His Asp Leu Met Leu Leu His Leu Glu Glu Pro Ala Lys
1               5                   10                  15

<210> SEQ ID NO 1129
<211> LENGTH: 15
<212> TYPE: PRT
<213> ORGANISM: Canis familiaris

<400> SEQUENCE: 1129

Val Thr Lys Phe Met Leu Cys Ala Gly Val Leu Glu Gly Lys Lys
1               5                   10                  15

<210> SEQ ID NO 1130
<211> LENGTH: 15
<212> TYPE: PRT
<213> ORGANISM: Plantago lanceolata

<400> SEQUENCE: 1130

His Ser Arg Asn Leu Ile Asn Glu Leu Ser Glu Arg Met Ala Gly
1               5                   10                  15

<210> SEQ ID NO 1131
<211> LENGTH: 15
<212> TYPE: PRT
<213> ORGANISM: Plantago lanceolata

<400> SEQUENCE: 1131

His Glu Asp Cys Glu Ile Lys Leu Val Lys Ser Ser Arg Pro Asp
1               5                   10                  15

<210> SEQ ID NO 1132
<211> LENGTH: 15
<212> TYPE: PRT
<213> ORGANISM: Plantago lanceolata

<400> SEQUENCE: 1132

Ile Lys Leu Val Lys Ser Ser Arg Pro Asp Cys Ser Glu Ile Pro
1               5                   10                  15

<210> SEQ ID NO 1133
<211> LENGTH: 15
<212> TYPE: PRT
<213> ORGANISM: Ambrosia trifida

<400> SEQUENCE: 1133

Met Lys Asn Ile Phe Met Leu Thr Leu Phe Ile Leu Ile Ile Thr
1               5                   10                  15

<210> SEQ ID NO 1134
<211> LENGTH: 15
<212> TYPE: PRT
<213> ORGANISM: Ambrosia trifida

<400> SEQUENCE: 1134

```
Met Leu Thr Leu Phe Ile Leu Ile Ile Thr Ser Thr Ile Lys Ala
1               5                   10                  15

<210> SEQ ID NO 1135
<211> LENGTH: 15
<212> TYPE: PRT
<213> ORGANISM: Ambrosia trifida

<400> SEQUENCE: 1135

Ile Leu Ile Ile Thr Ser Thr Ile Lys Ala Ile Gly Ser Thr Asn
1               5                   10                  15

<210> SEQ ID NO 1136
<211> LENGTH: 15
<212> TYPE: PRT
<213> ORGANISM: Ambrosia trifida

<400> SEQUENCE: 1136

Lys Gln Glu Asp Asp Gly Leu Cys Tyr Glu Gly Thr Asn Cys Gly
1               5                   10                  15

<210> SEQ ID NO 1137
<211> LENGTH: 15
<212> TYPE: PRT
<213> ORGANISM: Ambrosia trifida

<400> SEQUENCE: 1137

Gly Lys Tyr Cys Val Cys Tyr Asp Ser Lys Ala Ile Cys Asn Lys
1               5                   10                  15

<210> SEQ ID NO 1138
<211> LENGTH: 15
<212> TYPE: PRT
<213> ORGANISM: Poa pratensis

<400> SEQUENCE: 1138

Met Ala Ser Ser Ser Ser Val Leu Leu Val Val Ala Leu Phe Ala
1               5                   10                  15

<210> SEQ ID NO 1139
<211> LENGTH: 15
<212> TYPE: PRT
<213> ORGANISM: Poa pratensis

<400> SEQUENCE: 1139

Ser Val Leu Leu Val Val Ala Leu Phe Ala Val Phe Leu Gly Thr
1               5                   10                  15

<210> SEQ ID NO 1140
<211> LENGTH: 15
<212> TYPE: PRT
<213> ORGANISM: Poa pratensis

<400> SEQUENCE: 1140

Val Ala Leu Phe Ala Val Phe Leu Gly Thr Ala His Gly Ile Ala
1               5                   10                  15

<210> SEQ ID NO 1141
<211> LENGTH: 15
<212> TYPE: PRT
<213> ORGANISM: Poa pratensis

<400> SEQUENCE: 1141

Glu Pro Ile Ala Ala Tyr His Phe Asp Leu Ser Gly Lys Ala Phe
```

```
                 1               5                  10                 15

<210> SEQ ID NO 1142
<211> LENGTH: 15
<212> TYPE: PRT
<213> ORGANISM: Poa pratensis

<400> SEQUENCE: 1142

Lys Gly Ser Asn Pro Asn Tyr Leu Ala Leu Leu Val Lys Tyr Val
1               5                  10                 15

<210> SEQ ID NO 1143
<211> LENGTH: 15
<212> TYPE: PRT
<213> ORGANISM: Poa pratensis

<400> SEQUENCE: 1143

Asn Tyr Leu Ala Leu Leu Val Lys Tyr Val Thr Gly Asp Gly Asp
1               5                  10                 15

<210> SEQ ID NO 1144
<211> LENGTH: 15
<212> TYPE: PRT
<213> ORGANISM: Poa pratensis

<400> SEQUENCE: 1144

Met Ala Val Gln Lys Tyr Thr Val Ala Leu Phe Leu Thr Val Ala
1               5                  10                 15

<210> SEQ ID NO 1145
<211> LENGTH: 15
<212> TYPE: PRT
<213> ORGANISM: Poa pratensis

<400> SEQUENCE: 1145

Tyr Thr Val Ala Leu Phe Leu Thr Val Ala Leu Val Ala Gly Pro
1               5                  10                 15

<210> SEQ ID NO 1146
<211> LENGTH: 15
<212> TYPE: PRT
<213> ORGANISM: Poa pratensis

<400> SEQUENCE: 1146

Phe Leu Thr Val Ala Leu Val Ala Gly Pro Ala Ala Ser Tyr Ala
1               5                  10                 15

<210> SEQ ID NO 1147
<211> LENGTH: 15
<212> TYPE: PRT
<213> ORGANISM: Poa pratensis

<400> SEQUENCE: 1147

Gln Lys Leu Met Glu Asp Ile Asn Val Gly Phe Lys Ala Ala Val
1               5                  10                 15

<210> SEQ ID NO 1148
<211> LENGTH: 15
<212> TYPE: PRT
<213> ORGANISM: Poa pratensis

<400> SEQUENCE: 1148

Asp Ile Asn Val Gly Phe Lys Ala Ala Val Ala Ala Ala Ala Gly
1               5                  10                 15
```

<210> SEQ ID NO 1149
<211> LENGTH: 15
<212> TYPE: PRT
<213> ORGANISM: Poa pratensis

<400> SEQUENCE: 1149

Phe Lys Ala Ala Val Ala Ala Ala Gly Ala Pro Pro Ala Asp
1               5                   10                  15

<210> SEQ ID NO 1150
<211> LENGTH: 15
<212> TYPE: PRT
<213> ORGANISM: Poa pratensis

<400> SEQUENCE: 1150

Ala Pro Pro Ala Asp Lys Phe Lys Thr Phe Gln Ala Ala Phe Ser
1               5                   10                  15

<210> SEQ ID NO 1151
<211> LENGTH: 15
<212> TYPE: PRT
<213> ORGANISM: Poa pratensis

<400> SEQUENCE: 1151

Lys Phe Lys Thr Phe Gln Ala Ala Phe Ser Ala Ser Val Glu Ala
1               5                   10                  15

<210> SEQ ID NO 1152
<211> LENGTH: 15
<212> TYPE: PRT
<213> ORGANISM: Poa pratensis

<400> SEQUENCE: 1152

Pro Gly Phe Val Ser His Val Ala Ala Thr Ser Asp Ala Thr Tyr
1               5                   10                  15

<210> SEQ ID NO 1153
<211> LENGTH: 15
<212> TYPE: PRT
<213> ORGANISM: Poa pratensis

<400> SEQUENCE: 1153

Ala Thr Pro Glu Ala Lys Phe Asp Ser Phe Val Ala Ala Phe Thr
1               5                   10                  15

<210> SEQ ID NO 1154
<211> LENGTH: 15
<212> TYPE: PRT
<213> ORGANISM: Poa pratensis

<400> SEQUENCE: 1154

Lys Phe Asp Ser Phe Val Ala Ala Phe Thr Glu Ala Leu Arg Ile
1               5                   10                  15

<210> SEQ ID NO 1155
<211> LENGTH: 15
<212> TYPE: PRT
<213> ORGANISM: Poa pratensis

<400> SEQUENCE: 1155

Val Ala Ala Phe Thr Glu Ala Leu Arg Ile Ile Ala Gly Val Leu
1               5                   10                  15

<210> SEQ ID NO 1156

```
<211> LENGTH: 15
<212> TYPE: PRT
<213> ORGANISM: Poa pratensis

<400> SEQUENCE: 1156

Glu Ala Leu Arg Ile Ile Ala Gly Val Leu Lys Val His Ala Val
1               5                   10                  15

<210> SEQ ID NO 1157
<211> LENGTH: 15
<212> TYPE: PRT
<213> ORGANISM: Poa pratensis

<400> SEQUENCE: 1157

Ile Ala Gly Val Leu Lys Val His Ala Val Lys Pro Ile Thr Glu
1               5                   10                  15

<210> SEQ ID NO 1158
<211> LENGTH: 15
<212> TYPE: PRT
<213> ORGANISM: Poa pratensis

<400> SEQUENCE: 1158

Asp Lys Ile Asp Ala Ala Phe Lys Val Ala Ala Thr Ala Ala Asn
1               5                   10                  15

<210> SEQ ID NO 1159
<211> LENGTH: 15
<212> TYPE: PRT
<213> ORGANISM: Poa pratensis

<400> SEQUENCE: 1159

Ala Phe Lys Val Ala Ala Thr Ala Ala Asn Ala Ala Pro Ala Asn
1               5                   10                  15

<210> SEQ ID NO 1160
<211> LENGTH: 15
<212> TYPE: PRT
<213> ORGANISM: Poa pratensis

<400> SEQUENCE: 1160

Asp Lys Phe Thr Val Phe Glu Ala Ala Phe Asn Asn Ala Ile Lys
1               5                   10                  15

<210> SEQ ID NO 1161
<211> LENGTH: 15
<212> TYPE: PRT
<213> ORGANISM: Poa pratensis

<400> SEQUENCE: 1161

Phe Glu Ala Ala Phe Asn Asn Ala Ile Lys Glu Ser Thr Gly Gly
1               5                   10                  15

<210> SEQ ID NO 1162
<211> LENGTH: 15
<212> TYPE: PRT
<213> ORGANISM: Poa pratensis

<400> SEQUENCE: 1162

Glu Ser Thr Gly Gly Ala Tyr Asp Thr Tyr Lys Ser Ile Pro Ser
1               5                   10                  15

<210> SEQ ID NO 1163
<211> LENGTH: 15
<212> TYPE: PRT
```

-continued

<213> ORGANISM: Poa pratensis

<400> SEQUENCE: 1163

Ala Tyr Asp Thr Tyr Lys Ser Ile Pro Ser Leu Glu Ala Ala Val
1               5                   10                  15

<210> SEQ ID NO 1164
<211> LENGTH: 15
<212> TYPE: PRT
<213> ORGANISM: Poa pratensis

<400> SEQUENCE: 1164

Leu Glu Ala Ala Val Lys Gln Ala Tyr Ala Ala Thr Ile Ala Ala
1               5                   10                  15

<210> SEQ ID NO 1165
<211> LENGTH: 15
<212> TYPE: PRT
<213> ORGANISM: Poa pratensis

<400> SEQUENCE: 1165

Lys Gln Ala Tyr Ala Ala Thr Ile Ala Ala Ala Pro Glu Val Lys
1               5                   10                  15

<210> SEQ ID NO 1166
<211> LENGTH: 15
<212> TYPE: PRT
<213> ORGANISM: Poa pratensis

<400> SEQUENCE: 1166

Ala Pro Glu Val Lys Phe Ala Val Phe Lys Ala Ala Leu Thr Lys
1               5                   10                  15

<210> SEQ ID NO 1167
<211> LENGTH: 15
<212> TYPE: PRT
<213> ORGANISM: Poa pratensis

<400> SEQUENCE: 1167

Phe Ala Val Phe Lys Ala Ala Leu Thr Lys Ala Ile Thr Ala Met
1               5                   10                  15

<210> SEQ ID NO 1168
<211> LENGTH: 15
<212> TYPE: PRT
<213> ORGANISM: Poa pratensis

<400> SEQUENCE: 1168

Ala Ala Leu Thr Lys Ala Ile Thr Ala Met Ala Glu Val Gln Lys
1               5                   10                  15

<210> SEQ ID NO 1169
<211> LENGTH: 15
<212> TYPE: PRT
<213> ORGANISM: Artemisia vulgaris

<400> SEQUENCE: 1169

Met Ala Lys Cys Ser Tyr Val Phe Cys Ala Val Leu Leu Ile Phe
1               5                   10                  15

<210> SEQ ID NO 1170
<211> LENGTH: 15
<212> TYPE: PRT
<213> ORGANISM: Artemisia vulgaris -continued

<400> SEQUENCE: 1170

Tyr Val Phe Cys Ala Val Leu Leu Ile Phe Ile Val Ala Ile Gly
1               5                   10                  15

<210> SEQ ID NO 1171
<211> LENGTH: 15
<212> TYPE: PRT
<213> ORGANISM: Artemisia vulgaris

<400> SEQUENCE: 1171

Val Leu Leu Ile Phe Ile Val Ala Ile Gly Glu Met Glu Ala Ala
1               5                   10                  15

<210> SEQ ID NO 1172
<211> LENGTH: 15
<212> TYPE: PRT
<213> ORGANISM: Artemisia vulgaris

<400> SEQUENCE: 1172

Glu Lys Thr Ser Lys Thr Tyr Ser Gly Lys Cys Asp Asn Lys Lys
1               5                   10                  15

<210> SEQ ID NO 1173
<211> LENGTH: 15
<212> TYPE: PRT
<213> ORGANISM: Artemisia vulgaris

<400> SEQUENCE: 1173

Cys Phe Cys Tyr Phe Asp Cys Ser Lys Ser Pro Pro Gly Ala Thr
1               5                   10                  15

<210> SEQ ID NO 1174
<211> LENGTH: 15
<212> TYPE: PRT
<213> ORGANISM: Artemisia vulgaris

<400> SEQUENCE: 1174

Met Gly His Leu Gly Asn Phe Trp Leu Val Leu Ala Ile Ser Phe
1               5                   10                  15

<210> SEQ ID NO 1175
<211> LENGTH: 15
<212> TYPE: PRT
<213> ORGANISM: Artemisia vulgaris

<400> SEQUENCE: 1175

Asn Phe Trp Leu Val Leu Ala Ile Ser Phe Ala Ile Leu His Leu
1               5                   10                  15

<210> SEQ ID NO 1176
<211> LENGTH: 15
<212> TYPE: PRT
<213> ORGANISM: Artemisia vulgaris

<400> SEQUENCE: 1176

Leu Ala Ile Ser Phe Ala Ile Leu His Leu Ser His Ala His Glu
1               5                   10                  15

<210> SEQ ID NO 1177
<211> LENGTH: 15
<212> TYPE: PRT
<213> ORGANISM: Artemisia vulgaris

<400> SEQUENCE: 1177

```
Ala Gln Gly Ala Ile Asn Gly Ser Met Ala Val Gln Leu Trp Leu
1               5                   10                  15

<210> SEQ ID NO 1178
<211> LENGTH: 15
<212> TYPE: PRT
<213> ORGANISM: Artemisia vulgaris

<400> SEQUENCE: 1178

Thr Gln Ile Val Trp Ala Asn Ser Glu Arg Val Gly Cys Gly Arg
1               5                   10                  15

<210> SEQ ID NO 1179
<211> LENGTH: 15
<212> TYPE: PRT
<213> ORGANISM: Artemisia vulgaris

<400> SEQUENCE: 1179

Gly Trp Ala Tyr Ile Ile Val Cys Asn Tyr Asp Pro Pro Gly Asn
1               5                   10                  15

<210> SEQ ID NO 1180
<211> LENGTH: 15
<212> TYPE: PRT
<213> ORGANISM: Artemisia vulgaris

<400> SEQUENCE: 1180

Met Ala Ile Lys Met Met Lys Val Phe Cys Ile Met Val Val Cys
1               5                   10                  15

<210> SEQ ID NO 1181
<211> LENGTH: 15
<212> TYPE: PRT
<213> ORGANISM: Artemisia vulgaris

<400> SEQUENCE: 1181

Met Lys Val Phe Cys Ile Met Val Val Cys Met Val Val Ser Thr
1               5                   10                  15

<210> SEQ ID NO 1182
<211> LENGTH: 15
<212> TYPE: PRT
<213> ORGANISM: Artemisia vulgaris

<400> SEQUENCE: 1182

Ile Met Val Val Cys Met Val Val Ser Thr Ser Tyr Ala Glu Ser
1               5                   10                  15

<210> SEQ ID NO 1183
<211> LENGTH: 15
<212> TYPE: PRT
<213> ORGANISM: Artemisia vulgaris

<400> SEQUENCE: 1183

Met Val Val Ser Thr Ser Tyr Ala Glu Ser Ala Leu Thr Cys Ser
1               5                   10                  15

<210> SEQ ID NO 1184
<211> LENGTH: 15
<212> TYPE: PRT
<213> ORGANISM: Artemisia vulgaris

<400> SEQUENCE: 1184

Cys Leu Lys Ala Ser Phe Lys Ser Asn Lys Asp Leu Lys Ser Asp
1               5                   10                  15
```

```
<210> SEQ ID NO 1185
<211> LENGTH: 15
<212> TYPE: PRT
<213> ORGANISM: Artemisia vulgaris

<400> SEQUENCE: 1185

Phe Lys Ser Asn Lys Asp Leu Lys Ser Asp Phe Ala Val Pro Leu
1               5                   10                  15

<210> SEQ ID NO 1186
<211> LENGTH: 15
<212> TYPE: PRT
<213> ORGANISM: Artemisia vulgaris

<400> SEQUENCE: 1186

Asp Leu Lys Ser Asp Phe Ala Val Pro Leu Pro Ser Lys Cys Gly
1               5                   10                  15

<210> SEQ ID NO 1187
<211> LENGTH: 15
<212> TYPE: PRT
<213> ORGANISM: Artemisia vulgaris

<400> SEQUENCE: 1187

Glu Gly Thr Gly Gln His Leu Thr Ala Ala Ile Leu Gly Leu
1               5                   10                  15

<210> SEQ ID NO 1188
<211> LENGTH: 15
<212> TYPE: PRT
<213> ORGANISM: Artemisia vulgaris

<400> SEQUENCE: 1188

Gly Ile Ile Asn Glu Phe Asn Glu Val Gly Thr Leu Ala Pro Thr
1               5                   10                  15

<210> SEQ ID NO 1189
<211> LENGTH: 15
<212> TYPE: PRT
<213> ORGANISM: Artemisia vulgaris

<400> SEQUENCE: 1189

Gly Leu Phe Leu Gly Gly Ala Lys Tyr Met Val Leu Gln Gly Glu
1               5                   10                  15

<210> SEQ ID NO 1190
<211> LENGTH: 15
<212> TYPE: PRT
<213> ORGANISM: Artemisia vulgaris

<400> SEQUENCE: 1190

Gly Ala Lys Tyr Met Val Leu Gln Gly Glu Ala Gly Ala Val Ile
1               5                   10                  15

<210> SEQ ID NO 1191
<211> LENGTH: 15
<212> TYPE: PRT
<213> ORGANISM: Dactylis glomerata

<400> SEQUENCE: 1191

Ser Ser Val Leu Leu Val Val Ala Leu Phe Ala Val Phe Leu Gly
1               5                   10                  15
```

```
<210> SEQ ID NO 1192
<211> LENGTH: 15
<212> TYPE: PRT
<213> ORGANISM: Dactylis glomerata

<400> SEQUENCE: 1192

Val Val Ala Leu Phe Ala Val Phe Leu Gly Ser Ala His Gly Ile
1               5                   10                  15

<210> SEQ ID NO 1193
<211> LENGTH: 15
<212> TYPE: PRT
<213> ORGANISM: Dactylis glomerata

<400> SEQUENCE: 1193

Glu Glu Pro Ile Ala Pro Tyr His Phe Asp Leu Ser Gly His Ala
1               5                   10                  15

<210> SEQ ID NO 1194
<211> LENGTH: 15
<212> TYPE: PRT
<213> ORGANISM: Dactylis glomerata

<400> SEQUENCE: 1194

Pro Asn Tyr Leu Ala Leu Leu Val Lys Tyr Val Asp Gly Asp Gly
1               5                   10                  15

<210> SEQ ID NO 1195
<211> LENGTH: 15
<212> TYPE: PRT
<213> ORGANISM: Dactylis glomerata

<400> SEQUENCE: 1195

Ile Ala Leu Lys Glu Ser Trp Gly Ala Ile Trp Arg Val Asp Thr
1               5                   10                  15

<210> SEQ ID NO 1196
<211> LENGTH: 15
<212> TYPE: PRT
<213> ORGANISM: Dactylis glomerata

<400> SEQUENCE: 1196

Gly Ser Asp Glu Lys Asn Leu Ala Leu Ser Ile Lys Tyr Asn Lys
1               5                   10                  15

<210> SEQ ID NO 1197
<211> LENGTH: 15
<212> TYPE: PRT
<213> ORGANISM: Dactylis glomerata

<400> SEQUENCE: 1197

Asn Leu Ala Leu Ser Ile Lys Tyr Asn Lys Glu Gly Asp Ser Met
1               5                   10                  15

<210> SEQ ID NO 1198
<211> LENGTH: 15
<212> TYPE: PRT
<213> ORGANISM: Dactylis glomerata

<400> SEQUENCE: 1198

Ile Lys Tyr Asn Lys Glu Gly Asp Ser Met Ala Glu Val Glu Leu
1               5                   10                  15

<210> SEQ ID NO 1199
<211> LENGTH: 15
```

```
<212> TYPE: PRT
<213> ORGANISM: Dactylis glomerata

<400> SEQUENCE: 1199

Leu Trp Glu Val Lys Ser Ser Lys Pro Leu Thr Gly Pro Phe Asn
1               5                   10                  15

<210> SEQ ID NO 1200
<211> LENGTH: 15
<212> TYPE: PRT
<213> ORGANISM: Dactylis glomerata

<400> SEQUENCE: 1200

Asn Val Phe Asp Glu Val Ile Pro Thr Ala Phe Lys Ile Gly Thr
1               5                   10                  15

<210> SEQ ID NO 1201
<211> LENGTH: 15
<212> TYPE: PRT
<213> ORGANISM: Dactylis glomerata

<400> SEQUENCE: 1201

Ile Pro Thr Ala Phe Lys Ile Gly Thr Thr Tyr Thr Pro Glu Glu
1               5                   10                  15

<210> SEQ ID NO 1202
<211> LENGTH: 15
<212> TYPE: PRT
<213> ORGANISM: Dactylis glomerata

<400> SEQUENCE: 1202

Asp Ile Tyr Asn Tyr Met Glu Pro Tyr Val Ser Lys Val Asp Pro
1               5                   10                  15

<210> SEQ ID NO 1203
<211> LENGTH: 15
<212> TYPE: PRT
<213> ORGANISM: Dactylis glomerata

<400> SEQUENCE: 1203

Thr Ala Trp Val Asp Ser Gly Ala Gln Leu Gly Glu Leu Ser Tyr
1               5                   10                  15

<210> SEQ ID NO 1204
<211> LENGTH: 15
<212> TYPE: PRT
<213> ORGANISM: Dactylis glomerata

<400> SEQUENCE: 1204

Gly Glu Leu Ser Tyr Gly Val Leu Phe Asn Ile Gln Tyr Val Asn
1               5                   10                  15

<210> SEQ ID NO 1205
<211> LENGTH: 15
<212> TYPE: PRT
<213> ORGANISM: Dactylis glomerata

<400> SEQUENCE: 1205

Gly Val Leu Phe Asn Ile Gln Tyr Val Asn Tyr Trp Phe Ala Pro
1               5                   10                  15

<210> SEQ ID NO 1206
<211> LENGTH: 15
<212> TYPE: PRT
<213> ORGANISM: Penicillium chrysogenum
```

<400> SEQUENCE: 1206

Met Gly Phe Leu Lys Val Leu Ala Thr Ser Leu Ala Thr Leu Ala
1               5                   10                  15

<210> SEQ ID NO 1207
<211> LENGTH: 15
<212> TYPE: PRT
<213> ORGANISM: Penicillium chrysogenum

<400> SEQUENCE: 1207

Val Leu Ala Thr Ser Leu Ala Thr Leu Ala Val Val Asp Ala Gly
1               5                   10                  15

<210> SEQ ID NO 1208
<211> LENGTH: 15
<212> TYPE: PRT
<213> ORGANISM: Penicillium chrysogenum

<400> SEQUENCE: 1208

Ser Asn Thr Asp Ala Val Ile Pro Ser Ser Tyr Ile Val Val Met
1               5                   10                  15

<210> SEQ ID NO 1209
<211> LENGTH: 15
<212> TYPE: PRT
<213> ORGANISM: Penicillium chrysogenum

<400> SEQUENCE: 1209

Val Ile Pro Ser Ser Tyr Ile Val Val Met Asn Asp Asp Val Ser
1               5                   10                  15

<210> SEQ ID NO 1210
<211> LENGTH: 15
<212> TYPE: PRT
<213> ORGANISM: Penicillium chrysogenum

<400> SEQUENCE: 1210

Tyr Ile Val Val Met Asn Asp Asp Val Ser Thr Ala Glu Phe Ser
1               5                   10                  15

<210> SEQ ID NO 1211
<211> LENGTH: 15
<212> TYPE: PRT
<213> ORGANISM: Penicillium chrysogenum

<400> SEQUENCE: 1211

Pro Ala Val Lys Tyr Ile Glu Pro Asp Met Ile Val Asn Ala Thr
1               5                   10                  15

<210> SEQ ID NO 1212
<211> LENGTH: 15
<212> TYPE: PRT
<213> ORGANISM: Penicillium chrysogenum

<400> SEQUENCE: 1212

Ile Glu Pro Asp Met Ile Val Asn Ala Thr Ala Asn Val Val Gln
1               5                   10                  15

<210> SEQ ID NO 1213
<211> LENGTH: 15
<212> TYPE: PRT
<213> ORGANISM: Penicillium chrysogenum

<400> SEQUENCE: 1213

Ile Val Asn Ala Thr Ala Asn Val Val Gln Ser Asn Val Pro Ser
1               5                   10                  15

<210> SEQ ID NO 1214
<211> LENGTH: 15
<212> TYPE: PRT
<213> ORGANISM: Penicillium chrysogenum

<400> SEQUENCE: 1214

Trp Gly Leu Ala Arg Ile Ser Ser Lys Arg Thr Gly Thr Thr Ser
1               5                   10                  15

<210> SEQ ID NO 1215
<211> LENGTH: 15
<212> TYPE: PRT
<213> ORGANISM: Penicillium chrysogenum

<400> SEQUENCE: 1215

Tyr Gly Val Ala Lys Lys Ala Thr Leu Val Ala Val Lys Val Leu
1               5                   10                  15

<210> SEQ ID NO 1216
<211> LENGTH: 15
<212> TYPE: PRT
<213> ORGANISM: Penicillium chrysogenum

<400> SEQUENCE: 1216

Lys Ala Thr Leu Val Ala Val Lys Val Leu Gly Ala Asp Gly Ser
1               5                   10                  15

<210> SEQ ID NO 1217
<211> LENGTH: 15
<212> TYPE: PRT
<213> ORGANISM: Penicillium chrysogenum

<400> SEQUENCE: 1217

Asn Asp Ala Ala Ala Asn Val Val Lys Ser Gly Ile Phe Leu Ser
1               5                   10                  15

<210> SEQ ID NO 1218
<211> LENGTH: 15
<212> TYPE: PRT
<213> ORGANISM: Penicillium chrysogenum

<400> SEQUENCE: 1218

Asn Val Val Lys Ser Gly Ile Phe Leu Ser Val Ala Ala Gly Asn
1               5                   10                  15

<210> SEQ ID NO 1219
<211> LENGTH: 15
<212> TYPE: PRT
<213> ORGANISM: Penicillium chrysogenum

<400> SEQUENCE: 1219

Gly Ile Phe Leu Ser Val Ala Ala Gly Asn Glu Ala Glu Asn Ala
1               5                   10                  15

<210> SEQ ID NO 1220
<211> LENGTH: 15
<212> TYPE: PRT
<213> ORGANISM: Penicillium chrysogenum

<400> SEQUENCE: 1220

Ala Pro His Val Ala Gly Val Ala Ala Tyr Leu Met Ala Leu Glu

```
1               5                  10                 15

<210> SEQ ID NO 1221
<211> LENGTH: 15
<212> TYPE: PRT
<213> ORGANISM: Penicillium chrysogenum

<400> SEQUENCE: 1221

Gly Val Ala Ala Tyr Leu Met Ala Leu Glu Gly Val Ser Ala Gly
1               5                  10                 15

<210> SEQ ID NO 1222
<211> LENGTH: 15
<212> TYPE: PRT
<213> ORGANISM: Penicillium chrysogenum

<400> SEQUENCE: 1222

Asn Ala Cys Ala Arg Ile Val Gln Leu Ala Thr Ser Ser Ile Ser
1               5                  10                 15

<210> SEQ ID NO 1223
<211> LENGTH: 15
<212> TYPE: PRT
<213> ORGANISM: Penicillium chrysogenum

<400> SEQUENCE: 1223

Ile Val Gln Leu Ala Thr Ser Ser Ile Ser Arg Ala Pro Ser Gly
1               5                  10                 15

<210> SEQ ID NO 1224
<211> LENGTH: 15
<212> TYPE: PRT
<213> ORGANISM: Penicillium chrysogenum

<400> SEQUENCE: 1224

Met Lys Gly Phe Leu Ser Leu Thr Leu Leu Pro Leu Leu Val Ala
1               5                  10                 15

<210> SEQ ID NO 1225
<211> LENGTH: 15
<212> TYPE: PRT
<213> ORGANISM: Penicillium chrysogenum

<400> SEQUENCE: 1225

Ser Leu Thr Leu Leu Pro Leu Leu Val Ala Ala Ser Pro Val Ala
1               5                  10                 15

<210> SEQ ID NO 1226
<211> LENGTH: 15
<212> TYPE: PRT
<213> ORGANISM: Penicillium chrysogenum

<400> SEQUENCE: 1226

Pro Leu Leu Val Ala Ala Ser Pro Val Ala Val Asn Ser Ile His
1               5                  10                 15

<210> SEQ ID NO 1227
<211> LENGTH: 15
<212> TYPE: PRT
<213> ORGANISM: Penicillium chrysogenum

<400> SEQUENCE: 1227

Asn Asp Ala Ala Pro Ile Leu Ser Ser Met Thr Ser Lys Asp Ile
1               5                  10                 15
```

<210> SEQ ID NO 1228
<211> LENGTH: 15
<212> TYPE: PRT
<213> ORGANISM: Penicillium chrysogenum

<400> SEQUENCE: 1228

Ser Leu Phe Gly Phe Asp Phe Glu Ala Phe Met Gly Leu Lys His
1               5                   10                  15

<210> SEQ ID NO 1229
<211> LENGTH: 15
<212> TYPE: PRT
<213> ORGANISM: Penicillium chrysogenum

<400> SEQUENCE: 1229

Met Gly Leu Lys His Thr Phe His Ile Ala Gly Ser Leu Leu Gly
1               5                   10                  15

<210> SEQ ID NO 1230
<211> LENGTH: 15
<212> TYPE: PRT
<213> ORGANISM: Penicillium chrysogenum

<400> SEQUENCE: 1230

Thr Phe His Ile Ala Gly Ser Leu Leu Gly Tyr Ala Gly His Phe
1               5                   10                  15

<210> SEQ ID NO 1231
<211> LENGTH: 15
<212> TYPE: PRT
<213> ORGANISM: Penicillium chrysogenum

<400> SEQUENCE: 1231

Val Asp Ala Tyr Val Ile Asp Thr Gly Ala Asn Val Lys His Val
1               5                   10                  15

<210> SEQ ID NO 1232
<211> LENGTH: 15
<212> TYPE: PRT
<213> ORGANISM: Penicillium chrysogenum

<400> SEQUENCE: 1232

Lys Phe Gly Val Ala Lys Lys Ala Asn Val Tyr Ala Val Lys Val
1               5                   10                  15

<210> SEQ ID NO 1233
<211> LENGTH: 15
<212> TYPE: PRT
<213> ORGANISM: Penicillium chrysogenum

<400> SEQUENCE: 1233

Tyr Ala Val Lys Val Leu Arg Ser Asn Gly Ser Gly Thr Met Ser
1               5                   10                  15

<210> SEQ ID NO 1234
<211> LENGTH: 15
<212> TYPE: PRT
<213> ORGANISM: Penicillium chrysogenum

<400> SEQUENCE: 1234

Asp Lys Lys Phe Lys Gly Ser Val Ala Asn Met Ser Leu Gly Gly
1               5                   10                  15

<210> SEQ ID NO 1235

```
<211> LENGTH: 15
<212> TYPE: PRT
<213> ORGANISM: Penicillium chrysogenum

<400> SEQUENCE: 1235

Leu Asp Leu Ala Val Asn Ala Ala Val Asp Ala Gly Ile His Phe
1               5                   10                  15

<210> SEQ ID NO 1236
<211> LENGTH: 15
<212> TYPE: PRT
<213> ORGANISM: Penicillium chrysogenum

<400> SEQUENCE: 1236

Ala Gly Ile His Phe Ala Val Ala Ala Gly Asn Asp Asn Ala Asp
1               5                   10                  15

<210> SEQ ID NO 1237
<211> LENGTH: 15
<212> TYPE: PRT
<213> ORGANISM: Penicillium chrysogenum

<400> SEQUENCE: 1237

Ile Phe Ala Pro Gly Leu Asn Ile Leu Ser Thr Trp Val Gly Ser
1               5                   10                  15

<210> SEQ ID NO 1238
<211> LENGTH: 15
<212> TYPE: PRT
<213> ORGANISM: Penicillium chrysogenum

<400> SEQUENCE: 1238

Ser Met Ala Ser Pro His Ile Ala Gly Leu Leu Ala Tyr Tyr Val
1               5                   10                  15

<210> SEQ ID NO 1239
<211> LENGTH: 15
<212> TYPE: PRT
<213> ORGANISM: Penicillium chrysogenum

<400> SEQUENCE: 1239

His Ile Ala Gly Leu Leu Ala Tyr Tyr Val Ser Leu Ala Pro Ala
1               5                   10                  15

<210> SEQ ID NO 1240
<211> LENGTH: 15
<212> TYPE: PRT
<213> ORGANISM: Penicillium chrysogenum

<400> SEQUENCE: 1240

Thr Pro Lys Gln Leu Lys Ala Ala Leu Ile Ser Val Ala Thr Glu
1               5                   10                  15

<210> SEQ ID NO 1241
<211> LENGTH: 15
<212> TYPE: PRT
<213> ORGANISM: Penicillium chrysogenum

<400> SEQUENCE: 1241

Lys Ala Ala Leu Ile Ser Val Ala Thr Glu Gly Thr Leu Thr Asp
1               5                   10                  15

<210> SEQ ID NO 1242
<211> LENGTH: 15
<212> TYPE: PRT
```

<213> ORGANISM: Penicillium chrysogenum

<400> SEQUENCE: 1242

Ile Gly Ile Ile Ile Asp Ser Ala Glu Lys Ala Phe His Lys Glu
1               5                   10                  15

<210> SEQ ID NO 1243
<211> LENGTH: 15
<212> TYPE: PRT
<213> ORGANISM: Penicillium chrysogenum

<400> SEQUENCE: 1243

Ala Phe His Lys Glu Leu Gly Ala Ile Tyr Ser Glu Ile Lys Asp
1               5                   10                  15

<210> SEQ ID NO 1244
<211> LENGTH: 15
<212> TYPE: PRT
<213> ORGANISM: Juniperus oxycedrus

<400> SEQUENCE: 1244

Glu Leu Ala Asp Ile Leu Arg Ser Leu Gly Ser Asp Val Gly Glu
1               5                   10                  15

<210> SEQ ID NO 1245
<211> LENGTH: 15
<212> TYPE: PRT
<213> ORGANISM: Juniperus oxycedrus

<400> SEQUENCE: 1245

Gly Tyr Val Ser Leu Gln Glu Phe Val Asp Leu Asn Asn Lys Gly
1               5                   10                  15

<210> SEQ ID NO 1246
<211> LENGTH: 15
<212> TYPE: PRT
<213> ORGANISM: Juniperus oxycedrus

<400> SEQUENCE: 1246

Leu Ile Ser Val Glu Glu Phe Gln Thr Met Met Thr Ser Glu Met
1               5                   10                  15

<210> SEQ ID NO 1247
<211> LENGTH: 15
<212> TYPE: PRT
<213> ORGANISM: Salsola kali

<400> SEQUENCE: 1247

Glu Lys Val Lys Ile Glu Arg Leu His Pro Tyr Ile Thr Leu Tyr
1               5                   10                  15

<210> SEQ ID NO 1248
<211> LENGTH: 15
<212> TYPE: PRT
<213> ORGANISM: Salsola kali

<400> SEQUENCE: 1248

Glu Arg Leu His Pro Tyr Ile Thr Leu Tyr Gly Ile Asp Pro Lys
1               5                   10                  15

<210> SEQ ID NO 1249
<211> LENGTH: 15
<212> TYPE: PRT
<213> ORGANISM: Salsola kali

<400> SEQUENCE: 1249

Asn Arg Pro Thr Ile Thr Phe Ala Gly Thr Ala Ala Glu Phe Gly
1               5                   10                  15

<210> SEQ ID NO 1250
<211> LENGTH: 15
<212> TYPE: PRT
<213> ORGANISM: Salsola kali

<400> SEQUENCE: 1250

Ala Ala Glu Phe Gly Thr Val Asp Ser Ala Thr Leu Ile Val Glu
1               5                   10                  15

<210> SEQ ID NO 1251
<211> LENGTH: 15
<212> TYPE: PRT
<213> ORGANISM: Salsola kali

<400> SEQUENCE: 1251

Ser Asp Tyr Phe Val Gly Ala Asn Leu Ile Val Ser Asn Ser Ala
1               5                   10                  15

<210> SEQ ID NO 1252
<211> LENGTH: 15
<212> TYPE: PRT
<213> ORGANISM: Salsola kali

<400> SEQUENCE: 1252

Gly Ala Asn Leu Ile Val Ser Asn Ser Ala Pro Arg Pro Asp Gly
1               5                   10                  15

<210> SEQ ID NO 1253
<211> LENGTH: 15
<212> TYPE: PRT
<213> ORGANISM: Salsola kali

<400> SEQUENCE: 1253

Glu Gly Thr Val Asp Phe Ile Phe Gly Glu Ala Arg Ser Leu Tyr
1               5                   10                  15

<210> SEQ ID NO 1254
<211> LENGTH: 15
<212> TYPE: PRT
<213> ORGANISM: Salsola kali

<400> SEQUENCE: 1254

Phe Ile Phe Gly Glu Ala Arg Ser Leu Tyr Leu Asn Thr Glu Leu
1               5                   10                  15

<210> SEQ ID NO 1255
<211> LENGTH: 15
<212> TYPE: PRT
<213> ORGANISM: Salsola kali

<400> SEQUENCE: 1255

Leu Gly Arg Ala Trp Phe Glu Ala Ala Arg Val Val Phe Ser Tyr
1               5                   10                  15

<210> SEQ ID NO 1256
<211> LENGTH: 15
<212> TYPE: PRT
<213> ORGANISM: Salsola kali

<400> SEQUENCE: 1256

```
Phe Glu Ala Ala Arg Val Val Phe Ser Tyr Cys Asn Leu Ser Asp
1               5                   10                  15
```

<210> SEQ ID NO 1257
<211> LENGTH: 15
<212> TYPE: PRT
<213> ORGANISM: Salsola kali

<400> SEQUENCE: 1257

```
Ala Asp Ala Lys Thr Phe Thr Ser Leu Glu Tyr Ile Glu Ala Ala
1               5                   10                  15
```

<210> SEQ ID NO 1258
<211> LENGTH: 15
<212> TYPE: PRT
<213> ORGANISM: Salsola kali

<400> SEQUENCE: 1258

```
Phe Thr Ser Leu Glu Tyr Ile Glu Ala Ala Lys Trp Leu Leu Pro
1               5                   10                  15
```

<210> SEQ ID NO 1259
<211> LENGTH: 15
<212> TYPE: PRT
<213> ORGANISM: Salsola kali

<400> SEQUENCE: 1259

```
Glu Tyr Ile Glu Ala Ala Lys Trp Leu Leu Pro Pro Pro Lys Val
1               5                   10                  15
```

<210> SEQ ID NO 1260
<211> LENGTH: 15
<212> TYPE: PRT
<213> ORGANISM: Salsola kali

<400> SEQUENCE: 1260

```
Arg Thr Ile Phe Phe Asp Ala Tyr Leu Gly Thr Ser Tyr Val Ile
1               5                   10                  15
```

<210> SEQ ID NO 1261
<211> LENGTH: 15
<212> TYPE: PRT
<213> ORGANISM: Salsola kali

<400> SEQUENCE: 1261

```
Asp Ala Tyr Leu Gly Thr Ser Tyr Val Ile Val Ile Lys Glu Pro
1               5                   10                  15
```

<210> SEQ ID NO 1262
<211> LENGTH: 15
<212> TYPE: PRT
<213> ORGANISM: Salsola kali

<400> SEQUENCE: 1262

```
Thr Ser Tyr Val Ile Val Ile Lys Glu Pro Ala Glu Glu Phe Thr
1               5                   10                  15
```

<210> SEQ ID NO 1263
<211> LENGTH: 15
<212> TYPE: PRT
<213> ORGANISM: Salsola kali

<400> SEQUENCE: 1263

```
Lys Glu Pro Ala Glu Glu Phe Thr Thr Ile Ser Asp Ala Val Lys
1               5                   10                  15
```

<210> SEQ ID NO 1264
<211> LENGTH: 15
<212> TYPE: PRT
<213> ORGANISM: Salsola kali

<400> SEQUENCE: 1264

Ile Ser Tyr Arg Val Tyr Thr Leu Lys Glu Ile Glu Val Gly Thr
1               5                   10                  15

<210> SEQ ID NO 1265
<211> LENGTH: 15
<212> TYPE: PRT
<213> ORGANISM: Salsola kali

<400> SEQUENCE: 1265

Ile Glu Val Gly Thr Asp Tyr Phe Ser Ser Leu Lys Ile Gly
1               5                   10                  15

<210> SEQ ID NO 1266
<211> LENGTH: 15
<212> TYPE: PRT
<213> ORGANISM: Salsola kali

<400> SEQUENCE: 1266

Pro Val Tyr Arg Ala Met Leu Gln His Thr Pro Val Ala Ile Lys
1               5                   10                  15

<210> SEQ ID NO 1267
<211> LENGTH: 15
<212> TYPE: PRT
<213> ORGANISM: Salsola kali

<400> SEQUENCE: 1267

Pro Val Ala Ile Lys Val Leu Arg Pro Asn Val Ser Gln Gly Leu
1               5                   10                  15

<210> SEQ ID NO 1268
<211> LENGTH: 15
<212> TYPE: PRT
<213> ORGANISM: Salsola kali

<400> SEQUENCE: 1268

Leu Val Tyr Glu Tyr Met Glu Asn Gly Ser Leu Glu Asp Arg Leu
1               5                   10                  15

<210> SEQ ID NO 1269
<211> LENGTH: 15
<212> TYPE: PRT
<213> ORGANISM: Salsola kali

<400> SEQUENCE: 1269

Leu Glu Asp Arg Leu Phe Arg Lys Asn Asn Ser Pro Pro Ile Pro
1               5                   10                  15

<210> SEQ ID NO 1270
<211> LENGTH: 15
<212> TYPE: PRT
<213> ORGANISM: Salsola kali

<400> SEQUENCE: 1270

Trp Lys Leu Arg Phe Lys Ile Ala Ala Glu Ile Ala Ile Ala Leu
1               5                   10                  15

```
<210> SEQ ID NO 1271
<211> LENGTH: 15
<212> TYPE: PRT
<213> ORGANISM: Salsola kali

<400> SEQUENCE: 1271

Lys Ile Ala Ala Glu Ile Ala Ile Ala Leu Leu Phe Leu Arg Asp
1               5                   10                  15

<210> SEQ ID NO 1272
<211> LENGTH: 15
<212> TYPE: PRT
<213> ORGANISM: Salsola kali

<400> SEQUENCE: 1272

Ile Ala Ile Ala Leu Leu Phe Leu Arg Asp Ala Lys Pro Glu Pro
1               5                   10                  15

<210> SEQ ID NO 1273
<211> LENGTH: 15
<212> TYPE: PRT
<213> ORGANISM: Salsola kali

<400> SEQUENCE: 1273

Ile Leu Leu Asp Gly Asn Tyr Ile Ser Lys Ile Ala Asp Val Gly
1               5                   10                  15

<210> SEQ ID NO 1274
<211> LENGTH: 15
<212> TYPE: PRT
<213> ORGANISM: Salsola kali

<400> SEQUENCE: 1274

Ile Ala Asp Val Gly Leu Ala Arg Leu Val Pro Pro Thr Val Ala
1               5                   10                  15

<210> SEQ ID NO 1275
<211> LENGTH: 15
<212> TYPE: PRT
<213> ORGANISM: Salsola kali

<400> SEQUENCE: 1275

Lys Ser Asp Ile Tyr Ser Phe Gly Ile Ile Leu Leu Gln Leu Leu
1               5                   10                  15

<210> SEQ ID NO 1276
<211> LENGTH: 15
<212> TYPE: PRT
<213> ORGANISM: Salsola kali

<400> SEQUENCE: 1276

Ser Phe Gly Ile Ile Leu Leu Gln Leu Leu Thr Ala Arg Pro Pro
1               5                   10                  15

<210> SEQ ID NO 1277
<211> LENGTH: 15
<212> TYPE: PRT
<213> ORGANISM: Salsola kali

<400> SEQUENCE: 1277

Leu Leu Gln Leu Leu Thr Ala Arg Pro Pro Met Ala Leu Ser Tyr
1               5                   10                  15

<210> SEQ ID NO 1278
<211> LENGTH: 15
```

```
<212> TYPE: PRT
<213> ORGANISM: Salsola kali

<400> SEQUENCE: 1278

Asp Trp Pro Val Gln Glu Ala Leu Ser Leu Ala Gln Leu Ala Leu
1               5                   10                  15

<210> SEQ ID NO 1279
<211> LENGTH: 15
<212> TYPE: PRT
<213> ORGANISM: Salsola kali

<400> SEQUENCE: 1279

Glu Ala Leu Ser Leu Ala Gln Leu Ala Leu Lys Cys Cys Glu Gly
1               5                   10                  15

<210> SEQ ID NO 1280
<211> LENGTH: 15
<212> TYPE: PRT
<213> ORGANISM: Salsola kali

<400> SEQUENCE: 1280

Asp Ala Gly Ile Lys Tyr Ile Pro Ser Asn Thr Phe Ala Tyr Tyr
1               5                   10                  15

<210> SEQ ID NO 1281
<211> LENGTH: 15
<212> TYPE: PRT
<213> ORGANISM: Salsola kali

<400> SEQUENCE: 1281

Tyr Ile Pro Ser Asn Thr Phe Ala Tyr Tyr Asp Gln Val Leu Asp
1               5                   10                  15

<210> SEQ ID NO 1282
<211> LENGTH: 15
<212> TYPE: PRT
<213> ORGANISM: Salsola kali

<400> SEQUENCE: 1282

Gly Gly Glu Ile Gly Phe Asp Leu Tyr Phe Ser Met Ala Arg Gly
1               5                   10                  15

<210> SEQ ID NO 1283
<211> LENGTH: 15
<212> TYPE: PRT
<213> ORGANISM: Salsola kali

<400> SEQUENCE: 1283

Phe Asp Leu Tyr Phe Ser Met Ala Arg Gly Asn Ala Ser Leu Pro
1               5                   10                  15

<210> SEQ ID NO 1284
<211> LENGTH: 15
<212> TYPE: PRT
<213> ORGANISM: Salsola kali

<400> SEQUENCE: 1284

Lys Trp Phe Asp Thr Asn Tyr His Tyr Ile Val Pro Glu Leu Gly
1               5                   10                  15

<210> SEQ ID NO 1285
<211> LENGTH: 15
<212> TYPE: PRT
<213> ORGANISM: Salsola kali
```

<400> SEQUENCE: 1285

Pro Glu Val Lys Phe Ala Tyr Ser Ser His Lys Ala Val Asp Glu
1               5                   10                  15

<210> SEQ ID NO 1286
<211> LENGTH: 15
<212> TYPE: PRT
<213> ORGANISM: Salsola kali

<400> SEQUENCE: 1286

Lys Ala Val Asp Glu Tyr Lys Glu Ala Lys Ala Leu Gly Val Asp
1               5                   10                  15

<210> SEQ ID NO 1287
<211> LENGTH: 15
<212> TYPE: PRT
<213> ORGANISM: Salsola kali

<400> SEQUENCE: 1287

Val Gly Pro Val Ser Tyr Leu Leu Ser Lys Ala Ala Lys Gly
1               5                   10                  15

<210> SEQ ID NO 1288
<211> LENGTH: 15
<212> TYPE: PRT
<213> ORGANISM: Salsola kali

<400> SEQUENCE: 1288

Tyr Leu Leu Leu Ser Lys Ala Ala Lys Gly Val Glu Lys Ser Phe
1               5                   10                  15

<210> SEQ ID NO 1289
<211> LENGTH: 15
<212> TYPE: PRT
<213> ORGANISM: Salsola kali

<400> SEQUENCE: 1289

Lys Ala Ala Lys Gly Val Glu Lys Ser Phe Pro Leu Leu Ser Leu
1               5                   10                  15

<210> SEQ ID NO 1290
<211> LENGTH: 15
<212> TYPE: PRT
<213> ORGANISM: Salsola kali

<400> SEQUENCE: 1290

Val Glu Lys Ser Phe Pro Leu Leu Ser Leu Leu Pro Lys Ile Leu
1               5                   10                  15

<210> SEQ ID NO 1291
<211> LENGTH: 15
<212> TYPE: PRT
<213> ORGANISM: Salsola kali

<400> SEQUENCE: 1291

Pro Leu Leu Ser Leu Leu Pro Lys Ile Leu Pro Val Tyr Lys Glu
1               5                   10                  15

<210> SEQ ID NO 1292
<211> LENGTH: 15
<212> TYPE: PRT
<213> ORGANISM: Salsola kali

<400> SEQUENCE: 1292

Pro Val Tyr Lys Glu Val Ile Ala Glu Leu Lys Ala Ala Gly Ala
1               5                   10                  15

<210> SEQ ID NO 1293
<211> LENGTH: 15
<212> TYPE: PRT
<213> ORGANISM: Salsola kali

<400> SEQUENCE: 1293

Val Ile Ala Glu Leu Lys Ala Ala Gly Ala Ser Thr Ile Gln Phe
1               5                   10                  15

<210> SEQ ID NO 1294
<211> LENGTH: 15
<212> TYPE: PRT
<213> ORGANISM: Salsola kali

<400> SEQUENCE: 1294

Ser Thr Leu Ser Gly Leu Asn Val Leu Val Glu Thr Tyr Phe Ala
1               5                   10                  15

<210> SEQ ID NO 1295
<211> LENGTH: 15
<212> TYPE: PRT
<213> ORGANISM: Salsola kali

<400> SEQUENCE: 1295

Leu Asn Val Leu Val Glu Thr Tyr Phe Ala Asp Leu Thr Pro Glu
1               5                   10                  15

<210> SEQ ID NO 1296
<211> LENGTH: 15
<212> TYPE: PRT
<213> ORGANISM: Salsola kali

<400> SEQUENCE: 1296

Glu Thr Tyr Phe Ala Asp Leu Thr Pro Glu Ala Tyr Lys Thr Leu
1               5                   10                  15

<210> SEQ ID NO 1297
<211> LENGTH: 15
<212> TYPE: PRT
<213> ORGANISM: Salsola kali

<400> SEQUENCE: 1297

Ala Tyr Lys Thr Leu Val Ser Leu Asn Gly Val Thr Ala Phe Gly
1               5                   10                  15

<210> SEQ ID NO 1298
<211> LENGTH: 15
<212> TYPE: PRT
<213> ORGANISM: Salsola kali

<400> SEQUENCE: 1298

Val Thr Ala Phe Gly Phe Asp Leu Val Arg Gly Thr Lys Thr Leu
1               5                   10                  15

<210> SEQ ID NO 1299
<211> LENGTH: 15
<212> TYPE: PRT
<213> ORGANISM: Salsola kali

<400> SEQUENCE: 1299

Gly Phe Pro Ser Gly Lys Tyr Leu Phe Ala Gly Val Val Asp Gly

```
1               5                   10                  15
```

<210> SEQ ID NO 1300
<211> LENGTH: 15
<212> TYPE: PRT
<213> ORGANISM: Salsola kali

<400> SEQUENCE: 1300

```
Arg Asn Ile Trp Ala Asn Asp Leu Ala Ala Ser Leu Ala Thr Leu
1               5                   10                  15
```

<210> SEQ ID NO 1301
<211> LENGTH: 15
<212> TYPE: PRT
<213> ORGANISM: Salsola kali

<400> SEQUENCE: 1301

```
Asn Asp Leu Ala Ala Ser Leu Ala Thr Leu Gln Ser Leu Glu Ser
1               5                   10                  15
```

<210> SEQ ID NO 1302
<211> LENGTH: 15
<212> TYPE: PRT
<213> ORGANISM: Salsola kali

<400> SEQUENCE: 1302

```
Ser Leu Ala Thr Leu Gln Ser Leu Glu Ser Ile Val Gly Lys Asp
1               5                   10                  15
```

<210> SEQ ID NO 1303
<211> LENGTH: 15
<212> TYPE: PRT
<213> ORGANISM: Salsola kali

<400> SEQUENCE: 1303

```
Thr Lys Leu Asp Asp Glu Ile Lys Ser Trp Leu Ala Phe Ala Ala
1               5                   10                  15
```

<210> SEQ ID NO 1304
<211> LENGTH: 15
<212> TYPE: PRT
<213> ORGANISM: Salsola kali

<400> SEQUENCE: 1304

```
Glu Ile Lys Ser Trp Leu Ala Phe Ala Ala Gln Lys Val Leu Glu
1               5                   10                  15
```

<210> SEQ ID NO 1305
<211> LENGTH: 15
<212> TYPE: PRT
<213> ORGANISM: Salsola kali

<400> SEQUENCE: 1305

```
Leu Ala Phe Ala Ala Gln Lys Val Leu Glu Val Asn Ala Leu Ala
1               5                   10                  15
```

<210> SEQ ID NO 1306
<211> LENGTH: 15
<212> TYPE: PRT
<213> ORGANISM: Salsola kali

<400> SEQUENCE: 1306

```
Gln Lys Val Leu Glu Val Asn Ala Leu Ala Lys Ala Leu Ala Gly
1               5                   10                  15
```

```
<210> SEQ ID NO 1307
<211> LENGTH: 15
<212> TYPE: PRT
<213> ORGANISM: Salsola kali

<400> SEQUENCE: 1307

Gln Lys Asp Glu Ala Phe Phe Ser Ala Asn Ala Ala Ala Leu Ala
1               5                   10                  15

<210> SEQ ID NO 1308
<211> LENGTH: 15
<212> TYPE: PRT
<213> ORGANISM: Salsola kali

<400> SEQUENCE: 1308

Phe Phe Ser Ala Asn Ala Ala Ala Leu Ala Ser Arg Lys Ser Ser
1               5                   10                  15

<210> SEQ ID NO 1309
<211> LENGTH: 15
<212> TYPE: PRT
<213> ORGANISM: Salsola kali

<400> SEQUENCE: 1309

Glu Glu Tyr Val Lys Ala Ile Lys Glu Glu Ile Ser Lys Val Val
1               5                   10                  15

<210> SEQ ID NO 1310
<211> LENGTH: 15
<212> TYPE: PRT
<213> ORGANISM: Salsola kali

<400> SEQUENCE: 1310

Ile Ser Lys Val Val Lys Leu Gln Glu Glu Leu Asp Ile Asp Val
1               5                   10                  15

<210> SEQ ID NO 1311
<211> LENGTH: 15
<212> TYPE: PRT
<213> ORGANISM: Salsola kali

<400> SEQUENCE: 1311

Met Val Glu Tyr Phe Gly Glu Gln Leu Ser Gly Phe Ala Phe Thr
1               5                   10                  15

<210> SEQ ID NO 1312
<211> LENGTH: 15
<212> TYPE: PRT
<213> ORGANISM: Salsola kali

<400> SEQUENCE: 1312

Lys Ala Met Thr Val Phe Trp Ser Ser Leu Ala Gln Ser Met Thr
1               5                   10                  15

<210> SEQ ID NO 1313
<211> LENGTH: 15
<212> TYPE: PRT
<213> ORGANISM: Salsola kali

<400> SEQUENCE: 1313

Ser Arg Pro Met Lys Gly Met Leu Thr Gly Pro Val Thr Ile Leu
1               5                   10                  15

<210> SEQ ID NO 1314
```

```
<211> LENGTH: 15
<212> TYPE: PRT
<213> ORGANISM: Salsola kali

<400> SEQUENCE: 1314

Pro Val Thr Ile Leu Asn Trp Ser Phe Val Arg Asn Asp Gln Pro
1               5                   10                  15

<210> SEQ ID NO 1315
<211> LENGTH: 15
<212> TYPE: PRT
<213> ORGANISM: Salsola kali

<400> SEQUENCE: 1315

Arg His Glu Thr Cys Tyr Gln Ile Ala Leu Ala Ile Glu Asp Glu
1               5                   10                  15

<210> SEQ ID NO 1316
<211> LENGTH: 15
<212> TYPE: PRT
<213> ORGANISM: Salsola kali

<400> SEQUENCE: 1316

Lys Ala Gly Ile Asn Val Ile Gln Ile Asp Glu Ala Ala Leu Arg
1               5                   10                  15

<210> SEQ ID NO 1317
<211> LENGTH: 15
<212> TYPE: PRT
<213> ORGANISM: Salsola kali

<400> SEQUENCE: 1317

Val Ile Gln Ile Asp Glu Ala Ala Leu Arg Glu Gly Leu Pro Leu
1               5                   10                  15

<210> SEQ ID NO 1318
<211> LENGTH: 15
<212> TYPE: PRT
<213> ORGANISM: Salsola kali

<400> SEQUENCE: 1318

Gly Phe Tyr Leu Gln Trp Ala Val His Ser Phe Arg Ile Thr Asn
1               5                   10                  15

<210> SEQ ID NO 1319
<211> LENGTH: 15
<212> TYPE: PRT
<213> ORGANISM: Salsola kali

<400> SEQUENCE: 1319

Trp Ala Val His Ser Phe Arg Ile Thr Asn Val Gly Ile Gln Asp
1               5                   10                  15

<210> SEQ ID NO 1320
<211> LENGTH: 15
<212> TYPE: PRT
<213> ORGANISM: Salsola kali

<400> SEQUENCE: 1320

Ser Asn Phe Asn Asp Ile Ile His Ser Ile Ile Asp Met Asp Ala
1               5                   10                  15

<210> SEQ ID NO 1321
<211> LENGTH: 15
<212> TYPE: PRT
```

<213> ORGANISM: Salsola kali

<400> SEQUENCE: 1321

Ile Asp Met Asp Ala Asp Val Ile Thr Ile Glu Asn Ser Arg Ser
1               5                   10                  15

<210> SEQ ID NO 1322
<211> LENGTH: 15
<212> TYPE: PRT
<213> ORGANISM: Salsola kali

<400> SEQUENCE: 1322

Asp Val Ile Thr Ile Glu Asn Ser Arg Ser Asp Glu Lys Leu Leu
1               5                   10                  15

<210> SEQ ID NO 1323
<211> LENGTH: 15
<212> TYPE: PRT
<213> ORGANISM: Salsola kali

<400> SEQUENCE: 1323

Leu Ala Asp Arg Ile Arg Lys Met Leu Ala Val Leu Glu Ser Asn
1               5                   10                  15

<210> SEQ ID NO 1324
<211> LENGTH: 15
<212> TYPE: PRT
<213> ORGANISM: Salsola kali

<400> SEQUENCE: 1324

Arg Lys Met Leu Ala Val Leu Glu Ser Asn Val Leu Trp Val Asn
1               5                   10                  15

<210> SEQ ID NO 1325
<211> LENGTH: 15
<212> TYPE: PRT
<213> ORGANISM: Salsola kali

<400> SEQUENCE: 1325

Asn Glu Val Asn Pro Ala Leu Ser Asn Met Val Tyr Ala Ala Lys
1               5                   10                  15

<210> SEQ ID NO 1326
<211> LENGTH: 15
<212> TYPE: PRT
<213> ORGANISM: Salsola kali

<400> SEQUENCE: 1326

Val Asn Pro Ala Leu Ser Asn Met Val Tyr Ala Ala Lys Pro Ile
1               5                   10                  15

<210> SEQ ID NO 1327
<211> LENGTH: 15
<212> TYPE: PRT
<213> ORGANISM: Salsola kali

<400> SEQUENCE: 1327

Glu Gly Thr Asn Asn His Leu Thr Ala Ala Ala Ile Leu Gly Val
1               5                   10                  15

<210> SEQ ID NO 1328
<211> LENGTH: 15
<212> TYPE: PRT
<213> ORGANISM: Salsola kali -continued

```
<400> SEQUENCE: 1328

Gly Thr Lys Tyr Met Val Ile Gln Gly Glu Ala Gly Gln Val Ile
1               5                   10                  15

<210> SEQ ID NO 1329
<211> LENGTH: 15
<212> TYPE: PRT
<213> ORGANISM: Salsola kali

<400> SEQUENCE: 1329

Gln Ala Leu Ile Phe Gly Ile Tyr Asp Glu Pro Val Thr Pro Gly
1               5                   10                  15

<210> SEQ ID NO 1330
<211> LENGTH: 15
<212> TYPE: PRT
<213> ORGANISM: Lolium perenne

<400> SEQUENCE: 1330

Met Ala Ser Ser Ser Ser Val Leu Leu Val Val Ala Leu Phe Ala
1               5                   10                  15

<210> SEQ ID NO 1331
<211> LENGTH: 15
<212> TYPE: PRT
<213> ORGANISM: Lolium perenne

<400> SEQUENCE: 1331

Ser Val Leu Leu Val Val Ala Leu Phe Ala Val Phe Leu Gly Ser
1               5                   10                  15

<210> SEQ ID NO 1332
<211> LENGTH: 15
<212> TYPE: PRT
<213> ORGANISM: Lolium perenne

<400> SEQUENCE: 1332

Val Ala Leu Phe Ala Val Phe Leu Gly Ser Ala His Gly Ile Ala
1               5                   10                  15

<210> SEQ ID NO 1333
<211> LENGTH: 15
<212> TYPE: PRT
<213> ORGANISM: Lolium perenne

<400> SEQUENCE: 1333

Glu Pro Ile Ala Pro Tyr His Phe Asp Leu Ser Gly His Ala Phe
1               5                   10                  15

<210> SEQ ID NO 1334
<211> LENGTH: 15
<212> TYPE: PRT
<213> ORGANISM: Lolium perenne

<400> SEQUENCE: 1334

Lys Ala Ser Asn Pro Asn Tyr Leu Ala Ile Leu Val Lys Tyr Val
1               5                   10                  15

<210> SEQ ID NO 1335
<211> LENGTH: 15
<212> TYPE: PRT
<213> ORGANISM: Lolium perenne

<400> SEQUENCE: 1335
```

Asn Tyr Leu Ala Ile Leu Val Lys Tyr Val Asp Gly Asp Gly Asp
1               5                   10                  15

<210> SEQ ID NO 1336
<211> LENGTH: 15
<212> TYPE: PRT
<213> ORGANISM: Lolium perenne

<400> SEQUENCE: 1336

Lys Gln Gln Gly Ile Arg Tyr Ala Asn Pro Ile Ala Phe Phe Arg
1               5                   10                  15

<210> SEQ ID NO 1337
<211> LENGTH: 15
<212> TYPE: PRT
<213> ORGANISM: Lolium perenne

<400> SEQUENCE: 1337

Arg Tyr Ala Asn Pro Ile Ala Phe Phe Arg Lys Glu Pro Leu Lys
1               5                   10                  15

<210> SEQ ID NO 1338
<211> LENGTH: 15
<212> TYPE: PRT
<213> ORGANISM: Lolium perenne

<400> SEQUENCE: 1338

Ile Ala Phe Phe Arg Lys Glu Pro Leu Lys Glu Cys Gly Gly Ile
1               5                   10                  15

<210> SEQ ID NO 1339
<211> LENGTH: 15
<212> TYPE: PRT
<213> ORGANISM: Lolium perenne

<400> SEQUENCE: 1339

Asp Gly Val Trp Glu Ile Lys Ser Asp Lys Pro Leu Lys Gly Pro
1               5                   10                  15

<210> SEQ ID NO 1340
<211> LENGTH: 15
<212> TYPE: PRT
<213> ORGANISM: Lolium perenne

<400> SEQUENCE: 1340

Ile Lys Ser Asp Lys Pro Leu Lys Gly Pro Phe Asn Phe Arg Phe
1               5                   10                  15

<210> SEQ ID NO 1341
<211> LENGTH: 15
<212> TYPE: PRT
<213> ORGANISM: Lolium perenne

<400> SEQUENCE: 1341

Met Arg Asn Val Phe Asp Asp Val Val Pro Ala Asp Phe Lys Val
1               5                   10                  15

<210> SEQ ID NO 1342
<211> LENGTH: 15
<212> TYPE: PRT
<213> ORGANISM: Lolium perenne

<400> SEQUENCE: 1342

Ser Asp Ala Lys Thr Leu Val Leu Asn Ile Lys Tyr Thr Arg Pro
1               5                   10                  15

```
<210> SEQ ID NO 1343
<211> LENGTH: 15
<212> TYPE: PRT
<213> ORGANISM: Lolium perenne

<400> SEQUENCE: 1343

Leu Trp Glu Val Lys Ser Ala Lys Pro Leu Thr Gly Pro Met Asn
1               5                   10                  15

<210> SEQ ID NO 1344
<211> LENGTH: 15
<212> TYPE: PRT
<213> ORGANISM: Lolium perenne

<400> SEQUENCE: 1344

Asn Val Phe Asp Glu Val Ile Pro Thr Ala Phe Thr Val Gly Lys
1               5                   10                  15

<210> SEQ ID NO 1345
<211> LENGTH: 15
<212> TYPE: PRT
<213> ORGANISM: Lolium perenne

<400> SEQUENCE: 1345

Tyr Glu Gly Leu Ser Tyr Arg Ser Leu Gln Pro Glu Asn Phe Ala
1               5                   10                  15

<210> SEQ ID NO 1346
<211> LENGTH: 15
<212> TYPE: PRT
<213> ORGANISM: Lolium perenne

<400> SEQUENCE: 1346

Pro Glu Asn Phe Ala Val Val Asp Leu Asn Gln Met Arg Ala Val
1               5                   10                  15

<210> SEQ ID NO 1347
<211> LENGTH: 15
<212> TYPE: PRT
<213> ORGANISM: Lolium perenne

<400> SEQUENCE: 1347

Val Val Asp Leu Asn Gln Met Arg Ala Val Leu Val Asp Gly Lys
1               5                   10                  15

<210> SEQ ID NO 1348
<211> LENGTH: 15
<212> TYPE: PRT
<213> ORGANISM: Lolium perenne

<400> SEQUENCE: 1348

Gln Leu Gly Glu Leu Tyr Tyr Ala Ile Ser Lys Tyr Ser Arg Thr
1               5                   10                  15

<210> SEQ ID NO 1349
<211> LENGTH: 15
<212> TYPE: PRT
<213> ORGANISM: Lolium perenne

<400> SEQUENCE: 1349

Tyr Tyr Ala Ile Ser Lys Tyr Ser Arg Thr Leu Ala Phe Pro Ala
1               5                   10                  15
```

```
<210> SEQ ID NO 1350
<211> LENGTH: 15
<212> TYPE: PRT
<213> ORGANISM: Lolium perenne

<400> SEQUENCE: 1350

Lys Tyr Ser Arg Thr Leu Ala Phe Pro Ala Gly Val Cys Pro Thr
1               5                   10                  15

<210> SEQ ID NO 1351
<211> LENGTH: 15
<212> TYPE: PRT
<213> ORGANISM: Lolium perenne

<400> SEQUENCE: 1351

Gly Phe Gly Met Leu Leu Arg Lys Tyr Gly Ile Ala Ala Glu Asn
1               5                   10                  15

<210> SEQ ID NO 1352
<211> LENGTH: 15
<212> TYPE: PRT
<213> ORGANISM: Lolium perenne

<400> SEQUENCE: 1352

Leu Arg Lys Tyr Gly Ile Ala Ala Glu Asn Val Ile Asp Val Lys
1               5                   10                  15

<210> SEQ ID NO 1353
<211> LENGTH: 15
<212> TYPE: PRT
<213> ORGANISM: Lolium perenne

<400> SEQUENCE: 1353

Gly Gly Glu Ser Phe Gly Ile Val Val Ser Trp Gln Val Lys Leu
1               5                   10                  15

<210> SEQ ID NO 1354
<211> LENGTH: 15
<212> TYPE: PRT
<213> ORGANISM: Lolium perenne

<400> SEQUENCE: 1354

Gly Ile Val Val Ser Trp Gln Val Lys Leu Leu Pro Val Pro Pro
1               5                   10                  15

<210> SEQ ID NO 1355
<211> LENGTH: 15
<212> TYPE: PRT
<213> ORGANISM: Lolium perenne

<400> SEQUENCE: 1355

Val Asp Ile Ile Asn Lys Trp Gln Leu Val Ala Pro Gln Leu Pro
1               5                   10                  15

<210> SEQ ID NO 1356
<211> LENGTH: 15
<212> TYPE: PRT
<213> ORGANISM: Lolium perenne

<400> SEQUENCE: 1356

Ala Asp Leu Met Ile Arg Ile Ile Ala Met Gly Pro Lys Ala Thr
1               5                   10                  15

<210> SEQ ID NO 1357
<211> LENGTH: 15
```

```
<212> TYPE: PRT
<213> ORGANISM: Lolium perenne

<400> SEQUENCE: 1357

Asn Glu Met Ser Trp Ile Glu Ser Ile Pro Phe Val His Leu Gly
1               5                   10                  15

<210> SEQ ID NO 1358
<211> LENGTH: 15
<212> TYPE: PRT
<213> ORGANISM: Lolium perenne

<400> SEQUENCE: 1358

Asn Arg Asn Asn Thr Phe Lys Pro Phe Ala Glu Tyr Lys Ser Asp
1               5                   10                  15

<210> SEQ ID NO 1359
<211> LENGTH: 15
<212> TYPE: PRT
<213> ORGANISM: Lolium perenne

<400> SEQUENCE: 1359

Phe Lys Pro Phe Ala Glu Tyr Lys Ser Asp Tyr Val Tyr Glu Pro
1               5                   10                  15

<210> SEQ ID NO 1360
<211> LENGTH: 15
<212> TYPE: PRT
<213> ORGANISM: Lolium perenne

<400> SEQUENCE: 1360

Glu Tyr Lys Ser Asp Tyr Val Tyr Glu Pro Phe Pro Lys Ser Val
1               5                   10                  15

<210> SEQ ID NO 1361
<211> LENGTH: 15
<212> TYPE: PRT
<213> ORGANISM: Lolium perenne

<400> SEQUENCE: 1361

Ile Met Ile Phe Asp Pro Tyr Gly Ala Thr Ile Ser Ala Thr Pro
1               5                   10                  15

<210> SEQ ID NO 1362
<211> LENGTH: 15
<212> TYPE: PRT
<213> ORGANISM: Lolium perenne

<400> SEQUENCE: 1362

Phe Pro His Arg Lys Gly Val Leu Phe Asn Ile Gln Tyr Val Asn
1               5                   10                  15

<210> SEQ ID NO 1363
<211> LENGTH: 15
<212> TYPE: PRT
<213> ORGANISM: Lolium perenne

<400> SEQUENCE: 1363

Gly Val Leu Phe Asn Ile Gln Tyr Val Asn Tyr Trp Phe Ala Pro
1               5                   10                  15

<210> SEQ ID NO 1364
<211> LENGTH: 15
<212> TYPE: PRT
<213> ORGANISM: Lolium perenne
```

```
<400> SEQUENCE: 1364

Ile Gln Tyr Val Asn Tyr Trp Phe Ala Pro Gly Ala Gly Ala Ala
1               5                   10                  15

<210> SEQ ID NO 1365
<211> LENGTH: 15
<212> TYPE: PRT
<213> ORGANISM: Lolium perenne

<400> SEQUENCE: 1365

Lys Glu Ile Tyr Asn Tyr Met Glu Pro Tyr Val Ser Lys Asn Pro
1               5                   10                  15

<210> SEQ ID NO 1366
<211> LENGTH: 15
<212> TYPE: PRT
<213> ORGANISM: Lolium perenne

<400> SEQUENCE: 1366

Gly Gln Lys Tyr Phe Lys Gly Asn Phe Glu Arg Leu Ala Ile Thr
1               5                   10                  15

<210> SEQ ID NO 1367
<211> LENGTH: 15
<212> TYPE: PRT
<213> ORGANISM: Lolium perenne

<400> SEQUENCE: 1367

Met Ala Val Gln Lys His Thr Val Ala Leu Phe Leu Ala Val Ala
1               5                   10                  15

<210> SEQ ID NO 1368
<211> LENGTH: 15
<212> TYPE: PRT
<213> ORGANISM: Lolium perenne

<400> SEQUENCE: 1368

His Thr Val Ala Leu Phe Leu Ala Val Ala Leu Val Ala Gly Pro
1               5                   10                  15

<210> SEQ ID NO 1369
<211> LENGTH: 15
<212> TYPE: PRT
<213> ORGANISM: Lolium perenne

<400> SEQUENCE: 1369

Phe Leu Ala Val Ala Leu Val Ala Gly Pro Ala Ala Ser Tyr Ala
1               5                   10                  15

<210> SEQ ID NO 1370
<211> LENGTH: 15
<212> TYPE: PRT
<213> ORGANISM: Lolium perenne

<400> SEQUENCE: 1370

Leu Ile Glu Lys Ile Asn Ala Gly Phe Lys Ala Ala Val Ala Ala
1               5                   10                  15

<210> SEQ ID NO 1371
<211> LENGTH: 15
<212> TYPE: PRT
<213> ORGANISM: Lolium perenne

<400> SEQUENCE: 1371
```

Asn Ala Gly Phe Lys Ala Ala Val Ala Ala Ala Val Val Pro
1               5                   10                  15

<210> SEQ ID NO 1372
<211> LENGTH: 15
<212> TYPE: PRT
<213> ORGANISM: Lolium perenne

<400> SEQUENCE: 1372

Lys Thr Phe Val Glu Thr Phe Gly Thr Ala Thr Asn Lys Ala Phe
1               5                   10                  15

<210> SEQ ID NO 1373
<211> LENGTH: 15
<212> TYPE: PRT
<213> ORGANISM: Lolium perenne

<400> SEQUENCE: 1373

Thr Asn Lys Ala Phe Val Glu Gly Leu Ala Ser Gly Tyr Ala Asp
1               5                   10                  15

<210> SEQ ID NO 1374
<211> LENGTH: 15
<212> TYPE: PRT
<213> ORGANISM: Lolium perenne

<400> SEQUENCE: 1374

Leu Thr Ser Lys Leu Asp Ala Ala Leu Lys Leu Ala Tyr Glu Ala
1               5                   10                  15

<210> SEQ ID NO 1375
<211> LENGTH: 15
<212> TYPE: PRT
<213> ORGANISM: Lolium perenne

<400> SEQUENCE: 1375

Asp Ala Ala Leu Lys Leu Ala Tyr Glu Ala Ala Gln Gly Ala Thr
1               5                   10                  15

<210> SEQ ID NO 1376
<211> LENGTH: 15
<212> TYPE: PRT
<213> ORGANISM: Lolium perenne

<400> SEQUENCE: 1376

Pro Glu Ala Lys Tyr Asp Ala Tyr Val Ala Thr Leu Thr Glu Ala
1               5                   10                  15

<210> SEQ ID NO 1377
<211> LENGTH: 15
<212> TYPE: PRT
<213> ORGANISM: Lolium perenne

<400> SEQUENCE: 1377

Asp Ala Tyr Val Ala Thr Leu Thr Glu Ala Leu Arg Val Ile Ala
1               5                   10                  15

<210> SEQ ID NO 1378
<211> LENGTH: 15
<212> TYPE: PRT
<213> ORGANISM: Lolium perenne

<400> SEQUENCE: 1378

Thr Leu Thr Glu Ala Leu Arg Val Ile Ala Gly Thr Leu Glu Val
1               5                   10                  15

```
                    1               5               10              15

<210> SEQ ID NO 1379
<211> LENGTH: 15
<212> TYPE: PRT
<213> ORGANISM: Lolium perenne

<400> SEQUENCE: 1379

Val Asp Ala Ala Tyr Arg Thr Ala Ala Thr Ala Ala Asn Ala Ala
1               5                   10                  15

<210> SEQ ID NO 1380
<211> LENGTH: 15
<212> TYPE: PRT
<213> ORGANISM: Lolium perenne

<400> SEQUENCE: 1380

Phe Thr Val Phe Glu Asn Thr Phe Asn Asn Ala Ile Lys Val Ser
1               5                   10                  15

<210> SEQ ID NO 1381
<211> LENGTH: 15
<212> TYPE: PRT
<213> ORGANISM: Lolium perenne

<400> SEQUENCE: 1381

Asn Thr Phe Asn Asn Ala Ile Lys Val Ser Leu Gly Ala Ala Tyr
1               5                   10                  15

<210> SEQ ID NO 1382
<211> LENGTH: 15
<212> TYPE: PRT
<213> ORGANISM: Lolium perenne

<400> SEQUENCE: 1382

Ala Ile Lys Val Ser Leu Gly Ala Ala Tyr Asp Ser Tyr Lys Phe
1               5                   10                  15

<210> SEQ ID NO 1383
<211> LENGTH: 15
<212> TYPE: PRT
<213> ORGANISM: Lolium perenne

<400> SEQUENCE: 1383

Leu Gly Ala Ala Tyr Asp Ser Tyr Lys Phe Ile Pro Thr Leu Val
1               5                   10                  15

<210> SEQ ID NO 1384
<211> LENGTH: 15
<212> TYPE: PRT
<213> ORGANISM: Lolium perenne

<400> SEQUENCE: 1384

Asp Ser Tyr Lys Phe Ile Pro Thr Leu Val Ala Ala Val Lys Gln
1               5                   10                  15

<210> SEQ ID NO 1385
<211> LENGTH: 15
<212> TYPE: PRT
<213> ORGANISM: Lolium perenne

<400> SEQUENCE: 1385

Ile Pro Thr Leu Val Ala Ala Val Lys Gln Ala Tyr Ala Ala Lys
1               5                   10                  15
```

<210> SEQ ID NO 1386
<211> LENGTH: 15
<212> TYPE: PRT
<213> ORGANISM: Lolium perenne

<400> SEQUENCE: 1386

Ala Ala Val Lys Gln Ala Tyr Ala Ala Lys Gln Ala Thr Ala Pro
1               5                   10                  15

<210> SEQ ID NO 1387
<211> LENGTH: 15
<212> TYPE: PRT
<213> ORGANISM: Lolium perenne

<400> SEQUENCE: 1387

Glu Val Lys Tyr Thr Val Ser Glu Thr Ala Leu Lys Lys Ala Val
1               5                   10                  15

<210> SEQ ID NO 1388
<211> LENGTH: 15
<212> TYPE: PRT
<213> ORGANISM: Lolium perenne

<400> SEQUENCE: 1388

Leu Lys Lys Ala Val Thr Ala Met Ser Glu Ala Glu Lys Glu Ala
1               5                   10                  15

<210> SEQ ID NO 1389
<211> LENGTH: 15
<212> TYPE: PRT
<213> ORGANISM: Lolium perenne

<400> SEQUENCE: 1389

Pro Ala Ala Ala Tyr Ala Thr Ala Thr Pro Ala Ala Ala Thr Ala
1               5                   10                  15

<210> SEQ ID NO 1390
<211> LENGTH: 15
<212> TYPE: PRT
<213> ORGANISM: Lolium perenne

<400> SEQUENCE: 1390

Met Ala Val Gln Lys Tyr Thr Val Ala Leu Phe Leu Arg Arg Gly
1               5                   10                  15

<210> SEQ ID NO 1391
<211> LENGTH: 15
<212> TYPE: PRT
<213> ORGANISM: Lolium perenne

<400> SEQUENCE: 1391

Arg Ser Leu Arg Val Ile Ala Gly Ala Leu Glu Val His Ala Val
1               5                   10                  15

<210> SEQ ID NO 1392
<211> LENGTH: 15
<212> TYPE: PRT
<213> ORGANISM: Lolium perenne

<400> SEQUENCE: 1392

Asp Lys Ile Asp Ala Ala Phe Lys Ile Ala Ala Thr Ala Ala Asn
1               5                   10                  15

<210> SEQ ID NO 1393

```
<211> LENGTH: 15
<212> TYPE: PRT
<213> ORGANISM: Lolium perenne

<400> SEQUENCE: 1393

Ala Phe Lys Ile Ala Ala Thr Ala Ala Asn Ala Ala Pro Thr Asn
1               5                   10                  15

<210> SEQ ID NO 1394
<211> LENGTH: 15
<212> TYPE: PRT
<213> ORGANISM: Lolium perenne

<400> SEQUENCE: 1394

Asp Lys Phe Thr Val Phe Glu Ser Ala Phe Asn Lys Ala Leu Asn
1               5                   10                  15

<210> SEQ ID NO 1395
<211> LENGTH: 15
<212> TYPE: PRT
<213> ORGANISM: Lolium perenne

<400> SEQUENCE: 1395

Ala Pro Glu Val Lys Tyr Ala Val Phe Glu Ala Ala Leu Thr Lys
1               5                   10                  15

<210> SEQ ID NO 1396
<211> LENGTH: 15
<212> TYPE: PRT
<213> ORGANISM: Lolium perenne

<400> SEQUENCE: 1396

Tyr Ala Val Phe Glu Ala Ala Leu Thr Lys Ala Ile Thr Ala Met
1               5                   10                  15

<210> SEQ ID NO 1397
<211> LENGTH: 15
<212> TYPE: PRT
<213> ORGANISM: Lolium perenne

<400> SEQUENCE: 1397

Ala Ala Leu Thr Lys Ala Ile Thr Ala Met Thr Gln Ala Gln Lys
1               5                   10                  15

<210> SEQ ID NO 1398
<211> LENGTH: 15
<212> TYPE: PRT
<213> ORGANISM: Lolium perenne

<400> SEQUENCE: 1398

Leu Pro Pro Pro Leu Leu Val Val Gln Ser Leu Ile Ser Leu Leu
1               5                   10                  15

<210> SEQ ID NO 1399
<211> LENGTH: 15
<212> TYPE: PRT
<213> ORGANISM: Lolium perenne

<400> SEQUENCE: 1399

Pro Leu Leu Val Val Gln Ser Leu Ile Ser Leu Leu Ile Tyr Tyr
1               5                   10                  15

<210> SEQ ID NO 1400
<211> LENGTH: 15
<212> TYPE: PRT
```

<213> ORGANISM: Anthoxanthum odoratum

<400> SEQUENCE: 1400

Ile Ala Lys Val Pro Pro Gly Pro Asn Ile Thr Ala Thr Tyr Gly
1               5                   10                  15

<210> SEQ ID NO 1401
<211> LENGTH: 15
<212> TYPE: PRT
<213> ORGANISM: Anthoxanthum odoratum

<400> SEQUENCE: 1401

Asp Lys Trp Leu Asp Ala Lys Ser Thr Trp Tyr Gly Lys Pro Thr
1               5                   10                  15

<210> SEQ ID NO 1402
<211> LENGTH: 15
<212> TYPE: PRT
<213> ORGANISM: Anthoxanthum odoratum

<400> SEQUENCE: 1402

Trp Leu Asp Ala Lys Ser Thr Trp Tyr Gly Lys Pro Thr Gly Ala
1               5                   10                  15

<210> SEQ ID NO 1403
<211> LENGTH: 15
<212> TYPE: PRT
<213> ORGANISM: Ambrosia psilostachya

<400> SEQUENCE: 1403

Met Asn Asn Glu Lys Asn Val Ser Phe Glu Phe Ile Gly Ser Thr
1               5                   10                  15

<210> SEQ ID NO 1404
<211> LENGTH: 15
<212> TYPE: PRT
<213> ORGANISM: Ambrosia psilostachya

<400> SEQUENCE: 1404

Asn Val Ser Phe Glu Phe Ile Gly Ser Thr Asp Glu Val Asp Glu
1               5                   10                  15

<210> SEQ ID NO 1405
<211> LENGTH: 15
<212> TYPE: PRT
<213> ORGANISM: Ambrosia psilostachya

<400> SEQUENCE: 1405

Ile Lys Leu Leu Pro Cys Ala Trp Ala Gly Asn Val Cys Gly Glu
1               5                   10                  15

<210> SEQ ID NO 1406
<211> LENGTH: 15
<212> TYPE: PRT
<213> ORGANISM: Ambrosia psilostachya

<400> SEQUENCE: 1406

Gln Lys Cys Gly Lys Met Arg Met Asn Val Thr Lys Asn Thr Ile
1               5                   10                  15

<210> SEQ ID NO 1407
<211> LENGTH: 15
<212> TYPE: PRT
<213> ORGANISM: Quercus alba

```
<400> SEQUENCE: 1407

Ala Ser Val Ile Pro Pro Ala Arg Leu Phe Lys Ala Phe Val Leu
1               5                   10                  15

<210> SEQ ID NO 1408
<211> LENGTH: 15
<212> TYPE: PRT
<213> ORGANISM: Quercus alba

<400> SEQUENCE: 1408

Pro Ala Arg Leu Phe Lys Ala Phe Val Leu Asp Ser Asp Asn Leu
1               5                   10                  15

<210> SEQ ID NO 1409
<211> LENGTH: 15
<212> TYPE: PRT
<213> ORGANISM: Quercus alba

<400> SEQUENCE: 1409

Lys Ala Phe Val Leu Asp Ser Asp Asn Leu Ile Pro Lys Val Val
1               5                   10                  15

<210> SEQ ID NO 1410
<211> LENGTH: 15
<212> TYPE: PRT
<213> ORGANISM: Quercus alba

<400> SEQUENCE: 1410

Ala Ser Glu Val Phe Lys Ala Val Glu Ala Tyr Leu Val Ala His
1               5                   10                  15

<210> SEQ ID NO 1411
<211> LENGTH: 15
<212> TYPE: PRT
<213> ORGANISM: Quercus alba

<400> SEQUENCE: 1411

Lys Ala Val Glu Ala Tyr Leu Val Ala His Pro Asp Leu Tyr Lys
1               5                   10                  15

<210> SEQ ID NO 1412
<211> LENGTH: 15
<212> TYPE: PRT
<213> ORGANISM: Alternaria alternata

<400> SEQUENCE: 1412

Ile Ala Ser Leu Phe Ala Ala Ala Gly Leu Ala Ala Ala Ala Pro
1               5                   10                  15

<210> SEQ ID NO 1413
<211> LENGTH: 15
<212> TYPE: PRT
<213> ORGANISM: Alternaria alternata

<400> SEQUENCE: 1413

Ile Ala Ser Leu Phe Ala Ala Ala Gly Leu Ala Ala Ala Ala Pro
1               5                   10                  15

<210> SEQ ID NO 1414
<211> LENGTH: 15
<212> TYPE: PRT
<213> ORGANISM: Alternaria alternata

<400> SEQUENCE: 1414
```

```
Ala Ala Ala Gly Leu Ala Ala Ala Ala Pro Leu Glu Ser Arg Gln
1               5                   10                  15

<210> SEQ ID NO 1415
<211> LENGTH: 15
<212> TYPE: PRT
<213> ORGANISM: Alternaria alternata

<400> SEQUENCE: 1415

Ala Ala Ala Gly Leu Ala Ala Ala Ala Pro Leu Glu Ser Arg Gln
1               5                   10                  15

<210> SEQ ID NO 1416
<211> LENGTH: 15
<212> TYPE: PRT
<213> ORGANISM: Alternaria alternata

<400> SEQUENCE: 1416

Ala Ala Ala Gly Leu Ala Ala Ala Ala Pro Leu Glu Ser Arg Gln
1               5                   10                  15

<210> SEQ ID NO 1417
<211> LENGTH: 15
<212> TYPE: PRT
<213> ORGANISM: Alternaria alternata

<400> SEQUENCE: 1417

Lys Val Ser Asp Asp Ile Thr Tyr Val Ala Thr Ala Thr Leu Pro
1               5                   10                  15

<210> SEQ ID NO 1418
<211> LENGTH: 15
<212> TYPE: PRT
<213> ORGANISM: Alternaria alternata

<400> SEQUENCE: 1418

Lys Val Ser Asp Asp Ile Thr Tyr Val Ala Thr Ala Thr Leu Pro
1               5                   10                  15

<210> SEQ ID NO 1419
<211> LENGTH: 15
<212> TYPE: PRT
<213> ORGANISM: Alternaria alternata

<400> SEQUENCE: 1419

Lys Val Ser Asp Asp Ile Thr Tyr Val Ala Thr Ala Thr Leu Pro
1               5                   10                  15

<210> SEQ ID NO 1420
<211> LENGTH: 15
<212> TYPE: PRT
<213> ORGANISM: Alternaria alternata

<400> SEQUENCE: 1420

Lys Val Ser Asp Asp Ile Thr Tyr Val Ala Thr Ala Thr Leu Pro
1               5                   10                  15

<210> SEQ ID NO 1421
<211> LENGTH: 15
<212> TYPE: PRT
<213> ORGANISM: Alternaria alternata

<400> SEQUENCE: 1421

Lys Val Ser Asp Asp Ile Thr Tyr Val Ala Thr Ala Thr Leu Pro
1               5                   10                  15
```

<210> SEQ ID NO 1422
<211> LENGTH: 15
<212> TYPE: PRT
<213> ORGANISM: Alternaria alternata

<400> SEQUENCE: 1422

Lys Val Ser Asp Asp Ile Thr Tyr Val Ala Thr Ala Thr Leu Pro
1               5                   10                  15

<210> SEQ ID NO 1423
<211> LENGTH: 15
<212> TYPE: PRT
<213> ORGANISM: Alternaria alternata

<400> SEQUENCE: 1423

Ile Thr Tyr Val Ala Thr Ala Thr Leu Pro Asn Tyr Cys Arg Ala
1               5                   10                  15

<210> SEQ ID NO 1424
<211> LENGTH: 15
<212> TYPE: PRT
<213> ORGANISM: Alternaria alternata

<400> SEQUENCE: 1424

Ile Thr Tyr Val Ala Thr Ala Thr Leu Pro Asn Tyr Cys Arg Ala
1               5                   10                  15

<210> SEQ ID NO 1425
<211> LENGTH: 15
<212> TYPE: PRT
<213> ORGANISM: Alternaria alternata

<400> SEQUENCE: 1425

Ile Thr Tyr Val Ala Thr Ala Thr Leu Pro Asn Tyr Cys Arg Ala
1               5                   10                  15

<210> SEQ ID NO 1426
<211> LENGTH: 15
<212> TYPE: PRT
<213> ORGANISM: Alternaria alternata

<400> SEQUENCE: 1426

Ile Thr Tyr Val Ala Thr Ala Thr Leu Pro Asn Tyr Cys Arg Ala
1               5                   10                  15

<210> SEQ ID NO 1427
<211> LENGTH: 15
<212> TYPE: PRT
<213> ORGANISM: Alternaria alternata

<400> SEQUENCE: 1427

Ile Thr Tyr Val Ala Thr Ala Thr Leu Pro Asn Tyr Cys Arg Ala
1               5                   10                  15

<210> SEQ ID NO 1428
<211> LENGTH: 15
<212> TYPE: PRT
<213> ORGANISM: Alternaria alternata

<400> SEQUENCE: 1428

Ile Thr Tyr Val Ala Thr Ala Thr Leu Pro Asn Tyr Cys Arg Ala
1               5                   10                  15

<210> SEQ ID NO 1429
<211> LENGTH: 15
<212> TYPE: PRT
<213> ORGANISM: Alternaria alternata

<400> SEQUENCE: 1429

Ile Thr Tyr Val Ala Thr Ala Thr Leu Pro Asn Tyr Cys Arg Ala
1               5                   10                  15

<210> SEQ ID NO 1430
<211> LENGTH: 15
<212> TYPE: PRT
<213> ORGANISM: Alternaria alternata

<400> SEQUENCE: 1430

Gln Gly Val Ala Asp Ala Tyr Ile Thr Leu Val Thr Leu Pro Lys
1               5                   10                  15

<210> SEQ ID NO 1431
<211> LENGTH: 15
<212> TYPE: PRT
<213> ORGANISM: Alternaria alternata

<400> SEQUENCE: 1431

Gln Gly Val Ala Asp Ala Tyr Ile Thr Leu Val Thr Leu Pro Lys
1               5                   10                  15

<210> SEQ ID NO 1432
<211> LENGTH: 15
<212> TYPE: PRT
<213> ORGANISM: Alternaria alternata

<400> SEQUENCE: 1432

Gln Gly Val Ala Asp Ala Tyr Ile Thr Leu Val Thr Leu Pro Lys
1               5                   10                  15

<210> SEQ ID NO 1433
<211> LENGTH: 15
<212> TYPE: PRT
<213> ORGANISM: Alternaria alternata

<400> SEQUENCE: 1433

Gln Gly Val Ala Asp Ala Tyr Ile Thr Leu Val Thr Leu Pro Lys
1               5                   10                  15

<210> SEQ ID NO 1434
<211> LENGTH: 15
<212> TYPE: PRT
<213> ORGANISM: Alternaria alternata

<400> SEQUENCE: 1434

Gln Gly Val Ala Asp Ala Tyr Ile Thr Leu Val Thr Leu Pro Lys
1               5                   10                  15

<210> SEQ ID NO 1435
<211> LENGTH: 15
<212> TYPE: PRT
<213> ORGANISM: Alternaria alternata

<400> SEQUENCE: 1435

Val Ala Asp Ala Tyr Ile Thr Leu Val Thr Leu Pro Lys Ser Ser
1               5                   10                  15

<210> SEQ ID NO 1436
<211> LENGTH: 15

```
<212> TYPE: PRT
<213> ORGANISM: Alternaria alternata

<400> SEQUENCE: 1436

Val Ala Asp Ala Tyr Ile Thr Leu Val Thr Leu Pro Lys Ser Ser
1               5                   10                  15

<210> SEQ ID NO 1437
<211> LENGTH: 15
<212> TYPE: PRT
<213> ORGANISM: Alternaria alternata

<400> SEQUENCE: 1437

Val Ala Asp Ala Tyr Ile Thr Leu Val Thr Leu Pro Lys Ser Ser
1               5                   10                  15

<210> SEQ ID NO 1438
<211> LENGTH: 15
<212> TYPE: PRT
<213> ORGANISM: Alternaria alternata

<400> SEQUENCE: 1438

Val Ala Asp Ala Tyr Ile Thr Leu Val Thr Leu Pro Lys Ser Ser
1               5                   10                  15

<210> SEQ ID NO 1439
<211> LENGTH: 15
<212> TYPE: PRT
<213> ORGANISM: Alternaria alternata

<400> SEQUENCE: 1439

Met Ser Thr Ser Glu Leu Ala Thr Ser Tyr Ala Ala Leu Ile Leu
1               5                   10                  15

<210> SEQ ID NO 1440
<211> LENGTH: 15
<212> TYPE: PRT
<213> ORGANISM: Alternaria alternata

<400> SEQUENCE: 1440

Leu Ala Thr Ser Tyr Ala Ala Leu Ile Leu Ala Asp Asp Gly Val
1               5                   10                  15

<210> SEQ ID NO 1441
<211> LENGTH: 15
<212> TYPE: PRT
<213> ORGANISM: Alternaria alternata

<400> SEQUENCE: 1441

Lys Leu Gln Ser Leu Ile Lys Ala Ala Lys Ile Glu Glu Val Glu
1               5                   10                  15

<210> SEQ ID NO 1442
<211> LENGTH: 15
<212> TYPE: PRT
<213> ORGANISM: Alternaria alternata

<400> SEQUENCE: 1442

Gln Lys Leu Val Leu Phe Ala Val Lys Gly Thr Ala Thr Ser Thr
1               5                   10                  15

<210> SEQ ID NO 1443
<211> LENGTH: 15
<212> TYPE: PRT
<213> ORGANISM: Alternaria alternata
```

<400> SEQUENCE: 1443

Gly Gln Gln Tyr Leu Ala Trp Leu Asn Glu Lys Phe Lys Arg Ser
1               5                   10                  15

<210> SEQ ID NO 1444
<211> LENGTH: 15
<212> TYPE: PRT
<213> ORGANISM: Alternaria alternata

<400> SEQUENCE: 1444

Ile Asn Glu Leu Ile Ala Ser Gly Ser Glu Lys Leu Ala Ser Val
1               5                   10                  15

<210> SEQ ID NO 1445
<211> LENGTH: 15
<212> TYPE: PRT
<213> ORGANISM: Alternaria alternata

<400> SEQUENCE: 1445

Ile Asn Glu Leu Ile Ala Ser Gly Ser Glu Lys Leu Ala Ser Val
1               5                   10                  15

<210> SEQ ID NO 1446
<211> LENGTH: 15
<212> TYPE: PRT
<213> ORGANISM: Alternaria alternata

<400> SEQUENCE: 1446

Met Thr Ile Thr Lys Ile His Ala Arg Ser Val Tyr Asp Ser Arg
1               5                   10                  15

<210> SEQ ID NO 1447
<211> LENGTH: 15
<212> TYPE: PRT
<213> ORGANISM: Alternaria alternata

<400> SEQUENCE: 1447

Leu Gly Ala Asn Ala Ile Leu Gly Val Ser Met Ala Ile Ala Lys
1               5                   10                  15

<210> SEQ ID NO 1448
<211> LENGTH: 15
<212> TYPE: PRT
<213> ORGANISM: Alternaria alternata

<400> SEQUENCE: 1448

Met Ala Ile Ala Lys Ala Ala Ala Glu Lys Gly Val Pro Leu
1               5                   10                  15

<210> SEQ ID NO 1449
<211> LENGTH: 15
<212> TYPE: PRT
<213> ORGANISM: Alternaria alternata

<400> SEQUENCE: 1449

Gly Gly Arg Leu Ala Phe Gln Glu Phe Met Ile Val Pro Cys Glu
1               5                   10                  15

<210> SEQ ID NO 1450
<211> LENGTH: 15
<212> TYPE: PRT
<213> ORGANISM: Alternaria alternata

<400> SEQUENCE: 1450

Gly Gly Arg Leu Ala Phe Gln Glu Phe Met Ile Val Pro Cys Glu
1               5                   10                  15

<210> SEQ ID NO 1451
<211> LENGTH: 15
<212> TYPE: PRT
<213> ORGANISM: Alternaria alternata

<400> SEQUENCE: 1451

Gly Ala Glu Val Tyr Gln Lys Leu Lys Ala Leu Ala Lys Lys Thr
1               5                   10                  15

<210> SEQ ID NO 1452
<211> LENGTH: 15
<212> TYPE: PRT
<213> ORGANISM: Alternaria alternata

<400> SEQUENCE: 1452

Lys Ser Lys Trp Leu Thr Tyr Glu Gln Leu Ala Glu Met Tyr Lys
1               5                   10                  15

<210> SEQ ID NO 1453
<211> LENGTH: 15
<212> TYPE: PRT
<213> ORGANISM: Alternaria alternata

<400> SEQUENCE: 1453

Glu Ala Trp Ser Tyr Phe Phe Lys Thr Tyr Asp Gly Gln Ile Val
1               5                   10                  15

<210> SEQ ID NO 1454
<211> LENGTH: 15
<212> TYPE: PRT
<213> ORGANISM: Alternaria alternata

<400> SEQUENCE: 1454

Cys Asn Ala Leu Leu Leu Lys Val Asn Gln Ile Gly Thr Ile Thr
1               5                   10                  15

<210> SEQ ID NO 1455
<211> LENGTH: 15
<212> TYPE: PRT
<213> ORGANISM: Alternaria alternata

<400> SEQUENCE: 1455

Gly Ala Gly Trp Gly Val Met Val Ser His Arg Ser Gly Glu Thr
1               5                   10                  15

<210> SEQ ID NO 1456
<211> LENGTH: 15
<212> TYPE: PRT
<213> ORGANISM: Alternaria alternata

<400> SEQUENCE: 1456

Glu Arg Leu Ala Lys Leu Asn Gln Ile Leu Arg Ile Glu Glu Glu
1               5                   10                  15

<210> SEQ ID NO 1457
<211> LENGTH: 15
<212> TYPE: PRT
<213> ORGANISM: Alternaria alternata

<400> SEQUENCE: 1457

Ile Tyr Val Pro Leu Gly Tyr Lys Thr Ala Phe Ser Met Leu Ala

```
1               5                  10                 15
```

<210> SEQ ID NO 1458
<211> LENGTH: 15
<212> TYPE: PRT
<213> ORGANISM: Alternaria alternata

<400> SEQUENCE: 1458

```
Ala Gln Gly Lys Ala Phe Tyr Glu Ala Val Ala Lys Ala His Gln
1               5                  10                 15
```

<210> SEQ ID NO 1459
<211> LENGTH: 15
<212> TYPE: PRT
<213> ORGANISM: Alternaria alternata

<400> SEQUENCE: 1459

```
Ala Gln Gly Lys Ala Phe Tyr Glu Ala Val Ala Lys Ala His Gln
1               5                  10                 15
```

<210> SEQ ID NO 1460
<211> LENGTH: 15
<212> TYPE: PRT
<213> ORGANISM: Alternaria alternata

<400> SEQUENCE: 1460

```
Leu Phe Gln Val Ala Glu Thr Leu Pro Gln Glu Val Leu Asp Lys
1               5                  10                 15
```

<210> SEQ ID NO 1461
<211> LENGTH: 15
<212> TYPE: PRT
<213> ORGANISM: Alternaria alternata

<400> SEQUENCE: 1461

```
Ala Ile Val Tyr Tyr Ser Met Tyr Gly His Ile Lys Lys Met Ala
1               5                  10                 15
```

<210> SEQ ID NO 1462
<211> LENGTH: 15
<212> TYPE: PRT
<213> ORGANISM: Alternaria alternata

<400> SEQUENCE: 1462

```
Ala Ile Val Tyr Tyr Ser Met Tyr Gly His Ile Lys Lys Met Ala
1               5                  10                 15
```

<210> SEQ ID NO 1463
<211> LENGTH: 15
<212> TYPE: PRT
<213> ORGANISM: Alternaria alternata

<400> SEQUENCE: 1463

```
Glu Leu Lys Gly Ala Tyr Val Tyr Phe Ala Ser Asp Ala Ser Ser
1               5                  10                 15
```

<210> SEQ ID NO 1464
<211> LENGTH: 15
<212> TYPE: PRT
<213> ORGANISM: Alternaria alternata

<400> SEQUENCE: 1464

```
Gln Asp Ile Gln Lys Leu Trp His Ser Met Ile Pro Met Gly Arg
1               5                  10                 15
```

<210> SEQ ID NO 1465
<211> LENGTH: 15
<212> TYPE: PRT
<213> ORGANISM: Alternaria alternata

<400> SEQUENCE: 1465

Thr Gly Ser Leu Val Ile Thr Ser Ser Met Ser Gly His Ile Ala
1               5                   10                  15

<210> SEQ ID NO 1466
<211> LENGTH: 15
<212> TYPE: PRT
<213> ORGANISM: Aspergillus fumigatus

<400> SEQUENCE: 1466

Ala Arg Val Ile Tyr Thr Tyr Pro Asn Lys Val Phe Cys Gly Ile
1               5                   10                  15

<210> SEQ ID NO 1467
<211> LENGTH: 15
<212> TYPE: PRT
<213> ORGANISM: Aspergillus fumigatus

<400> SEQUENCE: 1467

Lys Asn Ile Val Lys Lys Thr Leu Glu Leu Phe Asn Glu Ile Ala
1               5                   10                  15

<210> SEQ ID NO 1468
<211> LENGTH: 15
<212> TYPE: PRT
<213> ORGANISM: Aspergillus fumigatus

<400> SEQUENCE: 1468

Leu Gly Gly Gly Tyr Ser Tyr Ala Phe Asn Asn Ala Val Glu Asn
1               5                   10                  15

<210> SEQ ID NO 1469
<211> LENGTH: 15
<212> TYPE: PRT
<213> ORGANISM: Aspergillus fumigatus

<400> SEQUENCE: 1469

Leu Asp Gly Phe Asn Trp Ala Val Asn Asp Ile Val Ser Lys Gly
1               5                   10                  15

<210> SEQ ID NO 1470
<211> LENGTH: 15
<212> TYPE: PRT
<213> ORGANISM: Aspergillus fumigatus

<400> SEQUENCE: 1470

Ala Asp Ser Leu Ala Lys Ala Ile Ser Ala Lys Val Pro Glu Ser
1               5                   10                  15

<210> SEQ ID NO 1471
<211> LENGTH: 15
<212> TYPE: PRT
<213> ORGANISM: Aspergillus fumigatus

<400> SEQUENCE: 1471

Ala Gln Leu Ser Ala Gly Ile Thr Ala Ala Ile Gln Lys Gly Ile
1               5                   10                  15

<210> SEQ ID NO 1472

```
<211> LENGTH: 15
<212> TYPE: PRT
<213> ORGANISM: Aspergillus fumigatus

<400> SEQUENCE: 1472

Ser Lys Lys Asp Lys Phe Val Ala Ala Asn Ala Gly Gly Thr Val
1               5                   10                  15

<210> SEQ ID NO 1473
<211> LENGTH: 15
<212> TYPE: PRT
<213> ORGANISM: Aspergillus fumigatus

<400> SEQUENCE: 1473

Ser Lys Lys Asp Lys Phe Val Ala Ala Asn Ala Gly Gly Thr Val
1               5                   10                  15

<210> SEQ ID NO 1474
<211> LENGTH: 15
<212> TYPE: PRT
<213> ORGANISM: Aspergillus fumigatus

<400> SEQUENCE: 1474

Ala Gly Gly Thr Val Tyr Glu Asp Leu Lys Ala Gln Tyr Thr Ala
1               5                   10                  15

<210> SEQ ID NO 1475
<211> LENGTH: 15
<212> TYPE: PRT
<213> ORGANISM: Aspergillus fumigatus

<400> SEQUENCE: 1475

Gly Gly Arg Leu Ala Phe Gln Glu Phe Met Ile Val Pro Asp Ser
1               5                   10                  15

<210> SEQ ID NO 1476
<211> LENGTH: 15
<212> TYPE: PRT
<213> ORGANISM: Aspergillus fumigatus

<400> SEQUENCE: 1476

Thr Asn Gly Ser Gln Phe Phe Ile Thr Thr Val Val Thr Ser Trp
1               5                   10                  15

<210> SEQ ID NO 1477
<211> LENGTH: 15
<212> TYPE: PRT
<213> ORGANISM: Aspergillus fumigatus

<400> SEQUENCE: 1477

Asp Thr Val Tyr Ala Thr Ile Asn Gly Val Leu Val Ser Trp Ile
1               5                   10                  15

<210> SEQ ID NO 1478
<211> LENGTH: 15
<212> TYPE: PRT
<213> ORGANISM: Cladosporium herbarum

<400> SEQUENCE: 1478

Ser Lys Val Gln Phe Asp Arg Ile Met Glu Tyr Ile Gln Ala Gly
1               5                   10                  15

<210> SEQ ID NO 1479
<211> LENGTH: 15
<212> TYPE: PRT
```

<213> ORGANISM: Cladosporium herbarum

<400> SEQUENCE: 1479

Met Lys Tyr Leu Ala Ala Phe Leu Leu Leu Gly Leu Ala Gly Asn
1               5                   10                  15

<210> SEQ ID NO 1480
<211> LENGTH: 15
<212> TYPE: PRT
<213> ORGANISM: Cladosporium herbarum

<400> SEQUENCE: 1480

Ala Phe Leu Leu Leu Gly Leu Ala Gly Asn Ser Ser Pro Ser Ala
1               5                   10                  15

<210> SEQ ID NO 1481
<211> LENGTH: 15
<212> TYPE: PRT
<213> ORGANISM: Cladosporium herbarum

<400> SEQUENCE: 1481

Ala Phe Leu Leu Leu Gly Leu Ala Gly Asn Ser Ser Pro Ser Ala
1               5                   10                  15

<210> SEQ ID NO 1482
<211> LENGTH: 15
<212> TYPE: PRT
<213> ORGANISM: Cladosporium herbarum

<400> SEQUENCE: 1482

Ile Leu Gly Val Ser Met Ala Val Ala Lys Ala Ala Ala Ala Glu
1               5                   10                  15

<210> SEQ ID NO 1483
<211> LENGTH: 15
<212> TYPE: PRT
<213> ORGANISM: Cladosporium herbarum

<400> SEQUENCE: 1483

Lys Arg Val Pro Leu Tyr Ala His Ile Ser Asp Leu Ser Gly Thr
1               5                   10                  15

<210> SEQ ID NO 1484
<211> LENGTH: 15
<212> TYPE: PRT
<213> ORGANISM: Cladosporium herbarum

<400> SEQUENCE: 1484

Gly Gly Arg Leu Ala Phe Gln Glu Phe Met Ile Val Pro Ser Gly
1               5                   10                  15

<210> SEQ ID NO 1485
<211> LENGTH: 15
<212> TYPE: PRT
<213> ORGANISM: Cladosporium herbarum

<400> SEQUENCE: 1485

Gly Gly Arg Leu Ala Phe Gln Glu Phe Met Ile Val Pro Ser Gly
1               5                   10                  15

<210> SEQ ID NO 1486
<211> LENGTH: 15
<212> TYPE: PRT
<213> ORGANISM: Cladosporium herbarum -continued

<400> SEQUENCE: 1486

Gly Gly Arg Leu Ala Phe Gln Glu Phe Met Ile Val Pro Ser Gly
1               5                   10                  15

<210> SEQ ID NO 1487
<211> LENGTH: 15
<212> TYPE: PRT
<213> ORGANISM: Cladosporium herbarum

<400> SEQUENCE: 1487

Phe Gln Glu Phe Met Ile Val Pro Ser Gly Ala Pro Ser Phe Thr
1               5                   10                  15

<210> SEQ ID NO 1488
<211> LENGTH: 15
<212> TYPE: PRT
<213> ORGANISM: Cladosporium herbarum

<400> SEQUENCE: 1488

Gly Ala Glu Val Tyr Gln Lys Leu Lys Ser Leu Thr Lys Lys Arg
1               5                   10                  15

<210> SEQ ID NO 1489
<211> LENGTH: 15
<212> TYPE: PRT
<213> ORGANISM: Cladosporium herbarum

<400> SEQUENCE: 1489

Ala Asp Gln Tyr Lys Gln Leu Ala Ala Lys Tyr Pro Ile Val Ser
1               5                   10                  15

<210> SEQ ID NO 1490
<211> LENGTH: 15
<212> TYPE: PRT
<213> ORGANISM: Cladosporium herbarum

<400> SEQUENCE: 1490

Glu Ala Trp Ser Tyr Phe Tyr Lys Thr Ser Gly Ser Asp Phe Gln
1               5                   10                  15

<210> SEQ ID NO 1491
<211> LENGTH: 15
<212> TYPE: PRT
<213> ORGANISM: Cladosporium herbarum

<400> SEQUENCE: 1491

Met Ala Pro Lys Ile Ala Ile Ile Phe Tyr Ser Thr Trp Gly His
1               5                   10                  15

<210> SEQ ID NO 1492
<211> LENGTH: 15
<212> TYPE: PRT
<213> ORGANISM: Cladosporium herbarum

<400> SEQUENCE: 1492

Ala Met Ser Thr Leu Ser His His Gly Ile Ile Tyr Val Pro Leu
1               5                   10                  15

<210> SEQ ID NO 1493
<211> LENGTH: 15
<212> TYPE: PRT
<213> ORGANISM: Cladosporium herbarum

<400> SEQUENCE: 1493

```
Gly Ala Ala Val Ala Ile Thr Tyr Ala Ser Arg Ala Gln Gly Ala
1               5                   10                  15

<210> SEQ ID NO 1494
<211> LENGTH: 15
<212> TYPE: PRT
<213> ORGANISM: Cladosporium herbarum

<400> SEQUENCE: 1494

Gln Ile Asp Ala Phe Ile Ala Asn Ala Gly Thr Ala Asp Ser
1               5                   10                  15

<210> SEQ ID NO 1495
<211> LENGTH: 15
<212> TYPE: PRT
<213> ORGANISM: Cladosporium herbarum

<400> SEQUENCE: 1495

Gln Ile Asp Ala Phe Ile Ala Asn Ala Gly Thr Ala Asp Ser
1               5                   10                  15

<210> SEQ ID NO 1496
<211> LENGTH: 15
<212> TYPE: PRT
<213> ORGANISM: Cladosporium herbarum

<400> SEQUENCE: 1496

Gly Thr Gly Ser Leu Val Ile Thr Ala Ser Met Ser Gly His Ile
1               5                   10                  15

<210> SEQ ID NO 1497
<211> LENGTH: 15
<212> TYPE: PRT
<213> ORGANISM: Cladosporium herbarum

<400> SEQUENCE: 1497

Gly Thr Gly Ser Leu Val Ile Thr Ala Ser Met Ser Gly His Ile
1               5                   10                  15

<210> SEQ ID NO 1498
<211> LENGTH: 15
<212> TYPE: PRT
<213> ORGANISM: Cladosporium herbarum

<400> SEQUENCE: 1498

Gly Cys Ile His Met Ala Arg Ser Leu Ala Asn Glu Trp Arg Asp
1               5                   10                  15

<210> SEQ ID NO 1499
<211> LENGTH: 15
<212> TYPE: PRT
<213> ORGANISM: Cladosporium herbarum

<400> SEQUENCE: 1499

Gly Cys Ile His Met Ala Arg Ser Leu Ala Asn Glu Trp Arg Asp
1               5                   10                  15

<210> SEQ ID NO 1500
<211> LENGTH: 15
<212> TYPE: PRT
<213> ORGANISM: Cladosporium herbarum

<400> SEQUENCE: 1500

Lys Glu Leu Lys Gly Ala Tyr Val Tyr Phe Ala Ser Asp Ala Ser
1               5                   10                  15
```

```
<210> SEQ ID NO 1501
<211> LENGTH: 15
<212> TYPE: PRT
<213> ORGANISM: Cladosporium herbarum

<400> SEQUENCE: 1501

Lys Glu Leu Lys Gly Ala Tyr Val Tyr Phe Ala Ser Asp Ala Ser
1               5                   10                  15

<210> SEQ ID NO 1502
<211> LENGTH: 15
<212> TYPE: PRT
<213> ORGANISM: Cladosporium herbarum

<400> SEQUENCE: 1502

Ala Tyr Val Tyr Phe Ala Ser Asp Ala Ser Thr Tyr Thr Thr Gly
1               5                   10                  15

<210> SEQ ID NO 1503
<211> LENGTH: 15
<212> TYPE: PRT
<213> ORGANISM: Penicillium chrysogenum

<400> SEQUENCE: 1503

Val Leu Ala Thr Ser Leu Ala Thr Leu Ala Val Val Asp Ala Gly
1               5                   10                  15

<210> SEQ ID NO 1504
<211> LENGTH: 15
<212> TYPE: PRT
<213> ORGANISM: Penicillium chrysogenum

<400> SEQUENCE: 1504

Tyr Ile Val Val Met Asn Asp Asp Val Ser Thr Ala Glu Phe Ser
1               5                   10                  15

<210> SEQ ID NO 1505
<211> LENGTH: 15
<212> TYPE: PRT
<213> ORGANISM: Penicillium chrysogenum

<400> SEQUENCE: 1505

Pro Ala Val Lys Tyr Ile Glu Pro Asp Met Ile Val Asn Ala Thr
1               5                   10                  15

<210> SEQ ID NO 1506
<211> LENGTH: 15
<212> TYPE: PRT
<213> ORGANISM: Penicillium chrysogenum

<400> SEQUENCE: 1506

Pro Ala Val Lys Tyr Ile Glu Pro Asp Met Ile Val Asn Ala Thr
1               5                   10                  15

<210> SEQ ID NO 1507
<211> LENGTH: 15
<212> TYPE: PRT
<213> ORGANISM: Penicillium chrysogenum

<400> SEQUENCE: 1507

Ile Val Asn Ala Thr Ala Asn Val Val Gln Ser Asn Val Pro Ser
1               5                   10                  15
```

```
<210> SEQ ID NO 1508
<211> LENGTH: 15
<212> TYPE: PRT
<213> ORGANISM: Penicillium chrysogenum

<400> SEQUENCE: 1508

Tyr Gly Val Ala Lys Lys Ala Thr Leu Val Ala Val Lys Val Leu
1               5                   10                  15

<210> SEQ ID NO 1509
<211> LENGTH: 15
<212> TYPE: PRT
<213> ORGANISM: Penicillium chrysogenum

<400> SEQUENCE: 1509

Asn Val Val Lys Ser Gly Ile Phe Leu Ser Val Ala Ala Gly Asn
1               5                   10                  15

<210> SEQ ID NO 1510
<211> LENGTH: 15
<212> TYPE: PRT
<213> ORGANISM: Penicillium chrysogenum

<400> SEQUENCE: 1510

Asn Val Val Lys Ser Gly Ile Phe Leu Ser Val Ala Ala Gly Asn
1               5                   10                  15

<210> SEQ ID NO 1511
<211> LENGTH: 15
<212> TYPE: PRT
<213> ORGANISM: Penicillium chrysogenum

<400> SEQUENCE: 1511

Gly Ile Phe Leu Ser Val Ala Ala Gly Asn Glu Ala Glu Asn Ala
1               5                   10                  15

<210> SEQ ID NO 1512
<211> LENGTH: 15
<212> TYPE: PRT
<213> ORGANISM: Penicillium chrysogenum

<400> SEQUENCE: 1512

Gly Ile Phe Leu Ser Val Ala Ala Gly Asn Glu Ala Glu Asn Ala
1               5                   10                  15

<210> SEQ ID NO 1513
<211> LENGTH: 15
<212> TYPE: PRT
<213> ORGANISM: Penicillium chrysogenum

<400> SEQUENCE: 1513

Ala Pro His Val Ala Gly Val Ala Ala Tyr Leu Met Ala Leu Glu
1               5                   10                  15

<210> SEQ ID NO 1514
<211> LENGTH: 15
<212> TYPE: PRT
<213> ORGANISM: Penicillium chrysogenum

<400> SEQUENCE: 1514

Ile Val Gln Leu Ala Thr Ser Ser Ile Ser Arg Ala Pro Ser Gly
1               5                   10                  15

<210> SEQ ID NO 1515
<211> LENGTH: 15
```

<212> TYPE: PRT
<213> ORGANISM: Penicillium chrysogenum

<400> SEQUENCE: 1515

Met Lys Gly Phe Leu Ser Leu Thr Leu Leu Pro Leu Leu Val Ala
1               5                   10                  15

<210> SEQ ID NO 1516
<211> LENGTH: 15
<212> TYPE: PRT
<213> ORGANISM: Penicillium chrysogenum

<400> SEQUENCE: 1516

Asn Asp Ala Ala Pro Ile Leu Ser Ser Met Thr Ser Lys Asp Ile
1               5                   10                  15

<210> SEQ ID NO 1517
<211> LENGTH: 15
<212> TYPE: PRT
<213> ORGANISM: Penicillium chrysogenum

<400> SEQUENCE: 1517

Thr Phe His Ile Ala Gly Ser Leu Leu Gly Tyr Ala Gly His Phe
1               5                   10                  15

<210> SEQ ID NO 1518
<211> LENGTH: 15
<212> TYPE: PRT
<213> ORGANISM: Penicillium chrysogenum

<400> SEQUENCE: 1518

Lys Phe Gly Val Ala Lys Lys Ala Asn Val Tyr Ala Val Lys Val
1               5                   10                  15

<210> SEQ ID NO 1519
<211> LENGTH: 15
<212> TYPE: PRT
<213> ORGANISM: Penicillium chrysogenum

<400> SEQUENCE: 1519

Lys Phe Gly Val Ala Lys Lys Ala Asn Val Tyr Ala Val Lys Val
1               5                   10                  15

<210> SEQ ID NO 1520
<211> LENGTH: 15
<212> TYPE: PRT
<213> ORGANISM: Penicillium chrysogenum

<400> SEQUENCE: 1520

Leu Asp Leu Ala Val Asn Ala Ala Val Asp Ala Gly Ile His Phe
1               5                   10                  15

<210> SEQ ID NO 1521
<211> LENGTH: 15
<212> TYPE: PRT
<213> ORGANISM: Penicillium chrysogenum

<400> SEQUENCE: 1521

Leu Asp Leu Ala Val Asn Ala Ala Val Asp Ala Gly Ile His Phe
1               5                   10                  15

<210> SEQ ID NO 1522
<211> LENGTH: 15
<212> TYPE: PRT
<213> ORGANISM: Penicillium chrysogenum

<400> SEQUENCE: 1522

Leu Asp Leu Ala Val Asn Ala Ala Val Asp Ala Gly Ile His Phe
1               5                   10                  15

<210> SEQ ID NO 1523
<211> LENGTH: 15
<212> TYPE: PRT
<213> ORGANISM: Penicillium chrysogenum

<400> SEQUENCE: 1523

Ala Gly Ile His Phe Ala Val Ala Ala Gly Asn Asp Asn Ala Asp
1               5                   10                  15

<210> SEQ ID NO 1524
<211> LENGTH: 15
<212> TYPE: PRT
<213> ORGANISM: Penicillium chrysogenum

<400> SEQUENCE: 1524

His Ile Ala Gly Leu Leu Ala Tyr Tyr Val Ser Leu Ala Pro Ala
1               5                   10                  15

<210> SEQ ID NO 1525
<211> LENGTH: 15
<212> TYPE: PRT
<213> ORGANISM: Penicillium chrysogenum

<400> SEQUENCE: 1525

Lys Ala Ala Leu Ile Ser Val Ala Thr Glu Gly Thr Leu Thr Asp
1               5                   10                  15

<210> SEQ ID NO 1526
<211> LENGTH: 15
<212> TYPE: PRT
<213> ORGANISM: Penicillium chrysogenum

<400> SEQUENCE: 1526

Ala Phe His Lys Glu Leu Gly Ala Ile Tyr Ser Glu Ile Lys Asp
1               5                   10                  15

<210> SEQ ID NO 1527
<211> LENGTH: 15
<212> TYPE: PRT
<213> ORGANISM: Penicillium chrysogenum

<400> SEQUENCE: 1527

Val Asp Ala Tyr Val Ile Asp Thr Gly Ala Asn Val Lys His Val
1               5                   10                  15

<210> SEQ ID NO 1528
<211> LENGTH: 15
<212> TYPE: PRT
<213> ORGANISM: Periplaneta americana

<400> SEQUENCE: 1528

Tyr Gly Ser Ile Phe His Phe Tyr Arg Leu Leu Val Gly His Val
1               5                   10                  15

<210> SEQ ID NO 1529
<211> LENGTH: 15
<212> TYPE: PRT
<213> ORGANISM: Periplaneta americana

<400> SEQUENCE: 1529

Phe Tyr Gln Leu Trp Lys Arg Ile Asp His Ile Val Gln Lys Tyr
1               5                   10                  15

<210> SEQ ID NO 1530
<211> LENGTH: 15
<212> TYPE: PRT
<213> ORGANISM: Periplaneta americana

<400> SEQUENCE: 1530

Tyr Thr Pro Asn Met Tyr Phe Lys Asp Val Val Ile Phe His Lys
1               5                   10                  15

<210> SEQ ID NO 1531
<211> LENGTH: 15
<212> TYPE: PRT
<213> ORGANISM: Felis catus

<400> SEQUENCE: 1531

Asp Glu Tyr Val Glu Gln Val Ala Gln Tyr Lys Ala Leu Pro Val
1               5                   10                  15

<210> SEQ ID NO 1532
<211> LENGTH: 15
<212> TYPE: PRT
<213> ORGANISM: Felis catus

<400> SEQUENCE: 1532

Asp Glu Tyr Val Glu Gln Val Ala Gln Tyr Lys Ala Leu Pro Val
1               5                   10                  15

<210> SEQ ID NO 1533
<211> LENGTH: 15
<212> TYPE: PRT
<213> ORGANISM: Felis catus

<400> SEQUENCE: 1533

Gln Val Ala Gln Tyr Lys Ala Leu Pro Val Val Leu Glu Asn Ala
1               5                   10                  15

<210> SEQ ID NO 1534
<211> LENGTH: 15
<212> TYPE: PRT
<213> ORGANISM: Felis catus

<400> SEQUENCE: 1534

Gln Val Ala Gln Tyr Lys Ala Leu Pro Val Val Leu Glu Asn Ala
1               5                   10                  15

<210> SEQ ID NO 1535
<211> LENGTH: 15
<212> TYPE: PRT
<213> ORGANISM: Felis catus

<400> SEQUENCE: 1535

Lys Ala Leu Pro Val Val Leu Glu Asn Ala Arg Ile Leu Lys Asn
1               5                   10                  15

<210> SEQ ID NO 1536
<211> LENGTH: 15
<212> TYPE: PRT
<213> ORGANISM: Felis catus

<400> SEQUENCE: 1536

Asn Ala Leu Ser Val Leu Asp Lys Ile Tyr Thr Ser Pro Leu Cys

<210> SEQ ID NO 1537
<211> LENGTH: 15
<212> TYPE: PRT
<213> ORGANISM: Felis catus

<400> SEQUENCE: 1537

Asn Ala Leu Ser Val Leu Asp Lys Ile Tyr Thr Ser Pro Leu Cys
1               5                   10                  15

<210> SEQ ID NO 1538
<211> LENGTH: 15
<212> TYPE: PRT
<213> ORGANISM: Felis catus

<400> SEQUENCE: 1538

Asn Ala Leu Ser Val Leu Asp Lys Ile Tyr Thr Ser Pro Leu Cys
1               5                   10                  15

<210> SEQ ID NO 1539
<211> LENGTH: 15
<212> TYPE: PRT
<213> ORGANISM: Felis catus

<400> SEQUENCE: 1539

Ala Glu Thr Cys Pro Ile Phe Tyr Asp Val Phe Phe Ala Val Ala
1               5                   10                  15

<210> SEQ ID NO 1540
<211> LENGTH: 15
<212> TYPE: PRT
<213> ORGANISM: Felis catus

<400> SEQUENCE: 1540

Ala Glu Thr Cys Pro Ile Phe Tyr Asp Val Phe Phe Ala Val Ala
1               5                   10                  15

<210> SEQ ID NO 1541
<211> LENGTH: 15
<212> TYPE: PRT
<213> ORGANISM: Felis catus

<400> SEQUENCE: 1541

Ala Glu Thr Cys Pro Ile Phe Tyr Asp Val Phe Phe Ala Val Ala
1               5                   10                  15

<210> SEQ ID NO 1542
<211> LENGTH: 15
<212> TYPE: PRT
<213> ORGANISM: Felis catus

<400> SEQUENCE: 1542

Ala Glu Thr Cys Pro Ile Phe Tyr Asp Val Phe Phe Ala Val Ala
1               5                   10                  15

<210> SEQ ID NO 1543
<211> LENGTH: 15
<212> TYPE: PRT
<213> ORGANISM: Felis catus

<400> SEQUENCE: 1543

Ala Glu Thr Cys Pro Ile Phe Tyr Asp Val Phe Phe Ala Val Ala
1               5                   10                  15

<210> SEQ ID NO 1544
<211> LENGTH: 15
<212> TYPE: PRT
<213> ORGANISM: Felis catus

<400> SEQUENCE: 1544

Ile Phe Tyr Asp Val Phe Phe Ala Val Ala Asn Gly Asn Glu Leu
1               5                   10                  15

<210> SEQ ID NO 1545
<211> LENGTH: 15
<212> TYPE: PRT
<213> ORGANISM: Felis catus

<400> SEQUENCE: 1545

Ile Phe Tyr Asp Val Phe Phe Ala Val Ala Asn Gly Asn Glu Leu
1               5                   10                  15

<210> SEQ ID NO 1546
<211> LENGTH: 15
<212> TYPE: PRT
<213> ORGANISM: Felis catus

<400> SEQUENCE: 1546

Ile Phe Tyr Asp Val Phe Phe Ala Val Ala Asn Gly Asn Glu Leu
1               5                   10                  15

<210> SEQ ID NO 1547
<211> LENGTH: 15
<212> TYPE: PRT
<213> ORGANISM: Felis catus

<400> SEQUENCE: 1547

Ile Phe Tyr Asp Val Phe Phe Ala Val Ala Asn Gly Asn Glu Leu
1               5                   10                  15

<210> SEQ ID NO 1548
<211> LENGTH: 15
<212> TYPE: PRT
<213> ORGANISM: Felis catus

<400> SEQUENCE: 1548

Ile Phe Tyr Asp Val Phe Phe Ala Val Ala Asn Gly Asn Glu Leu
1               5                   10                  15

<210> SEQ ID NO 1549
<211> LENGTH: 15
<212> TYPE: PRT
<213> ORGANISM: Felis catus

<400> SEQUENCE: 1549

Asn Gly Asn Glu Leu Leu Leu Asp Leu Ser Leu Thr Lys Val Asn
1               5                   10                  15

<210> SEQ ID NO 1550
<211> LENGTH: 15
<212> TYPE: PRT
<213> ORGANISM: Felis catus

<400> SEQUENCE: 1550

Asn Gly Asn Glu Leu Leu Leu Asp Leu Ser Leu Thr Lys Val Asn
1               5                   10                  15

<210> SEQ ID NO 1551

```
<210> SEQ ID NO 1551
<211> LENGTH: 15
<212> TYPE: PRT
<213> ORGANISM: Felis catus

<400> SEQUENCE: 1551

Tyr Val Glu Asn Gly Leu Ile Ser Arg Val Leu Asp Gly Leu Val
1               5                   10                  15

<210> SEQ ID NO 1552
<211> LENGTH: 15
<212> TYPE: PRT
<213> ORGANISM: Felis catus

<400> SEQUENCE: 1552

Val Phe Val Glu His Ile Lys Ala Leu Asp Asn Ser Ser Leu Ser
1               5                   10                  15

<210> SEQ ID NO 1553
<211> LENGTH: 15
<212> TYPE: PRT
<213> ORGANISM: Felis catus

<400> SEQUENCE: 1553

Tyr Thr Val Val Tyr Asp Gly Tyr Asn Val Phe Ser Ile Val Glu
1               5                   10                  15

<210> SEQ ID NO 1554
<211> LENGTH: 15
<212> TYPE: PRT
<213> ORGANISM: Felis catus

<400> SEQUENCE: 1554

Tyr Ile Leu Leu His Leu Leu Asn Phe Asp Lys Thr Arg Pro Phe
1               5                   10                  15

<210> SEQ ID NO 1555
<211> LENGTH: 15
<212> TYPE: PRT
<213> ORGANISM: Canis familiaris

<400> SEQUENCE: 1555

Gln Leu Phe Leu Gly Lys Tyr Leu Tyr Glu Ile Ala Arg Arg His
1               5                   10                  15

<210> SEQ ID NO 1556
<211> LENGTH: 15
<212> TYPE: PRT
<213> ORGANISM: Canis familiaris

<400> SEQUENCE: 1556

Pro Glu Leu Leu Tyr Tyr Ala Gln Gln Tyr Lys Gly Val Phe Ala
1               5                   10                  15

<210> SEQ ID NO 1557
<211> LENGTH: 15
<212> TYPE: PRT
<213> ORGANISM: Canis familiaris

<400> SEQUENCE: 1557

Lys Leu Gly Glu Tyr Gly Phe Gln Asn Ala Leu Leu Val Arg Tyr
1               5                   10                  15

<210> SEQ ID NO 1558
<211> LENGTH: 15
<212> TYPE: PRT
```

<213> ORGANISM: Canis familiaris

<400> SEQUENCE: 1558

Phe Leu Ser Val Val Leu Asn Arg Leu Cys Val Leu His Glu Lys
1               5                   10                  15

<210> SEQ ID NO 1559
<211> LENGTH: 15
<212> TYPE: PRT
<213> ORGANISM: Canis familiaris

<400> SEQUENCE: 1559

Phe Thr Phe His Ala Asp Leu Cys Thr Leu Pro Glu Ala Glu Lys
1               5                   10                  15

<210> SEQ ID NO 1560
<211> LENGTH: 15
<212> TYPE: PRT
<213> ORGANISM: Dermatophagoides farinae

<400> SEQUENCE: 1560

Ala Arg Lys Asn Phe Leu Glu Ser Leu Lys Tyr Val Glu Ala Asn
1               5                   10                  15

<210> SEQ ID NO 1561
<211> LENGTH: 15
<212> TYPE: PRT
<213> ORGANISM: Dermatophagoides farinae

<400> SEQUENCE: 1561

Phe Glu Gln Leu Lys Thr Gln Phe Asp Leu Asn Ala Glu Thr Ser
1               5                   10                  15

<210> SEQ ID NO 1562
<211> LENGTH: 15
<212> TYPE: PRT
<213> ORGANISM: Dermatophagoides farinae

<400> SEQUENCE: 1562

Gly Ser Cys Trp Ala Phe Ser Gly Val Ala Ala Thr Glu Ser Ala
1               5                   10                  15

<210> SEQ ID NO 1563
<211> LENGTH: 15
<212> TYPE: PRT
<213> ORGANISM: Dermatophagoides farinae

<400> SEQUENCE: 1563

Gly Ser Cys Trp Ala Phe Ser Gly Val Ala Ala Thr Glu Ser Ala
1               5                   10                  15

<210> SEQ ID NO 1564
<211> LENGTH: 15
<212> TYPE: PRT
<213> ORGANISM: Dermatophagoides farinae

<400> SEQUENCE: 1564

Phe Ser Gly Val Ala Ala Thr Glu Ser Ala Tyr Leu Ala Tyr Arg
1               5                   10                  15

<210> SEQ ID NO 1565
<211> LENGTH: 15
<212> TYPE: PRT
<213> ORGANISM: Dermatophagoides farinae

<400> SEQUENCE: 1565

Phe Ser Gly Val Ala Ala Thr Glu Ser Ala Tyr Leu Ala Tyr Arg
1               5                   10                  15

<210> SEQ ID NO 1566
<211> LENGTH: 15
<212> TYPE: PRT
<213> ORGANISM: Dermatophagoides farinae

<400> SEQUENCE: 1566

Ala Thr Glu Ser Ala Tyr Leu Ala Tyr Arg Asn Thr Ser Leu Asp
1               5                   10                  15

<210> SEQ ID NO 1567
<211> LENGTH: 15
<212> TYPE: PRT
<213> ORGANISM: Dermatophagoides farinae

<400> SEQUENCE: 1567

Ala Thr Glu Ser Ala Tyr Leu Ala Tyr Arg Asn Thr Ser Leu Asp
1               5                   10                  15

<210> SEQ ID NO 1568
<211> LENGTH: 15
<212> TYPE: PRT
<213> ORGANISM: Dermatophagoides farinae

<400> SEQUENCE: 1568

Leu Lys Ile Ala Thr Ala Lys Leu Glu Glu Ala Ser Gln Ser Ala
1               5                   10                  15

<210> SEQ ID NO 1569
<211> LENGTH: 15
<212> TYPE: PRT
<213> ORGANISM: Dermatophagoides farinae

<400> SEQUENCE: 1569

Val Glu Leu Glu Glu Glu Leu Arg Val Val Gly Asn Asn Leu Lys
1               5                   10                  15

<210> SEQ ID NO 1570
<211> LENGTH: 15
<212> TYPE: PRT
<213> ORGANISM: Dermatophagoides farinae

<400> SEQUENCE: 1570

Tyr Glu Gln Gln Ile Arg Ile Met Thr Ala Lys Leu Lys Glu Ala
1               5                   10                  15

<210> SEQ ID NO 1571
<211> LENGTH: 15
<212> TYPE: PRT
<213> ORGANISM: Dermatophagoides farinae

<400> SEQUENCE: 1571

Glu Leu Arg Val Lys Ile Ala Glu Leu Gln Lys Leu Gln His Glu
1               5                   10                  15

<210> SEQ ID NO 1572
<211> LENGTH: 15
<212> TYPE: PRT
<213> ORGANISM: Dermatophagoides farinae

<400> SEQUENCE: 1572

Gly Lys Tyr Lys Leu Glu Lys Ser Glu Lys Phe Asp Glu Phe Leu
1               5                   10                  15

<210> SEQ ID NO 1573
<211> LENGTH: 15
<212> TYPE: PRT
<213> ORGANISM: Dermatophagoides farinae

<400> SEQUENCE: 1573

Gly Phe Met Val Lys Thr Ala Ala Lys Thr Leu Lys Pro Thr Phe
1               5                   10                  15

<210> SEQ ID NO 1574
<211> LENGTH: 15
<212> TYPE: PRT
<213> ORGANISM: Dermatophagoides farinae

<400> SEQUENCE: 1574

Asn Asp Gln Tyr Ile Phe Arg Ser Leu Ser Thr Phe Lys Asn Thr
1               5                   10                  15

<210> SEQ ID NO 1575
<211> LENGTH: 15
<212> TYPE: PRT
<213> ORGANISM: Dermatophagoides farinae

<400> SEQUENCE: 1575

Phe Arg Ser Leu Ser Thr Phe Lys Asn Thr Glu Ala Lys Phe Lys
1               5                   10                  15

<210> SEQ ID NO 1576
<211> LENGTH: 15
<212> TYPE: PRT
<213> ORGANISM: Dermatophagoides farinae

<400> SEQUENCE: 1576

Val Arg Pro Phe Lys Met His Gly Asn Ser Asp Ile Lys Leu Met
1               5                   10                  15

<210> SEQ ID NO 1577
<211> LENGTH: 15
<212> TYPE: PRT
<213> ORGANISM: Dermatophagoides farinae

<400> SEQUENCE: 1577

Ile Pro Ile Gly His Thr Phe Phe Ile Trp Arg Ile Lys Gln
1               5                   10                  15

<210> SEQ ID NO 1578
<211> LENGTH: 15
<212> TYPE: PRT
<213> ORGANISM: Dermatophagoides farinae

<400> SEQUENCE: 1578

Phe Lys Leu Ser Ser Val Ile Leu Glu Asp Gly Lys Glu Val Glu
1               5                   10                  15

<210> SEQ ID NO 1579
<211> LENGTH: 15
<212> TYPE: PRT
<213> ORGANISM: Dermatophagoides farinae

<400> SEQUENCE: 1579

Glu Tyr Asp Ala Phe Asn Lys Ala Leu Ser Leu Asp Lys Lys Asp
1               5                   10                  15

<210> SEQ ID NO 1580
<211> LENGTH: 15
<212> TYPE: PRT
<213> ORGANISM: Dermatophagoides farinae

<400> SEQUENCE: 1580

Ile Ser Phe Val Lys Asn Gly Pro Leu Ser Arg Ala Asp Leu Asp
1               5                   10                  15

<210> SEQ ID NO 1581
<211> LENGTH: 15
<212> TYPE: PRT
<213> ORGANISM: Dermatophagoides farinae

<400> SEQUENCE: 1581

Phe Lys Ser Leu Phe Glu Ser Trp Gln Met Ser Glu Gln Glu Lys
1               5                   10                  15

<210> SEQ ID NO 1582
<211> LENGTH: 15
<212> TYPE: PRT
<213> ORGANISM: Dermatophagoides farinae

<400> SEQUENCE: 1582

Ile Thr Ser Ala Arg Leu Phe Arg Val Ser Arg Asn Gly Ile Phe
1               5                   10                  15

<210> SEQ ID NO 1583
<211> LENGTH: 15
<212> TYPE: PRT
<213> ORGANISM: Dermatophagoides farinae

<400> SEQUENCE: 1583

Val Met Asp Lys Ile Tyr Val Trp Ile Gly Asn Gln Phe Ala Glu
1               5                   10                  15

<210> SEQ ID NO 1584
<211> LENGTH: 15
<212> TYPE: PRT
<213> ORGANISM: Dermatophagoides farinae

<400> SEQUENCE: 1584

Ser Gly Arg Lys Phe Gln Pro Asn Gln Ile Ile Lys Leu Lys Gln
1               5                   10                  15

<210> SEQ ID NO 1585
<211> LENGTH: 15
<212> TYPE: PRT
<213> ORGANISM: Dermatophagoides farinae

<400> SEQUENCE: 1585

Thr Phe Val Val Ser Thr Val Asp Leu Met Thr Arg Tyr Gly Phe
1               5                   10                  15

<210> SEQ ID NO 1586
<211> LENGTH: 15
<212> TYPE: PRT
<213> ORGANISM: Dermatophagoides farinae

<400> SEQUENCE: 1586

His Thr Ser Phe Val Met Gly Val Thr Leu Pro Ala Thr Ile Ala
1               5                   10                  15

-continued

<210> SEQ ID NO 1587
<211> LENGTH: 15
<212> TYPE: PRT
<213> ORGANISM: Dermatophagoides farinae

<400> SEQUENCE: 1587

Val Val Val Thr Val Lys Leu Ile Gly Asp Asn Gly Val Leu Ala
1               5                   10                  15

<210> SEQ ID NO 1588
<211> LENGTH: 15
<212> TYPE: PRT
<213> ORGANISM: Dermatophagoides pteronyssinus

<400> SEQUENCE: 1588

Leu Ala Leu Ser Ala Val Tyr Ala Arg Pro Ser Ser Ile Lys Thr
1               5                   10                  15

<210> SEQ ID NO 1589
<211> LENGTH: 15
<212> TYPE: PRT
<213> ORGANISM: Dermatophagoides pteronyssinus

<400> SEQUENCE: 1589

Lys Ala Phe Asn Lys Ser Tyr Ala Thr Phe Glu Asp Glu Glu Ala
1               5                   10                  15

<210> SEQ ID NO 1590
<211> LENGTH: 15
<212> TYPE: PRT
<213> ORGANISM: Dermatophagoides pteronyssinus

<400> SEQUENCE: 1590

Ala Arg Lys Asn Phe Leu Glu Ser Val Lys Tyr Val Gln Ser Asn
1               5                   10                  15

<210> SEQ ID NO 1591
<211> LENGTH: 15
<212> TYPE: PRT
<213> ORGANISM: Dermatophagoides pteronyssinus

<400> SEQUENCE: 1591

Leu Glu Ser Val Lys Tyr Val Gln Ser Asn Gly Gly Ala Ile Asn
1               5                   10                  15

<210> SEQ ID NO 1592
<211> LENGTH: 15
<212> TYPE: PRT
<213> ORGANISM: Dermatophagoides pteronyssinus

<400> SEQUENCE: 1592

Gly Gly Ala Ile Asn His Leu Ser Asp Leu Ser Leu Asp Glu Phe
1               5                   10                  15

<210> SEQ ID NO 1593
<211> LENGTH: 15
<212> TYPE: PRT
<213> ORGANISM: Dermatophagoides pteronyssinus

<400> SEQUENCE: 1593

Glu Ile Asp Leu Arg Gln Met Arg Thr Val Thr Pro Ile Arg Met
1               5                   10                  15

<210> SEQ ID NO 1594
<211> LENGTH: 15

```
<212> TYPE: PRT
<213> ORGANISM: Dermatophagoides pteronyssinus

<400> SEQUENCE: 1594

Ser Cys Trp Ala Phe Ser Gly Val Ala Ala Thr Glu Ser Ala Tyr
1               5                   10                  15

<210> SEQ ID NO 1595
<211> LENGTH: 15
<212> TYPE: PRT
<213> ORGANISM: Dermatophagoides pteronyssinus

<400> SEQUENCE: 1595

Ser Cys Trp Ala Phe Ser Gly Val Ala Ala Thr Glu Ser Ala Tyr
1               5                   10                  15

<210> SEQ ID NO 1596
<211> LENGTH: 15
<212> TYPE: PRT
<213> ORGANISM: Dermatophagoides pteronyssinus

<400> SEQUENCE: 1596

Ser Gly Val Ala Ala Thr Glu Ser Ala Tyr Leu Ala Tyr Arg Asn
1               5                   10                  15

<210> SEQ ID NO 1597
<211> LENGTH: 15
<212> TYPE: PRT
<213> ORGANISM: Dermatophagoides pteronyssinus

<400> SEQUENCE: 1597

Ser Gly Val Ala Ala Thr Glu Ser Ala Tyr Leu Ala Tyr Arg Asn
1               5                   10                  15

<210> SEQ ID NO 1598
<211> LENGTH: 15
<212> TYPE: PRT
<213> ORGANISM: Dermatophagoides pteronyssinus

<400> SEQUENCE: 1598

Arg Gly Ile Glu Tyr Ile Gln His Asn Gly Val Val Gln Glu Ser
1               5                   10                  15

<210> SEQ ID NO 1599
<211> LENGTH: 15
<212> TYPE: PRT
<213> ORGANISM: Dermatophagoides pteronyssinus

<400> SEQUENCE: 1599

Arg Gly Ile Glu Tyr Ile Gln His Asn Gly Val Val Gln Glu Ser
1               5                   10                  15

<210> SEQ ID NO 1600
<211> LENGTH: 15
<212> TYPE: PRT
<213> ORGANISM: Dermatophagoides pteronyssinus

<400> SEQUENCE: 1600

Arg Glu Ala Leu Ala Gln Thr His Ser Ala Ile Ala Val Ile Ile
1               5                   10                  15

<210> SEQ ID NO 1601
<211> LENGTH: 15
<212> TYPE: PRT
<213> ORGANISM: Dermatophagoides pteronyssinus
```

<400> SEQUENCE: 1601

Arg Glu Ala Leu Ala Gln Thr His Ser Ala Ile Ala Val Ile Ile
1               5                   10                  15

<210> SEQ ID NO 1602
<211> LENGTH: 15
<212> TYPE: PRT
<213> ORGANISM: Dermatophagoides pteronyssinus

<400> SEQUENCE: 1602

Gln Thr His Ser Ala Ile Ala Val Ile Ile Gly Ile Lys Asp Leu
1               5                   10                  15

<210> SEQ ID NO 1603
<211> LENGTH: 15
<212> TYPE: PRT
<213> ORGANISM: Dermatophagoides pteronyssinus

<400> SEQUENCE: 1603

Asp Asn Gly Tyr Gly Tyr Phe Ala Ala Asn Ile Asp Leu Met Met
1               5                   10                  15

<210> SEQ ID NO 1604
<211> LENGTH: 15
<212> TYPE: PRT
<213> ORGANISM: Dermatophagoides pteronyssinus

<400> SEQUENCE: 1604

Phe Ala Phe Gly Tyr Phe Asn Gly Arg Ile Leu Gly Val Cys Pro
1               5                   10                  15

<210> SEQ ID NO 1605
<211> LENGTH: 15
<212> TYPE: PRT
<213> ORGANISM: Dermatophagoides pteronyssinus

<400> SEQUENCE: 1605

Asn Ala Met Asp Glu Ile Ile Lys Ser Thr Asp Ala Glu Pro Ala
1               5                   10                  15

<210> SEQ ID NO 1606
<211> LENGTH: 15
<212> TYPE: PRT
<213> ORGANISM: Dermatophagoides pteronyssinus

<400> SEQUENCE: 1606

Thr Gly Leu Pro Leu Met Tyr Lys Phe Gly Asp Asn Leu Val Val
1               5                   10                  15

<210> SEQ ID NO 1607
<211> LENGTH: 15
<212> TYPE: PRT
<213> ORGANISM: Dermatophagoides pteronyssinus

<400> SEQUENCE: 1607

Asn Gly Lys Leu His Leu Ser Leu Ile Asp Pro Ser Thr Leu Ser
1               5                   10                  15

<210> SEQ ID NO 1608
<211> LENGTH: 15
<212> TYPE: PRT
<213> ORGANISM: Dermatophagoides pteronyssinus

<400> SEQUENCE: 1608

Gln Gln Tyr Asp Ile Lys Tyr Thr Trp Asn Val Pro Lys Ile Ala
1               5                   10                  15

<210> SEQ ID NO 1609
<211> LENGTH: 15
<212> TYPE: PRT
<213> ORGANISM: Dermatophagoides pteronyssinus

<400> SEQUENCE: 1609

Thr Leu Ala Asn Pro Ile Leu Pro Ala Ser Pro Asn Ala Thr Ile
1               5                   10                  15

<210> SEQ ID NO 1610
<211> LENGTH: 15
<212> TYPE: PRT
<213> ORGANISM: Dermatophagoides pteronyssinus

<400> SEQUENCE: 1610

Glu Tyr Trp Ile Leu Thr Ala Ala His Cys Val Ala Gly Gln Thr
1               5                   10                  15

<210> SEQ ID NO 1611
<211> LENGTH: 15
<212> TYPE: PRT
<213> ORGANISM: Dermatophagoides pteronyssinus

<400> SEQUENCE: 1611

Ile Arg Tyr Asn Ser Leu Lys His Ser Leu Gly Gly Glu Lys Ile
1               5                   10                  15

<210> SEQ ID NO 1612
<211> LENGTH: 15
<212> TYPE: PRT
<213> ORGANISM: Dermatophagoides pteronyssinus

<400> SEQUENCE: 1612

Gly Gly Glu Lys Ile Ser Val Ala Lys Ile Phe Ala His Glu Lys
1               5                   10                  15

<210> SEQ ID NO 1613
<211> LENGTH: 15
<212> TYPE: PRT
<213> ORGANISM: Dermatophagoides pteronyssinus

<400> SEQUENCE: 1613

Ile Asp Asn Asp Ile Ala Leu Ile Lys Leu Lys Ser Pro Met Lys
1               5                   10                  15

<210> SEQ ID NO 1614
<211> LENGTH: 15
<212> TYPE: PRT
<213> ORGANISM: Dermatophagoides pteronyssinus

<400> SEQUENCE: 1614

Ser Glu Leu Arg Arg Val Asp Ile Ala Val Val Ser Arg Lys Glu
1               5                   10                  15

<210> SEQ ID NO 1615
<211> LENGTH: 15
<212> TYPE: PRT
<213> ORGANISM: Dermatophagoides pteronyssinus

<400> SEQUENCE: 1615

Phe Asp Phe Leu Leu Met Glu Arg Ile His Glu Gln Ile Lys Lys

```
<210> SEQ ID NO 1616
<211> LENGTH: 15
<212> TYPE: PRT
<213> ORGANISM: Dermatophagoides pteronyssinus

<400> SEQUENCE: 1616

Gly Glu Leu Ala Leu Phe Tyr Leu Gln Glu Gln Ile Asn His Phe
1               5                   10                  15

<210> SEQ ID NO 1617
<211> LENGTH: 15
<212> TYPE: PRT
<213> ORGANISM: Dermatophagoides pteronyssinus

<400> SEQUENCE: 1617

Asn Lys Ala Gly Val Arg Ile Tyr Val Asp Ile Val Leu Asn His
1               5                   10                  15

<210> SEQ ID NO 1618
<211> LENGTH: 15
<212> TYPE: PRT
<213> ORGANISM: Dermatophagoides pteronyssinus

<400> SEQUENCE: 1618

Asn Lys Ala Gly Val Arg Ile Tyr Val Asp Ile Val Leu Asn His
1               5                   10                  15

<210> SEQ ID NO 1619
<211> LENGTH: 15
<212> TYPE: PRT
<213> ORGANISM: Dermatophagoides pteronyssinus

<400> SEQUENCE: 1619

Arg Ile Tyr Val Asp Ile Val Leu Asn His Met Thr Gly Ala Gln
1               5                   10                  15

<210> SEQ ID NO 1620
<211> LENGTH: 15
<212> TYPE: PRT
<213> ORGANISM: Dermatophagoides pteronyssinus

<400> SEQUENCE: 1620

Ile Val Leu Asn His Met Thr Gly Ala Gln Ser Gly Lys Gly Thr
1               5                   10                  15

<210> SEQ ID NO 1621
<211> LENGTH: 15
<212> TYPE: PRT
<213> ORGANISM: Dermatophagoides pteronyssinus

<400> SEQUENCE: 1621

Pro Asp Asp Leu Arg Ser Ile Tyr Ser Arg Leu His Asn Leu Asn
1               5                   10                  15

<210> SEQ ID NO 1622
<211> LENGTH: 15
<212> TYPE: PRT
<213> ORGANISM: Dermatophagoides pteronyssinus

<400> SEQUENCE: 1622

Ser Ile Tyr Ser Arg Leu His Asn Leu Asn Lys Glu Phe Phe Pro
1               5                   10                  15
```

<210> SEQ ID NO 1623
<211> LENGTH: 15
<212> TYPE: PRT
<213> ORGANISM: Dermatophagoides pteronyssinus

<400> SEQUENCE: 1623

Ile Glu Phe Arg Phe Tyr Lys Glu Ile Thr Asn Val Phe Arg Gly
1               5                   10                  15

<210> SEQ ID NO 1624
<211> LENGTH: 15
<212> TYPE: PRT
<213> ORGANISM: Dermatophagoides pteronyssinus

<400> SEQUENCE: 1624

Ile Glu Phe Arg Phe Tyr Lys Glu Ile Thr Asn Val Phe Arg Gly
1               5                   10                  15

<210> SEQ ID NO 1625
<211> LENGTH: 15
<212> TYPE: PRT
<213> ORGANISM: Dermatophagoides pteronyssinus

<400> SEQUENCE: 1625

Asp Ala Leu Val Met Ile Asp Ser His Asp Leu Arg Val Gly His
1               5                   10                  15

<210> SEQ ID NO 1626
<211> LENGTH: 15
<212> TYPE: PRT
<213> ORGANISM: Dermatophagoides pteronyssinus

<400> SEQUENCE: 1626

Phe Glu Gly Arg Leu Leu Lys Ala Ala Thr Ala Phe Met Leu Ala
1               5                   10                  15

<210> SEQ ID NO 1627
<211> LENGTH: 15
<212> TYPE: PRT
<213> ORGANISM: Dermatophagoides pteronyssinus

<400> SEQUENCE: 1627

Phe Glu Gly Arg Leu Leu Lys Ala Ala Thr Ala Phe Met Leu Ala
1               5                   10                  15

<210> SEQ ID NO 1628
<211> LENGTH: 15
<212> TYPE: PRT
<213> ORGANISM: Dermatophagoides pteronyssinus

<400> SEQUENCE: 1628

Leu Lys Ala Ala Thr Ala Phe Met Leu Ala Trp Asn Tyr Gly Val
1               5                   10                  15

<210> SEQ ID NO 1629
<211> LENGTH: 15
<212> TYPE: PRT
<213> ORGANISM: Dermatophagoides pteronyssinus

<400> SEQUENCE: 1629

Ala Phe Met Leu Ala Trp Asn Tyr Gly Val Pro Arg Val Met Ser
1               5                   10                  15

<210> SEQ ID NO 1630

-continued

```
<211> LENGTH: 15
<212> TYPE: PRT
<213> ORGANISM: Dermatophagoides pteronyssinus

<400> SEQUENCE: 1630

Ala Phe Met Leu Ala Trp Asn Tyr Gly Val Pro Arg Val Met Ser
1               5                   10                  15

<210> SEQ ID NO 1631
<211> LENGTH: 15
<212> TYPE: PRT
<213> ORGANISM: Dermatophagoides pteronyssinus

<400> SEQUENCE: 1631

Pro Arg Val Met Ser Ser Tyr Phe Trp Asn Gln Ile Ile Lys Asp
1               5                   10                  15

<210> SEQ ID NO 1632
<211> LENGTH: 15
<212> TYPE: PRT
<213> ORGANISM: Dermatophagoides pteronyssinus

<400> SEQUENCE: 1632

Glu His Arg Trp Arg Glu Ile Tyr Asn Met Val Lys Phe Arg Met
1               5                   10                  15

<210> SEQ ID NO 1633
<211> LENGTH: 15
<212> TYPE: PRT
<213> ORGANISM: Dermatophagoides pteronyssinus

<400> SEQUENCE: 1633

Glu His Arg Trp Arg Glu Ile Tyr Asn Met Val Lys Phe Arg Met
1               5                   10                  15

<210> SEQ ID NO 1634
<211> LENGTH: 15
<212> TYPE: PRT
<213> ORGANISM: Dermatophagoides pteronyssinus

<400> SEQUENCE: 1634

Glu His Arg Trp Arg Glu Ile Tyr Asn Met Val Lys Phe Arg Met
1               5                   10                  15

<210> SEQ ID NO 1635
<211> LENGTH: 15
<212> TYPE: PRT
<213> ORGANISM: Dermatophagoides pteronyssinus

<400> SEQUENCE: 1635

Glu His Arg Trp Arg Glu Ile Tyr Asn Met Val Lys Phe Arg Met
1               5                   10                  15

<210> SEQ ID NO 1636
<211> LENGTH: 15
<212> TYPE: PRT
<213> ORGANISM: Dermatophagoides pteronyssinus

<400> SEQUENCE: 1636

Glu Ile Tyr Asn Met Val Lys Phe Arg Met Ile Ala Gly Gln Glu
1               5                   10                  15

<210> SEQ ID NO 1637
<211> LENGTH: 15
<212> TYPE: PRT
```

<213> ORGANISM: Dermatophagoides pteronyssinus

<400> SEQUENCE: 1637

Glu Ile Tyr Asn Met Val Lys Phe Arg Met Ile Ala Gly Gln Glu
1               5                   10                  15

<210> SEQ ID NO 1638
<211> LENGTH: 15
<212> TYPE: PRT
<213> ORGANISM: Dermatophagoides pteronyssinus

<400> SEQUENCE: 1638

Glu Ile Tyr Asn Met Val Lys Phe Arg Met Ile Ala Gly Gln Glu
1               5                   10                  15

<210> SEQ ID NO 1639
<211> LENGTH: 15
<212> TYPE: PRT
<213> ORGANISM: Dermatophagoides pteronyssinus

<400> SEQUENCE: 1639

Val Lys Phe Arg Met Ile Ala Gly Gln Glu Pro Val His Asn Trp
1               5                   10                  15

<210> SEQ ID NO 1640
<211> LENGTH: 15
<212> TYPE: PRT
<213> ORGANISM: Dermatophagoides pteronyssinus

<400> SEQUENCE: 1640

Tyr Gln Ile Ala Phe Ser Arg Gly Asn Arg Ala Phe Ile Ala Ile
1               5                   10                  15

<210> SEQ ID NO 1641
<211> LENGTH: 15
<212> TYPE: PRT
<213> ORGANISM: Dermatophagoides pteronyssinus

<400> SEQUENCE: 1641

Tyr Gln Ile Ala Phe Ser Arg Gly Asn Arg Ala Phe Ile Ala Ile
1               5                   10                  15

<210> SEQ ID NO 1642
<211> LENGTH: 15
<212> TYPE: PRT
<213> ORGANISM: Dermatophagoides pteronyssinus

<400> SEQUENCE: 1642

Ser Arg Gly Asn Arg Ala Phe Ile Ala Ile Asn Leu Gln Lys Asn
1               5                   10                  15

<210> SEQ ID NO 1643
<211> LENGTH: 15
<212> TYPE: PRT
<213> ORGANISM: Dermatophagoides pteronyssinus

<400> SEQUENCE: 1643

Tyr Val Gly His Asp Glu Phe Asp Ala Phe Val Ala Tyr His Ile
1               5                   10                  15

<210> SEQ ID NO 1644
<211> LENGTH: 15
<212> TYPE: PRT
<213> ORGANISM: Dermatophagoides pteronyssinus

```
<400> SEQUENCE: 1644

Glu Phe Asp Ala Phe Val Ala Tyr His Ile Gly Ala Arg Ile Val
1               5                   10                  15

<210> SEQ ID NO 1645
<211> LENGTH: 15
<212> TYPE: PRT
<213> ORGANISM: Dermatophagoides pteronyssinus

<400> SEQUENCE: 1645

Glu Phe Asp Ala Phe Val Ala Tyr His Ile Gly Ala Arg Ile Val
1               5                   10                  15

<210> SEQ ID NO 1646
<211> LENGTH: 15
<212> TYPE: PRT
<213> ORGANISM: Dermatophagoides pteronyssinus

<400> SEQUENCE: 1646

Phe Asp Ala Phe Val Ala Tyr His Ile Gly Ala Arg Ile Val Ser
1               5                   10                  15

<210> SEQ ID NO 1647
<211> LENGTH: 15
<212> TYPE: PRT
<213> ORGANISM: Dermatophagoides pteronyssinus

<400> SEQUENCE: 1647

Arg Lys Asp Leu Asp Ile Phe Glu Gln Tyr Asn Leu Glu Met Ala
1               5                   10                  15

<210> SEQ ID NO 1648
<211> LENGTH: 15
<212> TYPE: PRT
<213> ORGANISM: Dermatophagoides pteronyssinus

<400> SEQUENCE: 1648

Thr Leu Pro Thr Ile Leu Gln Ile Ala Ser Val Thr Lys Met Ser
1               5                   10                  15

<210> SEQ ID NO 1649
<211> LENGTH: 15
<212> TYPE: PRT
<213> ORGANISM: Dermatophagoides pteronyssinus

<400> SEQUENCE: 1649

Thr Ile Tyr Ser Asn Val Ala Asn Leu Arg Asn Trp Ile Ile Ser
1               5                   10                  15

<210> SEQ ID NO 1650
<211> LENGTH: 15
<212> TYPE: PRT
<213> ORGANISM: Dermatophagoides pteronyssinus

<400> SEQUENCE: 1650

Ser Asn Val Ala Asn Leu Arg Asn Trp Ile Ile Ser Asn Thr Val
1               5                   10                  15

<210> SEQ ID NO 1651
<211> LENGTH: 15
<212> TYPE: PRT
<213> ORGANISM: Alnus glutinosa

<400> SEQUENCE: 1651
```

Pro Ser Val Ile Pro Ala Ala Arg Leu Phe Lys Ala Phe Ile Leu
1               5                   10                  15

<210> SEQ ID NO 1652
<211> LENGTH: 15
<212> TYPE: PRT
<213> ORGANISM: Alnus glutinosa

<400> SEQUENCE: 1652

Ala Ala Arg Leu Phe Lys Ala Phe Ile Leu Asp Gly Asp Lys Leu
1               5                   10                  15

<210> SEQ ID NO 1653
<211> LENGTH: 15
<212> TYPE: PRT
<213> ORGANISM: Alnus glutinosa

<400> SEQUENCE: 1653

Gly Gly Ser Ile Leu Lys Ile Ser Asn Lys Phe His Thr Lys Gly
1               5                   10                  15

<210> SEQ ID NO 1654
<211> LENGTH: 15
<212> TYPE: PRT
<213> ORGANISM: Alnus glutinosa

<400> SEQUENCE: 1654

Gly Gly Ser Ile Leu Lys Ile Ser Asn Lys Phe His Thr Lys Gly
1               5                   10                  15

<210> SEQ ID NO 1655
<211> LENGTH: 15
<212> TYPE: PRT
<213> ORGANISM: Alnus glutinosa

<400> SEQUENCE: 1655

Ala Val Gly Leu Leu Lys Ala Val Glu Ser Tyr Leu Leu Ala His
1               5                   10                  15

<210> SEQ ID NO 1656
<211> LENGTH: 15
<212> TYPE: PRT
<213> ORGANISM: Betula pendula

<400> SEQUENCE: 1656

Tyr Glu Thr Glu Thr Thr Ser Val Ile Pro Ala Ala Arg Leu Phe
1               5                   10                  15

<210> SEQ ID NO 1657
<211> LENGTH: 15
<212> TYPE: PRT
<213> ORGANISM: Betula pendula

<400> SEQUENCE: 1657

Thr Ser Val Ile Pro Ala Ala Arg Leu Phe Lys Ala Phe Phe Leu
1               5                   10                  15

<210> SEQ ID NO 1658
<211> LENGTH: 15
<212> TYPE: PRT
<213> ORGANISM: Betula pendula

<400> SEQUENCE: 1658

Asp His Thr Asn Phe Lys Tyr Ser Tyr Ser Val Ile Glu Gly Gly
1               5                   10                  15

```
<210> SEQ ID NO 1659
<211> LENGTH: 15
<212> TYPE: PRT
<213> ORGANISM: Betula pendula

<400> SEQUENCE: 1659

Leu Glu Lys Ile Ser Asn Glu Ile Lys Ile Val Ala Thr Pro Asp
1               5                   10                  15

<210> SEQ ID NO 1660
<211> LENGTH: 15
<212> TYPE: PRT
<213> ORGANISM: Betula pendula

<400> SEQUENCE: 1660

Leu Glu Lys Ile Ser Asn Glu Ile Lys Ile Val Ala Thr Pro Asp
1               5                   10                  15

<210> SEQ ID NO 1661
<211> LENGTH: 15
<212> TYPE: PRT
<213> ORGANISM: Betula pendula

<400> SEQUENCE: 1661

Gly Gly Ser Ile Leu Lys Ile Ser Asn Lys Tyr His Thr Lys Gly
1               5                   10                  15

<210> SEQ ID NO 1662
<211> LENGTH: 15
<212> TYPE: PRT
<213> ORGANISM: Betula pendula

<400> SEQUENCE: 1662

Gly Gly Ser Ile Leu Lys Ile Ser Asn Lys Tyr His Thr Lys Gly
1               5                   10                  15

<210> SEQ ID NO 1663
<211> LENGTH: 15
<212> TYPE: PRT
<213> ORGANISM: Betula pendula

<400> SEQUENCE: 1663

Gly Gly Ser Ile Leu Lys Ile Ser Asn Lys Tyr His Thr Lys Gly
1               5                   10                  15

<210> SEQ ID NO 1664
<211> LENGTH: 15
<212> TYPE: PRT
<213> ORGANISM: Betula pendula

<400> SEQUENCE: 1664

Arg Ala Val Glu Ser Tyr Leu Leu Ala His Ser Asp Ala Tyr Asn
1               5                   10                  15

<210> SEQ ID NO 1665
<211> LENGTH: 15
<212> TYPE: PRT
<213> ORGANISM: Betula pendula

<400> SEQUENCE: 1665

Asp Gly Ser Val Trp Ala Gln Ser Ser Ser Phe Pro Gln Phe Lys
1               5                   10                  15
```

```
<210> SEQ ID NO 1666
<211> LENGTH: 15
<212> TYPE: PRT
<213> ORGANISM: Betula pendula

<400> SEQUENCE: 1666

Gly Leu His Leu Gly Gly Ile Lys Tyr Met Val Ile Gln Gly Glu
1               5                   10                  15

<210> SEQ ID NO 1667
<211> LENGTH: 15
<212> TYPE: PRT
<213> ORGANISM: Betula pendula

<400> SEQUENCE: 1667

Gly Ile Lys Tyr Met Val Ile Gln Gly Glu Ala Gly Ala Val Ile
1               5                   10                  15

<210> SEQ ID NO 1668
<211> LENGTH: 15
<212> TYPE: PRT
<213> ORGANISM: Betula pendula

<400> SEQUENCE: 1668

Leu Ser Arg Ala Leu Asn Leu Leu Gly Leu Glu Thr Asp Leu Ser
1               5                   10                  15

<210> SEQ ID NO 1669
<211> LENGTH: 15
<212> TYPE: PRT
<213> ORGANISM: Betula pendula

<400> SEQUENCE: 1669

Val Lys Ala Phe Lys Gln Val Asp Val Val Ile Ser Thr Val Gly
1               5                   10                  15

<210> SEQ ID NO 1670
<211> LENGTH: 15
<212> TYPE: PRT
<213> ORGANISM: Betula pendula

<400> SEQUENCE: 1670

Arg Thr Leu Asn Lys Ile Val Tyr Ile Lys Pro Ala Lys Asn Ile
1               5                   10                  15

<210> SEQ ID NO 1671
<211> LENGTH: 15
<212> TYPE: PRT
<213> ORGANISM: Betula pendula

<400> SEQUENCE: 1671

Arg Thr Leu Asn Lys Ile Val Tyr Ile Lys Pro Ala Lys Asn Ile
1               5                   10                  15

<210> SEQ

```
<212> TYPE: PRT
<213> ORGANISM: Betula pendula

<400> SEQUENCE: 1673

Ile Val Tyr Ile Lys Pro Ala Lys Asn Ile Tyr Ser Phe Asn Glu
1               5                   10                  15

<210> SEQ ID NO 1674
<211> LENGTH: 15
<212> TYPE: PRT
<213> ORGANISM: Betula pendula

<400> SEQUENCE: 1674

Pro Ala Lys Asn Ile Tyr Ser Phe Asn Glu Ile Val Ala Leu Trp
1               5                   10                  15

<210> SEQ ID NO 1675
<211> LENGTH: 15
<212> TYPE: PRT
<213> ORGANISM: Betula pendula

<400> SEQUENCE: 1675

Val Ile Leu Ala Ile Asn His Ser Val Phe Val Lys Gly Asp His
1               5                   10                  15

<210> SEQ ID NO 1676
<211> LENGTH: 15
<212> TYPE: PRT
<213> ORGANISM: Betula pendula

<400> SEQUENCE: 1676

Thr Asn Phe Glu Ile Glu Ala Ser Phe Gly Val Glu Ala Ser Glu
1               5                   10                  15

<210> SEQ ID NO 1677
<211> LENGTH: 15
<212> TYPE: PRT
<213> ORGANISM: Betula pendula

<400> SEQUENCE: 1677

Leu Tyr Pro Asp Val Lys Tyr Thr Thr Val Glu Glu Tyr Leu Gln
1               5                   10                  15

<210> SEQ ID NO 1678
<211> LENGTH: 15
<212> TYPE: PRT
<213> ORGANISM: Chamaecyparis obtusa

<400> SEQUENCE: 1678

Glu Arg Ser Leu Trp Ile Ile Phe Ser Lys Asn Leu Asn Ile Lys
1               5                   10                  15

<210> SEQ ID NO 1679
<211> LENGTH: 15
<212> TYPE: PRT
<213> ORGANISM: Chamaecyparis obtusa

<400> SEQUENCE: 1679

Glu Arg Ser Leu Trp Ile Ile Phe Ser Lys Asn Leu Asn Ile Lys
1               5                   10                  15

<210> SEQ ID NO 1680
<211> LENGTH: 15
<212> TYPE: PRT
<213> ORGANISM: Chamaecyparis obtusa
```

```
<400> SEQUENCE: 1680

Ile Ile Phe Ser Lys Asn Leu Asn Ile Lys Leu Asn Met Pro Leu
1               5                   10                  15

<210> SEQ ID NO 1681
<211> LENGTH: 15
<212> TYPE: PRT
<213> ORGANISM: Chamaecyparis obtusa

<400> SEQUENCE: 1681

Asn Leu Asn Ile Lys Leu Asn Met Pro Leu Tyr Ile Ala Gly Asn
1               5                   10                  15

<210> SEQ ID NO 1682
<211> LENGTH: 15
<212> TYPE: PRT
<213> ORGANISM: Chamaecyparis obtusa

<400> SEQUENCE: 1682

Asn His Phe Phe Asn His His Lys Val Met Leu Leu Gly His Ser
1               5                   10                  15

<210> SEQ ID NO 1683
<211> LENGTH: 15
<212> TYPE: PRT
<213> ORGANISM: Chamaecyparis obtusa

<400> SEQUENCE: 1683

Asn His Phe Phe Asn His His Lys Val Met Leu Leu Gly His Ser
1               5                   10                  15

<210> SEQ ID NO 1684
<211> LENGTH: 15
<212> TYPE: PRT
<213> ORGANISM: Chamaecyparis obtusa

<400> SEQUENCE: 1684

Asp Lys Ser Met Lys Val Thr Val Ala Phe Asn Gln Phe Gly Pro
1               5                   10                  15

<210> SEQ ID NO 1685
<211> LENGTH: 15
<212> TYPE: PRT
<213> ORGANISM: Chamaecyparis obtusa

<400> SEQUENCE: 1685

Met Ala Ala Val Ala Phe Leu Ala Leu Gln Leu Ile Val Met Ala
1               5                   10                  15

<210> SEQ ID NO 1686
<211> LENGTH: 15
<212> TYPE: PRT
<213> ORGANISM: Hesperocyparis arizonica

<400> SEQUENCE: 1686

Lys Ala Leu Trp Ile Ile Phe Ser Gln Asn Met Asn Ile Lys Leu
1               5                   10                  15

<210> SEQ ID NO 1687
<211> LENGTH: 15
<212> TYPE: PRT
<213> ORGANISM: Hesperocyparis arizonica

<400> SEQUENCE: 1687
```

```
Ile Phe Ser Gln Asn Met Asn Ile Lys Leu Gln Met Pro Leu Tyr
 1               5                  10                  15

<210> SEQ ID NO 1688
<211> LENGTH: 15
<212> TYPE: PRT
<213> ORGANISM: Hesperocyparis arizonica

<400> SEQUENCE: 1688

Ile Phe Ser Gln Asn Met Asn Ile Lys Leu Gln Met Pro Leu Tyr
 1               5                  10                  15

<210> SEQ ID NO 1689
<211> LENGTH: 15
<212> TYPE: PRT
<213> ORGANISM: Hesperocyparis arizonica

<400> SEQUENCE: 1689

Met Asn Ile Lys Leu Gln Met Pro Leu Tyr Val Ala Gly Tyr Lys
 1               5                  10                  15

<210> SEQ ID NO 1690
<211> LENGTH: 15
<212> TYPE: PRT
<213> ORGANISM: Hesperocyparis arizonica

<400> SEQUENCE: 1690

Met Asn Ile Lys Leu Gln Met Pro Leu Tyr Val Ala Gly Tyr Lys
 1               5                  10                  15

<210> SEQ ID NO 1691
<211> LENGTH: 15
<212> TYPE: PRT
<213> ORGANISM: Hesperocyparis arizonica

<400> SEQUENCE: 1691

Thr Ile Ser Asn Asn His Phe Phe Asn His His Lys Val Met Leu
 1               5                  10                  15

<210> SEQ ID NO 1692
<211> LENGTH: 15
<212> TYPE: PRT
<213> ORGANISM: Hesperocyparis arizonica

<400> SEQUENCE: 1692

His Phe Phe Asn His His Lys Val Met Leu Leu Gly His Asp Asp
 1               5                  10                  15

<210> SEQ ID NO 1693
<211> LENGTH: 15
<212> TYPE: PRT
<213> ORGANISM: Hesperocyparis arizonica

<400> SEQUENCE: 1693

Glu Asp Thr Asn Ile Tyr Asn Ser Asn Glu Ala Phe Lys Val Glu
 1               5                  10                  15

<210> SEQ ID NO 1694
<211> LENGTH: 15
<212> TYPE: PRT
<213> ORGANISM: Hesperocyparis arizonica

<400> SEQUENCE: 1694

Glu Asp Thr Asn Ile Tyr Asn Ser Asn Glu Ala Phe Lys Val Glu
```

-continued

```
1               5                   10                  15
```

<210> SEQ ID NO 1695
<211> LENGTH: 15
<212> TYPE: PRT
<213> ORGANISM: Hesperocyparis arizonica

<400> SEQUENCE: 1695

```
Glu Asp Thr Asn Ile Tyr Asn Ser Asn Glu Ala Phe Lys Val Glu
1               5                   10                  15
```

<210> SEQ ID NO 1696
<211> LENGTH: 15
<212> TYPE: PRT
<213> ORGANISM: Cupressus sempervirens

<400> SEQUENCE: 1696

```
Glu Lys Ala Leu Trp Ile Ile Phe Ser Gln Asn Met Asn Ile Lys
1               5                   10                  15
```

<210> SEQ ID NO 1697
<211> LENGTH: 15
<212> TYPE: PRT
<213> ORGANISM: Cupressus sempervirens

<400> SEQUENCE: 1697

```
Ile Ile Phe Ser Gln Asn Met Asn Ile Lys Leu Lys Met Pro Leu
1               5                   10                  15
```

<210> SEQ ID NO 1698
<211> LENGTH: 15
<212> TYPE: PRT
<213> ORGANISM: Cupressus sempervirens

<400> SEQUENCE: 1698

```
Ile Ile Phe Ser Gln Asn Met Asn Ile Lys Leu Lys Met Pro Leu
1               5                   10                  15
```

<210> SEQ ID NO 1699
<211> LENGTH: 15
<212> TYPE: PRT
<213> ORGANISM: Cupressus sempervirens

<400> SEQUENCE: 1699

```
Ile Ile Phe Ser Gln Asn Met Asn Ile Lys Leu Lys Met Pro Leu
1               5                   10                  15
```

<210> SEQ ID NO 1700
<211> LENGTH: 15
<212> TYPE: PRT
<213> ORGANISM: Cupressus sempervirens

<400> SEQUENCE: 1700

```
Asn Met Asn Ile Lys Leu Lys Met Pro Leu Tyr Val Ala Gly His
1               5                   10                  15
```

<210> SEQ ID NO 1701
<211> LENGTH: 15
<212> TYPE: PRT
<213> ORGANISM: Cupressus sempervirens

<400> SEQUENCE: 1701

```
Gly Pro Cys Leu Phe Met Arg Lys Val Ser His Val Ile Leu His
1               5                   10                  15
```

<210> SEQ ID NO 1702
<211> LENGTH: 15
<212> TYPE: PRT
<213> ORGANISM: Cupressus sempervirens

<400> SEQUENCE: 1702

Met Arg Lys Val Ser His Val Ile Leu His Gly Leu His Ile His
1               5                   10                  15

<210> SEQ ID NO 1703
<211> LENGTH: 15
<212> TYPE: PRT
<213> ORGANISM: Cupressus sempervirens

<400> SEQUENCE: 1703

Asn His Phe Phe Asn His His Lys Val Met Leu Leu Gly His Asp
1               5                   10                  15

<210> SEQ ID NO 1704
<211> LENGTH: 15
<212> TYPE: PRT
<213> ORGANISM: Cupressus sempervirens

<400> SEQUENCE: 1704

Asn His Phe Phe Asn His His Lys Val Met Leu Leu Gly His Asp
1               5                   10                  15

<210> SEQ ID NO 1705
<211> LENGTH: 15
<212> TYPE: PRT
<213> ORGANISM: Cupressus sempervirens

<400> SEQUENCE: 1705

Asp Lys Ser Met Lys Val Thr Val Ala Phe Asn Gln Phe Gly Pro
1               5                   10                  15

<210> SEQ ID NO 1706
<211> LENGTH: 15
<212> TYPE: PRT
<213> ORGANISM: Cupressus sempervirens

<400> SEQUENCE: 1706

Leu Val Ala Thr Ser Ala Ile Ser Leu His Met Gln Glu Ala Gly
1               5                   10                  15

<210> SEQ ID NO 1707
<211> LENGTH: 15
<212> TYPE: PRT
<213> ORGANISM: Fraxinus excelsior

<400> SEQUENCE: 1707

Asp Thr Cys Arg Ala Arg Phe Ile Thr Lys Leu Ser Glu Phe Ile
1               5                   10                  15

<210> SEQ ID NO 1708
<211> LENGTH: 15
<212> TYPE: PRT
<213> ORGANISM: Fraxinus excelsior

<400> SEQUENCE: 1708

Leu Ser Glu Phe Ile Thr Gly Ala Ser Val Arg Leu Gln Cys Arg
1               5                   10                  15

<210> SEQ ID NO 1709

-continued

```
<211> LENGTH: 15
<212> TYPE: PRT
<213> ORGANISM: Fraxinus excelsior

<400> SEQUENCE: 1709

Leu Gly Phe Phe Lys Lys Glu Ala Leu Pro Gln Cys Ala Gln Val
1               5                   10                  15

<210> SEQ ID NO 1710
<211> LENGTH: 15
<212> TYPE: PRT
<213> ORGANISM: Juniperus oxycedrus

<400> SEQUENCE: 1710

Glu Leu Ala Asp Ile Leu Arg Ser Leu Gly Ser Asp Val Gly Glu
1               5                   10                  15

<210> SEQ ID NO 1711
<211> LENGTH: 15
<212> TYPE: PRT
<213> ORGANISM: Juniperus oxycedrus

<400> SEQUENCE: 1711

Gly Tyr Val Ser Leu Gln Glu Phe Val Asp Leu Asn Asn Lys Gly
1               5                   10                  15

<210> SEQ ID NO 1712
<211> LENGTH: 15
<212> TYPE: PRT
<213> ORGANISM: Juniperus oxycedrus

<400> SEQUENCE: 1712

Gly Tyr Val Ser Leu Gln Glu Phe Val Asp Leu Asn Asn Lys Gly
1               5                   10                  15

<210> SEQ ID NO 1713
<211> LENGTH: 15
<212> TYPE: PRT
<213> ORGANISM: Juniperus oxycedrus

<400> SEQUENCE: 1713

Leu Ile Ser Val Glu Glu Phe Gln Thr Met Met Thr Ser Glu Met
1               5                   10                  15

<210> SEQ ID NO 1714
<211> LENGTH: 15
<212> TYPE: PRT
<213> ORGANISM: Phoenix dactylifera

<400> SEQUENCE: 1714

Ser Ser Ser Phe Pro Gln Phe Lys Ser Glu Glu Ile Thr Asn Ile
1               5                   10                  15

<210> SEQ ID NO 1715
<211> LENGTH: 15
<212> TYPE: PRT
<213> ORGANISM: Phoenix dactylifera

<400> SEQUENCE: 1715

Lys Tyr Met Val Ile Gln Gly Glu Pro Gly Ala Val Ile Arg Gly
1               5                   10                  15

<210> SEQ ID NO 1716
<211> LENGTH: 15
<212> TYPE: PRT
```

<213> ORGANISM: Phoenix dactylifera

<400> SEQUENCE: 1716

Gly Val Thr Val Lys Lys Thr Asn Gln Ala Leu Ile Phe Gly Ile
1               5                   10                  15

<210> SEQ ID NO 1717
<211> LENGTH: 15
<212> TYPE: PRT
<213> ORGANISM: Quercus alba

<400> SEQUENCE: 1717

Ala Ser Val Ile Pro Pro Ala Arg Leu Phe Lys Ala Phe Val Leu
1               5                   10                  15

<210> SEQ ID NO 1718
<211> LENGTH: 15
<212> TYPE: PRT
<213> ORGANISM: Quercus alba

<400> SEQUENCE: 1718

Ala Ser Val Ile Pro Pro Ala Arg Leu Phe Lys Ala Phe Val Leu
1               5                   10                  15

<210> SEQ ID NO 1719
<211> LENGTH: 15
<212> TYPE: PRT
<213> ORGANISM: Quercus alba

<400> SEQUENCE: 1719

Ala Ser Val Ile Pro Pro Ala Arg Leu Phe Lys Ala Phe Val Leu
1               5                   10                  15

<210> SEQ ID NO 1720
<211> LENGTH: 15
<212> TYPE: PRT
<213> ORGANISM: Quercus alba

<400> SEQUENCE: 1720

Ala Ser Val Ile Pro Pro Ala Arg Leu Phe Lys Ala Phe Val Leu
1               5                   10                  15

<210> SEQ ID NO 1721
<211> LENGTH: 15
<212> TYPE: PRT
<213> ORGANISM: Quercus alba

<400> SEQUENCE: 1721

Pro Ala Arg Leu Phe Lys Ala Phe Val Leu Asp Ser Asp Asn Leu
1               5                   10                  15

<210> SEQ ID NO 1722
<211> LENGTH: 15
<212> TYPE: PRT
<213> ORGANISM: Quercus alba

<400> SEQUENCE: 1722

Pro Ala Arg Leu Phe Lys Ala Phe Val Leu Asp Ser Asp Asn Leu
1               5                   10                  15

<210> SEQ ID NO 1723
<211> LENGTH: 15
<212> TYPE: PRT
<213> ORGANISM: Quercus alba

```
<400> SEQUENCE: 1723

Pro Ala Arg Leu Phe Lys Ala Phe Val Leu Asp Ser Asp Asn Leu
1               5                   10                  15

<210> SEQ ID NO 1724
<211> LENGTH: 15
<212> TYPE: PRT
<213> ORGANISM: Quercus alba

<400> SEQUENCE: 1724

Pro Ala Arg Leu Phe Lys Ala Phe Val Leu Asp Ser Asp Asn Leu
1               5                   10                  15

<210> SEQ ID NO 1725
<211> LENGTH: 15
<212> TYPE: PRT
<213> ORGANISM: Quercus alba

<400> SEQUENCE: 1725

Pro Ala Arg Leu Phe Lys Ala Phe Val Leu Asp Ser Asp Asn Leu
1               5                   10                  15

<210> SEQ ID NO 1726
<211> LENGTH: 15
<212> TYPE: PRT
<213> ORGANISM: Quercus alba

<400> SEQUENCE: 1726

Pro Ala Arg Leu Phe Lys Ala Phe Val Leu Asp Ser Asp Asn Leu
1               5                   10                  15

<210> SEQ ID NO 1727
<211> LENGTH: 15
<212> TYPE: PRT
<213> ORGANISM: Quercus alba

<400> SEQUENCE: 1727

Lys Ala Phe Val Leu Asp Ser Asp Asn Leu Ile Pro Lys Val Val
1               5                   10                  15

<210> SEQ ID NO 1728
<211> LENGTH: 15
<212> TYPE: PRT
<213> ORGANISM: Quercus alba

<400> SEQUENCE: 1728

Lys Ala Phe Val Leu Asp Ser Asp Asn Leu Ile Pro Lys Val Val
1               5                   10                  15

<210> SEQ ID NO 1729
<211> LENGTH: 15
<212> TYPE: PRT
<213> ORGANISM: Quercus alba

<400> SEQUENCE: 1729

Lys Ala Phe Val Leu Asp Ser Asp Asn Leu Ile Pro Lys Val Val
1               5                   10                  15

<210> SEQ ID NO 1730
<211> LENGTH: 15
<212> TYPE: PRT
<213> ORGANISM: Quercus alba

<400> SEQUENCE: 1730
```

Ala Ser Glu Val Phe Lys Ala Val Glu Ala Tyr Leu Val Ala His
1               5                   10                  15

<210> SEQ ID NO 1731
<211> LENGTH: 15
<212> TYPE: PRT
<213> ORGANISM: Quercus alba

<400> SEQUENCE: 1731

Ala Ser Glu Val Phe Lys Ala Val Glu Ala Tyr Leu Val Ala His
1               5                   10                  15

<210> SEQ ID NO 1732
<211> LENGTH: 15
<212> TYPE: PRT
<213> ORGANISM: Quercus alba

<400> SEQUENCE: 1732

Ala Ser Glu Val Phe Lys Ala Val Glu Ala Tyr Leu Val Ala His
1               5                   10                  15

<210> SEQ ID NO 1733
<211> LENGTH: 15
<212> TYPE: PRT
<213> ORGANISM: Quercus alba

<400> SEQUENCE: 1733

Lys Ala Val Glu Ala Tyr Leu Val Ala His Pro Asp Leu Tyr Lys
1               5                   10                  15

<210> SEQ ID NO 1734
<211> LENGTH: 15
<212> TYPE: PRT
<213> ORGANISM: Quercus alba

<400> SEQUENCE: 1734

Lys Ala Val Glu Ala Tyr Leu Val Ala His Pro Asp Leu Tyr Lys
1               5                   10                  15

<210> SEQ ID NO 1735
<211> LENGTH: 15
<212> TYPE: PRT
<213> ORGANISM: Quercus alba

<400> SEQUENCE: 1735

Lys Ala Val Glu Ala Tyr Leu Val Ala His Pro Asp Leu Tyr Lys
1               5                   10                  15

<210> SEQ ID NO 1736
<211> LENGTH: 15
<212> TYPE: PRT
<213> ORGANISM: Quercus alba

<400> SEQUENCE: 1736

Lys Ala Val Glu Ala Tyr Leu Val Ala His Pro Asp Leu Tyr Lys
1               5                   10                  15

<210> SEQ ID NO 1737
<211> LENGTH: 15
<212> TYPE: PRT
<213> ORGANISM: Anthoxanthum odoratum

<400> SEQUENCE: 1737

Ile Ala Lys Val Pro Pro Gly Pro Asn Ile Thr Ala Thr Tyr Gly
1               5                   10                  15

<210> SEQ ID NO 1738
<211> LENGTH: 15
<212> TYPE: PRT
<213> ORGANISM: Anthoxanthum odoratum

<400> SEQUENCE: 1738

Ile Ala Lys Val Pro Pro Gly Pro Asn Ile Thr Ala Thr Tyr Gly
1               5                   10                  15

<210> SEQ ID NO 1739
<211> LENGTH: 15
<212> TYPE: PRT
<213> ORGANISM: Anthoxanthum odoratum

<400> SEQUENCE: 1739

Ile Ala Lys Val Pro Pro Gly Pro Asn Ile Thr Ala Thr Tyr Gly
1               5                   10                  15

<210> SEQ ID NO 1740
<211> LENGTH: 15
<212> TYPE: PRT
<213> ORGANISM: Anthoxanthum odoratum

<400> SEQUENCE: 1740

Asp Lys Trp Leu Asp Ala Lys Ser Thr Trp Tyr Gly Lys Pro Thr
1               5                   10                  15

<210> SEQ ID NO 1741
<211> LENGTH: 15
<212> TYPE: PRT
<213> ORGANISM: Anthoxanthum odoratum

<400> SEQUENCE: 1741

Asp Lys Trp Leu Asp Ala Lys Ser Thr Trp Tyr Gly Lys Pro Thr
1               5                   10                  15

<210> SEQ ID NO 1742
<211> LENGTH: 15
<212> TYPE: PRT
<213> ORGANISM: Anthoxanthum odoratum

<400> SEQUENCE: 1742

Asp Lys Trp Leu Asp Ala Lys Ser Thr Trp Tyr Gly Lys Pro Thr
1               5                   10                  15

<210> SEQ ID NO 1743
<211> LENGTH: 15
<212> TYPE: PRT
<213> ORGANISM: Anthoxanthum odoratum

<400> SEQUENCE: 1743

Trp Leu Asp Ala Lys Ser Thr Trp Tyr Gly Lys Pro Thr Gly Ala
1               5                   10                  15

<210> SEQ ID NO 1744
<211> LENGTH: 15
<212> TYPE: PRT
<213> ORGANISM: Anthoxanthum odoratum

<400> SEQUENCE: 1744

Trp Leu Asp Ala Lys Ser Thr Trp Tyr Gly Lys Pro Thr Gly Ala
1               5                   10                  15

```
<210> SEQ ID NO 1745
<211> LENGTH: 15
<212> TYPE: PRT
<213> ORGANISM: Anthoxanthum odoratum

<400> SEQUENCE: 1745

Trp Leu Asp Ala Lys Ser Thr Trp Tyr Gly Lys Pro Thr Gly Ala
1               5                   10                  15

<210> SEQ ID NO 1746
<211> LENGTH: 15
<212> TYPE: PRT
<213> ORGANISM: Anthoxanthum odoratum

<400> SEQUENCE: 1746

Trp Leu Asp Ala Lys Ser Thr Trp Tyr Gly Lys Pro Thr Gly Ala
1               5                   10                  15

<210> SEQ ID NO 1747
<211> LENGTH: 15
<212> TYPE: PRT
<213> ORGANISM: Cynodon dactylon

<400> SEQUENCE: 1747

Met Leu Ala Val Val Ala Val Val Leu Ala Ser Met Val Gly Gly
1               5                   10                  15

<210> SEQ ID NO 1748
<211> LENGTH: 15
<212> TYPE: PRT
<213> ORGANISM: Cynodon dactylon

<400> SEQUENCE: 1748

Thr Val Trp Ala Gln Ser Ala Ala Phe Pro Ala Phe Lys Pro Glu
1               5                   10                  15

<210> SEQ ID NO 1749
<211> LENGTH: 15
<212> TYPE: PRT
<213> ORGANISM: Cynodon dactylon

<400> SEQUENCE: 1749

Thr Val Trp Ala Gln Ser Ala Ala Phe Pro Ala Phe Lys Pro Glu
1               5                   10                  15

<210> SEQ ID NO 1750
<211> LENGTH: 15
<212> TYPE: PRT
<213> ORGANISM: Cynodon dactylon

<400> SEQUENCE: 1750

Leu Arg Thr Leu Gly Ser Thr Ser Ala Asp Glu Val Gln Arg Met
1               5                   10                  15

<210> SEQ ID NO 1751
<211> LENGTH: 15
<212> TYPE: PRT
<213> ORGANISM: Dactylis glomerata

<400> SEQUENCE: 1751

Pro Asn Tyr Leu Ala Leu Leu Val Lys Tyr Val Asp Gly Asp Gly
1               5                   10                  15

<210> SEQ ID NO 1752
<211> LENGTH: 15
```

```
<212> TYPE: PRT
<213> ORGANISM: Dactylis glomerata

<400> SEQUENCE: 1752

Pro Asn Tyr Leu Ala Leu Leu Val Lys Tyr Val Asp Gly Asp Gly
1               5                   10                  15

<210> SEQ ID NO 1753
<211> LENGTH: 15
<212> TYPE: PRT
<213> ORGANISM: Dactylis glomerata

<400> SEQUENCE: 1753

Pro Asn Tyr Leu Ala Leu Leu Val Lys Tyr Val Asp Gly Asp Gly
1               5                   10                  15

<210> SEQ ID NO 1754
<211> LENGTH: 15
<212> TYPE: PRT
<213> ORGANISM: Dactylis glomerata

<400> SEQUENCE: 1754

Pro Asn Tyr Leu Ala Leu Leu Val Lys Tyr Val Asp Gly Asp Gly
1               5                   10                  15

<210> SEQ ID NO 1755
<211> LENGTH: 15
<212> TYPE: PRT
<213> ORGANISM: Dactylis glomerata

<400> SEQUENCE: 1755

Gly Ser Asp Glu Lys Asn Leu Ala Leu Ser Ile Lys Tyr Asn Lys
1               5                   10                  15

<210> SEQ ID NO 1756
<211> LENGTH: 15
<212> TYPE: PRT
<213> ORGANISM: Dactylis glomerata

<400> SEQUENCE: 1756

Gly Ser Asp Glu Lys Asn Leu Ala Leu Ser Ile Lys Tyr Asn Lys
1               5                   10                  15

<210> SEQ ID NO 1757
<211> LENGTH: 15
<212> TYPE: PRT
<213> ORGANISM: Dactylis glomerata

<400> SEQUENCE: 1757

Asn Leu Ala Leu Ser Ile Lys Tyr Asn Lys Glu Gly Asp Ser Met
1               5                   10                  15

<210> SEQ ID NO 1758
<211> LENGTH: 15
<212> TYPE: PRT
<213> ORGANISM: Dactylis glomerata

<400> SEQUENCE: 1758

Asn Leu Ala Leu Ser Ile Lys Tyr Asn Lys Glu Gly Asp Ser Met
1               5                   10                  15

<210> SEQ ID NO 1759
<211> LENGTH: 15
<212> TYPE: PRT
<213> ORGANISM: Dactylis glomerata
```

<400> SEQUENCE: 1759

Ile Pro Thr Ala Phe Lys Ile Gly Thr Thr Tyr Thr Pro Glu Glu
1               5                   10                  15

<210> SEQ ID NO 1760
<211> LENGTH: 15
<212> TYPE: PRT
<213> ORGANISM: Dactylis glomerata

<400> SEQUENCE: 1760

Asp Ile Tyr Asn Tyr Met Glu Pro Tyr Val Ser Lys Val Asp Pro
1               5                   10                  15

<210> SEQ ID NO 1761
<211> LENGTH: 15
<212> TYPE: PRT
<213> ORGANISM: Dactylis glomerata

<400> SEQUENCE: 1761

Asp Ile Tyr Asn Tyr Met Glu Pro Tyr Val Ser Lys Val Asp Pro
1               5                   10                  15

<210> SEQ ID NO 1762
<211> LENGTH: 15
<212> TYPE: PRT
<213> ORGANISM: Dactylis glomerata

<400> SEQUENCE: 1762

Asp Ile Tyr Asn Tyr Met Glu Pro Tyr Val Ser Lys Val Asp Pro
1               5                   10                  15

<210> SEQ ID NO 1763
<211> LENGTH: 15
<212> TYPE: PRT
<213> ORGANISM: Lolium perenne

<400> SEQUENCE: 1763

Met Ala Ser Ser Ser Ser Val Leu Leu Val Val Ala Leu Phe Ala
1               5                   10                  15

<210> SEQ ID NO 1764
<211> LENGTH: 15
<212> TYPE: PRT
<213> ORGANISM: Lolium perenne

<400> SEQUENCE: 1764

Val Ala Leu Phe Ala Val Phe Leu Gly Ser Ala His Gly Ile Ala
1               5                   10                  15

<210> SEQ ID NO 1765
<211> LENGTH: 15
<212> TYPE: PRT
<213> ORGANISM: Lolium perenne

<400> SEQUENCE: 1765

Glu Pro Ile Ala Pro Tyr His Phe Asp Leu Ser Gly His Ala Phe
1               5                   10                  15

<210> SEQ ID NO 1766
<211> LENGTH: 15
<212> TYPE: PRT
<213> ORGANISM: Lolium perenne

<400> SEQUENCE: 1766

Lys Ala Ser Asn Pro Asn Tyr Leu Ala Ile Leu Val Lys Tyr Val
1               5                   10                  15

<210> SEQ ID NO 1767
<211> LENGTH: 15
<212> TYPE: PRT
<213> ORGANISM: Lolium perenne

<400> SEQUENCE: 1767

Lys Ala Ser Asn Pro Asn Tyr Leu Ala Ile Leu Val Lys Tyr Val
1               5                   10                  15

<210> SEQ ID NO 1768
<211> LENGTH: 15
<212> TYPE: PRT
<213> ORGANISM: Lolium perenne

<400> SEQUENCE: 1768

Lys Ala Ser Asn Pro Asn Tyr Leu Ala Ile Leu Val Lys Tyr Val
1               5                   10                  15

<210> SEQ ID NO 1769
<211> LENGTH: 15
<212> TYPE: PRT
<213> ORGANISM: Lolium perenne

<400> SEQUENCE: 1769

Lys Gln Gln Gly Ile Arg Tyr Ala Asn Pro Ile Ala Phe Phe Arg
1               5                   10                  15

<210> SEQ ID NO 1770
<211> LENGTH: 15
<212> TYPE: PRT
<213> ORGANISM: Lolium perenne

<400> SEQUENCE: 1770

Arg Tyr Ala Asn Pro Ile Ala Phe Phe Arg Lys Glu Pro Leu Lys
1               5                   10                  15

<210> SEQ ID NO 1771
<211> LENGTH: 15
<212> TYPE: PRT
<213> ORGANISM: Lolium perenne

<400> SEQUENCE: 1771

Ile Ala Phe Phe Arg Lys Glu Pro Leu Lys Glu Cys Gly Gly Ile
1               5                   10                  15

<210> SEQ ID NO 1772
<211> LENGTH: 15
<212> TYPE: PRT
<213> ORGANISM: Lolium perenne

<400> SEQUENCE: 1772

Asp Gly Val Trp Glu Ile Lys Ser Asp Lys Pro Leu Lys Gly Pro
1               5                   10                  15

<210> SEQ ID NO 1773
<211> LENGTH: 15
<212> TYPE: PRT
<213> ORGANISM: Lolium perenne

<400> SEQUENCE: 1773

Asp Gly Val Trp Glu Ile Lys Ser Asp Lys Pro Leu Lys Gly Pro

```
1               5                   10                  15
```

<210> SEQ ID NO 1774
<211> LENGTH: 15
<212> TYPE: PRT
<213> ORGANISM: Lolium perenne

<400> SEQUENCE: 1774

```
Asp Gly Val Trp Glu Ile Lys Ser Asp Lys Pro Leu Lys Gly Pro
1               5                   10                  15
```

<210> SEQ ID NO 1775
<211> LENGTH: 15
<212> TYPE: PRT
<213> ORGANISM: Lolium perenne

<400> SEQUENCE: 1775

```
Asp Gly Val Trp Glu Ile Lys Ser Asp Lys Pro Leu Lys Gly Pro
1               5                   10                  15
```

<210> SEQ ID NO 1776
<211> LENGTH: 15
<212> TYPE: PRT
<213> ORGANISM: Lolium perenne

<400> SEQUENCE: 1776

```
Ile Lys Ser Asp Lys Pro Leu Lys Gly Pro Phe Asn Phe Arg Phe
1               5                   10                  15
```

<210> SEQ ID NO 1777
<211> LENGTH: 15
<212> TYPE: PRT
<213> ORGANISM: Lolium perenne

<400> SEQUENCE: 1777

```
Met Arg Asn Val Phe Asp Asp Val Val Pro Ala Asp Phe Lys Val
1               5                   10                  15
```

<210> SEQ ID NO 1778
<211> LENGTH: 15
<212> TYPE: PRT
<213> ORGANISM: Lolium perenne

<400> SEQUENCE: 1778

```
Met Arg Asn Val Phe Asp Asp Val Val Pro Ala Asp Phe Lys Val
1               5                   10                  15
```

<210> SEQ ID NO 1779
<211> LENGTH: 15
<212> TYPE: PRT
<213> ORGANISM: Lolium perenne

<400> SEQUENCE: 1779

```
Met Arg Asn Val Phe Asp Asp Val Val Pro Ala Asp Phe Lys Val
1               5                   10                  15
```

<210> SEQ ID NO 1780
<211> LENGTH: 15
<212> TYPE: PRT
<213> ORGANISM: Lolium perenne

<400> SEQUENCE: 1780

```
Ser Asp Ala Lys Thr Leu Val Leu Asn Ile Lys Tyr Thr Arg Pro
1               5                   10                  15
```

<210> SEQ ID NO 1781
<211> LENGTH: 15
<212> TYPE: PRT
<213> ORGANISM: Lolium perenne

<400> SEQUENCE: 1781

Ser Asp Ala Lys Thr Leu Val Leu Asn Ile Lys Tyr Thr Arg Pro
1               5                   10                  15

<210> SEQ ID NO 1782
<211> LENGTH: 15
<212> TYPE: PRT
<213> ORGANISM: Lolium perenne

<400> SEQUENCE: 1782

Ser Asp Ala Lys Thr Leu Val Leu Asn Ile Lys Tyr Thr Arg Pro
1               5                   10                  15

<210> SEQ ID NO 1783
<211> LENGTH: 15
<212> TYPE: PRT
<213> ORGANISM: Lolium perenne

<400> SEQUENCE: 1783

Leu Trp Glu Val Lys Ser Ala Lys Pro Leu Thr Gly Pro Met Asn
1               5                   10                  15

<210> SEQ ID NO 1784
<211> LENGTH: 15
<212> TYPE: PRT
<213> ORGANISM: Lolium perenne

<400> SEQUENCE: 1784

Leu Trp Glu Val Lys Ser Ala Lys Pro Leu Thr Gly Pro Met Asn
1               5                   10                  15

<210> SEQ ID NO 1785
<211> LENGTH: 15
<212> TYPE: PRT
<213> ORGANISM: Lolium perenne

<400> SEQUENCE: 1785

Asn Val Phe Asp Glu Val Ile Pro Thr Ala Phe Thr Val Gly Lys
1               5                   10                  15

<210> SEQ ID NO 1786
<211> LENGTH: 15
<212> TYPE: PRT
<213> ORGANISM: Lolium perenne

<400> SEQUENCE: 1786

Asn Val Phe Asp Glu Val Ile Pro Thr Ala Phe Thr Val Gly Lys
1               5                   10                  15

<210> SEQ ID NO 1787
<211> LENGTH: 15
<212> TYPE: PRT
<213> ORGANISM: Lolium perenne

<400> SEQUENCE: 1787

Pro Glu Asn Phe Ala Val Val Asp Leu Asn Gln Met Arg Ala Val
1               5                   10                  15

<210> SEQ ID NO 1788

```
<211> LENGTH: 15
<212> TYPE: PRT
<213> ORGANISM: Lolium perenne

<400> SEQUENCE: 1788

Leu Arg Lys Tyr Gly Ile Ala Ala Glu Asn Val Ile Asp Val Lys
1               5                   10                  15

<210> SEQ ID NO 1789
<211> LENGTH: 15
<212> TYPE: PRT
<213> ORGANISM: Lolium perenne

<400> SEQUENCE: 1789

Asn Glu Met Ser Trp Ile Glu Ser Ile Pro Phe Val His Leu Gly
1               5                   10                  15

<210> SEQ ID NO 1790
<211> LENGTH: 15
<212> TYPE: PRT
<213> ORGANISM: Lolium perenne

<400> SEQUENCE: 1790

Phe Pro His Arg Lys Gly Val Leu Phe Asn Ile Gln Tyr Val Asn
1               5                   10                  15

<210> SEQ ID NO 1791
<211> LENGTH: 15
<212> TYPE: PRT
<213> ORGANISM: Lolium perenne

<400> SEQUENCE: 1791

His Thr Val Ala Leu Phe Leu Ala Val Ala Leu Val Ala Gly Pro
1               5                   10                  15

<210> SEQ ID NO 1792
<211> LENGTH: 15
<212> TYPE: PRT
<213> ORGANISM: Lolium perenne

<400> SEQUENCE: 1792

Phe Leu Ala Val Ala Leu Val Ala Gly Pro Ala Ala Ser Tyr Ala
1               5                   10                  15

<210> SEQ ID NO 1793
<211> LENGTH: 15
<212> TYPE: PRT
<213> ORGANISM: Lolium perenne

<400> SEQUENCE: 1793

Leu Ile Glu Lys Ile Asn Ala Gly Phe Lys Ala Ala Val Ala Ala
1               5                   10                  15

<210> SEQ ID NO 1794
<211> LENGTH: 15
<212> TYPE: PRT
<213> ORGANISM: Lolium perenne

<400> SEQUENCE: 1794

Leu Ile Glu Lys Ile Asn Ala Gly Phe Lys Ala Ala Val Ala Ala
1               5                   10                  15

<210> SEQ ID NO 1795
<211> LENGTH: 15
<212> TYPE: PRT
```

<213> ORGANISM: Lolium perenne

<400> SEQUENCE: 1795

Leu Ile Glu Lys Ile Asn Ala Gly Phe Lys Ala Ala Val Ala Ala
1               5                   10                  15

<210> SEQ ID NO 1796
<211> LENGTH: 15
<212> TYPE: PRT
<213> ORGANISM: Lolium perenne

<400> SEQUENCE: 1796

Asn Ala Gly Phe Lys Ala Ala Val Ala Ala Ala Ala Val Val Pro
1               5                   10                  15

<210> SEQ ID NO 1797
<211> LENGTH: 15
<212> TYPE: PRT
<213> ORGANISM: Lolium perenne

<400> SEQUENCE: 1797

Asn Ala Gly Phe Lys Ala Ala Val Ala Ala Ala Ala Val Val Pro
1               5                   10                  15

<210> SEQ ID NO 1798
<211> LENGTH: 15
<212> TYPE: PRT
<213> ORGANISM: Lolium perenne

<400> SEQUENCE: 1798

Asn Ala Gly Phe Lys Ala Ala Val Ala Ala Ala Ala Val Val Pro
1               5                   10                  15

<210> SEQ ID NO 1799
<211> LENGTH: 15
<212> TYPE: PRT
<213> ORGANISM: Lolium perenne

<400> SEQUENCE: 1799

Lys Thr Phe Val Glu Thr Phe Gly Thr Ala Thr Asn Lys Ala Phe
1               5                   10                  15

<210> SEQ ID NO 1800
<211> LENGTH: 15
<212> TYPE: PRT
<213> ORGANISM: Lolium perenne

<400> SEQUENCE: 1800

Thr Asn Lys Ala Phe Val Glu Gly Leu Ala Ser Gly Tyr Ala Asp
1               5                   10                  15

<210> SEQ ID NO 1801
<211> LENGTH: 15
<212> TYPE: PRT
<213> ORGANISM: Lolium perenne

<400> SEQUENCE: 1801

Asp Ala Ala Leu Lys Leu Ala Tyr Glu Ala Ala Gln Gly Ala Thr
1               5                   10                  15

<210> SEQ ID NO 1802
<211> LENGTH: 15
<212> TYPE: PRT
<213> ORGANISM: Lolium perenne

```
<400> SEQUENCE: 1802

Pro Glu Ala Lys Tyr Asp Ala Tyr Val Ala Thr Leu Thr Glu Ala
1               5                   10                  15

<210> SEQ ID NO 1803
<211> LENGTH: 15
<212> TYPE: PRT
<213> ORGANISM: Lolium perenne

<400> SEQUENCE: 1803

Asp Ala Tyr Val Ala Thr Leu Thr Glu Ala Leu Arg Val Ile Ala
1               5                   10                  15

<210> SEQ ID NO 1804
<211> LENGTH: 15
<212> TYPE: PRT
<213> ORGANISM: Lolium perenne

<400> SEQUENCE: 1804

Asp Ala Tyr Val Ala Thr Leu Thr Glu Ala Leu Arg Val Ile Ala
1               5                   10                  15

<210> SEQ ID NO 1805
<211> LENGTH: 15
<212> TYPE: PRT
<213> ORGANISM: Lolium perenne

<400> SEQUENCE: 1805

Thr Leu Thr Glu Ala Leu Arg Val Ile Ala Gly Thr Leu Glu Val
1               5                   10                  15

<210> SEQ ID NO 1806
<211> LENGTH: 15
<212> TYPE: PRT
<213> ORGANISM: Lolium perenne

<400> SEQUENCE: 1806

Val Asp Ala Ala Tyr Arg Thr Ala Thr Ala Ala Asn Ala Ala
1               5                   10                  15

<210> SEQ ID NO 1807
<211> LENGTH: 15
<212> TYPE: PRT
<213> ORGANISM: Lolium perenne

<400> SEQUENCE: 1807

Phe Thr Val Phe Glu Asn Thr Phe Asn Asn Ala Ile Lys Val Ser
1               5                   10                  15

<210> SEQ ID NO 1808
<211> LENGTH: 15
<212> TYPE: PRT
<213> ORGANISM: Lolium perenne

<400> SEQUENCE: 1808

Asp Ser Tyr Lys Phe Ile Pro Thr Leu Val Ala Ala Val Lys Gln
1               5                   10                  15

<210> SEQ ID NO 1809
<211> LENGTH: 15
<212> TYPE: PRT
<213> ORGANISM: Lolium perenne

<400> SEQUENCE: 1809
```

Asp Ser Tyr Lys Phe Ile Pro Thr Leu Val Ala Ala Val Lys Gln
1               5                   10                  15

<210> SEQ ID NO 1810
<211> LENGTH: 15
<212> TYPE: PRT
<213> ORGANISM: Lolium perenne

<400> SEQUENCE: 1810

Ala Ala Val Lys Gln Ala Tyr Ala Ala Lys Gln Ala Thr Ala Pro
1               5                   10                  15

<210> SEQ ID NO 1811
<211> LENGTH: 15
<212> TYPE: PRT
<213> ORGANISM: Lolium perenne

<400> SEQUENCE: 1811

Glu Val Lys Tyr Thr Val Ser Glu Thr Ala Leu Lys Lys Ala Val
1               5                   10                  15

<210> SEQ ID NO 1812
<211> LENGTH: 15
<212> TYPE: PRT
<213> ORGANISM: Lolium perenne

<400> SEQUENCE: 1812

Leu Lys Lys Ala Val Thr Ala Met Ser Glu Ala Glu Lys Glu Ala
1               5                   10                  15

<210> SEQ ID NO 1813
<211> LENGTH: 15
<212> TYPE: PRT
<213> ORGANISM: Lolium perenne

<400> SEQUENCE: 1813

Pro Ala Ala Ala Tyr Ala Thr Ala Thr Pro Ala Ala Ala Thr Ala
1               5                   10                  15

<210> SEQ ID NO 1814
<211> LENGTH: 15
<212> TYPE: PRT
<213> ORGANISM: Lolium perenne

<400> SEQUENCE: 1814

Pro Ala Ala Ala Tyr Ala Thr Ala Thr Pro Ala Ala Ala Thr Ala
1               5                   10                  15

<210> SEQ ID NO 1815
<211> LENGTH: 15
<212> TYPE: PRT
<213> ORGANISM: Lolium perenne

<400> SEQUENCE: 1815

Ala Phe Lys Ile Ala Ala Thr Ala Ala Asn Ala Ala Pro Thr Asn
1               5                   10                  15

<210> SEQ ID NO 1816
<211> LENGTH: 15
<212> TYPE: PRT
<213> ORGANISM: Lolium perenne

<400> SEQUENCE: 1816

Ala Phe Lys Ile Ala Ala Thr Ala Ala Asn Ala Ala Pro Thr Asn
1               5                   10                  15

<210> SEQ ID NO 1817
<211> LENGTH: 15
<212> TYPE: PRT
<213> ORGANISM: Lolium perenne

<400> SEQUENCE: 1817

Ala Phe Lys Ile Ala Ala Thr Ala Ala Asn Ala Ala Pro Thr Asn
1               5                   10                  15

<210> SEQ ID NO 1818
<211> LENGTH: 15
<212> TYPE: PRT
<213> ORGANISM: Lolium perenne

<400> SEQUENCE: 1818

Asp Lys Phe Thr Val Phe Glu Ser Ala Phe Asn Lys Ala Leu Asn
1               5                   10                  15

<210> SEQ ID NO 1819
<211> LENGTH: 15
<212> TYPE: PRT
<213> ORGANISM: Lolium perenne

<400> SEQUENCE: 1819

Ala Ala Leu Thr Lys Ala Ile Thr Ala Met Thr Gln Ala Gln Lys
1               5                   10                  15

<210> SEQ ID NO 1820
<211> LENGTH: 15
<212> TYPE: PRT
<213> ORGANISM: Phalaris aquatica

<400> SEQUENCE: 1820

Pro Asn Tyr Leu Ala Leu Leu Val Lys Tyr Val Asp Gly Asp Gly
1               5                   10                  15

<210> SEQ ID NO 1821
<211> LENGTH: 15
<212> TYPE: PRT
<213> ORGANISM: Phalaris aquatica

<400> SEQUENCE: 1821

Pro Asn Tyr Leu Ala Leu Leu Val Lys Tyr Val Asp Gly Asp Gly
1               5                   10                  15

<210> SEQ ID NO 1822
<211> LENGTH: 15
<212> TYPE: PRT
<213> ORGANISM: Phalaris aquatica

<400> SEQUENCE: 1822

Pro Asn Tyr Leu Ala Leu Leu Val Lys Tyr Val Asp Gly Asp Gly
1               5                   10                  15

<210> SEQ ID NO 1823
<211> LENGTH: 15
<212> TYPE: PRT
<213> ORGANISM: Phalaris aquatica

<400> SEQUENCE: 1823

Pro Asn Tyr Leu Ala Leu Leu Val Lys Tyr Val Asp Gly Asp Gly
1               5                   10                  15

<210> SEQ ID NO 1824
<211> LENGTH: 15
<212> TYPE: PRT
<213> ORGANISM: Phalaris aquatica

<400> SEQUENCE: 1824

Ser Trp Gly Ala Ile Trp Arg Ile Asp Thr Pro Asp Lys Leu Thr
1               5                   10                  15

<210> SEQ ID NO 1825
<211> LENGTH: 15
<212> TYPE: PRT
<213> ORGANISM: Phalaris aquatica

<400> SEQUENCE: 1825

Asp Ala Ala Tyr Arg Val Ala Tyr Glu Ala Ala Glu Gly Ser Thr
1               5                   10                  15

<210> SEQ ID NO 1826
<211> LENGTH: 15
<212> TYPE: PRT
<213> ORGANISM: Phalaris aquatica

<400> SEQUENCE: 1826

Asp Ala Phe Ile Ala Ala Leu Thr Glu Ala Leu Arg Val Ile Ala
1               5                   10                  15

<210> SEQ ID NO 1827
<211> LENGTH: 15
<212> TYPE: PRT
<213> ORGANISM: Phalaris aquatica

<400> SEQUENCE: 1827

Asp Ala Phe Ile Ala Ala Leu Thr Glu Ala Leu Arg Val Ile Ala
1               5                   10                  15

<210> SEQ ID NO 1828
<211> LENGTH: 15
<212> TYPE: PRT
<213> ORGANISM: Phalaris aquatica

<400> SEQUENCE: 1828

Ala Leu Thr Glu Ala Leu Arg Val Ile Ala Gly Ala Phe Glu Val
1               5                   10                  15

<210> SEQ ID NO 1829
<211> LENGTH: 15
<212> TYPE: PRT
<213> ORGANISM: Phalaris aquatica

<400> SEQUENCE: 1829

Ala Ala Phe Lys Ile Ala Ala Thr Ala Ala Asn Ser Ala Pro Ala
1               5                   10                  15

<210> SEQ ID NO 1830
<211> LENGTH: 15
<212> TYPE: PRT
<213> ORGANISM: Phalaris aquatica

<400> SEQUENCE: 1830

Ala Ala Phe Lys Ile Ala Ala Thr Ala Ala Asn Ser Ala Pro Ala
1               5                   10                  15

<210> SEQ ID NO 1831
<211> LENGTH: 15

<212> TYPE: PRT
<213> ORGANISM: Phalaris aquatica

<400> SEQUENCE: 1831

Asn Asp Lys Phe Thr Val Phe Glu Gly Ala Phe Asn Lys Ala Ile
1               5                   10                  15

<210> SEQ ID NO 1832
<211> LENGTH: 15
<212> TYPE: PRT
<213> ORGANISM: Phalaris aquatica

<400> SEQUENCE: 1832

Asn Asp Lys Phe Thr Val Phe Glu Gly Ala Phe Asn Lys Ala Ile
1               5                   10                  15

<210> SEQ ID NO 1833
<211> LENGTH: 15
<212> TYPE: PRT
<213> ORGANISM: Phalaris aquatica

<400> SEQUENCE: 1833

Gly Ala Tyr Glu Thr Tyr Lys Phe Ile Pro Ser Leu Glu Ala Ala
1               5                   10                  15

<210> SEQ ID NO 1834
<211> LENGTH: 15
<212> TYPE: PRT
<213> ORGANISM: Phalaris aquatica

<400> SEQUENCE: 1834

Gly Ala Tyr Glu Thr Tyr Lys Phe Ile Pro Ser Leu Glu Ala Ala
1               5                   10                  15

<210> SEQ ID NO 1835
<211> LENGTH: 15
<212> TYPE: PRT
<213> ORGANISM: Phalaris aquatica

<400> SEQUENCE: 1835

Gly Ala Tyr Glu Thr Tyr Lys Phe Ile Pro Ser Leu Glu Ala Ala
1               5                   10                  15

<210> SEQ ID NO 1836
<211> LENGTH: 15
<212> TYPE: PRT
<213> ORGANISM: Phalaris aquatica

<400> SEQUENCE: 1836

Tyr Lys Phe Ile Pro Ser Leu Glu Ala Ala Val Lys Gln Ala Tyr
1               5                   10                  15

<210> SEQ ID NO 1837
<211> LENGTH: 15
<212> TYPE: PRT
<213> ORGANISM: Phalaris aquatica

<400> SEQUENCE: 1837

Tyr Lys Phe Ile Pro Ser Leu Glu Ala Ala Val Lys Gln Ala Tyr
1               5                   10                  15

<210> SEQ ID NO 1838
<211> LENGTH: 15
<212> TYPE: PRT
<213> ORGANISM: Phalaris aquatica

<400> SEQUENCE: 1838

Tyr Lys Phe Ile Pro Ser Leu Glu Ala Ala Val Lys Gln Ala Tyr
1               5                   10                  15

<210> SEQ ID NO 1839
<211> LENGTH: 15
<212> TYPE: PRT
<213> ORGANISM: Poa pratensis

<400> SEQUENCE: 1839

Glu Pro Ile Ala Ala Tyr His Phe Asp Leu Ser Gly Lys Ala Phe
1               5                   10                  15

<210> SEQ ID NO 1840
<211> LENGTH: 15
<212> TYPE: PRT
<213> ORGANISM: Poa pratensis

<400> SEQUENCE: 1840

Glu Pro Ile Ala Ala Tyr His Phe Asp Leu Ser Gly Lys Ala Phe
1               5                   10                  15

<210> SEQ ID NO 1841
<211> LENGTH: 15
<212> TYPE: PRT
<213> ORGANISM: Poa pratensis

<400> SEQUENCE: 1841

Glu Pro Ile Ala Ala Tyr His Phe Asp Leu Ser Gly Lys Ala Phe
1               5                   10                  15

<210> SEQ ID NO 1842
<211> LENGTH: 15
<212> TYPE: PRT
<213> ORGANISM: Poa pratensis

<400> SEQUENCE: 1842

Lys Gly Ser Asn Pro Asn Tyr Leu Ala Leu Leu Val Lys Tyr Val
1               5                   10                  15

<210> SEQ ID NO 1843
<211> LENGTH: 15
<212> TYPE: PRT
<213> ORGANISM: Poa pratensis

<400> SEQUENCE: 1843

Asn Tyr Leu Ala Leu Leu Val Lys Tyr Val Thr Gly Asp Gly Asp
1               5                   10                  15

<210> SEQ ID NO 1844
<211> LENGTH: 15
<212> TYPE: PRT
<213> ORGANISM: Poa pratensis

<400> SEQUENCE: 1844

Asp Lys Phe Thr Val Phe Glu Ala Ala Phe Asn Asn Ala Ile Lys
1               5                   10                  15

<210> SEQ ID NO 1845
<211> LENGTH: 15
<212> TYPE: PRT
<213> ORGANISM: Poa pratensis

<400> SEQUENCE: 1845

```
Gln Lys Leu Met Glu Asp Ile Asn Val Gly Phe Lys Ala Ala Val
1               5                   10                  15

<210> SEQ ID NO 1846
<211> LENGTH: 15
<212> TYPE: PRT
<213> ORGANISM: Poa pratensis

<400> SEQUENCE: 1846

Gln Lys Leu Met Glu Asp Ile Asn Val Gly Phe Lys Ala Ala Val
1               5                   10                  15

<210> SEQ ID NO 1847
<211> LENGTH: 15
<212> TYPE: PRT
<213> ORGANISM: Poa pratensis

<400> SEQUENCE: 1847

Asp Ile Asn Val Gly Phe Lys Ala Ala Val Ala Ala Ala Ala Gly
1               5                   10                  15

<210> SEQ ID NO 1848
<211> LENGTH: 15
<212> TYPE: PRT
<213> ORGANISM: Poa pratensis

<400> SEQUENCE: 1848

Asp Ile Asn Val Gly Phe Lys Ala Ala Val Ala Ala Ala Ala Gly
1               5                   10                  15

<210> SEQ ID NO 1849
<211> LENGTH: 15
<212> TYPE: PRT
<213> ORGANISM: Poa pratensis

<400> SEQUENCE: 1849

Asp Ile Asn Val Gly Phe Lys Ala Ala Val Ala Ala Ala Ala Gly
1               5                   10                  15

<210> SEQ ID NO 1850
<211> LENGTH: 15
<212> TYPE: PRT
<213> ORGANISM: Poa pratensis

<400> SEQUENCE: 1850

Asp Ile Asn Val Gly Phe Lys Ala Ala Val Ala Ala Ala Ala Gly
1               5                   10                  15

<210> SEQ ID NO 1851
<211> LENGTH: 15
<212> TYPE: PRT
<213> ORGANISM: Poa pratensis

<400> SEQUENCE: 1851

Phe Lys Ala Ala Val Ala Ala Ala Ala Gly Ala Pro Pro Ala Asp
1               5                   10                  15

<210> SEQ ID NO 1852
<211> LENGTH: 15
<212> TYPE: PRT
<213> ORGANISM: Poa pratensis

<400> SEQUENCE: 1852

Phe Lys Ala Ala Val Ala Ala Ala Ala Gly Ala Pro Pro Ala Asp
```

```
<210> SEQ ID NO 1853
<211> LENGTH: 15
<212> TYPE: PRT
<213> ORGANISM: Poa pratensis

<400> SEQUENCE: 1853

Phe Lys Ala Ala Val Ala Ala Ala Gly Ala Pro Pro Ala Asp
1               5                   10                  15

<210> SEQ ID NO 1854
<211> LENGTH: 15
<212> TYPE: PRT
<213> ORGANISM: Poa pratensis

<400> SEQUENCE: 1854

Ala Thr Pro Glu Ala Lys Phe Asp Ser Phe Val Ala Ala Phe Thr
1               5                   10                  15

<210> SEQ ID NO 1855
<211> LENGTH: 15
<212> TYPE: PRT
<213> ORGANISM: Poa pratensis

<400> SEQUENCE: 1855

Ala Thr Pro Glu Ala Lys Phe Asp Ser Phe Val Ala Ala Phe Thr
1               5                   10                  15

<210> SEQ ID NO 1856
<211> LENGTH: 15
<212> TYPE: PRT
<213> ORGANISM: Poa pratensis

<400> SEQUENCE: 1856

Ala Thr Pro Glu Ala Lys Phe Asp Ser Phe Val Ala Ala Phe Thr
1               5                   10                  15

<210> SEQ ID NO 1857
<211> LENGTH: 15
<212> TYPE: PRT
<213> ORGANISM: Poa pratensis

<400> SEQUENCE: 1857

Val Ala Ala Phe Thr Glu Ala Leu Arg Ile Ile Ala Gly Val Leu
1               5                   10                  15

<210> SEQ ID NO 1858
<211> LENGTH: 15
<212> TYPE: PRT
<213> ORGANISM: Poa pratensis

<400> SEQUENCE: 1858

Val Ala Ala Phe Thr Glu Ala Leu Arg Ile Ile Ala Gly Val Leu
1               5                   10                  15

<210> SEQ ID NO 1859
<211> LENGTH: 15
<212> TYPE: PRT
<213> ORGANISM: Poa pratensis

<400> SEQUENCE: 1859

Ala Phe Lys Val Ala Ala Thr Ala Ala Asn Ala Ala Pro Ala Asn
1               5                   10                  15
```

<210> SEQ ID NO 1860
<211> LENGTH: 15
<212> TYPE: PRT
<213> ORGANISM: Poa pratensis

<400> SEQUENCE: 1860

Ala Phe Lys Val Ala Ala Thr Ala Ala Asn Ala Ala Pro Ala Asn
1               5                   10                  15

<210> SEQ ID NO 1861
<211> LENGTH: 15
<212> TYPE: PRT
<213> ORGANISM: Poa pratensis

<400> SEQUENCE: 1861

Ala Phe Lys Val Ala Ala Thr Ala Ala Asn Ala Ala Pro Ala Asn
1               5                   10                  15

<210> SEQ ID NO 1862
<211> LENGTH: 15
<212> TYPE: PRT
<213> ORGANISM: Poa pratensis

<400> SEQUENCE: 1862

Ala Phe Lys Val Ala Ala Thr Ala Ala Asn Ala Ala Pro Ala Asn
1               5                   10                  15

<210> SEQ ID NO 1863
<211> LENGTH: 15
<212> TYPE: PRT
<213> ORGANISM: Poa pratensis

<400> SEQUENCE: 1863

Ala Phe Lys Val Ala Ala Thr Ala Ala Asn Ala Ala Pro Ala Asn
1               5                   10                  15

<210> SEQ ID NO 1864
<211> LENGTH: 15
<212> TYPE: PRT
<213> ORGANISM: Poa pratensis

<400> SEQUENCE: 1864

Ala Phe Lys Val Ala Ala Thr Ala Ala Asn Ala Ala Pro Ala Asn
1               5                   10                  15

<210> SEQ ID NO 1865
<211> LENGTH: 15
<212> TYPE: PRT
<213> ORGANISM: Poa pratensis

<400> SEQUENCE: 1865

Glu Ser Thr Gly Gly Ala Tyr Asp Thr Tyr Lys Ser Ile Pro Ser
1               5                   10                  15

<210> SEQ ID NO 1866
<211> LENGTH: 15
<212> TYPE: PRT
<213> ORGANISM: Poa pratensis

<400> SEQUENCE: 1866

Ala Tyr Asp Thr Tyr Lys Ser Ile Pro Ser Leu Glu Ala Ala Val
1               5                   10                  15

<210> SEQ ID NO 1867

-continued

```
<211> LENGTH: 15
<212> TYPE: PRT
<213> ORGANISM: Poa pratensis

<400> SEQUENCE: 1867

Ala Tyr Asp Thr Tyr Lys Ser Ile Pro Ser Leu Glu Ala Ala Val
1               5                   10                  15

<210> SEQ ID NO 1868
<211> LENGTH: 15
<212> TYPE: PRT
<213> ORGANISM: Poa pratensis

<400> SEQUENCE: 1868

Ala Tyr Asp Thr Tyr Lys Ser Ile Pro Ser Leu Glu Ala Ala Val
1               5                   10                  15

<210> SEQ ID NO 1869
<211> LENGTH: 15
<212> TYPE: PRT
<213> ORGANISM: Poa pratensis

<400> SEQUENCE: 1869

Leu Glu Ala Ala Val Lys Gln Ala Tyr Ala Ala Thr Ile Ala Ala
1               5                   10                  15

<210> SEQ ID NO 1870
<211> LENGTH: 15
<212> TYPE: PRT
<213> ORGANISM: Poa pratensis

<400> SEQUENCE: 1870

Leu Glu Ala Ala Val Lys Gln Ala Tyr Ala Ala Thr Ile Ala Ala
1               5                   10                  15

<210> SEQ ID NO 1871
<211> LENGTH: 15
<212> TYPE: PRT
<213> ORGANISM: Plantago lanceolata

<400> SEQUENCE: 1871

His Ser Arg Asn Leu Ile Asn Glu Leu Ser Glu Arg Met Ala Gly
1               5                   10                  15

<210> SEQ ID NO 1872
<211> LENGTH: 15
<212> TYPE: PRT
<213> ORGANISM: Plantago lanceolata

<400> SEQUENCE: 1872

His Ser Arg Asn Leu Ile Asn Glu Leu Ser Glu Arg Met Ala Gly
1               5                   10                  15

<210> SEQ ID NO 1873
<211> LENGTH: 15
<212> TYPE: PRT
<213> ORGANISM: Plantago lanceolata

<400> SEQUENCE: 1873

His Ser Arg Asn Leu Ile Asn Glu Leu Ser Glu Arg Met Ala Gly
1               5                   10                  15

<210> SEQ ID NO 1874
<211> LENGTH: 15
<212> TYPE: PRT
```

<213> ORGANISM: Plantago lanceolata

<400> SEQUENCE: 1874

Ile Lys Leu Val Lys Ser Ser Arg Pro Asp Cys Ser Glu Ile Pro
1               5                   10                  15

<210> SEQ ID NO 1875
<211> LENGTH: 15
<212> TYPE: PRT
<213> ORGANISM: Plantago lanceolata

<400> SEQUENCE: 1875

Ile Lys Leu Val Lys Ser Ser Arg Pro Asp Cys Ser Glu Ile Pro
1               5                   10                  15

<210> SEQ ID NO 1876
<211> LENGTH: 15
<212> TYPE: PRT
<213> ORGANISM: Ambrosia trifida

<400> SEQUENCE: 1876

Met Lys Asn Ile Phe Met Leu Thr Leu Phe Ile Leu Ile Ile Thr
1               5                   10                  15

<210> SEQ ID NO 1877
<211> LENGTH: 15
<212> TYPE: PRT
<213> ORGANISM: Ambrosia trifida

<400> SEQUENCE: 1877

Met Lys Asn Ile Phe Met Leu Thr Leu Phe Ile Leu Ile Ile Thr
1               5                   10                  15

<210> SEQ ID NO 1878
<211> LENGTH: 15
<212> TYPE: PRT
<213> ORGANISM: Ambrosia trifida

<400> SEQUENCE: 1878

Met Leu Thr Leu Phe Ile Leu Ile Ile Thr Ser Thr Ile Lys Ala
1               5                   10                  15

<210> SEQ ID NO 1879
<211> LENGTH: 15
<212> TYPE: PRT
<213> ORGANISM: Ambrosia trifida

<400> SEQUENCE: 1879

Met Leu Thr Leu Phe Ile Leu Ile Ile Thr Ser Thr Ile Lys Ala
1               5                   10                  15

<210> SEQ ID NO 1880
<211> LENGTH: 15
<212> TYPE: PRT
<213> ORGANISM: Ambrosia trifida

<400> SEQUENCE: 1880

Lys Gln Glu Asp Asp Gly Leu Cys Tyr Glu Gly Thr Asn Cys Gly
1               5                   10                  15

<210> SEQ ID NO 1881
<211> LENGTH: 15
<212> TYPE: PRT
<213> ORGANISM: Ambrosia trifida

<400> SEQUENCE: 1881

Gly Lys Tyr Cys Val Cys Tyr Asp Ser Lys Ala Ile Cys Asn Lys
1               5                   10                  15

<210> SEQ ID NO 1882
<211> LENGTH: 15
<212> TYPE: PRT
<213> ORGANISM: Salsola kali

<400> SEQUENCE: 1882

Glu Lys Val Lys Ile Glu Arg Leu His Pro Tyr Ile Thr Leu Tyr
1               5                   10                  15

<210> SEQ ID NO 1883
<211> LENGTH: 15
<212> TYPE: PRT
<213> ORGANISM: Salsola kali

<400> SEQUENCE: 1883

Ala Ala Glu Phe Gly Thr Val Asp Ser Ala Thr Leu Ile Val Glu
1               5                   10                  15

<210> SEQ ID NO 1884
<211> LENGTH: 15
<212> TYPE: PRT
<213> ORGANISM: Salsola kali

<400> SEQUENCE: 1884

Ser Asp Tyr Phe Val Gly Ala Asn Leu Ile Val Ser Asn Ser Ala
1               5                   10                  15

<210> SEQ ID NO 1885
<211> LENGTH: 15
<212> TYPE: PRT
<213> ORGANISM: Salsola kali

<400> SEQUENCE: 1885

Gly Ala Asn Leu Ile Val Ser Asn Ser Ala Pro Arg Pro Asp Gly
1               5                   10                  15

<210> SEQ ID NO 1886
<211> LENGTH: 15
<212> TYPE: PRT
<213> ORGANISM: Salsola kali

<400> SEQUENCE: 1886

Glu Gly Thr Val Asp Phe Ile Phe Gly Glu Ala Arg Ser Leu Tyr
1               5                   10                  15

<210> SEQ ID NO 1887
<211> LENGTH: 15
<212> TYPE: PRT
<213> ORGANISM: Salsola kali

<400> SEQUENCE: 1887

Glu Gly Thr Val Asp Phe Ile Phe Gly Glu Ala Arg Ser Leu Tyr
1               5                   10                  15

<210> SEQ ID NO 1888
<211> LENGTH: 15
<212> TYPE: PRT
<213> ORGANISM: Salsola kali

<400> SEQUENCE: 1888

Phe Ile Phe Gly Glu Ala Arg Ser Leu Tyr Leu Asn Thr Glu Leu
1               5                   10                  15

<210> SEQ ID NO 1889
<211> LENGTH: 15
<212> TYPE: PRT
<213> ORGANISM: Salsola kali

<400> SEQUENCE: 1889

Phe Ile Phe Gly Glu Ala Arg Ser Leu Tyr Leu Asn Thr Glu Leu
1               5                   10                  15

<210> SEQ ID NO 1890
<211> LENGTH: 15
<212> TYPE: PRT
<213> ORGANISM: Salsola kali

<400> SEQUENCE: 1890

Leu Gly Arg Ala Trp Phe Glu Ala Ala Arg Val Val Phe Ser Tyr
1               5                   10                  15

<210> SEQ ID NO 1891
<211> LENGTH: 15
<212> TYPE: PRT
<213> ORGANISM: Salsola kali

<400> SEQUENCE: 1891

Phe Glu Ala Ala Arg Val Val Phe Ser Tyr Cys Asn Leu Ser Asp
1               5                   10                  15

<210> SEQ ID NO 1892
<211> LENGTH: 15
<212> TYPE: PRT
<213> ORGANISM: Salsola kali

<400> SEQUENCE: 1892

Phe Thr Ser Leu Glu Tyr Ile Glu Ala Ala Lys Trp Leu Leu Pro
1               5                   10                  15

<210> SEQ ID NO 1893
<211> LENGTH: 15
<212> TYPE: PRT
<213> ORGANISM: Salsola kali

<400> SEQUENCE: 1893

Phe Thr Ser Leu Glu Tyr Ile Glu Ala Ala Lys Trp Leu Leu Pro
1               5                   10                  15

<210> SEQ ID NO 1894
<211> LENGTH: 15
<212> TYPE: PRT
<213> ORGANISM: Salsola kali

<400> SEQUENCE: 1894

Glu Tyr Ile Glu Ala Ala Lys Trp Leu Leu Pro Pro Pro Lys Val
1               5                   10                  15

<210> SEQ ID NO 1895
<211> LENGTH: 15
<212> TYPE: PRT
<213> ORGANISM: Salsola kali

<400> SEQUENCE: 1895

Arg Thr Ile Phe Phe Asp Ala Tyr Leu Gly Thr Ser Tyr Val Ile
1               5                   10                  15

<210> SEQ ID NO 1896
<211> LENGTH: 15
<212> TYPE: PRT
<213> ORGANISM: Salsola kali

<400> SEQUENCE: 1896

Asp Ala Tyr Leu Gly Thr Ser Tyr Val Ile Val Ile Lys Glu Pro
1               5                   10                  15

<210> SEQ ID NO 1897
<211> LENGTH: 15
<212> TYPE: PRT
<213> ORGANISM: Salsola kali

<400> SEQUENCE: 1897

Lys Ile Ala Ala Glu Ile Ala Ile Ala Leu Leu Phe Leu Arg Asp
1               5                   10                  15

<210> SEQ ID NO 1898
<211> LENGTH: 15
<212> TYPE: PRT
<213> ORGANISM: Salsola kali

<400> SEQUENCE: 1898

Ile Ala Ile Ala Leu Leu Phe Leu Arg Asp Ala Lys Pro Glu Pro
1               5                   10                  15

<210> SEQ ID NO 1899
<211> LENGTH: 15
<212> TYPE: PRT
<213> ORGANISM: Salsola kali

<400> SEQUENCE: 1899

Ser Phe Gly Ile Ile Leu Leu Gln Leu Leu Thr Ala Arg Pro Pro
1               5                   10                  15

<210> SEQ ID NO 1900
<211> LENGTH: 15
<212> TYPE: PRT
<213> ORGANISM: Salsola kali

<400> SEQUENCE: 1900

Phe Asp Leu Tyr Phe Ser Met Ala Arg Gly Asn Ala Ser Leu Pro
1               5                   10                  15

<210> SEQ ID NO 1901
<211> LENGTH: 15
<212> TYPE: PRT
<213> ORGANISM: Salsola kali

<400> SEQUENCE: 1901

Val Ile Ala Glu Leu Lys Ala Ala Gly Ala Ser Thr Ile Gln Phe
1               5                   10                  15

<210> SEQ ID NO 1902
<211> LENGTH: 15
<212> TYPE: PRT
<213> ORGANISM: Salsola kali

<400> SEQUENCE: 1902

Val Thr Ala Phe Gly Phe Asp Leu Val Arg Gly Thr Lys Thr Leu
1               5                   10                  15

```
<210> SEQ ID NO 1903
<211> LENGTH: 15
<212> TYPE: PRT
<213> ORGANISM: Salsola kali

<400> SEQUENCE: 1903

Ser Leu Ala Thr Leu Gln Ser Leu Glu Ser Ile Val Gly Lys Asp
1               5                   10                  15

<210> SEQ ID NO 1904
<211> LENGTH: 15
<212> TYPE: PRT
<213> ORGANISM: Salsola kali

<400> SEQUENCE: 1904

Thr Lys Leu Asp Asp Glu Ile Lys Ser Trp Leu Ala Phe Ala Ala
1               5                   10                  15

<210> SEQ ID NO 1905
<211> LENGTH: 15
<212> TYPE: PRT
<213> ORGANISM: Salsola kali

<400> SEQUENCE: 1905

Phe Phe Ser Ala Asn Ala Ala Ala Leu Ala Ser Arg Lys Ser Ser
1               5                   10                  15

<210> SEQ ID NO 1906
<211> LENGTH: 15
<212> TYPE: PRT
<213> ORGANISM: Salsola kali

<400> SEQUENCE: 1906

Gly Phe Tyr Leu Gln Trp Ala Val His Ser Phe Arg Ile Thr Asn
1               5                   10                  15

<210> SEQ ID NO 1907
<211> LENGTH: 15
<212> TYPE: PRT
<213> ORGANISM: Alternaria alternata

<400> SEQUENCE: 1907

Ile Ala Ser Leu Phe Ala Ala Ala Gly Leu Ala Ala Ala Ala Pro
1               5                   10                  15

<210> SEQ ID NO 1908
<211> LENGTH: 15
<212> TYPE: PRT
<213> ORGANISM: Alternaria alternata

<400> SEQUENCE: 1908

Ala Ala Ala Gly Leu Ala Ala Ala Ala Pro Leu Glu Ser Arg Gln
1               5                   10                  15

<210> SEQ ID NO 1909
<211> LENGTH: 15
<212> TYPE: PRT
<213> ORGANISM: Alternaria alternata

<400> SEQUENCE: 1909

Lys Val Ser Asp Asp Ile Thr Tyr Val Ala Thr Ala Thr Leu Pro
1               5                   10                  15

<210> SEQ ID NO 1910
<211> LENGTH: 15
```

```
<212> TYPE: PRT
<213> ORGANISM: Alternaria alternata

<400> SEQUENCE: 1910

Ile Thr Tyr Val Ala Thr Ala Thr Leu Pro Asn Tyr Cys Arg Ala
1               5                   10                  15

<210> SEQ ID NO 1911
<211> LENGTH: 15
<212> TYPE: PRT
<213> ORGANISM: Alternaria alternata

<400> SEQUENCE: 1911

Gln Gly Val Ala Asp Ala Tyr Ile Thr Leu Val Thr Leu Pro Lys
1               5                   10                  15

<210> SEQ ID NO 1912
<211> LENGTH: 15
<212> TYPE: PRT
<213> ORGANISM: Alternaria alternata

<400> SEQUENCE: 1912

Val Ala Asp Ala Tyr Ile Thr Leu Val Thr Leu Pro Lys Ser Ser
1               5                   10                  15

<210> SEQ ID NO 1913
<211> LENGTH: 15
<212> TYPE: PRT
<213> ORGANISM: Alternaria alternata

<400> SEQUENCE: 1913

Ile Asn Glu Leu Ile Ala Ser Gly Ser Glu Lys Leu Ala Ser Val
1               5                   10                  15

<210> SEQ ID NO 1914
<211> LENGTH: 15
<212> TYPE: PRT
<213> ORGANISM: Alternaria alternata

<400> SEQUENCE: 1914

Gly Gly Arg Leu Ala Phe Gln Glu Phe Met Ile Val Pro Cys Glu
1               5                   10                  15

<210> SEQ ID NO 1915
<211> LENGTH: 15
<212> TYPE: PRT
<213> ORGANISM: Alternaria alternata

<400> SEQUENCE: 1915

Ala Gln Gly Lys Ala Phe Tyr Glu Ala Val Ala Lys Ala His Gln
1               5                   10                  15

<210> SEQ ID NO 1916
<211> LENGTH: 15
<212> TYPE: PRT
<213> ORGANISM: Alternaria alternata

<400> SEQUENCE: 1916

Ala Ile Val Tyr Tyr Ser Met Tyr Gly His Ile Lys Lys Met Ala
1               5                   10                  15

<210> SEQ ID NO 1917
<211> LENGTH: 15
<212> TYPE: PRT
<213> ORGANISM: Aspergillus fumigatus
```

<400> SEQUENCE: 1917

Ser Lys Lys Asp Lys Phe Val Ala Ala Asn Ala Gly Gly Thr Val
1               5                   10                  15

<210> SEQ ID NO 1918
<211> LENGTH: 15
<212> TYPE: PRT
<213> ORGANISM: Cladosporium herbarum

<400> SEQUENCE: 1918

Ala Phe Leu Leu Leu Gly Leu Ala Gly Asn Ser Ser Pro Ser Ala
1               5                   10                  15

<210> SEQ ID NO 1919
<211> LENGTH: 15
<212> TYPE: PRT
<213> ORGANISM: Cladosporium herbarum

<400> SEQUENCE: 1919

Gly Gly Arg Leu Ala Phe Gln Glu Phe Met Ile Val Pro Ser Gly
1               5                   10                  15

<210> SEQ ID NO 1920
<211> LENGTH: 15
<212> TYPE: PRT
<213> ORGANISM: Cladosporium herbarum

<400> SEQUENCE: 1920

Gln Ile Asp Ala Phe Ile Ala Asn Ala Gly Thr Ala Asp Ser
1               5                   10                  15

<210> SEQ ID NO 1921
<211> LENGTH: 15
<212> TYPE: PRT
<213> ORGANISM: Cladosporium herbarum

<400> SEQUENCE: 1921

Gly Thr Gly Ser Leu Val Ile Thr Ala Ser Met Ser Gly His Ile
1               5                   10                  15

<210> SEQ ID NO 1922
<211> LENGTH: 15
<212> TYPE: PRT
<213> ORGANISM: Cladosporium herbarum

<400> SEQUENCE: 1922

Gly Cys Ile His Met Ala Arg Ser Leu Ala Asn Glu Trp Arg Asp
1               5                   10                  15

<210> SEQ ID NO 1923
<211> LENGTH: 15
<212> TYPE: PRT
<213> ORGANISM: Cladosporium herbarum

<400> SEQUENCE: 1923

Lys Glu Leu Lys Gly Ala Tyr Val Tyr Phe Ala Ser Asp Ala Ser
1               5                   10                  15

<210> SEQ ID NO 1924
<211> LENGTH: 15
<212> TYPE: PRT
<213> ORGANISM: Penicillium chrysogenum

<400> SEQUENCE: 1924

Pro Ala Val Lys Tyr Ile Glu Pro Asp Met Ile Val Asn Ala Thr
1               5                   10                  15

<210> SEQ ID NO 1925
<211> LENGTH: 15
<212> TYPE: PRT
<213> ORGANISM: Penicillium chrysogenum

<400> SEQUENCE: 1925

Gly Ile Phe Leu Ser Val Ala Ala Gly Asn Glu Ala Glu Asn Ala
1               5                   10                  15

<210> SEQ ID NO 1926
<211> LENGTH: 15
<212> TYPE: PRT
<213> ORGANISM: Penicillium chrysogenum

<400> SEQUENCE: 1926

Lys Phe Gly Val Ala Lys Lys Ala Asn Val Tyr Ala Val Lys Val
1               5                   10                  15

<210> SEQ ID NO 1927
<211> LENGTH: 15
<212> TYPE: PRT
<213> ORGANISM: Penicillium chrysogenum

<400> SEQUENCE: 1927

Leu Asp Leu Ala Val Asn Ala Ala Val Asp Ala Gly Ile His Phe
1               5                   10                  15

<210> SEQ ID NO 1928
<211> LENGTH: 15
<212> TYPE: PRT
<213> ORGANISM: Felis catus

<400> SEQUENCE: 1928

Asp Glu Tyr Val Glu Gln Val Ala Gln Tyr Lys Ala Leu Pro Val
1               5                   10                  15

<210> SEQ ID NO 1929
<211> LENGTH: 15
<212> TYPE: PRT
<213> ORGANISM: Felis catus

<400> SEQUENCE: 1929

Gln Val Ala Gln Tyr Lys Ala Leu Pro Val Val Leu Glu Asn Ala
1               5                   10                  15

<210> SEQ ID NO 1930
<211> LENGTH: 15
<212> TYPE: PRT
<213> ORGANISM: Felis catus

<400> SEQUENCE: 1930

Asn Ala Leu Ser Val Leu Asp Lys Ile Tyr Thr Ser Pro Leu Cys
1               5                   10                  15

<210> SEQ ID NO 1931
<211> LENGTH: 15
<212> TYPE: PRT
<213> ORGANISM: Felis catus

<400> SEQUENCE: 1931

Ala Glu Thr Cys Pro Ile Phe Tyr Asp Val Phe Phe Ala Val Ala

```
1               5                  10                 15

<210> SEQ ID NO 1932
<211> LENGTH: 15
<212> TYPE: PRT
<213> ORGANISM: Felis catus

<400> SEQUENCE: 1932

Ile Phe Tyr Asp Val Phe Phe Ala Val Ala Asn Gly Asn Glu Leu
1               5                  10                 15

<210> SEQ ID NO 1933
<211> LENGTH: 15
<212> TYPE: PRT
<213> ORGANISM: Felis catus

<400> SEQUENCE: 1933

Asn Gly Asn Glu Leu Leu Leu Asp Leu Ser Leu Thr Lys Val Asn
1               5                  10                 15

<210> SEQ ID NO 1934
<211> LENGTH: 15
<212> TYPE: PRT
<213> ORGANISM: Dermatophagoides farinae

<400> SEQUENCE: 1934

Gly Ser Cys Trp Ala Phe Ser Gly Val Ala Ala Thr Glu Ser Ala
1               5                  10                 15

<210> SEQ ID NO 1935
<211> LENGTH: 15
<212> TYPE: PRT
<213> ORGANISM: Dermatophagoides farinae

<400> SEQUENCE: 1935

Phe Ser Gly Val Ala Ala Thr Glu Ser Ala Tyr Leu Ala Tyr Arg
1               5                  10                 15

<210> SEQ ID NO 1936
<211> LENGTH: 15
<212> TYPE: PRT
<213> ORGANISM: Dermatophagoides pteronyssinus

<400> SEQUENCE: 1936

Ser Cys Trp Ala Phe Ser Gly Val Ala Ala Thr Glu Ser Ala Tyr
1               5                  10                 15

<210> SEQ ID NO 1937
<211> LENGTH: 15
<212> TYPE: PRT
<213> ORGANISM: Dermatophagoides pteronyssinus

<400> SEQUENCE: 1937

Ser Gly Val Ala Ala Thr Glu Ser Ala Tyr Leu Ala Tyr Arg Asn
1               5                  10                 15

<210> SEQ ID NO 1938
<211> LENGTH: 15
<212> TYPE: PRT
<213> ORGANISM: Dermatophagoides pteronyssinus

<400> SEQUENCE: 1938

Arg Gly Ile Glu Tyr Ile Gln His Asn Gly Val Val Gln Glu Ser
1               5                  10                 15
```

<210> SEQ ID NO 1939
<211> LENGTH: 15
<212> TYPE: PRT
<213> ORGANISM: Dermatophagoides pteronyssinus

<400> SEQUENCE: 1939

Arg Glu Ala Leu Ala Gln Thr His Ser Ala Ile Ala Val Ile Ile
1               5                   10                  15

<210> SEQ ID NO 1940
<211> LENGTH: 15
<212> TYPE: PRT
<213> ORGANISM: Dermatophagoides pteronyssinus

<400> SEQUENCE: 1940

Asn Lys Ala Gly Val Arg Ile Tyr Val Asp Ile Val Leu Asn His
1               5                   10                  15

<210> SEQ ID NO 1941
<211> LENGTH: 15
<212> TYPE: PRT
<213> ORGANISM: Dermatophagoides pteronyssinus

<400> SEQUENCE: 1941

Ile Val Leu Asn His Met Thr Gly Ala Gln Ser Gly Lys Gly Thr
1               5                   10                  15

<210> SEQ ID NO 1942
<211> LENGTH: 15
<212> TYPE: PRT
<213> ORGANISM: Dermatophagoides pteronyssinus

<400> SEQUENCE: 1942

Ile Glu Phe Arg Phe Tyr Lys Glu Ile Thr Asn Val Phe Arg Gly
1               5                   10                  15

<210> SEQ ID NO 1943
<211> LENGTH: 15
<212> TYPE: PRT
<213> ORGANISM: Dermatophagoides pteronyssinus

<400> SEQUENCE: 1943

Ala Phe Met Leu Ala Trp Asn Tyr Gly Val Pro Arg Val Met Ser
1               5                   10                  15

<210> SEQ ID NO 1944
<211> LENGTH: 15
<212> TYPE: PRT
<213> ORGANISM: Dermatophagoides pteronyssinus

<400> SEQUENCE: 1944

Glu His Arg Trp Arg Glu Ile Tyr Asn Met Val Lys Phe Arg Met
1               5                   10                  15

<210> SEQ ID NO 1945
<211> LENGTH: 15
<212> TYPE: PRT
<213> ORGANISM: Dermatophagoides pteronyssinus

<400> SEQUENCE: 1945

Glu Ile Tyr Asn Met Val Lys Phe Arg Met Ile Ala Gly Gln Glu
1               5                   10                  15

<210> SEQ ID NO 1946

```
<211> LENGTH: 15
<212> TYPE: PRT
<213> ORGANISM: Dermatophagoides pteronyssinus

<400> SEQUENCE: 1946

Tyr Gln Ile Ala Phe Ser Arg Gly Asn Arg Ala Phe Ile Ala Ile
1               5                   10                  15

<210> SEQ ID NO 1947
<211> LENGTH: 15
<212> TYPE: PRT
<213> ORGANISM: Dermatophagoides pteronyssinus

<400> SEQUENCE: 1947

Ser Arg Gly Asn Arg Ala Phe Ile Ala Ile Asn Leu Gln Lys Asn
1               5                   10                  15

<210> SEQ ID NO 1948
<211> LENGTH: 15
<212> TYPE: PRT
<213> ORGANISM: Dermatophagoides pteronyssinus

<400> SEQUENCE: 1948

Tyr Val Gly His Asp Glu Phe Asp Ala Phe Val Ala Tyr His Ile
1               5                   10                  15

<210> SEQ ID NO 1949
<211> LENGTH: 15
<212> TYPE: PRT
<213> ORGANISM: Dermatophagoides pteronyssinus

<400> SEQUENCE: 1949

Phe Asp Ala Phe Val Ala Tyr His Ile Gly Ala Arg Ile Val Ser
1               5                   10                  15

<210> SEQ ID NO 1950
<211> LENGTH: 15
<212> TYPE: PRT
<213> ORGANISM: Alnus glutinosa

<400> SEQUENCE: 1950

Pro Ser Val Ile Pro Ala Ala Arg Leu Phe Lys Ala Phe Ile Leu
1               5                   10                  15

<210> SEQ ID NO 1951
<211> LENGTH: 15
<212> TYPE: PRT
<213> ORGANISM: Alnus glutinosa

<400> SEQUENCE: 1951

Ala Ala Arg Leu Phe Lys Ala Phe Ile Leu Asp Gly Asp Lys Leu
1               5                   10                  15

<210> SEQ ID NO 1952
<211> LENGTH: 15
<212> TYPE: PRT
<213> ORGANISM: Alnus glutinosa

<400> SEQUENCE: 1952

Gly Gly Ser Ile Leu Lys Ile Ser Asn Lys Phe His Thr Lys Gly
1               5                   10                  15

<210> SEQ ID NO 1953
<211> LENGTH: 15
<212> TYPE: PRT
```

-continued

<213> ORGANISM: Betula pendula

<400> SEQUENCE: 1953

Leu Glu Lys Ile Ser Asn Glu Ile Lys Ile Val Ala Thr Pro Asp
1               5                   10                  15

<210> SEQ ID NO 1954
<211> LENGTH: 15
<212> TYPE: PRT
<213> ORGANISM: Betula pendula

<400> SEQUENCE: 1954

Gly Gly Ser Ile Leu Lys Ile Ser Asn Lys Tyr His Thr Lys Gly
1               5                   10                  15

<210> SEQ ID NO 1955
<211> LENGTH: 15
<212> TYPE: PRT
<213> ORGANISM: Betula pendula

<400> SEQUENCE: 1955

Arg Thr Leu Asn Lys Ile Val Tyr Ile Lys Pro Ala Lys Asn Ile
1               5                   10                  15

<210> SEQ ID NO 1956
<211> LENGTH: 15
<212> TYPE: PRT
<213> ORGANISM: Betula pendula

<400> SEQUENCE: 1956

Ile Val Tyr Ile Lys Pro Ala Lys Asn Ile Tyr Ser Phe Asn Glu
1               5                   10                  15

<210> SEQ ID NO 1957
<211> LENGTH: 15
<212> TYPE: PRT
<213> ORGANISM: Chamaecyparis obtusa

<400> SEQUENCE: 1957

Glu Arg Ser Leu Trp Ile Ile Phe Ser Lys Asn Leu Asn Ile Lys
1               5                   10                  15

<210> SEQ ID NO 1958
<211> LENGTH: 15
<212> TYPE: PRT
<213> ORGANISM: Chamaecyparis obtusa

<400> SEQUENCE: 1958

Asn Leu Asn Ile Lys Leu Asn Met Pro Leu Tyr Ile Ala Gly Asn
1               5                   10                  15

<210> SEQ ID NO 1959
<211> LENGTH: 15
<212> TYPE: PRT
<213> ORGANISM: Chamaecyparis obtusa

<400> SEQUENCE: 1959

Asn His Phe Phe Asn His His Lys Val Met Leu Leu Gly His Ser
1               5                   10                  15

<210> SEQ ID NO 1960
<211> LENGTH: 15
<212> TYPE: PRT
<213> ORGANISM: Cupressus arizonica

```
<400> SEQUENCE: 1960

Lys Ala Leu Trp Ile Ile Phe Ser Gln Asn Met Asn Ile Lys Leu
1               5                   10                  15

<210> SEQ ID NO 1961
<211> LENGTH: 15
<212> TYPE: PRT
<213> ORGANISM: Cupressus arizonica

<400> SEQUENCE: 1961

Ile Phe Ser Gln Asn Met Asn Ile Lys Leu Gln Met Pro Leu Tyr
1               5                   10                  15

<210> SEQ ID NO 1962
<211> LENGTH: 15
<212> TYPE: PRT
<213> ORGANISM: Cupressus arizonica

<400> SEQUENCE: 1962

Glu Asp Thr Asn Ile Tyr Asn Ser Asn Glu Ala Phe Lys Val Glu
1               5                   10                  15

<210> SEQ ID NO 1963
<211> LENGTH: 15
<212> TYPE: PRT
<213> ORGANISM: Cupressus sempervirens

<400> SEQUENCE: 1963

Glu Lys Ala Leu Trp Ile Ile Phe Ser Gln Asn Met Asn Ile Lys
1               5                   10                  15

<210> SEQ ID NO 1964
<211> LENGTH: 15
<212> TYPE: PRT
<213> ORGANISM: Cupressus sempervirens

<400> SEQUENCE: 1964

Ile Ile Phe Ser Gln Asn Met Asn Ile Lys Leu Lys Met Pro Leu
1               5                   10                  15

<210> SEQ ID NO 1965
<211> LENGTH: 15
<212> TYPE: PRT
<213> ORGANISM: Cupressus sempervirens

<400> SEQUENCE: 1965

Asn Met Asn Ile Lys Leu Lys Met Pro Leu Tyr Val Ala Gly His
1               5                   10                  15

<210> SEQ ID NO 1966
<211> LENGTH: 15
<212> TYPE: PRT
<213> ORGANISM: Cupressus sempervirens

<400> SEQUENCE: 1966

Asn His Phe Phe Asn His His Lys Val Met Leu Leu Gly His Asp
1               5                   10                  15

<210> SEQ ID NO 1967
<211> LENGTH: 15
<212> TYPE: PRT
<213> ORGANISM: Quercus alba

<400> SEQUENCE: 1967
```

```
Ala Ser Val Ile Pro Pro Ala Arg Leu Phe Lys Ala Phe Val Leu
1               5                   10                  15
```

<210> SEQ ID NO 1968
<211> LENGTH: 15
<212> TYPE: PRT
<213> ORGANISM: Quercus alba

<400> SEQUENCE: 1968

```
Pro Ala Arg Leu Phe Lys Ala Phe Val Leu Asp Ser Asp Asn Leu
1               5                   10                  15
```

<210> SEQ ID NO 1969
<211> LENGTH: 15
<212> TYPE: PRT
<213> ORGANISM: Quercus alba

<400> SEQUENCE: 1969

```
Lys Ala Phe Val Leu Asp Ser Asp Asn Leu Ile Pro Lys Val Val
1               5                   10                  15
```

<210> SEQ ID NO 1970
<211> LENGTH: 15
<212> TYPE: PRT
<213> ORGANISM: Quercus alba

<400> SEQUENCE: 1970

```
Ala Ser Glu Val Phe Lys Ala Val Glu Ala Tyr Leu Val Ala His
1               5                   10                  15
```

<210> SEQ ID NO 1971
<211> LENGTH: 15
<212> TYPE: PRT
<213> ORGANISM: Dactylis glomerata

<400> SEQUENCE: 1971

```
Pro Asn Tyr Leu Ala Leu Leu Val Lys Tyr Val Asp Gly Asp Gly
1               5                   10                  15
```

<210> SEQ ID NO 1972
<211> LENGTH: 15
<212> TYPE: PRT
<213> ORGANISM: Dactylis glomerata

<400> SEQUENCE: 1972

```
Gly Ser Asp Glu Lys Asn Leu Ala Leu Ser Ile Lys Tyr Asn Lys
1               5                   10                  15
```

<210> SEQ ID NO 1973
<211> LENGTH: 15
<212> TYPE: PRT
<213> ORGANISM: Dactylis glomerata

<400> SEQUENCE: 1973

```
Asn Leu Ala Leu Ser Ile Lys Tyr Asn Lys Glu Gly Asp Ser Met
1               5                   10                  15
```

<210> SEQ ID NO 1974
<211> LENGTH: 15
<212> TYPE: PRT
<213> ORGANISM: Dactylis glomerata

<400> SEQUENCE: 1974

```
Asp Ile Tyr Asn Tyr Met Glu Pro Tyr Val Ser Lys Val Asp Pro
1               5                   10                  15
```

```
<210> SEQ ID NO 1975
<211> LENGTH: 15
<212> TYPE: PRT
<213> ORGANISM: Lolium perenne

<400> SEQUENCE: 1975

Lys Ala Ser Asn Pro Asn Tyr Leu Ala Ile Leu Val Lys Tyr Val
1               5                   10                  15

<210> SEQ ID NO 1976
<211> LENGTH: 15
<212> TYPE: PRT
<213> ORGANISM: Lolium perenne

<400> SEQUENCE: 1976

Arg Tyr Ala Asn Pro Ile Ala Phe Phe Arg Lys Glu Pro Leu Lys
1               5                   10                  15

<210> SEQ ID NO 1977
<211> LENGTH: 15
<212> TYPE: PRT
<213> ORGANISM: Lolium perenne

<400> SEQUENCE: 1977

Ile Ala Phe Phe Arg Lys Glu Pro Leu Lys Glu Cys Gly Gly Ile
1               5                   10                  15

<210> SEQ ID NO 1978
<211> LENGTH: 15
<212> TYPE: PRT
<213> ORGANISM: Lolium perenne

<400> SEQUENCE: 1978

Asp Gly Val Trp Glu Ile Lys Ser Asp Lys Pro Leu Lys Gly Pro
1               5                   10                  15

<210> SEQ ID NO 1979
<211> LENGTH: 15
<212> TYPE: PRT
<213> ORGANISM: Lolium perenne

<400> SEQUENCE: 1979

Ile Lys Ser Asp Lys Pro Leu Lys Gly Pro Phe Asn Phe Arg Phe
1               5                   10                  15

<210> SEQ ID NO 1980
<211> LENGTH: 15
<212> TYPE: PRT
<213> ORGANISM: Lolium perenne

<400> SEQUENCE: 1980

Met Arg Asn Val Phe Asp Asp Val Val Pro Ala Asp Phe Lys Val
1               5                   10                  15

<210> SEQ ID NO 1981
<211> LENGTH: 15
<212> TYPE: PRT
<213> ORGANISM: Lolium perenne

<400> SEQUENCE: 1981

Ser Asp Ala Lys Thr Leu Val Leu Asn Ile Lys Tyr Thr Arg Pro
1               5                   10                  15
```

```
<210> SEQ ID NO 1982
<211> LENGTH: 15
<212> TYPE: PRT
<213> ORGANISM: Lolium perenne

<400> SEQUENCE: 1982

Leu Trp Glu Val Lys Ser Ala Lys Pro Leu Thr Gly Pro Met Asn
1               5                   10                  15

<210> SEQ ID NO 1983
<211> LENGTH: 15
<212> TYPE: PRT
<213> ORGANISM: Lolium perenne

<400> SEQUENCE: 1983

Asn Val Phe Asp Glu Val Ile Pro Thr Ala Phe Thr Val Gly Lys
1               5                   10                  15

<210> SEQ ID NO 1984
<211> LENGTH: 15
<212> TYPE: PRT
<213> ORGANISM: Lolium perenne

<400> SEQUENCE: 1984

Leu Ile Glu Lys Ile Asn Ala Gly Phe Lys Ala Ala Val Ala Ala
1               5                   10                  15

<210> SEQ ID NO 1985
<211> LENGTH: 15
<212> TYPE: PRT
<213> ORGANISM: Lolium perenne

<400> SEQUENCE: 1985

Asp Ala Tyr Val Ala Thr Leu Thr Glu Ala Leu Arg Val Ile Ala
1               5                   10                  15

<210> SEQ ID NO 1986
<211> LENGTH: 15
<212> TYPE: PRT
<213> ORGANISM: Lolium perenne

<400> SEQUENCE: 1986

Thr Leu Thr Glu Ala Leu Arg Val Ile Ala Gly Thr Leu Glu Val
1               5                   10                  15

<210> SEQ ID NO 1987
<211> LENGTH: 15
<212> TYPE: PRT
<213> ORGANISM: Lolium perenne

<400> SEQUENCE: 1987

Asp Ser Tyr Lys Phe Ile Pro Thr Leu Val Ala Ala Val Lys Gln
1               5                   10                  15

<210> SEQ ID NO 1988
<211> LENGTH: 15
<212> TYPE: PRT
<213> ORGANISM: Lolium perenne

<400> SEQUENCE: 1988

Pro Ala Ala Ala Tyr Ala Thr Ala Thr Pro Ala Ala Ala Thr Ala
1               5                   10                  15
```

<210> SEQ ID NO 1989
<211> LENGTH: 15
<212> TYPE: PRT
<213> ORGANISM: Lolium perenne

<400> SEQUENCE: 1989

Ala Phe Lys Ile Ala Ala Thr Ala Ala Asn Ala Ala Pro Thr Asn
1               5                   10                  15

<210> SEQ ID NO 1990
<211> LENGTH: 15
<212> TYPE: PRT
<213> ORGANISM: Phalaris aquatica

<400> SEQUENCE: 1990

Pro Asn Tyr Leu Ala Leu Leu Val Lys Tyr Val Asp Gly Asp Gly
1               5                   10                  15

<210> SEQ ID NO 1991
<211> LENGTH: 15
<212> TYPE: PRT
<213> ORGANISM: Phalaris aquatica

<400> SEQUENCE: 1991

Asp Ala Phe Ile Ala Ala Leu Thr Glu Ala Leu Arg Val Ile Ala
1               5                   10                  15

<210> SEQ ID NO 1992
<211> LENGTH: 15
<212> TYPE: PRT
<213> ORGANISM: Phalaris aquatica

<400> SEQUENCE: 1992

Ala Leu Thr Glu Ala Leu Arg Val Ile Ala Gly Ala Phe Glu Val
1               5                   10                  15

<210> SEQ ID NO 1993
<211> LENGTH: 15
<212> TYPE: PRT
<213> ORGANISM: Phalaris aquatica

<400> SEQUENCE: 1993

Ala Ala Phe Lys Ile Ala Ala Thr Ala Ala Asn Ser Ala Pro Ala
1               5                   10                  15

<210> SEQ ID NO 1994
<211> LENGTH: 15
<212> TYPE: PRT
<213> ORGANISM: Phalaris aquatica

<400> SEQUENCE: 1994

Asn Asp Lys Phe Thr Val Phe Glu Gly Ala Phe Asn Lys Ala Ile
1               5                   10                  15

<210> SEQ ID NO 1995
<211> LENGTH: 15
<212> TYPE: PRT
<213> ORGANISM: Phalaris aquatica

<400> SEQUENCE: 1995

Gly Ala Tyr Glu Thr Tyr Lys Phe Ile Pro Ser Leu Glu Ala Ala
1               5                   10                  15

```
<210> SEQ ID NO 1996
<211> LENGTH: 15
<212> TYPE: PRT
<213> ORGANISM: Phalaris aquatica

<400> SEQUENCE: 1996

Tyr Lys Phe Ile Pro Ser Leu Glu Ala Ala Val Lys Gln Ala Tyr
1               5                   10                  15

<210> SEQ ID NO 1997
<211> LENGTH: 15
<212> TYPE: PRT
<213> ORGANISM: Poa pratensis

<400> SEQUENCE: 1997

Glu Pro Ile Ala Ala Tyr His Phe Asp Leu Ser Gly Lys Ala Phe
1               5                   10                  15

<210> SEQ ID NO 1998
<211> LENGTH: 15
<212> TYPE: PRT
<213> ORGANISM: Poa pratensis

<400> SEQUENCE: 1998

Gln Lys Leu Met Glu Asp Ile Asn Val Gly Phe Lys Ala Ala Val
1               5                   10                  15

<210> SEQ ID NO 1999
<211> LENGTH: 15
<212> TYPE: PRT
<213> ORGANISM: Poa pratensis

<400> SEQUENCE: 1999

Asp Ile Asn Val Gly Phe Lys Ala Ala Val Ala Ala Ala Ala Gly
1               5                   10                  15

<210> SEQ ID NO 2000
<211> LENGTH: 15
<212> TYPE: PRT
<213> ORGANISM: Poa pratensis

<400> SEQUENCE: 2000

Phe Lys Ala Ala Val Ala Ala Ala Ala Gly Ala Pro Pro Ala Asp
1               5                   10                  15

<210> SEQ ID NO 2001
<211> LENGTH: 15
<212> TYPE: PRT
<213> ORGANISM: Poa pratensis

<400> SEQUENCE: 2001

Ala Thr Pro Glu Ala Lys Phe Asp Ser Phe Val Ala Ala Phe Thr
1               5                   10                  15

<210> SEQ ID NO 2002
<211> LENGTH: 15
<212> TYPE: PRT
<213> ORGANISM: Poa pratensis

<400> SEQUENCE: 2002

Val Ala Ala Phe Thr Glu Ala Leu Arg Ile Ile Ala Gly Val Leu
1               5                   10                  15
```

```
<210> SEQ ID NO 2003
<211> LENGTH: 15
<212> TYPE: PRT
<213> ORGANISM: Poa pratensis

<400> SEQUENCE: 2003

Ala Phe Lys Val Ala Ala Thr Ala Ala Asn Ala Ala Pro Ala Asn
1               5                   10                  15

<210> SEQ ID NO 2004
<211> LENGTH: 15
<212> TYPE: PRT
<213> ORGANISM: Poa pratensis

<400> SEQUENCE: 2004

Glu Ser Thr Gly Gly Ala Tyr Asp Thr Tyr Lys Ser Ile Pro Ser
1               5                   10                  15

<210> SEQ ID NO 2005
<211> LENGTH: 15
<212> TYPE: PRT
<213> ORGANISM: Poa pratensis

<400> SEQUENCE: 2005

Ala Tyr Asp Thr Tyr Lys Ser Ile Pro Ser Leu Glu Ala Ala Val
1               5                   10                  15

<210> SEQ ID NO 2006
<211> LENGTH: 15
<212> TYPE: PRT
<213> ORGANISM: Poa pratensis

<400> SEQUENCE: 2006

Leu Glu Ala Ala Val Lys Gln Ala Tyr Ala Ala Thr Ile Ala Ala
1               5                   10                  15

<210> SEQ ID NO 2007
<211> LENGTH: 15
<212> TYPE: PRT
<213> ORGANISM: Salsola kali

<400> SEQUENCE: 2007

Glu Gly Thr Val Asp Phe Ile Phe Gly Glu Ala Arg Ser Leu Tyr
1               5                   10                  15

<210> SEQ ID NO 2008
<211> LENGTH: 15
<212> TYPE: PRT
<213> ORGANISM: Salsola kali

<400> SEQUENCE: 2008

Phe Thr Ser Leu Glu Tyr Ile Glu Ala Ala Lys Trp Leu Leu Pro
1               5                   10                  15
```

EPITOPES FROM ALLERGEN PROTEINS AND METHODS AND USES FOR IMMUNE RESPONSE MODULATION

RELATED APPLICATION INFORMATION

This application is a continuation of U.S. application Ser. No. 14/376,757, filed Aug. 5, 2014, which is a U.S. National Phase of PCT/US2013/025201, filed Feb. 7, 2013, which claims priority to U.S. provisional application Ser. No. 61/596,166, filed Feb. 7, 2012, and U.S. provisional application Ser. No. 61/642,372, filed May 3, 2012, all applications of which are expressly incorporated herein by reference in their entirety.

GOVERNMENT SUPPORT

This invention received government support from the National Institutes Health contract NIAIDHHSN272200700048C and grant U19AI100275. The government has certain rights in the invention.

SEQUENCE LISTING

The instant application contains a Sequence Listing which has been submitted in ASCII format via EFS-Web and is hereby incorporated by reference in its entirety. Said ASCII copy, created on Feb. 6, 2013, is named 051501-0420333_SL.txt and is 405,771 bytes in size.

INTRODUCTION

Allergic reactions to common environmental allergens are associated with serious clinical manifestations, such as rhinitis and asthma, translating into high morbidity and societal costs. Furthermore, the incidence and prevalence of allergic disease is constantly rising. Current treatments for allergic disease are not fully satisfactory and, coincidentally, understanding of the fundamental aspects of allergic disease remains incomplete (1, 2).

Initiation and maintenance of allergic disease is due to a complex series of molecular events, including both innate and adaptive immunity. In terms of adaptive immunity, IgE is of particular importance. Its cross-linking by antigen is a main cause of the release of histamine and other mediators, and subsequent clinical manifestations of an allergic response. In fact, IgE reactivity is utilized to define the particular allergens contained in a given allergen source. However, in addition to IgE responses, T cells also vitally contribute to allergic disease. This contribution may be indirect, by promoting the production of IgE and the differentiation of eosinophils, or direct, through the release of various pro-inflammatory cytokines, such as IL-5, which promotes eosinophilic inflammation. A possible beneficial role of regulatory T cells (Tregs), resulting in suppression of allergic reactions, has also been indicated by several studies. Knowledge of the role of antigen specific T cells in allergic reactions in humans is limited, and detailed studies are hampered by a relative paucity of knowledge relating to the epitopes recognized by allergen-specific T cells.

Although there are reports of epitopes recognized by human T cells, for many allergen systems the information is either fragmentary or lacking altogether. Responses to complex allergens in humans are very heterogeneous and involve recognition of a large number of epitopes (3-18). At the same time, the most dominant and prevalent responses encompass a significant fraction of the response, and these dominant epitopes can be predicted on the basis of their capacity to bind, and be recognized in the context of, multiple HLA DR, DP and DQ allelic variants (3).

As disclosed herein, a large panel of allergen proteins derived from 28 common allergen sources, which included fungi (*Alternaria, Aspergillus, Cladosporuim* and *Penicillium*), trees (Alder, Ash, Birch, Black Walnut, Cypress, Juniper, Oak and Palm), grasses (Bermuda, Canary, Kentucky Blue, Orchard, Rye and Sweet Vernal), weeds (English Plantain, Giant Ragweed, Mugwort, Russian Thistle, and Western Ragweed) and various indoor allergens (American Cockroach, Cat dander, Dog dander and Dust Mites) was probed. Over 250 different antigenic regions were identified and provide the first actual epitope data for several allergen sources. As also disclosed herein, T cell responses to the allergens previously defined on the basis of IgE reactivity account for a variable, and in many cases a surprisingly small, fraction of T cell responses, suggesting that several antigens involved in T cell recognition are yet to be described.

SUMMARY

A panel of 133 allergens derived from 28 different sources, including fungi, trees, grasses, weeds and indoor allergens, was surveyed utilizing prediction of HLA class II binding peptides and ELISPOT assays with PBMC from allergic donors, resulting in the identification of 257 T cell epitopes. More than 90% of the epitopes were novel, and for 14 allergen sources were the first ever identified. The epitopes identified in the different allergen sources summed up to a variable fraction of the total extract response. In cases of allergens where the identified T cell epitopes accounted for a minor fraction of the extract response, fewer known protein sequences were available, suggesting that for "low epitope coverage" allergen sources, additional allergen proteins remain to be identified. IL-5 and IFN-γ responses were measured as prototype Th2 and Th1 responses, respectively. While in some cases (e.g., Orchard Grass, *Alternaria*, Cypress, and Russian Thistle) IL-5 production greatly exceeded IFN-γ, in others (e.g., *Aspergillus, Penicillum*, and Alder) the production of IFN-γ exceeded IL-5. Thus, different allergen sources are differentially polarized in terms of their capacity to recall production of Th1 versus Th2 associated lymphokines, and are associated with variable polarization of the responding T cells.

Disclosed herein is the most comprehensive survey of human allergen derived T cell epitopes. These epitopes can be used to characterize T cell responsiveness, T cell phenotype/T cell PLASTICITY as a function of seasonality, or as a result of SIT treatment or varying disease severity (asthma or rhinitis). In addition, these epitopes of allergens can be used in various clinical applications, for example, to modulate a T cell response or activity, to elicit, stimulate, induce, promote, increase or enhance an anti-allergen immune response, and to decrease, inhibit, suppress or reduce an anti-allergen immune response.

In accordance with the invention, provided are proteins and peptides that include, consist of or consist essentially of an amino acid sequence set forth in Table 7 (SEQ ID NOs:1,412-1,906, respectively, in order of appearance), or a variant thereof or derivative thereof. In accordance with the invention, also provided are proteins and peptides that include, consist of or consist essentially of an amino acid sequence set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance), or a variant or derivative thereof.

Proteins and peptides include subsequences, portions, homologues, variants, and derivatives of an amino acid sequence set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). In particular aspects, a subsequence, portion, homologue, variant or derivative is: a peptide of up to 30 amino acids in length and which comprises said amino acid sequence set forth in Table 7 (SEQ ID NOs:1,412-1,906, respectively, in order of appearance).). In other particular aspects, a subsequence, portion, homologue, variant or derivative is: a peptide from 7 to 30 amino acids in length, wherein at least 7 contiguous amino acids have at least 75% identity to at least 7 contiguous amino acids of said said amino acid sequence set forth in Table 7 (SEQ ID NOs:1, 412-1,906, respectively, in order of appearance).

In further embodiments, a protein or peptide does not consist of the sequence of Der f 1, Der f 2, Der p 1 and Der p 2 set forth in Table 7 (SEQ ID NOs:1,412-1,906, respectively, in order of appearance). In other embodiments, a protein or peptide is derived from a house dust mite allergen (e.g., an amino acid sequence of Der f 10 (SEQ ID NOs: 568-570), Der f 11 (SEQ ID NO:1571), Der f 13 (SEQ ID NOs:1572-1575), Der f 14 (SEQ ID NO:1576), Der f 16 (SEQ ID NOs:1577-1584), Der f 18 (SEQ ID NOs:1585-1586), Der p 3 (SEQ ID NOs:1609-1614), Der p 4 (SEQ ID NOs:1615-1646), Der p 5 (SEQ ID NO:647), Der p 9 (SEQ ID NOs:1648-1650) or Der p 14 (SEQ ID NOs:1604-1607) as specified in Table 7.

Proteins and peptides include allergen or antigen, and subsequences, portions, homologues, variants, and derivatives thereof. Proteins and peptides also include an amino acid sequence, variant or derivative thereof that elicits, stimulates, induces, promotes, increases or enhances an anti-allergen immune response. Proteins and peptides further include an amino acid sequence, variant or derivative thereof decreases, inhibits, suppresses or reduces an anti-allergen immune response (e.g., a T cell response or production of IgE antibody, stimulated, induced, increased or enhanced production of a lymphokine). Proteins and peptides moreover include an amino acid sequence, variant or derivative thereof that modulates a Th2 immune response. Proteins and peptides additionally include an amino acid sequence, variant or derivative thereof modulates production of a lymphokine or cytokine by a cell. Proteins and peptides still further include an amino acid sequence, variant or derivative thereof desensitizes, or improves, increases, or induces immunological tolerance of a subject to the allergen (e.g., to which the subject has been sensitized or is hypersensitive).

Proteins and peptides still moreover include an amino acid sequence, variant or derivative thereof modulates production of IL-5 (interleukin-5), IL-4 (interleukin-4), IL-10 (interleukin-10), IL-13 (interleukin-13), IL-17 (interleukin-17), or IFN-γ (interferon-gamma). Proteins and peptides yet additionally include an amino acid sequence, variant or derivative thereof increases, induces, elicits, or stimulates a Th2 immune response; increases, induce, elicits or stimulates production of a lymphokine by a cell; or increases, induces, elicits or stimulates production of IL-5 (interleukin-5), IL-4 (interleukin-4), IL-10 (interleukin-10), IL-13 (interleukin-13), IL-17 (interleukin-17), or IFN-γ (interferon-gamma). Such production can optionally be detected by an immunoassay, or is determined by contacting peripheral blood mononuclear cells (PBMC), such as PBMC's obtained from a subject allergic to an allergen or an organism from which the protein or peptide derives, with the protein or peptide followed by an immunoassay.

As disclosed herein, certain proteins and peptides include, consist of or consist essentially of an allergen or antigen. In particular aspects, an allergen or antigen is derived from or produced by Alder, *Alternaria* rot fungus, American cockroach, Dust mite, Ash, *Aspergillus fumigatus*, Bermuda grass, Birch, Black Walnut, Canary grass, Cat, *Cladosporium herbarum*, Common cypress, Cypress, Palm, Dog, English plantain, Giant ragweed, Japanese cypress, Kentucky blue grass, *Lolium perenne*, Mugwort weed, Orchard grass, *Penicillium chrysogenum*, Prickly juniper, Russian thistle, Rye grass, Sweet vernal grass, Western Ragweed or White oak.

As disclosed herein, in certain embodiments proteins and peptides have a length in a range of about 5-10, 10-15, 15-20, 20-25, 25-30, 30-35, 35-40, 45-50, 50-60, 60-70, 70-80, 90-100, 100-125, 125-150, 150-175, 175-200, 200-250, 250-300, or more amino acid residues. In other embodiments, proteins and peptides have a length in a range of up to 25 amino acids in length, or from about 7 to 20; 8 to 30; 8 to 25; 8 to 20; 9 to 30; 9 to 25; 9 to 20; 10 to 30; 10 to 25; 10 to 30 amino acid residues.

Proteins and peptides include isolated and purified forms. Proteins and peptides also include those immobilized on a substrate, as well as amino acid sequences, subsequences, portions, homologues, variants, and derivatives immobilized on a substrate.

Proteins and peptides can be included in compositions, for example, a pharmaceutical composition. In particular embodiments, a pharmaceutical composition is suitable for specific or non-specific immunotherapy, or is a vaccine composition Isolated nucleic acid (including isolated nucleic acid) encoding the proteins and peptides are also provided. Cells expressing a protein or peptide are further provided. Such cells include eukaryotic and prokaryotic cells, such as mammalian, insect, fungal and bacterial cells.

Methods and uses and medicaments of proteins and peptides of the invention are included. Such methods, uses and medicaments include modulating immune activity of a cell against an allergen; and desensitizing, inducing, eliciting, increasing or improving in the cell immunological tolerance to an allergen. In particular embodiments, a method or use includes contacting a cell with an amount of the protein or peptide of any one of the above-mentioned embodiments, sufficient to modulate the immune activity of the cell against the allergen (e.g., against an allergen from which the peptide or protein derives), or administering to a subject an allergen from which the peptide or protein derives in order to desensitize, induce, elicit, increase or improve immunological tolerance to the allergen or to modulate an immune response against an allergen in a subject (e.g., an allergen from which the peptide or protein derives).

Such methods, uses and medicaments also include reducing risk or providing a subject protection against an allergic reaction, allergic response, allergic disorder or allergic disease. In one embodiment, a method or use includes administering to the subject an amount of the protein or peptide sufficient to reduce risk or provide the subject with protection against the allergic reaction, allergic response, allergic disorder or allergic disease. Non-limiting examples of an allergic reaction or allergic response include allergic alveolitis, allergic bronchopulmonary aspergillosis, allergic conjunctivitis, allergic coryza, allergic dermatitis, allergic vasculitis, and allergic rhinitis.

Such methods, uses and medicaments further include treating an allergic reaction, allergic response, allergic disorder or allergic disease. In one embodiment, a method or use includes administering to the subject an amount of the protein or peptide, sufficient to treat the subject for the allergic response, allergic disorder or allergic disease.

In such methods, uses and medicaments, apeptide or protein can be derived from or based upon the allegen or can be derived from or based upon an allergen originating from the same organism as the allergen. More particularly, for example, a protein or peptide can be derived from or based upon an allergen causing the allergic reaction, allergic response, allergic disorder or allergic disease or said peptide derives from an allergen belonging to the same organism as the allergen causing said allergic reaction, allergic response, allergic disorder or allergic disease. Additionally, for example, a protein or peptide can be based upon or derived from an amino acid sequence set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance), or a variant or derivative thereof.

In various embodiments, a method or use desensitizes or induces, elicits, increases or improves immunological tolerance of a subject to an allergen of an organism or product of an organism in Table 1, Table 2, Table 3 or Table 4. In various other embodiments, a method or use desensitizes or induces, elicits, increases or improves immunological tolerance of a subject to an amino acid sequence set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1, 907-2,008, respectively, in order of appearance), or a variant or derivative thereof.

As set forth herein a protein, peptide, method, use or medicament can include administration or delivery by any means, systemically, regionally or locally. In particular aspects, a protein or peptide is administered cutaneously, subcutaneously, epicutaneously, intracutaneously, intramuscularly, intravenously, orally, mucosally, by inhalation or nasally. As also set forth herein a protein, peptide, method, use or medicament can include repeatedly contacting a cell with, or administering to a subject, the protein or peptide, multiple times.

Proteins and peptides can be used in diagnostic and detection methods and uses. In one embodiment, detecting an allergic response, or diagnosing an allergy in a subject, a method or use includes contacting a cell from the subject (which may be an ex vivo or in vivo cell) with a protein or peptide as set forth herein; and determining if the protein or peptide modulates an immune response or activity from the contacted cell. If the protein or peptide modulates an immune response or activity from the contacted cell (which may be an ex vivo or in vivo cell) detects an allergic response or indicates that the subject has an allergic response or an allergy. In particular aspects, modulation of immune response or activity is determined by assaying for a hypersensitive reaction or response, such as a cutaneous immunological hypersensitive reaction.

Subjects in accordance with invention include mammals, such as humans. In particular embodiments, a subject has exhibited a symptom of, or suffers from, an allergic reaction, allergic response, allergic disorder or allergic disease. In more particular embodiments, a subject has had an allergic reaction or allergic response to an allergen derived from or produced by Alder, *Alternaria* rot fungus, American cockroach, Dust mite, Ash, *Aspergillus fumigatus*, Bermuda grass, Birch, Black Walnut, Canary grass, Cat, *Cladosporium herbarum*, Common cypress, Cypress, Palm, Dog, English plantain, Giant ragweed, Japanese cypress, Kentucky blue grass, *Lolium perenne*, Mugwort weed, Orchard grass, *Penicillium chrysogenum*, Prickly juniper, Russian thistle, Rye grass, Sweet vernal grass, Western Ragweed or White oak. In further particular embodiments, a subject has had an allergic reaction or allergic response to an amino acid sequence set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance), or a variant or derivative thereof; or has had an allergic reaction or allergic response to a protein or peptide as set forth herein.

DETAILED DESCRIPTION

Figure 1:
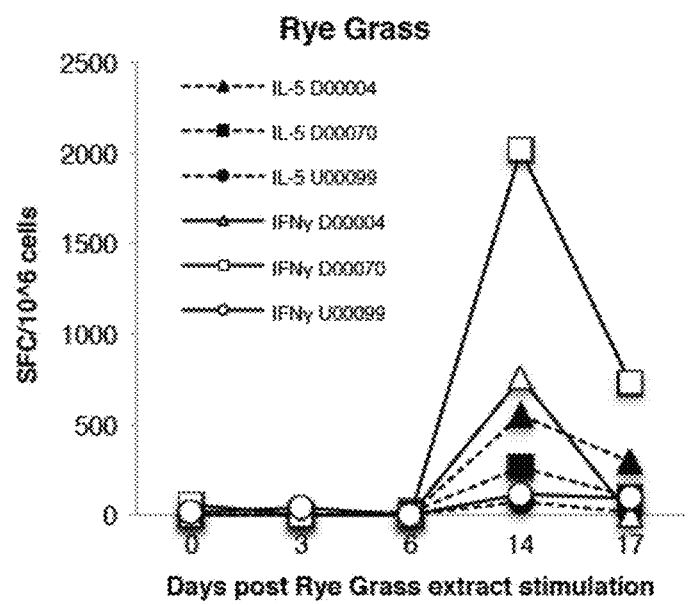
FIG. 1 shows that IFN-γ and IL-5 responses are optimally detected on day 14. IFN-γ and IL-5 responses to Rye Grass or *Alternaria* extract, in three correspondingly allergic donors each, were measured in ELISPOT assays on days 0, 3, 6, 14 and 17. The doses of individual extracts used for in vitro stimulation were chosen on the basis of initial dose titration studies, and were as shown in Table 6.
Figure 1:
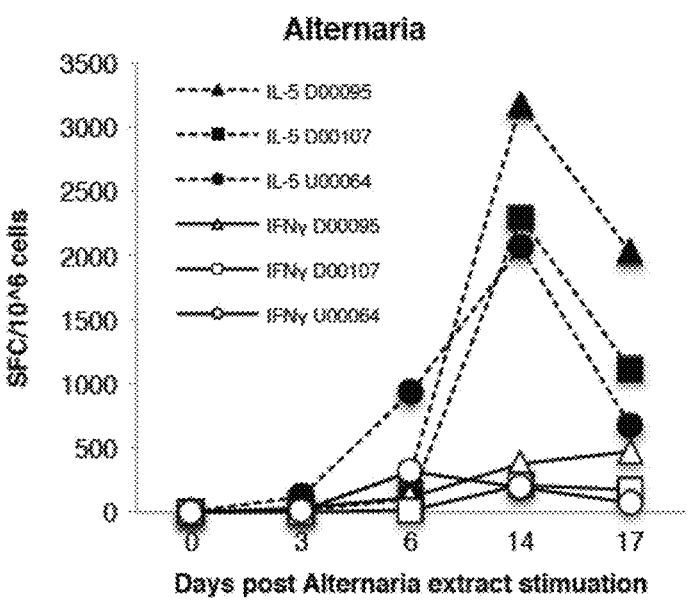

Thus, in accordance with the invention, there are provided proteins and peptides, or a subsequence, portion, homologue, variant or derivative thereof. In particular embodiments, proteins and peptides, subsequences, portions, homologues, variants or derivatives thereof are derived from or are based upon the amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1, 907-2,008, respectively, in order of appearance). Invention proteins and peptides, subsequences, portions, homologues, variants or derivatives thereof are useful for among other things in the methods and uses described herein.

In particular embodiments, the peptide consist of or consist essentially of an amino acid sequence of Table 7 (SEQ ID NOs:1,412-1,906, respectively, in order of appearance), Table 5 (SEQ ID NOs:1-1,411, respectively, in order of appearance), Table 8 (SEQ ID NOs:1,907-2,008, respectively, in order of appearance), or a variant thereof or derivative thereof. The variant or derivative may be a peptide of up to 30 amino acids in length which comprises said amino acid sequence set forth in Table 7 (SEQ ID NOs:1,412-1,906, respectively, in order of appearance), Table 5 (SEQ ID NOs:1-1,411, respectively, in order of appearance), Table 8 (SEQ ID NOs:1,907-2,008, respectively, in order of appearance). In other particular aspects, a variant is a peptide from 7 to 30 amino acids in length, wherein at least 7 contiguous amino acids have at least 75% identity, such as at least 80% or 85% identity, to at least 7 contiguous amino acids of said amino acid sequence set forth in Table 7 (SEQ ID NOs:1,412-1,906, respectively, in order of appearance), Table 5 (SEQ ID NOs:1-1,411, respectively, in order of appearance), Table 8 (SEQ ID NOs:1, 907-2,008, respectively, in order of appearance).

In still other embodiments, said variant peptide is up to 25 amino acids in length, such as up to 24, 23, 22, 21, 20, 19 or 19 amino acids in length. In particularly, said variant peptide is a peptide of 7 to 25 amino acids in length, such as 7 to 20; 8 to 30; 8 to 25; 8 to 20; 9 to 30; 9 to 25; 9 to 20; 10 to 30; 10 to 25; 10 to 20 amino acids in length and, wherein at least 7 contiguous amino acids have at least 75% identity, such as at least 80% or 85% identity, to at least 7 contiguous amino acids of said amino acid sequence set forth in Table 7 (SEQ ID NOs:1,412-1,906, respectively, in order of appearance), Table 5 (SEQ ID NOs:1-1,411, respectively, in order of appearance), Table 8 (SEQ ID NOs:1, 907-2,008, respectively, in order of appearance). In other embodiments, the variant peptide has at least 8, 9 or 10 amino acids having at least 75% (such as at least 80% or 85%) identity or homology to at least 8, 9, or 10 contiguous amino acids, respectively of said corresponding amino acid sequence.

In particular embodiments, a protein or peptide comprises, consists of or consists essentially of an amino acid sequence of Der f 10 (SEQ ID NOs:568-570), Der f 11 (SEQ ID NO:1571), Der f 13 (SEQ ID NOs:1572-1575), Der f 14 (SEQ ID NO:1576), Der f 16 (SEQ ID NOs:1577-1584), Der f 18 (SEQ ID NOs:1585-1586), Der p 3 (SEQ ID NOs:1609-1614), Der p 4 (SEQ ID NOs:1615-1646), Der p 5 (SEQ ID NO:647), Der p 9 (SEQ ID NOs:1648-1650) or Der p 14 (SEQ ID NOs:1604-1607) as specified in Table 7.

In still other particular embodiments, a protein or peptide does not consist of the sequence of the peptide does not consist of the sequence of Alt a 6 (SEQ ID NO:1455, Asp f 1 (SEQ ID NO:1466), Fel d 1 1 (SEQ ID NOs:1531, 1532, 1533, 1534, 1535, 1536, 1537, 1538), Fel d 1 2 (SEQ ID NOs:1539, 1540, 1541, 1542, 1543, 1544, 1545, 1546, 1547, 1548, 1549, 1550, 1551), Can f 3 (SEQ ID NOs:1557), Der f 1 (SEQ ID NOs:1562, 1563, 1564, 1565), Der f 2 (SEQ ID NO:1587), Der p1 (SEQ ID NOs:1591, 1593, 1594, 1595, 1596, 1597, 1598, 1599, 1600, 1601, 1602, 1603), Der p 2 (SEQ ID NO:1608), Aln g 1 (SEQ ID NOs:1653, 1654, 1655), Bet v 1 (SEQ ID NOs:1656, 1657, 1658, 1659, 1660, 1661, 1662, 1663, 1664), Bet v 2 (SEQ ID NO:1665), Cha o 1 (SEQ ID NOs:1678, 1679, 1680, 1681, 1682, 1683, 1684), Cup a 1 (SEQ ID NOs.: 1689, 1691, 1692), Cup s 1 (SEQ ID NOs.: 1700, 1701), Jun o 4 (SEQ ID NO:1710), Ant o 1 (SEQ ID NO:1743), Lol p 1 (SEQ ID NOs:1765, 1766, 1767, 1768), Lol p 11 (SEQ ID NO:1770), Lol p 5 1 (SEQ ID NOs:1793, 1794, 1795, 1796, 1797, 1798, 1802, 1803, 1804, 1805, 1807, 1808, 1809, 1811, 1812), Lol p 5 2 (SEQ ID NOs:1815, 1816, 1817, 1818, 1819), Pha a 1 (SEQ ID NO:1824), Pha a 5 (SEQ ID NOs:1831, 1833, 1836), Poa p 1 (SEQ ID NOs:1842, 1844), Poa p 5 (SEQ ID NOs:1845, 1846, 1847, 1848, 1849, 1850, 1851, 1852, 1853, 1854, 1855, 1856, 1859, 1860, 1861, 1862, 1863, 1864, 1865, 1866, 1867, 1868, 1869, 1870) or Amb t 5 (SEQ ID NO:1881) as set forth in Table 7.

As used herein, an "antigen" refers to a substance, including but not limited to a protein or peptide that elicits, induces, stimulates, promotes or enhances an immune response when administered to a subject. An immune response elicited by an antigen may include, but is not limited to, a B cell or a T cell response. An immune response can include a cellular response with a particular pattern of lymphokine/cytokine production (e.g., Th1, Th2), a humoral response (e.g., antibody production), or a combination thereof, to a particular antigen. For example, if a subject previously exposed to an allergen (i.e., is sensitized or is hypersensitive) comes into contact with the allergen again, allergic asthma may develop due to a Th2 response characterized by an increased production of type 2 cytokines (e.g., IL-4, IL-5, IL-9, and/or IL-13) secreted by CD4+ T lymphocytes.

As used herein an "epitope" refers to a region or part of an antigen that elicits an immune response when administered to a subject. In particular embodiments, an epitope may be comprised of a region or part of a protein or peptide set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). In particular aspects, an epitope is a T cell epitope, i.e., an epitope that elicits, stimulates, induces, promotes, increases or enhances a T cell activity, function or response.

An antigen, epitope, allergen, or composition thereof can modulate an undesired or abnormal inflammatory response. An antigen, epitope, allergen, or composition thereof as described herein may alter the Th2 response by, for example, shifting the immune response toward a Th1 phenotype that is less damaging. That is, an altered (or modulated) immune response can decrease, inhibit, suppress, or reduce sensitivity (desensitize) to an antigen, epitope, or allergen, or against inflammatory responses (e.g., allergy, asthma, rash, wheezing, coughing, eye irritation, etc.) caused by an antigen, epitope, or allergen.

Accordingly, non-limiting examples of antigens, allergens are peptides and proteins having defined amino acid sequences and which comprise T cell epitopes, i.e., elicit, stimulate, induce, promote, increase or enhance a T cell response or activity. Antigens and allergens can be analyzed to determine whether they include at least one T cell epitope using any number of assays (e.g. T cell proliferation assays, lymphokine secretion assays, T cell non-responsiveness studies, etc.).

The term "allergen" refers to an antigen which elicits, induces, stimulates, or enhances an immune response by a cell or the immune system of an exposed animal (e.g., human). An antigen is an allergen when the specific immune response is the development of enhanced sensitivity or a hypersensitivity to the antigen, but the antigen itself is not typically innately harmful. An allergen is therefore a particular type of antigen that can cause development of enhanced or increased sensitivity or hypersensitivity in a subject. For example, an allergen can elicit production of IgE antibodies in predisposed subjects. Other examples of responses elicited by allergens include T cell responses or activity, such as production of a lymphokine, cytokine, or effector function on other cells. Responses caused by allergens are also described, for example, in Mol. Biol. of Allergy and Immunology, ed. R. Bush, Immunology and Allergy Clinics of North American Series (August 1996). Although the terms "allergen" and "antigen" have a different meaning, reference to "allergen" herein includes reference to "antigen" and reference to "antigen" herein includes reference to "allergen."

Typically, allergens are organic substances, such as proteins, peptides, nucleotides, carbohydrates, lipids, fats, nucleic acid, and combinations or mixtures thereof. Allergen(s) as used herein include, but are not limited to a specific allergen protein, mixture of allergen proteins, an extract of an allergen, chemically or genetically manufactured allergen, or any combination thereof. Therefore, an "allergen" refers to allergen from plants (trees, weeds, crops, flowers, turf, grasses, etc., or parts thereof such as seeds, nuts, bark, pollen, leaves, etc.), or living or dead organisms (animals, bacterium, insects, mold, fungi, etc.) or products of organisms.

In certain embodiments, the proteins, peptides, subsequences, portions, homologues, variants and derivatives thereof, described herein stimulate, induce, promote, increase or enhance an immune response (for example, all or a part of a sequence in any of Table 5 (SEQ ID NOs:1-1, 411), Table 6, Table 7 (SEQ ID NOs:1,412-1,906) or Table 8 (SEQ ID NOs:1,907-2,008)). In particular embodiments, a protein or peptide is a T cell antigen, allergen or epitope. In further particular embodiments, a protein or peptide, or a subsequence, portion, homologue, variant or derivative thereof, elicits, stimulates, promotes, induces or enhances a T cell response, which may include but is not limited to a Th2 cell response.

As used herein, the term "immune response" includes T cell (cellular) mediated and/or B cell (humoral) mediated immune responses. Exemplary immune responses include T cell responses, e.g., lymphokine production, cytokine production and cellular cytotoxicity. T-cell responses include Th1 and/or Th2 responses. In addition, the term immune response includes responses that are indirectly effected by T cell activation, e.g., antibody production (humoral responses) and activation of cytokine responsive cells, e.g., eosinophils, macrophages. Immune cells involved in the immune response include lymphocytes, such as T cells (CD4+, CD8+, Th1 and Th2 cells) and B cells; antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer (NK) cells; myeloid cells, such as macrophages, eosinophils, mast cells, basophils, and granulocytes.

As set forth herein, a particular immunoglobulin (Ig) isotype may be produced in response to an antigen (allergen). For example, an "IgG antigen" refers to an antigen that induces an IgG antibody response. Likewise, an "IgE antigen" refers to an antigen that induces an IgE antibody response; an "IgA antigen" refers to an antigen that induces an IgA antibody response, and so forth. In certain embodiments, such an immunoglobulin (Ig) isotype produced in response to an antigen may also elicit production of other isotypes. For example, an IgG antigen may induce an IgG antibody response in combination with one more of an IgE, IgA, IgM or IgD antibody response. Accordingly, in certain embodiments, an IgG antigen may induce an IgG antibody response without inducing an IgE, IgA, IgM or IgD antibody response.

The invention encompasses methods and uses for reducing, decreasing, preventing the development of sensitization or hypersensitization to an antigen(s) or allergen(s). Accordingly, in other embodiments, a protein or peptide, subsequence, portion, homologue, variant or derivative thereof, decreases, inhibits, suppresses or reduces a T cell response, which may include but is not limited to a Th2 cell response. In certain embodiments, the T cell response is an anti-allergen immune response.

In accordance with another aspect of the invention there are provided a protein or peptide, a subsequence, portion, homologue, variant or derivative thereof, wherein the protein or peptide elicits, stimulates, induces, promotes, increases or enhances an anti-allergen immune response (for example, all or a part of a sequence in any of Table 5 (SEQ ID NOs:1-1,411), Table 6, Table 7 (SEQ ID NOs:1,412-1, 906) or Table 8 (SEQ ID NOs:1,907-2,008)). In another aspect, there are provided a protein or peptide, subsequence, portion, homologue, variant or derivative thereof, wherein the protein or peptide decreases, reduces, inhibits, suppresses or disrupts an anti-allergen immune response.

As will be understood by a person of skill in the art, a protein or a subsequence, portion, homologue, variant or derivative thereof as described herein, may elicit, stimulate, induce, promote, increase or enhance certain elements of an anti-allergen immune response while decreasing, reducing, inhibiting, suppressing or reducing other elements of the anti-allergen response, either contemporaneously or sequentially. In one non-limiting example, a protein or a subsequence, portion, homologue, variant or derivative thereof may elicit, stimulate, induce, promote, increase or enhance proliferation of regulatory T cells while decreasing, reducing, inhibiting, suppressing or reducing production of proinflammatory lymphokines/cytokines.

An "anti-allergen," "anti-protein," or "anti-peptide immune response" refers to an immune response that is particular or specific for the protein or peptide, e.g., allergen. In such instances, the response is specifically triggered (elicited, stimulated, increased, induced, or promoted) by the protein or peptide, e.g., allergen. Although "anti-allergen" immune response is specifically triggered by a given allergen, the immune response itself can be characterized by general features of immune responses, such as T cell (cellular) and/or B cell (humoral) immune responses, as set forth herein.

As disclosed herein, a protein, peptide, subsequence, portion, homologue, variant or derivative thereof, may elicit, stimulate, induce, promote, increase or enhance immunological tolerance to an antigen, including an allergen. In certain embodiments, a protein, peptide, subsequence, portion, homologue, variant or derivative thereof, described herein may elicit, stimulate, induce, promote, increase or enhance immunological tolerance to an allergen. Thus in certain embodiments a protein, peptide, subsequence, portion, homologue, variant or derivative thereof, described herein may be effective in use or treatment (e.g., therapeutic) of an allergic reaction or allergic immune response, including but not limited to an allergic response following a secondary or subsequent exposure of a subject to an antigen or allergen. In particular embodiments, immunological tolerance elicited, stimulated, induced, promoted, increased or enhanced from use or administration of the a protein, peptide, subsequence, portion, homologue, variant or derivative thereof, may involve modulation of T cell activity, including but not limited to CD4+ T cells, CD8+ T cells, Th1 cells, Th2 cells and regulatory T cells (Tregs). For example, immunological tolerance elicited, stimulated, induced, promoted, increased or enhanced from use or administration of a protein, peptide, subsequence, portion, homologue, variant or derivative thereof, may involve modulation of the production or activity of pro-inflammatory or anti-inflammatory lymphokines/cytokines produced by T cells. Thus, in accordance with certain aspects of the invention, there are provided proteins, peptides, subsequences, portions, homologues, variants and derivatives thereof, that elicits, stimulates, induces, promotes, increases or enhances immunological tolerance to an antigen or allergen.

An allergic reaction refers to a local or general reaction in a subject following contact with a specific antigen (e.g., allergen) to which the subject had been previously exposed and had become sensitized. The immunologic interaction of antigen (e.g., allergen) with sensitized lymphocytes (T cells) and/or antibody can give rise to inflammation and tissue damage. An allergy is an undesirable immune response or reaction that can therefore produce damage to self-tissues and cells, usually through inflammatory reactions.

One non-limiting example of an allergy is asthma. Asthma, which can be extrinsic or allergic asthma (also referred to as reactive airway disease), is an inflammatory disease of the lungs characterized by a generally reversible airway obstruction. Non-limiting features of allergic asthma include elevated concentrations of serum IgE, pulmonary eosinophilia, airway hyper-responsiveness, excessive airway mucus production, and airway remodeling marked by peribronchiolar collagen deposition and increases in airway smooth muscle mass. Other exemplary allergic reactions or inflammatory conditions include allergic alveolitis, allergic bronchopulmonary aspergillosis, allergic dermatitis, eczema, allergic conjunctivitis, allergic coryza, allergic vasculitis, rhinosinusitis, and allergic rhinitis.

Hypersensitivity or hyper-responsiveness used in reference to an immune response means an abnormal response or condition in which an antigen or allergen elicits an exaggerated immune response. For example, allergic asthma can result from repeated exposure to airborne allergens that trigger detrimental immunological responses, such as persistent inflammation in the bronchial wall, which can in turn cause structural and functional changes in the respiratory system. After allergen contact by sensitized subjects (i.e., those subjects that have already been exposed to the allergen), the immune response is dependent on CD4+T lymphocytes that are skewed to a T helper (Th) 2 phenotype. Th2 cytokines, for example, IL-4, IL-5, IL-9, and IL-13 are produced and are believed to contribute to asthma pathogenesis. For example, IL-4 drives the T helper response in favor of Th2, resulting in enhanced production of IgE; IL-5, which with granulocyte macrophage colony stimulating factor (GM-CSF) and IL-3, is important for the production of eosinophils; and IL-13, which is required for airway hyper-responsiveness and mucous metaplasia, which are downstream pathophysiological features that are closely linked with clinical asthma. All of these cytokines, together with TGF-beta have been implicated in airway remodeling. Increased numbers of airway eosinophils is also associated with disease severity, although the role of eosinophils in the pathology of asthma is not entirely understood, (see, e.g., Lee et al., *Science* 305:1773 (2004); Humbles et al., *Science* 305:1776 (2004)). The resulting structural and morphometric changes (remodeling) include subepithelial fibrosis, goblet cell hyperplasia and metaplasia, which result in functional consequences such as loss of distensibility of asthmatic airways, bronchial hyper-reactivity (even in the absence of the allergen), and an accelerated progressive decrease in forced expiratory volume at 1 second time intervals. Th2 cytokines may also prime and activate eosinophils to release proinflammatory agents, lipid mediators, and other cytokines thought to contribute to the observed tissue damage, remodeling, and hyper-responsiveness.

As used herein, the term "tolerance," "anergy," or "antigen (allergen)-specific tolerance" refers to a reduction, loss, inhibition, suppression or decrease, of T cells to T cell receptor-mediated stimulation by an allergen or antigen. The reduction can lead to reduced or non-responsiveness (insensitivity) of T cells to an allergen or antigen. Such insensitivity is generally antigen-specific and persists after exposure to the antigenic peptide has ceased. For example, tolerance in T cells is characterized by lack of lymphokine/cytokine production, e.g., IL-2, IFN-γ, or TNF-β. T-cell anergy occurs when T cells are exposed to antigen or allergen and receive a first signal (a T cell receptor or CD-3 mediated signal) in the absence of a second signal (a costimulatory signal). Under these conditions, re-exposure of the cells to the same antigen or allergen (even if re-exposure occurs in the presence of a costimulatory molecule) results in failure to produce cytokines and subsequently failure of T cells to proliferate. Thus, a failure to produce lymphokines/cytokines prevents proliferation. Tolerized T cells can, however, proliferate if cultured with cytokines (e.g., IL-2). For example, T cell anergy can also be observed by the lack of IL-2 production by T lymphocytes as measured by ELISA or by a proliferation assay using an indicator cell line.

As used herein, the term "immunological tolerance" refers to a) a decreased or reduced level of a specific immunological response (thought to be mediated at least in part by antigen-specific effector T lymphocytes, B lymphocytes, antibody, a combination); b) a delay in the onset or progression of a specific immunological response; or c) a reduced risk of the onset or progression of a specific immunological response to an antigen or allergen. "Specific" immunological tolerance occurs when tolerance is preferentially invoked against certain antigens (allergens) in comparison with other antigens (allergens). Tolerance is an active antigen dependent process and differs from non-specific immunosuppression and immunodeficiency.

An increase, improvement, enhancement or induction of "tolerance" refers to a decrease, reduction, inhibition, suppression, or limiting or controlling or clearing of specific immunological reactivity to an antigen as compared to reactivity to the antigen in a previous exposure to the same antigen. Thus in certain embodiments, a method or use of inducing immunological tolerance in a subject to an allergen includes elimination of an allergic response of the subject to the allergen. Immunological tolerance in a subject to an allergen can also be reflected by reducing the occurrence, frequency, severity, progression, or duration of an allergic response of the subject to the antigen or allergen.

While desirably tolerance can refer to non-reactivity to an antigen or allergen, tolerance need not be complete non-reactivity and can only be partial, and in any event is reflected by a decrease, inhibition, suppression or reduction in specific immunological reactivity to an antigen or allergen as compared to reactivity to the antigen or allergen in a previous exposure to the same antigen or allergen (or epitope thereof). Thus, in another embodiment, a method or use of inducing immunological tolerance in a subject to an allergen includes stabilizing or maintaining the level of an allergic response in the subject to the allergen.

Induction of immune tolerance (also referred to as desensitization), and the relative amount of immune tolerance, can be measured by methods disclosed herein or known to the skilled artisan. For example, induction of immune tolerance can be measured by modulation of lymphokine and/or cytokine level in said animal. As such, modulation can be an increase of a cytokine level, for instance an increase of a cytokine level at least 1.5, 2, 3 times or more relative to before said induction. Alternatively, modulation can be a decrease of the level of a particular cytokine level, for instance a decrease of the cytokine level is at least 1.5, 2, 3 times or more relative to before said induction. The lymphokines/cytokines chosen to measure can be from any relevant lymphokines/cytokines, such as IL-2, IL-5, IL-4, IL-6, IL-10, IL-12, IL-13, TNF-α, IFN-γ, IFN-α, TGF-β, MCP-1, RANK-L and Flt3L.

As disclosed herein, peptides and proteins of the invention are useful in methods and uses, for example, of "specific" immunotherapy. The term "specific" immunotherapy refers to a therapy particular or specific for the protein or peptide, e.g., allergen. To achieve "specific immunotherapy" an antigen is administered to a subject in order to achieve immunological tolerance of the subject to an antigen, including for example, an allergen. More particularly, specific immunotherapy may be conducted by administering an antigen derived from the antigen (e.g. allergen) against which immunological tolerance is sought. Alternatively, immunotherapy can be conducted by "non"-specific immunotherapy using a different antigen or protein than the antigen against which immunological tolerance is sought. Thus, in different embodiments, the antigen administered and antigen (e.g. allergen) against which immunological tolerance is sought may be the same protein, may be proteins of or produce by the same organism, or may be proteins of different organisms. In various embodiments, a method or use of specific immunotherapy reduces, inhibits, suppresses or decreases sensitivity or (hyper)sensitivity to the protein or peptide, e.g., allergen, or elicits, stimulates, increases, induces, promotes or improves tolerance of the protein or peptide, e.g., allergen. Typically a subject is administered a protein or peptide, e.g., allergen, for example, via a subcutaneous injection.

Methods and uses include multi-does regimens. For example, a method or use can begin with small doses of allergen, and the doses are increased for repeated contact or administration.

A variant or derivative of an antigen, including an allergen as described herein, or a subsequence or portion of an antigen or allergen, include molecules that are structurally similar and functionally similar (e.g., for example to any sequence in any of Table 5 (SEQ ID NOs:1-1,411), Table 6, Table 7 (SEQ ID NOs:1,412-1,906) or Table 8 (SEQ ID NOs:1,907-2,008)). A variant, derivative or subsequence of antigen or allergen is functionally similar to the antigen or allergen sequence if the variant, derivative or subsequence is capable of eliciting a detectable or measurable immune response, even if it is a reduced immune response compared to the nonvariant/non-derived or native sequence, which may be determined using methods, including animal models and in vitro assays, described herein and know to one of skill in the art. For example, an immune response may be determined by quantitative and/or qualitative determination of lymphokine/cytokine production (e.g., by T cells), antibody production (including class and/or isotype), cellular mobilization, migration or motility, and optionally in vivo, such as an animal model of antigen/allergen immune responsiveness. An immune response of variant, derivative or subsequence of antigen or allergen compared to the non-variant/non-derivatized/native full length antigen or allergen may be ascertained by analysis of a particular measure (such as lymphokine/cytokine production, immunoglobulin production, cell mobilization, migration, motility, etc.) and may be greater, less than or comparable, e.g., within 5%, 10%, 15%, or 20% or 25% of the immune response of non-variant/non-derivatized/native full length antigen or allergen. For example, levels of Th1 lymphokines/cytokines, such as IFN-γ, IL-2, and TNF-β and Th2 cytokines, such as IL-4, IL-5, IL-9, IL-10, and IL-13, may be determined according to methods described herein or known to one of skill in the art.

As disclosed herein, proteins and peptides, or a subsequence, portion, homologue, variant or derivative thereof include those having all or at least partial sequence identity to one or more exemplary proteins and peptides, or a subsequence, portion, homologue, variant or derivative thereof (e.g., sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). The term "identity" and "identical" and grammatical variations thereof, mean that two or more referenced entities are the same (e.g., peptides or polynucleotide molecules). Thus, where two proteins, peptides, subsequences, portions, homologues, variants or derivatives thereof are identical, they have the same amino acid sequence. The identity can be over a defined area (region or domain) of the sequence. "Areas, regions or domains" of homology or identity mean that a portion of two or more referenced entities share homology or are the same.

Invention proteins and peptides exclude certain proteins and peptides set forth in Table 7 as they are identical to proteins and peptides known in the art. In particular embodiments, at least proteins and peptides with sequences identical to the sequences of Alt a 6 (SEQ ID NO:1455, Asp f 1 (SEQ ID NO:1466), Fel d 1 1 (SEQ ID NOs:1531, 1532, 1533, 1534, 1535, 1536, 1537, 1538), Fel d 1 2 (SEQ ID NOs:1539, 1540, 1541, 1542, 1543, 1544, 1545, 1546, 1547, 1548, 1549, 1550, 1551), Can f 3 (SEQ ID NOs:1557), Der f 1 (SEQ ID NOs:1562, 1563, 1564, 1565), Der f 2 (SEQ ID NO:1587), Der p1 (SEQ ID NOs:1591, 1593, 1594, 1595, 1596, 1597, 1598, 1599, 1600, 1601, 1602, 1603), Der p 2 (SEQ ID NO:1608), Aln g 1 (SEQ ID NOs:1653, 1654, 1655), Bet v 1 (SEQ ID NOs:1656, 1657, 1658, 1659, 1660, 1661, 1662, 1663, 1664), Bet v 2 (SEQ ID NO:1665), Cha o 1 (SEQ ID NOs:1678, 1679, 1680, 1681, 1682, 1683, 1684), Cup a 1 (SEQ ID NOs:1689, 1691, 1692), Cup s 1 (SEQ ID NOs:1700, 1701), Jun o 4 (SEQ ID NO:1710), Ant o 1 (SEQ ID NO:1743), Lol p 1 (SEQ ID NOs:1765, 1766, 1767, 1768), Lol p 11 (SEQ ID NO:1770), Lol p 5 1 (SEQ ID NOs:1793, 1794, 1795, 1796, 1797, 1798, 1802, 1803, 1804, 1805, 1807, 1808, 1809, 1811, 1812), Lol p 5 2 (SEQ ID NOs:1815, 1816, 1817, 1818, 1819), Pha a 1 (SEQ ID NO:1824), Pha a 5 (SEQ ID NOs:1831, 1833, 1836), Poa p 1 (SEQ ID NOs:1842, 1844), Poa p 5 (SEQ ID NOs:1845, 1846, 1847, 1848, 1849, 1850, 1851, 1852, 1853, 1854, 1855, 1856, 1859, 1860, 1861, 1862, 1863, 1864, 1865, 1866, 1867, 1868, 1869, 1870) or Amb t 5 (SEQ ID NO:1881) as set forth in Table 7. In the event that proteins and peptides are excluded on the basis of identity to sequences known in the art, such as at least sequences of at least proteins and peptides with sequences identical to the sequences of Alt a 6 (SEQ ID NO:1455, Asp f 1 (SEQ ID NO:1466), Fel d 1 1 (SEQ ID NOs:1531, 1532, 1533, 1534, 1535, 1536, 1537, 1538), Fel d 1 2 (SEQ ID NOs:1539, 1540, 1541, 1542, 1543, 1544, 1545, 1546, 1547, 1548, 1549, 1550, 1551), Can f 3 (SEQ ID NOs:1557), Der f 1 (SEQ ID NOs:1562, 1563, 1564, 1565), Der f 2 (SEQ ID NO:1587), Der p1 (SEQ ID NOs:1591, 1593, 1594, 1595, 1596, 1597, 1598, 1599, 1600, 1601, 1602, 1603), Der p 2 (SEQ ID NO:1608), Aln g 1 (SEQ ID NOs:1653, 1654, 1655), Bet v 1 (SEQ ID NOs:1656, 1657, 1658, 1659, 1660, 1661, 1662, 1663, 1664), Bet v 2 (SEQ ID NO:1665), Cha o 1 (SEQ ID NOs:1678, 1679, 1680, 1681, 1682, 1683, 1684), Cup a 1 (SEQ ID NOs:1689, 1691, 1692), Cup s 1 (SEQ ID NOs:1700, 1701), Jun o 4 (SEQ ID NO:1710), Ant o 1 (SEQ ID NO:1743), Lol p 1 (SEQ ID NOs:1765, 1766, 1767, 1768), Lol p 11 (SEQ ID NO:1770), Lol p 5 1 (SEQ ID NOs:1793, 1794, 1795, 1796, 1797, 1798, 1802, 1803, 1804, 1805, 1807, 1808, 1809, 1811, 1812), Lol p 5 2 (SEQ ID NOs:1815, 1816, 1817, 1818, 1819), Pha a 1 (SEQ ID NO:1824), Pha a 5 (SEQ ID NOs:1831, 1833, 1836), Poa p 1 (SEQ ID NOs:1842, 1844), Poa p 5 (SEQ ID NOs:1845, 1846, 1847, 1848, 1849, 1850, 1851, 1852, 1853, 1854, 1855, 1856, 1859, 1860, 1861, 1862, 1863, 1864, 1865, 1866, 1867, 1868, 1869, 1870) or Amb t 5 (SEQ ID NO:1881) as set forth in Table 7, subsequences, portions, variants and derivatives thereof as set forth herein are not excluded. Furthermore, such proteins and peptides such as sequences of Alt a 6 (SEQ ID NO:1455, Asp f 1 (SEQ ID NO:1466), Fel d 1 1 (SEQ ID NOs:1531, 1532, 1533, 1534, 1535, 1536, 1537, 1538), Fel d 1 2 (SEQ ID NOs:1539, 1540, 1541, 1542, 1543, 1544, 1545, 1546, 1547, 1548, 1549, 1550, 1551), Can f 3 (SEQ ID NOs:1557), Der f 1 (SEQ ID NOs:1562, 1563, 1564, 1565), Der f 2 (SEQ ID NO:1587), Der p1 (SEQ ID NOs:1591, 1593, 1594, 1595, 1596, 1597, 1598, 1599, 1600, 1601, 1602, 1603), Der p 2 (SEQ ID NO:1608), Aln g 1 (SEQ ID NOs:1653, 1654, 1655), Bet v 1 (SEQ ID NOs:1656, 1657, 1658, 1659, 1660, 1661, 1662, 1663, 1664), Bet v 2 (SEQ ID NO:1665), Cha o 1 (SEQ ID NOs:1678, 1679, 1680, 1681, 1682, 1683, 1684), Cup a 1 (SEQ ID NOs:1689, 1691, 1692), Cup s 1 (SEQ ID NOs:1700, 1701), Jun o 4 (SEQ ID NO:1710), Ant o 1 (SEQ ID NO:1743), Lol p 1 (SEQ ID NOs:1765, 1766, 1767, 1768), Lol p 11 (SEQ ID NO:1770), Lol p 5 1 (SEQ ID NOs:1793, 1794, 1795, 1796, 1797, 1798, 1802, 1803, 1804, 1805, 1807, 1808, 1809, 1811, 1812), Lol p 5 2 (SEQ ID NOs:1815, 1816, 1817, 1818, 1819), Pha a 1 (SEQ ID NO:1824), Pha a 5 (SEQ ID NOs:1831, 1833, 1836), Poa p 1 (SEQ ID NOs:1842, 1844), Poa p 5 (SEQ ID NOs:1845, 1846, 1847, 1848, 1849, 1850, 1851, 1852, 1853, 1854, 1855, 1856, 1859, 1860, 1861, 1862, 1863, 1864, 1865, 1866, 1867, 1868, 1869, 1870) or Amb t 5 (SEQ ID NO:1881) as set forth in Table 7 may also be optionally included in the methods and uses set forth herein.

Identity can be determined by comparing each position in aligned sequences. A degree of identity between amino acid sequences is a function of the number of identical or matching amino acids at positions shared by the sequences, i.e. over a specified region. Optimal alignment of sequences for comparisons of identity may be conducted using a variety of algorithms, as are known in the art, including the ClustalW program, available at http://clustalw.genome.ad.jp, the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nml.nih.gov/). Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

As described herein, proteins and peptides include homologues (e.g., of any sequence in any of Table 5 (SEQ ID NOs:1-1,411), Table 6, Table 7 (SEQ ID NOs:1,412-1,906) or Table 8 (SEQ ID NOs:1,907-2,008)). A polypeptide sequence or polynucleotide sequence is a "homologue" of, or is "homologous" to, another sequence if the two sequences have substantial identity over a specified region and a functional activity of the sequences is preserved or conserved, at least in part (as used herein, the term 'homologous' does not infer evolutionary relatedness). Two polypeptide sequences or polynucleotide sequences are considered to have substantial identity if, when optimally aligned (with gaps permitted), they share at least about 40% sequence identity or greater (e.g. 45%, 50%, 55%, 60%, 65%, 70%, 75%, 80%, 85%, 90%, 95%, 96%, 97%, 98%, 99%, etc.) identify over a specific region, for example, over all or a part of a sequence in any of Table 5 (SEQ ID NOs:1-1,411), Table 6, Table 7 (SEQ ID NOs:1,412-1,906) or Table 8 (SEQ ID NOs:1,907-2,008), or if the sequences share defined functional motifs (e.g., epitopes). The percent identity can extend over the entire sequence length or a portion of the sequence (for example, over all or a part of a sequence in any of Table 5 (SEQ ID NOs:1-1,411), Table 6, Table 7 (SEQ ID NOs:1,412-1,906) or Table 8 (SEQ ID NOs:1,907-2,008)). In particular aspects, the length of the sequence sharing the percent identity is 2, 3, 4, 5 or more contiguous amino acids, e.g., 6, 7, 8, 9, 10, 11, 12, 13, 14, 15, 16, 17, 18, 19, 20, etc. contiguous amino acids (for example, over all or a part of a sequence in any of Table 5 (SEQ ID NOs:1-1,411), Table 6, Table 7 (SEQ ID NOs:1, 412-1,906) or Table 8 (SEQ ID NOs:1,907-2,008)). In additional particular aspects, the length of the sequence sharing the percent identity is 20 or more contiguous amino acids, e.g., 20, 21, 22, 23, 24, 25, 26, 27, 28, 29, 30, 31, 32, 33, 34, 35, etc. contiguous amino acids (for example, over all or a part of a sequence in any of Table 5 (SEQ ID NOs:1-1,411), Table 6, Table 7 (SEQ ID NOs:1,412-1,906) or Table 8 (SEQ ID NOs:1,907-2,008)). In further particular aspects, the length of the sequence sharing the percent identity is 35 or more contiguous amino acids, e.g., 35, 36, 37, 38, 39, 40, 41, 42, 43, 44, 45, 45, 47, 48, 49, 50, etc., contiguous amino acids (for example, over all or a part of a sequence in any of Table 5 (SEQ ID NOs:1-1,411), Table 6, Table 7 (SEQ ID NOs:1,412-1,906) or Table 8 (SEQ ID NOs:1,907-2,008)). In yet further particular aspects, the length of the sequence sharing the percent identity is 50 or more contiguous amino acids, e.g., 50-55, 55-60, 60-65, 65-70, 70-75, 75-80, 80-85, 85-90, 90-95, 95-100, etc. contiguous amino acids (for example, over all or a part of a sequence in any of Table 5 (SEQ ID NOs:1-1,411), Table 6, Table 7 (SEQ ID NOs:1,412-1,906) or Table 8 (SEQ ID NOs:1,907-2,008).

An "unrelated" or "non-homologous" sequence shares less than 30% identity. More particularly, shares less than about 25% identity, with a protein, peptide or polynucleotide of the invention over a specified region of homology.

A variant or derivative of a protein or peptide refers to a modified or variant form of the protein or peptide, or subsequence, portion or homologue thereof (for example, of all or a part of a sequence in any of Table 5 (SEQ ID NOs:1-1,411), Table 6, Table 7 (SEQ ID NOs:1,412-1,906) or Table 8 (SEQ ID NOs:1,907-2,008)). Such modified forms, such as amino acid deletions, additions and substitutions, of the proteins and peptides can also be used in the invention uses, methods and compositions, including methods for modulating an immune response, eliciting, stimulating, inducing, promoting, increasing, or enhancing immunological tolerance and protecting and treating subjects against an allergic reaction or response, as set forth herein.

Thus, in accordance with the invention, modified, variant and derivative forms of proteins, peptides, subsequences, portions, and homologues thereof are provided that have one or more functions or activities of unmodified, non-variant and non-derivatized forms of proteins and peptides. Such forms, referred to as "modifications", "variants" or "derivatives" and grammatical variations thereof deviate from a reference sequence. For example, as described herein, a protein, peptide, subsequence, portion, or homologue thereof may comprise, consist or consist essentially of an amino acid sequence that is a modification, variant, or derivative of a protein or an amino acid sequence set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). Such modifications, variants, or derivatives may have greater or less activity or function than a reference protein or peptide, such as ability to elicit, stimulate, induce, promote, increase, enhance, activate, modulate, inhibit, decreases, suppress, or reduce an immune response (e.g. a T cell response) or elicit, stimulate, induce, promote, increase or enhance immunological tolerance (desensitize) to an antigen or allergen. Thus, proteins, peptides, or subsequences, portions or homologues thereof include sequences having substantially the same, greater or less relative activity or function as a reference antigen or allergen (e.g., any of the proteins or peptides set forth in Table 5 (SEQ ID NOs:1-1, 411, respectively, in order of appearance), Table 6, Table 7 (SEQ ID NOs:1,412-1,906, respectively, in order of appearance) or Table 8 (SEQ ID NOs:1,907-2,008, respectively, in order of appearance) for example, an ability to elicit, stimulate, induce, promote, increase, enhance, activate, modulate, inhibit, suppress, decrease or reduce an immune response (e.g. a T cell response) or elicit, stimulate, induce, promote, increase or enhance immunological tolerance to an antigen or allergen in vitro or in vivo.

A variant or derivative therefore includes deletions, including truncations and fragments; insertions and additions, including tagged polypeptides and fusion proteins; substitutions, for example conservative substitutions, site-directed mutants and allelic variants; and modifications, including peptoids having one or more non-amino acyl groups (q.v., sugar, lipid, etc.) covalently linked to the peptide and post-translational modifications.

Non-limiting examples of modifications include one or more amino acid substitutions (e.g., 1, 2, 3, 4, 5, 6, 7, 8, 9, 10, 11, 12, 13, 14, 15, 16, 17, 18, 19, 20, 20-25, 25-30, 30-50, 50-100, or more residues), additions and insertions (e.g., 1, 2, 3, 4, 5, 6, 7, 8, 9, 10, 11, 12, 13, 14, 15, 16, 17, 18, 19, 20, 20-25, 25-30, 30-50, 50-100, or more residues) and deletions (e.g., 1, 2, 3, 4, 5, 6, 7, 8, 9, 10, 11, 12, 13, 14, 15, 16, 17, 18, 19, 20, 20-25, 25-30, 30-50, 50-100) of a reference protein, peptide, or subsequence or portion thereof (e.g., of any of the proteins or peptides set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). In particular embodiments, a modified or variant sequence retains at least part of a function or an activity of unmodified sequence, and can have less than, comparable, or greater, but at least a part of, a function or activity of a reference sequence, for example, the ability elicit, stimulate, induce, promote, increase, enhance, activate, modulate, inhibit, suppress, decrease, or reduce an immune response (e.g. a T cell response) or elicit, stimulate, induce, promote, increase or enhance immunological tolerance to an allergen. Such immune responses include, for example, among others, induced, increased, enhanced, stimulated, activated, modulated, inhibited, suppressed, decreased or reduced expression, production or activity of a cytokine (e.g., IL-5), an antibody (e.g. increase production of IgG antibodies, decrease production of IgE) or an immune cell (e.g. CD4+ T cell, CD8+ T cell, Th1 cell, Th2 cell or regulatory T cell).

Variants and derivatives of proteins and peptides include naturally-occurring polymorphisms or allelic variants, strain variants, as well as synthetic proteins and peptides that contain a limited number of conservative amino acid substitutions of the amino acid sequence. A variety of criteria can be used to indicate whether amino acids at a particular position in a protein or peptide are similar. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

Specific non-limiting examples of substitutions include conservative and non-conservative amino acid substitutions. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge, or are both hydrophilic or hydrophobic. For example, a conservative amino acid substitution is one in which an amino acid residue is replaced with an amino acid residue having a similar side chain, which include amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine, histidine); nonpolar side chains (e.g., alanine, valine, leucine, isoleucine, proline, phenylalanine, methionine, tryptophan); beta-branched side chains (e.g., threonine, valine, isoleucine), and aromatic side chains (e.g., tyrosine, phenylalanine, tryptophan). Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like. Proline, which is considered more difficult to classify, shares properties with amino acids that have aliphatic side chains (e.g., Leu, Val, Ile, and Ala). In certain circumstances, substitution of glutamine for glutamic acid or asparagine for aspartic acid may be considered a similar substitution in that glutamine and asparagine are amide derivatives of glutamic acid and aspartic acid, respectively. Conservative changes can also include the substitution of a chemically derivatized moiety for a non-derivatized residue, for example, by reaction of a functional side group of an amino acid. Variants and derivatives of proteins and peptides include forms having a limited number of one or more substituted residues.

An addition can be a covalent or non-covalent attachment of any type of molecule. Specific examples of additions include glycosylation, acetylation, phosphorylation, amidation, formylation, ubiquitination, and derivatization by protecting/blocking groups and any of numerous chemical modifications. Additional specific non-limiting examples of an addition are one or more additional amino acid residues. Accordingly, proteins, peptides, subsequences, portions, homologues, variants or derivatives thereof, can be a part of or contained within a larger molecule, such as another protein or peptide sequence, such as a fusion or chimera with a different (distinct) sequence.

In particular embodiments, an addition is a fusion (chimeric) sequence, an amino acid sequence having one or more molecules not normally present in a reference native (wild type) sequence covalently attached to the sequence. The term "chimeric" and grammatical variations thereof, when used in reference to a sequence, means that the sequence contains one or more portions that are derived from, obtained or isolated from, or based upon other physical or chemical entities. For example, a chimera of two or more different proteins may have one part a protein, peptide, subsequence, portion, homologue or variant thereof, and a second part of the chimera may be from a different sequence, or unrelated protein sequence.

Another particular example of a sequence having an amino acid addition is one in which a second heterologous sequence, i.e., heterologous functional domain is attached (covalent or non-covalent binding) that confers a distinct or complementary function. Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral), a metal (gold, silver), and radioisotope. For example, a tag such as T7 or polyhistidine can be attached in order to facilitate purification or detection of a protein, peptide, etc. Accordingly, there are provided proteins, peptides, subsequences, portions and homologues thereof, and a heterologous domain, wherein the heterologous functional domain confers a distinct function on the protein, peptide, subsequence, portion or homologue thereof.

Linkers, such as amino acid or peptidomimetic sequences may be inserted between the sequence and the addition (e.g., heterologous functional domain) so that the two entities maintain, at least in part, a distinct function or activity. Linkers may have one or more properties that include a flexible conformation, an inability to form an ordered secondary structure or a hydrophobic or charged character, which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329). Linkers further include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Further non-limiting examples of additions are detectable labels. Thus, in another embodiment, the invention provides proteins, peptides, subsequences, portions and homologues thereof, that are detectably labeled. Specific examples of detectable labels include fluorophores, chromophores, radioactive isotopes (e.g., $S^{35}$, $P^{32}$, $I^{125}$), electron-dense reagents, enzymes, ligands and receptors. Enzymes are typically detected by their activity. For example, horseradish peroxidase is usually detected by its ability to convert a substrate such as 3,3-',5,5-'-tetramethylbenzidine (TMB) to a blue pigment, which can be quantified.

Another non-limiting example of an addition is an insertion of an amino acid within any protein, peptide, subsequence, portion or homologue thereof (e.g., any protein or sequence set forth herein, such as in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). In particular embodiments, an insertion is of one or more amino acid residues inserted into the amino acid sequence of a protein or peptide, or subsequence, portion or homologue thereof, such as any protein or sequence set forth herein, such as in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance).

Modified and variant proteins, peptides, subsequences, portions or homologues thereof also include one or more D-amino acids substituted for L-amino acids (and mixtures thereof), structural and functional analogues, for example, peptidomimetics having synthetic or non-natural amino acids or amino acid analogues and derivatized forms. Modifications include cyclic structures such as an end-to-end amide bond between the amino and carboxy-terminus of the molecule or intra- or inter-molecular disulfide bond. Proteins, peptides, subsequences, portions and homologues thereof may be modified in vitro or in vivo, e.g., post-translationally modified to include, for example, sugar residues, phosphate groups, ubiquitin, fatty acids, lipids, etc.

Specific non-limiting examples of modified and variant proteins, peptides, subsequences, portions and homologues thereof include proteins or peptides comprising, consisting or consisting essentially of an amino acid sequence comprising at least one amino acid deletion from a full length protein or amino acid sequence set forth in any of Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). In particular embodiments, a protein, peptide, or subsequence, portion or homologue thereof is from about 2 to up to one amino acid less than the full length protein sequence. In additional particular embodiments, a protein subsequence or portion is from about 2 to 5, 5 to 10, 10 to 15, 15 to 20, 20 to 25, 25 to 50, 50 to 100 amino acids in length, provided that said subsequence or portion is at least one amino acid less in length than the full-length protein sequence.

The term "subsequence" or "portion" means a fragment or part of the full length molecule. A subsequence or portion therefore consists of one or more amino acids less than the full length protein or peptide. A subsequence or portion of can have one or more amino acids less than the full length protein or peptide internally or terminal amino acid deletions from either amino or carboxy-termini. Subsequences and portions can vary in size. For example, a subsequence or portion of a protein or peptide can be as small as an epitope capable of binding an antibody (i.e., about five amino acids) up to a polypeptide that is one amino acid less than the entire length of a reference protein or peptide.

As used herein, subsequences and portions may also include or consist of one or more amino acid additions or deletions, wherein the subsequence or portion does not comprise the full length native/wild type protein or peptide sequence. Accordingly, total subsequence or portion lengths can be greater than the length of the full length native/wild type protein or peptide, for example, where a protein or peptide subsequence is fused or forms a chimera with another polypeptide.

The invention provides isolated and/or purified proteins, peptides, subsequences, portions, homologues, variants or derivatives thereof. In particular embodiments, the isolated and/or purified proteins, peptides, subsequences, portions, homologues, variants or derivatives thereof, comprise, consist of or consist essentially of an amino acid sequence of a protein or peptide set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). In particular embodiments, the isolated and/or purified proteins, peptides, subsequences, portions, homologues, variants or derivatives thereof include a T cell epitope.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as fusions/chimeras, multimers/oligomers, modifications (e.g., phosphorylation, glycosylation, lipidation) or derivatized forms, or forms expressed in host cells produced by the hand of man.

An "isolated" composition (e.g., proteins, peptides, subsequences, portions, homologues, variants or derivatives thereof, for example, of any of Table 5 (SEQ ID NOs:1-1, 411, respectively, in order of appearance), Table 6, Table 7 (SEQ ID NOs:1,412-1,906, respectively, in order of appearance) or Table 8 (SEQ ID NOs:1,907-2,008, respectively, in order of appearance)) can also be "substantially pure" or "purified" when free of most or all of the materials with which it typically associates with in nature. Thus, an isolated protein, peptide, subsequence, portion, homologue, variant or derivative thereof, that also is substantially pure or purified does not include polypeptides or polynucleotides present among millions of other sequences, such as peptides of an peptide library or nucleic acids in a genomic or cDNA library, for example.

A "substantially pure" or "purified" composition can be combined with one or more other molecules. Thus, "substantially pure" or "purified" does not exclude combinations of compositions, such as combinations of proteins, peptides, subsequences, portions, homologues, variants or derivatives thereof (e.g., multiple proteins, peptides, subsequences, etc.), and other antigens, agents, drugs or therapies.

Proteins and peptide (e.g., antigens and allergens) can be prepared recombinantly, chemically synthesized, isolated from a biological material or source, and optionally modified, or any combination thereof. A biological material or source would include any organism of any proteins or peptide (e.g., antigen or allergen) set forth herein (e.g., as listed in Tables 1 to 8), or any part or product of any organism set forth herein (e.g., as listed in Tables 1 to 8). A biological material or source may further refer to a preparation in which the morphological integrity or physical state has been altered, modified or disrupted, for example, by dissection, dissociation, solubilization, fractionation, homogenization, biochemical or chemical extraction, pulverization, lyophilization, sonication or any other means of manipulating or processing a biological source or material. Subsequences, variants, homologues and derivatives can be prepared, for example, by substituting, deleting or adding one or more amino acid residues in the amino acid sequence of a protein, peptide, subsequence, portion or homologue thereof, and screening for biological activity, for example eliciting an immune response. A skilled person will understand how to make such derivatives or variants, using standard molecular biology techniques and methods, described for example in Sambrook et al. (2001) Molecular Cloning: a Laboratory Manual, 3$^{rd}$ ed., Cold Spring Harbour Laboratory Press).

The invention also provides protein or peptide (e.g., proteins, peptides, subsequences, portions, homologues, variants or derivatives thereof, for example, of any of Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance)), immobilized on or attached to a substrate. The protein or peptide (e.g., proteins, peptides, subsequences, portions, homologues, variants or derivatives thereof, for example, of any of Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance)) can optionally have a unique or distinct position or address on the substrate.

Substrates to which protein or peptide (e.g., proteins, peptides, subsequences, portions, homologues, variants or derivatives thereof, for example, of any of Table 5, Table 6, Table 7 or Table 8), can be immobilized or attached include essentially any physical entity such as a two dimensional surface that is permeable, semi-permeable or impermeable, either rigid or pliable and capable of either storing, binding to or having attached thereto or impregnated.

Substrates include dry solid medium (e.g., cellulose, polyester, nylon, or mixtures thereof etc.), such as glass, silica, plastic, polyethylene, polystyrene, polypropylene, polyacetate, polycarbonate, polyamide, polyester, polyurethane, or polyvinylchloride. Substrates include structures having sections, compartments, wells, containers, vessels or tubes, separated from each other to avoid or prevent cross-contamination or mixing with each other or with other reagents. Multi-well plates, which typically contain 6, 12, 26, 48, 96, to 1000 wells, are one particular non-limiting example of such a structure.

Substrates also include supports used for two- or three-dimensional arrays of sequences. The sequences are typically attached to the surface of the substrate (e.g., via a covalent bond) at defined positions (locations or addresses). Substrates can include a number of sequences, for example, 1, 2, 3, 4, 5, 5 to 10, 10 to 15, 15 to 20, 20 to 25, 25 to 30, 30 to 35, 35 to 40, 40 to 45, 45 to 50, 50 to 75, 75 to 100, 100 to 150, 150 to 200, 200 to 250, 250 to 300, up to all proteins, peptides, subsequences, portions, homologues, variants or derivatives thereof, listed in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). Such substrates, also referred to as "arrays," can have any protein density; the greater the density the greater the number of sequences that can be screened on a given chip. Substrates that include a two- or three-dimensional array of sequences, and individual protein sequences therein, may be coded in accordance with the invention.

The invention also provides nucleic acids encoding proteins, peptides, subsequences, portions, homologues, variants or derivatives thereof, for example, of amino acid sequences set forth in Table 5, Table 6, Table 7 or Table 8. Such nucleic acid sequences encode a sequence at least 40% or more (e.g., 45%, 50%, 55%, 60%, 65%, 70%, 75%, 80%, 85%, 90%, 95%, 96%, 97%, 98%, 99%) identical to an exemplary protein, peptide, subsequence, portion, homologue, variant or derivative thereof, for example, of any amino acid sequence set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). In an additional embodiment, a nucleic acid encodes a sequence having a modification, such as one or more amino acid additions (insertions), deletions or substitutions of protein, peptide, subsequence, portion, homologue, variant or derivative thereof, for example, of an amino acid sequence set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance) 8.

The terms "nucleic acid," "polynucleotide" and "polynucleotide" and the like refer to at least two or more ribo- or deoxy-ribonucleic acid base pairs (nucleotides/nucleosides) that are linked through a phosphoester bond or equivalent. Nucleic acids include polynucleotides and polynucleotides. Nucleic acids include single, double or triplex, circular or linear, molecules. Exemplary nucleic acids include but are not limited to: RNA, DNA, cDNA, genomic nucleic acid, naturally occurring and non-naturally occurring nucleic acid, e.g., synthetic nucleic acid.

Nucleic acids can be of various lengths. Nucleic acid lengths typically range from about 20 bases to 20 Kilobases (Kb), or any numerical value or range within or encompassing such lengths, 10 bases to 10 Kb, 1 to 5 Kb or less, 1000 to about 500 bases or less in length. Nucleic acids can also be shorter, for example, 100 to about 500 bases, or from about 12 to 24, 24 to 45, 45 to 90, 90 to 250, or about 250 to 500 bases in length, or any numerical value or range or value within or encompassing such lengths. In particular aspects, a nucleic acid sequence has a length from about 10-20, 20-30, 30-50, 50-100, 100-150, 150-200, 200-250, 250-300, 300-400, 400-500, 500-1000, 1000-2000 bases, or any numerical value or range within or encompassing such lengths. Shorter nucleic acids are commonly referred to as "oligonucleotides" or "probes" of single- or double-stranded DNA. However, there is no upper limit to the length of such oligonucleotides.

Nucleic acid sequences further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode proteins, peptides, subsequences, portions, homologues, variants or derivatives thereof, (e.g., substitutions, additions, insertions and deletions), for example, of amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance).

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to the encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as eukaryote or mammalian cell, yeast or bacteria, in an animal or in a plant).

Nucleic acid may be inserted into a nucleic acid construct in which expression of the nucleic acid is influenced or regulated by an "expression control element." An "expression control element" refers to a nucleic acid sequence element that regulates or influences expression of a nucleic acid sequence to which it is operatively linked. Expression control elements include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. Expression control elements include elements that activate transcription constitutively, that are inducible (i.e., require an external signal for activation), or derepressible (i.e., require a signal to turn transcription off; when the signal is no longer present, transcription is activated or "derepressed"), or specific for cell-types or tissues (i.e., tissue-specific control elements).

Nucleic acid can also be inserted into a plasmid for propagation into a host cell and for subsequent genetic manipulation. A plasmid is a nucleic acid that can be propagated in a host cell, plasmids may optionally contain expression control elements in order to drive expression of the nucleic acid encoding proteins, peptides, subsequences, portions, homologues, variants or derivatives thereof in the host cell. A vector is used herein synonymously with a plasmid and may also include an expression control element for expression in a host cell (e.g., expression vector). Plasmids and vectors generally contain at least an origin of replication for propagation in a cell and a promoter. Plasmids and vectors are therefore useful for genetic manipulation and expression of proteins, peptides, subsequences, portions, homologues, variants or derivatives thereof, for example, of amino acid sequences set forth in Table 5, Table 6, Table 7 or Table 8. Accordingly, vectors that include nucleic acids encoding or complementary to proteins, peptides, subsequences, portions, homologues, variants or derivatives thereof, for example, of amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance), are provided.

In accordance with the invention, there are provided particles (e.g., viral particles) and transformed host cells that express and/or are transformed with a nucleic acid that encodes and/or express proteins, peptides, subsequences, portions, homologues, variants or derivatives thereof, for example, of amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). Particles and transformed host cells include but are not limited to virions, and prokaryotic and eukaryotic cells such as bacteria, fungi (yeast), plant, insect, and animal (e.g., mammalian, including primate and human, CHO cells and hybridomas) cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression. The cells may be a primary cell isolate, cell culture (e.g., passaged, established or immortalized cell line), or part of a plurality of cells, or a tissue or organ ex vivo or in a subject (in vivo).

The term "transformed" or "transfected" when used in reference to a cell (e.g., a host cell) or organism, means a genetic change in a cell following incorporation of an exogenous molecule, for example, a protein or nucleic acid (e.g., a transgene) into the cell. Thus, a "transfected" or "transformed" cell is a cell into which, or a progeny thereof in which an exogenous molecule has been introduced by the hand of man, for example, by recombinant DNA techniques.

The nucleic acid or protein can be stably or transiently transfected or transformed (expressed) in the host cell and progeny thereof. The cell(s) can be propagated and the introduced protein expressed, or nucleic acid transcribed. A progeny of a transfected or transformed cell may not be identical to the parent cell, since there may be mutations that occur during replication.

Expression of proteins, peptides, subsequences, portions, homologues, variants or derivatives thereof and nucleic acid in particles or introduction into target cells (e.g., host cells) can also be carried out by methods known in the art. Non-limiting examples include osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (e.g., U.S. Pat. Nos. 4,844,904, 5,000,959, 4,863,740, and 4,975,282; and GIBCO-BRL, Gaithersburg, Md.). Piperazine based amphilic cationic lipids useful for gene therapy also are known (see, e.g., U.S. Pat. No. 5,861,397). Cationic lipid systems also are known (see, e.g., U.S. Pat. No. 5,459,127). Polymeric substances, microcapsules and colloidal dispersion systems such as liposomes are collectively referred to herein as "vesicles." Accordingly, viral and non-viral vector means delivery into cells are included.

Proteins, peptides, subsequences, portions, homologues, variants or derivatives thereof, for example, of amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance), are provided, can be employed in various methods and uses. Such methods and uses include, for example, administration in vitro and in vivo of one or more proteins, peptides, subsequences, portions, homologues, variants or derivatives thereof, such as the amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance), or subsequences, portions, homologues, variants or derivatives thereof. The methods and uses provided include methods and uses of modulating an immune response, including, among others, methods and uses of protecting and treating subjects against a disorder, disease; and methods and uses of providing specific immunotherapy; and methods and uses of diagnosis.

In particular embodiments, methods and uses include administration or delivery of a protein, peptide, subsequence, portion, homologue, variants or derivative thereof described herein (e.g., of any amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance)) to modulate an immune response in a subject, including, for example, modulating an immune response to an allergen or antigen.

As used herein, the term "modulate," means an alteration or effect on the term modified. For example, the term modulate can be used in various contexts to refer to an alteration or effect of an activity, a function, or expression of a polypeptide, gene or signaling pathway, or a physiological condition or response of an organism. In certain embodiments, modulating involves decreasing, reducing, inhibiting, suppressing or disrupting an immune response of a subject to an antigen or allergen. In other embodiments, modulating involves eliciting, stimulating, inducing, promoting, increasing or enhancing an immune response of a subject to an antigen or allergen. Thus, where the term "modulate" is used to modify the term "immune response against an allergen in a subject" this means that the immune response in the subject to the allergen is altered or affected (e.g., decreased, reduced, inhibited, suppressed, limited, controlled, prevented, elicited, promoted, stimulated, increased, induced, enhanced, etc.).

Methods and uses of modulating an immune response against an antigen or allergen as described herein may be used to provide a subject with protection against an allergic response or reaction to the allergen, or allergic disorder or allergic disease, or one or more physiological conditions, disorders, illnesses, diseases, symptoms or complications caused by or associated with the allergen. Accordingly, in other embodiments, methods and uses include administering a protein, peptide, subsequence, portion, homologue, variant or derivative thereof described herein (e.g., of any amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance)) to protect or treat a subject against an allergic response, allergic disorder or allergic disease, or one or more physiological conditions, disorders, illnesses, diseases, symptoms or complications caused by or associated with an allergen. In still other embodiments, methods and uses include administering or delivering a protein, peptide, subsequence, portion, homologue, variant or derivative thereof described herein (e.g., of any amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance)) to elicit, stimulate, induce, promote, increase or enhance immunological tolerance of a subject to an antigen or allergen.

In various embodiments, there are provided methods and uses of providing a subject with protection against an allergic response, allergic disorder or allergic disease, or one or more physiological conditions, disorders, illnesses, diseases, symptoms or complications caused by or associated with an allergen. In various aspects, a method or use includes administering to the subject an amount of a protein, peptide, subsequence, portion, homologue, variant or derivative thereof described herein (e.g., of any amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance)) sufficient to provide the subject with protection against the allergic response, allergic disorder or allergic disease, or one or more physiological conditions, disorders, illnesses, diseases, symptoms or complications caused by or associated with the allergen.

Methods and uses of the invention include providing a subject with protection against an antigen or allergen, or one or more physiological conditions, disorders, illnesses, diseases, symptoms or complications caused by or associated with the exposure to the antigen or allergen, such as vaccinating the subject to protect against an allergic response to the allergen, for example with any amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance). In certain embodiments, methods and uses include protecting the subject against an allergic response or reaction by inducing tolerance of the subject (desensitizing) to the allergen.

As used herein, the terms "protection", "protect" and grammatical variations thereof, when used in reference to an allergic response or one or more physiological conditions, disorders, illnesses, diseases, symptoms or complications caused by or associated with the exposure to allergen, means preventing an allergic response, reaction, or one or more physiological conditions, disorders, illnesses, diseases, symptoms or complications caused by or associated with the exposure to the allergen, or reducing or decreasing susceptibility to an allergic response, reaction, or one or more physiological conditions, disorders, illnesses, diseases, symptoms or complications caused by or associated with the exposure to the allergen.

An allergic response includes but is not limited to an allergic reaction, hypersensitivity, an inflammatory response or inflammation. In certain embodiments allergic response may involve one or more of cell infiltration, production of antibodies, production of cytokines, lymphokines, chemokines, interferons and interleukins, cell growth and maturation factors (e.g., differentiation factors), cell proliferation, cell differentiation, cell accumulation or migration (chemotaxis) and cell, tissue or organ damage or remodeling. In particular aspects, an allergic response may include Allergic rhinitis; Onchocercal dermatitis; Atopic dermatitis; allergic conjunctivitis; Drug reactions; Nodules, eosinophilia, rheumatism, dermatitis, rashes, hives, and swelling (NERDS); esophageal and a gastrointestinal allergy.

Allergic responses can occur systemically, or locally in any region, organ, tissue, or cell. In particular aspects, an allergic response occurs in the skin, the upper respiratory tract, the lower respiratory tract, pancreas, thymus, kidney, liver, spleen, muscle, nervous system, skeletal joints, eye, mucosal tissue, gut or bowel.

Methods and uses herein include treating a subject for an allergic response, allergic disorder or allergic disease, as well as one or more physiological conditions, disorders, illnesses, diseases, symptoms or complications caused by or associated with an allergen. Such methods and uses include administering to a subject an amount of a protein, peptide, subsequence, portion, homologue, variant or derivative thereof described herein (e.g., any amino acid sequence set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance)) sufficient to treat the subject for the allergic response, allergic disorder or allergic disease, or one or more physiological conditions, disorders, illnesses, diseases, symptoms or complications caused by or associated with the allergen.

As will be understood by a person skilled in the art, treating an allergic response, allergic disorder or allergic disease, or one or more physiological conditions, disorders, illnesses, diseases, symptoms or complications caused by or associated with an allergen may include decreasing, reducing, inhibiting, suppressing, limiting, controlling or clearing an allergic response, an allergic disorder or allergic disease, or one or more physiological conditions, disorders, illnesses, diseases, symptoms or complications caused by or associated with the allergen. Thus in certain embodiments, a method or use of treating a subject for a an allergic response, allergic disorder or allergic disease, or one or more physiological conditions, disorders, illnesses, diseases, symptoms or complications caused by or associated with an allergen comprises elimination of the allergic response, allergic disorder or allergic disease, or one or more physiological conditions, disorders, illnesses, diseases, symptoms or complications caused by or associated with the allergen from a subject. In other embodiments, a method or use of treating a subject for an allergic response, allergic disorder or allergic disease, or one or more physiological conditions, disorders, illnesses, diseases, symptoms or complications caused by or associated with an allergen includes reducing occurrence, frequency, severity, progression, or duration of the allergic response, allergic disorder or allergic disease, or one or more physiological conditions, disorders, illnesses, diseases, symptoms or complications caused by or associated with the allergen in the subject. In yet another embodiment, a method or use of treating a subject for an allergic response, allergic disorder or allergic disease, or one or more physiological conditions, disorders, illnesses, diseases, symptoms or complications caused by or associated with an allergen, includes stabilizing the allergic response, allergic disorder or allergic disease, or one or more physiological conditions, disorders, illnesses, diseases, symptoms or complications caused by or associated with the allergen in a subject by preventing an increase in the occurrence, frequency, severity, progression, or duration of the allergic response, allergic disorder or allergic disease, or one or more physiological conditions, disorders, illnesses, diseases, symptoms or complications caused by or associated with contact of the subject with an allergen.

Methods and use of the invention include treating or administering a subject previously exposed to an antigen or allergen. Thus, in certain embodiments, methods and uses are for treating or protecting a subject from an allergic response, allergic disorder or allergic disease, or one or more physiological conditions, disorders, illnesses, diseases, symptoms or complications caused by or associated with secondary or subsequent exposure to an antigen or allergen.

Physiological conditions, disorders, illnesses, diseases, symptoms or complications caused by or associated with an antigen/allergen treatable in accordance with the invention methods and uses include but are not limited to asthma, allergic asthma, bronchiolitis and pleuritis, Allergic rhinitis; Onchocercal dermatitis; Atopic dermatitis; allergic conjunctivitis; Drug reactions; Nodules, eosinophilia, rheumatism, dermatitis, rashes, hives, and swelling (NERDS); esophageal and a gastrointestinal allergy, Airway Obstruction, Apnea, Asbestosis, Atelectasis, Berylliosis, Bronchiectasis, Bronchiolitis, Bronchiolitis Obliterans Organizing Pneumonia, Bronchitis, Bronchopulmonary Dysplasia, Empyema, Pleural Empyema, Pleural Epiglottitis, Hemoptysis, Hypertension, Kartagener Syndrome, Meconium Aspiration, Pleural Effusion, Pleurisy, Pneumonia, Pneumothorax, Respiratory Distress Syndrome, Respiratory Hypersensitivity, Rhinoscleroma, Scimitar Syndrome, Severe Acute Respiratory Syndrome, Silicosis, Tracheal Stenosis, eosinophilic pleural effusions, Histiocytosis; chronic eosinophilic pneumonia; hypersensitivity pneumonitis; Allergic bronchopulmonary aspergillosis; Sarcoidosis; Idiopathic pulmonary fibrosis; pulmonary edema; pulmonary embolism; pulmonary emphysema; Pulmonary Hyperventilation; Pulmonary Alveolar Proteinosis; Chronic Obstructive Pulmonary Disease (COPD); Interstitial Lung Disease; and Topical eosinophilia.

Methods and uses of the invention further include inducing immunological tolerance of a subject to an antigen or allergen. In one embodiment, a method or use includes administering to the subject an amount of a protein, peptide, subsequence, portion, homologue, variant or derivative thereof described herein (e.g., any amino acid sequences set forth in Table 5 (SEQ ID NOs:1-1,411, respectively, in order of appearance), Table 6, Table 7 (SEQ ID NOs:1,412-1,906, respectively, in order of appearance) or Table 8 (SEQ ID NOs:1,907-2,008, respectively, in order of appearance)) sufficient to induce tolerance in the subject to the antigen or allergen.

In additional embodiments, a method or use of inducing immunological tolerance in a subject to an allergen includes a reduction in occurrence, frequency, severity, progression, or duration of physiological conditions, disorders, illnesses, diseases, symptoms or complications caused by or associated an allergic response to the allergen in the subject. Thus, in certain embodiments, inducing immunological tolerance can protect a subject against or treat a subject for an allergic response, allergic disorder or allergic disease, or one or more physiological conditions, disorders, illnesses, diseases, symptoms or complications caused by or associated with an antigen or allergen.

Methods and uses of inducing immunological tolerance described herein may include eliciting, stimulating, inducing, promoting, increasing or enhancing an immune response. In certain embodiments, inducing immunological tolerance may include eliciting, stimulating, inducing, promoting, increasing or enhancing an immune response that decreases, reduces, inhibits, suppresses, limits, controls or clears an allergic response. For example, in certain embodiments inducing immunological tolerance may include eliciting, stimulating, inducing, promoting, increasing or enhancing proliferation or activity of regulatory T cells. In other embodiments, inducing immunological tolerance may include eliciting, stimulating, inducing, promoting, increasing or enhancing an immune response that promotes an allergic response. As will be understood by a person of skill in the art, a method or use that elicits, stimulates, induces, promotes, increases or enhances an immune response that promotes an allergic response may still induce immunological tolerance by also eliciting, stimulating, inducing, promoting, increasing or enhancing an immune response that decreases, reduces, inhibits, suppresses, limits, controls or clears an allergic response. In particular embodiments, inducing immunological tolerance includes eliciting, stimulating, inducing, promoting, increasing or enhancing an immune responses that decreases, reduces, inhibits, suppresses, limits, controls or clears an allergic response that is stronger than the immune response that promotes an allergic response. In other embodiments, inducing immunological tolerance includes eliciting, stimulating, inducing, promoting, increasing or enhancing more immune responses that decrease, reduce, inhibit, suppress, limit, controls or clear an allergic response than immune responses that promote an allergic response.

Methods and uses of the invention include treating a subject via specific immunotherapy. In one embodiment, a method or use includes administering to the subject an amount of a protein, peptide, subsequence, portion, homologue, variant or derivative thereof described herein (e.g., any amino acid sequences set forth in Table 5 (SEQ ID NOs:1-1,411), Table 6, Table 7 (SEQ ID NOs:1,412-1,906) or Table 8 (SEQ ID NOs:1,907-2,008). In one aspect, an antigen (allergen) administered to a subject during specific immunotherapy to treat the subject is the same antigen (allergen) to which the subject has been sensitized or is hypersensitive (e.g., allergic). In another non-limiting aspect, an antigen (allergen) administered to a subject to treat the subject is a different antigen (allergen) to which the subject has been sensitized or is hypersensitive (e.g., allergic). Thus in different embodiments, the antigen administered and antigen (e.g., allergen) against which immunological tolerance is sought may be the same protein (antigen, allergen), may be proteins (antigens, allergens) of the same organism or may be proteins (antigens, allergens) of different organisms.

In accordance with the invention, methods and uses include therapeutic (following antigen/allergen exposure) and prophylactic (prior to antigen/allergen exposure) uses and methods. For example, therapeutic and prophylactic methods and uses of treating a subject for an allergic response, allergic disorder or allergic disease, or one or more physiological conditions, disorders, illnesses, diseases, symptoms or complications caused by or associated with an allergen, include but are not limited to treatment of a subject having or at risk of having an allergic response, allergic disorder or allergic disease, or one or more physiological conditions, disorders, illnesses, diseases, symptoms or complications caused by or associated with an allergen; treating a subject with an allergic response, allergic disorder or allergic disease, or one or more physiological conditions, disorders, illnesses, diseases, symptoms or complications caused by or associated with an allergen; and methods and uses of protecting a subject from an allergic response, allergic disorder or allergic disease, or one or more physiological conditions, disorders, illnesses, diseases, symptoms or complications caused by or associated with an antigen/allergen (e.g., provide the subject with protection against an allergic reaction to an allergen), to decrease or reduce the probability of an allergic response, allergic disorder or allergic disease, or one or more physiological conditions, disorders, illnesses, diseases, symptoms or complications caused by or associated with an allergen, in a subject and to decrease or reduce susceptibility of a subject to an allergic response, allergic disorder or allergic disease, or one or more physiological conditions, disorders, illnesses, diseases, symptoms or complications caused by or associated with an allergen, to inhibit or prevent an allergic response, allergic disorder or allergic disease, or one or more physiological conditions, disorders, illnesses, diseases, symptoms or complications caused by or associated with an allergen, in a subject. Accordingly, methods and uses can treat an allergic response, allergic disorder or allergic disease, or one or more physiological conditions, disorders, illnesses, diseases, symptoms or complications caused by or associated with an allergen, or provide a subject with protection from an allergic response, allergic disorder or allergic disease, or one or more physiological conditions, disorders, illnesses, diseases, symptoms or complications caused by or associated with an allergen (e.g., prophylactic protection).

As described herein, proteins, peptides, subsequences, portions, homologues, variants and derivatives thereof include T cell epitopes. In Accordingly, methods and uses of the invention include administering an amount of a protein, peptide, subsequence, portion, homologue, variant or derivative thereof (e.g., a T cell epitope) to a subject sufficient to provide the subject with protection against an allergic response, allergic disorder or allergic disease, or one or more physiological conditions, disorders, illnesses, diseases, symptoms or complications caused by or associated with an allergen. In another embodiment, a method includes administering an amount of a protein, peptide, subsequence, portion, homologue, variant or derivative thereof (e.g., a T cell epitope) to a subject sufficient to treat, vaccinate or immunize the subject against an allergic response, allergic disorder or allergic disease, or one or more physiological conditions, disorders, illnesses, diseases, symptoms or complications caused by or associated with an allergen.

In accordance with the invention, methods and uses of modulating anti-allergen activity of T cells, including but not limited to $CD8^+$ T cells, $CD4^+$ T cells, Th1 cells or Th2 cells, in a subject are provided. In one embodiment, a method or use includes administering to a subject an amount of a protein, peptide, subsequence, portion, homologue, variant or derivative thereof, such as a T cell epitope, sufficient to modulate Th2 cell activity in the subject.

In all methods and uses of the invention, any appropriate protein, peptide, subsequence, portion, homologue, variant or derivative thereof can be used or administered. In particular non-limiting examples, the protein, peptide, subsequence, portion, homologue, variant or derivative thereof comprises, consists of or consists essentially of an amino acid sequence of a protein or peptide set forth in Table 5 (SEQ ID NOs:1-1,411), Table 6, Table 7 (SEQ ID NOs:1,412-1,906) or Table 8 (SEQ ID NOs:1,907-2,008), or a subsequence, portion, homologue, variant or derivative thereof.

In certain embodiments, two or more proteins, peptides, subsequences, portions, homologues, variants or derivatives thereof, may be administered to a subject. In particular embodiments, a protein, peptide, subsequence, portion, homologue, variant or derivative thereof consists of or consists essentially of an amino acid sequence of a protein or peptide set forth in Table 5 (SEQ ID NOs:1-1,411), Table 6, Table 7 (SEQ ID NOs:1,412-1,906) or Table 8 (SEQ ID NOs:1,907-2,008), or subsequence, portion, homologue, variant or derivative thereof, and is administered with one or more other proteins, peptides, subsequences, portions, homologues, variants or derivatives thereof. Two or more proteins, peptides, subsequences, portions, homologues, variants or derivatives thereof may be administered as a combination composition, or administered separately, such as concurrently or in series or sequentially. Different proteins, peptides, subsequences, portions, homologues, variants or derivatives thereof, may be administered to a subject in the same amount, volume or concentration, or different amounts, volumes or concentrations. Thus, in certain embodiments, the subject may be administered the same amount of two or more different proteins, peptides, subsequences, portions, homologues, variants or derivatives thereof; and in other embodiments, the subject may be administered one protein, peptide, subsequence, portion, homologue, variant or derivative thereof in an amount, volume or concentration greater than one or more other protein, peptide, subsequence, portion, homologue, variant or derivative thereof administered to the subject.

Methods and uses of the invention include a favorable response or an improvement in one or more physiological conditions, disorders, illnesses, diseases, symptoms or complications caused by or associated with an antigen/allergen. In particular embodiments, a favorable response or improvement includes but is not limited to reduce, decrease, suppress, limit, control or inhibit an allergic response including reducing, decreasing, suppressing, limiting, controlling or inhibiting immune cell proliferation, function or activity, or eliciting, stimulating, inducing, promoting, increasing or enhancing immune cell proliferation or activity (e.g. regulatory T cells); or reduce, decrease, suppress, limit, control or inhibit the amount of allergen. In additional particular embodiments, an amount of a protein, peptide, subsequence, portion, homologue, variant or derivative thereof is sufficient to elicit, stimulate, induce, promote, increase or enhance or augment immunological tolerance to an allergen; or decrease, reduce, inhibit, suppress, prevent, control, or limit an allergic reaction or response. In further particular embodiments, an amount of a protein, peptide, subsequence, portion, homologue, variant or derivative thereof is sufficient to protect a subject from an allergic response or reduce, decrease, limit, control or inhibit susceptibility to an allergic response, allergic disorder or allergic disease, or one or more physiological conditions, disorders, illnesses, diseases, symptoms or complications caused by or associated with an allergen.

Methods and uses of the invention therefore include any therapeutic or beneficial effect. In various methods embodiments, an allergic response, allergic disorder or allergic disease, or one or more physiological conditions, disorders, illnesses, diseases, symptoms or complications caused by or associated with an allergen is reduced, decreased, inhibited, limited, delayed or prevented. Physiological conditions, disorders, illnesses and diseases associated with an antigen/allergen include but are not limited to asthma, allergic asthma, bronchiolitis and pleuritis, Allergic rhinitis; Onchocercal dermatitis; Atopic dermatitis; allergic conjunctivitis; Drug reactions; Nodules, eosinophilia, rheumatism, dermatitis, rashes, hives, and swelling (NERDS); esophageal and a gastrointestinal allergy, Airway Obstruction, Apnea, Asbestosis, Atelectasis, Berylliosis, Bronchiectasis, Bronchiolitis, Bronchiolitis Obliterans Organizing Pneumonia, Bronchitis, Bronchopulmonary Dysplasia, Empyema, Pleural Empyema, Pleural Epiglottitis, Hemoptysis, Hypertension, Kartagener Syndrome, Meconium Aspiration, Pleural Effusion, Pleurisy, Pneumonia, Pneumothorax, Respiratory Distress Syndrome, Respiratory Hypersensitivity, Rhinoscleroma, Scimitar Syndrome, Severe Acute Respiratory Syndrome, Silicosis, Tracheal Stenosis, eosinophilic pleural effusions, Histiocytosis; chronic eosinophilic pneumonia; hypersensitivity pneumonitis; Allergic bronchopulmonary aspergillosis; Sarcoidosis; Idiopathic pulmonary fibrosis; pulmonary edema; pulmonary embolism; pulmonary emphysema; Pulmonary Hyperventilation; Pulmonary Alveolar Proteinosis; Chronic Obstructive Pulmonary Disease (COPD); Interstitial Lung Disease; and Topical eosinophilia. Symptoms and complications associated with an allergen include but are not limited to cell infiltration, production of antibodies, production of cytokines, lymphokines, chemokines, interferons and interleukins, cell growth and maturation factors (e.g., differentiation factors), cell proliferation, cell differentiation, cell accumulation or migration and cell, tissue or organ damage or remodelling, allergic rhinitis; Onchocercal dermatitis; Atopic dermatitis; allergic conjunctivitis; Drug reactions; Nodules, eosinophilia, rheumatism, dermatitis, rashes, hives, and swelling (NERDS); esophageal and a gastrointestinal allergy. Additional symptoms of antigen/allergen exposure are known to one of skill in the art and treatment thereof in accordance with the invention is provided.

Methods and uses of the invention moreover include reducing, decreasing, inhibiting, delaying or preventing onset, progression, frequency, duration, severity, probability or susceptibility of one or more adverse symptoms, disorders, illnesses, diseases or complications caused by or associated with an antigen/allergen. In further various particular embodiments, methods and uses include improving, accelerating, facilitating, enhancing, augmenting, or hastening recovery of a subject from an allergic response, allergic disorder or allergic disease, or one or more physiological conditions, disorders, illnesses, diseases, symptoms or complications caused by or associated with an antigen/allergen. In yet additional various embodiments, methods and uses include stabilizing an allergic response, allergic disorder or allergic disease, or one or more physiological conditions, disorders, illnesses, diseases, symptoms or complications caused by or associated with an antigen/allergen.

A therapeutic or beneficial effect is therefore any objective or subjective measurable or detectable improvement or benefit provided to a particular subject. A therapeutic or beneficial effect can but need not be complete ablation of all or any allergic response, allergic disorder or allergic disease, or one or more physiological conditions, disorders, illnesses, diseases, symptoms or complications caused by or associated with an allergen. Thus, a satisfactory clinical endpoint is achieved when there is an incremental improvement or a partial reduction in an allergic response, allergic disorder or allergic disease, or one or more physiological conditions, disorders, illnesses, diseases, symptoms or complications caused by or associated with an allergen, or an inhibition, decrease, reduction, suppression, prevention, limit or control of worsening or progression of an allergic response, allergic disorder or allergic disease, or one or more physiological conditions, disorders, illnesses, diseases, symptoms or complications caused by or associated with an allergen, over a short or long duration (hours, days, weeks, months, etc.).

A therapeutic or beneficial effect also includes reducing or eliminating the need, dosage frequency or amount of a second therapeutic protocol or active such as another drug or other agent (e.g., anti-inflammatory) used for treating a subject having or at risk of having an allergic response, allergic disorder or allergic disease, or one or more physiological conditions, disorders, illnesses, diseases, symptoms or complications caused by or associated with an allergen. For example, reducing an amount of an adjunct therapy, such as a reduction or decrease of a treatment for an allergic response, allergic disorder or allergic disease, or one or more physiological conditions, disorders, illnesses, diseases, symptoms or complications caused by or associated with an allergen, or a specific immunotherapy, vaccination or immunization protocol is considered a beneficial effect. In addition, reducing or decreasing an amount of protein, peptide, subsequence, portion, homologue, variant or derivative thereof, used for specific immunotherapy, vaccination or immunization of a subject to provide protection to the subject is considered a beneficial effect.

As disclosed herein, invention proteins, peptides, subsequences, etc., can be used in methods of providing specific immunotherapy to a subject, such as a subject with or at risk of an allergic response, allergic disorder or allergic disease, or one or more physiological conditions, disorders, illnesses, diseases, symptoms or complications caused by or associated with an allergen. In one embodiment, a method or use includes administering to a subject an amount of a protein, peptide, subsequence, portion, homologue, variant or derivative thereof sufficient to elicit, stimulate, induce, promote, increase, enhance or augment immunological tolerance in the subject to an antigen/allergen. In another embodiment, a method includes administering to a subject an amount of a nucleic acid encoding all or a portion (e.g., a T cell epitope) of a protein, peptide, subsequence, portion, homologue, variant or derivative thereof sufficient to elicit, stimulate, induce, promote, increase, enhance or augment immunological tolerance of the subject to an allergen.

When an antigen(s) or allergen(s) is administered to induce tolerance, an amount or dose of the antigen or allergen to be administered, and the period of time required to achieve a desired outcome or result (e.g., to desensitize or develop tolerance to the antigen or allergen) can be determined by one skilled in the art. The antigen or allergen may be administered to the patient through any route known in the art, including, but not limited to oral, inhalation, sublingual, epicutaneous, intranasal, and/or parenteral routes (intravenous, intramuscular, subcutaneously, and intraperitoneal).

Methods and uses of the invention include administration of a protein, peptide, subsequence, portion, homologue, variant or derivative thereof to a subject prior to contact by or exposure to an allergen; administration prior to, substantially contemporaneously with or after a subject has been contacted by or exposed to an allergen; and administration prior to, substantially contemporaneously with or after an allergic response, allergic disorder or allergic disease, or one or more physiological conditions, disorders, illnesses, diseases, symptoms or complications caused by or associated with an allergen. A subject contacted by or exposed to an allergen may have contact or exposure over a period of 1-5, 5-10, 10-20, 20-30, 30-50, 50-100 hours, days, months, or years.

Invention compositions (e.g., proteins, peptides, subsequences, portions, homologues, variants or derivatives thereof, including T cell epitopes, for example, of an amino acid sequence of a protein or peptide set forth in Table 5 (SEQ ID NOs:1-1,411), Table 6, Table 7 (SEQ ID NOs:1,412-1,906) or Table 8 (SEQ ID NOs:1,907-2,008), methods and uses can be combined with any compound, agent, drug, treatment or other therapeutic regimen or protocol having a desired therapeutic, beneficial, additive, synergistic or complementary activity or effect. Exemplary combination compositions and treatments include multiple proteins, peptides, subsequences, portions, homologues, variants or derivatives thereof such as T cell epitopes as described herein (e.g., of an amino acid sequence of a protein or peptide set forth in Table 5 (SEQ ID NOs:1-1,411), Table 6, Table 7 (SEQ ID NOs:1,412-1,906) or Table 8 (SEQ ID NOs:1,907-2,008)), and second actives, such as anti-allergen compounds, agents, drugs, treatments and therapies, including but not limited to anti-histamines, anti-inflammatories, decongestants and corticosteroids as well as agents that assist, promote, stimulate or enhance efficacy. Such anti-allergen drugs, agents, treatments and therapies can be administered or performed prior to, substantially contemporaneously with or following any method or use described herein, for example, a therapeutic use or method of treating a subject for an allergic response, allergic disorder or allergic disease, or one or more physiological conditions, disorders, illnesses, diseases, symptoms or complications caused by or associated with an allergen, or a method or use of providing specific immunotherapy to a subject.

Accordingly, methods and uses include combinations of proteins, peptides, subsequences, portions, homologues, variants or derivatives thereof and second actives, and administering as a combination with a second active, or administered separately, such as concurrently or in series or sequentially (prior to or following) to administering a second active to a subject. The invention therefore provides combinations of one or more proteins, peptides, subsequences, portions, homologues, variants or derivatives thereof, in combination with a second active, including but not limited to any compound, agent, drug, therapeutic regimen, treatment protocol, process, remedy or composition, such as anti-histamine, anti-inflammatory, decongestant and corticosteroid, or immune tolerance stimulating, enhancing or augmenting protocol, or specific immunotherapy protocol set forth herein or known in the art. The compound, agent, drug, therapeutic regimen, treatment protocol, process, remedy or composition can be administered or performed prior to, substantially contemporaneously with or following administration of one or more proteins, peptides, subsequences, portions, homologues, variants or derivatives thereof, or a nucleic acid encoding all or a portion (e.g., a T cell epitope) of a protein, peptide, subsequence, portion, homologue, variant or derivative thereof, to a subject. Specific non-limiting examples of combination embodiments therefore include the foregoing or other compound, agent, drug, therapeutic regimen, treatment protocol, process, remedy or composition.

An exemplary combination is a protein, peptide, subsequence, portion, homologue, variant or derivative thereof, and a different protein, peptide, or subsequence, portion, homologue, variant or derivative thereof, of an amino acid sequence of a protein or peptide set forth in Table 5 (SEQ ID NOs:1-1,411), Table 6, Table 7 (SEQ ID NOs:1,412-1,906) or Table 8 (SEQ ID NOs:1,907-2,008). Another exemplary combination is a protein, peptide, subsequence, portion, homologue, variant or derivative thereof, and an immunological tolerance inducing molecule.

In invention methods and uses in which there is a desired outcome or effect, such as a therapeutic or prophylactic method or use that provides a benefit from treatment, protection, inducing immunological tolerance, vaccination or specific immunotherapy, a protein, peptide, subsequence, portion, homologue, variant or derivative thereof can be administered in a sufficient or effective amount. As used herein, a "sufficient amount" or "effective amount" or an "amount sufficient" or an "amount effective" refers to an amount that provides, in single (e.g., primary) or multiple (e.g., booster) doses, alone or in combination with one or more other compounds, treatments, therapeutic regimens or agents (e.g., a drug), a long term or a short term detectable or measurable improvement in a given subject or any objective or subjective benefit to a given subject of any degree or for any time period or duration (e.g., for minutes, hours, days, months, years, or cured).

An amount sufficient or an amount effective can but need not be provided in a single administration and can but need not be achieved by a particular protein, peptide, subsequence, portion, homologue, variant or derivative thereof, alone, optionally in a combination composition or method or use that includes a second active. In addition, an amount sufficient or an amount effective need not be sufficient or effective if given in single or multiple doses without a second or additional administration or dosage, since additional doses, amounts or duration above and beyond such doses, or additional antigens, compounds, drugs, agents, treatment or therapeutic regimens may be included in order to provide a given subject with a detectable or measurable improvement or benefit to the subject. For example, to increase, enhance, improve or optimize specific immunotherapy, after an initial or primary administration of one or more proteins, peptides, subsequences, portions, homologues, variants or derivative thereof, the subject can be administered one or more additional "boosters" of one or more proteins, peptides, subsequences, portions, homologues, variants or derivatives thereof. Such subsequent "booster" administrations can be of the same or a different type, formulation, dose, concentration, route, etc.

An amount sufficient or an amount effective need not be therapeutically or prophylactically effective in each and every subject treated, nor a majority of subjects treated in a given group or population. An amount sufficient or an amount effective means sufficiency or effectiveness in a particular subject, not a group of subjects or the general population. As is typical for such methods, different subjects will exhibit varied responses to a method of the invention, such as immunization, vaccination, specific immunotherapy and therapeutic treatments.

The term "subject" includes but is not limited to a subject at risk of allergen contact or exposure as well as a subject that has been contacted by or exposed to an allergen. A subject also includes those having or at risk of having or developing an immune response to an antigen or an allergen. Such subjects include mammalian animals (mammals), such as a non-human primate (apes, gibbons, gorillas, chimpanzees, orangutans, macaques), a domestic animal (dogs and cats), a farm animal (poultry such as chickens and ducks, horses, cows, goats, sheep, pigs), experimental animal (mouse, rat, rabbit, guinea pig) and humans. Subjects include animal disease models, for example, mouse and other animal models of allergic response known in the art.

Accordingly, subjects appropriate for treatment include those having or at risk of exposure to an antigen or allergen, also referred to as subjects in need of treatment. Subjects in need of treatment therefore include subjects that have been exposed to or contacted with an antigen or allergen, or that have an ongoing contact or exposure or have developed one or more adverse symptoms caused by or associated with an antigen or allergen, regardless of the type, timing or degree of onset, progression, severity, frequency, duration of the symptoms.

Target subjects and subjects in need of treatment also include those at risk of allergen exposure or contact or at risk of having exposure or contact to an allergen. Accordingly, subjects include those at increased or elevated (high) risk of an allergic reaction; has, or has previously had or is at risk of developing hypersensitivity to an allergen; and those that have or have previously had or is at risk of developing asthma.

The invention compositions, methods and uses are therefore applicable to treating a subject who is at risk of allergen exposure or contact but has not yet been exposed to or contacted with the allergen. Prophylactic uses and methods are therefore included. Target subjects for prophylaxis may be at increased risk (probability or susceptibility) of allergen exposure or contact as set forth herein. Such subjects are considered in need of treatment due to being at risk.

Subjects for prophylaxis need not be at increased risk but may be from the general population in which it is desired to protect a subject against an allergic response, allergic disorder or allergic disease, or one or more physiological conditions, disorders, illnesses, diseases, symptoms or complications caused by or associated with an allergen or to provide specific immunotherapy, for example. Such a subject that is desired to be protected against an allergic response, allergic disorder or allergic disease, or one or more physiological conditions, disorders, illnesses, diseases, symptoms or complications caused by or associated with an allergen or to be provided specific immunotherapy can be administered a protein, peptide, subsequence, portion, homologue, variant or derivative thereof. In another non-limiting example, a subject that is not specifically at risk of exposure to or contact by an allergen, but nevertheless desires protection against an allergic response, allergic disorder or allergic disease, or one or more physiological conditions, disorders, illnesses, diseases, symptoms or complications caused by or associated with an allergen, can be administered a protein, peptide, subsequence, portion, homologue, variant or derivative thereof. Such subjects are also considered in need of treatment.

"Prophylaxis" and grammatical variations thereof mean a method or use in which contact, administration or in vivo delivery to a subject is prior to contact with or exposure to an allergen. In certain situations it may not be known that a subject has been contacted with or exposed to an allergen, but administration or in vivo delivery to a subject can be performed prior to manifestation of an allergic response, allergic disorder or allergic disease, or one or more physiological conditions, disorders, illnesses, diseases, symptoms or complications caused by or associated with an allergen. For example, a subject can be provided protection against an allergic response, allergic disorder or allergic disease, or one or more physiological conditions, disorders, illnesses, diseases, symptoms or complications caused by or associated with an allergen or provided specific immunotherapy with a protein, peptide, subsequence, portion, homologue, variant or derivative thereof. In such case, a method or use can eliminate, prevent, inhibit, suppress, limit, decrease or reduce the probability of or susceptibility towards an allergic response, allergic disorder or allergic disease, or one or more physiological conditions, disorders, illnesses, diseases, symptoms or complications caused by or associated with an antigen/allergen.

"Prophylaxis" can also refer to a method or use in which contact, administration or in vivo delivery to a subject is prior to a secondary or subsequent exposure to an antigen/allergen. In such a situation, a subject may have had a prior contact or exposure to an allergen. In such subjects, an acute allergic reaction may but need not be resolved. Such a subject typically may have developed anti-allergen antibodies due to the prior exposure. Immunization or vaccination, by administration or in vivo delivery to such a subject, can be performed prior to a secondary or subsequent allergen exposure. Such a method or use can eliminate, prevent, inhibit, suppress, limit, decrease or reduce the probability of or susceptibility towards a secondary or subsequent allergic response, allergic disorder or allergic disease, or one or more physiological conditions, disorders, illnesses, diseases, symptoms or complications caused by or associated with an allergen. In certain embodiments, such a method or use includes providing specific immunotherapy to the subject to eliminate, prevent, inhibit, suppress, limit, decrease or reduce the probability of or susceptibility towards a secondary or subsequent allergic response, allergic disorder or allergic disease, or one or more physiological conditions, disorders, illnesses, diseases, symptoms or complications caused by or associated with an antigen/allergen.

Treatment of an allergic reaction or response can be at any time during the reaction or response. A protein, peptide, subsequence, portion, homologue, variant or derivative thereof, can be administered as a combination (e.g., with a second active), or separately concurrently or in sequence (sequentially) in accordance with the methods and uses described herein as a single or multiple dose e.g., one or more times hourly, daily, weekly, monthly or annually or between about 1 to 10 weeks, or for as long as appropriate, for example, to achieve a reduction in the onset, progression, severity, frequency, duration of one or more symptoms or complications associated with or caused by an allergic response, allergic disorder or allergic disease, or one or more physiological conditions, disorders, illnesses, diseases, symptoms or complications caused by or associated with an antigen/allergen.

Accordingly, methods and uses of the invention can be practiced one or more times (e.g., 1-10, 1-5 or 1-3 times) an hour, day, week, month, or year. The skilled artisan will know when it is appropriate to delay or discontinue administration. A non-limiting dosage schedule is 1-7 times per week, for 1, 2, 3, 4, 5, 6, 7, 8, 9, 10, 15, 20 or more weeks.

Doses can be based upon current existing protocols, empirically determined, using animal disease models or optionally in human clinical trials. Initial study doses can be based upon animal studies, e.g. a mouse, and the amount of protein, peptide, subsequence, portion, homologue, variant or derivative thereof, administered that is determined to be effective. Exemplary non-limiting amounts (doses) are in a range of about 0.1 mg/kg to about 100 mg/kg, and any numerical value or range or value within such ranges. Greater or lesser amounts (doses) can be administered, for example, 0.01-500 mg/kg, and any numerical value or range or value within such ranges. The dose can be adjusted according to the mass of a subject, and will generally be in a range from about 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, or more, two, three, four, or more times per hour, day, week, month or annually. A typical range will be from about 0.3 mg/kg to about 50 mg/kg, 0-25 mg/kg, or 1.0-10 mg/kg, or any numerical value or range or value within such ranges.

Doses can vary and depend upon whether the treatment is prophylactic or therapeutic, whether a subject has been previously exposed to the antigen/allergen, the onset, progression, severity, frequency, duration, probability of or susceptibility of the symptom, condition, pathology or complication, or vaccination or specific immunotherapy to which treatment is directed, the clinical endpoint desired, previous or simultaneous treatments, the general health, age, gender, race or immunological competency of the subject and other factors that will be appreciated by the skilled artisan. The skilled artisan will appreciate the factors that may influence the dosage and timing required to provide an amount sufficient for providing a therapeutic or prophylactic benefit.

Typically, for treatment, a protein, peptide, subsequence, portion, homologue, variant or derivative thereof, will be administered as soon as practical, typically within 1-2, 2-4, 4-12, 12-24 or 24-72 hours after a subject is exposed to or contacted with an allergen, or within 1-2, 2-4, 4-12, 12-24 or 24-48 hours after onset or development of one or more of an allergic response, allergic disorder or allergic disease, or one or more physiological conditions, disorders, illnesses, diseases, symptoms or complications caused by or associated with an antigen/allergen.

For prophylactic treatment in connection with vaccination or specific immunotherapy, proteins, peptides, subsequences, portions, homologues, variants or derivatives thereof, can be administered for a duration of 0-4 weeks, e.g., 2-3 weeks, prior to exposure to or contact by an allergen or at least within 1-2, 2-4, 4-12, 12-24, 24-48 or 48-72 hours prior to exposure to or contact by an allergen. For an acute allergic reaction, proteins, peptides, subsequences, portions, homologues, variants or derivatives thereof may be administered at any appropriate time.

The dose amount, number, frequency or duration may be proportionally increased or reduced, as indicated by the status of the subject. For example, whether the subject has an allergic response, whether the subject has been exposed to or contacted by an allergen or is merely at risk of allergen contact or exposure, whether the subject is a candidate for or will be vaccinated or provided specific immunotherapy. The dose amount, number, frequency or duration may be proportionally increased or reduced, as indicated by any adverse side effects, complications or other risk factors of the treatment or therapy.

In methods and uses of the invention, the route, dose, number and frequency of administrations, treatments, vaccinations and specific immunotherapy, and timing/intervals between treatment, vaccination and specific immunotherapy, and allergen exposure can be modified. Although rapid induction of immune responses or immunological tolerance is desired for developing protective emergency vaccines against an allergic response, allergic disorder or allergic disease, or one or more physiological conditions, disorders, illnesses, diseases, symptoms or complications caused by or associated with an allergen, in certain embodiments, a desirable treatment will elicit robust, long-lasting protection against an allergic response, allergic disorder or allergic disease, or one or more physiological conditions, disorders, illnesses, diseases, symptoms or complications caused by or associated with an allergen. Thus, in certain embodiments, invention compositions, methods and uses provide long-lasting protection against an allergic response, allergic disorder or allergic disease, or one or more physiological conditions, disorders, illnesses, diseases, symptoms or complications caused by or associated with an allergen. Specific immunotherapy strategies can provide long-lived protection against an allergic response, allergic disorder or allergic disease, or one or more physiological conditions, disorders, illnesses, diseases, symptoms or complications caused by or associated with an allergen depending on the level of induced immunological tolerance or a T cell response or activity.

Compositions, methods and uses include pharmaceutical compositions and formulations. In certain embodiments, a pharmaceutical composition includes one or more proteins, peptides, subsequences, portions, homologues, variants or derivatives thereof described herein (e.g., an amino acid sequence of a protein or peptide set forth in Table 5, Table 6, Table 7 or Table 8). In particular, aspects, such compositions and formulations may be a vaccine, including but not limited to a vaccine to protect against an allergic response, allergic disorder or allergic disease, or one or more physiological conditions, disorders, illnesses, diseases, symptoms or complications caused by or associated with an allergen.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

To increase an immune response, immunological tolerance or protection against an allergic response, allergic disorder or allergic disease, or one or more physiological conditions, disorders, illnesses, diseases, symptoms or complications caused by or associated with an allergen, proteins, peptides, subsequences, portions, homologues, variants or derivatives thereof, can be coupled to another protein such as ovalbumin or keyhole limpet hemocyanin (KLH), thyroglobulin or a toxin such as tetanus or cholera toxin. Proteins, peptides, subsequences, portions, homologues, variants or derivatives thereof can also be mixed with adjuvants.

Adjuvants include, for example: oil (mineral or organic) emulsion adjuvants such as Freund's complete (CFA) and incomplete adjuvant (IFA) (WO 95/17210; WO 98/56414; WO 99/12565; WO 99/11241; and U.S. Pat. No. 5,422,109); metal and metallic salts, such as aluminum and aluminum salts, such as aluminum phosphate or aluminum hydroxide, alum (hydrated potassium aluminum sulfate); bacterially derived compounds, such as Monophosphoryl lipid A and derivatives thereof (e.g., 3 De-O-acylated monophosphoryl lipid A, aka 3D-MPL or d3-MPL, to indicate that position 3 of the reducing end glucosamine is de-O-acylated, 3D-MPL consisting of the tri and tetra acyl congeners), and enterobacterial lipopolysaccharides (LPS); plant derived saponins and derivatives thereof, for example Quil A (isolated from the Quilaja *Saponaria* Molina tree, see, e.g., "Saponin adjuvants", Archiv. fur die gesamte Virusforschung, Vol. 44, Springer Verlag, Berlin, p 243-254; U.S. Pat. No. 5,057, 540), and fragments of Quil A which retain adjuvant activity without associated toxicity, for example QS7 and QS21 (also known as QA7 and QA21), as described in WO96/33739, for example; surfactants such as, soya lecithin and oleic acid; sorbitan esters such as sorbitan trioleate; and polyvinylpyrrolidone; oligonucleotides such as CpG (WO 96/02555, and WO 98/16247), polyriboA and polyriboU; block copolymers; and immunostimulatory cytokines such as GM-CSF and IL-1, and Muramyl tripeptide (MTP). Additional examples of adjuvants are described, for example, in "Vaccine Design—the subunit and adjuvant approach" (Edited by Powell, M. F. and Newman, M. J.; 1995, Pharmaceutical Biotechnology (Plenum Press, New York and London, ISBN 0-306-44867-X) entitled "Compendium of vaccine adjuvants and excipients" by Powell, M. F. and Newman M.

Cosolvents may be added to a protein, peptide, subsequence, portion, homologue, variant or derivative thereof, composition or formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters.

Supplementary compounds (e.g., preservatives, antioxidants, antimicrobial agents including biocides and biostats such as antibacterial, antiviral and antifungal agents) can also be incorporated into the compositions. Pharmaceutical compositions may therefore include preservatives, anti-oxidants and antimicrobial agents.

Preservatives can be used to inhibit microbial growth or increase stability of ingredients thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, ribavirin, valacyclovir, ganciclovir, 1,-D-ribofuranosyl-1,2,4-triazole-3 carboxamide, 9→2-hydroxyethoxy methylguanine, adamantanamine, 5-iodo-2'-deoxyuridine, trifluorothymidine, interferon and adenine arabinoside.

Pharmaceutical formulations and delivery systems appropriate for the compositions, methods and uses of the invention are known in the art (see, e.g., *Remington: The Science and Practice of Pharmacy* (2003) 20th ed., Mack Publishing Co., Easton, Pa.; *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms* (1993), Technonic Publishing Co., Inc., Lancaster, Pa.; Ansel ad Soklosa, *Pharmaceutical Calculations* (2001) 11th ed., Lippincott Williams & Wilkins, Baltimore, Md.; and Poznansky et al., *Drug Delivery Systems* (1980), R. L. Juliano, ed., Oxford, N.Y., pp. 253-315).

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include inhalation, respiration, intranasal, intubation, intrapulmonary instillation, oral, buccal, intrapulmonary, intradermal, topical, dermal, parenteral, sublingual, subcutaneous, intravascular, intrathecal, intraarticular, intracavity, transdermal, iontophoretic, intraocular, opthalmic, optical, intravenous (i.v.), intramuscular, intraglandular, intraorgan, or intralymphatic.

Formulations suitable for parenteral administration include aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

Methods and uses of the invention may be practiced by any mode of administration or delivery, or by any route, systemic, regional and local administration or delivery. Exemplary administration and delivery routes include intravenous (i.v.), intraperitoneal (i.p.), intrarterial, intramuscular, parenteral, subcutaneous, intra-pleural, topical, dermal, intradermal, transdermal, transmucosal, intra-cranial, intraspinal, rectal, oral (alimentary), mucosal, inhalation, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, or intralymphatic.

For oral administration, a composition can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, a composition can be delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

Invention proteins, peptides, subsequences, portions, homologues, variants or derivatives thereof optionally along with any adjunct agent, compound, drug, composition, whether active or inactive, etc., can be packaged in unit dosage form (capsules, tablets, troches, cachets, lozenges) for ease of administration and uniformity of dosage. A "unit dosage form" as used herein refers to physically discrete units suited as unitary dosages for the subject to be treated; each unit containing a predetermined quantity of active ingredient optionally in association with a pharmaceutical carrier (excipient, diluent, vehicle or filling agent) which, when administered in one or more doses, is calculated to produce a desired effect (e.g., prophylactic or therapeutic effect). Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Individual unit dosage forms can be included in multi-dose kits or containers. Pharmaceutical formulations can be packaged in single or multiple unit dosage form for ease of administration and uniformity of dosage.

The invention also provides methods of diagnosing and detecting an allergic response or allergy in a subject. The methods can be performed in solution, in solid phase, in silica, in vitro, in a cell, and in vivo. In one embodiment, a method includes contacting a cell (e.g., T cell) from the subject with a protein, peptide, subsequence, portion, homologue, variant or derivative thereof, as described herein (e.g., of an amino acid sequence of a protein or peptide set forth in Table 5 (SEQ ID NOs:1-1,411), Table 6, Table 7 (SEQ ID NOs:1,412-1,906) or Table 8 (SEQ ID NOs:1,907-2,008)); and determining if the protein or peptide modulates an immune response or activity of the contacted cell (e.g., T cell). A determination that the protein or peptide modulates an immune response or immune activity of the contacted cell indicates that the subject has an allergic response or an allergy, in particular, an allergy to the protein, peptide, subsequence, portion, homologue, variant or derivative thereof (e.g., of an amino acid sequence of a protein or peptide set forth in Table 5 (SEQ ID NOs:1-1,411), Table 6, Table 7 (SEQ ID NOs:1,412-1,906) or Table 8 (SEQ ID NOs:1,907-2,008)). In a particular aspect, the immune activity determined is Th2 cell reactivity. In another particular aspect, immune response or activity is determined by assaying for a cutaneous immunological hypersensitive reaction.

The terms "determining," "assaying" and "measuring" and grammatical variations thereof are used interchangeably herein and refer to either qualitative or quantitative determinations, or both qualitative and quantitative determinations, that involve manipulation or processing. When the terms are used in reference to measurement or detection, any means of assessing the relative amount, including the various methods set forth herein and known in the art, performed by the hand of man, is contemplated.

The invention provides kits including protein, peptide, subsequence, portion, homologue, variant or derivative thereof (e.g., of an amino acid sequence of a protein or peptide set forth in Table 5 (SEQ ID NOs:1-1,411), Table 6, Table 7 (SEQ ID NOs:1,412-1,906) or Table 8 (SEQ ID NOs:1,907-2,008)), combination compositions and pharmaceutical formulations thereof, packaged into suitable packaging material. Kits can be used in various in vitro, ex vivo and in vivo methods and uses, for example a treatment method or use as disclosed herein.

A kit typically includes a label or packaging insert including a description of the components or instructions for use in vitro, in vivo, or ex vivo, of the components therein. A kit can contain a collection of such components, e.g., a protein, peptide, subsequence, portion, homologue, variant or derivative thereof (e.g., of an amino acid sequence of a protein or peptide set forth in Table 5 (SEQ ID NOs:1-1,411), Table 6, Table 7 (SEQ ID NOs:1,412-1,906) or Table 8 (SEQ ID NOs:1,907-2,008)), alone, or in combination with another therapeutically useful composition (e.g., an immune modulatory drug).

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, use, treatment protocol or therapeutic regimen. Instructions can include dosage amounts, frequency or duration, and instructions for practicing any of the methods and uses, treatment protocols or therapeutic regimes set forth herein. Exemplary instructions include, instructions for modulating an immune response or activity of a cell against an allergen; modulating an immune response against an allergen in a subject; desensitizing, or inducing, eliciting, increasing or improving immunological tolerance to a protein or peptide allergen; reducing risk or providing a subject protection against an allergic reaction, allergic response, allergic disorder or allergic disease; treating an allergic reaction, allergic response, allergic disorder or allergic disease; or detecting an allergic response or diagnosing an allergy in a subject.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include other components. Each component of the kit can be enclosed within an individual container and all of the various containers can be within a single package. Invention kits can be designed for cold storage. Invention kits can further be designed to contain to the protein, peptide, subsequence, portion, homologue, variant or derivative thereof (e.g., of an amino acid sequence of a protein or peptide set forth in Table 5 (SEQ ID NOs:1-1,411), Table 6, Table 7 (SEQ ID NOs:1,412-1,906) or Table 8 (SEQ ID NOs:1,907-2,008)), or combination compositions or pharmaceutical compositions.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the invention is not entitled to antedate such publication by virtue of prior invention.

As used in this specification and the appended claims, the use of an indefinite article or the singular forms "a," "an" and "the" include plural reference unless the context clearly dictates otherwise. In addition, it should be understood that the individual peptides, proteins, antigens, allergens (referred to collectively as compositions), or groups of compositions, modeled or derived from the various components or combinations of the compositions, and substituents described herein, are disclosed by the application to the same extent as if each composition or group of compositions was set forth individually. Thus, selection of particular peptides, proteins, antigens, allergens, etc. is clearly within the scope of the invention.

As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs. As used herein, "about" means+ or −5%. The use of the alternative (e.g., "or") should be understood to mean one, both, or any combination thereof of the alternatives, i.e., "or" can also refer to "and."

As used in this specification and the appended claims, any concentration range, percentage range, ratio range or other integer range is to be understood to include the value of any integer within the recited range and, when appropriate, fractions thereof (such as one tenth and one hundredth of an integer), unless otherwise indicated. For example, although numerical values are often presented in a range format throughout this document, a range format is merely for convenience and brevity and should not be construed as an inflexible limitation on the scope of the invention. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, to illustrate, reference to a range of 90-100% includes 91-99%, 92-98%, 93-95%, 91-98%, 91-97%, 91-96%, 91-95%, 91-94%, 91-93%, and so forth. Reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 5-10, 10-20, 20-30, 30-40, 40-50, 50-75, 75-100, 100-150, and 150-175, includes ranges such as 5-20, 5-30, 5-40, 5-50, 5-75, 5-100, 5-150, 5-171, and 10-30, 10-40, 10-50, 10-75, 10-100, 10-150, 10-175, and 20-40, 20-50, 20-75, 20-100, 20-150, 20-175, and so forth. Further, for example, reference to a series of ranges of 2-72 hours, 2-48 hours, 4-24 hours, 4-18 hours and 6-12 hours, includes ranges of 2-6 hours, 2, 12 hours, 2-18 hours, 2-24 hours, etc., and 4-27 hours, 4-48 hours, 4-6 hours, etc.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. The invention is further exemplified by way of the following non-limited examples.

EXAMPLES

Example 1

This example includes a description of various materials and methods.

Patient Donor Population:

Patient recruitment for this study was performed at the University of California, San Diego (UCSD), and at National Jewish Health (NJH) in Denver, Colo., under each local IRB approved protocol, as well as LIAI Institutional Review Board IRB approved protocol VD1-059-0311 (Federal Wide Assurance #00000032). Informed consent, study ID numbers, clinical case histories and other information were collected and recorded by clinical investigators. Immediate hypersensitivity skin test reactivity to a panel of extracts from 28 common allergens, as well as positive (histamine), and negative controls (diluent), was determined by standard methods. Both wheal (mm) and flare (mm) were measured at 15 minutes. All volunteers were asked to provide a 5 ml serum sample and a unit of peripheral blood.

An allergic donor was defined based on a history of allergic rhinitis and a positive skin test (a wheal of at least 3 mm in diameter greater than the diluent negative control) to one or more of the allergens tested. A total of 87 allergic donors were investigated. The donor cohort included 45 females and 42 males, and ranged between 20-63 years of age. Of the 87 donors, 52 had rhinitis and another 29 were categorized as having rhinitis and asthma (6 were not classified).

The main goal was to identify a majority of the epitopes that are frequently recognized in the human population. By analyzing at least ten donors for each allergen of interest, the sample size is sufficient such that 80% of all epitopes that are recognized in 15% or more allergic individuals in the general population are expected to give a positive response in one or more of the ten individuals in our study (assuming a binomial distribution). Similarly, 95% of all epitopes recognized in 40% of the allergic population are expected to give responses in two or more individuals in the study. Based on these considerations, studying ten donors per allergen is sufficient to identify targets of frequent responses.

Bioinformatic Analyses:

Uniprot accession IDs for each of a panel of 28 common allergens were collected from the IUIS Allergen Nomenclature database, then used to retrieve sequences from the Uniprot database (Table 5, SEQ ID NOs:1-1,411). For those allergens without Uniprot IDs, we used the sequences provided by IUIS. If an allergen (e.g. Alt a1) had multiple sequences, a representative sequence for each allergen was selected. The representative sequence should have the longest length and greatest sequence coverage (or sequence identity >90%) compared to other sequences. If the sequence identity between two sequences that belong to the same allergen is <40%, both sequences were selected. As a result, 169 non-redundant sequences were identified.

Sequences, including isoforms, were then scanned for unique 15-mer peptides overlapping by 10 residues. Each peptide was then predicted for its capacity to bind to a panel of 20 of the most common HLA class II alleles (DPA1*0103/DPB1*0201, DPA1*0201/DPB1*0101, DPA1*0201/DPB1*0501, DPA1*0301/DPB1*0402, DQA1*0101/DQB1*0501, DQA1*0301/DQB1*0302, DQA1*0401/DQB1*0402, DQA1*0501/DQB1*0301, DRB1*0101, DRB1*0301, DRB1*0401, DRB1*0405, DRB1*0701, DRB1*0802, DRB1*1101, DRB1*1302, DRB1*1501, DRB3*0101, DRB4*0101, DRB5*0101) using the consensus prediction described in (19). Peptides with predicted binding scores in the top 20% for a given allele were considered potential binders, and the number of HLA molecules each peptide was predicted to bind was enumerated. All peptides predicted to bind 10 or more HLA molecules were selected for synthesis and further study.

To make sure each allergen is adequately represented in the peptide set, at least 2 peptides were included for each allergen. It was further stipulated that these 2 peptides should not be located in the first 20 residues (which likely contain signal sequences), and that the 2 peptides should not directly overlap (e.g. peptide 56-70 and 61-75). These additional requirements could be met for all but 4 proteins (Sec c 1, Sec c 20, Ant o 1, Dac g 2) for which only fragmentary sequence information was available. The complete list of Peptides is shown in Table 5.

Peptide Synthesis:

Peptides for screening studies were purchased from Mimotopes (Clayton, Victoria, Australia) and/or A and A (San Diego, Calif.) as crude material on a small (1 mg) scale. Peptides utilized as radiolabeled ligands were synthesized on larger scale, and purified (>95%) by reversed phase HPLC.

HLA Binding Assays:

Assays to quantitatively measure peptide binding to MHC class II molecules, based on the inhibition of binding of a high affinity radiolabeled peptide to purified MHC molecules, have been described in detail elsewhere (20). Briefly, MHC molecules were purified from EBV transformed homozygous cell lines by monoclonal Ab-based affinity chromatography. HLA-DR, DQ and DP molecules were captured by repeated passage of lysates over LB3.1 (anti-HLA-DR), SPV-L3 (anti-HLA-DQ) and B7/21 (anti-HLA-DP) columns.

For inhibition experiments, 0.1-1 nM of radiolabeled peptide was co-incubated at room temperature or 37° C. with 1 µM to 1 nM of purified MHC in the presence of a cocktail of protease inhibitors and various amounts of inhibitor peptide. Following a 2 to 4 day incubation, the percent of MHC bound radioactivity was determined by capturing MHC/peptide complexes on LB3.1 (DR), L243 (DR), HB180 (DR/DQ/DP), SPV-L3 (DQ) or B7/21 (DP) Ab coated Optiplates (Packard Instrument Co., Meriden, Conn.), and bound cpm measured using the TopCount (Packard Instrument Co.) microscintillation counter. Inhibitor peptides were tested in at least three or more independent assays at six different concentrations covering a 100,00-fold dose range. Under the conditions utilized, where [label]< [MHC] and IC50≥[MHC], the measured IC50 values are reasonable approximations of the true Kd values (21, 22).

PBMC Isolation and HLA Typing:

PBMC were obtained by density gradient centrifugation (Ficoll-Hypaque, Amerhsam Biosciences, Uppsala, Sweden) from one unit of blood (450 ml), according to manufacturer's instructions, and cryo-preserved for further analysis. An aliquot of serum was obtained for RAST IgE and IgG analyses (performed at NJMRC, Denver, Colo. & Phadia).

HLA typing was performed according to standard methods. Briefly, genomic DNA isolated from PBMC of the study subjects by standard techniques (QIAmp, Qiagen, Valencia, Calif.) was used for HLA typing. High resolution Luminex-based Sequence-Specific Oligonucleotide (SSO) typing for HLA Class I and Class II was utilized according the manufacturer's instructions (One Lambda, Canoga Park, Calif.). Where needed, PCR based Sequence-Specific Primer (SSP) typing methods were used to provide high resolution sub-typing (One Lambda, Canoga Park, Calif.).

In Vitro Expansion of Allergen-Specific T Cells:

PBMCs were cultured in RPMI 1640 (V Scientific, Tarzana, Calif.) supplemented with 5% human serum (Cellgro, Herndon, Va.) at a density of 2×106 cells/ml in 24-well plates (BD Biosciences, San Jose, Calif.) and stimulated with 2 to 50 µg/ml of allergen extract (Greer, Lenoir, N.C.) depending on the allergen (Table 6). Cells were kept at 37° C. in 5% CO2 and additional IL-2 (10 U/ml; eBioscience, San Diego, Calif.) was added every 3 days after initial antigenic stimulation. On day 14, cells were harvested and screened for reactivity against the allergen-specific peptide pools or individual peptides. LPS content of the various extracts was measured by Indoor Biotechnologies (Charlottesville, Va.) using standard Limulus Amebocyte Lysate (LAL) methodology.

ELISPOT Assays:

The production of IL-5 and IFN-γ was analyzed in ELISPOT assays. Flat-bottom 96-well nitrocellulose plates (Millipore, Bedford, Mass.) were prepared according to manufacturer's instructions and coated with 10 µg/ml anti-human IL-5 (Clone TRFK5; Mabtech, Cinncinati, Ohio) and anti-human IFN-γ (Clone 1-D1K; Mabtech, Cincinnati, Ohio). Cells were then incubated at a density of 1×105/well either with peptide pools or individual peptides (10 µg/ml), extract (2-50 µg/ml), PHA (10 µg/ml), or medium containing 0.1% DMSO (corresponding to the percentage of DMSO in the pools/peptides) as a control. After 24 hours, cells were removed, and plates were incubated with either 2 µg/ml biotinylated anti-human IL-5 Ab (Mabtech) and 1:200 HRP-conjugated antihuman IFN-γ Ab (Mabtech) at 37° C. After 2 hours, spots corresponding to the biotinylated Abs (IL-5) were developed by incubation with Alkaline Phosphatase-Complex (Vector Laboratories, Burlingame, Calif.) followed by incubation with Vector Blue Alkaline Phosphatase Substrate Kit III (Vector Laboratories) according to the manufacturer's instructions. Spots corresponding to the HRP-conjugated Ab (IFN-γ) were developed with 3-amino-9-ethylcarvazole solution (Sigma-Aldrich, St. Louis, Mo.). Spots were counted by computer-assisted image analysis (Zeiss, KS-ELISPOT reader, Munich, Germany).

Each assay was performed in triplicate. The level of statistical significance was determined with a Student's t-test using the mean of triplicate values of the response against relevant pools or individual peptides versus the response against the DMSO control. Criteria for peptide pool positivity were 100 spot-forming cells (SFCs)/106 PBMC, p≤0.05 and a stimulation index (SI)≥2, while criteria for individual peptide positivity were ≥20 SFC/106 PBMC, p≤0.05, and a SI≥2. The SFC/10^6 criteria utilized (in conjunction with also passing a T test with p<0.05, and a SI>2) have been used in several recent studies from our group (see, e.g., 16-19, 31-36). In particular, in the context of allergen epitope identification, a recent study analyzing responses to Timothy Grass allergens validated much of the methodology applied in the present study. Together, in these studies it was also noted that, in general, epitope pools yielding significant but relatively weaker responses (in the 20 to 100 SFC range) did not lead to the identification of significant and consistent responses at the level of individual peptides. For this reason, and because cells are often limiting, and pool deconvolution is the most demanding step in terms of cell requirement, in those studies, as well as in the present study, only pools yielding 100 SFC/10^6 were deconvoluted.

HLA Restriction:

To determine the HLA locus restriction of identified epitopes, mAb inhibition assays were performed as described previously (11, 37). Preliminary determinations were made on control T cell clones of known specificity to determine optimal antibody doses leading to complete inhibition of the specific clones, and not associated with inhibition of clones known to be restricted by a different HLA allele or locus. This antibody concentration was then utilized in experiments where a dose response of antigenic peptide was tested in the presence or absence of the specific antibodies. Experimental determinations were performed utilizing ELISPOT assays specific for the particular lymphokine utilized to originally identify the particular epitope mapped.

For each antigenic region/donor combination short-term T cell lines were derived by extract stimulation of triplicate cultures of 2-3 million cells. IL-2 was added 5-8 days following stimulation. After 14 days of stimulation with the corresponding allergen extract (2-50 µg/ml), the HLA locus that restricted the response to the specific lymphokine was determined by measuring the capacity of mAbs specific for HLA-DR, DP or DQ to inhibit (block) the response. For this, PBMCs were incubated with 10 µg/ml of mAbs (Strategic Biosolutions, Windham, Me.) against HLA-DR (LB3.1), DP (B7/21) or DQ (SVPL3) 30 minutes prior to addition of 10 µg/ml of peptide. Cytokine production induced by positive peptides was then measured in ELISPOT assays as described above. The pan MHC class I Ab (W6/32) was used as a control. The decrease (inhibition) in cytokine production in the presence of an HLA locus specific mAb, relative to production in the absence of mAb, was determined. A response was considered as restricted by HLA alleles at a specific locus when ≥50% inhibition of the response was observed in the presence of the corresponding mAb.

Example 2

This example includes a description of the identification of 257 different antigenic regions from common allergen sources.

T cell responses to complex allergens in humans are very heterogeneous and involve recognition of a large number of epitopes (3-18). Recent work demonstrated that the most dominant and prevalent responses could be predicted on the basis of their capacity to bind multiple HLA class II molecules. Here, this approach was used to investigate a large panel of allergen proteins derived from 28 different allergen sources.

This study broadly addressed inhalants and contact allergens, including allergens derived from fungi (*Alternaria, Aspergillus, Cladosporuim* and *Penicillium*), trees (Alder, Ash, Birch, Black Walnut, Cypress, Juniper, Oak and Palm), grasses (Bermuda, Canary, Kentucky Blue, Orchard, Rye and Sweet Vernal), weeds (English Plantain, Giant Ragweed, Mugwort, Russian Thistle, and Western Ragweed) and various indoor allergens (American Cockroach, Cat dander, Dog dander and Dust Mites) (Table 1). These allergen sources were selected because of their common diagnosis by extract reactivity in allergic patients at the two participating clinical sites, and availability in the IUIS database of at least some allergen protein sequences (a complete list of these allergen proteins is provided in Table 5 (SEQ ID NOs:1-1,411). The strategy was utilized to predict potential allergen derived T cell epitopes.

In the studies, In vitro stimulation for a 14-17 day period was utilized. As shown in FIG. 1, additional data from three individual donors for two different allergen sources (*Alternaria* and Rye Grass) demonstrate that both IFN-γ and IL-5 responses are optimally detected in the 14-17 day window. The doses of individual extracts used for In vitro stimulation were chosen on the basis of initial dose titration experiments. For each extract the magnitude of responses, as well as cell viability at the end of the In vitro stimulation step, were noted. For certain extracts toxicity (loss of viability) was observed. In all studies highest dose not associated with noticeable toxicity was used. The exact dose utilized for each extract source is shown in Table 6.

As described in the Materials and Methods, peptides ranking in the top 20% of predicted affinities for 10 or more of 20 common HLA class II alleles were selected for synthesis and further analysis. In total (see Table 1), 133 different proteins were analyzed, and a total of 1411 predicted promiscuous binders were synthesized, corresponding to an average of 10.6 peptides per protein. On average, about 50 peptides were made for each allergen source, with a range of 3 to 229 (a list of the peptides synthesized is also provided in Table 5 (SEQ ID NOs:1-1,411).

Short-term lines stimulated with extract, as described above, were tested with pools of 15-20 peptides from the proteins of the corresponding allergen, and then individual epitopes were identified by deconvolution of positive pools (11). The dose of peptide utilized in the experiments was selected based on the fact that for pools of 20 peptides, in which the initial individual peptide stocks are 40 mg/ml in 100% DMSO, the highest final concentration of each individual peptide that can be achieved, without reaching a total pool DMSO concentration that is toxic in the assay (0.25-0.5%), is 4-5 µg/ml. A dose of 10 µg/ml was used for experiments with single peptide stimulations. This is consistent with our experience in other systems (see, e.g., 11, 17, 21, 31, 33, 38), and is also a dose routinely used in the literature relating to stimulation of human class II restricted T cells.

Figure 2:
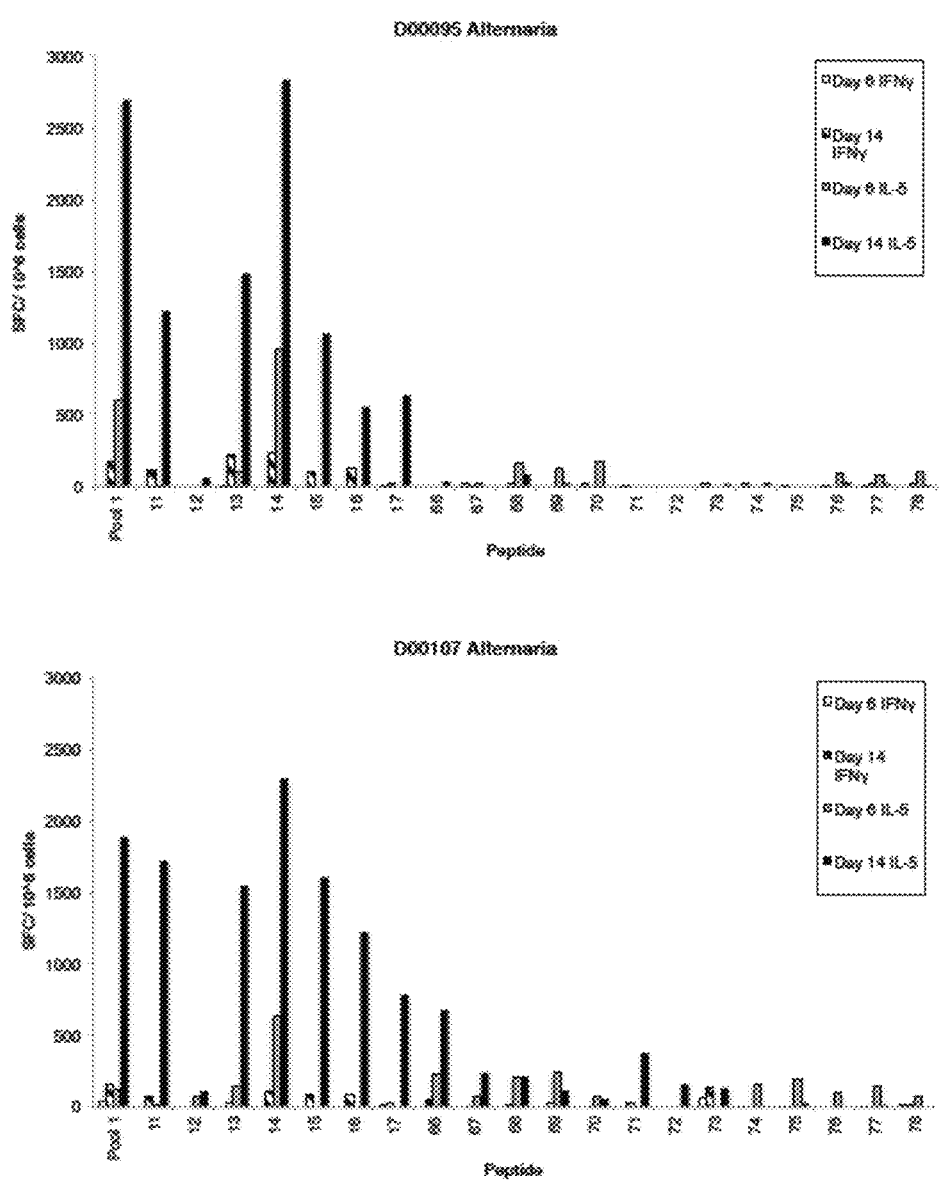
FIG. 2 shows a comparison of *Alternaria* epitopes identified on days 6 and 14 in two representative donors (D00095 and D00107). IL-5 or IFN-γ ELISPOT assays were performed, and positive responses defined, as described in Material and Methods. In terms of IL-5 responses in donor D00095, only peptide 14 was recognized on day 6; by day 14, peptides 11, 13, 14, 15, 16 and 17 were all positive. Similarly, in donor D00107 peptides 14 and 66 gave positive responses on days 6 and 14, while peptides 11, 12, 13, 15, 16, and 17 only gave responses on day 14. For IFN-γ, in both donors positive responses were only seen on day 14.

An additional issue to be addressed is whether different epitopes may be recognized on day 6 compared to day 14 of cultures. To address this issue, the pattern of epitopes identified was compared for two representative donors (D00095 and D00107) in the *Alternaria* system. The data, shown in FIG. 2, illustrate how the epitopes identified on day 6 were also identified on day 14. In addition, because of the stronger signal obtained on day 14, additional peptides that would have been missed on day 6 are revealed at the day 14 time-point.

Figure 3:
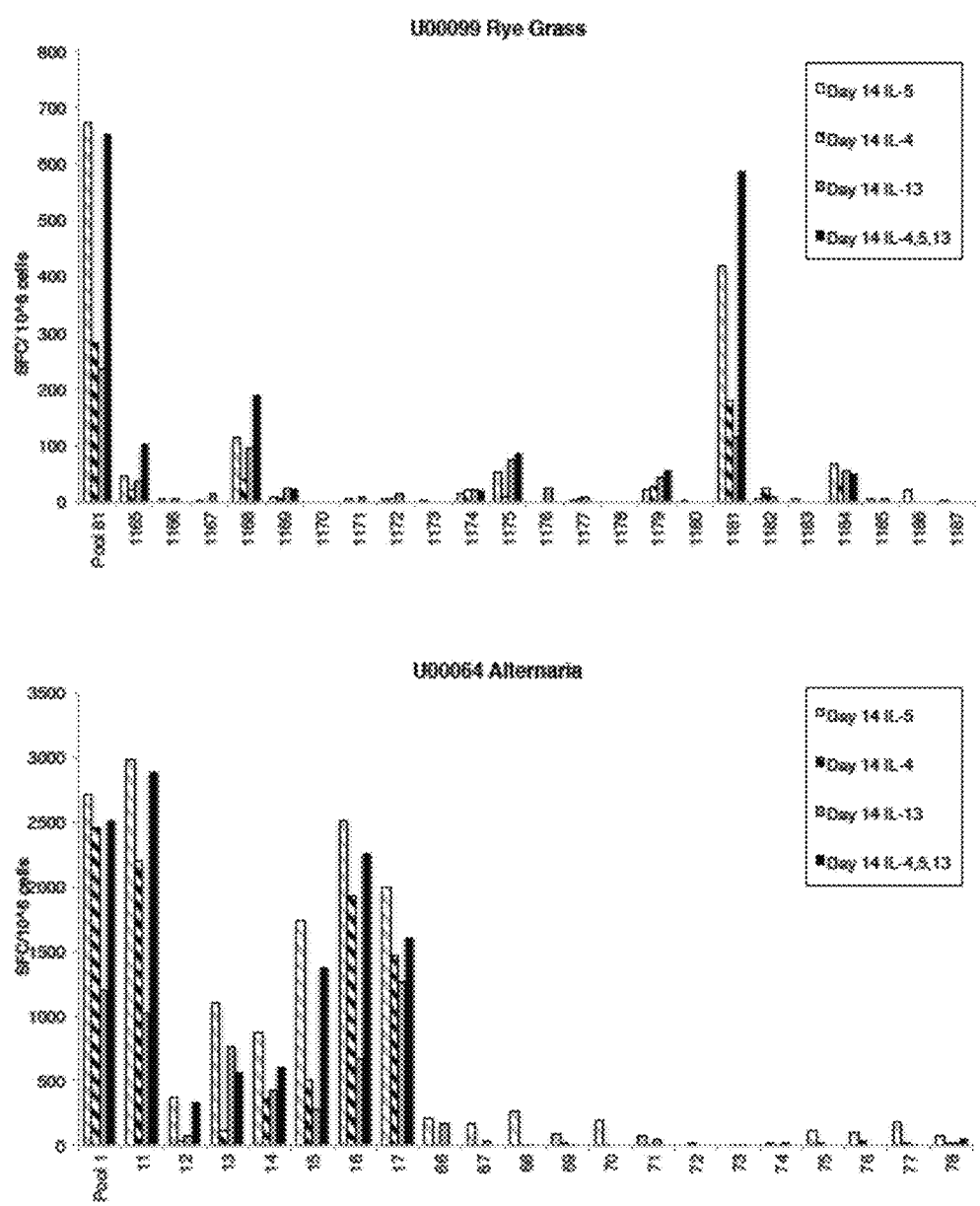
FIG. 3 shows a comparison of allergen epitope induced IL-4, -5 and -13 responses from cells in representative donors in response to *Alternaria* and Rye Grass peptides. Responses to IL-4, -5 and -13 were measured on day 14, as described herein. In donor U00064 *Alternaria* peptides 11, 13, 14, 15, 16, and 17 induced IL-5, IL-4 and IL-13 responses. Additionally, IL-5 responses were induced by peptides 12, 66, 67, 68 and 70. The data show that all epitopes inducing IL-4 and IL-13 responses also induced IL-5 responses. A similar pattern was noted in donor U00099 in response to Rye Grass peptides, where peptides 1168, 1175, 1181 and 1184 all induced IL-5 responses, and the same peptides encompassed all IL-4 and IL-13 responses.

Different lymphokines are differentially produced and regulated (39). However, in our experience, the epitopes that are recognized by IL-5 producing cells are essentially the same ones recognized by IL-4/IL-13 producing cells. Furthermore, IL-5 and IL-4/IL-13 producing cells are largely overlapping. Accordingly, the present study focused on IL-5 as a representative lymphokine of the Th2 lineage. To illustrate the rationale, FIG. 3 summarizes an analysis of IL-4, IL-5 and IL-13 producing cells in representative donors in response to *Alternaria* and Rye Grass peptides. These data demonstrate that, indeed, the epitopes recognized by IL-5 producing cells are the same ones recognized by IL-4/IL-13 producing cells. Furthermore, the data show that IL-5 and IL-4/IL-13 producing cells are largely overlapping and that there is little to gain by measuring all three lymphokines. Thus, while measuring all three lymphokines separately would be of obvious interest, it essentially doubles the number of cells required, and thus would not be easily compatible with the large number of allergens studied, and the relatively high-throughput nature of the assay strategy utilized in the present study.

PBMC from donors with positive skin tests to the allergen in question were restimulated In vitro with the various corresponding allergen extracts. Allergen extract stimulation was effective in most of the donors (94% overall, and on average across all sources; range 67 to 100% for the different extracts; Table 6). These short-term, extract-stimulated, lines were tested with pools of 15-20 peptides from the proteins of the corresponding allergen, and then individual epitopes were identified by deconvolution of positive pools (11). For each allergen source, we tested PBMCs from at least ten different allergic donors (range 10-15, average 11), as determined by skin test to the corresponding allergen. in standard dual ELISPOT assays detecting IFN-γ and IL-5.

Although this may be considered to be a limited number of donors, this number was chosen to enable identification of epitopes that are most frequently recognized in the donor population, consistent with the promiscuous HLA binding principle used to select the candidate epitopes. According to power calculations, by studying the response in 10 allergic donors, 80% of all epitopes that are recognized in 15% or more allergic individuals in the general population would be identified (assuming a binomial distribution). Similarly, 95% of all epitopes recognized in 40% of the allergic population are expected to give responses in two or more individuals in our study. This is consistent with the scope of the current investigation, which was to survey a large number of allergen sources, side-by-side, utilizing the same experimental design, and characterizing the most dominant responses.

In total, 322 peptides were positive in at least one donor. ELISPOT results from each individual peptide are presented in Table 7 (SEQ ID NOs:1,412-1,906). The high rate at which predicted peptides were found to be antigenic (322/1405=22.9%) demonstrates the power of the approach based on prediction of promiscuous HLA class II binding. Some epitopes were highly homologous because they were derived from allergen isoforms, or from the same allergen protein and covered largely overlapping regions. After removal of redundancies and consolidation of largely overlapping regions, a total of 289 unique epitopes, corresponding to 257 distinct antigenic regions, were identified (Table 1).

Example 3

This example includes a description of the allergen epitopes identified.

The sequences of the 257 antigenic regions identified were compared to the known human Class II/CD4 epitopes curated in the IEDB (www.iedb.org; (23)). To obtain a data set with characteristics comparable to the one obtained in the screening described herein, the IEDB was queried for all epitopes defined in human hosts, either ex vivo or by utilizing short-term lines, and for which CD4/class II restriction could either be demonstrated or inferred on the basis of the assay methodology. This analysis determined the extent to which the identified epitopes were novel or previously cited.

Overall, epitopes were identified for 25 of the 28 allergen sources studied. For 14 of the allergen sources, no epitope could be found in the IEDB that satisfied the criteria defined above for any of the epitopes identified for the allergen (Table 2A). By contrast, and as expected, in the cases of 11 other allergen sources which have been previously and more extensively studied, many of the epitopes identified mapped to regions reported as being antigenic in allergic patients (Table 2B). Nonetheless, in those cases, 84% of the epitopes identified had not been previously reported.

Conversely, only 38% of the epitopes already curated by the IEDB were re-identified by the present study. This is consistent with the results obtained in a Timothy Grass study, which estimated that the predictive approach would identify the most dominant and prevalently recognized epitopes, corresponding to about 50% of the total T cell response (3). Thus, the analysis presented in this section underscores the novel nature of a large number of the epitopes identified in the current study.

Example 4

This example includes an analysis of the distribution of epitopes identified as a function of the various allergen sources.

As mentioned above, allergen extract stimulation was effective in 95% of the donors. However, in some cases a relatively large number of epitopes were identified, while in other cases the screen revealed no, or only a few, epitopes. To quantitatively express these variations, for each allergen source the ratio of the total epitope specific IL-5 and IFNγ response to the total response observed against the corresponding crude allergen extract was calculated (Table 3).

In 16 cases the peptide specific responses corresponded to 15% or more of the response detected against the extract, while in 12 cases the peptide responses totaled less than this arbitrary threshold. Indeed, the 16 allergen sources associated with the larger total peptide responses accounted for 230 of the 257 (89%) epitope regions identified, and 74 of the 81 (91%) regions recognized by 2 or more donors (see also Table 7, SEQ ID NOs:1,412-1,906).

When the number of known allergenic proteins described in the IUIS database, and utilized for the present analysis, was scrutinized (Table 3), a correlation between the fraction of the extract response that could be attributed to the peptides studied, and the number of representative protein sequences available, became apparent. In other words, the sources for which the set of T cell epitopes identified accounted for only a minor fraction of the extract response were represented by fewer protein sequences (median 1.5) as compared to the sources where the epitopes accounted for a larger fraction of the extract response (median 5 protein sequences, RS=0.49; p=0.01). These results suggest that, in the cases of the "low epitope coverage" allergen sources, the number of antigenic T cell targets was too limited to allow for capture of the complexity of responses. Thus, it is likely that for these sources additional allergens exist.

Exceptions to this trend were noted, however. For example, in the case of White Oak, only one protein was represented in the IUIS. However, peptides from that one protein accounted for almost 50% of the extract response. Other instances where an appreciable fraction (21-47%) of the extract response was associated with just a few proteins were also noted. Indeed, as shown in Table 3, for 5 of the 16 allergens for which >15% of the extract response was identified with antigen specific peptide pools, only one or two proteins were available for study. These data suggest that for these allergen sources the major T cell epitopes are derived from a limited number of proteins. Conversely, it is remarkable that for some organisms, such as *Aspergillus*, where many proteins were scanned (n=23), only a few (n=1) were found to have epitopes. Finally, in some cases, such as American Cockroach, the paucity of epitopes might be reflective of the weak level of sensitization of the particular patient population investigated in this study, as judged by low skin test reactivity.

Example 5

This example includes a description of promiscuous restriction of dominant epitopes.

The next series of studies was focused on 74 epitope regions that were recognized in two or more donors and derived from the 16 allergen sources in which peptide specific responses could account for 15% or more of the responses detected with the extract. These more prominent epitopic regions, listed in Table 4, accounted for 70% of the total SFC response detected against all of the epitope regions identified from these 16 different allergen sources.

Figure 4:
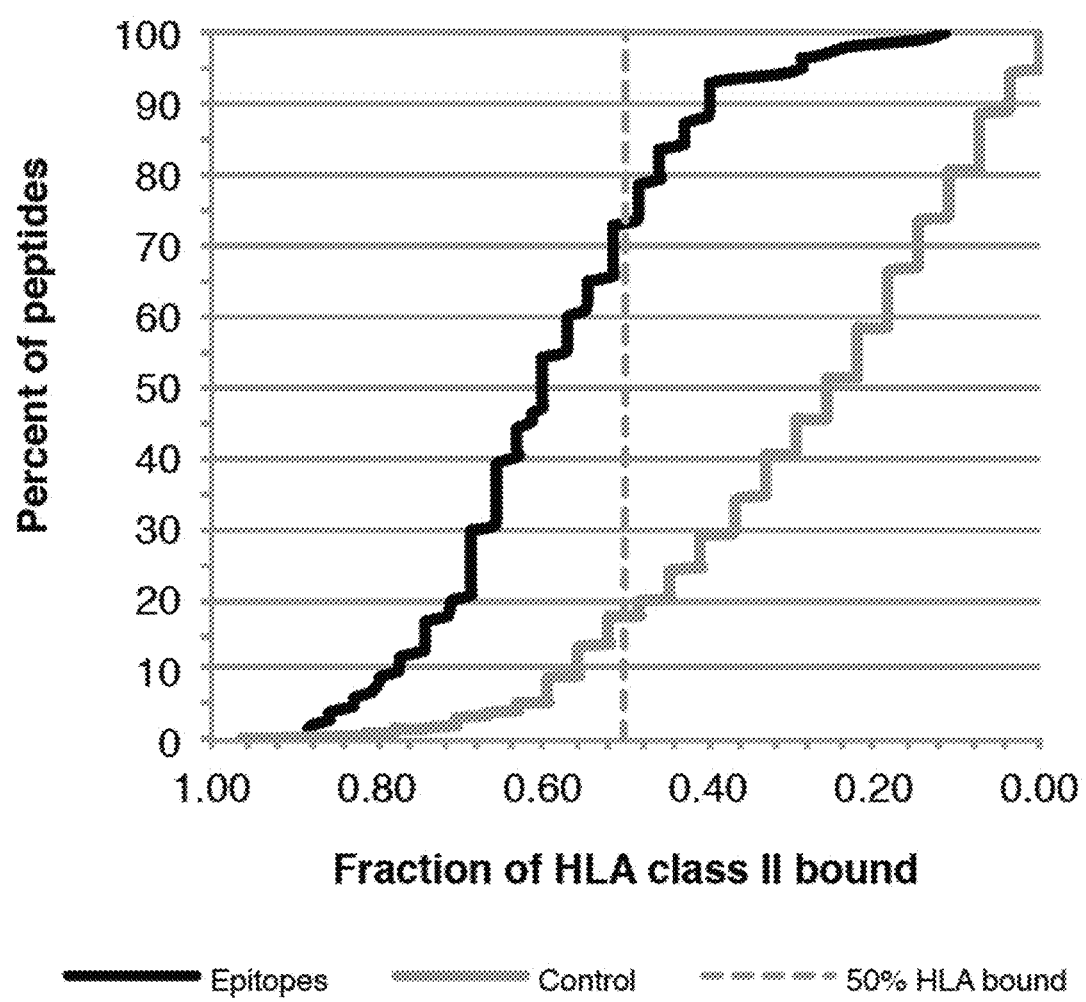
FIG. 4 shows promiscuous HLA binding capacity of dominant epitopes. Individual 15-mer epitopes (n=96) from the 74 epitope regions derived from the 16 allergen sources where peptide specific responses could account for 15% or more of the responses detected with the extract, and that were recognized in two or more donors, were tested for their capacity to bind a panel of 35 different DR, DP and DQ molecules. The cumulative percentage of epitopes (black line) binding various fractions of the class II panel is shown. 73% of the epitopes bound 50% or more of the molecules tested with an affinity of 1000 nM, or better. Also shown is the cumulative percentage of peptides in a control panel of 425 unbiased, non-redundant, peptides binding various fractions of the same class II panel; only 17% of the control peptides bound 50% or more of the molecules tested.

Each of the individual 15-mer peptides associated with these regions was tested for its capacity to bind a panel of 35 different DR, DP and DQ molecules representative of the most common allelic variants worldwide (24-26), including all 20 molecules comprising the prediction panel. It was found that 73% of the epitopes bound 50% or more of the molecules tested with an affinity of 1000 nM, or better (FIG. 4; binding data for each peptide is presented in Table 8, SEQ ID NOs:1,907-2,008). By contrast, in a control set of a panel of 425 unbiased, non-redundant, peptides representing 15-mers, overlapping by 10 residues, spanning the entire sequences of the *P. pratense* 1, 2, 3, 4, 5, 6, 7, 11, 12, and 13 pollen antigens, only 17% bound 50% or more of the same molecules. As the allergen-derived peptides tested herein were selected on the basis of predicted promiscuous HLA class II binding capacity, overall, these data support the validity of the predictive approach for identification of promiscuous binding peptides.

Based on the predictive approach taken and the data presented above, it was expected that a diverse set of HLA allelic variants would be restricting the T cell responses to the epitopes identified. To address this issue experimentally, the HLA locus restriction of the more frequently recognized epitopes was determined by inhibition experiments utilizing DR-, DP- and DQspecific antibodies. Locus restriction could be determined for a total of 65 antigenic regions (Table 4). In the remaining combinations (about a third of the cases), locus restriction could not be determined, either due to a scarcity of cells, low responses, or because 50% inhibition by locus specific mAb could not be achieved, perhaps reflective of promiscuous locus restriction at the level of individual donors.

Multiple restricting loci were observed in about a third of the cases (21/65; 32.3%). Furthermore, in 10 of the 17 (59%) cases where a single locus was indicated by the antibody inhibition experiments as restricting a specific epitope in multiple donors, no single allelic variant capable of binding the epitope In vitro was shared by all of the responding donors, thus implying intra-locus promiscuous restriction as well. Overall, the data presented in this section highlights the promiscuous restriction of the more prevalent and dominant epitopes identified.

Example 6

This example includes a description of studies showing that T cell responses to different allergen sources are differentially polarized.

Figure 5:
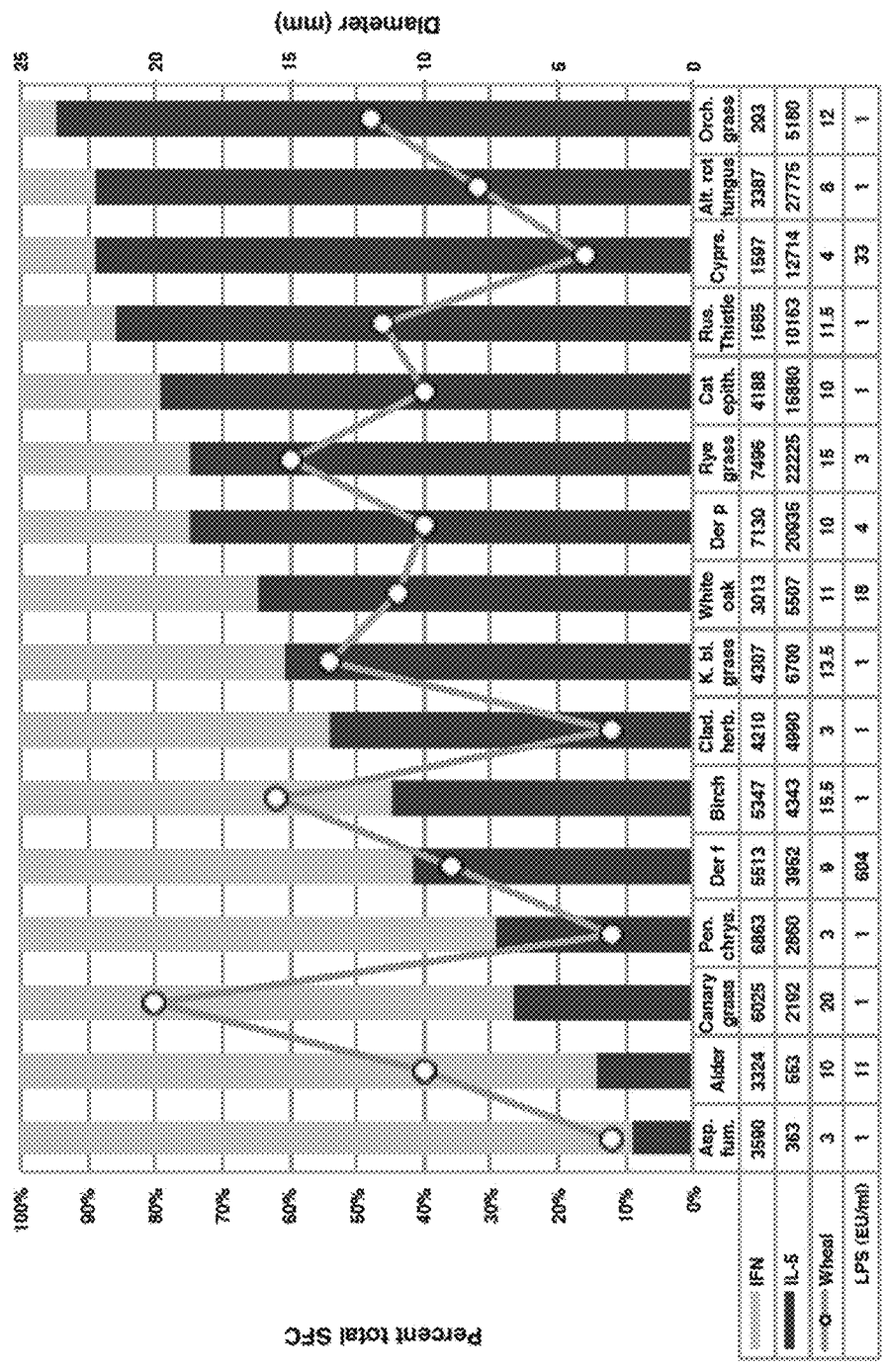
FIG. 5 shows T cell responses to different allergen sources are differentially polarized. Percentage of the total response to the various allergen sources attributable to IL-5 or IFN-γ, representative of Th2 and Th1 responses, respectively, are shown as a bar graph. Median whealsize (mm in diameter) measured in correspondingly allergic donors are plotted on the secondary axis.

As described herein, the epitope specific responses for the various allergen sources were determined by utilizing both IL-5 and IFN-γ ELISPOT assays. These lymphokines were chosen as prototype Th2 and Th1 responses, respectively. For each of the allergen sources, next the relative proportion of the response attributed to each of these two lymphokines was inspected. As expected, overall IL-5 production exceeded IFN-g production by a ratio of approximately 2:1. Interestingly, however, different patterns were noted for individual allergen sources (FIG. 5). In some cases (e.g., Orchard grass, *Alternaria*, Cypress, and Russian Thistle), IL-5 production exceeded IFN-g production by 5-10-fold. In other cases (e.g., *Aspergillus*, Penicillum, and Alder), the converse was noted, as production of IFN-g exceed IL-5 production by more than 3-10-fold. These results suggest that different allergen sources are associated with different degrees of polarization of the responding T cell subsets. It was hypothesized that differential polarization may correlate with the skin test response, such that a late phase skin response may associate more frequently with the Th1-type allergen/epitope. However, examination of the data revealed no discernable trend (FIG. 5).

Similarly, it was hypothesized that the polarization observed was due to the different allergenic extracts having different levels of LPS content. When the LPS content of the various extracts was measured (see the table embedded in FIG. 5) there was no correlation (r=0.14, −0.16 and −0.16 for IFNγ, IL-5 and the IFNγ/IL-5 ratio, respectively) between the LPS content the Th1/Th2 skewing we observed.

Figure 6:
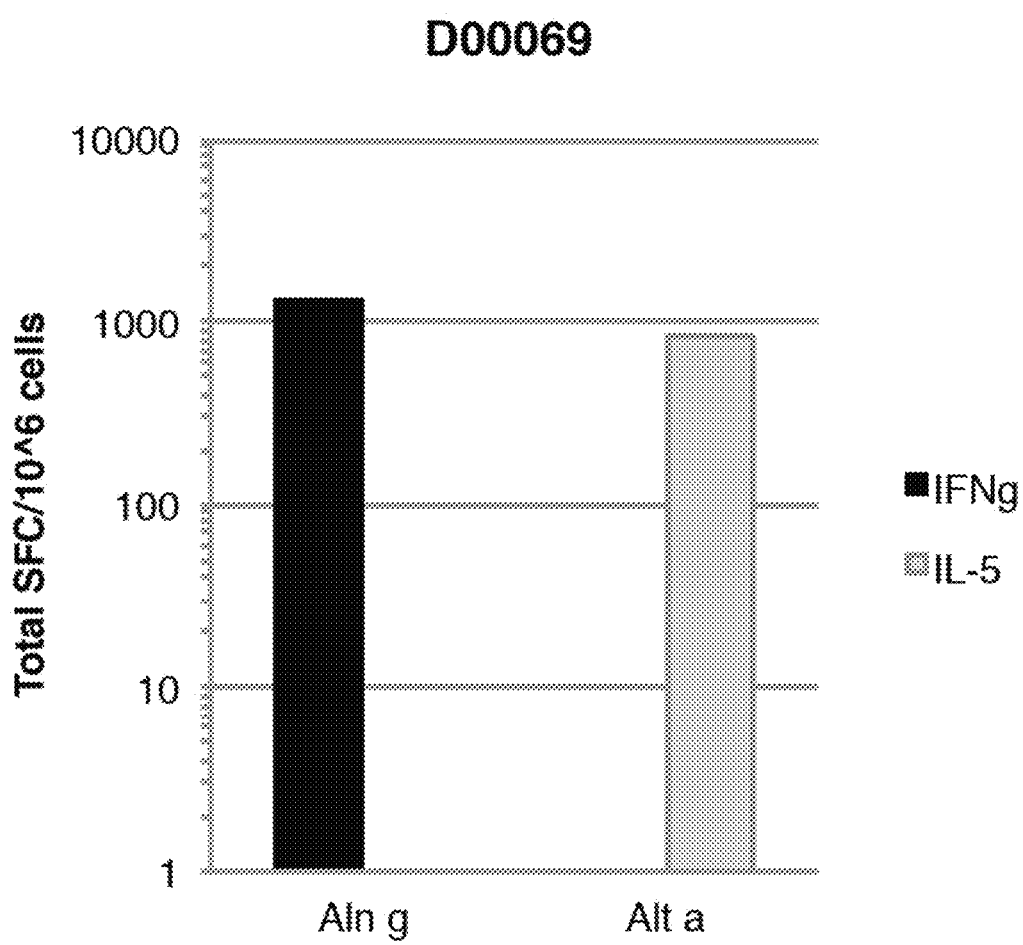
FIG. 6 shows polarized T cell responses to different allergens within an individual donor. IFNγ (black bars) and IL-5 (gray bars) responses, associated with Th1 and Th2 polarization, respectively, in donor D00069. As described, the T cell response, in terms of total SFC, to Aln g was associated only with only IFN-γ production, while the response to Alt a was only mediated by IL-5, highlighting the polarization of the responses to epitopes derived from Alder (Aln g) and *Alternaria* Rot Fungus (Alt a).

Strikingly, even within an individual donor, responses to different allergen sources could be differentially polarized, with responses to one allergen dominated by Th1 responses, and to a different allergen dominated by Th2 responses. An example of this type of situation is shown in FIG. 6, which depicts the T cell responses observed in a donor who responded to epitopes from Alder and *Alternaria* rot fungus, allergens associated with Th1 and Th2 polarization, respectively. As shown, the response by this donor to Alder (Aln g) was completely Th1, while the response to *Alternaria* (Alt a) was completely Th2.

Example 7

This example includes a description of methods of determining in vivo efficacy of proteins and peptides of the invention, in particular, for treatment of allergy.

Proteins and peptides of the invention are evaluated for efficacy in treatment of allergy in a mouse model. Six groups of BALB/cJ or HLA-transgenic mice are sensitized with repeat dosing of 1.5 micrograms of each whole allergen intranasally (in 25 uL) for 5×2 days over 2 weeks. This serves as a model system for investigation of allergic asthma caused by each whole allergen.

The sensitized mice are then left for one week before treatment with peptides of the invention. The treatment comprises intranasal delivery of allergen peptides followed 30 minutes later by intranasal delivery of allergen peptides daily for 5 days. Approximately 4 weeks later the mice are challenged with each whole allergen for 2 days (2×15 ug/25 uL intranasally) and outcomes are measured 48 hours later. 5 doses of allergen peptides are evaluated (10, 1, 0.1, 0.01 & 0.001 ug per peptide). Appropriate control experiments are conducted.

The outcomes measured are bronchial airway resistance following methacholine lung challenge (cm H2O/mL/s), a measure of respiratory function, and a quantitation of inflammatory cells in the bronchoalveolar lavage (BAL) fluid.

For measurement of airway resistance, 48 hours after intranasal challenge over 2 days (2×15 ug) with each whole allergen, total respiratory system resistance (Rrs) is measured in response to intranasal saline and increasing doses of intravenous methacholine (MCh) using the Flexivent rodent ventilator. Using the resulting Rrs-MCh dose-response curves, indices of airway reactivity (Slope Rrs) and maximal degree of bronchoconstriction at 25 MCh mg/mL (Max Rrs @ 25 mg/mL) are measured. Values are means+/−SE.

For quantitation of inflammatory cells, bronchoalveolar lavage fluid (BALF) is assessed for total and differential inflammatory cell counts. Sections of lung tissue are stained with hematoxylin and eosin (H&E) and morphometrically quantified using a custom computerized analysis system (Northern Eclipse).

Example 8

This example includes a description of a clinical trial protocol of proteins and peptides of the invention for treatment of allergy.

Proteins and peptides of the invention are analyzed in a randomized, placebo-controlled, blind clinical trial for efficacy in reducing allergic symptoms. The study design of the clinical trial is in accordance with good clinical practice guidelines.

Baseline skin responses to each allergen for all subjects are established using a Baseline Challenge between 6 and 8 days prior to study medication administration. Two intradermal injections of 0.010 HEP (histamine equivalent prick) units of commercially available standard allergen is administered, separated by a 30 minute time interval, into the volar surface of the left and right forearms respectively. Subjects are assessed to ensure that they experience a Late-Phase Skin Response (LPSR) to each whole allergen, and the magnitude of the baseline reaction is recorded as follows:

Eight hours after each injection the outline of any late-phase response is drawn onto the skin with a ballpoint pen. The longest and orthogonal diameters are measured and recorded for each response, and the area of the response in each arm is calculated. The average area of response in both arms of each subject is then calculated to provide the baseline reaction. Subjects who produced a suitable baseline reaction are assigned to dosing groups, randomized and entered into the Treatment Phase.

The Treatment Phase consists of a period of 21 days for each subject. During this period one group of subjects receives a single intradermal injection of either peptides of the invention (0.03, 0.3, 3, 12 nmol of each peptide per dose) or diluent placebo at Treatment Phase Visit 1 on day one. A cohort of 8 subjects receives treatment at each dose level (6 receives the peptides of the invention and 2 placebo). The first cohort of the intradermal group receives 0.03 nmol of each peptide in the mixture and each subsequent cohort in the group receives the next higher dose level.

Intradermal injections are made into the flexor surface of the left forearm. The total volume of the injection is 60 µL for all injections. After treatment, subjects have their skin response to whole allergen retested at Treatment Phase Visit 2 on day 21 (±3 days). Skin responses to whole allergen are assessed by measurement of the late-phase responses 8 hours following intradermal administration of 0.010 HEP (histamine equivalent prick) units of commercially available standard allergen as described above. The average area of response for both arms of each subject is then calculated as described above.

This average LPSR area after treatment is then compared to the baseline LPSR area for each subject. The overall change in LPSR area for all eight patients in each cohort is then evaluated.

Example 9

This example includes a discussion of the data.

Disclosed herein are results of a systematic survey of T cell epitopes derived from common allergens. This is believed to be the first such study simultaneously investigating 28 different common allergen sources with the same controlled and uniform technical approach. This approach is designed to allow relatively high throughput analysis, while still capturing a large fraction of the total class II restricted allergen specific T cell response, and has been validated in Timothy Grass (3) and German Cockroach systems. The approach is based on prediction of the peptides most likely to bind a panel of HLA molecules chosen to be representative of the most common HLA class II allelic variants at the DR, DP and DQ loci.

Each peptide was tested in at least ten donors specifically allergic to each allergen source. It was reasoned that this number of donors would be suitable to identify the more dominant, and more frequently recognized, epitopes, while at the same time allowing screening for a broad and diverse set of allergen sources. Nearly a quarter (322/1405=22.9%) of the predicted peptides were positive in at least one of the donors tested, thus further validating the approach, and illustrating its broad applicability to human inhalant and contact allergens, including fungus, tree, grass, weed and animal allergens.

The significance of the observations is highlighted by the comparison of these newly identified epitopes with those previously identified and described in the scientific literature and curated in the IEDB (23, 27). For 14 of the allergen sources, no human class II/CD4 epitope could be found in the IEDB that overlapped with any of the epitopes described herein. For 11 other allergen sources, which have been more extensively studied, no human class II/CD4 epitope could be found in the IEDB that overlapped with 84% of the epitopes identified. Conversely, when the data was analyzed to pinpoint the fraction of IEDB-contained epitopes that were re-identified in the course of the present study, it was found that, on average, 38% of the known epitopes were re-identified. This is consistent with the Timothy Grass and German Cockroach studies noted above, which estimated that the predictive approach would identify the most dominant and prevalently recognized epitopes, corresponding to about 50% of the total T cell response.

The epitopes most frequently recognized were characterized in terms of their HLA binding capacity to a panel of 35 different HLA class II molecules. This panel was chosen to be representative of the most common allelic variants in the general population at the HLA class II DR, DP and DQ loci (24-26). This data is of relevance, as the quantitative binding data to the various common HLA class II variants can be used to project the potential coverage by the various epitopes in patient populations of different ethnicities (26, 28, 29). The issue of restriction was addressed in experiments where the HLA class II restricting locus was determined by antibody inhibition experiments. It was found that about a third of the epitopes were restricted by multiple loci. Furthermore, it is estimated that at least 60% of the remaining epitopes are restricted by multiple allelic variants at a given locus. These results are not unexpected, given the fact that predicted promiscuous binding was utilized as a selection criterion for identifying candidate epitopes. Nonetheless, these observations underline the relevance of promiscuous epitope recognition in the context of HLA class II allergen-specific T cell responses.

A notable result of the side-by-side survey is that the identified epitopes account for a variable fraction of the response to a given allergen source, and that this fraction further correlates with how many different allergenic proteins have been described for that source. Thus, this data suggests that, at the T cell level, allergic responses target a relatively large number of antigens. Without being limited to any particular theory, future experiments may address whether this observation reflects the existence, for the allergen sources where only one or few specific sequences have been reported, of additional allergens recognized by IgE, and not yet identified. Alternatively, this may also reflect an incomplete overlap between the targets of T cell and IgE responses.

While some studies show a correlation between IL-5 levels and IgE (47), other studies do not (48). Thus, IgE or wheal responses may or may not be related to Th2 (i.e. IL-5) responses, and in our study these appear to depend upon the allergen studied. It was also observed that different allergen sources appear to elicit patterns of responses that are differentially polarized in terms of their Th1/Th2 balance, at least as judged by IL-5 (Th2) or IFN-γ (Th1) production. Strikingly, even within an individual donor, responses to different allergens could be differentially polarized, with responses to one allergen dominated by Th1 responses, and to a different allergen dominated by Th2 responses.

A similar phenomenon was observed with different allergenic proteins in the Timothy Grass system (11) following restimulation with pollen extract. A comparison of the LPS content of the various extracts used with the associated Th1/Th2 balances revealed no correlation, suggesting that the differential polarization observed is antigen specific, and not due to differential LPS content in the various extracts. The molecular basis for this effect is presently unclear and without being limited to any particular theory, might reflect differences in the relative concentrations and accessibility of the different allergens in the pollen and extract, their processing and presentation, and potentially the presence of distinct co-stimulatory signals associated with each allergen. The study of this mechanism might suggest avenues to influence or alter the lymphokine balance of Th responses, and thus potentially the outcome of responses in terms of IgE titers.

The epitopes identified herein are of use in several respects. First, the epitopes of the invention may be used to characterize T cell responses associated with allergic reactions, including characterization of changes in responding T cell phenotype/T cell plasticity as a function of seasonality, as a result of SIT treatment, or as a function of varying disease severity (asthma versus rhinitis). Secondly, T cell epitopes of the invention can be used to develop immunotherapeutic SIT treatments that could target T cell responses without the risks connected to administration of whole allergens capable of binding IgE, and that thus pose potential safety risks.

TABLE 1

Identification of 257 epitope regions from common allergen sources

| Allergen category | Allergen Source | Number of allergens | Number of peptides tested | Unique epitopes | Antigenic regions |
|---|---|---|---|---|---|
| Fungi | Alternaria Rot Fungus | 10 | 88 | 29 | 25 |
| | A. fumigatus | 23 | 229 | 11 | 11 |
| | C. herbarum | 6 | 53 | 15 | 15 |
| | P. chrysogenum | 2 | 38 | 18 | 18 |
| Grasses | Bermuda Grass | 5 | 21 | 3 | 3 |
| | Canary Grass | 2 | 20 | 9 | 7 |
| | Kentucky Blue Grass | 2 | 31 | 12 | 9 |
| | Orchard Grass | 4 | 15 | 5 | 4 |
| | Rye Grass | 6 | 70 | 34 | 30 |
| | Sweet Vernal Grass | 5 | 3 | 3 | 2 |
| Indoor allergens | American Cockroach | 5 | 79 | 3 | 3 |
| | Cat epithelia | 4 | 55 | 10 | 8 |
| | D. farinae | 11 | 160 | 23 | 22 |
| | D. pteronyssinus | 14 | 224 | 40 | 35 |
| | Dog epithelia | 4 | 44 | 5 | 5 |
| Trees | Alder | 2 | 11 | 4 | 3 |
| | Ash | 1 | 6 | 3 | 3 |
| | Birch | 6 | 47 | 14 | 13 |
| | Black Walnut | 2 | 22 | 0 | 0 |
| | Cypress | 5 | 65 | 16 | 12 |
| | Date Palm | 1 | 5 | 3 | 3 |
| | Prickly Juniper | 1 | 3 | 3 | 3 |
| | White Oak | 1 | 5 | 4 | 2 |
| Weeds | English Plantain | 1 | 3 | 2 | 2 |
| | Giant Ragweed | 1 | 5 | 4 | 3 |
| | Mugwort | 4 | 22 | 0 | 0 |
| | Russian Thistle | 4 | 83 | 16 | 16 |
| | Western Ragweed | 1 | 4 | 0 | 0 |
| | Total | 133 | 1411 | 289 | 257 |

TABLE 2

Novelty of the epitopes identified

A. Novel sources

| | Regions identified | | |
|---|---|---|---|
| Source | This study | IEDB | Novel |
| Alternaria Rot Fungus | 25 | 0 | 25 |
| P. chrysogenum | 18 | 0 | 18 |
| Russian Thistle | 16 | 0 | 16 |
| C. herbarum | 15 | 0 | 15 |
| Canary Grass | 7 | 0 | 7 |
| Orchard Grass | 4 | 0 | 4 |
| American Cockroach | 3 | 0 | 3 |
| Ash | 3 | 0 | 3 |
| Prickly Juniper | 3 | 0 | 3 |
| Date Palm | 3 | 0 | 3 |

TABLE 2-continued

Novelty of the epitopes identified

| | | | |
|---|---|---|---|
| Giant Ragweed | 3 | 0 | 3 |
| White Oak | 2 | 0 | 2 |
| Sweet Vernal Grass | 2 | 0 | 2 |
| English Plantain | 2 | 0 | 2 |
| Total | 106 | 0 | 106 |

B. Sources for which epitopes were previously described

| Source | This study | IEDB | Overlap | Novel | % Novel | % IEDB reidentified |
|---|---|---|---|---|---|---|
| Alder | 3 | 3 | 2 | 1 | 33.3 | 66.7 |
| D. farina | 22 | 7 | 2 | 20 | 90.9 | 28.6 |
| A. fumigatus | 11 | 3 | 1 | 10 | 90.9 | 33.3 |
| Bermuda Grass | 3 | 5 | 0 | 3 | 100.0 | 0.0 |
| Birch | 13 | 7 | 3 | 10 | 76.9 | 42.9 |
| Cat epithelia | 8 | 4 | 4 | 4 | 50.0 | 100.0 |
| Dog epithelia | 5 | 5 | 0 | 5 | 100.0 | 0.0 |
| D. pteronyssinus | 35 | 8 | 5 | 30 | 85.7 | 62.5 |
| Japanese Cypress | 12 | 10 | 3 | 9 | 75.0 | 30.0 |
| Kentucky Blue Grass | 9 | 7 | 2 | 7 | 77.8 | 28.6 |
| Rye Grass | 30 | 4 | 2 | 28 | 93.3 | 50.0 |
| Total | 151 | 63 | 24 | 127 | 84.1 | 38.1 |

TABLE 3

Heterogeneity in epitope coverage of the different allergen sources

| Allergen Source | Regions | Response (SFC) Peptide | Response (SFC) Extract | % Peptide/Extract | IUIS Proteins |
|---|---|---|---|---|---|
| Rye Grass | 30 | 29722 | 19437 | 152.9 | 4 |
| D. pteronyssinus | 35 | 28129 | 22505 | 125.0 | 14 |
| D. farinae | 22 | 9402 | 9707 | 96.9 | 11 |
| Alternaria Rot Fungus | 25 | 31162 | 35207 | 88.5 | 10 |
| Cypress | 12 | 14310 | 18160 | 78.8 | 5 |
| Cat epithelia | 8 | 20068 | 28607 | 70.2 | 5 |
| Birch | 13 | 9690 | 17110 | 56.6 | 6 |
| White Oak | 2 | 8520 | 18067 | 47.2 | 1 |
| Canary Grass | 7 | 8217 | 22054 | 37.3 | 2 |
| P. chrysogenum | 18 | 9723 | 26643 | 36.5 | 2 |
| Russian Thistle | 16 | 11848 | 32723 | 36.2 | 5 |
| C. herbarum | 15 | 9200 | 31020 | 29.7 | 6 |
| Kentucky Blue Grass | 9 | 11007 | 39232 | 28.1 | 7 |
| Alder | 3 | 3877 | 14384 | 27.0 | 2 |
| Orchard Grass | 4 | 5474 | 25990 | 21.1 | 2 |
| A. fumigatus | 11 | 3953 | 23180 | 17.1 | 23 |
| Median | 12.5 | 9707 | 22843 | 42.2 | 5.0 |
| Juniper | 3 | 1033 | 17540 | 5.9 | 1 |
| Sweet Vernal Grass | 2 | 1667 | 35263 | 4.7 | 5 |
| Ash | 3 | 767 | 17073 | 4.5 | 1 |
| Bermuda Grass | 3 | 903 | 21083 | 4.3 | 2 |
| English Plantain | 2 | 688 | 16963 | 4.1 | 1 |
| Giant Ragweed | 3 | 533 | 13960 | 3.8 | 1 |
| American Cockroach | 3 | 690 | 27854 | 2.5 | 5 |
| Dog epithelia | 5 | 353 | 14616 | 2.4 | 4 |
| Date Palm | 3 | 233 | 23417 | 1.0 | 1 |
| Black Walnut | 0 | 0 | 28913 | 0.0 | 2 |
| Mugwort | 0 | 0 | 21793 | 0.0 | 4 |
| Western Ragweed | 0 | 0 | 16733 | 0.0 | 1 |
| Median | 3 | 611 | 19312 | 3.1 | 1.5 |

TABLE 4

HLA restriction of prevalently recognized epitope regions

| Organism | Source | Donors responding | % responding | Total SFC | Region restriction(s) DR | DQ | DP |
|---|---|---|---|---|---|---|---|
| Alt. Rot Fungus | Alt a 1 (6-25) | 4 | 33.3 | 5572 | 4 | 0 | 0 |
| | Alt a 1 (116-135) | 7 | 58.3 | 7450 | 3 | 3 | 0 |
| | Alt a 1 (141-157) | 5 | 41.7 | 5768 | 5 | 0 | 0 |
| | Alt a 5 (51-65) | 2 | 16.7 | 3450 | 1 | 0 | 0 |
| | Alt a 6 (161-175) | 2 | 16.7 | 1238 | 0 | 0 | 1 |
| | Alt a 7 (6-20) | 2 | 16.7 | 727 | 1 | 0 | 0 |
| | Alt a 7 (190-204) | 2 | 16.7 | 397 | 0 | 0 | 0 |
| A. fumigatus | Asp f 17 (91-105) | 2 | 18.2 | 813 | 1 | 0 | 0 |
| C. herbarum | Cla h 5 (6-20) | 2 | 20.0 | 247 | 0 | 0 | 0 |
| | Cla h 6 (161-175) | 3 | 30.0 | 2082 | 1 | 0 | 1 |
| | Cla h 8 (101-115) | 2 | 20.0 | 317 | 0 | 0 | 0 |

TABLE 4-continued

HLA restriction of prevalently recognized epitope regions

| Organism | Source | Donors responding | % responding | Total SFC | DR | DQ | DP |
|---|---|---|---|---|---|---|---|
| | Cla h 8 (151-165) | 2 | 20.0 | 470 | 1 | 0 | 0 |
| | Cla h 8 (181-195) | 2 | 20.0 | 817 | 0 | 0 | 0 |
| | Cla h 8 (236-250) | 2 | 20.0 | 4067 | 1 | 1 | 0 |
| P. chrysogenum | Pen ch 13 (101-115) | 2 | 20.0 | 677 | 1 | 0 | 0 |
| | Pen ch 13 (271-285) | 2 | 20.0 | 1463 | 1 | 0 | 0 |
| | Pen ch 18 (226-240) | 2 | 20.0 | 607 | 1 | 0 | 0 |
| | Pen ch 18 (291-305) | 3 | 30.0 | 2480 | 2 | 0 | 0 |
| Cat epithelia | Fel d 1 (41-60) | 3 | 27.3 | 6065 | 3 | 0 | 0 |
| | Fel d 1 (78-92) | 3 | 27.3 | 3453 | 3 | 0 | 0 |
| | Fel d 1 (21-40) | 6 | 54.5 | 7128 | 2 | 0 | 2 |
| | Fel d 1 (36-50) | 2 | 18.2 | 2837 | 1 | 0 | 0 |
| D. farinae | Der f 1 (131-150) | 2 | 20.0 | 1448 | 2 | 0 | 0 |
| D. pteronyssinus | Der p 1 (131-150) | 2 | 18.2 | 2417 | 2 | 1 | 0 |
| | Der p 1 (176-190) | 2 | 18.2 | 890 | 2 | 0 | 0 |
| | Der p 1 (226-240) | 2 | 18.2 | 2783 | 1 | 1 | 0 |
| | Der p 4 (96-120) | 3 | 27.3 | 3877 | 2 | 0 | 0 |
| | Der p 4 (251-265) | 2 | 18.2 | 763 | 0 | 0 | 1 |
| | Der p 4 (321-335) | 2 | 18.2 | 1570 | 0 | 1 | 0 |
| | Der p 4 (381-400) | 4 | 36.4 | 2573 | 2 | 0 | 0 |
| | Der p 4 (411-430) | 2 | 18.2 | 1117 | 0 | 0 | 1 |
| | Der p 4 (482-502) | 2 | 18.2 | 1160 | 1 | 0 | 0 |
| Alder | Aln g 1 (11-30) | 2 | 16.7 | 2036 | 0 | 1 | 1 |
| | Aln g 1 (111-125) | 2 | 16.7 | 1244 | 1 | 1 | 0 |
| Birch | Bet v 1 (96-110) | 2 | 20.0 | 462 | 0 | 0 | 0 |
| | Bet v 1 (111-125) | 3 | 30.0 | 1132 | 2 | 0 | 0 |
| | Bet v 6 (211-230) | 2 | 20.0 | 807 | 0 | 1 | 0 |
| Cypress | Cha o 1 (86-110) | 3 | 30.0 | 1922 | 1 | 0 | 0 |
| | Cha o 1 (211-225) | 2 | 20.0 | 835 | 0 | 0 | 0 |
| | Cup a 1 (71-90) | 3 | 30.0 | 3067 | 1 | 0 | 0 |
| | Cup a 1 (316-330) | 3 | 30.0 | 740 | 1 | 1 | 0 |
| | Cup s 1 (91-115) | 3 | 30.0 | 3627 | 1 | 0 | 0 |
| | Cup s 1 (211-225) | 2 | 20.0 | 1650 | 1 | 0 | 0 |
| White Oak | Que a 1 (11-35) | 8 | 61.5 | 7183 | 1 | 0 | 3 |
| | Que a 1 (141-155) | 4 | 30.8 | 1337 | 1 | 0 | 1 |
| Orchard Grass | Dac g 1 (181-195) | 4 | 36.4 | 2795 | 2 | 0 | 0 |
| | Dac g 2 (11-30) | 2 | 18.2 | 1917 | 1 | 0 | 0 |
| | Dac g 4 (1-15) | 3 | 27.3 | 482 | 0 | 0 | 0 |
| Rye Grass | Lol p 1 (176-190) | 3 | 27.3 | 1180 | 1 | 0 | 0 |
| | Lol p 2 (51-70) | 4 | 36.4 | 1163 | 3 | 0 | 0 |
| | Lol p 2 (76-90) | 3 | 27.3 | 1253 | 0 | 2 | 0 |
| | Lol p 3 (11-25) | 3 | 27.3 | 2070 | 2 | 0 | 0 |
| | Lol p 3 (51-65) | 2 | 18.2 | 1803 | 1 | 0 | 0 |
| | Lol p 3 (76-90) | 2 | 18.2 | 3342 | 0 | 0 | 0 |
| | Lol p 5 (71-85) | 3 | 27.3 | 3325 | 0 | 2 | 1 |
| | Lol p 5 (156-175) | 3 | 27.3 | 3437 | 0 | 2 | 0 |
| | Lol p 5 (236-250) | 2 | 18.2 | 460 | 0 | 0 | 0 |
| | Lol p 5 (306-320) | 2 | 18.2 | 1695 | 0 | 1 | 0 |
| | Lol p 5 (181-195) | 3 | 27.3 | 2260 | 1 | 1 | 1 |
| | Lol p 11 (116-135) | 2 | 18.2 | 2393 | 0 | 0 | 1 |
| Canary Grass | Pha a 1 (186-200) | 4 | 40.0 | 2095 | 3 | 1 | 0 |
| | Pha a 5 (121-140) | 3 | 30.0 | 1680 | 1 | 1 | 0 |
| | Pha a 5 (166-180) | 2 | 20.0 | 2222 | 0 | 1 | 1 |
| | Pha a 5 (181-195) | 2 | 20.0 | 493 | 2 | 0 | 0 |
| | Pha a 5 (201-220) | 4 | 40.0 | 1502 | 3 | 1 | 0 |
| Ken. Blue Grass | Poa p 1 (121-135) | 3 | 25.0 | 1357 | 1 | 0 | 0 |
| | Poa p 5 (51-75) | 7 | 58.3 | 3528 | 0 | 1 | 1 |
| | Poa p 5 (121-135) | 3 | 25.0 | 435 | 1 | 0 | 0 |
| | Poa p 5 (131-145) | 2 | 16.7 | 243 | 1 | 0 | 0 |
| | Poa p 5 (176-190) | 6 | 50.0 | 1862 | 3 | 0 | 1 |
| | Poa p 5 (211-230) | 4 | 33.3 | 1738 | 3 | 0 | 0 |
| | Poa p 5 (221-235) | 2 | 16.7 | 1370 | 1 | 0 | 0 |
| Russian Thistle | Sal k 1 (191-205) | 2 | 20.0 | 2060 | 0 | 1 | 1 |
| | Sal k 1 (321-335) | 2 | 20.0 | 1947 | 1 | 0 | 1 |

TABLE 5

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Alder | 3517 | Aln g 1 | P38948 | 730050 | 1 | MGVFNYEAETPSVIP | 15 | 3324.0008 |
| Alder | 3517 | Aln g 1 | P38948 | 730050 | 11 | PSVIPAARLFKAFIL | 15 | 3324.0004 |
| Alder | 3517 | Aln g 1 | P38948 | 730050 | 16 | AARLFKAFILDGDKL | 15 | 3324.0003 |
| Alder | 3517 | Aln g 1 | P38948 | 730050 | 76 | DRVNFKYSFSVIEGG | 15 | 3324.0002 |
| Alder | 3517 | Aln g 1 | P38948 | 730050 | 111 | GGSILKISNKFHTKG | 15 | 3324.0007 |
| Alder | 3517 | Aln g 1 | P38948 | 730050 | 136 | IEKEKAVGLLKAVES | 15 | 3324.0006 |
| Alder | 3517 | Aln g 1 | P38948 | 730050 | 141 | AVGLLKAVESYLLAH | 15 | 3324.0001 |
| Alder | 3517 | Aln g 1 | P38948 | 730050 | 146 | KAVESYLLAHSDAYN | 15 | 3324.0005 |
| Alder | 3517 | Aln g 4 | 081701 | 14423845 | 56 | TDGDGFISFQEFTNF | 15 | 3324.0010 |
| Alder | 3517 | Aln g 4 | 081701 | 14423845 | 61 | FISFQEFTNFARANR | 15 | 3324.0009 |
| Alder | 3517 | Aln g 4 | 081701 | 14423845 | 71 | ARANRGLVKDVAKIF | 15 | 3337.0001 |
| Alternaria rot fungus | 5599 | Alt a 1 | P79085 | 14423645 | 1 | MQFTTIASLFAAAGL | 15 | 3324.0012 |
| Alternaria rot fungus | 5599 | Alt a 1 | P79085 | 14423645 | 6 | IASLFAAAGLAAAAP | 15 | 3324.0015 |
| Alternaria rot fungus | 5599 | Alt a 1 | P79085 | 14423645 | 11 | AAAGLAAAAPLESRQ | 15 | 3324.0017 |
| Alternaria rot fungus | 5599 | Alt a 1 | P79085 | 14423645 | 111 | KVSDDITYVATATLP | 15 | 3324.0013 |
| Alternaria rot fungus | 5599 | Alt a 1 | P79085 | 14423645 | 116 | ITYVATATLPNYCRA | 15 | 3324.0014 |
| Alternaria rot fungus | 5599 | Alt a 1 | P79085 | 14423645 | 141 | QGVADAYITLVTLPK | 15 | 3324.0011 |
| Alternaria rot fungus | 5599 | Alt a 1 | P79085 | 14423645 | 143 | VADAYITLVTLPKSS | 15 | 3324.0016 |
| Alternaria rot fungus | 5599 | Alt a 10 | P42041 | 76666767 | 16 | QPTGLFINNEFVKAV | 15 | 3324.0023 |
| Alternaria rot fungus | 5599 | Alt a 10 | P42041 | 76666767 | 56 | DVDIAVAARKAFNG | 15 | 3324.0032 |
| Alternaria rot fungus | 5599 | Alt a 10 | P42041 | 76666767 | 81 | GKLLNKLADLFEKNA | 15 | 3324.0022 |
| Alternaria rot fungus | 5599 | Alt a 10 | P42041 | 76666767 | 141 | DTAPDSFNYIRKEPI | 15 | 3324.0021 |
| Alternaria rot fungus | 5599 | Alt a 10 | P42041 | 76666767 | 146 | SFNYIRKEPIGVCGQ | 15 | 3324.0033 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Alternaria rot fungus | 5599 | Alt a 10 | P42041 | 76666767 | 161 | IIPWNFPILMWSWKI | 15 | 3324.0019 |
| Alternaria rot fungus | 5599 | Alt a 10 | P42041 | 76666767 | 301 | GSRIYVQEEIYDKFI | 15 | 3324.0025 |
| Alternaria rot fungus | 5599 | Alt a 10 | P42041 | 76666767 | 306 | VQEEIYDKFIQRFKE | 15 | 3324.0024 |
| Alternaria rot fungus | 5599 | Alt a 10 | P42041 | 76666767 | 311 | YDKFIQRFKERAAQN | 15 | 3324.0028 |
| Alternaria rot fungus | 5599 | Alt a 10 | P42041 | 76666767 | 341 | VSQLQFDRIMGYIEE | 15 | 3324.0034 |
| Alternaria rot fungus | 5599 | Alt a 10 | P42041 | 76666767 | 371 | GDKGYFIEPTIFSNV | 15 | 3324.0018 |
| Alternaria rot fungus | 5599 | Alt a 10 | P42041 | 76666767 | 421 | YGLAAAVHTSNLTTA | 15 | 3324.0031 |
| Alternaria rot fungus | 5599 | Alt a 10 | P42041 | 76666767 | 431 | NLTTAIEVANALRAG | 15 | 3324.0027 |
| Alternaria rot fungus | 5599 | Alt a 10 | P42041 | 76666767 | 436 | IEVANALRAGTVWVN | 15 | 3324.0030 |
| Alternaria rot fungus | 5599 | Alt a 10 | P42041 | 76666767 | 446 | TVWNSYNTLHWQLP | 15 | 3324.0020 |
| Alternaria rot fungus | 5599 | Alt a 10 | P42041 | 76666767 | 476 | AALDNYIQTKTVSIR | 15 | 3324.0026 |
| Alternaria rot fungus | 5599 | Alt a 10 | P42041 | 76666767 | 481 | YIQTKTVSIRLGDVL | 15 | 3324.0029 |
| Alternaria rot fungus | 5599 | Alt a 12 | P49148 | 1350779 | 1 | MSTSELATSYAALIL | 15 | 3324.0036 |
| Alternaria rot fungus | 5599 | Alt a 12 | P49148 | 1350779 | 6 | LATSYAALILADDGV | 15 | 3324.0035 |
| Alternaria rot fungus | 5599 | Alt a 12 | P49148 | 1350779 | 26 | KLQSLIKAAKIEEVE | 15 | 3324.0037 |
| Alternaria rot fungus | 5599 | Alt a 12 | P49148 | 1350779 | 41 | PIWTTLFAKALEGKD | 15 | 3324.0039 |
| Alternaria rot fungus | 5599 | Alt a 12 | P49148 | 1350779 | 76 | LLLRWRAADAAPAAE | 15 | 3324.0038 |
| Alternaria rot fungus | 5599 | Alt a 13 | Q6R4B4 | 41057621 | 6 | SELAVQKLVLFAVKG | 15 | 3324.0041 |
| Alternaria rot fungus | 5599 | Alt a 13 | Q6R4B4 | 41057621 | 11 | QKLVLFAVKGTATST | 15 | 3324.0044 |
| Alternaria rot fungus | 5599 | Alt a 13 | Q6R4B4 | 41057621 | 26 | HNTVRPLILLDELGV | 15 | 3324.0049 |
| Alternaria rot fungus | 5599 | Alt a 13 | Q6R4B4 | 41057621 | 76 | DTLRAWESTSTLMYI | 15 | 3324.0048 |
| Alternaria rot fungus | 5599 | Alt a 13 | Q6R4B4 | 41057621 | 111 | INNWLTLHTAALGPT | 15 | 3324.0043 |
| Alternaria rot fungus | 5599 | Alt a 13 | Q6R4B4 | 41057621 | 126 | AKYWLYFYKLHPEKL | 15 | 3324.0040 |
| Alternaria rot fungus | 5599 | Alt a 13 | Q6R4B4 | 41057621 | 141 | PKTIEKLRSNITVQY | 15 | 3324.0051 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Alternaria rot fungus | 5599 | Alt a 13 | Q6R4B4 | 41057621 | 146 | KLRSNITVQYDILER | 15 | 3324.0050 |
| Alternaria rot fungus | 5599 | Alt a 13 | Q6R4B4 | 41057621 | 166 | GQQYLAWLNEKFKRS | 15 | 3324.0045 |
| Alternaria rot fungus | 5599 | Alt a 13 | Q6R4B4 | 41057621 | 171 | AWLNEKFKRSSYNRR | 15 | 3324.0042 |
| Alternaria rot fungus | 5599 | Alt a 13 | Q6R4B4 | 41057621 | 191 | LCYEKYRRVVRAGVK | 15 | 3324.0046 |
| Alternaria rot fungus | 5599 | Alt a 13 | Q6R4B4 | 41057621 | 201 | RAGVKVAQTARVVCP | 15 | 3324.0047 |
| Alternaria rot fungus | 5599 | Alt a 3 | P78983 | 1850544 | 41 | SAKNALESYAYSLRN | 15 | 3324.0053 |
| Alternaria rot fungus | 5599 | Alt a 3 | P78983 | 1850544 | 46 | LESYAYSLRNTLSDS | 15 | 3324.0052 |
| Alternaria rot fungus | 5599 | Alt a 3 | P78983 | 1850544 | 91 | ATKDEYESQQKELEG | 15 | 3337.0002 |
| Alternaria rot fungus | 5599 | Alt a 4 | Q00002 | 1006624 | 26 | ADKVVLVAYFAADDK | 15 | 3324.0054 |
| Alternaria rot fungus | 5599 | Alt a 4 | Q00002 | 1006624 | 56 | NFLFGATNDAALAKA | 15 | 3324.0061 |
| Alternaria rot fungus | 5599 | Alt a 4 | Q00002 | 1006624 | 96 | MRTYPRLRKVASTPL | 15 | 3324.0060 |
| Alternaria rot fungus | 5599 | Alt a 4 | Q00002 | 1006624 | 101 | RLRKVASTPLIGEVG | 15 | 3324.0059 |
| Alternaria rot fungus | 5599 | Alt a 4 | Q00002 | 1006624 | 116 | PETYAGYMAAGIPLA | 15 | 3337.0057 |
| Alternaria rot fungus | 5599 | Alt a 4 | Q00002 | 1006624 | 121 | GYMAAGIPLAYIFAE | 15 | 3324.0056 |
| Alternaria rot fungus | 5599 | Alt a 4 | Q00002 | 1006624 | 126 | GIPLAYIFAETPEER | 15 | 3324.0058 |
| Alternaria rot fungus | 5599 | Alt a 4 | Q00002 | 1006624 | 156 | GEINFATIDAKSFGQ | 15 | 3324.0062 |
| Alternaria rot fungus | 5599 | Alt a 4 | Q00002 | 1006624 | 286 | DELSKLVTIAKVDAT | 15 | 3324.0063 |
| Alternaria rot fungus | 5599 | Alt a 4 | Q00002 | 1006624 | 306 | DEIQGFLPSSLFPLA | 15 | 3324.0055 |
| Alternaria rot fungus | 5599 | Alt a 5 | P42037 | 467617 | 1 | MKHLAAYLLLGLGGN | 15 | 3324.0064 |
| Alternaria rot fungus | 5599 | Alt a 5 | P42037 | 467617 | 21 | ADVKAVLESVGIEAD | 15 | 3337.0003 |
| Alternaria rot fungus | 5599 | Alt a 5 | P42037 | 467617 | 51 | INELIASGSEKLASV | 15 | 3324.0065 |
| Alternaria rot fungus | 5599 | Alt a 6 | Q9HDT3 | 14423684 | 1 | MTTKIHARSVYDSR | 15 | 3324.0075 |
| Alternaria rot fungus | 5599 | Alt a 6 | Q9HDT3 | 14423684 | 106 | LGANAILGVSMAIAK | 15 | 3324.0069 |
| Alternaria rot fungus | 5599 | Alt a 6 | Q9HDT3 | 14423684 | 111 | ILGVSMAIAKAAAAE | 15 | 3324.0070 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Alternaria rot fungus | 5599 | Alt a 6 | Q9HDT3 | 14423684 | 116 | MAIAKAAAEKGVPL | 15 | 3324.0074 |
| Alternaria rot fungus | 5599 | Alt a 6 | Q9HDT3 | 14423684 | 161 | GGRLAFQEFMIVPCE | 15 | 3324.0073 |
| Alternaria rot fungus | 5599 | Alt a 6 | Q9HDT3 | 14423684 | 186 | GAEVYQKLKALAKT | 15 | 3324.0072 |
| Alternaria rot fungus | 5599 | Alt a 6 | Q9HDT3 | 14423684 | 241 | IKIAMDVASSEFYKA | 15 | 3324.0077 |
| Alternaria rot fungus | 5599 | Alt a 6 | Q9HDT3 | 14423684 | 271 | KSKWLTYEQLAEMYK | 15 | 3324.0068 |
| Alternaria rot fungus | 5599 | Alt a 6 | Q9HDT3 | 14423684 | 306 | EAWSYFFKTYDGQIV | 15 | 3324.0067 |
| Alternaria rot fungus | 5599 | Alt a 6 | Q9HDT3 | 14423684 | 336 | IELKSCNALLLKVNQ | 15 | 3324.0066 |
| Alternaria rot fungus | 5599 | Alt a 6 | Q9HDT3 | 14423684 | 341 | CNALLLKVNQIGTIT | 15 | 3324.0071 |
| Alternaria rot fungus | 5599 | Alt a 6 | Q9HDT3 | 14423684 | 366 | GAGWGVMVSHRSGET | 15 | 3324.0078 |
| Alternaria rot fungus | 5599 | Alt a 6 | Q9HDT3 | 14423684 | 406 | ERLAKLNQILRIEEE | 15 | 3324.0076 |
| Alternaria rot fungus | 5599 | Alt a 7 | P42058 | 467619 | 6 | AIVYYSMYGHIKKMA | 15 | 3324.0085 |
| Alternaria rot fungus | 5599 | Alt a 7 | P42058 | 467619 | 31 | GGDAKLFQVAETLPQ | 15 | 3324.0082 |
| Alternaria rot fungus | 5599 | Alt a 7 | P42058 | 467619 | 36 | LFQVAETLPQEVLDK | 15 | 3324.0084 |
| Alternaria rot fungus | 5599 | Alt a 7 | P42058 | 467619 | 66 | PAVLEEFDGILFGIP | 15 | 3324.0087 |
| Alternaria rot fungus | 5599 | Alt a 7 | P42058 | 467619 | 106 | FWGKYAGVFVSTGTL | 15 | 3324.0086 |
| Alternaria rot fungus | 5599 | Alt a 7 | P42058 | 467619 | 141 | IYVPLGYKTAFSMLA | 15 | 3324.0079 |
| Alternaria rot fungus | 5599 | Alt a 7 | P42058 | 467619 | 146 | GYKTAFSMLANLDEV | 15 | 3324.0081 |
| Alternaria rot fungus | 5599 | Alt a 7 | P42058 | 467619 | 181 | SELELNIAQAQGKAF | 15 | 3324.0083 |
| Alternaria rot fungus | 5599 | Alt a 7 | P42058 | 467619 | 190 | AQGKAFYEAVAKAHQ | 15 | 3324.0080 |
| Alternaria rot fungus | 5599 | Alt a 8 | P0C0Y4 | 23344707 | 6 | PQATELKDLFSLKGK | 15 | 3324.0090 |
| Alternaria rot fungus | 5599 | Alt a 8 | P0C0Y4 | 23344707 | 11 | LKDLFSLKGKVVIVT | 15 | 3324.0091 |
| Alternaria rot fungus | 5599 | Alt a 8 | P0C0Y4 | 23344707 | 46 | ADLAITYNSRAEGAE | 15 | 3324.0094 |
| Alternaria rot fungus | 5599 | Alt a 8 | P0C0Y4 | 23344707 | 151 | TGSLVITSSMSGHIA | 15 | 3324.0093 |
| Alternaria rot fungus | 5599 | Alt a 8 | P0C0Y4 | 23344707 | 176 | VAKAGCIHLAKSLAN | 15 | 3324.0096 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Alternaria rot fungus | 5599 | Alt a 8 | P0C0Y4 | 23344707 | 181 | CIHLAKSLANEWRDF | 15 | 3324.0095 |
| Alternaria rot fungus | 5599 | Alt a 8 | P0C0Y4 | 23344707 | 216 | QDIQKLWHSMIPMGR | 15 | 3324.0092 |
| Alternaria rot fungus | 5599 | Alt a 8 | P0C0Y4 | 23344707 | 236 | ELKGAYVYFASDASS | 15 | 3324.0088 |
| Alternaria rot fungus | 5599 | Alt a 8 | P0C0Y4 | 23344707 | 241 | YVYFASDASSYCTGS | 15 | 3324.0089 |
| American cockroach | 6978 | Per a 1 | O18527 | 2231297 | 1 | INEIHSIIGLPPFVP | 15 | 3324.1371 |
| American cockroach | 6978 | Per a 1 | O18527 | 2231297 | 41 | DELKALFQEKLETSP | 15 | 3324.1356 |
| American cockroach | 6978 | Per a 1 | O18527 | 2231297 | 51 | LETSPDFKALYDAIR | 15 | 3324.1378 |
| American cockroach | 6978 | Per a 1 | O18527 | 2231297 | 56 | DFKALYDAIRSPEFQ | 15 | 3324.1375 |
| American cockroach | 6978 | Per a 1 | O18527 | 2231297 | 66 | SPEFQSIISTLNAMQ | 15 | 3324.1359 |
| American cockroach | 6978 | Per a 1 | O18527 | 2231297 | 71 | SIISTLNAMQRSEHH | 15 | 3324.1357 |
| American cockroach | 6978 | Per a 1 | O18527 | 2231297 | 91 | KGVDVDHFIQLIRAL | 15 | 3324.1363 |
| American cockroach | 6978 | Per a 1 | O18527 | 2231297 | 96 | DHFIQLIRALFGLSR | 15 | 3324.1347 |
| American cockroach | 6978 | Per a 1 | O18527 | 2231297 | 101 | LIRALFGLSRAARNL | 15 | 3324.1364 |
| American cockroach | 6978 | Per a 1 | O18527 | 2231297 | 106 | FGLSRAARNLQDDLN | 15 | 3324.1369 |
| American cockroach | 6978 | Per a 1 | O18527 | 2231297 | 116 | QDDLNDFLHSLEPIS | 15 | 3324.1373 |
| American cockroach | 6978 | Per a 1 | O18527 | 2231297 | 151 | LHADDFHKIITTIEA | 15 | 3324.1379 |
| American cockroach | 6978 | Per a 1 | O18527 | 2231297 | 156 | FHKIITTIEALPEFA | 15 | 3324.1351 |
| American cockroach | 6978 | Per a 1 | O18527 | 2231297 | 166 | LPEFANFYNFLKEHG | 15 | 3324.1355 |
| American cockroach | 6978 | Per a 1 | O18527 | 2231297 | 171 | NFYNFLKEHGLDVVD | 15 | 3324.1372 |
| American cockroach | 6978 | Per a 1 | O18527 | 2231297 | 181 | LDVVDYINEIHSIIG | 15 | 3324.1361 |
| American cockroach | 6978 | Per a 1 | O18527 | 2231297 | 186 | YINEIHSIIGLPPFV | 15 | 3324.1365 |
| American cockroach | 6978 | Per a 1 | O18527 | 2231297 | 211 | VGINGLIDDVIAILP | 15 | 3324.1368 |
| American cockroach | 6978 | Per a 1 | O18527 | 2231297 | 216 | LIDDVIAILPVDELK | 15 | 3324.1362 |
| American cockroach | 6978 | Per a 1 | O18527 | 2231297 | 221 | IAILPVDELKALFQE | 15 | 3324.1370 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| American cockroach | 6978 | Per a 1 | O18527 | 2231297 | 226 | VDELKALFQEKLETS | 15 | 3324.1360 |
| American cockroach | 6978 | Per a 1 | O18527 | 2231297 | 241 | PDFKALYDAIRSPEF | 15 | 3324.1380 |
| American cockroach | 6978 | Per a 1 | O18527 | 2231297 | 251 | RSPEFQSIISTLNAM | 15 | 3324.1381 |
| American cockroach | 6978 | Per a 1 | O18527 | 2231297 | 306 | DLNDFLALIPTDQIL | 15 | 3324.1348 |
| American cockroach | 6978 | Per a 1 | O18527 | 2231297 | 311 | LALIPTDQILAIAMD | 15 | 3324.1377 |
| American cockroach | 6978 | Per a 1 | O18527 | 2231297 | 316 | TDQILAIAMDYLAND | 15 | 3324.1354 |
| American cockroach | 6978 | Per a 1 | O18527 | 2231297 | 321 | AIAMDYLANDAEVQE | 15 | 3324.1374 |
| American cockroach | 6978 | Per a 1 | O18527 | 2231297 | 331 | AEVQELVAYLQSDDF | 15 | 3324.1350 |
| American cockroach | 6978 | Per a 1 | O18527 | 2231297 | 341 | QSDDFHKIITTIEAL | 15 | 3324.1353 |
| American cockroach | 6978 | Per a 1 | O18527 | 2231297 | 346 | HKIITTIERALPEFAN | 15 | 3324.1352 |
| American cockroach | 6978 | Per a 1 | O18527 | 2231297 | 356 | PEFANFYNFLKEHGL | 15 | 3324.1349 |
| American cockroach | 6978 | Per a 1 | O18527 | 2231297 | 361 | FYNFLKEHGLDVVDY | 15 | 3324.1376 |
| American cockroach | 6978 | Per a 1 | O18527 | 2231297 | 371 | DVVDYINEIHSIIGL | 15 | 3324.1358 |
| American cockroach | 6978 | Per a 1 | O18527 | 2231297 | 431 | DFKALYDAIDLRSSR | 15 | 3324.1366 |
| American cockroach | 6978 | Per a 1 | O18527 | 2231297 | 432 | FKALYDAIDLRSSRA | 15 | 3324.1367 |
| American cockroach | 6978 | Per a 10 | Q1M0X9 | 60678799 | 1 | MLRYIVLASLIACSL | 15 | 3324.1382 |
| American cockroach | 6978 | Per a 10 | Q1M0X9 | 60678799 | 6 | VLASLIACSLSAVPK | 15 | 3324.1386 |
| American cockroach | 6978 | Per a 10 | Q1M0X9 | 60678799 | 41 | YPYQLSFEYYGSHMC | 15 | 3324.1383 |
| American cockroach | 6978 | Per a 10 | Q1M0X9 | 60678799 | 96 | HQATQLIANPNYDYY | 15 | 3324.1393 |
| American cockroach | 6978 | Per a 10 | Q1M0X9 | 60678799 | 106 | NYDYYTIDFDVAVAR | 15 | 3324.1388 |
| American cockroach | 6978 | Per a 10 | Q1M0X9 | 60678799 | 111 | TIDFDVAVARVSPAF | 15 | 3324.1385 |
| American cockroach | 6978 | Per a 10 | Q1M0X9 | 60678799 | 116 | VAVARVSPAFSYGTG | 15 | 3324.1389 |
| American cockroach | 6978 | Per a 10 | Q1M0X9 | 60678799 | 161 | TLPSQLQVVSVPIVS | 15 | 3324.1387 |
| American cockroach | 6978 | Per a 10 | Q1M0X9 | 60678799 | 166 | LQVVSVPIVSRSECN | 15 | 3324.1390 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| American cockroach | 6978 | Per a 10 | Q1M0X9 | 60678799 | 236 | PGVYSNVASLKGFIT | 15 | 3324.1392 |
| American cockroach | 6978 | Per a 10 | Q1M0X9 | 60678799 | 241 | NVASLKGFITEQTGV | 15 | 3324.1391 |
| American cockroach | 6978 | Per a 10 | Q1M0X9 | 60678799 | 242 | VASLKGFITEQTGVN | 15 | 3324.1384 |
| American cockroach | 6978 | Per a 3 | Q25640 | 1580794 | 1 | LNAFNMYFRYIYPTW | 15 | 3324.1401 |
| American cockroach | 6978 | Per a 3 | Q25640 | 1580794 | 6 | MYFRYIYPTWFNTTL | 15 | 3324.1397 |
| American cockroach | 6978 | Per a 3 | Q25640 | 1580794 | 31 | QFYYTHQIYARYFL | 15 | 3324.1399 |
| American cockroach | 6978 | Per a 3 | Q25640 | 1580794 | 36 | YHQIYARYFLERLSN | 15 | 3324.1398 |
| American cockroach | 6978 | Per a 3 | Q25640 | 1580794 | 41 | ARYFLERLSNSLPDV | 15 | 3324.1395 |
| American cockroach | 6978 | Per a 3 | Q25640 | 1580794 | 56 | KPFQYSKPLKTGYNP | 15 | 3324.1409 |
| American cockroach | 6978 | Per a 3 | Q25640 | 1580794 | 91 | NIDLFYVSDIKNYES | 15 | 3324.1411 |
| American cockroach | 6978 | Per a 3 | Q25640 | 1580794 | 141 | GTSNSPYQYFYGSIF | 15 | 3324.1408 |
| American cockroach | 6978 | Per a 3 | Q25640 | 1580794 | 146 | PYQYFYGSIFHFYRL | 15 | 3324.1402 |
| American cockroach | 6978 | Per a 3 | Q25640 | 1580794 | 151 | YGSIFHFYRLLVGHV | 15 | 3324.1394 |
| American cockroach | 6978 | Per a 3 | Q25640 | 1580794 | 156 | HFYRLLVGHVVDPYH | 15 | 3324.1412 |
| American cockroach | 6978 | Per a 3 | Q25640 | 1580794 | 191 | FYQLWKRIDHIVQKY | 15 | 3324.1404 |
| American cockroach | 6978 | Per a 3 | Q25640 | 1580794 | 196 | KRIDHIVQKYKNRLP | 15 | 3324.1410 |
| American cockroach | 6978 | Per a 3 | Q25640 | 1580794 | 231 | KLYTYFEHFEHSLGN | 15 | 3324.1405 |
| American cockroach | 6978 | Per a 3 | Q25640 | 1580794 | 236 | FEHFEHSLGNAMYLG | 15 | 3324.1413 |
| American cockroach | 6978 | Per a 3 | Q25640 | 1580794 | 271 | PFTYNIEVSSDKAQD | 15 | 3324.1414 |
| American cockroach | 6978 | Per a 3 | Q25640 | 1580794 | 281 | DKAQDVYVRIFLGPK | 15 | 3324.1407 |
| American cockroach | 6978 | Per a 3 | Q25640 | 1580794 | 346 | YRNLFKKVSDALEGK | 15 | 3324.1403 |
| American cockroach | 6978 | Per a 3 | Q25640 | 1580794 | 386 | GGQTFTFYVIVTPYV | 15 | 3324.1396 |
| American cockroach | 6978 | Per a 3 | Q25640 | 1580794 | 391 | TFYVIVTPYVKQDEH | 15 | 3324.1400 |
| American cockroach | 6978 | Per a 3 | Q25640 | 1580794 | 446 | YTPNMYFKDVVIFHK | 15 | 3324.1415 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| American cockroach | 6978 | Per a 3 | Q25640 | 1580794 | 451 | YFKDVVIFHKKYDEV | 15 | 3324.1406 |
| American cockroach | 6978 | Per a 6 | Q1M0Y3 | 60678791 | 6 | DEQIQLLKKAFDAFD | 15 | 3324.1420 |
| American cockroach | 6978 | Per a 6 | Q1M0Y3 | 60678791 | 31 | MVGTILEMLGHPLDD | 15 | 3324.1418 |
| American cockroach | 6978 | Per a 6 | Q1M0Y3 | 60678791 | 61 | GELEFQEFVTLAARF | 15 | 3324.1417 |
| American cockroach | 6978 | Per a 6 | Q1M0Y3 | 60678791 | 66 | QEFVTLAARFLVEED | 15 | 3324.1416 |
| American cockroach | 6978 | Per a 6 | Q1M0Y3 | 60678791 | 101 | GYITTTVLREILKEL | 15 | 3324.1419 |
| American cockroach | 6978 | Per a 6 | Q1M0Y3 | 60678791 | 106 | TVLREILKELDDKLT | 15 | 3324.1421 |
| American cockroach | 6978 | Per a 7 | Q9UB83 | 4468639 | 101 | RSEERLATATAKLAE | 15 | 3324.1423 |
| American cockroach | 6978 | Per a 7 | Q9UB83 | 4468639 | 191 | VELEEELRVVGNNLK | 15 | 3324.1425 |
| American cockroach | 6978 | Per a 7 | Q9UB83 | 4468639 | 216 | LREEEYKQQIKTLTT | 15 | 3324.1424 |
| American cockroach | 6978 | Per a 7 | Q9UB83 | 4468639 | 221 | YKQQIKTLTTRLKEA | 15 | 3324.1422 |
| Ash | 38873 | Fra e 1 | Q6U740 | 34978692 | 21 | DTCRARFITKLSEFI | 15 | 3324.1102 |
| Ash | 38873 | Fra e 1 | Q6U740 | 34978692 | 26 | RFITKLSEFITGASV | 15 | 3324.1101 |
| Ash | 38873 | Fra e 1 | Q6U740 | 34978692 | 31 | LSEFITGASVRLQCR | 15 | 3324.1105 |
| Ash | 38873 | Fra e 1 | Q6U740 | 34978692 | 76 | NEFCEITLLSSGRKD | 15 | 3324.1106 |
| Ash | 38873 | Fra e 1 | Q6U740 | 34978692 | 101 | KPSLKFILNTVNGTT | 15 | 3324.1103 |
| Ash | 38873 | Fra e 1 | Q6U740 | 34978692 | 121 | LGFPKKEALPQCAQV | 15 | 3324.1104 |
| Aspergillus fumigatus | 330879 | Asp f 1 | P67875 | 66845737 | 1 | MVAIKNLFLLAATAV | 15 | 3324.0121 |
| Aspergillus fumigatus | 330879 | Asp f 1 | P67875 | 66845737 | 6 | NLFLLAATAVSVLAA | 15 | 3324.0122 |
| Aspergillus fumigatus | 330879 | Asp f 1 | P67875 | 66845737 | 46 | DKRLLYSQAKAESNS | 15 | 3324.0123 |
| Aspergillus fumigatus | 330879 | Asp f 1 | P67875 | 66845737 | 116 | DDHYLLEFPTFPDGH | 15 | 3337.0014 |
| Aspergillus fumigatus | 330879 | Asp f 1 | P67875 | 66845737 | 146 | ARVIYTYPNKVFCGI | 15 | 3324.0124 |
| Aspergillus fumigatus | 330879 | Asp f 10 | Q12547(IUIS) | 85541049 | 1 | MVVFSKVIAVVVGLS | 15 | 3324.0128 |
| Aspergillus fumigatus | 330879 | Asp f 10 | Q12547(IUIS) | 85541049 | 6 | KVTAVVVGLSTIVSA | 15 | 3324.0129 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Aspergillus fumigatus | 330879 | Asp f 10 | Q12547(IUIS) | 85541049 | 11 | VVGLSTIVSAVPVVQ | 15 | 3324.0126 |
| Aspergillus fumigatus | 330879 | Asp f 10 | Q12547(IUIS) | 85541049 | 16 | TIVSAVPVVQPRKGF | 15 | 3324.0134 |
| Aspergillus fumigatus | 330879 | Asp f 10 | Q12547(IUIS) | 85541049 | 26 | PRKGFTINQVARPVT | 15 | 3324.0136 |
| Aspergillus fumigatus | 330879 | Asp f 10 | Q12547(IUIS) | 85541049 | 41 | NKKTVNLPAVYANAL | 15 | 3324.0132 |
| Aspergillus fumigatus | 330879 | Asp f 10 | Q12547(IUIS) | 85541049 | 46 | NLPAVYANALTKYGG | 15 | 3324.0131 |
| Aspergillus fumigatus | 330879 | Asp f 10 | Q12547(IUIS) | 85541049 | 61 | TVPDSVKAAASSGSA | 15 | 3324.0137 |
| Aspergillus fumigatus | 330879 | Asp f 10 | Q12547(IUIS) | 85541049 | 106 | ADLWFSSELSASQS | 15 | 3324.0127 |
| Aspergillus fumigatus | 330879 | Asp f 10 | Q12547(IUIS) | 85541049 | 171 | VEAASHISSQFVQDK | 15 | 3324.0125 |
| Aspergillus fumigatus | 330879 | Asp f 10 | Q12547(IUIS) | 85541049 | 186 | DNDGLLGLAFSSINT | 15 | 3324.0133 |
| Aspergillus fumigatus | 330879 | Asp f 10 | Q12547(IUIS) | 85541049 | 191 | LGLAFSSINTVSPRP | 15 | 3324.0135 |
| Aspergillus fumigatus | 330879 | Asp f 10 | Q12547(IUIS) | 85541049 | 221 | LFAVTLKYHAPGTYD | 15 | 3324.0130 |
| Aspergillus fumigatus | 746128 | Asp f 11 | Q9Y7F6 |  | 11 | VFPDVEYAPVGTAET | 15 | 3324.0143 |
| Aspergillus fumigatus | 746128 | Asp f 11 | Q9Y7F6 | 5019414 | 26 | KVGRIVFNLFDKDVP | 15 | 3324.0144 |
| Aspergillus fumigatus | 746128 | Asp f 11 | Q9Y7F6 | 5019414 | 61 | STFHRIIPNFMIQGG | 15 | 3324.0140 |
| Aspergillus fumigatus | 746128 | Asp f 11 | Q9Y7F6 | 5019414 | 101 | KHDKKGILSMANAGP | 15 | 3324.0141 |
| Aspergillus fumigatus | 746128 | Asp f 11 | Q9Y7F6 | 5019414 | 116 | NTNGSQFFITTAVTS | 15 | 3324.0138 |
| Aspergillus fumigatus | 746128 | Asp f 11 | Q9Y7F6 | 5019414 | 121 | QFFITTAVTSWLDGK | 15 | 3324.0139 |
| Aspergillus fumigatus | 746128 | Asp f 11 | Q9Y7F6 | 5019414 | 146 | KSYSVVKEIEALGSS | 15 | 3324.0142 |
| Aspergillus fumigatus | 330879 | Asp f 12 | P40292 | 1930153 | 1 | MSSETFEFQAEISQL | 15 | 3324.0177 |
| Aspergillus fumigatus | 330879 | Asp f 12 | P40292 | 1930153 | 6 | FEFQAEISQLLSLII | 15 | 3324.0146 |
| Aspergillus fumigatus | 330879 | Asp f 12 | P40292 | 1930153 | 11 | EISQLLSLIINTVYS | 15 | 3324.0151 |
| Aspergillus fumigatus | 330879 | Asp f 12 | P40292 | 1930153 | 16 | LSLIINTVYSNKEIF | 15 | 3324.0165 |
| Aspergillus fumigatus | 330879 | Asp f 12 | P40292 | 1930153 | 26 | NKEIFLRELISNASD | 15 | 3324.0147 |
| Aspergillus fumigatus | 330879 | Asp f 12 | P40292 | 1930153 | 31 | LRELISNASDALDKI | 15 | 3324.0156 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Aspergillus fumigatus | 330879 | Asp f 12 | P40292 | 1930153 | 41 | ALDLKRYQSLSDPTK | 15 | 3324.0172 |
| Aspergillus fumigatus | 330879 | Asp f 12 | P40292 | 1930153 | 96 | IARSGTKQFMEALSA | 15 | 3324.0173 |
| Aspergillus fumigatus | 330879 | Asp f 12 | P40292 | 1930153 | 101 | TKQFMEALSAGADIS | 15 | 3324.0180 |
| Aspergillus fumigatus | 330879 | Asp f 12 | P40292 | 1930153 | 116 | MIGQFGVGFYSAYLV | 15 | 3324.0166 |
| Aspergillus fumigatus | 330879 | Asp f 12 | P40292 | 1930153 | 121 | GVGFYSAYLVADRVT | 15 | 3324.0149 |
| Aspergillus fumigatus | 330879 | Asp f 12 | P40292 | 1930153 | 126 | SAYLVADRVTVVSKN | 15 | 3324.0171 |
| Aspergillus fumigatus | 330879 | Asp f 12 | P40292 | 1930153 | 171 | TKILHLKDEQTDYL | 15 | 3324.0179 |
| Aspergillus fumigatus | 330879 | Asp f 12 | P40292 | 1930153 | 191 | KEVVRKHSEFISYPI | 15 | 3324.0161 |
| Aspergillus fumigatus | 330879 | Asp f 12 | P40292 | 1930153 | 196 | KHSEFISYPIYLHVL | 15 | 3324.0155 |
| Aspergillus fumigatus | 330879 | Asp f 12 | P40292 | 1930153 | 281 | ITQEEYASFYKSLSN | 15 | 3324.0152 |
| Aspergillus fumigatus | 330879 | Asp f 12 | P40292 | 1930153 | 301 | LAVKHFSVEGQLEFR | 15 | 3324.0170 |
| Aspergillus fumigatus | 330879 | Asp f 12 | P40292 | 1930153 | 311 | QLEFRAILYVPKRAP | 15 | 3324.0150 |
| Aspergillus fumigatus | 330879 | Asp f 12 | P40292 | 1930153 | 336 | NNIKLYVRRVFITDD | 15 | 3324.0157 |
| Aspergillus fumigatus | 330879 | Asp f 12 | P40292 | 1930153 | 341 | YVRRVFITDDATDLI | 15 | 3324.0158 |
| Aspergillus fumigatus | 330879 | Asp f 12 | P40292 | 1930153 | 391 | KNIVKKTLELFNEIA | 15 | 3324.0175 |
| Aspergillus fumigatus | 330879 | Asp f 12 | P40292 | 1930153 | 406 | EDREQFDKFYSAFSK | 15 | 3324.0159 |
| Aspergillus fumigatus | 330879 | Asp f 12 | P40292 | 1930153 | 411 | FDKFYSAFSKNIKLG | 15 | 3324.0154 |
| Aspergillus fumigatus | 330879 | Asp f 12 | P40292 | 1930153 | 436 | LAKLLRYQSTKSGDE | 15 | 3324.0176 |
| Aspergillus fumigatus | 330879 | Asp f 12 | P40292 | 1930153 | 466 | KQIYYITGESIKAVA | 15 | 3324.0164 |
| Aspergillus fumigatus | 330879 | Asp f 12 | P40292 | 1930153 | 476 | IKAVAKSPFLDSLKQ | 15 | 3324.0174 |
| Aspergillus fumigatus | 330879 | Asp f 12 | P40292 | 1930153 | 491 | KNFEVLFLVDPIDEY | 15 | 3324.0163 |
| Aspergillus fumigatus | 330879 | Asp f 12 | P40292 | 1930153 | 541 | EKEYENLAKSLKNIL | 15 | 3324.0160 |
| Aspergillus fumigatus | 330879 | Asp f 12 | P40292 | 1930153 | 546 | NLAKSLKNILGDKVE | 15 | 3324.0178 |
| Aspergillus fumigatus | 330879 | Asp f 12 | P40292 | 1930153 | 581 | GWSANMERIMKAQAL | 15 | 3324.0167 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Aspergillus fumigatus | 330879 | Asp f 12 | P40292 | 1930153 | 586 | MERIMKAQALRDTSM | 15 | 3324.0168 |
| Aspergillus fumigatus | 330879 | Asp f 12 | P40292 | 1930153 | 631 | ENDRTVKSITQLLFE | 15 | 3324.0153 |
| Aspergillus fumigatus | 330879 | Asp f 12 | P40292 | 1930153 | 636 | VKSITQLLFETSLLV | 15 | 3324.0145 |
| Aspergillus fumigatus | 330879 | Asp f 12 | P40292 | 1930153 | 641 | QLLFETSLLVSGFTI | 15 | 3324.0148 |
| Aspergillus fumigatus | 330879 | Asp f 12 | P40292 | 1930153 | 661 | FAERIHKLVSLGLNI | 15 | 3324.0162 |
| Aspergillus fumigatus | 330879 | Asp f 12 | P40292 | 1930153 | 666 | HKLVSLGLNIDERAE | 15 | 3324.0169 |
| Aspergillus fumigatus | 330879 | Asp f 13 | P28296 | 83305202 | 1 | MLSIKRTLLLLGAVL | 15 | 3324.0183 |
| Aspergillus fumigatus | 330879 | Asp f 13 | P28296 | 83305202 | 6 | RTLLLLGAVLPAVFG | 15 | 3324.0181 |
| Aspergillus fumigatus | 330879 | Asp f 13 | P28296 | 83305202 | 81 | KSYKIKDFAAYAGSF | 15 | 3324.0189 |
| Aspergillus fumigatus | 330879 | Asp f 13 | P28296 | 83305202 | 111 | HVEEDQIWYLDALTT | 15 | 3324.0182 |
| Aspergillus fumigatus | 330879 | Asp f 13 | P28296 | 83305202 | 116 | QIWYLDALTTQKGAP | 15 | 3324.0186 |
| Aspergillus fumigatus | 330879 | Asp f 13 | P28296 | 83305202 | 141 | QASTDYIYDTSAGAG | 15 | 3324.0187 |
| Aspergillus fumigatus | 330879 | Asp f 13 | P28296 | 83305202 | 146 | YIYDTSAGAGTYAYV | 15 | 3324.0195 |
| Aspergillus fumigatus | 330879 | Asp f 13 | P28296 | 83305202 | 211 | KTNLLSVKVFQGESS | 15 | 3324.0185 |
| Aspergillus fumigatus | 330879 | Asp f 13 | P28296 | 83305202 | 216 | SVKVFQGESSTSI | 15 | 3324.0193 |
| Aspergillus fumigatus | 330879 | Asp f 13 | P28296 | 83305202 | 231 | LDGFNWAVNDIVSKG | 15 | 3324.0192 |
| Aspergillus fumigatus | 330879 | Asp f 13 | P28296 | 83305202 | 256 | LGGGYSYAFNNAVEN | 15 | 3324.0190 |
| Aspergillus fumigatus | 330879 | Asp f 13 | P28296 | 83305202 | 296 | SAPNALTVAAINKSN | 15 | 3324.0194 |
| Aspergillus fumigatus | 330879 | Asp f 13 | P28296 | 83305202 | 351 | ATPHIVGLSVYLMGL | 15 | 3324.0184 |
| Aspergillus fumigatus | 330879 | Asp f 13 | P28296 | 83305202 | 356 | VGLSVYLMGLENLSG | 15 | 3324.0188 |
| Aspergillus fumigatus | 330879 | Asp f 13 | P28296 | 83305202 | 361 | YLMGLENLSGPAAVT | 15 | 3324.0191 |
| Aspergillus fumigatus | 330879 | Asp f 15 | O60022 | 66853233 | 1 | MKFTTPISLISLFVS | 15 | 3324.0197 |
| Aspergillus fumigatus | 330879 | Asp f 15 | O60022 | 66853233 | 6 | PISLISLFVSSALAA | 15 | 3324.0196 |
| Aspergillus fumigatus | 330879 | Asp f 15 | O60022 | 66853233 | 11 | SLFVSSALAAPTPEN | 15 | 3324.0198 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Aspergillus fumigatus | 330879 | Asp f 15 | O60022 | 66853233 | 91 | GKCYKLQYEQNTIYV | 15 | 3324.0202 |
| Aspergillus fumigatus | 330879 | Asp f 15 | O60022 | 66853233 | 96 | LQYEQNTIYVTAIDA | 15 | 3324.0201 |
| Aspergillus fumigatus | 330879 | Asp f 15 | O60022 | 66853233 | 101 | NTIYVTAIDAAPGGF | 15 | 3324.0200 |
| Aspergillus fumigatus | 330879 | Asp f 15 | O60022 | 66853233 | 111 | APGGFNIATSAMDQL | 15 | 3324.0199 |
| Aspergillus fumigatus | 746128 | Asp f 16 | O74682 (IUIS) | 3643812 | 1 | MYFKYTAALAAVLP | 15 | 3324.0204 |
| Aspergillus fumigatus | 746128 | Asp f 16 | O74682 (IUIS) | 3643812 | 6 | TAAALAAVLPLCSAQ | 15 | 3324.0205 |
| Aspergillus fumigatus | 746128 | Asp f 16 | O74682 (IUIS) | 3643812 | 81 | PTIDTDFYFFFGKAE | 15 | 3324.0206 |
| Aspergillus fumigatus | 746128 | Asp f 16 | O74682 (IUIS) | 3643812 | 86 | DFYFFFGKAEVVMKA | 15 | 3324.0203 |
| Aspergillus fumigatus | 746128 | Asp f 16 | O74682 (IUIS) | 3643812 | 196 | PQTPMRLRLAAGPAA | 15 | 3324.0207 |
| Aspergillus fumigatus | 746128 | Asp f 17 | O60025 | 2980819 | 11 | VGVISDISAQTSALA | 15 | 3324.0208 |
| Aspergillus fumigatus | 746128 | Asp f 17 | O60025 | 2980819 | 91 | SKKDKFVAANAGGTV | 15 | 3324.0212 |
| Aspergillus fumigatus | 746128 | Asp f 17 | O60025 | 2980819 | 101 | AGGTVYEDLKAQYTA | 15 | 3324.0213 |
| Aspergillus fumigatus | 746128 | Asp f 17 | O60025 | 2980819 | 111 | AQYTAADSLAKAISA | 15 | 3324.0214 |
| Aspergillus fumigatus | 746128 | Asp f 17 | O60025 | 2980819 | 116 | ADSLAKAISAKVPES | 15 | 3324.0209 |
| Aspergillus fumigatus | 746128 | Asp f 17 | O60025 | 2980819 | 131 | LSDIAAQLSAGITAA | 15 | 3324.0211 |
| Aspergillus fumigatus | 746128 | Asp f 17 | O60025 | 2980819 | 136 | AQLSAGITAAIQKGI | 15 | 3324.0210 |
| Aspergillus fumigatus | 330879 | Asp f 18 | P87184 | 66851354 | 1 | MKGYLSLSILPLLVA | 15 | 3324.0217 |
| Aspergillus fumigatus | 330879 | Asp f 18 | P87184 | 66851354 | 6 | SLSILPLLVAASPVV | 15 | 3324.0218 |
| Aspergillus fumigatus | 330879 | Asp f 18 | P87184 | 66851354 | 11 | PLLVAASPVVDSIH | 15 | 3324.0221 |
| Aspergillus fumigatus | 330879 | Asp f 18 | P87184 | 66851354 | 26 | NGAAPILSSMNAKEV | 15 | 3324.0231 |
| Aspergillus fumigatus | 330879 | Asp f 18 | P87184 | 66851354 | 46 | VVFKKHVNAESAAAH | 15 | 3324.0224 |
| Aspergillus fumigatus | 330879 | Asp f 18 | P87184 | 66851354 | 61 | HSWVQDIHSAQNERV | 15 | 3324.0220 |
| Aspergillus fumigatus | 330879 | Asp f 18 | P87184 | 66851354 | 91 | LGLKNTFDIAGSLVG | 15 | 3324.0227 |
| Aspergillus fumigatus | 330879 | Asp f 18 | P87184 | 66851354 | 96 | TFDIAGSLVGYSGHF | 15 | 3324.0233 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Aspergillus fumigatus | 330879 | Asp f 18 | P87184 | 66851354 | 236 | YAVKVLRSSGSGTMS | 15 | 3324.0225 |
| Aspergillus fumigatus | 330879 | Asp f 18 | P87184 | 66851354 | 276 | KGFKGSVANMSLGGG | 15 | 3324.0229 |
| Aspergillus fumigatus | 330879 | Asp f 18 | P87184 | 66851354 | 291 | KSRTLEAAVNAGVEA | 15 | 3324.0230 |
| Aspergillus fumigatus | 330879 | Asp f 18 | P87184 | 66851354 | 301 | AGVEAGLHFAVAAGN | 15 | 3324.0222 |
| Aspergillus fumigatus | 330879 | Asp f 18 | P87184 | 66851354 | 381 | MASPHIAGLLAYFVS | 15 | 3324.0219 |
| Aspergillus fumigatus | 330879 | Asp f 18 | P87184 | 66851354 | 386 | IAGLLAYFVSLQPSK | 15 | 3324.0215 |
| Aspergillus fumigatus | 330879 | Asp f 18 | P87184 | 66851354 | 411 | PKKLKKDIIAIATQG | 15 | 3324.0232 |
| Aspergillus fumigatus | 330879 | Asp f 18 | P87184 | 66851354 | 416 | KDIIAIATQGALTDI | 15 | 3324.0216 |
| Aspergillus fumigatus | 330879 | Asp f 18 | P87184 | 66851354 | 451 | IIASGGYKVNASVKD | 15 | 3324.0226 |
| Aspergillus fumigatus | 330879 | Asp f 18 | P87184 | 66851354 | 476 | KLLTEELGAIYSEIH | 15 | 3324.0223 |
| Aspergillus fumigatus | 330879 | Asp f 18 | P87184 | 66851354 | 481 | ELGAIYSEIHDAAVA | 15 | 3324.0228 |
| Aspergillus fumigatus | 330879 | Asp f 2 | P79017 | 66849502 | 1 | MAALLRLAVLLPLAA | 15 | 3324.0236 |
| Aspergillus fumigatus | 330879 | Asp f 2 | P79017 | 66849502 | 6 | RLAVLLPLAAPLVAT | 15 | 3324.0235 |
| Aspergillus fumigatus | 330879 | Asp f 2 | P79017 | 66849502 | 16 | PLVATLPTSPVPIAA | 15 | 3324.0242 |
| Aspergillus fumigatus | 330879 | Asp f 2 | P79017 | 66849502 | 36 | EPVFFSWDAGAVTSF | 15 | 3324.0238 |
| Aspergillus fumigatus | 330879 | Asp f 2 | P79017 | 66849502 | 41 | SWDAGAVTSFPIHSS | 15 | 3324.0239 |
| Aspergillus fumigatus | 330879 | Asp f 2 | P79017 | 66849502 | 156 | TTRRWLVSMCSQGYT | 15 | 3324.0243 |
| Aspergillus fumigatus | 330879 | Asp f 2 | P79017 | 66849502 | 206 | YDEVIALAKSNGTES | 15 | 3324.0241 |
| Aspergillus fumigatus | 330879 | Asp f 2 | P79017 | 66849502 | 221 | THDSEALQYFALEAY | 15 | 3324.0240 |
| Aspergillus fumigatus | 330879 | Asp f 2 | P79017 | 66849502 | 226 | ALQYFALEAYAFDIA | 15 | 3324.0234 |
| Aspergillus fumigatus | 330879 | Asp f 2 | P79017 | 66849502 | 231 | ALEAYAFDIAAPGVG | 15 | 3324.0237 |
| Aspergillus fumigatus | 330879 | Asp f 22 | Q96X30 | 13925873 | 1 | MPISKIHARSVYDSR | 15 | 3324.0256 |
| Aspergillus fumigatus | 330879 | Asp f 22 | Q96X30 | 13925873 | 106 | LGANAILGVSLAVAK | 15 | 3324.0245 |
| Aspergillus fumigatus | 330879 | Asp f 22 | Q96X30 | 13925873 | 111 | ILGVSLAVAKAGAAE | 15 | 3324.0248 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Aspergillus fumigatus | 330879 | Asp f 22 | Q96X30 | 13925873 | 161 | GGRLAFQEFMIVPDS | 15 | 3324.0252 |
| Aspergillus fumigatus | 330879 | Asp f 22 | Q96X30 | 13925873 | 166 | FQEFMIVPDSAPSFS | 15 | 3324.0251 |
| Aspergillus fumigatus | 330879 | Asp f 22 | Q96X30 | 13925873 | 186 | GAEVYQKLKALAKKK | 15 | 3324.0254 |
| Aspergillus fumigatus | 330879 | Asp f 22 | Q96X30 | 13925873 | 241 | IKIAMDVASSEFYKA | 15 | 3324.0255 |
| Aspergillus fumigatus | 330879 | Asp f 22 | Q96X30 | 13925873 | 271 | PSKWLTYEQLADLYK | 15 | 3324.0247 |
| Aspergillus fumigatus | 330879 | Asp f 22 | Q96X30 | 13925873 | 281 | ADLYKSLAAKYPIVS | 15 | 3324.0244 |
| Aspergillus fumigatus | 330879 | Asp f 22 | Q96X30 | 13925873 | 306 | EAWSYFYKTSDFQIV | 15 | 3324.0250 |
| Aspergillus fumigatus | 330879 | Asp f 22 | Q96X30 | 13925873 | 336 | IELKSCNALLLKVNQ | 15 | 3324.0246 |
| Aspergillus fumigatus | 330879 | Asp f 22 | Q96X30 | 13925873 | 341 | CNALLLKVNQIGTLT | 15 | 3324.0249 |
| Aspergillus fumigatus | 330879 | Asp f 22 | Q96X30 | 13925873 | 406 | ERLAKLNQILRIEEE | 15 | 3324.0253 |
| Aspergillus fumigatus | 330879 | Asp f 23 | Q8NKF4 | 66853155 | 71 | EIVEAVTIIETPPLV | 15 | 3324.0259 |
| Aspergillus fumigatus | 330879 | Asp f 23 | Q8NKF4 | 66853155 | 96 | PRGLRSLTTVWAEHL | 15 | 3324.0257 |
| Aspergillus fumigatus | 330879 | Asp f 23 | Q8NKF4 | 66853155 | 151 | RIKKYCTVVRLAHT | 15 | 3324.0260 |
| Aspergillus fumigatus | 330879 | Asp f 23 | Q8NKF4 | 66853155 | 156 | CTVVRLAHTQIRKT | 15 | 3324.0258 |
| Aspergillus fumigatus | 330879 | Asp f 27 | Q4WWX5 | 71000343 | 1 | MVVKTFFDITIDGQP | 15 | 3324.0265 |
| Aspergillus fumigatus | 330879 | Asp f 27 | Q4WWX5 | 71000343 | 21 | FKLFDEVVPKTVENF | 15 | 3324.0266 |
| Aspergillus fumigatus | 330879 | Asp f 27 | Q4WWX5 | 71000343 | 46 | GYKGSSFHRIIPQFM | 15 | 3324.0261 |
| Aspergillus fumigatus | 330879 | Asp f 27 | Q4WWX5 | 71000343 | 51 | SFHRIIPQFMLQGGD | 15 | 3324.0263 |
| Aspergillus fumigatus | 330879 | Asp f 27 | Q4WWX5 | 71000343 | 91 | HDKPGLLSMANAGKN | 15 | 3324.0267 |
| Aspergillus fumigatus | 330879 | Asp f 27 | Q4WWX5 | 71000343 | 106 | TNGSQFFITTVVTSW | 15 | 3324.0262 |
| Aspergillus fumigatus | 330879 | Asp f 27 | Q4WWX5 | 71000343 | 111 | FFITTVVTSWLDGAH | 15 | 3324.0264 |
| Aspergillus fumigatus | 746128 | Asp f 28 | Q1RQJ1 | 91680607 | 11 | NPIIYKALTSSGPVV | 15 | 3324.0270 |
| Aspergillus fumigatus | 746128 | Asp f 28 | Q1RQJ1 | 91680607 | 46 | LSEKYSNVRFIQVDV | 15 | 3324.0271 |
| Aspergillus fumigatus | 746128 | Asp f 28 | Q1RQJ1 | 91680607 | 66 | VAHEMNIRAMPTFVL | 15 | 3324.0268 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Aspergillus fumigatus | 746128 | Asp f 28 | Q1RQJ1 | 91680607 | 71 | NIRAMPTFVLYKDGQ | 15 | 3324.0269 |
| Aspergillus fumigatus | 330879 | Asp f 29 | Q4WV97 | 70997545 | 41 | SPVFQRLSTSEEFKN | 15 | 3324.0273 |
| Aspergillus fumigatus | 330879 | Asp f 29 | Q4WV97 | 70997545 | 56 | AKFYEIDVDELSEVA | 15 | 3324.0272 |
| Aspergillus fumigatus | 330879 | Asp f 29 | Q4WV97 | 70997545 | 96 | ANPPALEAAIKAHVA | 15 | 3337.0015 |
| Aspergillus fumigatus | 330879 | Asp f 3 | O43099 | 2769700 | 46 | KKVILFALPGAFTPV | 15 | 3324.0274 |
| Aspergillus fumigatus | 330879 | Asp f 3 | O43099 | 2769700 | 81 | VDVVAVLAYNDAYM | 15 | 3324.0275 |
| Aspergillus fumigatus | 330879 | Asp f 3 | O43099 | 2769700 | 86 | VLAYNDAYVMSAWGK | 15 | 3324.0277 |
| Aspergillus fumigatus | 330879 | Asp f 3 | O43099 | 2769700 | 106 | GDDILFLSDPDARFS | 15 | 3324.0279 |
| Aspergillus fumigatus | 330879 | Asp f 3 | O43099 | 2769700 | 141 | HGKITYAALEPAKNH | 15 | 3324.0278 |
| Aspergillus fumigatus | 330879 | Asp f 3 | O43099 | 2769700 | 154 | NHLEFSSAETVLKHL | 15 | 3324.0276 |
| Aspergillus fumigatus | 746128 | Asp f 34 | A4FSH5 | 133920236 | 1 | MQIKSFVLAASAAAT | 15 | 3324.0280 |
| Aspergillus fumigatus | 746128 | Asp f 34 | A4FSH5 | 133920236 | 6 | FVLAASAAATASAAA | 15 | 3324.0281 |
| Aspergillus fumigatus | 746128 | Asp f 34 | A4FSH5 | 133920236 | 26 | NKYFGIVAIHSGSAV | 15 | 3324.0283 |
| Aspergillus fumigatus | 746128 | Asp f 34 | A4FSH5 | 133920236 | 31 | IVAIHSGSAVQYQPF | 15 | 3324.0282 |
| Aspergillus fumigatus | 746128 | Asp f 34 | A4FSH5 | 133920236 | 36 | SGSAVQYQPFSAAKS | 15 | 3324.0287 |
| Aspergillus fumigatus | 746128 | Asp f 34 | A4FSH5 | 133920236 | 41 | QYQPFSAAKSSIFAG | 15 | 3324.0286 |
| Aspergillus fumigatus | 746128 | Asp f 34 | A4FSH5 | 133920236 | 71 | ATFYIQDGSLYLYAA | 15 | 3324.0285 |
| Aspergillus fumigatus | 746128 | Asp f 34 | A4FSH5 | 133920236 | 76 | QDGSLYLYAASATPQ | 15 | 3324.0284 |
| Aspergillus fumigatus | 330879 | Asp f 4 | O60024 | 70989331 | 1 | MQLKNSMLLLTALAA | 15 | 3324.0289 |
| Aspergillus fumigatus | 330879 | Asp f 4 | O60024 | 70989331 | 6 | SMLLLTALAAGSSVA | 15 | 3324.0290 |
| Aspergillus fumigatus | 330879 | Asp f 4 | O60024 | 70989331 | 41 | DTVYATINGVLVSWI | 15 | 3324.0288 |
| Aspergillus fumigatus | 330879 | Asp f 4 | O60024 | 70989331 | 186 | TGWYGNSALTLHLEA | 15 | 3324.0291 |
| Aspergillus fumigatus | 330879 | Asp f 4 | O60024 | 70989331 | 276 | GELCSIISHGLSKVI | 15 | 3324.0293 |
| Aspergillus fumigatus | 330879 | Asp f 4 | O60024 | 70989331 | 286 | LSKVIDAYTADLAGV | 15 | 3324.0292 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Aspergillus fumigatus | 330879 | Asp f 5 | P46075 | 3776613 | 1 | MRGLLLAGALALPAS | 15 | 3324.0297 |
| Aspergillus fumigatus | 330879 | Asp f 5 | P46075 | 3776613 | 6 | LAGALALPASVFAHP | 15 | 3324.0311 |
| Aspergillus fumigatus | 330879 | Asp f 5 | P46075 | 3776613 | 31 | TVDLNAFRLKSLAKY | 15 | 3324.0299 |
| Aspergillus fumigatus | 330879 | Asp f 5 | P46075 | 3776613 | 36 | AFRLKSLAKYVNATE | 15 | 3324.0300 |
| Aspergillus fumigatus | 330879 | Asp f 5 | P46075 | 3776613 | 41 | SLAKYVNATETVIEA | 15 | 3324.0313 |
| Aspergillus fumigatus | 330879 | Asp f 5 | P46075 | 3776613 | 61 | PFKPQSYVEVATQHV | 15 | 3324.0317 |
| Aspergillus fumigatus | 330879 | Asp f 5 | P46075 | 3776613 | 121 | GKDGKVFSYGNSFYT | 15 | 3324.0306 |
| Aspergillus fumigatus | 330879 | Asp f 5 | P46075 | 3776613 | 181 | ESVFKGVSGTVSDP | 15 | 3324.0314 |
| Aspergillus fumigatus | 330879 | Asp f 5 | P46075 | 3776613 | 196 | KAKLVYFVKDDGTLA | 15 | 3324.0308 |
| Aspergillus fumigatus | 330879 | Asp f 5 | P46075 | 3776613 | 221 | SNWLLTYIDAKSGEE | 15 | 3324.0298 |
| Aspergillus fumigatus | 330879 | Asp f 5 | P46075 | 3776613 | 306 | SYLNNYRPSSSSLSF | 15 | 3324.0318 |
| Aspergillus fumigatus | 330879 | Asp f 5 | P46075 | 3776613 | 316 | SSLSFKYPYSVSSSP | 15 | 3324.0309 |
| Aspergillus fumigatus | 330879 | Asp f 5 | P46075 | 3776613 | 331 | PSSYIDASIIQLFYT | 15 | 3324.0294 |
| Aspergillus fumigatus | 330879 | Asp f 5 | P46075 | 3776613 | 336 | DASIIQLFYTANIYH | 15 | 3324.0296 |
| Aspergillus fumigatus | 330879 | Asp f 5 | P46075 | 3776613 | 341 | QLFYTANIYHDLLYT | 15 | 3324.0304 |
| Aspergillus fumigatus | 330879 | Asp f 5 | P46075 | 3776613 | 346 | ANIYHDLLYTLGFTE | 15 | 3324.0310 |
| Aspergillus fumigatus | 330879 | Asp f 5 | P46075 | 3776613 | 376 | GNDYVILNAQDGSGT | 15 | 3324.0315 |
| Aspergillus fumigatus | 330879 | Asp f 5 | P46075 | 3776613 | 426 | IVIHEYTHGLSNRLT | 15 | 3324.0307 |
| Aspergillus fumigatus | 330879 | Asp f 5 | P46075 | 3776613 | 461 | WSDFMATAIRLKPGD | 15 | 3324.0319 |
| Aspergillus fumigatus | 330879 | Asp f 5 | P46075 | 3776613 | 491 | AGGIRQYPYSTSLST | 15 | 3324.0302 |
| Aspergillus fumigatus | 330879 | Asp f 5 | P46075 | 3776613 | 506 | NPLTYTSVNSLNAVH | 15 | 3324.0316 |
| Aspergillus fumigatus | 330879 | Asp f 5 | P46075 | 3776613 | 516 | LNAVHAIGTVWASML | 15 | 3324.0312 |
| Aspergillus fumigatus | 330879 | Asp f 5 | P46075 | 3776613 | 521 | AIGTVWASMLYEVLW | 15 | 3324.0305 |
| Aspergillus fumigatus | 330879 | Asp f 5 | P46075 | 3776613 | 526 | WASMLYEVLWNLIDK | 15 | 3324.0295 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Aspergillus fumigatus | 330879 | Asp f 5 | P46075 | 3776613 | 556 | PTDGKYLAMKLVMDG | 15 | 3324.0303 |
| Aspergillus fumigatus | 330879 | Asp f 5 | P46075 | 3776613 | 576 | CNPNFVQARDAILDA | 15 | 3324.0301 |
| Aspergillus fumigatus | 330879 | Asp f 6 | Q92450 | 18158811 | 11 | PYPYDALQPYISQQI | 15 | 3324.0322 |
| Aspergillus fumigatus | 330879 | Asp f 6 | Q92450 | 18158811 | 16 | ALQPYISQQIMELHH | 15 | 3324.0321 |
| Aspergillus fumigatus | 330879 | Asp f 6 | Q92450 | 18158811 | 31 | KKHHQTYVNGLNAAL | 15 | 3324.0326 |
| Aspergillus fumigatus | 330879 | Asp f 6 | Q92450 | 18158811 | 36 | TYVNGLNAALEAQKK | 15 | 3324.0323 |
| Aspergillus fumigatus | 330879 | Asp f 6 | Q92450 | 18158811 | 56 | DVPKLVSVQQAIKFN | 15 | 3324.0325 |
| Aspergillus fumigatus | 330879 | Asp f 6 | Q92450 | 18158811 | 61 | VSVQQAIKFNGGGHI | 15 | 3324.0328 |
| Aspergillus fumigatus | 330879 | Asp f 6 | Q92450 | 18158811 | 111 | FDKFKDAFNTTLLGI | 15 | 3324.0324 |
| Aspergillus fumigatus | 330879 | Asp f 6 | Q92450 | 18158811 | 166 | EHAYYLQYLNDKASY | 15 | 3324.0320 |
| Aspergillus fumigatus | 330879 | Asp f 6 | Q92450 | 18158811 | 171 | LQYLNDKASYAKGIW | 15 | 3324.0327 |
| Aspergillus fumigatus | 330879 | Asp f 7 | O42799 | 2879888 | 1 | MAPIFKSLALVSALF | 15 | 3324.0332 |
| Aspergillus fumigatus | 330879 | Asp f 7 | O42799 | 2879888 | 6 | KSLALVSALFAAISS | 15 | 3324.0330 |
| Aspergillus fumigatus | 330879 | Asp f 7 | O42799 | 2879888 | 11 | VSALFAAISSAAPVN | 15 | 3324.0331 |
| Aspergillus fumigatus | 330879 | Asp f 7 | O42799 | 2879888 | 96 | TQPSVATFIPVAAAA | 15 | 3324.0334 |
| Aspergillus fumigatus | 330879 | Asp f 7 | O42799 | 2879888 | 101 | ATFIPVAAAAAADS | 15 | 3324.0333 |
| Aspergillus fumigatus | 330879 | Asp f 7 | O42799 | 2879888 | 176 | LTYYDTATSASAPSS | 15 | 3324.0335 |
| Aspergillus fumigatus | 330879 | Asp f 7 | O42799 | 2879888 | 196 | DGFSENVVALPVGIM | 15 | 3324.0329 |
| Aspergillus fumigatus | 330879 | Asp f 8 | Q9UUZ6 | 9887212 | 1 | MKHLAAYLLLALAGN | 15 | 3324.0336 |
| Aspergillus fumigatus | 330879 | Asp f 8 | Q9UUZ6 | 9887212 | 6 | AYLLLALAGNTSPSS | 15 | 3324.0337 |
| Aspergillus fumigatus | 330879 | Asp f 8 | Q9UUZ6 | 9887212 | 21 | EDVKAVLSSVGIDAD | 15 | 3324.0338 |
| Aspergillus fumigatus | 330879 | Asp f 8 | Q9UUZ6 | 9887212 | 36 | EERLNKLIAELEGKD | 15 | 3337.0016 |
| Aspergillus fumigatus | 330879 | Asp f 8 | Q9UUZ6 | 9887212 | 51 | LQELIAEGSTKLASV | 15 | 3324.0339 |
| Aspergillus fumigatus | 330879 | Asp f 9 | O42800 (IUIS) | 85540942 | 1 | KRSFILRSADMYFKY | 15 | 3324.0342 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Aspergillus fumigatus | 330879 | Asp f 9 | O42800(IUIS) | 85540942 | 6 | LRSADMYFKYTAAAL | 15 | 3324.0343 |
| Aspergillus fumigatus | 330879 | Asp f 9 | O42800(IUIS) | 85540942 | 11 | MYFKYTAAALAAVLP | 15 | 3324.0341 |
| Aspergillus fumigatus | 330879 | Asp f 9 | O42800(IUIS) | 85540942 | 16 | TAAALAAVLPLCSAQ | 15 | 3324.0344 |
| Aspergillus fumigatus | 330879 | Asp f 9 | O42800(IUIS) | 85540942 | 51 | STYTADFTSASALDQ | 15 | 3324.0346 |
| Aspergillus fumigatus | 330879 | Asp f 9 | O42800(IUIS) | 85540942 | 91 | PTIDTDFYFFGKAE | 15 | 3324.0345 |
| Aspergillus fumigatus | 330879 | Asp f 9 | O42800(IUIS) | 85540942 | 96 | DFYFFGKAEVVMKA | 15 | 3324.0340 |
| Bermuda grass | 28909 | Cyn d 1 | Q947S4 | 16076697 | 1 | MLAVVAVVLASMVGG | 15 | 3324.0633 |
| Bermuda grass | 28909 | Cyn d 1 | Q947S4 | 16076697 | 111 | ITDKNYEHIAAYHFD | 15 | 3324.0637 |
| Bermuda grass | 28909 | Cyn d 1 | Q947S4 | 16076697 | 116 | YEHIAAYHFDLSGKA | 15 | 3324.0634 |
| Bermuda grass | 28909 | Cyn d 1 | Q947S4 | 16076697 | 141 | DKLRKAGELMLQFRR | 15 | 3324.0635 |
| Bermuda grass | 28909 | Cyn d 1 | Q947S4 | 16076697 | 176 | PNYLALLVKYAAGDG | 15 | 3324.0636 |
| Bermuda grass | 28909 | Cyn d 12 | O04725 | 2154728 | 31 | TVWAQSAAFPAFKPE | 15 | 3324.0639 |
| Bermuda grass | 28909 | Cyn d 12 | O04725 | 2154728 | 66 | FLGPTKYMVIQGEPG | 15 | 3324.0640 |
| Bermuda grass | 28909 | Cyn d 12 | O04725 | 2154728 | 71 | KYMVIQGEPGAVIRG | 15 | 3324.0638 |
| Bermuda grass | 28909 | Cyn d 15 | Q7XYF2 | 32344781 | 1 | MATLTFPVLLATMVG | 15 | 3324.0641 |
| Bermuda grass | 28909 | Cyn d 15 | Q7XYF2 | 32344781 | 6 | FPVLLATMVGHAWCV | 15 | 3324.0642 |
| Bermuda grass | 28909 | Cyn d 15 | Q7XYF2 | 32344781 | 21 | NIIFHVEESSPKFAL | 15 | 3324.0643 |
| Bermuda grass | 28909 | Cyn d 15 | Q7XYF2 | 32344781 | 71 | KPLKGPLNIRLRAEG | 15 | 3337.0021 |
| Bermuda grass | 28909 | Cyn d 23 | Q7XYF3 | 32344779 | 1 | MAKVIAIILVATMVT | 15 | 3324.0644 |
| Bermuda grass | 28909 | Cyn d 23 | Q7XYF3 | 32344779 | 6 | AIILVATMVTAALVP | 15 | 3324.0645 |
| Bermuda grass | 28909 | Cyn d 23 | Q7XYF3 | 32344779 | 11 | ATMVTAALVPIECAT | 15 | 3324.0648 |
| Bermuda grass | 28909 | Cyn d 23 | Q7XYF3 | 32344779 | 56 | DAAVNLMAMSFICIG | 15 | 3324.0646 |
| Bermuda grass | 28909 | Cyn d 23 | Q7XYF3 | 32344779 | 61 | LMAMSFICIGWAKKA | 15 | 3324.0647 |
| Bermuda grass | 28909 | Cyn d 23 | Q7XYF3 | 32344779 | 91 | AADQVLAAAPAHKYK | 15 | 3324.0649 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Bermuda grass | 28909 | Cyn d 7 | P94092 | 14423848 | 26 | ELTDALRTLGSTSAD | 15 | 3324.0651 |
| Bermuda grass | 28909 | Cyn d 7 | P94092 | 14423848 | 31 | LRTLGSTSADEVQRM | 15 | 3324.0652 |
| Bermuda grass | 28909 | Cyn d 7 | P94092 | 14423848 | 56 | FIDFDEFISFCNANP | 15 | 3324.0650 |
| Birch | 3505 | Bet v 1 | O23754 | 2414158 | 6 | YETETTSVIPAARLF | 15 | 3324.0351 |
| Birch | 3505 | Bet v 1 | O23754 | 2414158 | 11 | TSVIPAARLFKAFFL | 15 | 3324.0349 |
| Birch | 3505 | Bet v 1 | O23754 | 2414158 | 76 | DHTNFKYSYSVIEGG | 15 | 3324.0350 |
| Birch | 3505 | Bet v 1 | O23754 | 2414158 | 96 | LEKISNEIKIVATPD | 15 | 3324.0353 |
| Birch | 3505 | Bet v 1 | O23754 | 2414158 | 111 | GGSILKISNKYHTKG | 15 | 3324.0352 |
| Birch | 3505 | Bet v 1 | O23754 | 2414158 | 141 | GETLLRAVESYLLAH | 15 | 3324.0347 |
| Birch | 3505 | Bet v 1 | O23754 | 2414158 | 146 | RAVESYLLAHSDAYN | 15 | 3324.0348 |
| Birch | 3505 | Bet v 2 | P25816 | 157830684 | 31 | DGSVWAQSSSFPQFK | 15 | 3324.0355 |
| Birch | 3505 | Bet v 2 | P25816 | 157830684 | 66 | GLHLGGIKYMVIQGE | 15 | 3324.0356 |
| Birch | 3505 | Bet v 2 | P25816 | 157830684 | 71 | GIKYMVIQGEAGAVI | 15 | 3324.0354 |
| Birch | 3505 | Bet v 3 | P43187 | 257675827 | 26 | NSSFRLRSESLNTLR | 15 | 3324.0358 |
| Birch | 3505 | Bet v 3 | P43187 | 257675827 | 31 | LRSESLNTLRLRRIF | 15 | 3324.0360 |
| Birch | 3505 | Bet v 3 | P43187 | 257675827 | 36 | LNTLRLRRIFDLFDK | 15 | 3324.0361 |
| Birch | 3505 | Bet v 3 | P43187 | 257675827 | 56 | ITVDELSRALNLLGL | 15 | 3324.0359 |
| Birch | 3505 | Bet v 3 | P43187 | 257675827 | 61 | LSRALNLLGLETDLS | 15 | 3324.0364 |
| Birch | 3505 | Bet v 3 | P43187 | 257675827 | 91 | GLQPEDFISLHQSLN | 15 | 3324.0357 |
| Birch | 3505 | Bet v 3 | P43187 | 257675827 | 96 | DFISLHQSLNDSYFA | 15 | 3324.0365 |
| Birch | 3505 | Bet v 3 | P43187 | 257675827 | 146 | GDGYISARELQMVLG | 15 | 3324.0366 |
| Birch | 3505 | Bet v 3 | P43187 | 257675827 | 171 | DRVEKMIVSVDSNRD | 15 | 3324.0362 |
| Birch | 3505 | Bet v 3 | P43187 | 257675827 | 191 | FEFKDMMRSVLVRSS | 15 | 3324.0363 |
| Birch | 3505 | Bet v 4 | Q39419 | 2051993 | 31 | ELGEALKTLGSITPD | 15 | 3324.0367 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Birch | 3505 | Bet v 4 | Q39419 | 2051993 | 61 | FISFQEFTDFGRANR | 15 | 3324.0368 |
| Birch | 3505 | Bet v 4 | Q39419 | 2051993 | 71 | GRANRGLLKDVAKIF | 15 | 3337.0017 |
| Birch | 3505 | Bet v 6 | Q9FUW6 | 10764491 | 16 | IGKFIVEASAKSGHP | 15 | 3324.0375 |
| Birch | 3505 | Bet v 6 | Q9FUW6 | 10764491 | 46 | GKLVEKFKGLGVTLL | 15 | 3324.0374 |
| Birch | 3505 | Bet v 6 | Q9FUW6 | 10764491 | 51 | KFKGLGVTLLHGDLY | 15 | 3324.0376 |
| Birch | 3505 | Bet v 6 | Q9FUW6 | 10764491 | 71 | VKAFKQVDVVISTVG | 15 | 3324.0384 |
| Birch | 3505 | Bet v 6 | Q9FUW6 | 10764491 | 76 | QVDVVISTVGHLQLA | 15 | 3324.0389 |
| Birch | 3505 | Bet v 6 | Q9FUW6 | 10764491 | 86 | HLQLADQVKIIAAIK | 15 | 3324.0381 |
| Birch | 3505 | Bet v 6 | Q9FUW6 | 10764491 | 91 | DQVKIIAAIKEAGNI | 15 | 3324.0377 |
| Birch | 3505 | Bet v 6 | Q9FUW6 | 10764491 | 101 | EAGNIKRFPSEFGN | 15 | 3324.0385 |
| Birch | 3505 | Bet v 6 | Q9FUW6 | 10764491 | 141 | EAEGIPYTVSSNFF | 15 | 3324.0370 |
| Birch | 3505 | Bet v 6 | Q9FUW6 | 10764491 | 146 | PYTVVSSNFFAGYFL | 15 | 3324.0383 |
| Birch | 3505 | Bet v 6 | Q9FUW6 | 10764491 | 151 | SSNFFAGYFLPTLAQ | 15 | 3324.0373 |
| Birch | 3505 | Bet v 6 | Q9FUW6 | 10764491 | 156 | AGYFLPTLAQPGLTS | 15 | 3324.0388 |
| Birch | 3505 | Bet v 6 | Q9FUW6 | 10764491 | 206 | RTLNKIVYIKPAKNI | 15 | 3324.0387 |
| Birch | 3505 | Bet v 6 | Q9FUW6 | 10764491 | 211 | IVYIKPAKNIYSFNE | 15 | 3324.0386 |
| Birch | 3505 | Bet v 6 | Q9FUW6 | 10764491 | 216 | PAKNIYSFNEIVALW | 15 | 3324.0372 |
| Birch | 3505 | Bet v 6 | Q9FUW6 | 10764491 | 221 | YSFNEIVALWEKKIG | 15 | 3324.0371 |
| Birch | 3505 | Bet v 6 | Q9FUW6 | 10764491 | 256 | PIPINVILAINHSVF | 15 | 3324.0369 |
| Birch | 3505 | Bet v 6 | Q9FUW6 | 10764491 | 261 | VILAINHSVFVKGDH | 15 | 3324.0380 |
| Birch | 3505 | Bet v 6 | Q9FUW6 | 10764491 | 276 | TNFEIEASFGVEASE | 15 | 3324.0379 |
| Birch | 3505 | Bet v 6 | Q9FUW6 | 10764491 | 291 | LYPDVKYTTVEEYLQ | 15 | 3324.0382 |
| Birch | 3505 | Bet v 6 | Q9FUW6 | 10764491 | 294 | DVKYTTVEEYLQQFV | 15 | 3324.0378 |
| Birch | 3505 | Bet v 7 | P81531 (IUIS) | 21431524 | 51 | GKPLHYKKSSFHRVI | 15 | 3324.0390 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Birch | 3505 | Bet v 7 | P81531(IUIS) | 21431524 | 101 | TGPGLSMANAGPGT | 15 | 3337.0018 |
| Birch | 3505 | Bet v 7 | P81531(IUIS) | 21431524 | 116 | NGSQFFICTAKTEWL | 15 | 3324.0391 |
| Black walnut | 16719 | Jug n 1 | Q7Y1C2 | 31321942 | 6 | KCIFHTFSLTMARLA | 15 | 3324.1111 |
| Black walnut | 16719 | Jug n 1 | Q7Y1C2 | 31321942 | 11 | TFSLTMARLATLAAL | 15 | 3324.1110 |
| Black walnut | 16719 | Jug n 1 | Q7Y1C2 | 31321942 | 16 | MARLATLAALLVALL | 15 | 3324.1108 |
| Black walnut | 16719 | Jug n 1 | Q7Y1C2 | 31321942 | 21 | TLAALLVALLFVANA | 15 | 3324.1109 |
| Black walnut | 16719 | Jug n 1 | Q7Y1C2 | 31321942 | 26 | LVALLFVANAAAFRT | 15 | 3324.1107 |
| Black walnut | 16719 | Jug n 1 | Q7Y1C2 | 31321942 | 31 | FVANAAAFRTTITTM | 15 | 3324.1112 |
| Black walnut | 16719 | Jug n 1 | Q7Y1C2 | 31321942 | 36 | AAFRTTITTMEIDED | 15 | 3324.1114 |
| Black walnut | 16719 | Jug n 1 | Q7Y1C2 | 31321942 | 71 | LNHCQYYLRQQSRSG | 15 | 3324.1113 |
| Black walnut | 16719 | Jug n 2 | Q7Y1C1 | 31321944 | 66 | RHNPYYFHSQSIRSR | 15 | 3324.1119 |
| Black walnut | 16719 | Jug n 2 | Q7Y1C1 | 31321944 | 86 | GEVKYLERFAERTEL | 15 | 3324.1122 |
| Black walnut | 16719 | Jug n 2 | Q7Y1C1 | 31321944 | 96 | ERTELLRGIENYRVV | 15 | 3324.1121 |
| Black walnut | 16719 | Jug n 2 | Q7Y1C1 | 31321944 | 101 | LRGIENYRVVILDAN | 15 | 3324.1118 |
| Black walnut | 16719 | Jug n 2 | Q7Y1C1 | 31321944 | 106 | NYRVVILDANPNTFM | 15 | 3324.1125 |
| Black walnut | 16719 | Jug n 2 | Q7Y1C1 | 31321944 | 191 | GQVREYYAAGAKSPD | 15 | 3324.1126 |
| Black walnut | 16719 | Jug n 2 | Q7Y1C1 | 31321944 | 206 | QSYLRVFSNDILVAA | 15 | 3324.1115 |
| Black walnut | 16719 | Jug n 2 | Q7Y1C1 | 31321944 | 211 | VFSNDILVAALNTPR | 15 | 3324.1116 |
| Black walnut | 16719 | Jug n 2 | Q7Y1C1 | 31321944 | 301 | LQEMDVLVNYAEIKR | 15 | 3324.1123 |
| Black walnut | 16719 | Jug n 2 | Q7Y1C1 | 31321944 | 366 | TGRFQKVTARLARGD | 15 | 3324.1124 |
| Black walnut | 16719 | Jug n 2 | Q7Y1C1 | 31321944 | 381 | IFVIPAGHPIAITAS | 15 | 3324.1128 |
| Black walnut | 16719 | Jug n 2 | Q7Y1C1 | 31321944 | 411 | NNQRNFLAGQNSIIN | 15 | 3324.1117 |
| Black walnut | 16719 | Jug n 2 | Q7Y1C1 | 31321944 | 416 | FLAGQNSIINQLERE | 15 | 3324.1120 |
| Black walnut | 16719 | Jug n 2 | Q7Y1C1 | 31321944 | 446 | IFESQMESYFVPTER | 15 | 3324.1127 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Canary grass | 28479 | Pha a 1 | Q41260 | 2498576 | 1 | MMKMVCSSSSSLLV | 15 | 3324.1430 |
| Canary grass | 28479 | Pha a 1 | Q41260 | 2498576 | 11 | SSLLVVAALLAVFVG | 15 | 3324.1426 |
| Canary grass | 28479 | Pha a 1 | Q41260 | 2498576 | 16 | VAALLAVFVGSAQGI | 15 | 3324.1427 |
| Canary grass | 28479 | Pha a 1 | Q41260 | 2498576 | 126 | EEPIAPYHFDLSGHA | 15 | 3324.1429 |
| Canary grass | 28479 | Pha a 1 | Q41260 | 2498576 | 186 | PNYLALLVKYVDGDG | 15 | 3324.1428 |
| Canary grass | 28479 | Pha a 1 | Q41260 | 2498576 | 221 | SWGAIWRIDTPDKLT | 15 | 3337.0039 |
| Canary grass | 28479 | Pha a 5 | P56164 | 1246117 | 1 | MAVQKYTMALFLAVA | 15 | 3324.1434 |
| Canary grass | 28479 | Pha a 5 | P56164 | 1246117 | 6 | YTMALFLAVALVAGP | 15 | 3324.1431 |
| Canary grass | 28479 | Pha a 5 | P56164 | 1246117 | 11 | FLAVALVAGPAAPTP | 15 | 3324.1438 |
| Canary grass | 28479 | Pha a 5 | P56164 | 1246117 | 101 | DAAYRVAYEAAEGST | 15 | 3324.1443 |
| Canary grass | 28479 | Pha a 5 | P56164 | 1246117 | 116 | PEAKYDAFIAALTEA | 15 | 3324.1435 |
| Canary grass | 28479 | Pha a 5 | P56164 | 1246117 | 121 | DAFIAALTEALRVIA | 15 | 3324.1432 |
| Canary grass | 28479 | Pha a 5 | P56164 | 1246117 | 126 | ALTEALRVIAGAFEV | 15 | 3324.1437 |
| Canary grass | 28479 | Pha a 5 | P56164 | 1246117 | 161 | VDKIDAAFKIAATAA | 15 | 3324.1440 |
| Canary grass | 28479 | Pha a 5 | P56164 | 1246117 | 166 | AAFKIAATAANSAPA | 15 | 3324.1441 |
| Canary grass | 28479 | Pha a 5 | P56164 | 1246117 | 181 | NDKFTVFEGAFNKAI | 15 | 3324.1442 |
| Canary grass | 28479 | Pha a 5 | P56164 | 1246117 | 201 | GAYETYKFIPSLEAA | 15 | 3324.1433 |
| Canary grass | 28479 | Pha a 5 | P56164 | 1246117 | 206 | YKFIPSLEAAVKQAY | 15 | 3324.1436 |
| Canary grass | 28479 | Pha a 5 | P56164 | 1246117 | 216 | VKQAYGATVARAPEV | 15 | 3324.1444 |
| Canary grass | 28479 | Pha a 5 | P56164 | 1246117 | 226 | RAPEVKYAVPEAGLT | 15 | 3324.1439 |
| Cat epithelia | 9685 | Fel d 11 | P30438 | 146387241 | 1 | MKGACVLVLLWAALL | 15 | 3324.1047 |
| Cat epithelia | 9685 | Fel d 11 | P30438 | 146387241 | 6 | VLVLLWAALLLISGG | 15 | 3324.1046 |
| Cat epithelia | 9685 | Fel d 11 | P30438 | 146387241 | 41 | DEYVEQVAQYKALPV | 15 | 3324.1049 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Cat epithelia | 9685 | Fel d 11 | P30438 | 146387241 | 46 | QVAQYKALPVVLENA | 15 | 3324.1051 |
| Cat epithelia | 9685 | Fel d 11 | P30438 | 146387241 | 51 | KALPVVLENARILKN | 15 | 3324.1048 |
| Cat epithelia | 9685 | Fel d 11 | P30438 | 146387241 | 78 | NALSVLDKIYTSPLC | 15 | 3324.1050 |
| Cat epithelia | 9685 | Fel d 12 | P30440 | 146387241 | 1 | MRGALLVLALLVTQA | 15 | 3324.1054 |
| Cat epithelia | 9685 | Fel d 12 | P30440 | 146387241 | 6 | LVLALLVTQALGVKM | 15 | 3324.1053 |
| Cat epithelia | 9685 | Fel d 12 | P30440 | 146387241 | 21 | AETCPIFYDVFFAVA | 15 | 3324.1056 |
| Cat epithelia | 9685 | Fel d 12 | P30440 | 146387241 | 26 | IFYDVFFAVANGNEL | 15 | 3324.1052 |
| Cat epithelia | 9685 | Fel d 12 | P30440 | 146387241 | 36 | NGNELLLDLSLTKVN | 15 | 3324.1055 |
| Cat epithelia | 9685 | Fel d 12 | P30440 | 146387241 | 66 | YVENGLISRVLDGLV | 15 | 3324.1057 |
| Cat epithelia | 9685 | Fel d 2 | P49064 | 30962111 | 1 | MKWVTFISLLLLFSS | 15 | 3324.1058 |
| Cat epithelia | 9685 | Fel d 2 | P49064 | 30962111 | 6 | FISLLLFSSAYSRG | 15 | 3324.1063 |
| Cat epithelia | 9685 | Fel d 2 | P49064 | 30962111 | 41 | EHFRGLVLVAFSQYL | 15 | 3324.1060 |
| Cat epithelia | 9685 | Fel d 2 | P49064 | 30962111 | 46 | LVLVAFSQYLQQCPF | 15 | 3324.1061 |
| Cat epithelia | 9685 | Fel d 2 | P49064 | 30962111 | 61 | EDHVKLVNEVTEFAK | 15 | 3324.1075 |
| Cat epithelia | 9685 | Fel d 2 | P49064 | 30962111 | 156 | QRFLGKYLYEIARRH | 15 | 3324.1069 |
| Cat epithelia | 9685 | Fel d 2 | P49064 | 30962111 | 161 | KYLYEIARRHPYFYA | 15 | 3324.1068 |
| Cat epithelia | 9685 | Fel d 2 | P49064 | 30962111 | 166 | IARRHPYFYAPELLY | 15 | 3324.1070 |
| Cat epithelia | 9685 | Fel d 2 | P49064 | 30962111 | 171 | PYFYAPELLYYAEEY | 15 | 3324.1078 |
| Cat epithelia | 9685 | Fel d 2 | P49064 | 30962111 | 231 | GERAFKAWSVARLSQ | 15 | 3324.1059 |
| Cat epithelia | 9685 | Fel d 2 | P49064 | 30962111 | 246 | KFPKAEFAEISKLVT | 15 | 3324.1077 |
| Cat epithelia | 9685 | Fel d 2 | P49064 | 30962111 | 346 | AKDVFLGTFLYEYSR | 15 | 3324.1074 |
| Cat epithelia | 9685 | Fel d 2 | P49064 | 30962111 | 351 | LGTFLYEYSRRHPEY | 15 | 3324.1076 |
| Cat epithelia | 9685 | Fel d 2 | P49064 | 30962111 | 361 | RHPEYSVSLLLRLAK | 15 | 3324.1062 |
| Cat epithelia | 9685 | Fel d 2 | P49064 | 30962111 | 366 | SVSLLLRLAKEYEAT | 15 | 3324.1071 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Cat epithelia | 9685 | Fel d 2 | P49064 | 30962111 | 396 | HVFDEFKPLVEEPHN | 15 | 3324.1072 |
| Cat epithelia | 9685 | Fel d 2 | P49064 | 30962111 | 421 | KLGEYGFQNALLVRY | 15 | 3324.1065 |
| Cat epithelia | 9685 | Fel d 2 | P49064 | 30962111 | 426 | GFQNALLVRYTKKVP | 15 | 3324.1080 |
| Cat epithelia | 9685 | Fel d 2 | P49064 | 30962111 | 471 | SCAEDYLSVVLNRLC | 15 | 3324.1064 |
| Cat epithelia | 9685 | Fel d 2 | P49064 | 30962111 | 476 | YLSVVLNRLCVLHEK | 15 | 3324.1066 |
| Cat epithelia | 9685 | Fel d 2 | P49064 | 30962111 | 506 | VNRRPCFSALQVDET | 15 | 3324.1081 |
| Cat epithelia | 9685 | Fel d 2 | P49064 | 30962111 | 531 | FTFHADLCTLPEAEK | 15 | 3324.1079 |
| Cat epithelia | 9685 | Fel d 2 | P49064 | 30962111 | 546 | QIKKQSALVELLKHK | 15 | 3324.1073 |
| Cat epithelia | 9685 | Fel d 2 | P49064 | 30962111 | 594 | EEGPKLVAAAQAALA | 15 | 3324.1067 |
| Cat epithelia | 9685 | Fel d 3 | Q8WNR9 | 17939981 | 31 | TNETYQKFEAIEYKT | 15 | 3324.1087 |
| Cat epithelia | 9685 | Fel d 3 | Q8WNR9 | 17939981 | 41 | 1EYKTQVVAGINYY1 | 15 | 3324.1083 |
| Cat epithelia | 9685 | Fel d 3 | Q8WNR9 | 17939981 | 46 | QVVAGINYYIKVQVD | 15 | 3324.1086 |
| Cat epithelia | 9685 | Fel d 3 | Q8WNR9 | 17939981 | 51 | INYYIKVQVDDNRYI | 15 | 3324.1084 |
| Cat epithelia | 9685 | Fel d 3 | Q8WNR9 | 17939981 | 61 | DNRYIHIKVFKGLPV | 15 | 3324.1082 |
| Cat epithelia | 9685 | Fel d 3 | Q8WNR9 | 17939981 | 66 | HIKVFKGLPVQDSSL | 15 | 3324.1085 |
| Cat epithelia | 9685 | Fel d 4 | Q5VFH6 | 45775300 | 1 | MKLLLLCLGLILVCA | 15 | 3324.1096 |
| Cat epithelia | 9685 | Fel d 4 | Q5VFH6 | 45775300 | 31 | ISGEWYSILLASDVK | 15 | 3324.1088 |
| Cat epithelia | 9685 | Fel d 4 | Q5VFH6 | 45775300 | 36 | YSILLASDVKEKIEE | 15 | 3324.1094 |
| Cat epithelia | 9685 | Fel d 4 | Q5VFH6 | 45775300 | 51 | NGSMRVFVEHIKALD | 15 | 3324.1098 |
| Cat epithelia | 9685 | Fel d 4 | Q5VFH6 | 45775300 | 56 | VFVEHIKALDNSSLS | 15 | 3324.1090 |
| Cat epithelia | 9685 | Fel d 4 | Q5VFH6 | 45775300 | 61 | IKALDNSSLSFVFHT | 15 | 3324.1091 |
| Cat epithelia | 9685 | Fel d 4 | Q5VFH6 | 45775300 | 96 | YTVVYDGYNVFSIVE | 15 | 3324.1100 |
| Cat epithelia | 9685 | Fel d 4 | Q5VFH6 | 45775300 | 101 | DGYNVFSIVETVYDE | 15 | 3324.1097 |
| Cat epithelia | 9685 | Fel d 4 | Q5VFH6 | 45775300 | 106 | FSIVETVYDEYILLH | 15 | 3324.1095 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Cat epithelia | 9685 | Fel d 4 | Q5VFH6 | 45775300 | 111 | TVYDEYILHLLNFD | 15 | 3324.1089 |
| Cat epithelia | 9685 | Fel d 4 | Q5VFH6 | 45775300 | 116 | YILLHLLNFDKTRPF | 15 | 3324.1093 |
| Cat epithelia | 9685 | Fel d 4 | Q5VFH6 | 45775300 | 121 | LLNFDKTRPFQLVEF | 15 | 3324.1092 |
| Cat epithelia | 9685 | Fel d 4 | Q5VFH6 | 45775300 | 126 | KTRPFQLVEFYAREP | 15 | 3324.1099 |
| Cladosporium herbarum | 29918 | Cla h 10 | P40108 | 291047712 | 16 | QPTGLFINNEFVKGQ | 15 | 3324.0559 |
| Cladosporium herbarum | 29918 | Cla h 10 | P40108 | 291047712 | 56 | DVDIAVAARKAFEG | 15 | 3324.0561 |
| Cladosporium herbarum | 29918 | Cla h 10 | P40108 | 291047712 | 81 | GKLLNNLANLFEKNI | 15 | 3324.0552 |
| Cladosporium herbarum | 29918 | Cla h 10 | P40108 | 291047712 | 86 | NLANLFEKNIDLLAA | 15 | 3324.0565 |
| Cladosporium herbarum | 29918 | Cla h 10 | P40108 | 291047712 | 91 | FEKNIDLLAAVESLD | 15 | 3324.0555 |
| Cladosporium herbarum | 29918 | Cla h 10 | P40108 | 291047712 | 166 | PLLMWAWKIGPAIAC | 15 | 3324.0558 |
| Cladosporium herbarum | 29918 | Cla h 10 | P40108 | 291047712 | 191 | QTPLGGLVAASLVKE | 15 | 3324.0557 |
| Cladosporium herbarum | 29918 | Cla h 10 | P40108 | 291047712 | 246 | RTILKAAASSNLKKV | 15 | 3324.0566 |
| Cladosporium herbarum | 29918 | Cla h 10 | P40108 | 291047712 | 281 | AISWNFGIFFNHGQ | 15 | 3324.0553 |
| Cladosporium herbarum | 29918 | Cla h 10 | P40108 | 291047712 | 341 | SKVQFDRIMEYIQAG | 15 | 3324.0560 |
| Cladosporium herbarum | 29918 | Cla h 10 | P40108 | 291047712 | 371 | DKGYFIEPTIFSNVT | 15 | 3324.0554 |
| Cladosporium herbarum | 29918 | Cla h 10 | P40108 | 291047712 | 386 | EDMKIVKEEIFGPVC | 15 | 3324.0556 |
| Cladosporium herbarum | 29918 | Cla h 10 | P40108 | 291047712 | 416 | NASTYGLAAAVHTKN | 15 | 3324.0564 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Cladosporium herbarum | 29918 | Cla h 10 | P40108 | 291047712 | 431 | LNTAIEVSNALKAGT | 15 | 3324.0563 |
| Cladosporium herbarum | 29918 | Cla h 10 | P40108 | 291047712 | 441 | LKAGTVWNTYNTLH | 15 | 3324.0562 |
| Cladosporium herbarum | 29918 | Cla h 12 | P50344 | 1710589 | 1 | MSAELASSYAALIL | 15 | 3324.0569 |
| Cladosporium herbarum | 29918 | Cla h 12 | P50344 | 1710589 | 6 | LASSYAALILADEGL | 15 | 3324.0567 |
| Cladosporium herbarum | 29918 | Cla h 12 | P50344 | 1710589 | 21 | EITADKLQALISAAK | 15 | 3324.0568 |
| Cladosporium herbarum | 29918 | Cla h 12 | P50344 | 1710589 | 26 | KLQALISAAKVPEIE | 15 | 3324.0570 |
| Cladosporium herbarum | 29918 | Cla h 12 | P50344 | 1710589 | 36 | VPEIEPIWTSLFAKA | 15 | 3324.0571 |
| Cladosporium herbarum | 29918 | Cla h 12 | P50344 | 1710589 | 41 | PIWTSLFAKALEGKD | 15 | 3324.0572 |
| Cladosporium herbarum | 29918 | Cla h 5 | P42039 | 5777795 | 1 | MKYLAAFLLLGLAGN | 15 | 3324.0573 |
| Cladosporium herbarum | 29918 | Cla h 5 | P42039 | 5777795 | 6 | AFLLLGLAGNSSPSA | 15 | 3324.0576 |
| Cladosporium herbarum | 29918 | Cla h 5 | P42039 | 5777795 | 21 | EDIKTVLSSVGIDAD | 15 | 3324.0574 |
| Cladosporium herbarum | 29918 | Cla h 5 | P42039 | 5777795 | 46 | LEGKDINELISSGSE | 15 | 3324.0577 |
| Cladosporium herbarum | 29918 | Cla h 5 | P42039 | 5777795 | 51 | INELISSGSEKLASV | 15 | 3324.0575 |
| Cladosporium herbarum | 29918 | Cla h 6 | P42040 | 467660 | 1 | MPISKIHSRYVYDSR | 15 | 3324.0587 |
| Cladosporium herbarum | 29918 | Cla h 6 | P42040 | 467660 | 66 | VANVNEIIAPALIKE | 15 | 3324.0584 |
| Cladosporium herbarum | 29918 | Cla h 6 | P42040 | 467660 | 106 | IGANAILGVSMAVAK | 15 | 3324.0579 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Cladosporium herbarum | 29918 | Cla h 6 | P42040 | 467660 | 111 | ILGVSMAVAKAAAE | 15 | 3324.0586 |
| Cladosporium herbarum | 29918 | Cla h 6 | P42040 | 467660 | 126 | KRVPLYAHISDLSGT | 15 | 3324.0590 |
| Cladosporium herbarum | 29918 | Cla h 6 | P42040 | 467660 | 161 | GGRLAFQEFMIVPSG | 15 | 3324.0588 |
| Cladosporium herbarum | 29918 | Cla h 6 | P42040 | 467660 | 166 | FQEFMIVPSGAPSFT | 15 | 3324.0581 |
| Cladosporium herbarum | 29918 | Cla h 6 | P42040 | 467660 | 186 | GAEVYQKLKSLTKKR | 15 | 3324.0585 |
| Cladosporium herbarum | 29918 | Cla h 6 | P42040 | 467660 | 241 | IKIAMDVASSEFYKA | 15 | 3324.0589 |
| Cladosporium herbarum | 29918 | Cla h 6 | P42040 | 467660 | 271 | KSKWITYEQLADQYK | 15 | 3324.0594 |
| Cladosporium herbarum | 29918 | Cla h 6 | P42040 | 467660 | 281 | ADQYKQLAAKYPIVS | 15 | 3324.0593 |
| Cladosporium herbarum | 29918 | Cla h 6 | P42040 | 467660 | 306 | EAWSYFYKTSGSDFQ | 15 | 3324.0580 |
| Cladosporium herbarum | 29918 | Cla h 6 | P42040 | 467660 | 341 | KACNALLLKVNQIGT | 15 | 3324.0578 |
| Cladosporium herbarum | 29918 | Cla h 6 | P42040 | 467660 | 346 | LLLKVNQIGTITEAI | 15 | 3324.0591 |
| Cladosporium herbarum | 29918 | Cla h 6 | P42040 | 467660 | 366 | SFAAGWGVMVSHRSG | 15 | 3324.0583 |
| Cladosporium herbarum | 29918 | Cla h 6 | P42040 | 467660 | 386 | TIADIVGLRAGQIK | 15 | 3324.0592 |
| Cladosporium herbarum | 29918 | Cla h 6 | P42040 | 467660 | 411 | AKLNQILRIEEELGD | 15 | 3324.0582 |
| Cladosporium herbarum | 29918 | Cla h 7 | P42059 | 1168970 | 1 | MAPKIAIIFYSTWGH | 15 | 3324.0597 |
| Cladosporium herbarum | 29918 | Cla h 7 | P42059 | 1168970 | 131 | AMSTLSHHGIIYVPL | 15 | 3337.0019 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Cladosporium herbarum | 29918 | Cla h 7 | P42059 | 1168970 | 141 | IYVPLGYKTFHLLG | 15 | 3324.0595 |
| Cladosporium herbarum | 29918 | Cla h 7 | P42059 | 1168970 | 190 | QGKAFYEAVAKVNFQ | 15 | 3324.0596 |
| Cladosporium herbarum | 29918 | Cla h 8 | P0C0Y5 | 296863443 | 46 | GAAVAITYASRAQGA | 15 | 3324.0600 |
| Cladosporium herbarum | 29918 | Cla h 8 | P0C0Y5 | 296863443 | 101 | QIDAPIANAGATADS | 15 | 3324.0601 |
| Cladosporium herbarum | 29918 | Cla h 8 | P0C0Y5 | 296863443 | 151 | GTGSLVITASMSGHI | 15 | 3324.0603 |
| Cladosporium herbarum | 29918 | Cla h 8 | P0C0Y5 | 296863443 | 181 | GCIHMARSLANEWRD | 15 | 3324.0602 |
| Cladosporium herbarum | 29918 | Cla h 8 | P0C0Y5 | 296863443 | 236 | KELKGAYVFASDAS | 15 | 3324.0598 |
| Cladosporium herbarum | 29918 | Cla h 8 | P0C0Y5 | 296863443 | 241 | AYVFASDASTYTTG | 15 | 3324.0599 |
| Cypress | 13415 | Cha o 1 | Q96385 | 219928905 | 1 | MASCTLLAVLVFLCA | 15 | 3324.0519 |
| Cypress | 13415 | Cha o 1 | Q96385 | 219928905 | 6 | LLAVLVFLCAIVSCF | 15 | 3324.0518 |
| Cypress | 13415 | Cha o 1 | Q96385 | 219928905 | 86 | ERSLWIIFSKNLNIK | 15 | 3324.0517 |
| Cypress | 13415 | Cha o 1 | Q96385 | 219928905 | 91 | IIFSKNLNIKLNMPL | 15 | 3324.0522 |
| Cypress | 13415 | Cha o 1 | Q96385 | 219928905 | 96 | NLNIKLNMPLYIAGN | 15 | 3324.0523 |
| Cypress | 13415 | Cha o 1 | Q96385 | 219928905 | 126 | GPCLFMRTVSHVILH | 15 | 3324.0520 |
| Cypress | 13415 | Cha o 1 | Q96385 | 219928905 | 131 | MRTVSHVILHGLNIH | 15 | 3324.0528 |
| Cypress | 13415 | Cha o 1 | Q96385 | 219928905 | 151 | VSGNVLISEASGVVP | 15 | 3324.0526 |
| Cypress | 13415 | Cha o 1 | Q96385 | 219928905 | 196 | LVDVTLASTGVTISN | 15 | 3324.0524 |
| Cypress | 13415 | Cha o 1 | Q96385 | 219928905 | 211 | NHFFNHHKVMLLGHS | 15 | 3324.0521 |
| Cypress | 13415 | Cha o 1 | Q96385 | 219928905 | 231 | DKSMKVTVAFNQFGP | 15 | 3324.0525 |
| Cypress | 13415 | Cha o 1 | Q96385 | 219928905 | 256 | YGLIHVANNNYDPWS | 15 | 3324.0527 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Cypress | 13415 | Cha o 2 | Q7M1E7 | 47606004 | 1 | MGMKFMAAVAFLALQ | 15 | 3324.0531 |
| Cypress | 13415 | Cha o 2 | Q7M1E7 | 47606004 | 6 | MAAVAFLALQLIVMA | 15 | 3324.0529 |
| Cypress | 13415 | Cha o 2 | Q7M1E7 | 47606004 | 11 | FLALQLIVMAAAEDQ | 15 | 3324.0532 |
| Cypress | 13415 | Cha o 2 | Q7M1E7 | 47606004 | 31 | LDSDIEQYLRSNRSL | 15 | 3324.0544 |
| Cypress | 13415 | Cha o 2 | Q7M1E7 | 47606004 | 36 | EQYLRSNRSLKKLVH | 15 | 3324.0538 |
| Cypress | 13415 | Cha o 2 | Q7M1E7 | 47606004 | 76 | EAFATTWNAACKKAS | 15 | 3324.0551 |
| Cypress | 13415 | Cha o 2 | Q7M1E7 | 47606004 | 81 | TWNAACKKASAVLLV | 15 | 3324.0547 |
| Cypress | 13415 | Cha o 2 | Q7M1E7 | 47606004 | 86 | CKKASAVLLVPANKK | 15 | 3324.0534 |
| Cypress | 13415 | Cha o 2 | Q7M1E7 | 47606004 | 96 | PANKKFFVNNLVFRG | 15 | 3324.0533 |
| Cypress | 13415 | Cha o 2 | Q7M1E7 | 47606004 | 131 | ARWKNSKIWLQFAQL | 15 | 3324.0542 |
| Cypress | 13415 | Cha o 2 | Q7M1E7 | 47606004 | 136 | SKIWLQFAQLTDFNL | 15 | 3324.0530 |
| Cypress | 13415 | Cha o 2 | Q7M1E7 | 47606004 | 181 | NRPTAIKIDYSKSVT | 15 | 3324.0545 |
| Cypress | 13415 | Cha o 2 | Q7M1E7 | 47606004 | 186 | IKIDYSKSVTVKELT | 15 | 3324.0535 |
| Cypress | 13415 | Cha o 2 | Q7M1E7 | 47606004 | 196 | VKELTLMNSPEFHLV | 15 | 3324.0550 |
| Cypress | 13415 | Cha o 2 | Q7M1E7 | 47606004 | 236 | IDIFASKRPHIEKCV | 15 | 3324.0539 |
| Cypress | 13415 | Cha o 2 | Q7M1E7 | 47606004 | 296 | HVHVNRAKFIDTQNG | 15 | 3324.0543 |
| Cypress | 13415 | Cha o 2 | Q7M1E7 | 47606004 | 321 | GLASYITYENVEMIN | 15 | 3324.0537 |
| Cypress | 13415 | Cha o 2 | Q7M1E7 | 47606004 | 331 | VEMINSENPILINQF | 15 | 3324.0549 |
| Cypress | 13415 | Cha o 2 | Q7M1E7 | 47606004 | 336 | SENPILINQFYCTSA | 15 | 3324.0540 |
| Cypress | 13415 | Cha o 2 | Q7M1E7 | 47606004 | 366 | TYKNIHGTSATAAAI | 15 | 3324.0548 |
| Cypress | 13415 | Cha o 2 | Q7M1E7 | 47606004 | 376 | TAAAIQLMCSDSVPC | 15 | 3324.0536 |
| Cypress | 13415 | Cha o 2 | Q7M1E7 | 47606004 | 391 | TGIQLSNVSLKLTSG | 15 | 3324.0541 |
| Cypress | 13415 | Cha o 2 | Q7M1E7 | 47606004 | 481 | QPCKPKLIIVHPNKP | 15 | 3324.0546 |
| Cypress | 49011 | Cup a 1 | Q9SCG9 | 9087167 | 66 | KALWIIFSQNMNIKL | 15 | 3324.0604 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Cypress | 49011 | Cup a 1 | Q9SCG9 | 9087167 | 71 | IFSQMNIKLQMPLY | 15 | 3324.0607 |
| Cypress | 49011 | Cup a 1 | Q9SCG9 | 9087167 | 76 | MNIKLQMPLYVAGYK | 15 | 3324.0613 |
| Cypress | 49011 | Cup a 1 | Q9SCG9 | 9087167 | 106 | PCLFMRKASHVILHG | 15 | 3324.0608 |
| Cypress | 49011 | Cup a 1 | Q9SCG9 | 9087167 | 131 | LGDVLVSESIGVEPV | 15 | 3324.0610 |
| Cypress | 49011 | Cup a 1 | Q9SCG9 | 9087167 | 186 | TISNNHFFNHHKVML | 15 | 3324.0612 |
| Cypress | 49011 | Cup a 1 | Q9SCG9 | 9087167 | 191 | HFFNHHKVMLLGHDD | 15 | 3324.0605 |
| Cypress | 49011 | Cup a 1 | Q9SCG9 | 9087167 | 211 | KSMKVTVAFNQFGPN | 15 | 3324.0609 |
| Cypress | 49011 | Cup a 1 | Q9SCG9 | 9087167 | 231 | PRARYGLVHVANNNY | 15 | 3324.0611 |
| Cypress | 49011 | Cup a 1 | Q9SCG9 | 9087167 | 316 | EDTNIYNSNEAFKVE | 15 | 3324.0606 |
| Cypress | 13469 | Cup s 1 | Q9M4S2 | 257321241 | 1 | MDSPCLIAVLVFLCA | 15 | 3324.0617 |
| Cypress | 13469 | Cup s 1 | Q9M4S2 | 257321241 | 6 | LIAVLVFLCAIVSCY | 15 | 3324.0614 |
| Cypress | 13469 | Cup s 1 | Q9M4S2 | 257321241 | 11 | VFLCAIVSCYSDNPI | 15 | 3324.0625 |
| Cypress | 13469 | Cup s 1 | Q9M4S2 | 257321241 | 86 | EKALWIIFSQMNNIK | 15 | 3324.0615 |
| Cypress | 13469 | Cup s 1 | Q9M4S2 | 257321241 | 91 | IIFSQMNIKLKMPL | 15 | 3324.0618 |
| Cypress | 13469 | Cup s 1 | Q9M4S2 | 257321241 | 96 | NMNIKLKMPLYVAGH | 15 | 3324.0624 |
| Cypress | 13469 | Cup s 1 | Q9M4S2 | 257321241 | 126 | GPCLFMRKVSHVILH | 15 | 3324.0619 |
| Cypress | 13469 | Cup s 1 | Q9M4S2 | 257321241 | 131 | MRKVSHVILHGLHIH | 15 | 3324.0621 |
| Cypress | 13469 | Cup s 1 | Q9M4S2 | 257321241 | 151 | VLGNVLVSESIGVEP | 15 | 3324.0627 |
| Cypress | 13469 | Cup s 1 | Q9M4S2 | 257321241 | 211 | NHFFNHHKVMLLGHD | 15 | 3324.0616 |
| Cypress | 13469 | Cup s 1 | Q9M4S2 | 257321241 | 231 | DKSMKVTVAFNQFGP | 15 | 3324.0622 |
| Cypress | 13469 | Cup s 1 | Q9M4S2 | 257321241 | 256 | YGLVHVANNNYDQWN | 15 | 3324.0626 |
| Cypress | 13469 | Cup s 1 | Q9M4S2 | 257321241 | 336 | TEETNIYTSNEAFKV | 15 | 3324.0620 |
| Cypress | 13469 | Cup s 1 | Q9M4S2 | 257321241 | 346 | EAFKVENGNLAPQLT | 15 | 3324.0623 |
| Cypress | 13469 | Cup s 3 | Q69CS2 | 38456226 | 1 | MARVSELALLLVATS | 15 | 3324.0629 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Cypress | 13469 | Cup s 3 | Q69CS2 | 38456226 | 6 | ELALLLVATSAISLH | 15 | 3324.0628 |
| Cypress | 13469 | Cup s 3 | Q69CS2 | 38456226 | 11 | LVATSAISLHMQEAG | 15 | 3324.0630 |
| Cypress | 13469 | Cup s 3 | Q69CS2 | 38456226 | 56 | TWTVNLAAGTASARF | 15 | 3324.0632 |
| Cypress | 13469 | Cup s 3 | Q69CS2 | 38456226 | 116 | DYYDVSLVDGFNIPL | 15 | 3337.0020 |
| Cypress | 13469 | Cup s 3 | Q69CS2 | 38456226 | 121 | SLVDGFNIPLAINPT | 15 | 3324.0631 |
| Date palm | 42345 | Pho d 2 | Q8L5D8 | 21322677 | 36 | SSSFPQFKSEEITNI | 15 | 3324.1549 |
| Date palm | 42345 | Pho d 2 | Q8L5D8 | 21322677 | 61 | APTGLYLGSTKYMVI | 15 | 3324.1548 |
| Date palm | 42345 | Pho d 2 | Q8L5D8 | 21322677 | 66 | YLGSTKYMVIQGEPG | 15 | 3324.1546 |
| Date palm | 42345 | Pho d 2 | Q8L5D8 | 21322677 | 71 | KYMVIQGEPGAVIRG | 15 | 3324.1547 |
| Date palm | 42345 | Pho d 2 | Q8L5D8 | 21322677 | 91 | GVTVKKTNQALIFGI | 15 | 3324.1550 |
| Dermatophagoides farinae | 6954 | Der f 1 | A1YW11 | 119633260 | 1 | MKFVLAIASLLVLST | 15 | 3324.0664 |
| Dermatophagoides farinae | 6954 | Der f 1 | A1YW11 | 119633260 | 6 | AIASLLVLSTVYARP | 15 | 3324.0665 |
| Dermatophagoides farinae | 6954 | Der f 1 | A1YW11 | 119633260 | 11 | LVLSTVYARPASIKT | 15 | 3324.0677 |
| Dermatophagoides farinae | 6954 | Der f 1 | A1YW11 | 119633260 | 26 | FEEFKKAFNKNYATV | 15 | 3324.0681 |
| Dermatophagoides farinae | 6954 | Der f 1 | A1YW11 | 119633260 | 46 | ARKNFLESLKYVEAN | 15 | 3324.0668 |
| Dermatophagoides farinae | 6954 | Der f 1 | A1YW11 | 119633260 | 61 | KGAINHLSDLSLDEF | 15 | 3324.0683 |
| Dermatophagoides farinae | 6954 | Der f 1 | A1YW11 | 119633260 | 71 | SLDEFKNRYLMSAEA | 15 | 3324.0672 |
| Dermatophagoides farinae | 6954 | Der f 1 | A1YW11 | 119633260 | 76 | KNRYLMSAEAFEQLK | 15 | 3324.0667 |
| Dermatophagoides farinae | 6954 | Der f 1 | A1YW11 | 119633260 | 81 | MSAEAFEQLKTQFDL | 15 | 3324.0684 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides farinae | 6954 | Der f 1 | A1YW11 | 119633260 | 86 | FEQLKTQFDLNAETS | 15 | 3324.0682 |
| Dermatophagoides farinae | 6954 | Der f 1 | A1YW11 | 119633260 | 131 | GSCWAFSGVAATESA | 15 | 3324.0670 |
| Dermatophagoides farinae | 6954 | Der f 1 | A1YW11 | 119633260 | 136 | FSGVAATESAYLAYR | 15 | 3324.0666 |
| Dermatophagoides farinae | 6954 | Der f 1 | A1YW11 | 119633260 | 141 | ATESAYLAYRNTSLD | 15 | 3324.0674 |
| Dermatophagoides farinae | 6954 | Der f 1 | A1YW11 | 119633260 | 146 | YLAYRNTSLDLSEQE | 15 | 3324.0673 |
| Dermatophagoides farinae | 6954 | Der f 1 | A1YW11 | 119633260 | 176 | PRGIEYIQQNGVVEE | 15 | 3324.0679 |
| Dermatophagoides farinae | 6954 | Der f 1 | A1YW11 | 119633260 | 221 | PDVKQIREALTQTHT | 15 | 3324.0685 |
| Dermatophagoides farinae | 6954 | Der f 1 | A1YW11 | 119633260 | 231 | TQTHTAIAVIIGIKD | 15 | 3324.0680 |
| Dermatophagoides farinae | 6954 | Der f 1 | A1YW11 | 119633260 | 241 | IGIKDLRAFQHYDGR | 15 | 3324.0676 |
| Dermatophagoides farinae | 6954 | Der f 1 | A1YW11 | 119633260 | 296 | GDSGYGYFQAGNNLM | 15 | 3324.0669 |
| Dermatophagoides farinae | 6954 | Der f 1 | A1YW11 | 119633260 | 301 | GYFQAGNNLMMIEQY | 15 | 3324.0671 |
| Dermatophagoides farinae | 6954 | Der f 1 | A1YW11 | 119633260 | 306 | GNNLMMIEQYPYVVI | 15 | 3324.0675 |
| Dermatophagoides farinae | 6954 | Der f 1 | A1YW11 | 119633260 | 307 | NNLMMIEQYPYVVIM | 15 | 3324.0678 |
| Dermatophagoides farinae | 6954 | Der f 10 | Q23939 | 42559584 | 101 | RSEERLKIATAKLEE | 15 | 3324.0686 |
| Dermatophagoides farinae | 6954 | Der f 10 | Q23939 | 42559584 | 106 | LKIATAKLEEASQSA | 15 | 3324.0689 |
| Dermatophagoides farinae | 6954 | Der f 10 | Q23939 | 42559584 | 191 | VELEEELRVVGNNLK | 15 | 3324.0690 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides farinae | 6954 | Der f 10 | Q23939 | 42559584 | 216 | QREEAYEQQIRIMTA | 15 | 3324.0688 |
| Dermatophagoides farinae | 6954 | Der f 10 | Q23939 | 42559584 | 221 | YEQQIRIMTAKLKEA | 15 | 3324.0687 |
| Dermatophagoides farinae | 6954 | Der f 11 | Q96720 | 42559514 | 11 | KLRKLLEDVHIESEE | 15 | 3324.0719 |
| Dermatophagoides farinae | 6954 | Der f 11 | Q96720 | 42559514 | 61 | KFQAEVFELLAQLET | 15 | 3324.0692 |
| Dermatophagoides farinae | 6954 | Der f 11 | Q96720 | 42559514 | 66 | VFELLAQLETANKEK | 15 | 3324.0696 |
| Dermatophagoides farinae | 6954 | Der f 11 | Q96720 | 42559514 | 96 | ELNIKIEEINRTVIE | 15 | 3324.0713 |
| Dermatophagoides farinae | 6954 | Der f 11 | Q96720 | 42559514 | 101 | IEEINRTVIELTSHK | 15 | 3324.0718 |
| Dermatophagoides farinae | 6954 | Der f 11 | Q96720 | 42559514 | 131 | EVKLQLDNANHLKTQ | 15 | 3324.0716 |
| Dermatophagoides farinae | 6954 | Der f 11 | Q96720 | 42559514 | 136 | LDNANHLKTQIAQQL | 15 | 3324.0699 |
| Dermatophagoides farinae | 6954 | Der f 11 | Q96720 | 42559514 | 141 | HLKTQIAQQLEDTRH | 15 | 3324.0717 |
| Dermatophagoides farinae | 6954 | Der f 11 | Q96720 | 42559514 | 171 | AHTLEVELESLKVQL | 15 | 3324.0709 |
| Dermatophagoides farinae | 6954 | Der f 11 | Q96720 | 42559514 | 191 | ARLELERQLTKANGD | 15 | 3324.0711 |
| Dermatophagoides farinae | 6954 | Der f 11 | Q96720 | 42559514 | 226 | ELRRKMAQKISEYEE | 15 | 3324.0714 |
| Dermatophagoides farinae | 6954 | Der f 11 | Q96720 | 42559514 | 236 | SEYEEQLRALLNKCS | 15 | 3324.0710 |
| Dermatophagoides farinae | 6954 | Der f 11 | Q96720 | 42559514 | 256 | KSRLQSEVEVLIMDL | 15 | 3324.0720 |
| Dermatophagoides farinae | 6954 | Der f 11 | Q96720 | 42559514 | 261 | SEVEVLIMDLEKATR | 15 | 3324.0706 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides farinae | 6954 | Der f 11 | Q96720 | 42559514 | 281 | EKRVAQLEKINLDLK | 15 | 3324.0697 |
| Dermatophagoides farinae | 6954 | Der f 11 | Q96720 | 42559514 | 311 | ELRVKIAELQKLQHE | 15 | 3324.0715 |
| Dermatophagoides farinae | 6954 | Der f 11 | Q96720 | 42559514 | 316 | IAELQKLQHEYEKLR | 15 | 3324.0704 |
| Dermatophagoides farinae | 6954 | Der f 11 | Q96720 | 42559514 | 376 | DELSAAYKEAETLRK | 15 | 3324.0703 |
| Dermatophagoides farinae | 6954 | Der f 11 | Q96720 | 42559514 | 396 | NQRLIAELAQVRHDY | 15 | 3324.0698 |
| Dermatophagoides farinae | 6954 | Der f 11 | Q96720 | 42559514 | 421 | IEALRKQYQIEIEQL | 15 | 3324.0693 |
| Dermatophagoides farinae | 6954 | Der f 11 | Q96720 | 42559514 | 426 | KQYQIEIEQLNMRLA | 15 | 3324.0695 |
| Dermatophagoides farinae | 6954 | Der f 11 | Q96720 | 42559514 | 431 | EIEQLNMRLAEAEAK | 15 | 3324.0712 |
| Dermatophagoides farinae | 6954 | Der f 11 | Q96720 | 42559514 | 451 | ARLKKKYQAQITELE | 15 | 3324.0691 |
| Dermatophagoides farinae | 6954 | Der f 11 | Q96720 | 42559514 | 456 | KYQAQITELELSLDA | 15 | 3324.0721 |
| Dermatophagoides farinae | 6954 | Der f 11 | Q96720 | 42559514 | 481 | TIKKQALQITELQAH | 15 | 3324.0702 |
| Dermatophagoides farinae | 6954 | Der f 11 | Q96720 | 42559514 | 521 | QAELEEMRIALEQAN | 15 | 3324.0701 |
| Dermatophagoides farinae | 6954 | Der f 11 | Q96720 | 42559514 | 531 | LEQANRAKRQAEQLH | 15 | 3324.0722 |
| Dermatophagoides farinae | 6954 | Der f 11 | Q96720 | 42559514 | 556 | TTINVNLASAKSKLE | 15 | 3324.0708 |
| Dermatophagoides farinae | 6954 | Der f 11 | Q96720 | 42559514 | 566 | KSKLESEFSALQADY | 15 | 3324.0705 |
| Dermatophagoides farinae | 6954 | Der f 11 | Q96720 | 42559514 | 596 | KLTIELKSTKDLLIE | 15 | 3324.0694 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides farinae | 6954 | Der f 11 | Q96720 | 42559514 | 601 | LKSTKDLLIEEQERL | 15 | 3324.0700 |
| Dermatophagoides farinae | 6954 | Der f 11 | Q96720 | 42559514 | 616 | VKLETVKKSLEQEVR | 15 | 3324.0723 |
| Dermatophagoides farinae | 6954 | Der f 11 | Q96720 | 42559514 | 631 | TLHVRIEBVEANALA | 15 | 3324.0707 |
| Dermatophagoides farinae | 6954 | Der f 13 | Q1M2P5 | 37958167 | 6 | GKYKLEKSEKFDEFL | 15 | 3324.0727 |
| Dermatophagoides farinae | 6954 | Der f 13 | Q1M2P5 | 37958167 | 26 | GFMVKTAAKTLKPTF | 15 | 3324.0725 |
| Dermatophagoides farinae | 6954 | Der f 13 | Q1M2P5 | 37958167 | 46 | NDQYIFRSLSTFKNT | 15 | 3324.0724 |
| Dermatophagoides farinae | 6954 | Der f 13 | Q1M2P5 | 37958167 | 51 | FRSLSTFKNTEAKPK | 15 | 3324.0726 |
| Dermatophagoides farinae | 6954 | Der f 14 | Q94507 | 1545803 | 16 | TRRVAELTAVGSPS | 15 | 3324.0735 |
| Dermatophagoides farinae | 6954 | Der f 14 | Q94507 | 1545803 | 51 | KSPHEFNTEFTIHA | 15 | 3324.0731 |
| Dermatophagoides farinae | 6954 | Der f 14 | Q94507 | 1545803 | 91 | DKENNVRKNQLNLQY | 15 | 3324.0737 |
| Dermatophagoides farinae | 6954 | Der f 14 | Q94507 | 1545803 | 96 | VRKNQLNLQYKFAGD | 15 | 3324.0734 |
| Dermatophagoides farinae | 6954 | Der f 14 | Q94507 | 1545803 | 116 | VDYENEFSNLKRSS | 15 | 3324.0738 |
| Dermatophagoides farinae | 6954 | Der f 14 | Q94507 | 1545803 | 141 | AKYMSSHPPILNHKV | 15 | 3324.0736 |
| Dermatophagoides farinae | 6954 | Der f 14 | Q94507 | 1545803 | 146 | SHPPILNHKVNIQFK | 15 | 3324.0733 |
| Dermatophagoides farinae | 6954 | Der f 14 | Q94507 | 1545803 | 151 | LNHKVNIQFKYRPFK | 15 | 3324.0730 |
| Dermatophagoides farinae | 6954 | Der f 14 | Q94507 | 1545803 | 156 | NIQFKYRPFKVNELN | 15 | 3324.0732 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides farinae | 6954 | Der f 14 | Q94507 | 1545803 | 181 | HKFQLMRNSQIEVEE | 15 | 3324.0728 |
| Dermatophagoides farinae | 6954 | Der f 14 | Q94507 | 1545803 | 196 | VRPFKMHGNSDIKLM | 15 | 3324.0739 |
| Dermatophagoides farinae | 6954 | Der f 14 | Q94507 | 1545803 | 311 | KIFINHKSEMTKPTN | 15 | 3324.0729 |
| Dermatophagoides farinae | 6954 | Der f 15 | Q9U6R7 | 21444331 | 1 | MKTIYAILSIMACIG | 15 | 3324.0740 |
| Dermatophagoides farinae | 6954 | Der f 15 | Q9U6R7 | 21444331 | 6 | AILSIMACIGLMNAS | 15 | 3324.0744 |
| Dermatophagoides farinae | 6954 | Der f 15 | Q9U6R7 | 21444331 | 11 | MACIGLMNASIKRDH | 15 | 3324.0746 |
| Dermatophagoides farinae | 6954 | Der f 15 | Q9U6R7 | 21444331 | 91 | SWEKRGYERFNNLRL | 15 | 3324.0747 |
| Dermatophagoides farinae | 6954 | Der f 15 | Q9U6R7 | 21444331 | 96 | GYERFNNLRLKNPEL | 15 | 3324.0743 |
| Dermatophagoides farinae | 6954 | Der f 15 | Q9U6R7 | 21444331 | 106 | KNPELTTMISLGGWY | 15 | 3324.0753 |
| Dermatophagoides farinae | 6954 | Der f 15 | Q9U6R7 | 21444331 | 131 | ANPTYRQQFIQSVLD | 15 | 3324.0755 |
| Dermatophagoides farinae | 6954 | Der f 15 | Q9U6R7 | 21444331 | 136 | RQQFIQSVLDFLQEY | 15 | 3324.0741 |
| Dermatophagoides farinae | 6954 | Der f 15 | Q9U6R7 | 21444331 | 171 | IDKQNYLALVRELKD | 15 | 3324.0745 |
| Dermatophagoides farinae | 6954 | Der f 15 | Q9U6R7 | 21444331 | 176 | YLALVRELKDAFEPH | 15 | 3324.0756 |
| Dermatophagoides farinae | 6954 | Der f 15 | Q9U6R7 | 21444331 | 186 | AFEPHGYLLTAAVSP | 15 | 3324.0754 |
| Dermatophagoides farinae | 6954 | Der f 15 | Q9U6R7 | 21444331 | 231 | GWENFYGHNAPLYKR | 15 | 3324.0748 |
| Dermatophagoides farinae | 6954 | Der f 15 | Q9U6R7 | 21444331 | 251 | ELHTYFNVNYTMHYY | 15 | 3324.0742 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides farinae | 6954 | Der f 15 | Q9U6R7 | 21444331 | 256 | FNVNYTMHYLNNGA | 15 | 3324.0750 |
| Dermatophagoides farinae | 6954 | Der f 15 | Q9U6R7 | 21444331 | 316 | LSYIELCQLFQKEEW | 15 | 3324.0749 |
| Dermatophagoides farinae | 6954 | Der f 15 | Q9U6R7 | 21444331 | 361 | KLAFLKELGVSGVMV | 15 | 3324.0751 |
| Dermatophagoides farinae | 6954 | Der f 15 | Q9U6R7 | 21444331 | 391 | NPLLNKVHNMINGDE | 15 | 3324.0752 |
| Dermatophagoides farinae | 6954 | Der f 16 | Q8MVU3 | 21591547 | 6 | KNFDVIPIGHTFFFI | 15 | 3324.0777 |
| Dermatophagoides farinae | 6954 | Der f 16 | Q8MVU3 | 21591547 | 11 | IPIGHTFFFIWRIKQ | 15 | 3324.0772 |
| Dermatophagoides farinae | 6954 | Der f 16 | Q8MVU3 | 21591547 | 16 | TFFFIWRIKQFELVP | 15 | 3324.0761 |
| Dermatophagoides farinae | 6954 | Der f 16 | Q8MVU3 | 21591547 | 21 | WRIKQFELVPVPKED | 15 | 3324.0759 |
| Dermatophagoides farinae | 6954 | Der f 16 | Q8MVU3 | 21591547 | 111 | EIEEFESRQFSSYFK | 15 | 3324.0774 |
| Dermatophagoides farinae | 6954 | Der f 16 | Q8MVU3 | 21591547 | 121 | SSYFKNGIIYLKGGY | 15 | 3324.0760 |
| Dermatophagoides farinae | 6954 | Der f 16 | Q8MVU3 | 21591547 | 171 | VMNNGDVFILLVPNF | 15 | 3324.0768 |
| Dermatophagoides farinae | 6954 | Der f 16 | Q8MVU3 | 21591547 | 176 | DVFILLVPNFVFVWT | 15 | 3324.0757 |
| Dermatophagoides farinae | 6954 | Der f 16 | Q8MVU3 | 21591547 | 181 | LVPNFVFVWTGKHSN | 15 | 3324.0773 |
| Dermatophagoides farinae | 6954 | Der f 16 | Q8MVU3 | 21591547 | 211 | SELNRFKLSSVILED | 15 | 3324.0758 |
| Dermatophagoides farinae | 6954 | Der f 16 | Q8MVU3 | 21591547 | 216 | FKLSSVILEDGKEVE | 15 | 3324.0767 |
| Dermatophagoides farinae | 6954 | Der f 16 | Q8MVU3 | 21591547 | 236 | EYDAFNKALSLDKKD | 15 | 3324.0775 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides farinae | 6954 | Der f 16 | Q8MVU3 | 21591547 | 291 | ISFVKNGPLSRADLD | 15 | 3324.0776 |
| Dermatophagoides farinae | 6954 | Der f 16 | Q8MVU3 | 21591547 | 336 | IKYAMELINKKKYPN | 15 | 3324.0771 |
| Dermatophagoides farinae | 6954 | Der f 16 | Q8MVU3 | 21591547 | 361 | DESVEFKSLFESWQM | 15 | 3324.0770 |
| Dermatophagoides farinae | 6954 | Der f 16 | Q8MVU3 | 21591547 | 366 | FKSLFESWQMSEQEK | 15 | 3324.0763 |
| Dermatophagoides farinae | 6954 | Der f 16 | Q8MVU3 | 21591547 | 376 | SEQEKITSARLFRVS | 15 | 3324.0769 |
| Dermatophagoides farinae | 6954 | Der f 16 | Q8MVU3 | 21591547 | 381 | ITSARLFRVSRNGIF | 15 | 3324.0764 |
| Dermatophagoides farinae | 6954 | Der f 16 | Q8MVU3 | 21591547 | 416 | VMDKIYVWIGNQFAE | 15 | 3324.0766 |
| Dermatophagoides farinae | 6954 | Der f 16 | Q8MVU3 | 21591547 | 421 | YVWIGNQFAERIADE | 15 | 3324.0762 |
| Dermatophagoides farinae | 6954 | Der f 16 | Q8MVU3 | 21591547 | 451 | SGRKFQPNQIIKLKQ | 15 | 3324.0765 |
| Dermatophagoides farinae | 6954 | Der f 18 | Q86R84 | 27550039 | 1 | MTRPSLTVLAVLAAC | 15 | 3324.0778 |
| Dermatophagoides farinae | 6954 | Der f 18 | Q86R84 | 27550039 | 6 | LTVLAVLAACFGSNI | 15 | 3324.0779 |
| Dermatophagoides farinae | 6954 | Der f 18 | Q86R84 | 27550039 | 56 | SLCTHIVYSYFGIDA | 15 | 3324.0786 |
| Dermatophagoides farinae | 6954 | Der f 18 | Q86R84 | 27550039 | 61 | IVYSYFGIDAATHEI | 15 | 3324.0780 |
| Dermatophagoides farinae | 6954 | Der f 18 | Q86R84 | 27550039 | 71 | ATHEIKLLDEYLMKD | 15 | 3324.0783 |
| Dermatophagoides farinae | 6954 | Der f 18 | Q86R84 | 27550039 | 121 | EHYRETFVVSTVDLM | 15 | 3324.0787 |
| Dermatophagoides farinae | 6954 | Der f 18 | Q86R84 | 27550039 | 126 | TFVVSTVDLMTRYGF | 15 | 3324.0790 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides farinae | 6954 | Der f 18 | Q86R84 | 27550039 | 171 | HTSFVMGVTLPATIA | 15 | 3324.0789 |
| Dermatophagoides farinae | 6954 | Der f 18 | Q86R84 | 27550039 | 196 | SNYDFMNVLSLDYT | 15 | 3324.0781 |
| Dermatophagoides farinae | 6954 | Der f 18 | Q86R84 | 27550039 | 241 | HKMVMAVPFYARTWI | 15 | 3324.0792 |
| Dermatophagoides farinae | 6954 | Der f 18 | Q86R84 | 27550039 | 246 | AVPFYARTWILEKMN | 15 | 3324.0785 |
| Dermatophagoides farinae | 6954 | Der f 18 | Q86R84 | 27550039 | 281 | DGFLSYNELCVQIQA | 15 | 3324.0782 |
| Dermatophagoides farinae | 6954 | Der f 18 | Q86R84 | 27550039 | 306 | HDNTAIYAVYVHSNH | 15 | 3324.0791 |
| Dermatophagoides farinae | 6954 | Der f 18 | Q86R84 | 27550039 | 311 | IYAVYVHSNHAEWIS | 15 | 3324.0788 |
| Dermatophagoides farinae | 6954 | Der f 18 | Q86R84 | 27550039 | 366 | PLLHAIQSNYYHGVV | 15 | 3324.0784 |
| Dermatophagoides farinae | 6954 | Der f 2 | Q00855 | 83755018 | 1 | MISKILCLSLLVAAV | 15 | 3324.0794 |
| Dermatophagoides farinae | 6954 | Der f 2 | Q00855 | 83755018 | 6 | LCLSLLVAAVVADQV | 15 | 3324.0793 |
| Dermatophagoides farinae | 6954 | Der f 2 | Q00855 | 83755018 | 51 | PFTLEALFDANQNTK | 15 | 3324.0795 |
| Dermatophagoides farinae | 6954 | Der f 2 | Q00855 | 83755018 | 101 | QQYDIKYTWNVPKIA | 15 | 3324.0796 |
| Dermatophagoides farinae | 6954 | Der f 2 | Q00855 | 83755018 | 121 | VVVTVKLIGDNGVLA | 15 | 3337.0026 |
| Dermatophagoides farinae | 6954 | Der f 3 | P49275 | 1311457 | 1 | MMLTIVVLLAANIL | 15 | 3324.0798 |
| Dermatophagoides farinae | 6954 | Der f 3 | P49275 | 1311457 | 6 | IVVLLAANILATPIL | 15 | 3324.0797 |
| Dermatophagoides farinae | 6954 | Der f 3 | P49275 | 1311457 | 11 | AANILATPILPSSPN | 15 | 3324.0803 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides farinae | 6954 | Der f 3 | P49275 | 1311457 | 36 | AGDCPYQISLQSSSH | 15 | 3324.0804 |
| Dermatophagoides farinae | 6954 | Der f 3 | P49275 | 1311457 | 41 | YQISLQSSSHFCGGS | 15 | 3324.0802 |
| Dermatophagoides farinae | 6954 | Der f 3 | P49275 | 1311457 | 56 | ILDEYWILTAAHCVN | 15 | 3324.0800 |
| Dermatophagoides farinae | 6954 | Der f 3 | P49275 | 1311457 | 76 | KLSIRYNTLKHASGG | 15 | 3324.0799 |
| Dermatophagoides farinae | 6954 | Der f 3 | P49275 | 1311457 | 111 | NDVALIKLKTPMTLD | 15 | 3324.0801 |
| Dermatophagoides farinae | 6954 | Der f 6 | P49276 | 14424450 | 1 | MIKIFLVTILIVITV | 15 | 3324.0805 |
| Dermatophagoides farinae | 6954 | Der f 6 | P49276 | 14424450 | 6 | LVTILIVITVTVDAR | 15 | 3324.0807 |
| Dermatophagoides farinae | 6954 | Der f 6 | P49276 | 14424450 | 26 | QPKWAYLDSNEFPRS | 15 | 3324.0810 |
| Dermatophagoides farinae | 6954 | Der f 6 | P49276 | 14424450 | 61 | APFQISLLKDYLIMK | 15 | 3324.0806 |
| Dermatophagoides farinae | 6954 | Der f 6 | P49276 | 14424450 | 66 | SLLKDYLIMKRHMCG | 15 | 3324.0811 |
| Dermatophagoides farinae | 6954 | Der f 6 | P49276 | 14424450 | 141 | KTIIILPNPVVPSTN | 15 | 3324.0809 |
| Dermatophagoides farinae | 6954 | Der f 6 | P49276 | 14424450 | 265 | TRPKYYLDWITKNIV | 15 | 3324.0808 |
| Dermatophagoides farinae | 6954 | Der f 7 | Q26456 | 1311689 | 1 | MMKFLLIAAVAFVAV | 15 | 3324.0812 |
| Dermatophagoides farinae | 6954 | Der f 7 | Q26456 | 1311689 | 6 | LIAAVAFVAVSADPI | 15 | 3324.0813 |
| Dermatophagoides farinae | 6954 | Der f 7 | Q26456 | 1311689 | 11 | AFVAVSADPIHYDKI | 15 | 3324.0818 |
| Dermatophagoides farinae | 6954 | Der f 7 | Q26456 | 1311689 | 111 | IVSMEYDLAYKLGDL | 15 | 3324.0817 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides farinae | 6954 | Der f 7 | Q26456 | 1311689 | 131 | VISDIQDFVVALSLE | 15 | 3324.0819 |
| Dermatophagoides farinae | 6954 | Der f 7 | Q26456 | 1311689 | 136 | QDFVVALSLEISDEG | 15 | 3324.0814 |
| Dermatophagoides farinae | 6954 | Der f 7 | Q26456 | 1311689 | 156 | SFEVRQFANVVNHIG | 15 | 3324.0815 |
| Dermatophagoides farinae | 6954 | Der f 7 | Q26456 | 1311689 | 161 | QFANVVNHIGGLSIL | 15 | 3324.0822 |
| Dermatophagoides farinae | 6954 | Der f 7 | Q26456 | 1311689 | 166 | VNHIGGLSILDPIFG | 15 | 3324.0821 |
| Dermatophagoides farinae | 6954 | Der f 7 | Q26456 | 1311689 | 171 | GLSILDPIFGVLSDV | 15 | 3324.0820 |
| Dermatophagoides farinae | 6954 | Der f 7 | Q26456 | 1311689 | 176 | DPIFGVLSDVLTAIF | 15 | 3324.0816 |
| Dermatophagoides pteronyssinus | 6956 | Der p 1 | P08176 | 83754033 | 1 | MKIVLAIASLLALSA | 15 | 3324.0823 |
| Dermatophagoides pteronyssinus | 6956 | Der p 1 | P08176 | 83754033 | 6 | AIASLLALSAVYARP | 15 | 3324.0826 |
| Dermatophagoides pteronyssinus | 6956 | Der p 1 | P08176 | 83754033 | 11 | LALSAVYARPSSIKT | 15 | 3324.0828 |
| Dermatophagoides pteronyssinus | 6956 | Der p 1 | P08176 | 83754033 | 31 | KAFNKSYATPEDEEA | 15 | 3324.0834 |
| Dermatophagoides pteronyssinus | 6956 | Der p 1 | P08176 | 83754033 | 46 | ARKNFLESVKYVQSN | 15 | 3324.0839 |
| Dermatophagoides pteronyssinus | 6956 | Der p 1 | P08176 | 83754033 | 51 | LESVKYVQSNGGAIN | 15 | 3324.0838 |
| Dermatophagoides pteronyssinus | 6956 | Der p 1 | P08176 | 83754033 | 61 | GGAINHLSDLSLDEF | 15 | 3324.0842 |
| Dermatophagoides pteronyssinus | 6956 | Der p 1 | P08176 | 83754033 | 71 | SLDEFKNRFLMSAEA | 15 | 3324.0830 |
| Dermatophagoides pteronyssinus | 6956 | Der p 1 | P08176 | 83754033 | 76 | KNRFLMSAEAFEHLK | 15 | 3324.0824 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 1 | P08176 | 83754033 | 81 | MSAEAFEHLKTQFDL | 15 | 3324.0844 |
| Dermatophagoides pteronyssinus | 6956 | Der p 1 | P08176 | 83754033 | 86 | FEHLKTQFDLNAETN | 15 | 3324.0841 |
| Dermatophagoides pteronyssinus | 6956 | Der p 1 | P08176 | 83754033 | 111 | EIDLRQMRTVTPIRM | 15 | 3324.0836 |
| Dermatophagoides pteronyssinus | 6956 | Der p 1 | P08176 | 83754033 | 131 | SCWAFSGVAATESAY | 15 | 3324.0832 |
| Dermatophagoides pteronyssinus | 6956 | Der p 1 | P08176 | 83754033 | 136 | SGVAATESAYLAYRN | 15 | 3324.0829 |
| Dermatophagoides pteronyssinus | 6956 | Der p 1 | P08176 | 83754033 | 141 | TESAYLAYRNQSLDL | 15 | 3324.0825 |
| Dermatophagoides pteronyssinus | 6956 | Der p 1 | P08176 | 83754033 | 176 | RGIEYIQHNGVVQES | 15 | 3324.0831 |
| Dermatophagoides pteronyssinus | 6956 | Der p 1 | P08176 | 83754033 | 186 | VVQESYYRVVAREQS | 15 | 3324.0833 |
| Dermatophagoides pteronyssinus | 6956 | Der p 1 | P08176 | 83754033 | 211 | ISNYCQIYPPNVNKI | 15 | 3324.0837 |
| Dermatophagoides pteronyssinus | 6956 | Der p 1 | P08176 | 83754033 | 226 | REALAQTHSAIAVI | 15 | 3324.0840 |
| Dermatophagoides pteronyssinus | 6956 | Der p 1 | P08176 | 83754033 | 231 | QTHSAIAVIIGIKDL | 15 | 3324.0835 |
| Dermatophagoides pteronyssinus | 6956 | Der p 1 | P08176 | 83754033 | 296 | DNGYGYFAANIDLMM | 15 | 3324.0827 |
| Dermatophagoides pteronyssinus | 6956 | Der p 1 | P08176 | 83754033 | 306 | IDLMMIEEYPYVVIL | 15 | 3324.0843 |
| Dermatophagoides pteronyssinus | 6956 | Der p 10 | O18416 | 2440053 | 101 | RSEERLKIATAKLEE | 15 | 3324.0845 |
| Dermatophagoides pteronyssinus | 6956 | Der p 10 | O18416 | 2440053 | 106 | LKIATAKLEEASQSA | 15 | 3324.0847 |
| Dermatophagoides pteronyssinus | 6956 | Der p 10 | O18416 | 2440053 | 191 | VELEEELRVVGNNLK | 15 | 3324.0848 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 10 | O18416 | 2440053 | 221 | HEQQIRIMTKLKEA | 15 | 3324.0846 |
| Dermatophagoides pteronyssinus | 6956 | Der p 11 | Q6Y2F9 | 37778944 | 61 | AELQIQVMSLSERLE | 15 | 3324.0856 |
| Dermatophagoides pteronyssinus | 6956 | Der p 11 | Q6Y2F9 | 37778944 | 146 | QKFQAEVFELLSQLE | 15 | 3324.0855 |
| Dermatophagoides pteronyssinus | 6956 | Der p 11 | Q6Y2F9 | 37778944 | 151 | EVFELLSQLETANKE | 15 | 3324.0850 |
| Dermatophagoides pteronyssinus | 6956 | Der p 11 | Q6Y2F9 | 37778944 | 176 | LEYTVHELNIKIEEI | 15 | 3324.0873 |
| Dermatophagoides pteronyssinus | 6956 | Der p 11 | Q6Y2F9 | 37778944 | 181 | HELNIKIEEINRTVI | 15 | 3324.0869 |
| Dermatophagoides pteronyssinus | 6956 | Der p 11 | Q6Y2F9 | 37778944 | 216 | HEVKLQLDNANHLKQ | 15 | 3324.0859 |
| Dermatophagoides pteronyssinus | 6956 | Der p 11 | Q6Y2F9 | 37778944 | 226 | NHLKQQIAQQLEDTR | 15 | 3324.0853 |
| Dermatophagoides pteronyssinus | 6956 | Der p 11 | Q6Y2F9 | 37778944 | 276 | EARLELERQLTKANG | 15 | 3324.0866 |
| Dermatophagoides pteronyssinus | 6956 | Der p 11 | Q6Y2F9 | 37778944 | 311 | EELRRKMAQKISEYE | 15 | 3324.0867 |
| Dermatophagoides pteronyssinus | 6956 | Der p 11 | Q6Y2F9 | 37778944 | 346 | QSEVEVLIMDLEKAA | 15 | 3324.0874 |
| Dermatophagoides pteronyssinus | 6956 | Der p 11 | Q6Y2F9 | 37778944 | 351 | VLIMDLEKAAAHAQQ | 15 | 3324.0876 |
| Dermatophagoides pteronyssinus | 6956 | Der p 11 | Q6Y2F9 | 37778944 | 481 | KNQRLIAELAQVRHD | 15 | 3324.0851 |
| Dermatophagoides pteronyssinus | 6956 | Der p 11 | Q6Y2F9 | 37778944 | 506 | EIEALRKQYQIEIEQ | 15 | 3324.0852 |
| Dermatophagoides pteronyssinus | 6956 | Der p 11 | Q6Y2F9 | 37778944 | 511 | RKQYQIEIEQLNMRL | 15 | 3324.0854 |
| Dermatophagoides pteronyssinus | 6956 | Der p 11 | Q6Y2F9 | 37778944 | 516 | IEIEQLNMRLAEAEA | 15 | 3324.0871 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 11 | Q6Y2F9 | 37778944 | 536 | IARLKKKYQAQITEL | 15 | 3324.0870 |
| Dermatophagoides pteronyssinus | 6956 | Der p 11 | Q6Y2F9 | 37778944 | 541 | KKYQAQITELELSLD | 15 | 3324.0860 |
| Dermatophagoides pteronyssinus | 6956 | Der p 11 | Q6Y2F9 | 37778944 | 566 | KTIKKQALQITELQA | 15 | 3324.0872 |
| Dermatophagoides pteronyssinus | 6956 | Der p 11 | Q6Y2F9 | 37778944 | 611 | EEMRIALEQASRAKR | 15 | 3324.0858 |
| Dermatophagoides pteronyssinus | 6956 | Der p 11 | Q6Y2F9 | 37778944 | 636 | VRVNELTTINVNLAS | 15 | 3324.0864 |
| Dermatophagoides pteronyssinus | 6956 | Der p 11 | Q6Y2F9 | 37778944 | 641 | LTTINVNLASAKSKL | 15 | 3324.0861 |
| Dermatophagoides pteronyssinus | 6956 | Der p 11 | Q6Y2F9 | 37778944 | 646 | VNLASAKSKLESEFS | 15 | 3324.0877 |
| Dermatophagoides pteronyssinus | 6956 | Der p 11 | Q6Y2F9 | 37778944 | 651 | AKSKLESEFSALQAD | 15 | 3324.0857 |
| Dermatophagoides pteronyssinus | 6956 | Der p 11 | Q6Y2F9 | 37778944 | 681 | QKLTIELKSTKDLLI | 15 | 3324.0849 |
| Dermatophagoides pteronyssinus | 6956 | Der p 11 | Q6Y2F9 | 37778944 | 686 | ELKSTKDLLIEEQER | 15 | 3324.0868 |
| Dermatophagoides pteronyssinus | 6956 | Der p 11 | Q6Y2F9 | 37778944 | 701 | LVKLETVKKSLEQEV | 15 | 3324.0862 |
| Dermatophagoides pteronyssinus | 6956 | Der p 11 | Q6Y2F9 | 37778944 | 716 | RTLHVRIEBVEANAL | 15 | 3324.0875 |
| Dermatophagoides pteronyssinus | 6956 | Der p 11 | Q6Y2F9 | 37778944 | 731 | AGGKRVIAKLESRIR | 15 | 3324.0863 |
| Dermatophagoides pteronyssinus | 6956 | Der p 11 | Q6Y2F9 | 37778944 | 836 | DQAESNLSFIRAKHR | 15 | 3324.0865 |
| Dermatophagoides pteronyssinus | 6956 | Der p 14 | Q8N0N0 | 20385544 | 31 | AQSTVVYSLDAKTVL | 15 | 3324.0886 |
| Dermatophagoides pteronyssinus | 6956 | Der p 14 | Q8N0N0 | 20385544 | 36 | VYSLDAKTVLTPRDS | 15 | 3324.0936 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 14 | Q8N0N0 | 20385544 | 61 | VAFVSDCEAVLRLQN | 15 | 3324.0923 |
| Dermatophagoides pteronyssinus | 6956 | Der p 14 | Q8N0N0 | 20385544 | 66 | DCEAVLRLQNVAIDG | 15 | 3324.0912 |
| Dermatophagoides pteronyssinus | 6956 | Der p 14 | Q8N0N0 | 20385544 | 96 | FAFGYFNGRILGVCP | 15 | 3324.0914 |
| Dermatophagoides pteronyssinus | 6956 | Der p 14 | Q8N0N0 | 20385544 | 116 | DWSLNVKKAIVSSLQ | 15 | 3324.0888 |
| Dermatophagoides pteronyssinus | 6956 | Der p 14 | Q8N0N0 | 20385544 | 121 | VKKAIVSSLQALSDG | 15 | 3324.0880 |
| Dermatophagoides pteronyssinus | 6956 | Der p 14 | Q8N0N0 | 20385544 | 236 | KPVHMSYVKMMLKQN | 15 | 3324.0926 |
| Dermatophagoides pteronyssinus | 6956 | Der p 14 | Q8N0N0 | 20385544 | 286 | EVLKKLCSEITEPQA | 15 | 3324.0913 |
| Dermatophagoides pteronyssinus | 6956 | Der p 14 | Q8N0N0 | 20385544 | 306 | FTFQKLVDKLRYLSA | 15 | 3324.0915 |
| Dermatophagoides pteronyssinus | 6956 | Der p 14 | Q8N0N0 | 20385544 | 311 | LVDKLRYLSAEETAS | 15 | 3324.0909 |
| Dermatophagoides pteronyssinus | 6956 | Der p 14 | Q8N0N0 | 20385544 | 341 | RLRLFLDASAFAAS | 15 | 3324.0879 |
| Dermatophagoides pteronyssinus | 6956 | Der p 14 | Q8N0N0 | 20385544 | 346 | FLDASAFAASDGSIR | 15 | 3324.0907 |
| Dermatophagoides pteronyssinus | 6956 | Der p 14 | Q8N0N0 | 20385544 | 371 | LSITRSTALFTVAAI | 15 | 3324.0882 |
| Dermatophagoides pteronyssinus | 6956 | Der p 14 | Q8N0N0 | 20385544 | 376 | STALFTVAAIKAAPN | 15 | 3324.0878 |
| Dermatophagoides pteronyssinus | 6956 | Der p 14 | Q8N0N0 | 20385544 | 391 | KETVQVLLPVIASEK | 15 | 3324.0900 |
| Dermatophagoides pteronyssinus | 6956 | Der p 14 | Q8N0N0 | 20385544 | 406 | TIRPMLLGFSVLVRR | 15 | 3324.0902 |
| Dermatophagoides pteronyssinus | 6956 | Der p 14 | Q8N0N0 | 20385544 | 436 | DARDAYLARLAVARD | 15 | 3324.0904 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 14 | Q8N0N0 | 20385544 | 441 | YLARLAVARDASERM | 15 | 3324.0897 |
| Dermatophagoides pteronyssinus | 6956 | Der p 14 | Q8N0N0 | 20385544 | 451 | ASERMTIVRALENLN | 15 | 3324.0903 |
| Dermatophagoides pteronyssinus | 6956 | Der p 14 | Q8N0N0 | 20385544 | 456 | TIVRALENLNVNTDG | 15 | 3324.0933 |
| Dermatophagoides pteronyssinus | 6956 | Der p 14 | Q8N0N0 | 20385544 | 476 | NAMDEIIKSTDAEPA | 15 | 3324.0918 |
| Dermatophagoides pteronyssinus | 6956 | Der p 14 | Q8N0N0 | 20385544 | 486 | DAEPAMRAAAVNALP | 15 | 3324.0924 |
| Dermatophagoides pteronyssinus | 6956 | Der p 14 | Q8N0N0 | 20385544 | 536 | MSHIKDLFAVKGECM | 15 | 3324.0917 |
| Dermatophagoides pteronyssinus | 6956 | Der p 14 | Q8N0N0 | 20385544 | 551 | KNYVLTYVDNLKKSK | 15 | 3324.0891 |
| Dermatophagoides pteronyssinus | 6956 | Der p 14 | Q8N0N0 | 20385544 | 631 | LKELVEFQVTQSGFD | 15 | 3324.0883 |
| Dermatophagoides pteronyssinus | 6956 | Der p 14 | Q8N0N0 | 20385544 | 646 | RELNNAMSLLEKKSF | 15 | 3324.0932 |
| Dermatophagoides pteronyssinus | 6956 | Der p 14 | Q8N0N0 | 20385544 | 651 | AMSLLEKKSFQSVMQ | 15 | 3324.0911 |
| Dermatophagoides pteronyssinus | 6956 | Der p 14 | Q8N0N0 | 20385544 | 656 | EKKSFQSVMQFLRDM | 15 | 3324.0905 |
| Dermatophagoides pteronyssinus | 6956 | Der p 14 | Q8N0N0 | 20385544 | 661 | QSVMQFLRDMLKMLS | 15 | 3324.0895 |
| Dermatophagoides pteronyssinus | 6956 | Der p 14 | Q8N0N0 | 20385544 | 666 | FLRDMLKMLSQIRKN | 15 | 3324.0889 |
| Dermatophagoides pteronyssinus | 6956 | Der p 14 | Q8N0N0 | 20385544 | 671 | LKMLSQIRKNADDNH | 15 | 3324.0927 |
| Dermatophagoides pteronyssinus | 6956 | Der p 14 | Q8N0N0 | 20385544 | 736 | LDSKLVLPTITGLPL | 15 | 3324.0908 |
| Dermatophagoides pteronyssinus | 6956 | Der p 14 | Q8N0N0 | 20385544 | 746 | TGLPLMYKPGDNLVV | 15 | 3324.0922 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 14 | Q8NON0 | 20385544 | 811 | MIDMNVQKQEHSLLV | 15 | 3324.0928 |
| Dermatophagoides pteronyssinus | 6956 | Der p 14 | Q8NON0 | 20385544 | 816 | VQKQEHSLLVRFNMK | 15 | 3324.0935 |
| Dermatophagoides pteronyssinus | 6956 | Der p 14 | Q8NON0 | 20385544 | 836 | TVMRFKQSLREKRAT | 15 | 3324.0920 |
| Dermatophagoides pteronyssinus | 6956 | Der p 14 | Q8NON0 | 20385544 | 901 | KEVTALELMLKSETQ | 15 | 3324.0901 |
| Dermatophagoides pteronyssinus | 6956 | Der p 14 | Q8NON0 | 20385544 | 916 | DKTRRYIAEMTAVGS | 15 | 3324.0921 |
| Dermatophagoides pteronyssinus | 6956 | Der p 14 | Q8NON0 | 20385544 | 971 | NLKMHMDLPNVLQAD | 15 | 3324.0929 |
| Dermatophagoides pteronyssinus | 6956 | Der p 14 | Q8NON0 | 20385544 | 996 | NNVRKNRLNLQYKFA | 15 | 3324.0930 |
| Dermatophagoides pteronyssinus | 6956 | Der p 14 | Q8NON0 | 20385544 | 1021 | ENEFLFNLKRSSKEK | 15 | 3324.0925 |
| Dermatophagoides pteronyssinus | 6956 | Der p 14 | Q8NON0 | 20385544 | 1041 | YRAKYMSSHFPILNH | 15 | 3324.0910 |
| Dermatophagoides pteronyssinus | 6956 | Der p 14 | Q8NON0 | 20385544 | 1051 | PILNHKVNVQFKYRP | 15 | 3324.0919 |
| Dermatophagoides pteronyssinus | 6956 | Der p 14 | Q8NON0 | 20385544 | 1061 | FKYRPFKVNELNLEG | 15 | 3324.0906 |
| Dermatophagoides pteronyssinus | 6956 | Der p 14 | Q8NON0 | 20385544 | 1081 | LQHKFRLMRNSQMEV | 15 | 3324.0892 |
| Dermatophagoides pteronyssinus | 6956 | Der p 14 | Q8NON0 | 20385544 | 1211 | DKKIFITHKTEMTKP | 15 | 3324.0887 |
| Dermatophagoides pteronyssinus | 6956 | Der p 14 | Q8NON0 | 20385544 | 1271 | LFYENYLTVHKGGKL | 15 | 3324.0885 |
| Dermatophagoides pteronyssinus | 6956 | Der p 14 | Q8NON0 | 20385544 | 1291 | RNDRKILLDLDNALS | 15 | 3324.0896 |
| Dermatophagoides pteronyssinus | 6956 | Der p 14 | Q8NON0 | 20385544 | 1296 | ILLDLDNALSPREGT | 15 | 3324.0890 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 14 | Q8N0N0 | 20385544 | 1346 | NGKLHLSLIDPSTLS | 15 | 3324.0894 |
| Dermatophagoides pteronyssinus | 6956 | Der p 14 | Q8N0N0 | 20385544 | 1351 | LSLIDPSTLSLVTKA | 15 | 3324.0893 |
| Dermatophagoides pteronyssinus | 6956 | Der p 14 | Q8N0N0 | 20385544 | 1511 | GKLEGVLSRKVPSHL | 15 | 3324.0916 |
| Dermatophagoides pteronyssinus | 6956 | Der p 14 | Q8N0N0 | 20385544 | 1516 | VLSRKVPSHLTLETP | 15 | 3324.0934 |
| Dermatophagoides pteronyssinus | 6956 | Der p 14 | Q8N0N0 | 20385544 | 1566 | PGVQYKIIGNGKIKD | 15 | 3324.0931 |
| Dermatophagoides pteronyssinus | 6956 | Der p 14 | Q8N0N0 | 20385544 | 1636 | FDPHRAYYINWISSI | 15 | 3324.0899 |
| Dermatophagoides pteronyssinus | 6956 | Der p 14 | Q8N0N0 | 20385544 | 1641 | AYYINWISSIRKYIQ | 15 | 3324.0898 |
| Dermatophagoides pteronyssinus | 6956 | Der p 14 | Q8N0N0 | 20385544 | 1646 | WISSIRKYIQNFIVE | 15 | 3324.0884 |
| Dermatophagoides pteronyssinus | 6956 | Der p 14 | Q8N0N0 | 20385544 | 1648 | SSIRKYIQNFIVEDH | 15 | 3324.0881 |
| Dermatophagoides pteronyssinus | 6956 | Der p 2 | P49278 | 21465916 | 1 | MMYKILCLSLLVAAV | 15 | 3324.0937 |
| Dermatophagoides pteronyssinus | 6956 | Der p 2 | P49278 | 21465916 | 6 | LCLSLLVAAVARDQV | 15 | 3324.0938 |
| Dermatophagoides pteronyssinus | 6956 | Der p 2 | P49278 | 21465916 | 46 | IHRGKPFQLEAVFEA | 15 | 3324.0939 |
| Dermatophagoides pteronyssinus | 6956 | Der p 2 | P49278 | 21465916 | 51 | PFQLEAVFEANQNTK | 15 | 3324.0941 |
| Dermatophagoides pteronyssinus | 6956 | Der p 2 | P49278 | 21465916 | 101 | QQYDIKYTWNVPKIA | 15 | 3324.0940 |
| Dermatophagoides pteronyssinus | 6956 | Der p 20 | DERP20SEQ | 188485735 | 26 | LLKKYLTRDVFDQLK | 15 | 3324.0943 |
| Dermatophagoides pteronyssinus | 6956 | Der p 20 | DERP20SEQ | 188485735 | 31 | LTRDVFDQLKNKKTD | 15 | 3324.0944 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 20 | DERP20SEQ | 188485735 | 71 | DAQSYKTFAALFDPI | 15 | 3324.0942 |
| Dermatophagoides pteronyssinus | 6956 | Der p 20 | DERP20SEQ | 188485735 | 76 | KTFAALFDPIIDDYH | 15 | 3324.0945 |
| Dermatophagoides pteronyssinus | 6956 | Der p20 | DERP20SEQ | 188485735 | 131 | LNGYPFNPMLTEAQY | 15 | 3324.0946 |
| Dermatophagoides pteronyssinus | 6956 | Der p 21 | Q2L7C5 | 85687540 | 1 | MKFIITLFAAIVMAA | 15 | 3324.0947 |
| Dermatophagoides pteronyssinus | 6956 | Der p 21 | Q2L7C5 | 85687540 | 6 | TLFAAIVMAAAVSGF | 15 | 3324.0949 |
| Dermatophagoides pteronyssinus | 6956 | Der p 21 | Q2L7C5 | 85687540 | 11 | IVMAAAVSGFIVGDK | 15 | 3324.0951 |
| Dermatophagoides pteronyssinus | 6956 | Der p 21 | Q2L7C5 | 85687540 | 26 | KEDEWRMAFDRLMME | 15 | 3324.0954 |
| Dermatophagoides pteronyssinus | 6956 | Der p 21 | Q2L7C5 | 85687540 | 31 | RMAFDRLMMEELETK | 15 | 3324.0956 |
| Dermatophagoides pteronyssinus | 6956 | Der p 21 | Q2L7C5 | 85687540 | 51 | KGLLHLSEQYKELEK | 15 | 3324.0955 |
| Dermatophagoides pteronyssinus | 6956 | Der p 21 | Q2L7C5 | 85687540 | 86 | MKGALKFFEMEAKRT | 15 | 3324.0950 |
| Dermatophagoides pteronyssinus | 6956 | Der p 21 | Q2L7C5 | 85687540 | 106 | ERYNYEFALESIKLL | 15 | 3324.0948 |
| Dermatophagoides pteronyssinus | 6956 | Der p 21 | Q2L7C5 | 85687540 | 111 | EFALESIKLLIKKLD | 15 | 3324.0952 |
| Dermatophagoides pteronyssinus | 6956 | Der p 21 | Q2L7C5 | 85687540 | 116 | SIKLLIKKLDELAKK | 15 | 3324.0953 |
| Dermatophagoides pteronyssinus | 6956 | Der p 3 | P39675 | 729315 | 1 | MIIYNLIVLLLAIN | 15 | 3324.0957 |
| Dermatophagoides pteronyssinus | 6956 | Der p 3 | P39675 | 729315 | 6 | ILIVLLAINTLANP | 15 | 3324.0958 |
| Dermatophagoides pteronyssinus | 6956 | Der p 3 | P39675 | 729315 | 11 | LLAINTLANPILPAS | 15 | 3324.0962 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 3 | P39675 | 729315 | 16 | TLANPILPASPNATI | 15 | 3324.0969 |
| Dermatophagoides pteronyssinus | 6956 | Der p 3 | P39675 | 729315 | 41 | CPYQISLQSSSHFCG | 15 | 3324.0961 |
| Dermatophagoides pteronyssinus | 6956 | Der p 3 | P39675 | 729315 | 56 | GTILDEYWILTAAHC | 15 | 3324.0959 |
| Dermatophagoides pteronyssinus | 6956 | Der p 3 | P39675 | 729315 | 61 | EYWILTAAHCVAGQT | 15 | 3324.0966 |
| Dermatophagoides pteronyssinus | 6956 | Der p 3 | P39675 | 729315 | 76 | ASKLSIRYNSLKHSL | 15 | 3324.0963 |
| Dermatophagoides pteronyssinus | 6956 | Der p 3 | P39675 | 729315 | 81 | IRYNSLKHSLGGEKI | 15 | 3324.0968 |
| Dermatophagoides pteronyssinus | 6956 | Der p 3 | P39675 | 729315 | 91 | GGEKISVAKIFAHEK | 15 | 3324.0964 |
| Dermatophagoides pteronyssinus | 6956 | Der p 3 | P39675 | 729315 | 111 | IDNDIALIKLKSPMK | 15 | 3324.0967 |
| Dermatophagoides pteronyssinus | 6956 | Der p 3 | P39675 | 729315 | 116 | ALIKLKSPMKLNQKN | 15 | 3324.0965 |
| Dermatophagoides pteronyssinus | 6956 | Der p 3 | P39675 | 729315 | 166 | SELRRVDIAVVSRKE | 15 | 3324.0960 |
| Dermatophagoides pteronyssinus | 6956 | Der p 4 | Q9Y197 | 5059162 | 1 | KYHNPHFIGNRSVIT | 15 | 3324.0983 |
| Dermatophagoides pteronyssinus | 6956 | Der p4 | Q9Y197 | 5059162 | 6 | HFIGNRSVITHLMEW | 15 | 3324.0982 |
| Dermatophagoides pteronyssinus | 6956 | Der p 4 | Q9Y197 | 5059162 | 86 | NKAGVRIYVDIVLNH | 15 | 3324.0981 |
| Dermatophagoides pteronyssinus | 6956 | Der p 4 | Q9Y197 | 5059162 | 91 | RIYVDIVLNHMTGAQ | 15 | 3324.0988 |
| Dermatophagoides pteronyssinus | 6956 | Der p 4 | Q9Y197 | 5059162 | 96 | IVLNHMTGAQSGKGT | 15 | 3324.0987 |
| Dermatophagoides pteronyssinus | 6956 | Der p 4 | Q9Y197 | 5059162 | 176 | QVDFLNHLIDIGVAG | 15 | 3324.0984 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 4 | Q9Y197 | 5059162 | 201 | PDDLRSIYSRLHNLN | 15 | 3324.0979 |
| Dermatophagoides pteronyssinus | 6956 | Der p 4 | Q9Y197 | 5059162 | 206 | SIYSRLHNLNKEFFP | 15 | 3324.0989 |
| Dermatophagoides pteronyssinus | 6956 | Der p 4 | Q9Y197 | 5059162 | 221 | ENSQPFIYHETIYYG | 15 | 3324.0990 |
| Dermatophagoides pteronyssinus | 6956 | Der p 4 | Q9Y197 | 5059162 | 251 | IEFRFYKEITNVFRG | 15 | 3324.0976 |
| Dermatophagoides pteronyssinus | 6956 | Der p 4 | Q9Y197 | 5059162 | 286 | DALVMIDSHDLRVGH | 15 | 3324.0992 |
| Dermatophagoides pteronyssinus | 6956 | Der p 4 | Q9Y197 | 5059162 | 311 | FEGRLLKAATAFMLA | 15 | 3324.0973 |
| Dermatophagoides pteronyssinus | 6956 | Der p 4 | Q9Y197 | 5059162 | 316 | LKAATAFMLAWNYGV | 15 | 3324.0972 |
| Dermatophagoides pteronyssinus | 6956 | Der p 4 | Q9Y197 | 5059162 | 321 | AFMLAWNYGVPRVMS | 15 | 3324.0977 |
| Dermatophagoides pteronyssinus | 6956 | Der p 4 | Q9Y197 | 5059162 | 331 | PRVMSSYFWNQIIKD | 15 | 3324.0991 |
| Dermatophagoides pteronyssinus | 6956 | Der p 4 | Q9Y197 | 5059162 | 381 | EHRWREIYNMVKFRM | 15 | 3324.0986 |
| Dermatophagoides pteronyssinus | 6956 | Der p 4 | Q9Y197 | 5059162 | 386 | EIYNMVKFRMIAGQE | 15 | 3324.0978 |
| Dermatophagoides pteronyssinus | 6956 | Der p 4 | Q9Y197 | 5059162 | 391 | VKFRMIAGQEPVHNW | 15 | 3324.0993 |
| Dermatophagoides pteronyssinus | 6956 | Der p 4 | Q9Y197 | 5059162 | 411 | YQIAFSRGNRAFIAI | 15 | 3324.0980 |
| Dermatophagoides pteronyssinus | 6956 | Der p 4 | Q9Y197 | 5059162 | 416 | SRGNRAFIAINLQKN | 15 | 3324.0974 |
| Dermatophagoides pteronyssinus | 6956 | Der p 4 | Q9Y197 | 5059162 | 421 | AFIAINLQKNQQNLQ | 15 | 3324.0985 |
| Dermatophagoides pteronyssinus | 6956 | Der p 4 | Q9Y197 | 5059162 | 476 | YVGHDEFDAFVAYHI | 15 | 3324.0975 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 4 | Q9Y197 | 5059162 | 481 | EFDAFVAYHIGARIV | 15 | 3324.0970 |
| Dermatophagoides pteronyssinus | 6956 | Der p 4 | Q9Y197 | 5059162 | 482 | FDAFVAYHIGARIVS | 15 | 3324.0971 |
| Dermatophagoides pteronyssinus | 6956 | Der p 5 | P14004V | 1352238 | 6 | KDPKPLKKISIMKFI | 15 | 3324.0999 |
| Dermatophagoides pteronyssinus | 6956 | Der p 5 | P14004V | 1352238 | 11 | LKKISIMKFIIAFFV | 15 | 3324.0996 |
| Dermatophagoides pteronyssinus | 6956 | Der p 5 | P14004V | 1352238 | 16 | IMKFIIAFFVATLAV | 15 | 3324.0994 |
| Dermatophagoides pteronyssinus | 6956 | Der p 5 | P14004V | 1352238 | 21 | IAFFVATLAVMTVSG | 15 | 3324.0995 |
| Dermatophagoides pteronyssinus | 6956 | Der p 5 | P14004V | 1352238 | 46 | FDFLLMERIHEQIKK | 15 | 3324.0998 |
| Dermatophagoides pteronyssinus | 6956 | Der p 5 | P14004V | 1352238 | 61 | GELALFYLQEQINHF | 15 | 3324.0997 |
| Dermatophagoides pteronyssinus | 6956 | Der p 5 | P14004V | 1352238 | 66 | FYLQEQINHFEEKPT | 15 | 3324.1000 |
| Dermatophagoides pteronyssinus | 6956 | Der p 5 | P14004V | 1352238 | 106 | DRLMQRKDLDIFEQY | 15 | 3324.1002 |
| Dermatophagoides pteronyssinus | 6956 | Der p 5 | P14004V | 1352238 | 111 | RKDLDIFEQYNLEMA | 15 | 3324.1001 |
| Dermatophagoides pteronyssinus | 6956 | Der p 6 | P49277(IUIS) | 1352239 | 1 | MIKIITTILIITVV | 15 | 3324.1003 |
| Dermatophagoides pteronyssinus | 6956 | Der p 6 | P49277(IUIS) | 1352239 | 6 | TTILIITVVDCRF | 15 | 3324.1004 |
| Dermatophagoides pteronyssinus | 6956 | Der p 6 | P49277(IUIS) | 1352239 | 26 | PKWSYLDSLPASSSM | 15 | 3324.1005 |
| Dermatophagoides pteronyssinus | 6956 | Der p 6 | P49277(IUIS) | 1352239 | 36 | ASSSMMNDNSSPIAG | 15 | 3337.0027 |
| Dermatophagoides pteronyssinus | 6956 | Der p 7 | P49273 | 292659601 | 1 | MMKLLIAAAFVAV | 15 | 3324.1006 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 7 | P49273 | 292659601 | 6 | LIAAAFVAVSADPI | 15 | 3324.1007 |
| Dermatophagoides pteronyssinus | 6956 | Der p 7 | P49273 | 292659601 | 11 | AFVAVSADPIHYDKI | 15 | 3324.1012 |
| Dermatophagoides pteronyssinus | 6956 | Der p 7 | P49273 | 292659601 | 111 | VVSMEYDLAYKLGDL | 15 | 3324.1015 |
| Dermatophagoides pteronyssinus | 6956 | Der p 7 | P49273 | 292659601 | 131 | VISDIQDFVVELSLE | 15 | 3324.1019 |
| Dermatophagoides pteronyssinus | 6956 | Der p 7 | P49273 | 292659601 | 136 | QDFVVELSLEVSEEG | 15 | 3324.1009 |
| Dermatophagoides pteronyssinus | 6956 | Der p 7 | P49273 | 292659601 | 151 | NMTLTSFEVRQFANV | 15 | 3324.1014 |
| Dermatophagoides pteronyssinus | 6956 | Der p 7 | P49273 | 292659601 | 156 | SFEVRQFANVVNHIG | 15 | 3324.1010 |
| Dermatophagoides pteronyssinus | 6956 | Der p 7 | P49273 | 292659601 | 161 | QFANVVNHIGGLSIL | 15 | 3324.1016 |
| Dermatophagoides pteronyssinus | 6956 | Der p 7 | P49273 | 292659601 | 166 | VNHIGGLSILDPIFA | 15 | 3324.1013 |
| Dermatophagoides pteronyssinus | 6956 | Der p 7 | P49273 | 292659601 | 171 | GLSILDPIFAVLSDV | 15 | 3324.1011 |
| Dermatophagoides pteronyssinus | 6956 | Der p 7 | P49273 | 292659601 | 176 | DPIFAVLSDVLTAIF | 15 | 3324.1008 |
| Dermatophagoides pteronyssinus | 6956 | Der p 7 | P49273 | 292659601 | 186 | LTAIFQDTVRAEMTK | 15 | 3324.1018 |
| Dermatophagoides pteronyssinus | 6956 | Der p 7 | P49273 | 292659601 | 196 | AEMTKVLAPAFKKEL | 15 | 3324.1017 |
| Dermatophagoides pteronyssinus | 6956 | Der p 8 | P46419 | 1170095 | 16 | QPIRLLLTYSGVDFV | 15 | 3324.1025 |
| Dermatophagoides pteronyssinus | 6956 | Der p 8 | P46419 | 1170095 | 46 | EWLNEKFNLGLDFPN | 15 | 3324.1029 |
| Dermatophagoides pteronyssinus | 6956 | Der p 8 | P46419 | 1170095 | 66 | DGDMKMTQTFAILRY | 15 | 3324.1027 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 8 | P46419 | 1170095 | 71 | MTQTFAILRYLGRKY | 15 | 3324.1022 |
| Dermatophagoides pteronyssinus | 6956 | Der p 8 | P46419 | 1170095 | 136 | LKLMSKFVGEHAFIA | 15 | 3324.1023 |
| Dermatophagoides pteronyssinus | 6956 | Der p 8 | P46419 | 1170095 | 141 | KFVGEHAFIAGANIS | 15 | 3324.1021 |
| Dermatophagoides pteronyssinus | 6956 | Der p 8 | P46419 | 1170095 | 146 | HAFIAGANISYVDFN | 15 | 3324.1020 |
| Dermatophagoides pteronyssinus | 6956 | Der p 8 | P46419 | 1170095 | 156 | YVDFNLYEYLCHVKV | 15 | 3324.1026 |
| Dermatophagoides pteronyssinus | 6956 | Der p 8 | P46419 | 1170095 | 171 | MVPEVFGQPENLKRY | 15 | 3324.1024 |
| Dermatophagoides pteronyssinus | 6956 | Der p 8 | P46419 | 1170095 | 181 | NLKRYVERMESLPRV | 15 | 3324.1028 |
| Dermatophagoides pteronyssinus | 6956 | Der p 9 | Q7Z163 | 31745576 | 1 | MKFMILFALIAIGTS | 15 | 3324.1030 |
| Dermatophagoides pteronyssinus | 6956 | Der p 9 | Q7Z163 | 31745576 | 6 | LFALIAIGTSVAIGE | 15 | 3324.1038 |
| Dermatophagoides pteronyssinus | 6956 | Der p 9 | Q7Z163 | 31745576 | 31 | ITEKFPWMINEPLND | 15 | 3324.1034 |
| Dermatophagoides pteronyssinus | 6956 | Der p 9 | Q7Z163 | 31745576 | 56 | ASPGDAVYQIALFRK | 15 | 3324.1041 |
| Dermatophagoides pteronyssinus | 6956 | Der p 9 | Q7Z163 | 31745576 | 61 | AVYQIALFRKDSFTC | 15 | 3324.1044 |
| Dermatophagoides pteronyssinus | 6956 | Der p 9 | Q7Z163 | 31745576 | 76 | GGSLISSRTVLTAAH | 15 | 3324.1042 |
| Dermatophagoides pteronyssinus | 6956 | Der p 9 | Q7Z163 | 31745576 | 96 | EATPSYFKIRYNTLD | 15 | 3324.1031 |
| Dermatophagoides pteronyssinus | 6956 | Der p 9 | Q7Z163 | 31745576 | 101 | YFKIRYNTLDRTNGP | 15 | 3324.1032 |
| Dermatophagoides pteronyssinus | 6956 | Der p 9 | Q7Z163 | 31745576 | 121 | KIYRHNLYSSSPIDY | 15 | 3324.1045 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dermatophagoides pteronyssinus | 6956 | Der p 9 | Q7Z163 | 31745576 | 131 | SPIDYDVATLILSQP | 15 | 3324.1033 |
| Dermatophagoides pteronyssinus | 6956 | Der p 9 | Q7Z163 | 31745576 | 136 | DVATLILSQPFTPSA | 15 | 3324.1037 |
| Dermatophagoides pteronyssinus | 6956 | Der p 9 | Q7Z163 | 31745576 | 181 | TLPTILQIASVTKMS | 15 | 3324.1036 |
| Dermatophagoides pteronyssinus | 6956 | Der p 9 | Q7Z163 | 31745576 | 201 | STVVGSVNAITNRMLC | 15 | 3324.1035 |
| Dermatophagoides pteronyssinus | 6956 | Der p 9 | Q7Z163 | 31745576 | 251 | STKYPTIYSNVANLR | 15 | 3324.1039 |
| Dermatophagoides pteronyssinus | 6956 | Der p 9 | Q7Z163 | 31745576 | 256 | TIYSNVANLRNWIIS | 15 | 3324.1040 |
| Dermatophagoides pteronyssinus | 6956 | Der p 9 | Q7Z163 | 31745576 | 259 | SNVANLRNWIISNTV | 15 | 3324.1043 |
| Dog epithelia | 9615 | Can f 1 | O18873 | 29292148 | 1 | MKTLLLTIGFSLIAI | 15 | 3324.0474 |
| Dog epithelia | 9615 | Can f 1 | O18873 | 29292148 | 6 | LTIGFSLIAILQAQD | 15 | 3324.0473 |
| Dog epithelia | 9615 | Can f 1 | O18873 | 29292148 | 11 | SLIAILQAQDTPALG | 15 | 3324.0475 |
| Dog epithelia | 9615 | Can f 1 | O18873 | 29292148 | 31 | VSGKWYLKAMTADQE | 15 | 3324.0478 |
| Dog epithelia | 9615 | Can f 1 | O18873 | 29292148 | 36 | YLKAMTADQEVPEKP | 15 | 3324.0480 |
| Dog epithelia | 9615 | Can f 1 | O18873 | 29292148 | 91 | PGKTAYEGQRVVFI | 15 | 3324.0479 |
| Dog epithelia | 9615 | Can f 1 | O18873 | 29292148 | 96 | AYEGQRVVFIQPSPV | 15 | 3324.0476 |
| Dog epithelia | 9615 | Can f 1 | O18873 | 29292148 | 101 | RVVFIQPSPVRDHYI | 15 | 3324.0477 |
| Dog epithelia | 9615 | Can f 2 | O18874 | 3121746 | 1 | MQLLLLTVGLALICG | 15 | 3324.0482 |
| Dog epithelia | 9615 | Can f 2 | O18874 | 3121746 | 36 | RWHSVALASNKSDLI | 15 | 3324.0484 |
| Dog epithelia | 9615 | Can f 2 | O18874 | 3121746 | 51 | KPWGHFRVFIHSMSA | 15 | 3324.0483 |
| Dog epithelia | 9615 | Can f 2 | O18874 | 3121746 | 56 | FRVFIHSMSAKDGNL | 15 | 3324.0485 |
| Dog epithelia | 9615 | Can f 2 | O18874 | 3121746 | 81 | QCEKVSLTAFKTATS | 15 | 3324.0486 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dog epithelia | 9615 | Can f 2 | O18874 | 3121746 | 86 | SLTAFKTATSNKFDL | 15 | 3324.0489 |
| Dog epithelia | 9615 | Can f 2 | O18874 | 3121746 | 116 | KSYLILYMINQYNDD | 15 | 3324.0481 |
| Dog epithelia | 9615 | Can f 2 | O18874 | 3121746 | 121 | LYMINQYNDDTSLVA | 15 | 3324.0488 |
| Dog epithelia | 9615 | Can f 2 | O18874 | 3121746 | 131 | TSLVAHLMVRDLSRQ | 15 | 3324.0487 |
| Dog epithelia | 9615 | Can f 3 | P49822 | 56757408 | 1 | MKWVTFISLFFLFSS | 15 | 3324.0490 |
| Dog epithelia | 9615 | Can f 3 | P49822 | 56757408 | 6 | FISLFFLFSSAYSRG | 15 | 3324.0491 |
| Dog epithelia | 9615 | Can f 3 | P49822 | 56757408 | 21 | LVRREAYKSEIAHRY | 15 | 3324.0511 |
| Dog epithelia | 9615 | Can f 3 | P49822 | 56757408 | 41 | EHPRGLVLVAFSQYL | 15 | 3324.0493 |
| Dog epithelia | 9615 | Can f 3 | P49822 | 56757408 | 46 | LVLVAFSQYLQQCPF | 15 | 3324.0496 |
| Dog epithelia | 9615 | Can f 3 | P49822 | 56757408 | 156 | QLFLGKYLYEIARRH | 15 | 3324.0499 |
| Dog epithelia | 9615 | Can f 3 | P49822 | 56757408 | 161 | KYLYEIARRHPYFYA | 15 | 3324.0501 |
| Dog epithelia | 9615 | Can f 3 | P49822 | 56757408 | 166 | IARRHPYFYAPELLY | 15 | 3324.0502 |
| Dog epithelia | 9615 | Can f 3 | P49822 | 56757408 | 171 | PYFYAPELLYYAQQY | 15 | 3324.0506 |
| Dog epithelia | 9615 | Can f 3 | P49822 | 56757408 | 176 | PELLYYAQQYKGVFA | 15 | 3324.0508 |
| Dog epithelia | 9615 | Can f 3 | P49822 | 56757408 | 206 | lEALREKVLLSSAKE | 15 | 3324.0510 |
| Dog epithelia | 9615 | Can f 3 | P49822 | 56757408 | 231 | GDRAFKAWSVARLSQ | 15 | 3324.0495 |
| Dog epithelia | 9615 | Can f 3 | P49822 | 56757408 | 346 | AKDVFLGTFLYEYAR | 15 | 3324.0507 |
| Dog epithelia | 9615 | Can f 3 | P49822 | 56757408 | 351 | LGTFLYEYARRHPEY | 15 | 3324.0504 |
| Dog epithelia | 9615 | Can f 3 | P49822 | 56757408 | 361 | RHPEYSVSLLLRLAK | 15 | 3324.0497 |
| Dog epithelia | 9615 | Can f 3 | P49822 | 56757408 | 366 | SVSLLLRLAKEYEAT | 15 | 3324.0505 |
| Dog epithelia | 9615 | Can f 3 | P49822 | 56757408 | 396 | KVLDEFKPlVDEPQN | 15 | 3324.0503 |
| Dog epithelia | 9615 | Can f 3 | P49822 | 56757408 | 421 | KLGEYGFQNALLVRY | 15 | 3324.0498 |
| Dog epithelia | 9615 | Can f 3 | P49822 | 56757408 | 471 | SCAEDFLSVVLNRLC | 15 | 3324.0494 |
| Dog epithelia | 9615 | Can f 3 | P49822 | 56757408 | 476 | FLSVVLNRLCVLHEK | 15 | 3324.0500 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Dog epithelia | 9615 | Can f 3 | P49822 | 56757408 | 531 | FTFHADLCTLPEAEK | 15 | 3324.0509 |
| Dog epithelia | 9615 | Can f 3 | P49822 | 56757408 | 594 | EEGPKLVAAAQAALV | 15 | 3324.0492 |
| Dog epithelia | 9615 | Can f 5 | P09582 | 50979094 | 1 | MWFLALCLAMSLGWT | 15 | 3324.0513 |
| Dog epithelia | 9615 | Can f 5 | P09582 | 50979094 | 86 | EGQLVQVRKSFIHPL | 15 | 3324.0514 |
| Dog epithelia | 9615 | Can f 5 | P09582 | 50979094 | 91 | QVRKSFIHPLYKTKV | 15 | 3324.0512 |
| Dog epithelia | 9615 | Can f 5 | P09582 | 50979094 | 116 | RSHDLMLLHLEEPAK | 15 | 3324.0515 |
| Dog epithelia | 9615 | Can f 5 | P09582 | 50979094 | 191 | VTKFMLCAGVLEGKK | 15 | 3324.0516 |
| English plantain | 39414 | Pla l 1 | P82242 | 14422363 | 21 | HSRNLINELSERMAG | 15 | 3324.1552 |
| English plantain | 39414 | Pla l 1 | P82242 | 14422363 | 71 | HEDCEIKLVKSSRPD | 15 | 3324.1551 |
| English plantain | 39414 | Pla l 1 | P82242 | 14422363 | 76 | IKLVKSSRPDCSEIP | 15 | 3337.0044 |
| Giant ragweed | 4214 | Amb t 5 | P10414 | 1184267 | 1 | MKNIFMLTLFILIIT | 15 | 3324.0099 |
| Giant ragweed | 4214 | Amb t 5 | P10414 | 1184267 | 6 | MLTLFILIITSTIKA | 15 | 3324.0100 |
| Giant ragweed | 4214 | Amb t 5 | P10414 | 1184267 | 11 | ILIITSTIKAIGSTN | 15 | 3324.0101 |
| Giant ragweed | 4214 | Amb t 5 | P10414 | 1184267 | 31 | KQEDDGLCYEGTNCG | 15 | 3337.0006 |
| Giant ragweed | 4214 | Amb t 5 | P10414 | 1184267 | 56 | GKYCVCYDSKAICNK | 15 | 3337.0007 |
| Kentucky blue grass | 4545 | Poa p 1 | Q9ZP03 | 4090265 | 1 | MASSSSVLLVVALFA | 15 | 3324.1554 |
| Kentucky blue grass | 4545 | Poa p 1 | Q9ZP03 | 4090265 | 6 | SVLLVVALFAVFLGT | 15 | 3324.1553 |
| Kentucky blue grass | 4545 | Poa p 1 | Q9ZP03 | 4090265 | 11 | VALFAVFLGTAHGIA | 15 | 3324.1555 |
| Kentucky blue grass | 4545 | Poa p 1 | Q9ZP03 | 4090265 | 121 | EPIAAYHFDLSGKAF | 15 | 3324.1556 |
| Kentucky blue grass | 4545 | Poa p 1 | Q9ZP03 | 4090265 | 176 | KGSNPNYLALLVKYV | 15 | 3324.1557 |
| Kentucky blue grass | 4545 | Poa p 1 | Q9ZP03 | 4090265 | 181 | NYLALLVKVVTGDGD | 15 | 3324.1558 |
| Kentucky blue grass | 4545 | Poa p 5 | Q9FPR0 | 11991227 | 1 | MAVQKYTVALFLTVA | 15 | 3324.1565 |
| Kentucky blue grass | 4545 | Poa p 5 | Q9FPR0 | 11991227 | 6 | YTVALFLTVALVAGP | 15 | 3324.1561 |
| Kentucky blue grass | 4545 | Poa p 5 | Q9FPR0 | 11991227 | 11 | FLTVALVAGPAASYA | 15 | 3324.1572 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Kentucky blue grass | 4545 | Poa p 5 | Q9FPR0 | 11991227 | 51 | QKLMEDINVGFKAAV | 15 | 3324.1580 |
| Kentucky blue grass | 4545 | Poa p 5 | Q9FPR0 | 11991227 | 56 | DINVGFKAAVAAAAG | 15 | 3324.1571 |
| Kentucky blue grass | 4545 | Poa p 5 | Q9FPR0 | 11991227 | 61 | FKAAVAAAAGAPPAD | 15 | 3324.1575 |
| Kentucky blue grass | 4545 | Poa p 5 | Q9FPR0 | 11991227 | 71 | APPADKFKTFQAAFS | 15 | 3324.1568 |
| Kentucky blue grass | 4545 | Poa p 5 | Q9FPR0 | 11991227 | 76 | KFKTFQAAFSASVEA | 15 | 3324.1560 |
| Kentucky blue grass | 4545 | Poa p 5 | Q9FPR0 | 11991227 | 101 | PGFVSHVAATSDATY | 15 | 3324.1573 |
| Kentucky blue grass | 4545 | Poa p 5 | Q9FPR0 | 11991227 | 121 | ATPEAKFDSFVAAFT | 15 | 3324.1570 |
| Kentucky blue grass | 4545 | Poa p 5 | Q9FPR0 | 11991227 | 126 | KFDSFVAAFTEALRI | 15 | 3324.1559 |
| Kentucky blue grass | 4545 | Poa p 5 | Q9FPR0 | 11991227 | 131 | VAAFTEALRIIAGVL | 15 | 3324.1576 |
| Kentucky blue grass | 4545 | Poa p 5 | Q9FPR0 | 11991227 | 136 | EALRIIAGVLKVHAV | 15 | 3324.1566 |
| Kentucky blue grass | 4545 | Poa p 5 | Q9FPR0 | 11991227 | 141 | IAGVLKVHAVKPITE | 15 | 3324.1581 |
| Kentucky blue grass | 4545 | Poa p 5 | Q9FPR0 | 11991227 | 171 | DKIDAAFKVAATAAN | 15 | 3324.1569 |
| Kentucky blue grass | 4545 | Poa p 5 | Q9FPR0 | 11991227 | 176 | AFKVAATANAAPAN | 15 | 3324.1578 |
| Kentucky blue grass | 4545 | Poa p 5 | Q9FPR0 | 11991227 | 191 | DKFTVFEAAFNNAIK | 15 | 3324.1562 |
| Kentucky blue grass | 4545 | Poa p 5 | Q9FPR0 | 11991227 | 196 | FEAAFNNAIKESTGG | 15 | 3324.1574 |
| Kentucky blue grass | 4545 | Poa p 5 | Q9FPR0 | 11991227 | 206 | ESTGGAYDTYKSIPS | 15 | 3324.1583 |
| Kentucky blue grass | 4545 | Poa p 5 | Q9FPR0 | 11991227 | 211 | AYDTYKSIPSLEAAV | 15 | 3324.1579 |
| Kentucky blue grass | 4545 | Poa p 5 | Q9FPR0 | 11991227 | 221 | LEAAVKQAYAATIAA | 15 | 3324.1564 |
| Kentucky blue grass | 4545 | Poa p 5 | Q9FPR0 | 11991227 | 226 | KQAYAATIAAAPEVK | 15 | 3324.1582 |
| Kentucky blue grass | 4545 | Poa p 5 | Q9FPR0 | 11991227 | 236 | APEVKFAVFKAALTK | 15 | 3324.1567 |
| Kentucky blue grass | 4545 | Poa p 5 | Q9FPR0 | 11991227 | 241 | FAVFKAALTKAITAM | 15 | 3324.1563 |
| Kentucky blue grass | 4545 | Poa p 5 | Q9FPR0 | 11991227 | 246 | AALTKAITAMAEVQK | 15 | 3324.1577 |
| Mugwort | 4220 | Art v 1 | Q842X5 | 27818335 | 1 | MAKCSYVFCAVLLIF | 15 | 3324.0106 |
| Mugwort | 4220 | Art v 1 | Q842X5 | 27818335 | 6 | YVFCAVLLIFIVAIG | 15 | 3324.0104 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Mugwort | 4220 | Art v 1 | Q842X5 | 27818335 | 11 | VLLIFIVAIGEMEAA | 15 | 3324.0105 |
| Mugwort | 4220 | Art v 1 | Q842X5 | 27818335 | 31 | EKTSKTYSGKCDNKK | 15 | 3337.0009 |
| Mugwort | 4220 | Art v 1 | Q842X5 | 27818335 | 71 | CFCYFDCSKSPPGAT | 15 | 3337.0010 |
| Mugwort | 4220 | Art v 2 | A6GVD5 | 148887203 | 1 | MGHIGNFWLVLAISF | 15 | 3324.0109 |
| Mugwort | 4220 | Art v 2 | A6GVD5 | 148887203 | 6 | NFWLVLAISFAILHL | 15 | 3324.0107 |
| Mugwort | 4220 | Art v 2 | A6GVD5 | 148887203 | 11 | LAISFAILHLSHAHE | 15 | 3324.0108 |
| Mugwort | 4220 | Art v 2 | A6GVD5 | 148887203 | 86 | AQGAINGSMAVQLWL | 15 | 3324.0111 |
| Mugwort | 4220 | Art v 2 | A6GVD5 | 148887203 | 121 | TQIVWANSERVGCGR | 15 | 3337.0011 |
| Mugwort | 4220 | Art v 2 | A6GVD5 | 148887203 | 141 | GWAYIIVCNYDPPGN | 15 | 3324.0110 |
| Mugwort | 4220 | Art v 3 | C4MGH1 | 189544590 | 1 | MAIKMMKVFCIMVVC | 15 | 3324.0112 |
| Mugwort | 4220 | Art v 3 | C4MGH1 | 189544590 | 6 | MKVFCIMVVCMVVST | 15 | 3324.0116 |
| Mugwort | 4220 | Art v 3 | C4MGH1 | 189544590 | 11 | IMVVCMVVSTSYAES | 15 | 3324.0114 |
| Mugwort | 4220 | Art v 3 | C4MGH1 | 189544590 | 16 | MVVSTSYAESALTCS | 15 | 3324.0117 |
| Mugwort | 4220 | Art v 3 | C4MGH1 | 189544590 | 76 | CLKASFKSNKDLKSD | 15 | 3337.0012 |
| Mugwort | 4220 | Art v 3 | C4MGH1 | 189544590 | 81 | FKSNKDLKSDFAVPL | 15 | 3324.0115 |
| Mugwort | 4220 | Art v 3 | C4MGH1 | 189544590 | 86 | DLKSDFAVPLPSKCG | 15 | 3324.0113 |
| Mugwort | 4220 | Arty 4 | Q8H2C8 | 73621416 | 16 | EGTQQHLTAAAILGL | 15 | 3324.0119 |
| Mugwort | 4220 | Arty 4 | Q8H2C8 | 73621416 | 51 | GIINEFNEVGTLAPT | 15 | 3337.0013 |
| Mugwort | 4220 | Arty 4 | Q8H2C8 | 73621416 | 66 | GLFLGGAKYMVLQGE | 15 | 3324.0120 |
| Mugwort | 4220 | Arty 4 | Q8H2C8 | 73621416 | 71 | GAKYMVLQGEAGAVI | 15 | 3324.0118 |
| Orchard grass | 4509 | Dac g 1 | Q7XAX7 | 18093991 | 6 | SSVLLVVALFAVFLG | 15 | 3324.0653 |
| Orchard grass | 4509 | Dac g 1 | Q7XAX7 | 18093991 | 11 | VVALFAVFLGSAHGI | 15 | 3324.0654 |
| Orchard grass | 4509 | Dac g 1 | Q7XAX7 | 18093991 | 121 | EEPIAPYHFDLSGHA | 15 | 3324.0656 |
| Orchard grass | 4509 | Dac g 1 | Q7XAX7 | 18093991 | 181 | PNYLALLVKYVDGDG | 15 | 3324.0655 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Orchard grass | 4509 | Dac g 1 | Q7XAX7 | 18093991 | 211 | IALKESWGAIWRVDT | 15 | 3337.0022 |
| Orchard grass | 4509 | Dac g 2 | Q41183 | 255657 | 11 | GSDEKNLALSIKYNK | 15 | 3324.0657 |
| Orchard grass | 4509 | Dac g 2 | Q41183 | 255657 | 16 | NLALSIKYNKEGDSM | 15 | 3324.0658 |
| Orchard grass | 4509 | Dac g 2 | Q41183 | 255657 | 21 | IKYNKEGDSMAEVEL | 15 | 3337.0023 |
| Orchard grass | 4509 | Dac g 3 | P93124 | 14423759 | 51 | LWEVKSSKPLTGPFN | 15 | 3337.0024 |
| Orchard grass | 4509 | Dac g 3 | P93124 | 14423759 | 76 | NVFDEVIPTAFKIGT | 15 | 3324.0659 |
| Orchard grass | 4509 | Dac g 3 | P93124 | 14423759 | 82 | IPTAFKIGTTYTPEE | 15 | 3324.0660 |
| Orchard grass | 4509 | Dac g 4 | P82946 | 32363463 | 1 | DIYNYMEPYVSKVDP | 15 | 3324.0663 |
| Orchard grass | 4509 | Dac g 4 | P82946 | 32363463 | 26 | TAWDSGAQLGELSY | 15 | 3337.0025 |
| Orchard grass | 4509 | Dac g 4 | P82946 | 32363463 | 36 | GELSYGVLFNIQYVN | 15 | 3324.0662 |
| Orchard grass | 4509 | Dac g 4 | P82946 | 32363463 | 41 | GVLFNIQYVNYWFAP | 15 | 3324.0661 |
| Penicillium chrysogenum | 5076 | Pen ch 13 | Q9URR2 | 6684758 | 1 | MGFLKVLATSLATLA | 15 | 3324.1295 |
| Penicillium chrysogenum | 5076 | Pen ch 13 | Q9URR2 | 6684758 | 6 | VLATSLATLAVVDAG | 15 | 3324.1300 |
| Penicillium chrysogenum | 5076 | Pen ch 13 | Q9URR2 | 6684758 | 26 | SNTDAVIPSSYIVVM | 15 | 3324.1309 |
| Penicillium chrysogenum | 5076 | Pen ch 13 | Q9URR2 | 6684758 | 31 | VIPSSYIVVMNDDVS | 15 | 3324.1310 |
| Penicillium chrysogenum | 5076 | Pen ch 13 | Q9URR2 | 6684758 | 36 | YIVVMNDDVSTAEFS | 15 | 3324.1311 |
| Penicillium chrysogenum | 5076 | Pen ch 13 | Q9URR2 | 6684758 | 101 | PAVKYIEPDMIVNAT | 15 | 3324.1304 |
| Penicillium chrysogenum | 5076 | Pen ch 13 | Q9URR2 | 6684758 | 106 | IEPDMIVNATANVVQ | 15 | 3324.1298 |
| Penicillium chrysogenum | 5076 | Pen ch 13 | Q9URR2 | 6684758 | 111 | IVNATANVVQSNVPS | 15 | 3324.1306 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Penicillium chrysogenurn | 5076 | Pen ch 13 | Q9URR2 | 6684758 | 126 | WGLARISSKRTGTTS | 15 | 3324.1312 |
| Penicillium chrysogenurn | 5076 | Pen ch 13 | Q9URR2 | 6684758 | 201 | YGVAKKATLVAVKVL | 15 | 3324.1305 |
| Penicillium chrysogenurn | 5076 | Pen ch 13 | Q9URR2 | 6684758 | 206 | KATLVAVKVLGADGS | 15 | 3324.1307 |
| Penicillium chrysogenurn | 5076 | Pen ch 13 | Q9URR2 | 6684758 | 261 | NDAAANVVKSGIFLS | 15 | 3324.1308 |
| Penicillium chrysogenurn | 5076 | Pen ch 13 | Q9URR2 | 6684758 | 266 | NVVKSGIFLSVAAGN | 15 | 3324.1299 |
| Penicillium chrysogenurn | 5076 | Pen ch 13 | Q9URR2 | 6684758 | 271 | GIFLSVAAGNEAENA | 15 | 3324.1303 |
| Penicillium chrysogenurn | 5076 | Pen ch 13 | Q9URR2 | 6684758 | 346 | APHVAGVAAYLMALE | 15 | 3324.1296 |
| Penicillium chrysogenurn | 5076 | Pen ch 13 | Q9URR2 | 6684758 | 351 | GVAAYLMALEGVSAG | 15 | 3324.1297 |
| Penicillium chrysogenurn | 5076 | Pen ch 13 | Q9URR2 | 6684758 | 366 | NACARIVQLATSSIS | 15 | 3324.1301 |
| Penicillium chrysogenurn | 5076 | Pen ch 13 | Q9URR2 | 6684758 | 371 | IVQLATSSISRAPSG | 15 | 3324.1302 |
| Penicillium chrysogenurn | 5076 | Pen ch 18 | Q9P8G3 | 7963902 | 1 | MKGFLSLTLLPLLVA | 15 | 3324.1314 |
| Penicillium chrysogenurn | 5076 | Pen ch 18 | Q9P8G3 | 7963902 | 6 | SLTLLPLLVAASPVA | 15 | 3324.1315 |
| Penicillium chrysogenurn | 5076 | Pen ch 18 | Q9P8G3 | 7963902 | 11 | PLLVAASPVAVNSIH | 15 | 3324.1319 |
| Penicillium chrysogenurn | 5076 | Pen ch 18 | Q9P8G3 | 7963902 | 26 | NDAAPILSSMTSKDI | 15 | 3324.1332 |
| Penicillium chrysogenurn | 5076 | Pen ch 18 | Q9P8G3 | 7963902 | 81 | SLFGFDFEAFMGLKH | 15 | 3324.1316 |
| Penicillium chrysogenurn | 5076 | Pen ch 18 | Q9P8G3 | 7963902 | 91 | MGLKHTFHIAGSLLG | 15 | 3324.1318 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Penicillium chrysogenum | 5076 | Pen ch 18 | Q9P8G3 | 7963902 | 96 | TFHIAGSLLGYAGHF | 15 | 3324.1323 |
| Penicillium chrysogenum | 5076 | Pen ch 18 | Q9P8G3 | 7963902 | 176 | VDAYVIDTGANVKHV | 15 | 3324.1327 |
| Penicillium chrysogenum | 5076 | Pen ch 18 | Q9P8G3 | 7963902 | 226 | KFGVAKKANVYAVKV | 15 | 3324.1330 |
| Penicillium chrysogenum | 5076 | Pen ch 18 | Q9P8G3 | 7963902 | 236 | YAVKVLRSNGSGTMS | 15 | 3324.1320 |
| Penicillium chrysogenum | 5076 | Pen ch 18 | Q9P8G3 | 7963902 | 271 | DKKFPKGSVANMSLGG | 15 | 3324.1329 |
| Penicillium chrysogenum | 5076 | Pen ch 18 | Q9P8G3 | 7963902 | 291 | LDLAVNAAVDAGIHF | 15 | 3324.1331 |
| Penicillium chrysogenum | 5076 | Pen ch 18 | Q9P8G3 | 7963902 | 301 | AGIHFAVAAGNDNAD | 15 | 3324.1324 |
| Penicillium chrysogenum | 5076 | Pen ch 18 | Q9P8G3 | 7963902 | 351 | IFAPGLNILSTWVGS | 15 | 3324.1325 |
| Penicillium chrysogenum | 5076 | Pen ch 18 | Q9P8G3 | 7963902 | 376 | SMASPHIAGLLAYYV | 15 | 3324.1321 |
| Penicillium chrysogenum | 5076 | Pen ch 18 | Q9P8G3 | 7963902 | 381 | HIAGLLAYYVSLAPA | 15 | 3324.1313 |
| Penicillium chrysogenum | 5076 | Pen ch 18 | Q9P8G3 | 7963902 | 406 | TPKQLKAALISVATE | 15 | 3324.1317 |
| Penicillium chrysogenum | 5076 | Pen ch 18 | Q9P8G3 | 7963902 | 411 | KAALISVATEGTLTD | 15 | 3324.1326 |
| Penicillium chrysogenum | 5076 | Pen ch 18 | Q9P8G3 | 7963902 | 466 | IGIIIDSAEKAFHKE | 15 | 3324.1322 |
| Penicillium chrysogenum | 5076 | Pen ch 18 | Q9P8G3 | 7963902 | 476 | AFHKELGAIYSEIKD | 15 | 3324.1328 |
| Prickly juniper | 69008 | Jun o 4 | O64943 | 5391446 | 46 | ELADILRSLGSDVGE | 15 | 3324.1129 |
| Prickly juniper | 69008 | Jun o 4 | O64943 | 5391446 | 76 | GYVSLQEFVDLNNKG | 15 | 3324.1131 |
| Prickly juniper | 69008 | Jun o 4 | O64943 | 5391446 | 146 | LISVEEFQTMMTSEM | 15 | 3324.1130 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Russian thistle | 151250 | Sal k 11 | Q17ST3 | 59895730 | 81 | EKVKIERLHPYITLY | 15 | 3324.1599 |
| Russian thistle | 151250 | Sal k 11 | Q17ST3 | 59895730 | 86 | ERLHPYITLYGIDPK | 15 | 3324.1597 |
| Russian thistle | 151250 | Sal k 11 | Q17ST3 | 59895730 | 101 | NRPTITFAGTAAEFG | 15 | 3324.1595 |
| Russian thistle | 151250 | Sal k 11 | Q17ST3 | 59895730 | 111 | AAEFGTVDSATLIVE | 15 | 3324.1596 |
| Russian thistle | 151250 | Sal k 11 | Q17ST3 | 59895730 | 126 | SDYFVGANLIVSNSA | 15 | 3324.1594 |
| Russian thistle | 151250 | Sal k 11 | Q17ST3 | 59895730 | 131 | GANLIVSNSAPRPDG | 15 | 3324.1601 |
| Russian thistle | 151250 | Sal k 11 | Q17ST3 | 59895730 | 191 | EGTVDFIFGEARSLY | 15 | 3324.1590 |
| Russian thistle | 151250 | Sal k 11 | Q17ST3 | 59895730 | 196 | FIFGEARSLYLNTEL | 15 | 3324.1591 |
| Russian thistle | 151250 | Sal k 11 | Q17ST3 | 59895730 | 251 | LGRAWFEAARVVFSY | 15 | 3324.1592 |
| Russian thistle | 151250 | Sal k 11 | Q17ST3 | 59895730 | 256 | FEAARVVFSYCNLSD | 15 | 3324.1593 |
| Russian thistle | 151250 | Sal k 11 | Q17ST3 | 59895730 | 316 | ADAKTFTSLEYIEAA | 15 | 3324.1598 |
| Russian thistle | 151250 | Sal k 11 | Q17ST3 | 59895730 | 321 | FTSLEYIEAAKWLLP | 15 | 3324.1589 |
| Russian thistle | 151250 | Sal k 11 | Q17ST3 | 59895730 | 325 | EYIEAAKWLLPPPKV | 15 | 3324.1600 |
| Russian thistle | 151250 | Sal k 12 | P83181 | 25090947 | 11 | RTIFFDAYLGTSYVI | 15 | 3324.1602 |
| Russian thistle | 151250 | Sal k 12 | P83181 | 25090947 | 16 | DAYLGTSYVIVIKEP | 15 | 3324.1603 |
| Russian thistle | 151250 | Sal k 12 | P83181 | 25090947 | 21 | TSYVIVIKEPAEEFT | 15 | 3324.1604 |
| Russian thistle | 151250 | Sal k 12 | P83181 | 25090947 | 28 | KEPAEEFTTISDAVK | 15 | 3337.0045 |
| Russian thistle | 151250 | Sal k 2 | Q8L5K9 | 22726221 | 56 | ISYRVYTLKEIEVGT | 15 | 3324.1617 |
| Russian thistle | 151250 | Sal k 2 | Q8L5K9 | 22726221 | 66 | IEVGTDYFSSSLKIG | 15 | 3324.1616 |
| Russian thistle | 151250 | Sal k 2 | Q8L5K9 | 22726221 | 86 | PVYRAMLQHTPVAIK | 15 | 3324.1610 |
| Russian thistle | 151250 | Sal k 2 | Q8L5K9 | 22726221 | 96 | PVAIKVLRPNVSQGL | 15 | 3324.1615 |
| Russian thistle | 151250 | Sal k 2 | Q8L5K9 | 22726221 | 141 | LVYEYMENGSLEDRL | 15 | 3324.1614 |
| Russian thistle | 151250 | Sal k 2 | Q8L5K9 | 22726221 | 151 | LEDRLFRKNNSPPIP | 15 | 3324.1620 |
| Russian thistle | 151250 | Sal k 2 | Q8L5K9 | 22726221 | 166 | WKLRFKIAAEIAIAL | 15 | 3324.1607 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Russian thistle | 151250 | Sal k 2 | Q8L5K9 | 22726221 | 171 | KIAEIAIALLFLRD | 15 | 3324.1606 |
| Russian thistle | 151250 | Sal k 2 | Q8L5K9 | 22726221 | 176 | IAIALLFLRDAKPEP | 15 | 3324.1608 |
| Russian thistle | 151250 | Sal k 2 | Q8L5K9 | 22726221 | 201 | ILLDGNYISKIADVG | 15 | 3324.1612 |
| Russian thistle | 151250 | Sal k 2 | Q8L5K9 | 22726221 | 211 | IADVGLARLVPPTVA | 15 | 3324.1619 |
| Russian thistle | 151250 | Sal k 2 | Q8L5K9 | 22726221 | 256 | KSDIYSFGIILLQLL | 15 | 3324.1605 |
| Russian thistle | 151250 | Sal k 2 | Q8L5K9 | 22726221 | 261 | SFGIILLQLLTARPP | 15 | 3324.1609 |
| Russian thistle | 151250 | Sal k 2 | Q8L5K9 | 22726221 | 266 | LLQLLTARPPMALSY | 15 | 3324.1613 |
| Russian thistle | 151250 | Sal k 2 | Q8L5K9 | 22726221 | 301 | DWPVQEALSLAQLAL | 15 | 3324.1611 |
| Russian thistle | 151250 | Sal k 2 | Q8L5K9 | 22726221 | 306 | EALSLAQLALKCCEG | 15 | 3324.1618 |
| Russian thistle | 151250 | Sal k 3 | C1KEU0 | 225810599 | 51 | DAGIKYIPSNTFAYY | 15 | 3324.1622 |
| Russian thistle | 151250 | Sal k 3 | C1KEU0 | 225810599 | 56 | YIPSNTFAYYDQVLD | 15 | 3324.1667 |
| Russian thistle | 151250 | Sal k 3 | C1KEU0 | 225810599 | 86 | GGEIGFDLYFSMARG | 15 | 3324.1642 |
| Russian thistle | 151250 | Sal k 3 | C1KEU0 | 225810599 | 91 | FDLYFSMARGNASLP | 15 | 3324.1653 |
| Russian thistle | 151250 | Sal k 3 | C1KEU0 | 225810599 | 111 | KWFDTNYHYIVPELG | 15 | 3324.1654 |
| Russian thistle | 151250 | Sal k 3 | C1KEU0 | 225810599 | 126 | PEVKFAYSSHKAVDE | 15 | 3324.1644 |
| Russian thistle | 151250 | Sal k 3 | C1KEU0 | 225810599 | 136 | KAVDEYKEAKALGVD | 15 | 3324.1662 |
| Russian thistle | 151250 | Sal k 3 | C1KEU0 | 225810599 | 156 | VGPVSYLLLSKAAKG | 15 | 3324.1651 |
| Russian thistle | 151250 | Sal k 3 | C1KEU0 | 225810599 | 161 | YLLLSKAAKGVEKSF | 15 | 3324.1659 |
| Russian thistle | 151250 | Sal k 3 | C1KEU0 | 225810599 | 166 | KAAKGVEKSFPLLSL | 15 | 3324.1643 |
| Russian thistle | 151250 | Sal k 3 | C1KEU0 | 225810599 | 171 | VEKSFPLLSLLPKIL | 15 | 3324.1631 |
| Russian thistle | 151250 | Sal k 3 | C1KEU0 | 225810599 | 176 | PLLSLLPKILPVYKE | 15 | 3324.1645 |
| Russian thistle | 151250 | Sal k 3 | C1KEU0 | 225810599 | 186 | PVYKEVIAELKAAGA | 15 | 3324.1634 |
| Russian thistle | 151250 | Sal k 3 | C1KEU0 | 225810599 | 191 | VIAELKAAGASTIQF | 15 | 3324.1632 |
| Russian thistle | 151250 | Sal k 3 | C1KEU0 | 225810599 | 231 | STLSGLNVLVETYFA | 15 | 3324.1664 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Russian thistle | 151250 | Sal k 3 | C1KEU0 | 225810599 | 236 | LNVLVETYFADLTPE | 15 | 3324.1655 |
| Russian thistle | 151250 | Sal k 3 | C1KEU0 | 225810599 | 241 | ETYFADLTPEAYKTL | 15 | 3324.1641 |
| Russian thistle | 151250 | Sal k 3 | C1KEU0 | 225810599 | 251 | AYKTLVSLNGVTAFG | 15 | 3324.1652 |
| Russian thistle | 151250 | Sal k 3 | C1KEU0 | 225810599 | 261 | VTAFGFDLVRGTKTL | 15 | 3324.1640 |
| Russian thistle | 151250 | Sal k 3 | C1KEU0 | 225810599 | 281 | GFPSGKYLFAGVVDG | 15 | 3324.1648 |
| Russian thistle | 151250 | Sal k 3 | C1KEU0 | 225810599 | 296 | RNIWANDLAASLATL | 15 | 3324.1638 |
| Russian thistle | 151250 | Sal k 3 | C1KEU0 | 225810599 | 301 | NDLAASLATLQSLES | 15 | 3324.1628 |
| Russian thistle | 151250 | Sal k 3 | C1KEU0 | 225810599 | 306 | SLATLQSLESIVGKD | 15 | 3324.1647 |
| Russian thistle | 151250 | Sal k 3 | C1KEU0 | 225810599 | 341 | TKLDDEIKSWLAFAA | 15 | 3324.1630 |
| Russian thistle | 151250 | Sal k 3 | C1KEU0 | 225810599 | 346 | EIKSWLAFAAQKVLE | 15 | 3324.1621 |
| Russian thistle | 151250 | Sal k 3 | C1KEU0 | 225810599 | 351 | LAFAAQKVLEVNALA | 15 | 3324.1623 |
| Russian thistle | 151250 | Sal k 3 | C1KEU0 | 225810599 | 356 | QKVLEVNALAKALAG | 15 | 3324.1657 |
| Russian thistle | 151250 | Sal k 3 | C1KEU0 | 225810599 | 371 | QKDEAFFSANAAALA | 15 | 3324.1624 |
| Russian thistle | 151250 | Sal k 3 | C1KEU0 | 225810599 | 376 | FFSANAAALASRKSS | 15 | 3324.1636 |
| Russian thistle | 151250 | Sal k 3 | C1KEU0 | 225810599 | 461 | EEYVKAIKEEISKVV | 15 | 3324.1627 |
| Russian thistle | 151250 | Sal k 3 | C1KEU0 | 225810599 | 471 | ISKVVKLQEELDIDV | 15 | 3324.1661 |
| Russian thistle | 151250 | Sal k 3 | C1KEU0 | 225810599 | 496 | MVEYFGEQLSGFAFT | 15 | 3324.1639 |
| Russian thistle | 151250 | Sal k 3 | C1KEU0 | 225810599 | 536 | KAMTVFWSSLAQSMT | 15 | 3324.1633 |
| Russian thistle | 151250 | Sal k 3 | C1KEU0 | 225810599 | 551 | SRPMKGMLTGPVTIL | 15 | 3324.1663 |
| Russian thistle | 151250 | Sal k 3 | C1KEU0 | 225810599 | 561 | PVTILNWSFVRNDQP | 15 | 3324.1646 |
| Russian thistle | 151250 | Sal k 3 | C1KEU0 | 225810599 | 576 | RHETCYQIALAIEDE | 15 | 3324.1629 |
| Russian thistle | 151250 | Sal k 3 | C1KEU0 | 225810599 | 596 | KAGINVIQIDEAALR | 15 | 3324.1650 |
| Russian thistle | 151250 | Sal k 3 | C1KEU0 | 225810599 | 601 | VIQIDEAALREGLPL | 15 | 3324.1665 |
| Russian thistle | 151250 | Sal k 3 | C1KEU0 | 225810599 | 621 | GFYLQWAVHSFRITN | 15 | 3324.1625 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Russian thistle | 151250 | Sal k 3 | C1KEU0 | 225810599 | 626 | WAVHSFRITNVGIQD | 15 | 3324.1635 |
| Russian thistle | 151250 | Sal k 3 | C1KEU0 | 225810599 | 651 | SNFNDIIHSIIDMDA | 15 | 3324.1658 |
| Russian thistle | 151250 | Sal k 3 | C1KEU0 | 225810599 | 661 | IDMDADVITIENSRS | 15 | 3324.1649 |
| Russian thistle | 151250 | Sal k 3 | C1KEU0 | 225810599 | 666 | DVITIENSRSDEKLL | 15 | 3324.1660 |
| Russian thistle | 151250 | Sal k 3 | C1KEU0 | 225810599 | 711 | LADRIRKMLAVLESN | 15 | 3324.1637 |
| Russian thistle | 151250 | Sal k 3 | C1KEU0 | 225810599 | 716 | RKMLAVLESNVLWVN | 15 | 3324.1626 |
| Russian thistle | 151250 | Sal k 3 | C1KEU0 | 225810599 | 741 | NEVNPALSNMVYAAK | 15 | 3324.1656 |
| Russian thistle | 151250 | Sal k 3 | C1KEU0 | 225810599 | 743 | VNPALSNMVYAAKPI | 15 | 3324.1666 |
| Russian thistle | 151250 | Sal k 4 | C6JWH0 | 239916566 | 16 | EGTNNHLTAAAILGV | 15 | 3324.1669 |
| Russian thistle | 151250 | Sal k 4 | C6JWH0 | 239916566 | 71 | GTKYMVIQGEAGQVI | 15 | 3324.1668 |
| Russian thistle | 151250 | Sal k 4 | C6JWH0 | 239916566 | 101 | QALIFGIYDEPVTPG | 15 | 3337.0046 |
| Rye grass | 4522 | Lol p 1 | P14946 | 126385 | 1 | MASSSSVLLVVALFA | 15 | 3324.1133 |
| Rye grass | 4522 | Lol p 1 | P14946 | 126385 | 6 | SVLLVVALFAVFLGS | 15 | 3324.1132 |
| Rye grass | 4522 | Lol p 1 | P14946 | 126385 | 11 | VALFAVFLGSAHGIA | 15 | 3324.1134 |
| Rye grass | 4522 | Lol p 1 | P14946 | 126385 | 121 | EPIAPYHFDLSGHAF | 15 | 3337.0028 |
| Rye grass | 4522 | Lol p 1 | P14946 | 126385 | 176 | KASNPNYLAILVKYV | 15 | 3324.1135 |
| Rye grass | 4522 | Lol p 1 | P14946 | 126385 | 181 | NYLAILVKYVDGDGD | 15 | 3324.1136 |
| Rye grass | 4522 | Lol p 11 | Q7M1X5 | 47605808 | 106 | KQQGIRYANPIAFFR | 15 | 3324.1137 |
| Rye grass | 4522 | Lol p 11 | Q7M1X5 | 47605808 | 111 | RYANPIAFFRKEPLK | 15 | 3324.1138 |
| Rye grass | 4522 | Lol p 11 | Q7M1X5 | 47605808 | 116 | IAFFRKEPLKECGGI | 15 | 3337.0029 |
| Rye grass | 4522 | Lol p 2 | P14947 | 126386 | 51 | DGVWEIKSDKPLKGP | 15 | 3324.1139 |
| Rye grass | 4522 | Lol p 2 | P14947 | 126386 | 56 | IKSDKPLKGPFNFRF | 15 | 3324.1140 |
| Rye grass | 4522 | Lol p 2 | P14947 | 126386 | 76 | MRNVFDDVVPADFKV | 15 | 3337.0030 |
| Rye grass | 4522 | Lol p 3 | P14948 | 126387 | 11 | SDAKTLVLNIKYTRP | 15 | 3324.1142 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Rye grass | 4522 | Lol p 3 | P14948 | 126387 | 51 | LWEVKSAKPLTGPMN | 15 | 3337.0031 |
| Rye grass | 4522 | Lol p 3 | P14948 | 126387 | 76 | NVFDEVIPTAFTVGK | 15 | 3324.1141 |
| Rye grass | 4522 | Lol p 4 | Q5TIW3 | 55859464 | 21 | YEGLSYRSLQPENFA | 15 | 3324.1161 |
| Rye grass | 4522 | Lol p 4 | Q5TIW3 | 55859464 | 31 | PENFAVVDLNQMRAV | 15 | 3324.1159 |
| Rye grass | 4522 | Lol p 4 | Q5TIW3 | 55859464 | 36 | VVDLNQMRAVLVDGK | 15 | 3324.1160 |
| Rye grass | 4522 | Lol p 4 | Q5TIW3 | 55859464 | 61 | QLGELYYAISKYSRT | 15 | 3324.1146 |
| Rye grass | 4522 | Lol p 4 | Q5TIW3 | 55859464 | 66 | YYAISKYSRTLAPPA | 15 | 3324.1147 |
| Rye grass | 4522 | Lol p 4 | Q5TIW3 | 55859464 | 71 | KYSRTLAPPAGVCPT | 15 | 3324.1164 |
| Rye grass | 4522 | Lol p 4 | Q5TIW3 | 55859464 | 96 | GFGMLLRKYGIAAEN | 15 | 3324.1157 |
| Rye grass | 4522 | Lol p 4 | Q5TIW3 | 55859464 | 101 | LRKYGIAAENVIDVK | 15 | 3324.1145 |
| Rye grass | 4522 | Lol p 4 | Q5TIW3 | 55859464 | 141 | GGESFGIVVSWQVKL | 15 | 3324.1153 |
| Rye grass | 4522 | Lol p 4 | Q5TIW3 | 55859464 | 146 | GIVVSWQVKLLPVPP | 15 | 3324.1156 |
| Rye grass | 4522 | Lol p 4 | Q5TIW3 | 55859464 | 176 | VDIINKWQLVAPQLP | 15 | 3324.1143 |
| Rye grass | 4522 | Lol p 4 | Q5TIW3 | 55859464 | 191 | ADLMRIIAMGPKAT | 15 | 3324.1155 |
| Rye grass | 4522 | Lol p 4 | Q5TIW3 | 55859464 | 236 | NEMSWIESIPFVHLG | 15 | 3324.1151 |
| Rye grass | 4522 | Lol p 4 | Q5TIW3 | 55859464 | 261 | NRNNTFKPFAEYKSD | 15 | 3324.1158 |
| Rye grass | 4522 | Lol p 4 | Q5TIW3 | 55859464 | 266 | FKPFAEYKSDYVYEP | 15 | 3324.1148 |
| Rye grass | 4522 | Lol p 4 | Q5TIW3 | 55859464 | 271 | EYKSDYVYEPFPKSV | 15 | 3324.1162 |
| Rye grass | 4522 | Lol p 4 | Q5TIW3 | 55859464 | 301 | IMIFDPYGATISATP | 15 | 3324.1149 |
| Rye grass | 4522 | Lol p 4 | Q5TIW3 | 55859464 | 321 | FPHRKGVLFNIQYVN | 15 | 3324.1152 |
| Rye grass | 4522 | Lol p 4 | Q5TIW3 | 55859464 | 326 | GVLFNIQYVNYWFAP | 15 | 3324.1144 |
| Rye grass | 4522 | Lol p 4 | Q5TIW3 | 55859464 | 331 | IQYVNYWFAPGAGAA | 15 | 3324.1150 |
| Rye grass | 4522 | Lol p 4 | Q5TIW3 | 55859464 | 351 | KEIYNYMEPYVSKNP | 15 | 3324.1154 |
| Rye grass | 4522 | Lol p 4 | Q5TIW3 | 55859464 | 396 | GQKYFKGNFERLAIT | 15 | 3324.1163 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Rye grass | 4522 | Lol p 51 | Q40237 | 2498582 | 1 | MAVQKHTVALFLAVA | 15 | 3324.1172 |
| Rye grass | 4522 | Lol p 51 | Q40237 | 2498582 | 6 | HTVALFLAVALVAGP | 15 | 3324.1166 |
| Rye grass | 4522 | Lol p 51 | Q40237 | 2498582 | 11 | FLAVALVAGPAASYA | 15 | 3324.1170 |
| Rye grass | 4522 | Lol p 51 | Q40237 | 2498582 | 71 | LIEKINAGFKAAVAA | 15 | 3324.1175 |
| Rye grass | 4522 | Lol p 51 | Q40237 | 2498582 | 76 | NAGFKAAVAAAAVVP | 15 | 3324.1168 |
| Rye grass | 4522 | Lol p 51 | Q40237 | 2498582 | 96 | KTFVETFGTATNKAF | 15 | 3324.1171 |
| Rye grass | 4522 | Lol p 51 | Q40237 | 2498582 | 106 | TNKAFVEGLASGYAD | 15 | 3324.1186 |
| Rye grass | 4522 | Lol p 51 | Q40237 | 2498582 | 126 | LTSKLDAALKLAYEA | 15 | 3324.1187 |
| Rye grass | 4522 | Lol p 51 | Q40237 | 2498582 | 131 | DAALKLAYEAAQGAT | 15 | 3324.1169 |
| Rye grass | 4522 | Lol p 51 | Q40237 | 2498582 | 146 | PEAKYDAYVATLTEA | 15 | 3324.1180 |
| Rye grass | 4522 | Lol p 51 | Q40237 | 2498582 | 151 | DAYVATLTEALRVIA | 15 | 3324.1167 |
| Rye grass | 4522 | Lol p 51 | Q40237 | 2498582 | 156 | TLTEALRVIAGTLEV | 15 | 3324.1185 |
| Rye grass | 4522 | Lol p 51 | Q40237 | 2498582 | 196 | VDAAYRTAATAANAA | 15 | 3324.1181 |
| Rye grass | 4522 | Lol p 51 | Q40237 | 2498582 | 216 | FTVFENTFNNAIKVS | 15 | 3324.1179 |
| Rye grass | 4522 | Lol p 51 | Q40237 | 2498582 | 221 | NTFNNAIKVSLGAAY | 15 | 3324.1176 |
| Rye grass | 4522 | Lol p 51 | Q40237 | 2498582 | 226 | AIKVSLGAAYDSYKF | 15 | 3324.1173 |
| Rye grass | 4522 | Lol p 51 | Q40237 | 2498582 | 231 | LGAAYDSYKFIPTLV | 15 | 3324.1174 |
| Rye grass | 4522 | Lol p 51 | Q40237 | 2498582 | 236 | DSYKFIPTLVAAVKQ | 15 | 3324.1165 |
| Rye grass | 4522 | Lol p 51 | Q40237 | 2498582 | 241 | IPTLVAAVKQAYAAK | 15 | 3324.1182 |
| Rye grass | 4522 | Lol p 51 | Q40237 | 2498582 | 246 | AAVKQAYAAKQATAP | 15 | 3324.1177 |
| Rye grass | 4522 | Lol p 51 | Q40237 | 2498582 | 261 | EVKYTVSETALKKAV | 15 | 3324.1178 |
| Rye grass | 4522 | Lol p 51 | Q40237 | 2498582 | 271 | LKKAVTAMSEAEKEA | 15 | 3324.1183 |
| Rye grass | 4522 | Lol p 51 | Q40237 | 2498582 | 306 | PAAAYATATPAAATA | 15 | 3324.1184 |
| Rye grass | 4522 | Lol p 52 | Q40240 | 485371 | 1 | MAVQKYTVALFLRRG | 15 | 3324.1195 |

TABLE 5-continued

Complete list of peptides synthesized.

| Organism | Taxonomy ID | Source protein | SwissProt ID | GI number | Position | Sequence (SEQ. ID. NOs.: 1-1,411, in order of appearance) | Len. | Peptide ID |
|---|---|---|---|---|---|---|---|---|
| Rye grass | 4522 | Lol p 52 | Q40240 | 485371 | 141 | RSLRVIAGALEVHAV | 15 | 3324.1190 |
| Rye grass | 4522 | Lol p 52 | Q40240 | 485371 | 176 | DKIDAAFKIAATAAN | 15 | 3324.1192 |
| Rye grass | 4522 | Lol p 52 | Q40240 | 485371 | 181 | AFKIAATANAAPTN | 15 | 3324.1197 |
| Rye grass | 4522 | Lol p 52 | Q40240 | 485371 | 196 | DKFTVFESAFNKALN | 15 | 3324.1191 |
| Rye grass | 4522 | Lol p 52 | Q40240 | 485371 | 241 | APEVKYAVFEAALTK | 15 | 3324.1188 |
| Rye grass | 4522 | Lol p 52 | Q40240 | 485371 | 246 | YAVFEAALTKAITAM | 15 | 3324.1194 |
| Rye grass | 4522 | Lol p 52 | Q40240 | 485371 | 251 | AALTKAITAMTQAQK | 15 | 3324.1196 |
| Rye grass | 4522 | Lol p 52 | Q40240 | 485371 | 291 | LPPPLLVVQSLISLL | 15 | 3324.1193 |
| Rye grass | 4522 | Lol p 52 | Q40240 | 485371 | 294 | PLLVVQSLISLLIYY | 15 | 3324.1189 |
| Sweet vernal grass | 29661 | Ant o 1 | Q7M1X6 | 75139986 | 1 | IAKVPPGPNITATYG | 15 | 3324.0103 |
| Sweet vernal grass | 29661 | Ant o 1 | Q7M1X6 | 75139986 | 16 | DKWLDAKSTWYGKPT | 15 | 3324.0102 |
| Sweet vernal grass | 29661 | Ant o 1 | Q7M1X6 | 75139986 | 18 | WLDAKSTWYGKPTGA | 15 | 3337.0008 |
| Western ragweed | 29715 | Amb p 5 | P43174 | 1171001 | 1 | MNNEKNVSFEFIGST | 15 | 3324.0097 |
| Western ragweed | 29715 | Amb p 5 | P43174 | 1171001 | 6 | NVSFEFIGSTDEVDE | 15 | 3324.0098 |
| Western ragweed | 29715 | Amb p 5 | P43174 | 1171001 | 21 | IKLLPCAWAGNVCGE | 15 | 3337.0004 |
| Western ragweed | 29715 | Amb p 5 | P43174 | 1171001 | 63 | QKCGKMRMNVTKNTI | 15 | 3337.0005 |
| White oak | 3513 | Que a 1 | B6RQS2 | 167472849 | 11 | ASVIPPARLFKAFVL | 15 | 3324.1587 |
| White oak | 3513 | Que a 1 | B6RQS2 | 167472849 | 16 | PARLFKAFVLDSDNL | 15 | 3324.1585 |
| White oak | 3513 | Que a 1 | B6RQS2 | 167472849 | 21 | KAFVLDSDNLIPKVV | 15 | 3324.1588 |
| White oak | 3513 | Que a 1 | B6RQS2 | 167472849 | 141 | ASEVFKAVEAYLVAH | 15 | 3324.1584 |
| White oak | 3513 | Que a 1 | B6RQS2 | 167472849 | 146 | KAVEAYLVAHPDLYK | 15 | 3324.1586 |

TABLE 6

Summary of responses to allergen extracts

| Allergen | Concentration (µg/ml) | Donor | Wheal (mm) | Response to extract (SFC) IFNg | IL-5 | Total | Evaluation | Summary Tested | Positive | % Positive | |
|---|---|---|---|---|---|---|---|---|---|---|---|
| Alder | 50 | D00069 | 12 | 3407 | 667 | 4073 | + | 12 | 11 | 91.7 | |
| | | U00110 | 10 | 220 | 3 | 223 | + | | | | |
| | | U00122 | 10 | 597 | 1860 | 2457 | + | | | | Alder |
| | | U00047 | 10 | 70 | 297 | 367 | + | | | | *Alternaria* |
| | | U00046 | 10 | 1323 | 197 | 1520 | + | | | | American cockroach |
| | | U00050 | 10 | 987 | 100 | 1087 | + | | | | Ash |
| | | U00054 | 10 | 1123 | 830 | 1953 | + | | | | *Aspergillus fumigatus* |
| | | U00064 | 10 | 200 | 30 | 230 | + | | | | Bermuda |
| | | U00075 | 3 | 227 | 10 | 237 | + | | | | Birch |
| | | U00039 | 10 | 33 | 0 | 33 | − | | | | Black walnut |
| | | U00032 | 10 | 997 | 198 | 1194 | + | | | | Canary grass |
| | | U00115 | 10 | 1010 | 0 | 1010 | + | | | | Cat epithelia |
| *Alternaria* rot fungus | 2 | D00069 | 15 | 33 | 2460 | 2493 | + | 12 | 12 | 100.0 | *Cladosporium* |
| | | U00119 | 3 | 953 | 3370 | 4323 | + | | | | Cypress |
| | | U00122 | 10 | 2573 | 1310 | 3883 | + | | | | *D. farinae* |
| | | U00064 | 7 | 677 | 2280 | 2957 | + | | | | *D. pteronyssinus* |
| | | U00102 | 7 | 1197 | 1580 | 2777 | + | | | | Dog epithelia |
| | | D00095 | 9 | 1157 | 2400 | 3557 | + | | | | English plantain |
| | | U00032 | 8 | 173 | 203 | 377 | + | | | | German cockroach |
| | | U00129 | 3 | 207 | 3183 | 3390 | + | | | | Giant ragweed |
| | | D00003 | 8 | 1760 | 2913 | 4673 | + | | | | Juniper |
| | | U00075 | 8 | 540 | 2460 | 3000 | + | | | | Kentucky blue |
| | | U00097 | 5 | 2827 | 593 | 3420 | + | | | | Mugwort |
| | | D00107 | 14 | 43 | 313 | 357 | + | | | | Oak |
| Ash | 50 | D00069 | 15 | 170 | 0 | 170 | + | 14 | 11 | 78.6 | Olive |
| | | U00089 | 12 | 600 | 310 | 910 | + | | | | Orchard |
| | | D00052 | 9 | 567 | 143 | 710 | + | | | | Palm |
| | | U00058 | 3 | 0 | 0 | 0 | − | | | | Penicillium |
| | | U00109 | 20 | 1860 | 1180 | 3040 | + | | | | Russian thistle |
| | | U00122 | 12 | 1473 | 1180 | 2653 | + | | | | Rye |
| | | U00047 | 10 | 210 | 887 | 1097 | + | | | | Sweet vernal grass |
| | | U00046 | 10 | 170 | 0 | 170 | + | | | | Timothy |
| | | U00102 | 3 | 7 | 3 | 10 | − | | | | Western ragweed |
| | | D00026 | 25 | 2177 | 480 | 2657 | + | | | | Wheat |
| | | U00115 | 10 | 107 | 40 | 147 | − | | | | |
| | | D00007 | 9 | 567 | 33 | 600 | + | | | | |
| | | D00047 | 20 | 1833 | 2313 | 4147 | + | | | | |
| | | D00027 | 12 | 763 | 0 | 763 | + | | | | |
| *A. fumigatus* | 5 | U00109 | 3 | 2853 | 217 | 3070 | + | 11 | 11 | 100.0 | |
| | | U00122 | 3 | 2610 | 2250 | 4860 | + | | | | |
| | | D00045 | 8 | 1383 | 47 | 1430 | + | | | | |
| | | U00047 | 3 | 593 | 30 | 623 | + | | | | |
| | | U00050 | 3 | 1997 | 530 | 2527 | + | | | | |
| | | U00129 | 3 | 720 | 600 | 1320 | + | | | | |
| | | U00075 | 3 | 1407 | 57 | 1463 | + | | | | |
| | | U00085 | 3 | 1260 | 57 | 1317 | + | | | | |
| | | U00103 | 3 | 1250 | 63 | 1313 | + | | | | |
| | | U00113 | 3 | 3393 | 10 | 3403 | + | | | | |
| | | U00121 | 3 | 1500 | 353 | 1853 | + | | | | |
| American cockroach | 25 | U00109 | 3 | 2853 | 217 | 3070 | + | 11 | 11 | 100.0 | |
| | | U00122 | 3 | 2610 | 2250 | 4860 | + | | | | |
| | | D00045 | 8 | 1383 | 47 | 1430 | + | | | | |
| | | U00047 | 3 | 593 | 30 | 623 | + | | | | |
| | | U00050 | 3 | 1997 | 530 | 2527 | + | | | | |
| | | U00129 | 3 | 720 | 600 | 1320 | + | | | | |
| | | U00075 | 3 | 1407 | 57 | 1463 | + | | | | |
| | | U00085 | 3 | 1260 | 57 | 1317 | + | | | | |
| | | U00103 | 3 | 1250 | 63 | 1313 | + | | | | |
| | | U00113 | 3 | 3393 | 10 | 3403 | + | | | | |
| | | U00121 | 3 | 1500 | 353 | 1853 | + | | | | |
| Brermuda grass | 50 | D00070 | 11 | 2010 | 97 | 2107 | + | 11 | 11 | 100.0 | |
| | | U00089 | 15 | 2450 | 510 | 2960 | + | | | | |
| | | D00004 | 20 | 1833 | 547 | 2380 | + | | | | |
| | | D00039 | 17 | 2020 | 507 | 2527 | + | | | | |
| | | D00094 | 20 | 33 | 2100 | 2133 | + | | | | |
| | | D00102 | 13 | 213 | 1073 | 1287 | + | | | | |
| | | D00067 | 14 | 1580 | 23 | 1603 | + | | | | |
| | | U00054 | 10 | 1457 | 0 | 1457 | + | | | | |
| | | U00099 | 10 | 1380 | 603 | 1983 | + | | | | |
| | | D00042 | 17 | 973 | 23 | 997 | + | | | | |
| | | D00104 | 11 | 1620 | 30 | 1650 | + | | | | |

TABLE 6-continued

Summary of responses to allergen extracts

| Allergen | Concentration (µg/ml) | Donor | Wheal (mm) | Response to extract (SFC) | | | Evaluation | Summary | | |
|---|---|---|---|---|---|---|---|---|---|---|
| | | | | IFNg | IL-5 | Total | | Tested | Positive | % Positive |
| Birch | 50 | U00110 | 20 | 307 | 207 | 513 | + | 10 | 10 | 100.0 |
| | | U00047 | 10 | 380 | 1840 | 2220 | + | | | |
| | | D00026 | 25 | 2603 | 407 | 3010 | + | | | |
| | | U00115 | 10 | 617 | 87 | 703 | + | | | |
| | | U00103 | 7 | 2547 | 1190 | 3737 | + | | | |
| | | D00073 | 19 | 680 | 33 | 713 | + | | | |
| | | D00067 | 16 | 2690 | 387 | 3077 | + | | | |
| | | D00065 | 19 | 1083 | 97 | 1180 | + | | | |
| | | D00094 | 15 | 350 | 2710 | 3060 | + | | | |
| | | U00053 | 10 | 1580 | 327 | 1907 | + | | | |
| Black walnut | 50 | U00110 | 10 | 1410 | 1910 | 3320 | + | 10 | 10 | 100.0 |
| | | U00080 | 5 | 2233 | 2193 | 4427 | + | | | |
| | | D00094 | 17 | 793 | 1557 | 2350 | + | | | |
| | | U00115 | 5 | 1810 | 2183 | 3993 | + | | | |
| | | D00003 | 6 | 903 | 843 | 1747 | + | | | |
| | | U00075 | 8 | 163 | 2177 | 2340 | + | | | |
| | | U00092 | 5 | 2110 | 967 | 3077 | + | | | |
| | | U00097 | 6 | 2670 | 0 | 2670 | + | | | |
| | | U00072 | | 0 | 1463 | 1463 | + | | | |
| | | U00137 | 4 | 1330 | 2197 | 3527 | + | | | |
| Canary grass | 50 | D00070 | 21 | 2770 | 1183 | 3953 | + | 10 | 10 | 100.0 |
| | | U00089 | 10 | 1813 | 910 | 2723 | + | | | |
| | | U00110 | 20 | 163 | 67 | 230 | + | | | |
| | | U00099 | 20 | 2267 | 340 | 2607 | + | | | |
| | | U00106 | 18 | 677 | 1297 | 1973 | + | | | |
| | | D00004 | 35 | 1253 | 2520 | 3773 | + | | | |
| | | U00117 | 7 | 1573 | 53 | 1627 | + | | | |
| | | D00052 | 17 | 1670 | 1803 | 3473 | + | | | |
| | | D00036 | 20 | 787 | 487 | 1273 | + | | | |
| | | U00029 | 20 | 421 | 0 | 421 | + | | | |
| Cat epithelia | 50 | D00069 | 10 | 2037 | 2353 | 4390 | + | 11 | 11 | 100.0 |
| | | U00106 | 12 | 653 | 2063 | 2717 | + | | | |
| | | D00004 | 8 | 785 | 1005 | 1790 | + | | | |
| | | U00079 | 8 | 1177 | 2100 | 3277 | + | | | |
| | | D00073 | 15 | 700 | 1113 | 1813 | + | | | |
| | | U00047 | 15 | 307 | 1933 | 2240 | + | | | |
| | | U00046 | 10 | 737 | 2620 | 3357 | + | | | |
| | | U00029 | 25 | 1380 | 1363 | 2743 | + | | | |
| | | U00128 | 10 | 2220 | 2073 | 4293 | + | | | |
| | | U00126 | 8 | 440 | 320 | 760 | + | | | |
| | | U00107 | 10 | 820 | 407 | 1227 | + | | | |
| C. herbarum | 5 | U00079 | 3 | 1703 | 3917 | 5620 | + | 10 | 10 | 100.0 |
| | | U00110 | 3 | 640 | 2040 | 2680 | + | | | |
| | | U00122 | 4 | 2060 | 2640 | 4700 | + | | | |
| | | D00073 | 16 | 1297 | 990 | 2287 | + | | | |
| | | U00083 | 8 | 2270 | 53 | 2323 | + | | | |
| | | U00102 | 16 | 2207 | 387 | 2593 | + | | | |
| | | U00101 | 3 | 1760 | 1963 | 3723 | + | | | |
| | | U00128 | 3 | 2933 | 0 | 2933 | + | | | |
| | | U00129 | 3 | 1397 | 1287 | 2683 | + | | | |
| | | U00107 | 3 | 1213 | 263 | 1477 | + | | | |
| Cypress | 50 | D00052 | 5 | 977 | 797 | 1773 | + | 10 | 8 | 80.0 |
| | | U00110 | 3 | 97 | 0 | 97 | − | | | |
| | | D00026 | 20 | 2207 | 1653 | 3860 | + | | | |
| | | D00102 | 12 | 250 | 1283 | 1533 | + | | | |
| | | U00092 | 3 | 937 | 240 | 1177 | + | | | |
| | | D00008 | 9 | 30 | 2297 | 2327 | + | | | |
| | | D00107 | 10 | 1223 | 1473 | 2697 | + | | | |
| | | U00075 | 3 | 230 | 1340 | 1570 | + | | | |
| | | U00125 | 3 | 43 | 10 | 53 | − | | | |
| | | U00034 | 3 | 2827 | 247 | 3073 | + | | | |
| D. farinae | 50 | D00069 | 16 | 1303 | 30 | 1333 | + | 10 | 9 | 90.0 |
| | | U00099 | 10 | 767 | 270 | 1037 | + | | | |
| | | U00117 | 5 | 823 | 237 | 1060 | + | | | |
| | | U00110 | 10 | 207 | 0 | 207 | + | | | |
| | | U00093 | 8 | 817 | 217 | 1033 | + | | | |
| | | U00112 | 8 | 343 | 0 | 343 | + | | | |
| | | U00131 | 10 | 553 | 0 | 553 | + | | | |
| | | U00102 | 3 | 130 | 10 | 140 | − | | | |
| | | U00050 | 10 | 540 | 240 | 780 | + | | | |
| | | U00124 | 8 | 907 | 1640 | 2547 | + | | | |

TABLE 6-continued

Summary of responses to allergen extracts

| Allergen | Concentration (μg/ml) | Donor | Wheal (mm) | Response to extract (SFC) | | | Evaluation | Summary | | |
|---|---|---|---|---|---|---|---|---|---|---|
| | | | | IFNg | IL-5 | Total | | Tested | Positive | % Positive |
| D. pteronyssinus | 50 | U00117 | 6 | 2397 | 2883 | 5280 | + | 11 | 11 | 100.0 |
| | | U00093 | 10 | 1167 | 0 | 1167 | + | | | |
| | | U00112 | 8 | 217 | 0 | 217 | + | | | |
| | | U00131 | 8 | 1283 | 303 | 1587 | + | | | |
| | | D00002 | 15 | 663 | 137 | 800 | + | | | |
| | | U00050 | 12 | 1580 | 357 | 1937 | + | | | |
| | | U00102 | 5 | 267 | 40 | 307 | + | | | |
| | | U00128 | 20 | 163 | 330 | 493 | + | | | |
| | | U00023 | 10 | 860 | 2173 | 3033 | + | | | |
| | | U00124 | 8 | 2323 | 2100 | 4423 | + | | | |
| | | U00108 | 15 | 1343 | 1917 | 3260 | + | | | |
| Dog epithelia | 50 | U00079 | 3 | 283 | 47 | 330 | + | 10 | 10 | 100.0 |
| | | U00117 | 3 | 1843 | 223 | 2067 | + | | | |
| | | U00110 | 3 | 190 | 33 | 223 | + | | | |
| | | U00108 | 3 | 1150 | 400 | 1550 | + | | | |
| | | U00023 | 4 | 1460 | 817 | 2277 | + | | | |
| | | U00069 | 5 | 453 | 113 | 567 | + | | | |
| | | U00101 | 3 | 903 | 703 | 1607 | + | | | |
| | | U00129 | 3 | 2110 | 0 | 2110 | + | | | |
| | | D00107 | 10 | 297 | 1447 | 1743 | + | | | |
| | | U00075 | 3 | 1453 | 390 | 1843 | + | | | |
| English plantain | 50 | D00069 | 10 | 2547 | 2513 | 5060 | + | 10 | 8 | 80.0 |
| | | D00004 | 9 | 1650 | 1230 | 2880 | + | | | |
| | | U00110 | 8 | 60 | 13 | 73 | − | | | |
| | | D00073 | 21 | 240 | 20 | 260 | + | | | |
| | | D00094 | 19 | 1167 | 1650 | 2817 | + | | | |
| | | U00054 | 10 | 987 | 743 | 1730 | + | | | |
| | | U00075 | 3 | 657 | 530 | 1187 | + | | | |
| | | U00069 | 5 | 83 | 50 | 133 | − | | | |
| | | U00102 | 8 | 380 | 243 | 623 | + | | | |
| | | U00072 | 5 | 1467 | 733 | 2200 | + | | | |
| Giant ragweed | 50 | D00002 | 13 | 1760 | 120 | 1880 | + | 10 | 10 | 100.0 |
| | | D00094 | 20 | 173 | 793 | 967 | + | | | |
| | | U00047 | 10 | 647 | 1297 | 1943 | + | | | |
| | | D00095 | 12 | 1407 | 160 | 1567 | + | | | |
| | | D00007 | 8 | 1160 | 43 | 1203 | + | | | |
| | | D00100 | 10 | 1060 | 457 | 1517 | + | | | |
| | | D00045 | 14 | 1870 | 130 | 2000 | + | | | |
| | | D00084 | 10 | 843 | 1050 | 1893 | + | | | |
| | | D00096 | 13 | 287 | 0 | 287 | + | | | |
| | | U00054 | 8 | 687 | 17 | 703 | + | | | |
| Juniper | 20 | D00052 | 8 | 37 | 0 | 37 | − | 10 | 8 | 80.0 |
| | | D00060 | 9 | 1530 | 2413 | 3943 | + | | | |
| | | U00032 | 10 | 153 | 123 | 277 | + | | | |
| | | D00073 | 21 | 0 | 0 | 0 | − | | | |
| | | U00099 | 8 | 190 | 2147 | 2337 | + | | | |
| | | D00027 | 6 | 153 | 687 | 840 | + | | | |
| | | D00068 | 15 | 540 | 2717 | 3257 | + | | | |
| | | U00034 | 3 | 637 | 1450 | 2087 | + | | | |
| | | D00084 | 13 | 183 | 2227 | 2410 | + | | | |
| | | U00098 | 3 | 2023 | 330 | 2353 | + | | | |
| Kentucky blue grass | 50 | D00070 | 27 | 1543 | 683 | 2227 | + | 12 | 12 | 100.0 |
| | | U00089 | 12 | 2750 | 2060 | 4810 | + | | | |
| | | U00106 | 10 | 2215 | 2927 | 5142 | + | | | |
| | | D00004 | 22 | 2417 | 1813 | 4230 | + | | | |
| | | U00036 | 10 | 1553 | 2097 | 3650 | + | | | |
| | | U00102 | 20 | 773 | 2290 | 3063 | + | | | |
| | | U00032 | 25 | 1730 | 1813 | 3543 | + | | | |
| | | D00054 | 10 | 3133 | 2353 | 5487 | + | | | |
| | | U00115 | 8 | 1490 | 713 | 2203 | + | | | |
| | | U00101 | 8 | 1083 | 2297 | 3380 | + | | | |
| | | U00110 | 20 | 800 | 543 | 1343 | + | | | |
| | | U00034 | 10 | 423 | 1837 | 2260 | + | | | |
| Mugwort | 50 | U00122 | 12 | 850 | 523 | 1373 | + | 10 | 10 | 100.0 |
| | | D00061 | 17 | 2283 | 1503 | 3787 | + | | | |
| | | D00095 | 8 | 843 | 423 | 1267 | + | | | |
| | | D00007 | 17 | 1887 | 1277 | 3163 | + | | | |
| | | D00041 | 12 | 2670 | 1603 | 4273 | + | | | |
| | | D00042 | 11 | 933 | 230 | 1163 | + | | | |
| | | D00047 | 16 | 1213 | 1273 | 2487 | + | | | |
| | | U00103 | 8 | 533 | 53 | 587 | + | | | |
| | | U00118 | 6 | 2083 | 1410 | 3493 | + | | | |
| | | D00104 | 17 | 160 | 40 | 200 | + | | | |

TABLE 6-continued

Summary of responses to allergen extracts

| Allergen | Concentration (µg/ml) | Donor | Wheal (mm) | Response to extract (SFC) | | | Evaluation | Summary | | |
|---|---|---|---|---|---|---|---|---|---|---|
| | | | | IFNg | IL-5 | Total | | Tested | Positive | % Positive |
| White Oak | 25 | D00069 | 13 | 483 | 1873 | 2357 | + | 12 | 8 | 66.7 |
| | | D00004 | 13 | 540 | 587 | 1127 | + | | | |
| | | D00052 | 11 | 110 | 10 | 120 | − | | | |
| | | D00026 | 21 | 760 | 340 | 1100 | + | | | |
| | | D00078 | 15 | 153 | 320 | 473 | + | | | |
| | | U00047 | 10 | 0 | 2933 | 2933 | + | | | |
| | | U00103 | 8 | 40 | 0 | 40 | − | | | |
| | | U00115 | 8 | 23 | 0 | 23 | − | | | |
| | | D00094 | 19 | 23 | 3583 | 3607 | + | | | |
| | | U00110 | 8 | 77 | 47 | 123 | − | | | |
| | | U00072 | 5 | 1113 | 1390 | 2503 | + | | | |
| | | D00067 | 11 | 1273 | 1183 | 2457 | + | | | |
| Orchard grass | 50 | D00070 | 29 | 2107 | 350 | 2457 | + | 11 | 11 | 100.0 |
| | | U00089 | 5 | 2570 | 2253 | 4823 | + | | | |
| | | U00110 | 20 | 357 | 930 | 1287 | + | | | |
| | | U00099 | 10 | 37 | 2433 | 2470 | + | | | |
| | | U00106 | 12 | 510 | 463 | 973 | + | | | |
| | | D00004 | 25 | 1690 | 2263 | 3953 | + | | | |
| | | U00036 | 10 | 1310 | 280 | 1590 | + | | | |
| | | U00058 | 8 | 760 | 687 | 1447 | + | | | |
| | | D00042 | 18 | 1260 | 1160 | 2420 | + | | | |
| | | U00102 | 20 | 957 | 1543 | 2500 | + | | | |
| | | U00101 | 12 | 1050 | 1020 | 2070 | + | | | |
| Date Palm | 50 | D00069 | 9 | 1927 | 2517 | 4443 | + | 10 | 9 | 90.0 |
| | | U00075 | 3 | 873 | 1347 | 2220 | + | | | |
| | | U00046 | 10 | 2437 | 1597 | 4033 | + | | | |
| | | U00050 | 10 | 1040 | 1863 | 2903 | + | | | |
| | | U00054 | 10 | 1010 | 940 | 1950 | + | | | |
| | | D00045 | 24 | 2223 | 110 | 2333 | + | | | |
| | | U00110 | 10 | 43 | 20 | 63 | − | | | |
| | | U00036 | 8 | 1127 | 23 | 1150 | + | | | |
| | | D00035 | 5 | 2223 | 100 | 2323 | + | | | |
| | | D00084 | 13 | 1963 | 33 | 1997 | + | | | |
| P. chrysogenum | 5 | D00052 | 11 | 570 | 890 | 1460 | + | 10 | 10 | 100.0 |
| | | U00036 | 3 | 2363 | 237 | 2600 | + | | | |
| | | U00109 | 3 | 837 | 633 | 1470 | + | | | |
| | | U00122 | 3 | 3870 | 2423 | 6293 | + | | | |
| | | U00050 | 3 | 460 | 973 | 1433 | + | | | |
| | | U00047 | 3 | 1570 | 263 | 1833 | + | | | |
| | | U00118 | 6 | 1710 | 1363 | 3073 | + | | | |
| | | U00129 | 3 | 2183 | 1330 | 3513 | + | | | |
| | | U00132 | 3 | 2167 | 837 | 3003 | + | | | |
| | | U00137 | 3 | 1587 | 377 | 1963 | + | | | |
| Russian thistle | 50 | U00089 | 12 | 1610 | 1750 | 3360 | + | 10 | 9 | 90.0 |
| | | D00060 | 11 | 2170 | 1803 | 3973 | + | | | |
| | | U00106 | 10 | 2907 | 2493 | 5400 | + | | | |
| | | U00109 | 20 | 1310 | 3383 | 4693 | + | | | |
| | | U00047 | 10 | 220 | 1153 | 1373 | + | | | |
| | | D00047 | 24 | 1720 | 2623 | 4343 | + | | | |
| | | D00079 | 19 | 1480 | 1280 | 2760 | + | | | |
| | | U00054 | 10 | 1490 | 927 | 2417 | + | | | |
| | | U00110 | 10 | 13 | 3 | 17 | − | | | |
| | | U00118 | 14 | 1563 | 2823 | 4387 | + | | | |
| Rye grass | 50 | D00070 | 25 | 2580 | 1523 | 4103 | + | 11 | 11 | 100.0 |
| | | U00089 | 12 | 1153 | 410 | 1563 | + | | | |
| | | U00110 | 18 | 183 | 67 | 250 | + | | | |
| | | U00099 | 20 | 0 | 2307 | 2307 | + | | | |
| | | U00106 | 15 | 618 | 1786 | 2404 | + | | | |
| | | D00004 | 16 | 1107 | 1607 | 2713 | + | | | |
| | | U00117 | 4 | 253 | 87 | 340 | + | | | |
| | | U00036 | 10 | 363 | 153 | 517 | + | | | |
| | | U00054 | 15 | 943 | 403 | 1347 | + | | | |
| | | U00125 | 25 | 403 | 1007 | 1410 | + | | | |
| | | D00041 | 15 | 2060 | 423 | 2483 | + | | | |
| Sweet vernal grass | 50 | U00099 | 10 | 1943 | 2960 | 4903 | + | 15 | 14 | 93.3 |
| | | U00106 | 12 | 2443 | 1570 | 4013 | + | | | |
| | | D00004 | 26 | 1907 | 830 | 2737 | + | | | |
| | | U00079 | 7 | 30 | 23 | 53 | − | | | |
| | | D00052 | 19 | 1543 | 1673 | 3217 | + | | | |
| | | U00036 | 15 | 1313 | 1177 | 2490 | + | | | |
| | | U00058 | 12 | 1087 | 1143 | 2230 | + | | | |
| | | U00110 | 13 | 103 | 110 | 213 | + | | | |
| | | U00102 | 10 | 143 | 407 | 550 | + | | | |
| | | U00050 | 10 | 1397 | 860 | 2257 | + | | | |

TABLE 6-continued

Summary of responses to allergen extracts

| Allergen | Concentration (µg/ml) | Donor | Wheal (mm) | Response to extract (SFC) | | | Evaluation | Summary | | |
|---|---|---|---|---|---|---|---|---|---|---|
| | | | | IFNg | IL-5 | Total | | Tested | Positive | % Positive |
| Western ragweed | 50 | U00054 | 15 | 273 | 53 | 327 | + | 10 | 10 | 100.0 |
| | | U00016 | 10 | 2413 | 1483 | 3897 | + | | | |
| | | D00042 | 14 | 2090 | 1943 | 4033 | + | | | |
| | | U00101 | 12 | 1740 | 63 | 1803 | + | | | |
| | | U00075 | 20 | 1787 | 753 | 2540 | + | | | |
| | | D00070 | 23 | 1820 | 1950 | 3770 | + | | | |
| | | D00094 | 24 | 83 | 707 | 790 | + | | | |
| | | D00007 | 11 | 1137 | 493 | 1630 | + | | | |
| | | D00079 | 19 | 320 | 713 | 1033 | + | | | |
| | | D00102 | 19 | 413 | 1740 | 2153 | + | | | |
| | | D00100 | 16 | 1690 | 443 | 2133 | + | | | |
| | | U00092 | 5 | 267 | 2020 | 2287 | + | | | |
| | | D00045 | 10 | 563 | 380 | 943 | + | | | |
| | | D00084 | 20 | 83 | 80 | 163 | + | | | |
| | | U00098 | 7 | 1707 | 123 | 1830 | + | | | |
| Total | | | | | | | | 304 | 286 | 94.1 |
| Criteria of positivity: Total SFC ≥ 150 | | | | | | | | | Average: | 94.3 |

TABLE 7

Positive donor/peptide responses

| Category | Organism | Antigen | Position | Sequence (SEQ ID NOs: 1,412-1,906, in order of appearance) | Peptide ID | Region ID | Donor | Response (SFC/10^6) IFNg | IL-5 | Total |
|---|---|---|---|---|---|---|---|---|---|---|
| Fungi | Alternaria rot fungus | Alt a 1 | 6 | IASLFAAAGLAAAAP | 3324.0015 | 1.01 | U00129 | | 1830 | 1830 |
| | | Alt a 1 | 6 | IASLFAAAGLAAAAP | 3324.0015 | 1.01 | U00064 | | 93 | 93 |
| | | Alt a 1 | 11 | AAAGLAAAAPLESRQ | 3324.0017 | 1.01 | D00003 | | 87 | 87 |
| | | Alt a 1 | 11 | AAAGLAAAAPLESRQ | 3324.0017 | 1.01 | D00095 | | 1298 | 1298 |
| | | Alt a 1 | 11 | AAAGLAAAAPLESRQ | 3324.0017 | 1.01 | D00064 | | 2357 | 2357 |
| | | Alt a 1 | 111 | KVSDDITYVATATLP | 3324.0013 | 1.02 | U00122 | 197 | | 197 |
| | | Alt a 1 | 111 | KVSDDITYVATATLP | 3324.0013 | 1.02 | D00069 | | 53 | 53 |
| | | Alt a 1 | 111 | KVSDDITYVATATLP | 3324.0013 | 1.02 | D00095 | | 1468 | 1468 |
| | | Alt a 1 | 111 | KVSDDITYVATATLP | 3324.0013 | 1.02 | U00064 | | 123 | 123 |
| | | Alt a 1 | 111 | KVSDDITYVATATLP | 3324.0013 | 1.02 | U00075 | | 1310 | 1310 |
| | | Alt a 1 | 111 | KVSDDITYVATATLP | 3324.0013 | 1.02 | U00097 | | 712 | 712 |
| | | Alt a 1 | 116 | ITYVATATLPNYCRA | 3324.0014 | 1.02 | D00095 | | 2563 | 2563 |
| | | Alt a 1 | 116 | ITYVATATLPNYCRA | 3324.0014 | 1.02 | D00069 | | 327 | 327 |
| | | Alt a 1 | 116 | ITYVATATLPNYCRA | 3324.0014 | 1.02 | D00107 | 157 | 1123 | 1280 |
| | | Alt a 1 | 116 | ITYVATATLPNYCRA | 3324.0014 | 1.02 | U00064 | | 797 | 797 |
| | | Alt a 1 | 116 | ITYVATATLPNYCRA | 3324.0014 | 1.02 | U00075 | | 1405 | 1405 |
| | | Alt a 1 | 116 | ITYVATATLPNYCRA | 3324.0014 | 1.02 | U00097 | | 882 | 882 |
| | | Alt a 1 | 116 | ITYVATATLPNYCRA | 3324.0014 | 1.02 | U00122 | 133 | | 133 |
| | | Alt a 1 | 141 | QGVADAYITLVTLPK | 3324.0011 | 1.03 | D00095 | | 623 | 623 |
| | | Alt a 1 | 141 | QGVADAYITLVTLPK | 3324.0011 | 1.03 | D00003 | 397 | 1768 | 2165 |
| | | Alt a 1 | 141 | QGVADAYITLVTLPK | 3324.0011 | 1.03 | U00064 | | 1777 | 1777 |
| | | Alt a 1 | 141 | QGVADAYITLVTLPK | 3324.0011 | 1.03 | D00129 | | 670 | 670 |
| | | Alt a 1 | 141 | QGVADAYITLVTLPK | 3324.0011 | 1.03 | D00107 | | 298 | 298 |
| | | Alt a 1 | 143 | VADAYITLVTLPKSS | 3324.0016 | 1.03 | U00075 | | 533 | 533 |
| | | Alt a 1 | 143 | VADAYITLVTLPKSS | 3324.0016 | 1.03 | D00095 | | 1728 | 1728 |
| | | Alt a 1 | 143 | VADAYITLVTLPKSS | 3324.0016 | 1.03 | D00003 | | 353 | 353 |
| | | Alt a 1 | 143 | VADAYITLVTLPKSS | 3324.0016 | 1.03 | U00064 | | 1323 | 1323 |
| | | Alt a 12 | 1 | MSTSELATSYAALIL | 3324.0036 | 1.04 | U00075 | 370 | 1513 | 1883 |
| | | Alt a 12 | 6 | LATSYAALILADDGV | 3324.0035 | 1.04 | U00075 | 540 | 703 | 1243 |
| | | Alt a 12 | 26 | KLQSLIKAAKIEEVE | 3324.0037 | 1.05 | U00075 | | 80 | 80 |
| | | Alt a 13 | 11 | QKLVLFAVKGTATST | 3324.0044 | 1.06 | U00075 | | 70 | 70 |
| | | Alt a 13 | 166 | GQQYLAWLNEKFKRS | 3324.0045 | 1.07 | U00075 | | 63 | 63 |
| | | Alt a 5 | 51 | INELIASGSEKLASV | 3324.0065 | 1.08 | U00075 | | 337 | 337 |
| | | Alt a 5 | 51 | INELIASGSEKLASV | 3324.0065 | 1.08 | U00102 | | 3113 | 3113 |
| | | Alt a 6 | 1 | MTITKIHARSVYDSR | 3324.0075 | 1.09 | U00064 | | 47 | 47 |
| | | Alt a 6 | 106 | LGANAIGVSMAIAK | 3324.0069 | 1.10 | D00095 | | 418 | 418 |
| | | Alt a 6 | 116 | MAIAKAAAAEKGVPL | 3324.0074 | 1.11 | U00129 | | 63 | 63 |
| | | Alt a 6 | 161 | GGRLAFQEFMIVPCE | 3324.0073 | 1.12 | D00069 | | 328 | 328 |
| | | Alt a 6 | 161 | GGRLAFQEFMIVPCE | 3324.0073 | 1.12 | D00107 | 807 | 103 | 910 |
| | | Alt a 6 | 186 | GAEVYQKLKALAKKT | 3324.0072 | 1.13 | D00069 | | 173 | 173 |
| | | Alt a 6 | 271 | KSKWLTYEQLAEMYK | 3324.0068 | 1.14 | U00064 | | 47 | 47 |
| | | Alt a 6 | 306 | EAWSYFFKTYDGQIV | 3324.0067 | 1.15 | U00129 | | 90 | 90 |
| | | Alt a 6 | 341 | CNALLLKVNQIGTIT | 3324.0071 | 1.16 | U00129 | | 1223 | 1223 |

TABLE 7-continued

Positive donor/peptide responses

| Category | Organism | Antigen | Position | Sequence (SEQ ID NOs: 1,412-1,906, in order of appearance) | Peptide ID | Region ID | Donor | Response (SFC/10^6) IFNg | Response (SFC/10^6) IL-5 | Response (SFC/10^6) Total |
|---|---|---|---|---|---|---|---|---|---|---|
| | | Alt a 6 | 366 | GAGWGVMVSHRSGET | 3324.0078 | 1.17 | D00003 | | 63 | 63 |
| | | Alt a 6 | 406 | ERLAKLNQILRIEEE | 3324.0076 | 1.18 | U00075 | 1080 | | 1080 |
| | | Alt a 7 | 141 | IYVPLGYKTAFSMLA | 3324.0079 | 1.19 | U00122 | 103 | | 103 |
| | | Alt a 7 | 190 | AQGKAFYEAVAKAHQ | 3324.0080 | 1.19 | D00003 | | 290 | 290 |
| | | Alt a 7 | 190 | AQGKAFYEAVAKAHQ | 3324.0080 | 1.20 | U00122 | 107 | | 107 |
| | | Alt a 7 | 36 | LFQVAETLPQEVLDK | 3324.0084 | 1.21 | D00003 | | 170 | 170 |
| | | Alt a 7 | 6 | AIVYYSMYGHIKKMA | 3324.0085 | 1.22 | D00003 | | 137 | 137 |
| | | Alt a 7 | 6 | AIVYYSMYGHIKKMA | 3324.0085 | 1.22 | D00003 | | 590 | 590 |
| | | Alt a 8 | 236 | ELKGAYVYFASDASS | 3324.0088 | 1.23 | U00075 | | 247 | 247 |
| | | Alt a 8 | 216 | QDIQKLWHSMIPMGR | 3324.0092 | 1.24 | D00003 | | 190 | 190 |
| | | Alt a 8 | 151 | TGSLVITSSMSGHIA | 3324.0093 | 1.25 | U00097 | | 378 | 378 |
| | Aspergillus fumigatus | Asp f 1 | 146 | ARVIYTYPNKVFCGI | 3324.0124 | 1.26 | U00109 | 318 | 87 | 405 |
| | | Asp f 12 | 391 | KNIVKKTLELFNEIA | 3324.0175 | 1.27 | U00109 | 83 | | 83 |
| | | Asp f 13 | 256 | LGGGYSYAFNNAVEN | 3324.0190 | 1.28 | U00122 | 442 | | 442 |
| | | Asp f 13 | 231 | LDGFNWAVNDIVSKG | 3324.0192 | 1.29 | U00122 | 507 | 277 | 783 |
| | | Asp f 17 | 116 | ADSLAKAISAKVPES | 3324.0209 | 1.30 | U00050 | 477 | | 477 |
| | | Asp f 17 | 136 | AQLSAGITAAIQKGI | 3324.0210 | 1.31 | U00121 | 171 | | 171 |
| | | Asp f 17 | 91 | SKKDKFVAANAGGTV | 3324.0212 | 1.32 | U00113 | 157 | | 157 |
| | | Asp f 17 | 91 | SKKDKFVAANAGGTV | 3324.0212 | 1.32 | U00109 | 657 | | 657 |
| | | Asp f 17 | 101 | AGGTVYEDLKAQYTA | 3324.0213 | 1.33 | U00113 | 200 | | 200 |
| | | Asp f 22 | 161 | GGRLAFQEFMIVPDS | 3324.0252 | 1.34 | U00050 | 380 | | 380 |
| | | Asp f 27 | 106 | TNGSQFFITTVVTSW | 3324.0262 | 1.35 | U00109 | 87 | | 87 |
| | | Asp f 4 | 41 | DTVYATINGVLVSWI | 3324.0288 | 1.36 | U00109 | 112 | | 112 |
| | | Asp f 4 | 341 | SKVQPFDRIMEYIQAG | 3324.0560 | 1.37 | U00110 | | 113 | 113 |
| | Cladosporium herbarum | Cla h 10 | 1 | MKYLAAFLLLGLAGN | 3324.0573 | 1.38 | U00107 | | 43 | 43 |
| | | Cla h 5 | 6 | AFLLLGLAGNSSPSA | 3324.0576 | 1.38 | U00107 | 103 | | 103 |
| | | Cla h 5 | 6 | AFLLLGLAGNSSPSA | 3324.0576 | 1.38 | U00122 | | 143 | 143 |
| | | Cla h 5 | 111 | ILGVSMAVAKAAAAE | 3324.0586 | 1.39 | U00128 | 177 | | 177 |
| | | Cla h 6 | 126 | KRVPLYAHISDLSGT | 3324.0590 | 1.40 | U00129 | | 67 | 67 |
| | | Cla h 6 | 161 | GGRLAFQEFMIVPSG | 3324.0588 | 1.41 | U00101 | | 130 | 130 |
| | | Cla h 6 | 161 | GGRLAFQEFMIVPSG | 3324.0588 | 1.41 | U00110 | 833 | 157 | 990 |
| | | Cla h 6 | 161 | GGRLAFQEFMIVPSG | 3324.0588 | 1.41 | U00128 | 962 | | 962 |
| | | Cla h 6 | 166 | FQEFMIVPSGAPSFT | 3324.0581 | 1.41 | U00128 | 277 | | 277 |
| | | Cla h 6 | 186 | GAEVYQKLKSLTKKR | 3324.0585 | 1.42 | U00128 | 343 | | 343 |
| | | Cla h 6 | 281 | ADQYKQLAAKYPIVS | 3324.0593 | 1.43 | U00110 | | 53 | 53 |
| | | Cla h 6 | 306 | EAWSYFYKTSGSDFQ | 3324.0580 | 1.44 | D00073 | 70 | | 70 |
| | | Cla h 7 | 1 | MAPKIAIIFYSTWGH | 3324.0597 | 1.45 | U00128 | 112 | | 112 |
| | | Cla h 7 | 131 | AMSTLSHHGIIYVPL | 3337.0019 | 1.46 | U00128 | 117 | | 117 |
| | | Cla h 8 | 46 | GAAVAITYASRAQGA | 3324.0600 | 1.47 | D00073 | 150 | | 150 |
| | | Cla h 8 | 101 | QIDAFIANAGATADS | 3324.0601 | 1.48 | D00073 | 230 | | 230 |
| | | Cla h 8 | 101 | QIDAFIANAGATADS | 3324.0601 | 1.48 | U00107 | 87 | | 87 |
| | | Cla h 8 | 151 | GTGSLVITASMSGHI | 3324.0603 | 1.49 | U00079 | | 420 | 420 |
| | | Cla h 8 | 151 | GTGSLVITASMSGHI | 3324.0603 | 1.49 | U00107 | | 50 | 50 |
| | | Cla h 8 | 181 | GCIHMARSLANEWRD | 3324.0602 | 1.50 | U00079 | | 130 | 130 |
| | | Cla h 8 | 181 | GCIHMARSLANEWRD | 3324.0602 | 1.50 | U00107 | 500 | 187 | 687 |

TABLE 7-continued

Positive donor/peptide responses

| Category | Organism | Antigen | Position | Sequence (SEQ ID NOs: 1,412-1,906, in order of appearance) | Peptide ID | Region ID | Donor | Response (SFC/10^6) | | |
|---|---|---|---|---|---|---|---|---|---|---|
| | | | | | | | | IFNg | IL-5 | Total |
| | Penicillium chrysogenum | Cla h 8 | 236 | KELKGAYVFASDAS | 3324.0598 | 1.51 | U00079 | | 3540 | 3540 |
| | | Cla h 8 | 236 | KELKGAYVFASDAS | 3324.0598 | 1.51 | U00128 | 527 | | 527 |
| | | Cla h 8 | 241 | AYVFASDASTYTTG | 3324.0599 | 1.51 | U00079 | | 2003 | 2003 |
| | | Pen ch 13 | 6 | VLATSLATLAVVDAG | 3324.1300 | 1.52 | U00050 | 170 | | 170 |
| | | Pen ch 13 | 36 | YIVVMNDDVSTAEFS | 3324.1311 | 1.53 | U00050 | 140 | | 140 |
| | | Pen ch 13 | 101 | PAVKYIEPDMIVNAI | 3324.1304 | 1.54 | U00050 | 263 | | 263 |
| | | Pen ch 13 | 101 | PAVKYIEPDMIVNAT | 3324.1304 | 1.54 | U00137 | 413 | | 413 |
| | | Pen ch 13 | 111 | IVNATANVVQSNVPS | 3324.1306 | 1.55 | U00137 | 353 | | 353 |
| | | Pen ch 13 | 201 | YGVAKKATLVAVKVL | 3324.1305 | 1.56 | U00137 | 320 | | 320 |
| | | Pen ch 13 | 266 | NVVKSGIFLSVAAGN | 3324.1299 | 1.57 | U00050 | 173 | | 173 |
| | | Pen ch 13 | 266 | NVVKSGIFLSVAAGN | 3324.1299 | 1.57 | U00137 | 400 | | 400 |
| | | Pen ch 13 | 271 | GIFLSVAAGNEAENA | 3324.1303 | 1.57 | U00050 | 213 | | 213 |
| | | Pen ch 13 | 271 | GIFLSVAAGNEAENA | 3324.1303 | 1.57 | U00137 | 1250 | | 1250 |
| | | Pen ch 13 | 346 | APHVAGVAAYLMALE | 3324.1296 | 1.58 | U00137 | 333 | | 333 |
| | | Pen ch 13 | 371 | IVQLATSSISRAPSG | 3324.1302 | 1.59 | U00137 | 310 | | 310 |
| | | Pen ch 18 | 1 | MKGFLsLTLLPLLVA | 3324.1314 | 1.60 | U00109 | 193 | | 193 |
| | | Pen ch 18 | 26 | NDAAPILsSMTSKDI | 3324.1332 | 1.61 | U00047 | | 200 | 200 |
| | | Pen ch 18 | 96 | TFHIAGSLLGYAGHF | 3324.1323 | 1.62 | U00047 | | 240 | 240 |
| | | Pen ch 18 | 226 | KFGVAKKANVYAVKV | 3324.1330 | 1.63 | U00047 | | 360 | 360 |
| | | Pen ch 18 | 226 | KFGVAKKANVYAVKV | 3324.1330 | 1.63 | U00122 | | 247 | 247 |
| | | Pen ch 18 | 291 | LDLAVNAAVDAGIHF | 3324.1331 | 1.64 | U00047 | | 280 | 280 |
| | | Pen ch 18 | 291 | LDLAVNAAVDAGIHF | 3324.1331 | 1.64 | U00109 | 1237 | 427 | 1663 |
| | | Pen ch 18 | 301 | AGIHFAVAAGNDNAD | 3324.1324 | 1.65 | U00122 | | 537 | 537 |
| | | Pen ch 18 | 381 | HIAGLLAYYVSLAPA | 3324.1313 | 1.66 | U00109 | 207 | | 207 |
| | | Pen ch 18 | 411 | KAALISVATEGTLTD | 3324.1326 | 1.67 | U00047 | | 250 | 250 |
| | | Pen ch 18 | 476 | AFHKELGAIYSEIKD | 3324.1328 | 1.68 | U00047 | | 320 | 320 |
| | | Pen ch 18 | 176 | VDAYVIDTGANVKHV | 3324.1327 | 1.69 | U00109 | 343 | | 343 |
| | | Pen ch 18 | | | | | U00132 | 1117 | | 1117 |
| Indoor allergens | American cockroach | Per a 3 | 151 | YGSIPHFYRLLVGHV | 3324.1394 | 2.01 | D00054 | 160 | | 160 |
| | | Per a 3 | 191 | FYQLWKRIDHIVQKY | 3324.1404 | 2.02 | D00054 | 350 | | 350 |
| | | Per a 3 | 446 | YTPNMYFKDVVIFHK | 3324.1415 | 2.03 | D00054 | 180 | | 180 |
| | Cat | Fel d 11 | 41 | DEYVEQVAQYKALPV | 3324.1049 | 2.15 | D00073 | | 120 | 120 |
| | | Fel d 11 | 41 | DEYVEQVAQYKALPV | 3324.1049 | 2.15 | U00046 | | 270 | 270 |
| | | Fel d 11 | 46 | QVAQYKALPVVLENA | 3324.1051 | 2.15 | U00046 | | 2622 | 2622 |
| | | Fel d 11 | 46 | QVAQYKALPVVLENA | 3324.1051 | 2.15 | U00079 | | 3323 | 3323 |
| | | Fel d 11 | 51 | KALPVVLENARILKN | 3324.1048 | 2.15 | U00046 | | 660 | 660 |
| | | Fel d 11 | 78 | NALSVLDKIYTSPLC | 3324.1050 | 2.16 | D00073 | 587 | 980 | 1567 |
| | | Fel d 11 | 78 | NALSVLDKIYTSPLC | 3324.1050 | 2.16 | U00029 | 823 | 213 | 1037 |
| | | Fel d 11 | 78 | NALSVLDKIYTSPLC | 3324.1050 | 2.16 | U00079 | | 850 | 850 |
| | | Fel d 12 | 21 | AETCPIFYDVFFAVA | 3324.1056 | 2.17 | D00073 | 1477 | 997 | 2473 |
| | | Fel d 12 | 21 | AETCPIFYDVFFAVA | 3324.1056 | 2.17 | D00069 | | 503 | 503 |
| | | Fel d 12 | 21 | AETCPIFYDVFFAVA | 3324.1056 | 2.17 | U00046 | | 1797 | 1797 |
| | | Fel d 12 | 21 | AETCPIFYDVFFAVA | 3324.1056 | 2.17 | U00106 | | 557 | 557 |
| | | Fel d 12 | 21 | AETCPIFYDVFFAVA | 3324.1056 | 2.17 | U00128 | 570 | | 570 |

TABLE 7-continued

Positive donor/peptide responses

| Category | Organism | Antigen | Position | Sequence (SEQ ID NOs: 1,412-1,906, in order of appearance) | Peptide ID | Region ID | Donor | Response (SFC/10^6) IFNg | Response (SFC/10^6) IL-5 | Response (SFC/10^6) Total |
|---|---|---|---|---|---|---|---|---|---|---|
| | | Fel d 12 | 26 | IFYDVFFAVANGNEL | 3324.1052 | 2.17 | U00079 | | 903 | 903 |
| | | Fel d 12 | 26 | IFYDVFFAVANGNEL | 3324.1052 | 2.17 | U00128 | 115 | | 115 |
| | | Fel d 12 | 26 | IFYDVFFAVANGNEL | 3324.1052 | 2.17 | U00106 | | 1337 | 1337 |
| | | Fel d 12 | 26 | IFYDVFFAVANGNEL | 3324.1052 | 2.17 | D00069 | | 237 | 237 |
| | | Fel d 12 | 26 | IFYDVFFAVANGNEL | 3324.1052 | 2.17 | U00046 | | 1530 | 1530 |
| | | Fel d 12 | 36 | NGNELLLDLSLTKVN | 3324.1055 | 2.18 | U00106 | | 100 | 100 |
| | | Fel d 12 | 36 | NGNELLLDLSLTKVN | 3324.1055 | 2.18 | D00073 | 1187 | 1550 | 2737 |
| | | Fel d 12 | 66 | YVENGLISRVLDGLV | 3324.1057 | 2.19 | U00079 | | 183 | 183 |
| | | Fel d 4 | 56 | VFVEHIKALDNSSLS | 3324.1090 | 2.20 | U00029 | | 58 | 58 |
| | | Fel d 4 | 96 | YTVVYDGYNVFSIVE | 3324.1100 | 2.21 | U00029 | | 270 | 270 |
| | | Fel d 4 | 116 | YILLHLLNFDKTRPF | 3324.1093 | 2.22 | U00029 | | 73 | 73 |
| | Dog | Can f 3 | 156 | QLFLGKYLYEIARRH | 3324.0499 | 2.23 | U00117 | 77 | | 77 |
| | | Can f 3 | 176 | PELLYYAQQYKGVFA | 3324.0508 | 2.24 | U00117 | 53 | | 53 |
| | | Can f 3 | 421 | KLGEYGFQNALLVRY | 3324.0498 | 2.25 | U00117 | 87 | | 87 |
| | | Can f 3 | 476 | FLSVVLNRLCVLHEK | 3324.0500 | 2.26 | U00117 | 77 | | 77 |
| | | Can f 3 | 531 | FTFHADLCTLPEAEK | 3324.0509 | 2.27 | U00117 | 60 | | 60 |
| D. farinae | | Der f 1 | 46 | ARKNFLESLKYVEAN | 3324.0668 | 2.28 | U00117 | 67 | | 67 |
| | | Der f 1 | 86 | FEQLKTQFDLNAETS | 3324.0682 | 2.29 | U00117 | 70 | | 70 |
| | | Der f 1 | 131 | GSCWAFSGVAATESA | 3324.0670 | 2.30 | U00050 | 297 | 542 | 838 |
| | | Der f 1 | 131 | GSCWAFSGVAATESA | 3324.0670 | 2.30 | U00117 | 470 | | 470 |
| | | Der f 1 | 136 | FSGVAATESAYLAYR | 3324.0666 | 2.30 | U00117 | 610 | | 610 |
| | | Der f 1 | 136 | FSGVAATESAYLAYR | 3324.0666 | 2.30 | U00050 | 343 | 77 | 420 |
| | | Der f 1 | 141 | ATESAYLAYRNTSLD | 3324.0674 | 2.30 | U00050 | 217 | | 217 |
| | | Der f 1 | 141 | ATESAYLAYRNTSLD | 3324.0674 | 2.30 | U00117 | 80 | | 80 |
| | | Der f 1 | 106 | LKIATAKLEEASQSA | 3324.0689 | 2.31 | D00069 | 67 | | 67 |
| | | Der f 10 | 191 | VELEEELRVVGNNLK | 3324.0690 | 2.32 | D00069 | 70 | | 70 |
| | | Der f 10 | 221 | YEQQIRIMTAKLKEA | 3324.0687 | 2.33 | D00069 | 60 | | 60 |
| | | Der f 11 | 311 | ELRVKIAELQKLQHE | 3324.0715 | 2.34 | U00131 | 433 | | 433 |
| | | Der f 13 | 6 | GKYKLEKSEKFDEFL | 3324.0727 | 2.35 | U00124 | | 240 | 240 |
| | | Der f 13 | 26 | GFMVKTAAKTLKPTF | 3324.0725 | 2.36 | U00124 | | 2600 | 2600 |
| | | Der f 13 | 46 | NDQYIFRSLSTFKNT | 3324.0724 | 2.37 | U00124 | | 487 | 487 |
| | | Der f 13 | 51 | FRSLSTFKNTEAKFK | 3324.0726 | 2.37 | U00124 | | 570 | 570 |
| | | Der f 14 | 196 | VRPFKMHGNSDIKLM | 3324.0739 | 2.38 | U00050 | 647 | | 647 |
| | | Der f 16 | 11 | IPIGHTFFFIWRIKQ | 3324.0772 | 2.39 | U00099 | 160 | | 160 |
| | | Der f 16 | 216 | FKLSSVILEDGKEVE | 3324.0767 | 2.40 | U00099 | 177 | | 177 |
| | | Der f 16 | 236 | EYDAFNKALSLDKKD | 3324.0775 | 2.41 | U00099 | 230 | | 230 |
| | | Der f 16 | 291 | ISFVVKNGPLSRADLD | 3324.0776 | 2.42 | U00099 | 183 | | 183 |
| | | Der f 16 | 366 | FKSLFESWQMSEQEK | 3324.0763 | 2.43 | U00099 | 230 | | 230 |
| | | Der f 16 | 381 | ITSARLFRVSRNGIF | 3324.0764 | 2.44 | U00099 | 223 | | 223 |
| | | Der f 16 | 416 | VMDKIYVWIGNQFAE | 3324.0766 | 2.45 | U00099 | 160 | | 160 |
| | | Der f 16 | 451 | SGRKFQPNQIIKLKQ | 3324.0765 | 2.46 | U00093 | 1560 | | 1560 |
| | | Der f 18 | 126 | TFVVSTVDLMTRYGF | 3324.0790 | 2.47 | D00069 | 63 | | 63 |
| | | Der f 18 | 171 | HTSFVMGVTLPATIA | 3324.0789 | 2.48 | D00069 | 143 | | 143 |
| | | Der f 2 | 121 | VVVTVKLIGDNGVLA | 3337.0026 | 2.49 | D00069 | 63 | | 63 |

TABLE 7-continued

Positive donor/peptide responses

| Category | Organism | Antigen | Position | Sequence (SEQ ID NOs: 1,412-1,906, in order of appearance) | Peptide ID | Region ID | Donor | Response (SFC/10^6) | | |
|---|---|---|---|---|---|---|---|---|---|---|
| | | | | | | | | IFNg | IL-5 | Total |
| D. pteronyssinus | | Der p 1 | 11 | LALSAVYARPSSIKT | 3324.0828 | 2.50 | U00050 | 267 | 77 | 343 |
| | | Der p 1 | 31 | KAFNKSYATFEDEEA | 3324.0834 | 2.51 | U00050 | 1563 | 703 | 2267 |
| | | Der p 1 | 46 | ARKNFLESVKYVQSN | 3324.0839 | 2.52 | U00108 | | 487 | 487 |
| | | Der p 1 | 51 | LESVKYVQSNGGAIN | 3324.0838 | 2.53 | U00117 | | 467 | 467 |
| | | Der p 1 | 61 | GGAINHLSDLSLDEF | 3324.0842 | 2.54 | U00050 | 170 | 603 | 773 |
| | | Der p 1 | 111 | EIDLRQMRTVTPIRM | 3324.0836 | 2.55 | U00117 | 120 | 613 | 733 |
| | | Der p 1 | 131 | SCWAFSGVAATESAY | 3324.0832 | 2.56 | U00050 | 843 | 460 | 1303 |
| | | Der p 1 | 131 | SCWAFSGVAATESAY | 3324.0832 | 2.56 | U00117 | 233 | 773 | 1007 |
| | | Der p 1 | 136 | SGVAATESAYLAYRN | 3324.0829 | 2.56 | U00117 | 340 | 347 | 687 |
| | | Der p 1 | 136 | SGVAATESAYLAYRN | 3324.0829 | 2.56 | U00050 | 237 | 167 | 403 |
| | | Der p 1 | 176 | RGIEYIQHNGVVQES | 3324.0831 | 2.57 | U00117 | | 567 | 567 |
| | | Der p 1 | 176 | RGIEYIQHNGVVQES | 3324.0831 | 2.57 | U00117 | 220 | 103 | 323 |
| | | Der p 1 | 226 | REALAQTHSAIAVII | 3324.0840 | 2.58 | U00050 | 1407 | 477 | 1883 |
| | | Der p 1 | 226 | REALAQTHSAIAVII | 3324.0840 | 2.58 | U00117 | | 900 | 900 |
| | | Der p 1 | 231 | QTHSAIAVIIGIKDL | 3324.0835 | 2.58 | U00117 | | 317 | 317 |
| | | Der p 1 | 296 | DNGYGYFAANIDLMM | 3324.0827 | 2.59 | U00117 | | 53 | 53 |
| | | Der p 14 | 96 | FAFGYFNGRILGVCP | 3324.0914 | 2.60 | U00093 | 133 | | 133 |
| | | Der p 14 | 476 | NAMDEIIKSTDAEPA | 3324.0918 | 2.61 | U00117 | 260 | | 260 |
| | | Der p 14 | 746 | TGLPLMYKFGDNLVV | 3324.0922 | 2.62 | U00131 | 247 | | 247 |
| | | Der p 14 | 1346 | NGKLHLSLIDPSTLS | 3324.0894 | 2.63 | U00102 | 460 | | 460 |
| | | Der p 2 | 101 | QQYDIKYTWNVPKIA | 3324.0940 | 2.64 | U00117 | | 1333 | 1333 |
| | | Der p 3 | 16 | TLANPILPASPNATI | 3324.0969 | 2.65 | U00108 | | 167 | 167 |
| | | Der p 3 | 61 | EYWILTAAHCVAGQT | 3324.0966 | 2.66 | U00108 | | 203 | 203 |
| | | Der p 3 | 81 | IRYNSLKHSLGGEKI | 3324.0968 | 2.67 | U00108 | | 137 | 137 |
| | | Der p 3 | 91 | GGEKISVAKIFAHEK | 3324.0964 | 2.68 | U00108 | | 137 | 137 |
| | | Der p 3 | 111 | IDNDIALIKLKSPMK | 3324.0967 | 2.69 | U00108 | | 187 | 187 |
| | | Der p 3 | 166 | SELRRVDIAVVSRKE | 3324.0960 | 2.70 | U00108 | | 120 | 120 |
| | | Der p 4 | 46 | FDFLLMERIHEQIKK | 3324.0998 | 2.71 | U00108 | | 143 | 143 |
| | | Der p 4 | 61 | GELALFYLQEQINHF | 3324.0997 | 2.72 | U00108 | | 1113 | 1113 |
| | | Der p 4 | 86 | NKAGVRIYVDIVLNH | 3324.0981 | 2.73 | U00108 | 93 | 2017 | 2110 |
| | | Der p 4 | 86 | NKAGVRIYVDIVLNH | 3324.0981 | 2.73 | U00128 | | 1260 | 1260 |
| | | Der p 4 | 91 | RIYVDIVLNHMTGAQ | 3324.0988 | 2.73 | U00108 | | 117 | 117 |
| | | Der p 4 | 96 | IVLNHMTGAQSGKGT | 3324.0987 | 2.73 | U00117 | | 507 | 507 |
| | | Der p 4 | 201 | PDDLRSIYSRLHNLN | 3324.0979 | 2.74 | U00108 | | 177 | 177 |
| | | Der p 4 | 206 | SIYSRLHNLNKEFFP | 3324.0989 | 2.74 | U00108 | | 117 | 117 |
| | | Der p 4 | 251 | IEFRFYKEITNVFRG | 3324.0976 | 2.75 | U00108 | | 153 | 153 |
| | | Der p 4 | 251 | IEFRFYKEITNVFRG | 3324.0976 | 2.75 | U00117 | | 610 | 610 |
| | | Der p 4 | 286 | DALVMIDSHDLRVGH | 3324.0992 | 2.76 | U00128 | | 290 | 290 |
| | | Der p 4 | 311 | FEGRLLKAATAFMLA | 3324.0973 | 2.77 | U00108 | | 113 | 113 |
| | | Der p 4 | 311 | FEGRLLKAATAFMLA | 3324.0973 | 2.77 | U00108 | | 953 | 953 |
| | | Der p 4 | 316 | LKAATAFMLAWNYGV | 3324.0972 | 2.77 | U00117 | | 757 | 757 |
| | | Der p 4 | 321 | AFMLAWNYGVPRVMS | 3324.0977 | 2.77 | U00117 | | 1413 | 1413 |
| | | Der p 4 | 321 | AFMLAWNYGVPRVMS | 3324.0977 | 2.77 | U00108 | | 157 | 157 |
| | | Der p 4 | 331 | PRVMSSYFWNQIIKD | 3324.0991 | 2.78 | U00117 | | 152 | 152 |
| | | Der p 4 | 381 | EHRWREIYNMVKFRM | 3324.0986 | 2.79 | U00128 | | 300 | 300 |

TABLE 7-continued

Positive donor/peptide responses

| Category | Organism | Antigen | Position | Sequence (SEQ ID NOs: 1,412-1,906, in order of appearance) | Peptide ID | Region ID | Donor | Response (SFC/10^6) IFNg | Response (SFC/10^6) IL-5 | Response (SFC/10^6) Total |
|---|---|---|---|---|---|---|---|---|---|---|
| | | Der p 4 | 381 | EHRWREIYNMVKFRM | 3324.0986 | 2.79 | U00093 | 1007 | | 1007 |
| | | Der p 4 | 381 | EHRWREIYNMVKFRM | 3324.0986 | 2.79 | U00108 | | 80 | 80 |
| | | Der p 4 | 381 | EHRWREIYNMVKFRM | 3324.0986 | 2.79 | U00117 | | 402 | 402 |
| | | Der p 4 | 386 | EIYNMVKFRMIAGQE | 3324.0978 | 2.79 | U00108 | | 167 | 167 |
| | | Der p 4 | 386 | EIYNMVKFRMIAGQE | 3324.0978 | 2.79 | U00117 | | 1100 | 1100 |
| | | Der p 4 | 386 | EIYNMVKFRMIAGQE | 3324.0978 | 2.79 | U00093 | 667 | | 667 |
| | | Der p 4 | 391 | VKFRMIAGQEPVHNW | 3324.0993 | 2.79 | U00117 | | 92 | 92 |
| | | Der p 4 | 411 | YQIAFSRGNRAFIAI | 3324.0980 | 2.80 | U00117 | | 177 | 177 |
| | | Der p 4 | 411 | YQIAFSRGNRAFIAI | 3324.0980 | 2.80 | U00117 | | 380 | 380 |
| | | Der p 4 | 416 | SRGNRAFIAINLQKN | 3324.0974 | 2.80 | U00117 | | 940 | 940 |
| | | Der p 4 | 476 | YVGHDEFDAFVAYHI | 3324.0975 | 2.81 | U00117 | | 973 | 973 |
| | | Der p 4 | 481 | EFDAFVAYHIGARIV | 3324.0970 | 2.81 | U00108 | | 123 | 123 |
| | | Der p 4 | 481 | EFDAFVAYHIGARIV | 3324.0970 | 2.81 | U00117 | | 763 | 763 |
| | | Der p 4 | 482 | FDAFVAYHIGARIVS | 3324.0971 | 2.81 | U00108 | | 187 | 187 |
| | | Der p 5 | 111 | RKDLDIFEQYNLEMA | 3324.1001 | 8.82 | U00108 | | 117 | 117 |
| | | Der p 9 | 181 | TLPTILQIASVTKMS | 3324.1036 | 2.83 | U00108 | | 120 | 120 |
| | | Der p 9 | 256 | TIYSNVANLRNWIIS | 3324.1040 | 2.84 | U00108 | | 297 | 297 |
| | | Der p 9 | 259 | SNVANLRNWIISNTV | 3324.1043 | 2.84 | U00108 | | 177 | 177 |
| Trees | Alder | Aln g 1 | 11 | PSVIPAARLFKAFIL | 3324.0004 | 3.01 | D00069 | 683 | | 683 |
| | | Aln g 1 | 16 | AARLFKAFILDGDKL | 3324.0003 | 3.01 | U00110 | 800 | 553 | 1353 |
| | | Aln g 1 | 111 | GGSILKISNKFHTKG | 3324.0007 | 3.02 | U00032 | 887 | | 887 |
| | | Aln g 1 | 111 | GGSILKISNKFHTKG | 3324.0007 | 3.02 | U00110 | 357 | | 357 |
| | | Aln g 1 | 141 | AVGLLKAVESYLLAH | 3324.0001 | 3.03 | D00069 | 597 | 597 | |
| | Birch | Bet v 1 | 6 | YETETTSVIPAARLF | 3324.0351 | 3.04 | D00094 | | 403 | 403 |
| | | Bet v 1 | 11 | TSVIPAARLFKAFFL | 3324.0349 | 3.04 | D00094 | | 427 | 427 |
| | | Bet v 1 | 76 | DHTNFKYSYSVIEGG | 3324.0350 | 3.05 | D00094 | | 413 | 413 |
| | | Bet v 1 | 96 | LEKISNEIKIVATPD | 3324.0353 | 3.06 | D00067 | 92 | | 92 |
| | | Bet v 1 | 96 | LEKISNEIKIVATPD | 3324.0353 | 3.06 | D00094 | | 370 | 370 |
| | | Bet v 1 | 111 | GGSILKISNKYHTKG | 3324.0352 | 3.07 | D00094 | | 280 | 280 |
| | | Bet v 1 | 111 | GGSILKISNKYHTKG | 3324.0352 | 3.07 | D00067 | 612 | | 612 |
| | | Bet v 1 | 111 | GGSILKISNKYHTKG | 3324.0352 | 3.07 | D00073 | 240 | | 240 |
| | | Bet v 1 | 146 | RAVESYLLAHSDAYN | 3324.0348 | 3.08 | D00094 | | 293 | 293 |
| | | Bet v 2 | 31 | DGSVWAQSSSFPQFK | 3324.0355 | 3.09 | D00094 | | 1953 | 1953 |
| | | Bet v 2 | 66 | GLHLGGIKYMVIQGE | 3324.0356 | 3.10 | D00094 | | 440 | 440 |
| | | Bet v 2 | 71 | GIKYMVIQGEAGAVI | 3324.0354 | 3.10 | D00094 | | 350 | 350 |
| | | Bet v 3 | 61 | LSRAINLLGLETDLS | 3324.0364 | 3.11 | D00094 | | 167 | 167 |
| | | Bet v 6 | 71 | VKAFKQVDVVISTVG | 3324.0384 | 3.12 | U00053 | 1007 | | 1007 |
| | | Bet v 6 | 206 | RTLNKIVYIKPAKNI | 3324.0387 | 3.13 | U00053 | 580 | | 580 |
| | | Bet v 6 | 206 | RTLNKIVYIKPAKNI | 3324.0387 | 3.13 | U00103 | 140 | | 140 |
| | | Bet v 6 | 211 | IVYIKPAKNIYSFNE | 3324.0386 | 3.13 | U00103 | 227 | | 227 |
| | | Bet v 6 | 211 | IVYIKPAKNIYSFNE | 3324.0386 | 3.13 | U00053 | 487 | | 487 |
| | | Bet v 6 | 216 | PAKNIYSFNEIVALW | 3324.0372 | 3.13 | U00103 | 67 | | 67 |
| | | Bet v 6 | 261 | VILAINHSVFVKGDH | 3324.0380 | 3.14 | U00103 | 1410 | | 1410 |

TABLE 7-continued

Positive donor/peptide responses

| Category | Organism | Antigen | Position | Sequence (SEQ ID NOs: 1,412-1,906, in order of appearance) | Peptide ID | Region ID | Donor | Response (SFC/10^6) IFNg | Response (SFC/10^6) IL-5 | Response (SFC/10^6) Total |
|---|---|---|---|---|---|---|---|---|---|---|
| | | Bet v 6 | 276 | TNFEIEASFGVEASE | 3324.0379 | 3.15 | U00103 | 1113 | | 1113 |
| | | Bet v 6 | 291 | LYPDVKYTTVEEYLQ | 3324.0382 | 3.16 | U00103 | 67 | 67 | 117 |
| | Cypress | Cha o 1 | 86 | ERSLWIIFSKNLNIK | 3324.0517 | 3.17 | U00075 | | 117 | 117 |
| | | Cha o 1 | 86 | ERSLWIIFSKNLNIK | 3324.0517 | 3.17 | D00052 | 97 | | 97 |
| | | Cha o 1 | 91 | IIFSKNLNIKLNMPL | 3324.0522 | 3.17 | D00008 | | 863 | 863 |
| | | Cha o 1 | 96 | NLNIKLNMPLYIAGN | 3324.0523 | 3.17 | D00008 | | 1708 | 1708 |
| | | Cha o 1 | 211 | NHFFNHHKVMLLGHS | 3324.0521 | 3.18 | D00008 | | 778 | 778 |
| | | Cha o 1 | 211 | NHFFNHHKVMLLGHS | 3324.0521 | 3.18 | D00052 | 57 | | 57 |
| | | Cha o 1 | 231 | DKSMKVTAFNQFGP | 3324.0525 | 3.19 | D00008 | | 323 | 323 |
| | | Cha o 2 | 6 | MAAVAFLALQLIVMA | 3324.0529 | 3.20 | D00008 | | 283 | 283 |
| | | Cha o 2 | 66 | KALWIIFSQNMNIKL | 3324.0604 | 3.21 | U00034 | 390 | | 390 |
| | | Cup a 1 | 71 | IFSQNMNIKLQMPLY | 3324.0607 | 3.21 | D00008 | | 2607 | 2607 |
| | | Cup a 1 | 71 | IFSQNMNIKLQMPLY | 3324.0607 | 3.21 | D00102 | 70 | | 70 |
| | | Cup a 1 | 76 | MNIKLQMPLYVAGYK | 3324.0613 | 3.21 | D00008 | | 652 | 652 |
| | | Cup a 1 | 76 | MNIKLQMPLYVAGYK | 3324.0613 | 3.21 | U00034 | 120 | | 120 |
| | | Cup a 1 | 186 | TISNNHFFNHHKVML | 3324.0612 | 3.22 | D00008 | | 542 | 542 |
| | | Cup a 1 | 191 | HFFNHHKVMLLGHDD | 3324.0605 | 3.22 | D00008 | | 992 | 992 |
| | | Cup a 1 | 316 | EDTNIYNSNEAFKVE | 3324.0606 | 3.23 | D00008 | | 427 | 427 |
| | | Cup a 1 | 316 | EDTNIYNSNEAFKVE | 3324.0606 | 3.23 | D00052 | 240 | | 240 |
| | | Cup a 1 | 316 | EDTNIYNSNEAFKVE | 3324.0606 | 3.23 | D00102 | 73 | | 73 |
| | | Cup a 1 | 86 | EKALWIIFSQNMNIK | 3324.0615 | 3.24 | D00052 | 333 | | 400 |
| | | Cup s 1 | 91 | IIFSQNMNIKLKMPL | 3324.0618 | 3.24 | D00102 | 80 | 67 | 80 |
| | | Cup s 1 | 91 | IIFSQNMNIKLKMPL | 3324.0618 | 3.24 | D00008 | | 3067 | 3067 |
| | | Cup s 1 | 91 | IIFSQNMNIKLKMPL | 3324.0618 | 3.24 | D00052 | 73 | | 73 |
| | | Cup s 1 | 96 | NMNIKLKMPLYVAGH | 3324.0624 | 3.24 | D00008 | | 3147 | 3147 |
| | | Cup s 1 | 126 | GPCLFMRKVSHVILH | 3324.0619 | 3.25 | D00008 | | 687 | 687 |
| | | Cup s 1 | 131 | MRKVSHVILHGLHIH | 3324.0621 | 3.25 | D00008 | | 642 | 642 |
| | | Cup s 1 | 211 | NHFFNHHKVMLLGHD | 3324.0616 | 3.26 | D00008 | | 1427 | 1427 |
| | | Cup s 1 | 211 | NHFFNHHKVMLLGHD | 3324.0616 | 3.26 | D00052 | 173 | 50 | 223 |
| | | Cup s 1 | 231 | DKSMKVTAFNQFGP | 3324.0622 | 3.27 | D00008 | | 102 | 102 |
| | | Cup s 3 | 11 | LVATSAISLHMQEAG | 3324.0630 | 3.28 | D00102 | 83 | | 83 |
| Ash | | Fra e 1 | 21 | DTCRARFITKLSEFI | 3324.1102 | 3.29 | U00047 | | 67 | 67 |
| | | Fra e 1 | 31 | LSEFITGASVRLQCR | 3324.1105 | 3.30 | U00058 | | 73 | 73 |
| | | Fra e 1 | 121 | LGFFKKEALPQCAQV | 3324.1104 | 3.31 | U00047 | 53 | 573 | 627 |
| Prickly juniper | | Jun o 4 | 46 | ELADILRSLGSDVGE | 3324.1129 | 3.32 | U00099 | | 380 | 380 |
| | | Jun o 4 | 76 | GYVSLQEFVDLNNKG | 3324.1131 | 3.33 | D00068 | | 80 | 80 |
| | | Jun o 4 | 76 | GYVSLQEFVDLNNKG | 3324.1131 | 3.33 | U00099 | | 420 | 420 |
| | | Jun o 4 | 146 | LISVEEFQTMMTSEM | 3324.1130 | 3.34 | U00099 | | 153 | 153 |
| Date palm | | Pho d 2 | 36 | SSSFPQFKSEEITNI | 3324.1549 | 3.37 | U00050 | | 77 | 77 |
| | | Pho d 2 | 71 | KYMVIQGEPGAVIRG | 3324.1547 | 3.38 | U00050 | | 63 | 63 |
| | | Pho d 2 | 91 | GVTVKKTNQALIFGI | 3324.1550 | 3.39 | U00050 | | 93 | 93 |
| White oak | | Que a 1 | 11 | ASVIPPARLFKAFVL | 3324.1587 | 3.40 | D00026 | 273 | | 273 |
| | | Que a 1 | 11 | ASVIPPARLFKAFVL | 3324.1587 | 3.40 | D00067 | 127 | 203 | 330 |
| | | Que a 1 | 11 | ASVIPPARLFKAFVL | 3324.1587 | 3.40 | D00078 | | 97 | 97 |
| | | Que a 1 | 11 | ASVIPPARLFKAFVL | 3324.1587 | 3.40 | U00047 | | 100 | 100 |

TABLE 7-continued

Positive donor/peptide responses

| Category | Organism | Antigen | Sequence (SEQ ID NOs: 1,412-1,906, in order of appearance) | Position | Peptide ID | Region ID | Donor | Response (SFC/10^6) IFNg | Response (SFC/10^6) IL-5 | Response (SFC/10^6) Total |
|---|---|---|---|---|---|---|---|---|---|---|
| | | Que a 1 | PARLFKAFVLDSDNL | 16 | 3324.1585 | 3.40 | U00047 | | 170 | 170 |
| | | Que a 1 | PARLFKAFVLDSDNL | 16 | 3324.1585 | 3.40 | U00110 | 1877 | 890 | 2767 |
| | | Que a 1 | PARLFKAFVLDSDNL | 16 | 3324.1585 | 3.40 | U00115 | | 1790 | 1790 |
| | | Que a 1 | PARLFKAFVLDSDNL | 16 | 3324.1585 | 3.40 | D00078 | 393 | 190 | 583 |
| | | Que a 1 | PARLFKAFVLDSDNL | 16 | 3324.1585 | 3.40 | D00072 | 180 | 520 | 700 |
| | | Que a 1 | KAFVLDSDNLIPKVV | 21 | 3324.1588 | 3.40 | D00004 | | 70 | 70 |
| | | Que a 1 | KAFVLDSDNLIPKVV | 21 | 3324.1588 | 3.40 | D00004 | | 123 | 123 |
| | | Que a 1 | KAFVLDSDNLIPKVV | 21 | 3324.1588 | 3.40 | D00072 | 200 | 947 | 1147 |
| | | Que a 1 | KAFVLDSDNLIPKVV | 21 | 3324.1588 | 3.40 | D00078 | | 57 | 57 |
| | | Que a 1 | ASEVFKAVEAYLVAH | 141 | 3324.1584 | 3.41 | U00047 | | 207 | 207 |
| | | Que a 1 | ASEVFKAVEAYLVAH | 141 | 3324.1584 | 3.41 | U00072 | 143 | 890 | 1033 |
| | | Que a 1 | ASEVFKAVEAYLVAH | 141 | 3324.1584 | 3.41 | D00004 | | 97 | 97 |
| | | Que a 1 | KAVEAYLVAHPDLYK | 146 | 3324.1586 | 3.41 | D00004 | | 83 | 83 |
| | | Que a 1 | KAVEAYLVAHPDLYK | 146 | 3324.1586 | 3.41 | D00067 | | 53 | 53 |
| | | Que a 1 | KAVEAYLVAHPDLYK | 146 | 3324.1586 | 3.41 | D00047 | | 143 | 143 |
| | | Que a 1 | KAVEAYLVAHPDLYK | 146 | 3324.1586 | 3.41 | U00072 | 110 | 443 | 553 |
| Grasses | Sweet vernal grass | Ant o 1 | IAKVPPGPNITATYG | 1 | 3324.0103 | 4.01 | U00054 | 153 | | 153 |
| | | Ant o 1 | IAKVPPGPNITATYG | 1 | 3324.0103 | 4.01 | U00058 | 223 | | 223 |
| | | Ant o 1 | IAKVPPGPNITATYG | 1 | 3324.0103 | 4.01 | U00106 | 267 | | 267 |
| | | Ant o 1 | DKWLDAKSTWYGKPT | 16 | 3324.0102 | 4.02 | U00050 | 447 | 147 | 593 |
| | | Ant o 1 | DKWLDAKSTWYGKPT | 16 | 3324.0102 | 4.02 | U00106 | 233 | | 233 |
| | | Ant o 1 | DKWLDAKSTWYGKPT | 16 | 3324.0102 | 4.02 | U00054 | 123 | | 123 |
| | | Ant o 1 | WLDAKSTWYGKPTGA | 18 | 3337.0008 | 4.02 | U00054 | 140 | | 140 |
| | | Ant o 1 | WLDAKSTWYGKPTGA | 18 | 3337.0008 | 4.02 | U00075 | | 57 | 57 |
| | | Ant o 1 | WLDAKSTWYGKPTGA | 18 | 3337.0008 | 4.02 | U00050 | 283 | | 283 |
| | | Ant o 1 | WLDAKSTWYGKPTGA | 18 | 3337.0008 | 4.02 | U00106 | 163 | | 163 |
| | Bermuda grass | Cyn d 1 | MLAVVAVVLASMVGG | 1 | 3324.0633 | 4.03 | U00089 | 227 | | 227 |
| | | Cyn d 12 | TVWAQSAAFPAFKPE | 31 | 3324.0639 | 4.04 | D00104 | 463 | | 463 |
| | | Cyn d 12 | TVWAQSAAFPAFKPE | 31 | 3324.0639 | 4.04 | U00054 | 100 | | 100 |
| | | Cyn d 7 | LRTLGSTSADEVQRM | 31 | 3324.0652 | 4.05 | U00054 | 113 | | 113 |
| | Orchard grass | Dac g 1 | PNYLALLVKYVDGDG | 181 | 3324.0655 | 4.06 | U00099 | | 957 | 957 |
| | | Dac g 1 | PNYLALLVKYVDGDG | 181 | 3324.0655 | 4.06 | U00102 | 110 | 353 | 463 |
| | | Dac g 1 | PNYLALLVKYVDGDG | 181 | 3324.0655 | 4.06 | U00036 | | 83 | 83 |
| | | Dac g 2 | GSDEKNLALSIKYNK | 11 | 3324.0657 | 4.07 | D00042 | | 1292 | 1292 |
| | | Dac g 2 | GSDEKNLALSIKYNK | 11 | 3324.0657 | 4.07 | U00110 | | 1000 | 1000 |
| | | Dac g 2 | GSDEKNLALSIKYNK | 11 | 3324.0657 | 4.07 | U00058 | | 693 | 693 |
| | | Dac g 2 | NLALSIKYNKEGDSM | 16 | 3324.0658 | 4.07 | U00058 | | 917 | 917 |
| | | Dac g 2 | NLALSIKYNKEGDSM | 16 | 3324.0658 | 4.07 | U00110 | | 853 | 853 |
| | | Dac g 3 | IPTAFKIGTTYTPEE | 82 | 3324.0660 | 4.08 | U00036 | 110 | 170 | 280 |
| | | Dac g 4 | DIYNYMEPYVSKVDP | 1 | 3324.0663 | 4.09 | U00036 | 73 | | 73 |
| | | Dac g 4 | DIYNYMEPYVSKVDP | 1 | 3324.0663 | 4.09 | U00089 | | 302 | 302 |
| | | Dac g 4 | DIYNYMEPYVSKVDP | 1 | 3324.0663 | 4.09 | U00102 | | 107 | 107 |

TABLE 7-continued

Positive donor/peptide responses

| Category | Organism | Antigen | Position | Sequence (SEQ ID NOs: 1,412-1,906, in order of appearance) | Peptide ID | Region ID | Donor | Response (SFC/10^6) IFNg | Response (SFC/10^6) IL-5 | Response (SFC/10^6) Total |
|---|---|---|---|---|---|---|---|---|---|---|
| Rye grass | | Lol p 1 | 1 | MASSSVLLVVALFA | 3324.1133 | 4.10 | U00125 | 53 | | 53 |
| | | Lol p 1 | 11 | VALFAVFLGSAHGIA | 3324.1134 | 4.11 | U00099 | | 208 | 208 |
| | | Lol p 1 | 121 | EPIAPYHFDLSGHAF | 3337.0028 | 4.12 | U00099 | 157 | 97 | 253 |
| | | Lol p 1 | 176 | KASNPNYLAILVKYV | 3324.1135 | 4.13 | U00099 | | 837 | 837 |
| | | Lol p 1 | 176 | KASNPNYLAILVKYV | 3324.1135 | 4.13 | U00106 | 157 | 100 | 257 |
| | | Lol p 1 | 176 | KASNPNYLAILVKYV | 3324.1135 | 4.13 | U00125 | | 87 | 87 |
| | | Lol p 1 | 106 | KQQGIRYANPIAFFR | 3324.1137 | 4.13 | U00125 | | 123 | 123 |
| | | Lol p 11 | 111 | RYANPIAFFRKEPLK | 3324.1138 | 4.14 | U00125 | 440 | 1697 | 2137 |
| | | Lol p 11 | 111 | IAFFRKEPLKECGGI | 3337.0029 | 4.14 | U00125 | 77 | 180 | 257 |
| | | Lol p 11 | 116 | DGVWEIKSDKPLKGP | 3324.1139 | 4.15 | U00106 | 103 | | 103 |
| | | Lol p 2 | 51 | DGVWEIKSDKPLKGP | 3324.1139 | 4.15 | U00125 | 83 | 83 | 167 |
| | | Lol p 2 | 51 | DGVWEIKSDKPLKGP | 3324.1139 | 4.15 | D00004 | | 577 | 577 |
| | | Lol p 2 | 51 | DGVWEIKSDKPLKGP | 3324.1139 | 4.15 | D00125 | | 287 | 287 |
| | | Lol p 2 | 51 | IKSDKPLKGPFNFRF | 3324.1140 | 4.15 | U00110 | | 317 | 317 |
| | | Lol p 2 | 56 | MRNVFDDVVPADFKV | 3337.0030 | 4.16 | U00110 | 103 | 110 | 213 |
| | | Lol p 2 | 76 | MRNVFDDVVPADFKV | 3337.0030 | 4.16 | D00070 | | 133 | 133 |
| | | Lol p 2 | 76 | MRNVFDDVVPADFKV | 3337.0030 | 4.16 | U00125 | 460 | 447 | 907 |
| | | Lol p 2 | 76 | SDAKTLVLNIKYTRP | 3324.1142 | 4.17 | D00036 | | 227 | 227 |
| | | Lol p 3 | 11 | SDAKTLVLNIKYTRP | 3324.1142 | 4.17 | D00004 | | 147 | 147 |
| | | Lol p 3 | 11 | SDAKTLVLNIKYTRP | 3324.1142 | 4.17 | U00110 | 150 | 1547 | 1697 |
| | | Lol p 3 | 11 | LWEVKSAKPLTGPMN | 3337.0031 | 4.18 | U00106 | 90 | | 90 |
| | | Lol p 3 | 51 | LWEVKSAKPLTGPMN | 3337.0031 | 4.18 | U00125 | 703 | 1010 | 1713 |
| | | Lol p 3 | 51 | NVFDEVIPTAFTVGK | 3324.1141 | 4.19 | U00099 | | 2258 | 2258 |
| | | Lol p 3 | 76 | NVFDEVIPTAFTVGK | 3324.1141 | 4.19 | U00125 | 263 | 820 | 1083 |
| | | Lol p 4 | 31 | PENFAVVDLNQMRAV | 3324.1159 | 4.20 | U00117 | 75 | | 75 |
| | | Lol p 4 | 101 | LRKYGIAAENVIDVK | 3324.1145 | 4.21 | U00117 | 50 | | 50 |
| | | Lol p 4 | 236 | NEMSWIESIPFVHLG | 3324.1151 | 4.22 | U00117 | 1933 | | 1933 |
| | | Lol p 4 | 321 | FPHRKGVLFNIQYVN | 3324.1152 | 4.23 | U00117 | 100 | | 100 |
| | | Lol p 51 | 6 | HTVALFLAVALVAGP | 3324.1166 | 4.24 | U00106 | 53 | | 53 |
| | | Lol p 51 | 11 | FLAVALVAGPAASYA | 3324.1170 | 4.24 | U00106 | | 63 | 63 |
| | | Lol p 51 | 71 | LIEKINAGFKAAVAA | 3324.1175 | 4.25 | D00070 | 960 | 900 | 1860 |
| | | Lol p 51 | 71 | LIEKINAGFKAAVAA | 3324.1175 | 4.25 | U00099 | | 1202 | 1202 |
| | | Lol p 51 | 71 | LIEKINAGFKAAVAA | 3324.1175 | 4.25 | U00106 | | 263 | 263 |
| | | Lol p 51 | 76 | NAGFKAAVAAAAVVP | 3324.1168 | 4.25 | D00070 | 850 | 873 | 1723 |
| | | Lol p 51 | 76 | NAGFKAAVAAAAVVP | 3324.1168 | 4.25 | U00099 | | 977 | 977 |
| | | Lol p 51 | 76 | NAGFKAAVAAAAVVP | 3324.1168 | 4.25 | U00106 | | 248 | 248 |
| | | Lol p 51 | 96 | KTFVETFGTATNKAF | 3324.1171 | 4.26 | U00106 | 73 | | 73 |
| | | Lol p 51 | 106 | TNKAFVEGLASGYAD | 3324.1186 | 4.27 | U00099 | | 287 | 287 |
| | | Lol p 51 | 131 | DAALKLAYEAAQGAT | 3324.1169 | 4.28 | D00070 | 120 | | 120 |
| | | Lol p 51 | 146 | PEAKYDAYVATLTEA | 3324.1180 | 4.29 | D00070 | 227 | | 227 |
| | | Lol p 51 | 151 | DAYVATLTEALRVIA | 3324.1167 | 4.29 | D00070 | 1017 | 410 | 1427 |
| | | Lol p 51 | 151 | DAYVATLTEALRVIA | 3324.1167 | 4.29 | U00106 | | 1743 | 1743 |

TABLE 7-continued

Positive donor/peptide responses

| Category | Organism | Antigen | Position | Sequence (SEQ ID NOs: 1,412-1,906, in order of appearance) | Peptide ID | Region ID | Donor | Response (SFC/10^6) IFNg | Response (SFC/10^6) IL-5 | Response (SFC/10^6) Total |
|---|---|---|---|---|---|---|---|---|---|---|
| | | Lol p 51 | 156 | TLTEALRVIAGTLEV | 3324.1185 | 4.29 | U00099 | | 267 | 267 |
| | | Lol p 51 | 196 | VDAAYRTAATAANAA | 3324.1181 | 4.30 | U00106 | | 383 | 383 |
| | | Lol p 51 | 216 | FTVFENTFNNAIKVS | 3324.1179 | 4.31 | U00099 | | 87 | 87 |
| | | Lol p 51 | 236 | DSYKFIPTLVAAVKQ | 3324.1165 | 4.32 | U00099 | | 382 | 382 |
| | | Lol p 51 | 236 | DSYKFIPTLVAAVKQ | 3324.1165 | 4.32 | U00106 | | 78 | 78 |
| | | Lol p 51 | 246 | AAVKQAYAAKQATAP | 3324.1177 | 4.33 | U00106 | 43 | | 43 |
| | | Lol p 51 | 261 | EVKYTVSETALKKAV | 3324.1178 | 4.34 | U00106 | | 333 | 333 |
| | | Lol p 51 | 271 | LKKAVTAMSEAEKEA | 3324.1183 | 4.35 | U00106 | | 128 | 128 |
| | | Lol p 51 | 306 | PAAAYATATPAAATA | 3324.1184 | 4.36 | U00106 | 58 | | 58 |
| | | Lol p 51 | 306 | PAAAYATATPAAATA | 3324.1184 | 4.36 | U00099 | | 1637 | 1637 |
| | | Lol p 52 | 181 | AFKIAATAANAAPTN | 3324.1197 | 4.37 | D00004 | | 1200 | 1200 |
| | | Lol p 52 | 181 | AFKIAATAANAAPTN | 3324.1197 | 4.37 | U00106 | | 887 | 887 |
| | | Lol p 52 | 181 | AFKIAATAANAAPTN | 3324.1197 | 4.37 | D00070 | 173 | | 173 |
| | | Lol p 52 | 196 | DKFTVFESAFNKALN | 3324.1191 | 4.38 | U00106 | | 97 | 97 |
| | | Lol p 52 | 251 | AALTKAITAMTQAQK | 3324.1196 | 4.39 | U00099 | | 998 | 998 |
| Canary grass | | Pha a 1 | 186 | PNYLALLVKYVDGDG | 3324.1428 | 4.40 | D00052 | 153 | 132 | 285 |
| | | Pha a 1 | 186 | PNYLALLVKYVDGDG | 3324.1428 | 4.40 | U00106 | | 323 | 323 |
| | | Pha a 1 | 186 | PNYLALLVKYVDGDG | 3324.1428 | 4.40 | D00070 | 147 | | 147 |
| | | Pha a 1 | 186 | PNYLALLVKYVDGDG | 3324.1428 | 4.40 | U00029 | 1340 | | 1340 |
| | | Pha a 1 | 221 | SWGAIWRIDTPDKLT | 3337.0039 | 4.41 | U00106 | 155 | | 155 |
| | | Pha a 5 | 101 | DAAYRVAYEAAEGST | 3324.1443 | 4.42 | U00117 | 70 | | 70 |
| | | Pha a 5 | 121 | DAFIAALTEALRVIA | 3324.1432 | 4.43 | U00029 | 713 | | 713 |
| | | Pha a 5 | 121 | DAFIAALTEALRVIA | 3324.1432 | 4.43 | D00052 | | 540 | 540 |
| | | Pha a 5 | 126 | ALTEALRVIAGAFEV | 3324.1437 | 4.43 | D00070 | 427 | | 427 |
| | | Pha a 5 | 166 | AAFKIAATAANSAPA | 3324.1441 | 4.44 | U00029 | 2018 | | 2018 |
| | | Pha a 5 | 166 | AAFKIAATAANSAPA | 3324.1441 | 4.44 | U00099 | 208 | 203 | 203 |
| | | Pha a 5 | 181 | NDKFTVFEGAFNKAI | 3324.1442 | 4.45 | D00029 | 153 | 400 | 400 |
| | | Pha a 5 | 181 | NDKFTVFEGAFNKAI | 3324.1442 | 4.45 | U00117 | 93 | | 93 |
| | | Pha a 5 | 201 | GAYETYKFIPSLEAA | 3324.1433 | 4.46 | D00052 | 208 | | 208 |
| | | Pha a 5 | 201 | GAYETYKFIPSLEAA | 3324.1433 | 4.46 | U00029 | 153 | | 153 |
| | | Pha a 5 | 201 | GAYETYKFIPSLEAA | 3324.1433 | 4.46 | D00070 | 513 | 290 | 803 |
| | | Pha a 5 | 206 | YKFIPSLEAAVKQAY | 3324.1436 | 4.46 | D00070 | 187 | 57 | 243 |
| | | Pha a 5 | 206 | YKFIPSLEAAVKQAY | 3324.1436 | 4.46 | U00099 | 193 | | 193 |
| Kentucky blue grass | | Poa p 1 | 121 | EPIAAYHFDLSGKAF | 3324.1556 | 4.79 | D00004 | 297 | | 297 |
| | | Poa p 1 | 121 | EPIAAYHFDLSGKAF | 3324.1556 | 4.79 | U00032 | | 183 | 183 |
| | | Poa p 1 | 121 | EPIAAYHFDLSGKAF | 3324.1556 | 4.79 | U00102 | | 877 | 877 |
| | | Poa p 1 | 176 | KGSNPNYLALLVKVV | 3324.1557 | 4.80 | U00102 | | 290 | 290 |
| | | Poa p 1 | 181 | NYLALLVKVVTGDGD | 3324.1558 | 4.80 | U00102 | | 80 | 80 |
| | | Poa p 1 | 191 | DKFTVFEAAFNNAIK | 3324.1562 | 4.81 | U00101 | | 183 | 183 |
| | | Poa p 5 | 51 | QKLMEDINVGFKAAV | 3324.1580 | 4.82 | U00101 | 317 | | 317 |
| | | Poa p 5 | 51 | QKLMEDINVGFKAAV | 3324.1580 | 4.82 | U00110 | 283 | 107 | 390 |

TABLE 7-continued

Positive donor/peptide responses

| Category | Organism | Antigen | Position | Sequence (SEQ ID NOs: 1,412-1,906, in order of appearance) | Peptide ID | Region ID | Donor | Response (SFC/10^6) | | |
|---|---|---|---|---|---|---|---|---|---|---|
| | | | | | | | | IFNg | IL-5 | Total |
| | | Poa p 5 | 56 | DINVGFKAAVAAAAG | 3324.1571 | 4.82 | U00106 | | 397 | 397 |
| | | Poa p 5 | 56 | DINVGFKAAVAAAAG | 3324.1571 | 4.82 | U00115 | 47 | | 47 |
| | | Poa p 5 | 56 | DINVGFKAAVAAAAG | 3324.1571 | 4.82 | U00034 | | 1057 | 1057 |
| | | Poa p 5 | 56 | DINVGFKAAVAAAAG | 3324.1571 | 4.82 | U00102 | 1183 | | 1183 |
| | | Poa p 5 | 61 | FKAAVAAAAGAPPAD | 3324.1575 | 4.82 | U00032 | | 138 | 138 |
| | | Poa p 5 | 61 | FKAAVAAAAGAPPAD | 3324.1575 | 4.82 | U00034 | | 327 | 327 |
| | | Poa p 5 | 61 | FKAAVAAAAGAPPAD | 3324.1575 | 4.82 | U00102 | 230 | | 230 |
| | | Poa p 5 | 121 | ATPEAKFDSFVAAFT | 3324.1570 | 4.82 | U00102 | | 238 | 238 |
| | | Poa p 5 | 121 | ATPEAKFDSFVAAFT | 3324.1570 | 4.82 | U00115 | 80 | | 80 |
| | | Poa p 5 | 121 | ATPEAKFDSFVAAFT | 3324.1570 | 4.83 | U00102 | 117 | | 117 |
| | | Poa p 5 | 131 | VAAFTEALRIIAGVL | 3324.1576 | 4.84 | U00115 | 117 | | 117 |
| | | Poa p 5 | 131 | VAAFTEALRIIAGVL | 3324.1576 | 4.84 | U00102 | 127 | | 127 |
| | | Poa p 5 | 176 | AFKVAATAANAAPAN | 3324.1578 | 4.85 | U00032 | 127 | 548 | 675 |
| | | Poa p 5 | 176 | AFKVAATAANAAPAN | 3324.1578 | 4.85 | U00110 | 100 | | 100 |
| | | Poa p 5 | 176 | AFKVAATAANAAPAN | 3324.1578 | 4.85 | U00034 | | 107 | 107 |
| | | Poa p 5 | 176 | AFKVAATAANAAPAN | 3324.1578 | 4.85 | U00106 | | 820 | 820 |
| | | Poa p 5 | 176 | AFKVAATAANAAPAN | 3324.1578 | 4.85 | U00102 | 83 | | 83 |
| | | Poa p 5 | 206 | ESTGAYDTYKSIPS | 3324.1583 | 4.85 | U00115 | 77 | | 77 |
| | | Poa p 5 | 211 | AYDTYKSIPSLEAAV | 3324.1579 | 4.86 | U00102 | | 157 | 157 |
| | | Poa p 5 | 211 | AYDTYKSIPSLEAAV | 3324.1579 | 4.86 | U00115 | | 98 | 98 |
| | | Poa p 5 | 211 | AYDTYKSIPSLEAAV | 3324.1579 | 4.86 | U00101 | 163 | | 163 |
| | | Poa p 5 | 211 | AYDTYKSIPSLEAAV | 3324.1579 | 4.86 | U00106 | | 1320 | 1320 |
| | | Poa p 5 | 221 | LEAAVKQAYAATIAA | 3324.1564 | 4.87 | U00115 | | 180 | 180 |
| | | Poa p 5 | 221 | LEAAVKQAYAATIAA | 3324.1564 | 4.87 | U00102 | 1190 | | 1190 |
| English plantain | | Pla l 1 | 21 | HSRNLINELSERMAG | 3324.1552 | 5.01 | D00004 | | 118 | 118 |
| | | Pla l 1 | 21 | HSRNLINELSERMAG | 3324.1552 | 5.01 | U00072 | | 190 | 190 |
| | | Pla l 1 | 21 | HSRNLINELSERMAG | 3324.1552 | 5.01 | U00102 | | 57 | 57 |
| | | Pla l 1 | 76 | IKLVKSSRPDCSEIP | 3337.0044 | 5.02 | D00004 | 90 | | 90 |
| | | Pla l 1 | 76 | IKLVKSSRPDCSEIP | 3337.0044 | 5.02 | U00072 | | 233 | 233 |
| Giant ragweed | | Amb t 5 | 1 | MKNIFMLTLFILIIT | 3324.0099 | 5.03 | D00002 | | 57 | 57 |
| | | Amb t 5 | 1 | MKNIFMLTLFILIIT | 3324.0099 | 5.03 | D00095 | 77 | | 77 |
| | | Amb t 5 | 6 | MLTLFILIITSTIKA | 3324.0100 | 5.03 | D00007 | 63 | | 63 |
| | | Amb t 5 | 6 | MLTLFILIITSTIKA | 3324.0100 | 5.04 | D00096 | 167 | | 167 |
| | | Amb t 5 | 31 | KQEDDGLCYEGTNCG | 3337.0006 | 5.05 | D00096 | 123 | | 123 |
| | | Amb t 5 | 56 | GKYCVCYDSKAICNK | 3337.0007 | 5.05 | D00007 | 47 | | 47 |
| Russian thistle | | Sal k 11 | 81 | EKVKIERLHPYITLY | 3324.1599 | 5.06 | D00047 | | 260 | 260 |
| | | Sal k 11 | 111 | AAEFGTVDSATLIVE | 3324.1596 | 5.07 | D00047 | | 3003 | 3003 |
| | | Sal k 11 | 126 | SDYPVGANLIVSNSA | 3324.1594 | 5.08 | D00047 | | 920 | 920 |
| | | Sal k 11 | 131 | GANLIVSNSAPRPDG | 3324.1601 | 5.08 | D00047 | | 147 | 147 |
| | | Sal k 11 | 191 | EGTVDFIFGEARSLY | 3324.1590 | 5.09 | D00047 | 397 | 1300 | 1697 |
| | | Sal k 11 | 191 | EGTVDFIFGEARSLY | 3324.1590 | 5.09 | U00106 | | 363 | 363 |
| | | Sal k 11 | 196 | FIFGEARSLYLNTEL | 3324.1591 | 5.09 | D00047 | | 500 | 500 |

TABLE 7-continued

Positive donor/peptide responses

| Category | Organism | Antigen | Position | Sequence (SEQ ID NOs: 1,412-1,906, in order of appearance) | Peptide ID | Region ID | Donor | Response (SFC/10^6) | | |
|---|---|---|---|---|---|---|---|---|---|---|
| | | | | | | | | IFNg | IL-5 | Total |
| | | Sal k 11 | 196 | FIFGEARSLYLNTEL | 3324.1591 | 5.09 | U00106 | | 133 | 133 |
| | | Sal k 11 | 251 | LGRAWFEAARVVFSY | 3324.1592 | 5.10 | D00047 | 120 | 1430 | 1550 |
| | | Sal k 11 | 256 | FEAARVVFSYCNLSD | 3324.1593 | 5.10 | D00047 | | 363 | 363 |
| | | Sal k 11 | 321 | FTSLEYIEAAKWLLP | 3324.1589 | 5.11 | D00047 | 310 | 1433 | 1743 |
| | | Sal k 11 | 321 | FTSLEYIEAAKWLLP | 3324.1589 | 5.11 | U00106 | | 203 | 203 |
| | | Sal k 11 | 325 | EYIEAAKWLLPPPKV | 3324.1600 | 5.11 | D00047 | | 980 | 980 |
| | | Sal k 12 | 11 | RTIFFDAYLGTSYVI | 3324.1602 | 5.12 | D00047 | | 433 | 433 |
| | | Sal k 12 | 16 | DAYLGTSYVIVIKEP | 3324.1603 | 5.12 | D00047 | | 290 | 290 |
| | | Sal k 2 | 171 | KIAEBIAIALLFLRD | 3324.1606 | 5.13 | D00047 | | 90 | 90 |
| | | Sal k 2 | 176 | IAIALLFLRDAKPEP | 3324.1608 | 5.13 | D00047 | | 97 | 97 |
| | | Sal k 2 | 261 | SFGIILLQLLTARPP | 3324.1609 | 5.14 | D00047 | | 103 | 103 |
| | | Sal k 3 | 91 | FDLYFSMARGNASLP | 3324.1653 | 5.15 | D00047 | 343 | | 343 |
| | | Sal k 3 | 191 | VIAELKAAGASTIQF | 3324.1632 | 5.16 | D00047 | | 313 | 313 |
| | | Sal k 3 | 261 | VTAFGFDLVRGTKTL | 3324.1640 | 5.17 | D00047 | | 73 | 73 |
| | | Sal k 3 | 306 | SLATLQSLESIVGKD | 3324.1647 | 5.18 | D00047 | 228 | | 228 |
| | | Sal k 3 | 341 | TKLDDEIKSWLAFAA | 3324.1630 | 5.19 | D00047 | | 87 | 87 |
| | | Sal k 3 | 376 | FFSANAAALASRKSS | 3324.1636 | 5.20 | D00047 | 93 | | 93 |
| | | Sal k 3 | 621 | GFYLQWAVHSFRITN | 3324.1625 | 5.21 | D00047 | 193 | 143 | 337 |

TABLE 8

HLA class II binding patterns of prevalently recognized epitope regions

| | Region: peptide information | | | | | | HLA DR binding capacity (IC$_{50}$ nM) | | | | |
|---|---|---|---|---|---|---|---|---|---|---|---|
| Region ID | Organism | Souce protein | Acc. no. | Pos | Sequence (SEQ ID NOs: 1,907-2,008 in order of appearance) | Peptide ID | DRB1* 0101 | DRB1* 0301 | DRB1* 0401 | DRB1* 0404 | DRB1* 0405 |
| 1.01 | Alt. rot fungus | Alt a 1 | P79085 | 6 | IASLFAAAGLAAAAP | 3324.0015 | 2.0 | 32079 | 9.1 | 5.6 | 1814 |
| 1.01 | Alt. rot fungus | Alt a 1 | P79085 | 11 | AAAGLAAAAPLESRQ | 3324.0017 | 18 | 919 | 37 | 5.0 | 340 |
| 1.02 | Alt. rot fungus | Alt a 1 | P79085 | 111 | KVSDDITYVATATLP | 3324.0013 | 127 | 642 | 208 | 5875 | 234 |
| 1.02 | Alt. rot fungus | Alt a 1 | P79085 | 116 | ITYVATATLPNYCRA | 3324.0014 | 21 | 5584 | 7.0 | 78 | 14654 |
| 1.03 | Alt. rot fungus | Alt a 1 | P79085 | 141 | QGVADAYITLVTLPK | 3324.0011 | 151 | 8348 | 106 | 423 | 175 |
| 1.03 | Alt. rot fungus | Alt a 1 | P79085 | 143 | VADAYITLVTLPKSS | 3324.0016 | 6.5 | 2797 | 6.3 | 5.0 | 34 |
| 1.08 | Alt. rot fungus | Alt a 5 | P42037 | 51 | INELIASGSEKLASV | 3324.0065 | 6.7 | 32 | 78 | 71 | 110 |
| 1.12 | Alt. rot fungus | Alt a 6 | Q9HDT3 | 161 | GGRLAFQEFMIVPCE | 3324.0073 | 238 | 2520 | 708 | 479 | 215 |
| 1.20 | Alt. rot fungus | Alt a 7 | P42058 | 190 | AQGKAFYEAVAKAHQ | 3324.0080 | 56 | 4114 | 60 | 102 | 200 |
| 1.22 | Alt. rot fungus | Alt a 7 | P42058 | 6 | AIVYYSMYGHIKKMA | 3324.0085 | 5.2 | 16530 | 882 | 248 | 781 |
| 1.32 | A. fumigatus | Asp f 17 | O60025 | 91 | SKKDKFVAANAGGTV | 3324.0212 | 3.6 | 40660 | 206 | 1107 | 91 |
| 1.38 | C. herbarum | Cla h 5 | P42039 | 6 | AFILLGLAGNSSPSA | 3324.0576 | 0.96 | 50000 | 7.5 | 683 | 900 |
| 1.41 | C. herbarum | Cla h 6 | P42040 | 161 | GGRLAFQEFMIVPSG | 3324.0588 | 486 | 5286 | 549 | 820 | 952 |
| 1.48 | C. herbarum | Cla h 8 | P0C0Y5 | 101 | QIDAFIANAGATADS | 3324.0601 | 1.7 | 150 | 6716 | 6451 | 6807 |
| 1.49 | C. herbarum | Cla h 8 | P0C0Y5 | 151 | GTGSLVITASMSGHI | 3324.0603 | 49 | 3530 | 6.6 | 7.6 | 162 |
| 1.50 | C. herbarum | Cla h 8 | P0C0Y5 | 181 | GCIHMARSLANEWRD | 3324.0602 | 24 | 2757 | 33 | 7.8 | 128 |
| 1.51 | C. herbarum | Cla h 8 | P0C0Y5 | 236 | KELKGAVYYFASDAS | 3324.0598 | 4.8 | 2317 | 10 | 5806 | 6569 |
| 1.54 | P. chrysogenum | Pen ch13 | Q9URR2 | 101 | PAVKYIEPDMIVNAT | 3324.1304 | 128 | 64 | 120 | | 233 |
| 1.57 | P. chrysogenum | Pen ch13 | Q9URR2 | 271 | GIFLSVAAGNEAENA | 3324.1303 | 6.9 | 3592 | 28 | 63 | 942 |
| 1.63 | P. chrysogenum | Pen ch18 | Q9P8G3 | 226 | KFGVAKKANVYAVKV | 3324.1330 | 18 | 9196 | 616 | 108 | 4648 |
| 1.64 | P. chrysogenum | Pen ch18 | Q9P8G3 | 291 | LDLAVNAAVDAGIHF | 3324.1331 | 58 | 780 | 521 | 78 | 1356 |

TABLE 8-continued

HLA class II binding patterns of prevalently recognized epitope regions

| | | | | | | | | | | | | |
|---|---|---|---|---|---|---|---|---|---|---|---|---|
| 2.15 | Cat epithelia | Fel d 1 1 | P30438 | 41 | DEVEQVAQYKALPV | 3324.1049 | 4.8 | 9240 | 41 | 1246 | 795 |
| 2.15 | Cat epithelia | Fel d 1 1 | P30438 | 46 | QVAQYKALPVVLENA | 3324.1051 | 1.4 | 19151 | 59 | 6110 | 9334 |
| 2.16 | Cat epithelia | Fel d 1 1 | P30438 | 78 | NALSVLDKIYTSPLC | 3324.1050 | 89 | 320 | 169 | 97 | 445 |
| 2.17 | Cat epithelia | Fel d 1 2 | P30440 | 21 | AETCPIFYDVFPAVA | 3324.1056 | 766 | 71 | 442 | 271 | 556 |
| 2.17 | Cat epithelia | Fel d 1 2 | P30440 | 26 | IFYDVFFAVANGNEL | 3324.1052 | 14 | 5343 | 377 | 183 | 6079 |
| 2.18 | Cat epithelia | Fel d 1 2 | P30440 | 36 | NGNELLLDLSLTKVN | 3324.1055 | 663 | 19 | 451 | 102 | 926 |
| 2.30 | D. forinae | Der f 1 | A1YW11 | 131 | GSCWAFSGVAATESA | 3324.0670 | 42 | 38891 | 23 | 1616 | 238 |
| 2.30 | D. farinae | Der f 1 | A1YW11 | 136 | FSGVAATESAYLAYR | 3324.0666 | 8.8 | 5135 | 62 | 482 | 507 |
| 2.56 | D. pteronyssinus | Der p 1 | P08176 | 131 | SCWAFSGVAATESAY | 3324.0832 | 11 | 25798 | 49 | | 267 |
| 2.56 | D. pteronyssinus | Der p 1 | P08176 | 136 | SGVAATESAYLAYRN | 3324.0829 | 9.6 | 2816 | 127 | | 903 |
| 2.57 | D. pteronyssinus | Der p 1 | P08176 | 176 | RGIEYIQHNGVVQES | 3324.0831 | 223 | 1145 | 84 | | 341 |
| 2.58 | D. pteronyssinus | Der p 1 | P08176 | 226 | REALAQTHSAIAVII | 3324.0840 | 11 | 4216 | 25 | | 962 |
| 2.73 | D. pteronyssinus | Der p 4 | Q9Y197 | 86 | NKAGVRIIVDIVLNH | 3324.0981 | 951 | 275 | 332 | 93 | 181 |
| 2.73 | D. pteronyssinus | Der p 4 | Q9Y197 | 96 | IVLNHMTGAQSGKGT | 3324.0987 | 1.2 | 14905 | 6688 | 27 | 5537 |
| 2.75 | D. pteronyssinus | Der p 4 | Q9Y197 | 251 | IEFRFYKEITNVFRG | 3324.0976 | 7.6 | 516 | 14 | 583 | 75 |
| 2.77 | D. pteronyssinus | Der p 4 | Q9Y197 | 321 | AFMLAWNYGVPRVMS | 3324.0977 | 1.6 | 49 | 82 | 628 | 66 |
| 2.79 | D. pteronyssinus | Der p 4 | Q9Y197 | 381 | EHRWREIYNMVKFRM | 3324.0986 | 131 | 706 | 170 | 252 | 331 |
| 2.79 | D. pteronyssinus | Der p 4 | Q9Y197 | 386 | EIYNMVKFRMIAGQE | 3324.0978 | 27 | 665 | 317 | 84 | 79 |
| 2.80 | D. pteronyssinus | Der p 4 | Q9Y197 | 411 | YQIAFSRGNRAFIAI | 3324.0980 | 1.7 | 117 | 14 | | 27 |
| 2.80 | D. pteronyssinus | Der p 4 | Q9Y197 | 416 | SRGNRAFIAINLQKN | 3324.0974 | 24 | 615 | 92 | 415 | 160 |
| 2.81 | D. pteronyssinus | Der p 4 | Q9Y197 | 476 | YVGHDEFDAFVAYHI | 3324.0975 | 19 | 8516 | 1172 | 1970 | 667 |
| 2.81 | D. pteronyssinus | Der p 4 | Q9Y197 | 482 | FDAFVAYHIGARIVS | 3324.0971 | 0.75 | 7274 | 248 | 1425 | 466 |
| 3.01 | Alder | Aln g 1 | P38948 | 11 | PSVIPAARLFKAFIL | 3324.0004 | 13 | 56 | 666 | 444 | 221 |
| 3.01 | Alder | Aln g 1 | P38948 | 16 | AARLFKAFILDGDKL | 3324.0003 | 70 | 1069 | 525 | 706 | 19 |
| 3.02 | Alder | Aln g 1 | P38948 | 111 | GGSILKISNKFHTKG | 3324.0007 | 19 | 32 | 84 | 12 | 126 |
| 3.06 | Birch | Bet v 1 | O23754 | 96 | LEKISNEIKIVATPD | 3324.0353 | 182 | 1362 | 5260 | 269 | 1693 |

TABLE 8-continued

HLA class II binding patterns of prevalently recognized epitope regions

| | | | | | | | | | | | | |
|---|---|---|---|---|---|---|---|---|---|---|---|---|
| 3.07 | Birch | Bet v 1 | O23754 | 111 | GGSILKISNKYHTKG | 3324.0352 | 12 | 78 | 140 | 52 | 87 |
| 3.13 | Birch | Bet v 6 | Q9FUW6 | 206 | RTLNKIVVIKPAKNI | 3324.0387 | 4.5 | 979 | 74 | 13 | 156 |
| 3.13 | Birch | Bet v 6 | Q9FUW6 | 211 | IVVIKPAKNIYSFNE | 3324.0386 | 2.0 | 504 | 5.1 | 7.8 | 63 |
| 3.17 | Cypress | Cha o 1 | Q96385 | 86 | ERSLWIIFSKNLNIK | 3324.0517 | 1.3 | 57 | 56 | 14 | 17 |
| 3.17 | Cypress | Cha o 1 | Q96385 | 96 | NLNIKLNMPLYIAGN | 3324.0523 | 528 | 15393 | 27672 | 3563 | 3490 |
| 3.18 | Cypress | Cha o 1 | Q96385 | 211 | NHFFNHHKVMLLGHS | 3324.0521 | 65 | 6873 | 208 | 277 | 157 |
| 3.21 | Cypress | Cup a 1 | Q9SCG9 | 66 | KALWIIFSQNMNIKL | 3324.0604 | 831 | 4445 | 294 | 404 | 1484 |
| 3.21 | Cypress | Cup a 1 | Q9SCG9 | 71 | IFSQNMNIKLQMPLY | 3324.0607 | 106 | 86 | 212 | 245 | 433 |
| 3.23 | Cypress | Cup a 1 | Q9SCG9 | 316 | EDTNIYNSNEAPKVE | 3324.0606 | 25 | 263 | 617 | 3139 | 4994 |
| 3.24 | Cypress | Cup a 1 | Q9SCG9 | 86 | EKALWIIFSQNMNIK | 3324.0615 | 64 | 878 | 312 | 196 | 427 |
| 3.24 | Cypress | Cup s 1 | Q9M4S2 | 86 | IIFSQNMNIKLKMPL | 3324.0618 | 115 | 568 | 6397 | 6342 | 8675 |
| 3.24 | Cypress | Cup s 1 | Q9M4S2 | 91 | NMNIKLKMPLYVAGH | 3324.0624 | 7.6 | 4211 | 4828 | 998 | 2537 |
| 3.26 | Cypress | Cup s 1 | Q9M4S2 | 96 | NHFFNHHKVMLLGHD | 3324.0616 | 24 | 22741 | 71 | 2257 | 573 |
| 3.40 | White oak | Que a 1 | B6RQS2 | 11 | ASVIPPARLFKAFVL | 3324.1587 | 29 | 778 | 384 | 43 | 92 |
| 3.40 | White oak | Que a 1 | B6RQS2 | 16 | PARLFKAFVLDSDNL | 3324.1585 | 98 | 92 | 16 | 15 | 28 |
| 3.40 | White oak | Que a 1 | B6RQS2 | 21 | KAFVLDSDNLIPKVV | 3324.1588 | 24 | 7.6 | 4.9 | 49 | 39 |
| 3.41 | White oak | Que a 1 | B6RQS2 | 141 | ASEVFKAVEAYLVAH | 3324.1584 | 0.95 | 778 | 49 | 7871 | 5866 |
| 4.06 | Orchard grass | Dac g 1 | Q7XAX7 | 181 | PNYIALLVKYVDGDG | 3324.0655 | 7.8 | 11727 | 315 | 1084 | 72 |
| 4.07 | Orchard grass | Dac g 2 | Q41183 | 11 | GSDEKNLALSIKYNK | 3324.0657 | 110 | 98 | 2656 | 3379 | 3409 |
| 4.07 | Orchard grass | Dac g 2 | Q41183 | 16 | NLALSIKYNKEGDSM | 3324.0658 | 768 | 275 | 2078 | 2339 | 1425 |
| 4.09 | Orchard grass | Dac g 4 | P82946 | 1 | DIYNYMEPYVSKVDP | 3324.0663 | 13 | 50000 | 102 | 22853 | 5897 |
| 4.13 | Rye grass | Lol p 1 | P14946 | 176 | KASNPNYLAILVKYV | 3324.1135 | 3.0 | 14228 | 221 | 3.0 | 124 |
| 4.14 | Rye grass | Lol p 11 | Q7M1X5 | 111 | RYANPIAFFRKEPLK | 3324.1138 | 19 | 1487 | 255 | 464 | 1961 |
| 4.14 | Rye grass | Lol p 11 | Q7M1X5 | 116 | IAFFRKEPLKECCGI | 3337.0029 | 71 | 1218 | 298 | 3198 | 413 |
| 4.15 | Rye grass | Lol p 2 | P14947 | 51 | DGVWEIKSDKPLKGP | 3324.1139 | 1394 | 84 | 67 | 262 | 9793 |
| 4.15 | Rye grass | Lol p 2 | P14947 | 56 | IKSDKPLKGPFNFRF | 3324.1140 | 666 | 2270 | 710 | 5959 | 8878 |

TABLE 8-continued

HLA class II binding patterns of prevalently recognized epitope regions

| | | | | | | | | | | | | |
|---|---|---|---|---|---|---|---|---|---|---|---|---|
| 4.16 | Rye grass | Lol p 2 | P14947 | 76 | MRNVFDDVVPADFKV | 3337.0030 | 707 | 22 | 788 | 5700 | 1650 |
| 4.17 | Rye grass | Lol p 3 | P14948 | 11 | SDAKTLVLNIKYTRP | 3337.1142 | 1552 | 283 | 9616 | 1376 | 14819 |
| 4.18 | Rye grass | Lol p 3 | P14948 | 51 | LWEVKSAKPLTGPMN | 3337.0031 | 91 | 475 | 585 | 157 | 7244 |
| 4.19 | Rye grass | Lol p 3 | P14948 | 76 | NVFDEVIPTAFTVGK | 3337.1141 | 292 | 1398 | 1374 | 4295 | 4254 |
| 4.25 | Rye grass | Lol p 5 1 | Q40237 | 71 | LIEKINAGFKAAVAA | 3324.1175 | 36 | 190 | 484 | 341 | 3095 |
| 4.29 | Rye grass | Lol p 5 1 | Q40237 | 151 | DAYVATLTEALRVIA | 3324.1167 | 10 | 577 | 98 | 996 | 837 |
| 4.29 | Rye grass | Lol p 5 1 | Q40237 | 156 | TLTEALRVIAGTLEV | 3324.1185 | 47 | 1223 | 110 | 103 | 6389 |
| 4.32 | Rye grass | Lol p 5 1 | Q40237 | 236 | DSYKFIPTLVAAVKQ | 3324.1165 | 1.1 | 1654 | 3.9 | 6042 | 8523 |
| 4.36 | Rye grass | Lol p 5 1 | Q40237 | 306 | PAAAYATATPAAATA | 3324.1184 | 0.60 | 11254 | 1.0 | 10 | 568 |
| 4.37 | Rye grass | Lol p 5 2 | Q40240 | 181 | APFKIAATAANAAPTN | 3324.1197 | 1.7 | 2824 | 0.75 | 2.1 | 586 |
| 4.40 | Canary grass | Pha a 1 | Q41260 | 186 | PNYLALLVKYVDGDG | 3324.1428 | 6.1 | 12592 | 1032 | 650 | 42 |
| 4.43 | Canary grass | Pha a 5 | P56164 | 121 | DAFIAALTEALRVIA | 3324.1432 | 1.5 | 21 | 7.9 | 4.5 | 2.4 |
| 4.43 | Canary grass | Pha a 5 | P56164 | 126 | ALTEALRVIAGAFEV | 3324.1437 | 19 | 3994 | 6712 | 101 | 666 |
| 4.44 | Canary grass | Pha a 5 | P56164 | 166 | AAFKIAATAANSAPA | 3324.1441 | 0.62 | 1366 | 0.96 | 1.3 | 16 |
| 4.45 | Canary grass | Pha a 5 | P56164 | 181 | NDKFTVFEGAFNKAI | 3324.1442 | 13 | 7870 | 47 | 71 | 96 |
| 4.46 | Canary grass | Pha a 5 | P56164 | 201 | GAYETYKFIPSLEAA | 3324.1433 | 1.5 | 2291 | 5.6 | 722 | 5901 |
| 4.46 | Canary grass | Pha a 5 | P56164 | 206 | YKFIPSLEAAVKQAY | 3324.1436 | 1.3 | 532 | 4.2 | 54 | 6911 |
| 4.79 | Kentucky blue grass | Poa p 1 | Q9ZP03 | 121 | EPIAAYHFDLSGKAF | 3324.1556 | 3.0 | 2447 | 4.7 | 460 | 6859 |
| 4.82 | Kentucky blue grass | Poa p 5 | Q9FPR0 | 51 | QKLMEDINVGFKAAV | 3324.1580 | 15 | 3.4 | 105 | 6410 | 6660 |
| 4.82 | Kentucky blue grass | Poa p 5 | Q9FPR0 | 56 | DINVGFKAAVAAAAG | 3324.1571 | 1.5 | 7971 | 13 | 53 | 615 |
| 4.82 | Kentucky blue grass | Poa p 5 | Q9FPR0 | 61 | FKAAVAAAAGAPPAD | 3324.1575 | 2.2 | 50000 | 100 | 1254 | 11606 |
| 4.83 | Kentucky blue grass | Poa p 5 | Q9FPR0 | 121 | ATPEAKFDSFVAAFT | 3324.1570 | 102 | 4730 | 59 | 1256 | 726 |
| 4.84 | Kentucky blue grass | Poa p 5 | Q9FPR0 | 131 | VAAFTEALRIIAGVL | 3324.1576 | 59 | 4940 | 328 | 348 | 1013 |
| 4.85 | Kentucky blue grass | Poa p 5 | Q9FPR0 | 176 | APFKVAATAANAAPAN | 3324.1578 | 14 | 43392 | 10 | 6066 | 398 |
| 4.86 | Kentucky blue grass | Poa p 5 | Q9FPR0 | 206 | ESTGGAYDTYKSIPS | 3324.1583 | 170 | 1197 | 54 | 4381 | 7674 |
| 4.86 | Kentucky blue grass | Poa p 5 | Q9FPR0 | 211 | AYDTYKSIPSLEAAV | 3324.1579 | 1.7 | 4684 | 2.5 | 65 | 5999 |

TABLE 8-continued

HLA class II binding patterns of prevalently recognized epitope regions

| | Kentucky blue grass 4.87 | | Poa p 5 | Q9FPRO | 221 LEAAVKQAYAATIAA | 3324.1564 | 4.1 | 163 | 300 | 3110 | | | |
| --- | --- | --- | --- | --- | --- | --- | --- | --- | --- | --- | --- | --- | --- |
| | 5.09 Russian thistle | | Sal k 11 | Q175T3 | 191 EGTVDFIFGEARSLY | 3324.1590 | 1.5 | 419 | 21 | 2888 | | | |
| | 5.11 Russian thistle | | Sal k 11 | Q175T3 | 321 FTSLEYIEAAKWLLP | 3324.1589 | 105 | 621 | 823 | 477 | | | |
| Peptide ID | DRB1*0701 | DRB1*0802 | DRB1*0901 | DRB1*1001 | DRB1*1101 | DRB1*1201 | DRB1*1302 | DRB1*1501 | DRB1*1602 | DRB3*0101 | DRB3*0202 | DRB4*0101 | DRB5*0101 |
| 3324.0015 | 1007 | 45 | 62 | 12 | 1262 | 10995 | 3251 | 11 | 871 | 46138 | 4645 | 301 | 746 |
| 3324.0017 | 532 | 15 | 128 | 15 | 924 | 17178 | 5638 | 148 | 956 | 50000 | 1043 | 28 | 135 |
| 3324.0013 | 66 | 151 | 178 | 291 | 883 | 7666 | 52 | 478 | 856 | 6000 | 5275 | 1159 | 1756 |
| 3324.0014 | 32 | 10 | 121 | 1.4 | 16 | 994 | 1012 | 1232 | 504 | 1325 | 8.7 | 4417 | 68 |
| 3324.0011 | 585 | 42 | 749 | 79 | 90 | 7907 | 3934 | 86 | 3403 | 3672 | 3832 | 627 | 81 |
| 3324.0016 | 4890 | 7.9 | 315 | 23 | 16 | 5300 | 5151 | 122 | 436 | 13047 | 324 | 58 | 8.3 |
| 3324.0065 | 30 | 312 | 11 | 56 | 1312 | 8620 | 4.1 | 14 | 237 | 3736 | 8.5 | 193 | 138 |
| 3324.0073 | 476 | 3199 | 782 | 568 | 6086 | 3836 | 178 | 344 | 3918 | 12846 | 2123 | 24 | 2781 |
| 3324.0080 | 176 | 5.1 | 170 | 56 | 29 | 17697 | 3652 | 1230 | 2135 | 32587 | 3230 | 548 | 38 |
| 3324.0085 | 345 | 25 | 50 | 87 | 82 | 1639 | 191 | 1.1 | 491 | 21576 | 2686 | 186 | 4.3 |
| 3324.0212 | 35 | 50 | 12 | 18 | 716 | 50000 | 0.35 | 1167 | 350 | 203 | 783 | 6746 | 129 |
| 3324.0576 | 21427 | 86 | 14 | 0.92 | 207 | 674 | 48 | 67 | 115 | 50000 | 29 | 98 | 363 |
| 3324.0588 | 393 | 42 | 63 | 47 | 1050 | 7350 | 7.1 | 3552 | 380 | 8985 | 1087 | 4.0 | 3599 |
| 3324.0601 | 1186 | 11 | 0.62 | 58 | 357 | 14150 | 0.79 | 146 | 14 | 31 | 3.5 | 920 | 3843 |
| 3324.0603 | 6.3 | 498 | 202 | 74 | 262 | 1558 | 0.52 | 71 | 99 | 5715 | 1554 | 594 | 3279 |
| 3324.0602 | 19 | 94 | 152 | 8.9 | 38 | 402 | 77 | 52 | 186 | 3902 | 61 | 270 | 122 |
| 3324.0598 | 174 | 16 | 4.5 | 8.6 | 702 | 1169 | 106 | 71 | 36 | 90 | 696 | 8.3 | 904 |
| 3324.1304 | 69 | 6101 | 342 | 10 | 539 | 5431 | 23 | 64 | 515 | 1413 | 926 | 4.9 | 363 |
| 3324.1303 | 90 | 54 | 57 | 4.0 | 663 | 26989 | 70 | 227 | 70 | 10285 | 96 | 107 | 75 |
| 3324.1330 | 15 | 2.6 | 79 | 31 | 39 | 1160 | 45 | 61 | 399 | 19072 | 1165 | 36 | 38 |
| 3324.1331 | 510 | 135 | 336 | 830 | 5469 | 3112 | 1.2 | 1247 | 6275 | 56 | 10 | 4.6 | 19692 |

TABLE 8-continued

HLA class II binding patterns of prevalently recognized epitope regions

| | | | | | | | | | | | | | |
|---|---|---|---|---|---|---|---|---|---|---|---|---|---|
| 3324.1049 | 62 | 208 | 107 | 5.8 | 779 | 76 | 644 | 8.3 | 99 | 3223 | 425 | 2106 | 15 |
| 3324.1051 | 77 | 90 | 37 | 10 | 499 | 114 | 1116 | 19 | 101 | 7529 | 1007 | 1739 | 902 |
| 3324.1050 | 174 | 33 | 591 | 40 | 166 | 780 | 325 | 73 | 627 | 287 | 2461 | 157 | 1112 |
| 3324.1056 | 1112 | 1213 | 2567 | 265 | 7993 | 738 | 40 | 688 | 1173 | 240 | 5759 | 2410 | 17988 |
| 3324.1052 | 25 | 114 | 56 | 81 | 5450 | 6429 | 35 | 284 | 555 | 889 | 941 | 50000 | 506 |
| 3324.1055 | 945 | 425 | 408 | 415 | 6739 | 1806 | 208 | 840 | 2471 | 103 | 1870 | 406 | 1633 |
| 3324.0670 | 216 | 84 | 47 | 31 | 11595 | 32537 | 38812 | 178 | 501 | 50000 | 524 | 38259 | 3721 |
| 3324.0666 | 17 | 78 | 20 | 34 | 4770 | 32626 | 958 | 68 | 65 | 50000 | 13194 | 8441 | 823 |
| 3324.0832 | 70 | 8721 | 29 | 0.39 | 563 | 15767 | 50000 | 827 | 70 | 50000 | 615 | 3875 | 503 |
| 3324.0829 | 33 | 9532 | 66 | 7.7 | 647 | 12480 | 1342 | 52 | 110 | 50000 | 2256 | 454 | 611 |
| 3324.0831 | 123 | 783 | 246 | 61 | 810 | 654 | 71 | 178 | 384 | 50000 | 1020 | 223 | 3872 |
| 3324.0840 | 1.8 | 963 | 4.2 | 61 | 453 | 1179 | 13 | 13 | 124 | 50000 | 3764 | 438 | 2201 |
| 3324.0981 | 919 | 376 | 4205 | 73 | 2403 | 2559 | 231 | 70 | 94 | 116 | 4601 | 113 | 7898 |
| 3324.0987 | 208 | 94 | 44 | 14 | 365 | 5198 | 215 | 1386 | 4775 | 50000 | 236 | 118 | 799 |
| 3324.0976 | 72 | 1.9 | 45 | 12 | 700 | 10622 | 79 | 3.9 | 14 | 69 | 3489 | 463 | 15 |
| 3324.0977 | 12 | 5.6 | 5.7 | 54 | 155 | 903 | 3.8 | 6.5 | 9.2 | 855 | 7.2 | 57 | 25 |
| 3324.0986 | 295 | 41 | 1010 | 92 | 64 | 87 | 306 | 105 | 170 | 5036 | 1745 | 48 | 5.4 |
| 3324.0978 | 8.9 | 6.2 | 120 | 11 | 9.4 | 109 | 200 | 38 | 75 | 6603 | 1665 | 163 | 285 |
| 3324.0980 | 1.2 | 8491 | 2.5 | 1.7 | 55 | 881 | 0.15 | 1.7 | 24 | 1125 | 6.1 | 4.9 | 9.4 |
| 3324.0974 | 118 | 69 | 38 | 4.1 | 1145 | 3589 | 6.1 | 29 | 114 | 1497 | 6.0 | 3.7 | 52 |
| 3324.0975 | 0.81 | 3.7 | 11 | 15 | 68 | 1340 | 122 | 6.3 | 281 | 1238 | 2680 | 107 | 39 |
| 3324.0971 | 0.73 | 1.1 | 1.2 | 38 | 37 | 241 | 2.5 | 0.46 | 16 | 5339 | 19 | 743 | 1.6 |
| 3324.0004 | 5.0 | 55 | 38 | 1.1 | 30 | 831 | 1054 | 1.5 | 150 | 1657 | 2038 | 67 | 213 |
| 3324.0003 | 9.6 | 224 | 272 | 3.3 | 3827 | 987 | 12310 | 4.2 | 354 | 75 | 4320 | 30 | 57 |
| 3324.0007 | 113 | 5.3 | 302 | 42 | 11 | 1272 | 606 | 2.0 | 606 | 13748 | 3140 | 66 | 15 |
| 3324.0353 | 205 | 244 | 875 | 595 | 137 | 2320 | 48 | 318 | 425 | 4859 | 779 | 320 | 1637 |

TABLE 8-continued

HLA class II binding patterns of prevalently recognized epitope regions

| | | | | | | | | | | | | | |
|---|---|---|---|---|---|---|---|---|---|---|---|---|---|
| 3324.0352 | 558 | 6.2 | 92 | 393 | 15 | 1192 | 28 | 4.6 | 323 | 4855 | 5846 | 202 | 36 |
| 3324.0387 | 19 | 1.5 | 9.2 | 7.0 | 44 | 420 | 0.84 | 28 | 146 | 530 | 16 | 4.6 | 24 |
| 3324.0386 | 14 | 2.8 | 4.4 | 2.0 | 14 | 44 | 2.8 | 5.8 | 46 | 268 | 2.4 | 1.1 | 18 |
| 3324.0517 | 4.6 | 7.4 | 15 | 84 | 19 | 93 | 0.43 | 1.3 | 25 | 1218 | 112 | 71 | 106 |
| 3324.0523 | 544 | 159 | 795 | 878 | 6105 | 5877 | 1.2 | 203 | 6265 | 7305 | 378 | 718 | 9501 |
| 3324.0521 | 12 | 22 | 105 | 124 | 215 | 2806 | 60 | 124 | 660 | 10863 | 557 | 24 | 2408 |
| 3324.0604 | 153 | 1898 | 222 | 88 | 3252 | 3488 | 13 | 582 | 378 | 2626 | 275 | 128 | 582 |
| 3324.0607 | 536 | 30 | 284 | 175 | 226 | 52 | 5.9 | 654 | 1012 | 503 | 3.0 | 0.23 | 1960 |
| 3324.0606 | 46 | 6524 | 48 | 580 | 11359 | 5992 | 0.84 | 100 | 2661 | 105 | 25 | 7518 | 1139 |
| 3324.0615 | 173 | 875 | 82 | 45 | 1519 | 820 | 15 | 50 | 195 | 2736 | 706 | 12 | 2176 |
| 3324.0618 | 115 | 65 | 958 | 593 | 143 | 654 | 15 | 127 | 1146 | 2187 | 5.6 | 626 | 200 |
| 3324.0624 | 6151 | 21 | 243 | 125 | 98 | 206 | 225 | 10 | 559 | 18149 | 1152 | 152 | 639 |
| 3324.0616 | 3.4 | 5.7 | 66 | 14 | 237 | 2932 | 200 | 142 | 914 | 7250 | 549 | 11 | 2201 |
| 3324.1587 | 1.5 | 82 | 15 | 0.69 | 390 | 503 | 680 | 3.9 | 62 | 1634 | 2477 | 30 | 218 |
| 3324.1585 | 14 | 259 | 61 | 3.9 | 1005 | 1952 | 433 | 13 | 83 | 6.2 | 1094 | 14 | 502 |
| 3324.1588 | 40 | 287 | 74 | 25 | 1174 | 1287 | 0.64 | 43 | 71 | 1.0 | 15 | 892 | 65 |
| 3324.1584 | 17 | 19 | 6.7 | 1.6 | 61 | 485 | 70 | 4.0 | 15 | 253 | 8.8 | 576 | 36 |
| 3324.0655 | 114 | 47 | 72 | 11 | 133 | 284 | 4777 | 82 | 177 | 34528 | 674 | 415 | 587 |
| 3324.0657 | 439 | 25 | 851 | 149 | 452 | 1575 | 97 | 136 | 847 | 14129 | 1034 | 1803 | 1268 |
| 3324.0658 | 1853 | 37 | 2776 | 109 | 115 | 5675 | 116 | 487 | 1518 | 6679 | 4791 | 4795 | 3590 |
| 3324.0663 | 23453 | 311 | 344 | 9.4 | 748 | 8160 | 6384 | 70 | 2529 | 26539 | 28096 | 17451 | 190 |
| 3324.1135 | 7.4 | 2.0 | 34 | 11 | 46 | 165 | 5.8 | 3.4 | 99 | 1513 | 9.5 | 83 | 139 |
| 3324.1138 | 382 | 25 | 240 | 62 | 895 | 574 | 347 | 62 | 136 | 3842 | 2250 | 562 | 52 |
| 3337.0029 | 3495 | 6.8 | 953 | 280 | 383 | 8867 | 1666 | 122 | 472 | 915 | 11381 | 1770 | 109 |
| 3324.1139 | 30936 | 462 | 35386 | 8804 | 11353 | 50000 | 101 | 2247 | 326 | 719 | 18619 | 6923 | 1638 |
| 3324.1140 | 1109 | 3400 | 2041 | 573 | 18417 | 8883 | 178 | 1162 | 961 | 1470 | 1642 | 6585 | 33683 |

TABLE 8-continued

HLA class II binding patterns of prevalently recognized epitope regions

| | | | | | | | | | | | | | |
|---|---|---|---|---|---|---|---|---|---|---|---|---|---|
| 3337.0030 | 443 | 535 | 9626 | 705 | 11119 | 36345 | 1132 | 3375 | 6726 | 855 | 8286 | 7473 | 1392 |
| 3337.1142 | 3764 | 65 | 22025 | 4945 | 89 | 6223 | 410 | 2440 | 7796 | 22005 | 5168 | 2463 | 20103 |
| 3337.0031 | 360 | 57 | 836 | 99 | 2649 | 14985 | 347 | 664 | 8426 | 24579 | 24793 | 31 | 792 |
| 3324.1141 | 282 | 5203 | 2919 | 819 | 23345 | 11051 | 3895 | 3693 | 6185 | 9896 | 5681 | 148 | 37968 |
| 3324.1175 | 557 | 343 | 60 | 26 | 1833 | 4177 | 57 | 48 | 247 | 8694 | 126 | 907 | 10 |
| 3324.1167 | 13 | 246 | 72 | 8.5 | 915 | 1302 | 12 | 387 | 273 | 223 | 52 | 342 | 200 |
| 3324.1185 | 14 | 187 | 69 | 33 | 1724 | 1319 | 76 | 423 | 1068 | 4464 | 1511 | 429 | 3337 |
| 3324.1165 | 16 | 6.1 | 6.1 | 4.7 | 23 | 8323 | 46 | 285 | 190 | 1680 | 8.8 | 1454 | 16 |
| 3324.1184 | 161 | 2.5 | 4.7 | 1.3 | 250 | 50000 | 3198 | 1529 | 162 | 10938 | 183 | 320 | 75 |
| 3324.1197 | 11 | 3.4 | 8.4 | 0.45 | 84 | 8528 | 2.7 | 96 | 28 | 17319 | 62 | 67 | 144 |
| 3324.1428 | 173 | 42 | 82 | 21 | 165 | 269 | 144 | 92 | 196 | 5040 | 876 | 98 | 1102 |
| 3324.1432 | 1.1 | 66 | 6.8 | 0.37 | 33 | 11 | 12 | 1.3 | 7.6 | 13 | 8.5 | 73 | 0.36 |
| 3324.1437 | 8.4 | 60 | 71 | 28 | 263 | 212 | 69 | 147 | 815 | 13812 | 27576 | 113 | 323 |
| 3324.1441 | 6.8 | 1.7 | 2.9 | 0.91 | 14 | 2382 | 1.8 | 29 | 23 | 738 | 0.61 | 11 | 6.9 |
| 3324.1442 | 8.4 | 166 | 24 | 1.6 | 723 | 9786 | 171 | 8.3 | 33 | 631 | 82 | 475 | 0.51 |
| 3324.1433 | 15 | 19 | 13 | 2.3 | 83 | 735 | 661 | 45 | 341 | 1088 | 125 | 992 | 74 |
| 3324.1436 | 21 | 60 | 25 | 9.4 | 130 | 1030 | 704 | 685 | 71 | 1738 | 107 | 828 | 27 |
| 3324.1556 | 28 | 65 | 7.8 | 30 | 588 | 704 | 1774 | 2.6 | 108 | 1.4 | 92 | 0.12 | 87 |
| 3324.1580 | 474 | 315 | 58 | 195 | 634 | 10790 | 5.1 | 44 | 156 | 4.7 | 41 | 82 | 561 |
| 3324.1571 | 37 | 4.8 | 8.9 | 7.3 | 619 | 7888 | 621 | 12 | 308 | 3192 | 864 | 796 | 111 |
| 3324.1575 | 101 | 43 | 5.6 | 13 | 2286 | 7531 | 3458 | 519 | 334 | 14700 | 2418 | 3857 | 140 |
| 3324.1570 | 98 | 240 | 65 | 31 | 13650 | 12428 | 109 | 67 | 875 | 2253 | 3475 | 85 | 683 |
| 3324.1576 | 41 | 42 | 101 | 83 | 73 | 1212 | 262 | 436 | 734 | 17847 | 1590 | 73 | 2246 |
| 3324.1578 | 52 | 49 | 73 | 3.2 | 325 | 13571 | 108 | 852 | 577 | 50000 | 95 | 374 | 460 |
| 3324.1583 | 519 | 189 | 514 | 56 | 5761 | 50000 | 815 | 573 | 335 | 513 | 1381 | 11481 | 3460 |
| 3324.1579 | 57 | 17 | 39 | 4.1 | 29 | 19306 | 1894 | 61 | 5.7 | 7820 | 177 | 4373 | 104 |

TABLE 8-continued

HLA class II binding patterns of prevalently recognized epitope regions

| Peptide ID | DQB1*0201 | DQB1*0202 | DQB1*0301 | DQB1*0302 | DQB1*0402 | DQB1*0501 | DQB1*0502 | DQB1*0503 | DQB1*0602 | DPB1*0101 | DPB1*0201 | DPB1*0301 | DPB1*0401 | DPB1*0402 | DPB1*0501 | DPB1*1401 | DPB1*2001 |
|---|---|---|---|---|---|---|---|---|---|---|---|---|---|---|---|---|---|
| | | | HLA DQ binding capacity (IC50 nM) | | | | | | | | | HLA DP binding capacity (IC50 nM) | | | | | |
| 3324.1564 | 1.8 | | 317 | 5.3 | | 147 | 3363 | 5474 | 0.27 | | 50 | 2335 | 356 | 1308 | 11 | | 234 |
| 3324.1590 | 14 | | 105 | 9.1 | | 278 | 1641 | 772 | 258 | | 18 | 1982 | 198 | 939 | 5972 | | 114 |
| 3324.1589 | 177 | | 528 | 382 | | 98 | 1307 | 6237 | 62 | | 544 | 5053 | 122 | 744 | 2140 | | 164 |
| 3324.0015 | 4120 | 1055 | 2.8 | 3010 | 2402 | 24056 | 7019 | 7261 | 103 | 6156 | 2492 | 61 | 28038 | 582 | 3718 | 234 | 2089 |
| 3324.0017 | 1853 | 50000 | 1.2 | 393 | 118 | 50000 | 8005 | 223 | 21 | 3370 | 357 | 71 | 40712 | 19838 | 463 | 125 | 184 |
| 3324.0013 | 123 | 8362 | 1144 | 2052 | 543 | 23106 | 25813 | 19392 | 2143 | 1768 | 18050 | 685 | 1614 | 3389 | 1286 | 4372 | 12845 |
| 3324.0014 | 823 | 3845 | 59 | 764 | 170 | 17589 | 8971 | 14205 | 2232 | 988 | 969 | 241 | 2994 | 2258 | 1867 | 1139 | 200 |
| 3324.0011 | 1812 | 31720 | 1315 | 1045 | 459 | 8010 | 6014 | 9102 | 4947 | 444 | 7728 | 16881 | 2009 | 509 | 72 | 3388 | 8828 |
| 3324.0016 | 570 | 7017 | 370 | 1743 | 1061 | 5103 | 7746 | 1117 | 70 | 40 | 11996 | 1124 | 2501 | 1065 | 7.1 | 1432 | 8647 |
| 3324.0065 | 5008 | 6578 | 72 | 4893 | 1877 | 34647 | 25918 | 7535 | 302 | 527 | 2734 | 3549 | 2738 | 1177 | 329 | 50 | 7505 |
| 3324.0073 | 299 | 32061 | 710 | 564 | 1183 | 23 | 178 | 4943 | 1289 | 47 | 35 | 5073 | 51 | 69 | 477 | 3088 | 7642 |
| 3324.0080 | 8948 | 50000 | 694 | 2674 | 1674 | 345 | 1365 | 157 | 2356 | 39 | 104 | 36 | 412 | 685 | 45 | 938 | 77 |
| 3324.0085 | 5789 | 6241 | 417 | 32021 | 50000 | 392 | 3255 | 1662 | 3352 | 33 | 32 | 107 | 72 | 145 | 47 | 398 | 1294 |
| 3324.0212 | 5873 | 3328 | 16 | 2657 | 416 | 50000 | 1381 | 162 | 26891 | 22256 | 2956 | 1824 | 11512 | 50000 | 5627 | 7611 | 2587 |
| 3324.0576 | 3864 | 8356 | 12 | 11230 | 66 | 5484 | 718 | 557 | 792 | 1437 | 112 | 406 | 1910 | 232 | 8188 | 4054 | 143 |
| 3324.0588 | 1989 | 50000 | 2502 | 2619 | 2807 | 68 | 4947 | 2437 | 1515 | 202 | 57 | 1091 | 37 | 268 | 83 | 9666 | 29599 |
| 3324.0601 | 482 | 3501 | 17 | 1024 | 57 | 11040 | 819 | 84 | 737 | 6173 | 2559 | 8817 | 1880 | 19500 | 36023 | 1876 | 2378 |
| 3324.0603 | 3922 | 114 | 31 | 11509 | 5287 | 6135 | 27045 | 13832 | 484 | 12974 | 26959 | 129 | 7104 | 10715 | 8303 | 36 | 1562 |
| 3324.0602 | 1048 | 301 | 41 | 1650 | 116 | 3078 | 673 | 649 | 174 | 5570 | 8054 | 695 | 21959 | 32474 | 6254 | 3885 | 1270 |
| 3324.0598 | 306 | 1225 | 23 | 1472 | 781 | 1043 | 4672 | 518 | 12 | 181 | 57 | 1578 | 60 | 537 | 1556 | 2384 | 1247 |
| 3324.1304 | 47 | 283 | | 822 | 1314 | 119 | 1961 | 1786 | 549 | 234 | | 1013 | | 91 | 389 | 170 | 503 |

TABLE 8-continued

HLA class II binding patterns of prevalently recognized epitope regions

| ID | | | | | | | | | | | | | | | | | |
|---|---|---|---|---|---|---|---|---|---|---|---|---|---|---|---|---|---|
| 3324.1303 | 121 | 4717 | 33 | 52 | 102 | 3957 | 50000 | 50000 | 370 | 549 | 108 | 5.0 | 204 | 3667 | 6490 | 70 | 146 |
| 3324.1330 | 994 | 9490 | 114 | 12547 | 1199 | 28997 | 10107 | 8157 | 1583 | 1773 | 501 | 812 | 5008 | 4599 | 3553 | 50000 | 2723 |
| 3324.1331 | 87 | 361 | 19 | 138 | 12 | 128 | 583 | 1149 | 480 | 6381 | 5052 | 273 | 9176 | 6632 | 8028 | 43033 | 5533 |
| 3324.1049 | 512 | 630 | 5346 | 1188 | 806 | 147 | 2523 | 337 | 140 | 1670 | 1120 | 1036 | 533 | 26784 | 16357 | 1149 | 17743 |
| 3324.1051 | 661 | 21374 | 5072 | 150 | 46 | 434 | 552 | 610 | 1596 | 3517 | 1808 | 14 | 14857 | 20869 | 3802 | 65 | 806 |
| 3324.1050 | 2628 | 1593 | 6450 | 3675 | 611 | 687 | 3312 | 5835 | 1000 | 251 | 575 | 3147 | 349 | 32 | 152 | 3094 | 1360 |
| 3324.1056 | 132 | 2101 | 108 | 209 | 75 | 36 | 464 | 263 | 2273 | 3.1 | 8.1 | 1740 | 5.6 | 28 | 520 | 92 | 3965 |
| 3324.1052 | 198 | 28703 | 19 | 320 | 329 | 872 | 6652 | 8127 | 1134 | 3268 | 89 | 344 | 242 | 5175 | 5558 | 3247 | 1232 |
| 3324.1055 | 2585 | 8017 | 3528 | 1981 | 3942 | 629 | 2865 | 9367 | 10904 | 180 | 841 | 5014 | 590 | 844 | 57 | 1445 | 15456 |
| 3324.0670 | 97 | 5447 | 24 | 249 | 84 | 5340 | 9320 | 7931 | 1334 | 9878 | 9311 | 18 | 14425 | 6224 | 17163 | 13775 | 396 |
| 3324.0666 | 65 | 156 | 44 | 1137 | 76 | 3429 | 1209 | 4191 | 2016 | 8430 | 8262 | 276 | 1443 | 20587 | 8843 | 6182 | 1186 |
| 3324.0832 | 92 | 21 | | | 61 | 6535 | 4402 | 8426 | 136 | 1362 | | 20 | | 3908 | 9552 | 652 | 7.7 |
| 3324.0829 | 210 | 871 | | 3429 | 2855 | 496 | 2997 | 5141 | 1136 | 1205 | | 1601 | | 20081 | 4927 | 9417 | 449 |
| 3324.0831 | 263 | 32412 | | 1188 | 723 | 8536 | 1139 | 12278 | 859 | 1625 | | 4341 | | 7397 | 35246 | 50000 | 726 |
| 3324.0840 | 536 | 629 | | 1377 | 1848 | 436 | 2459 | 32124 | 291 | 232 | | 1017 | | 32 | 3999 | 1219 | 310 |
| 3324.0981 | 2215 | 15466 | 1201 | 4845 | 12990 | 54 | 4508 | 8099 | 5125 | 258 | 220 | 2.5 | 2722 | 1368 | 1602 | 1317 | 17 |
| 3324.0987 | 29771 | 50000 | 228 | 8351 | 3184 | 26479 | 50000 | 12133 | 65 | 15476 | 2227 | 505 | 16086 | 25757 | 3452 | 15612 | 2929 |
| 3324.0976 | 227 | 6202 | 531 | 2740 | 2505 | 668 | 5519 | 4366 | 318 | 419 | 35 | 123 | 3334 | 14 | 45 | 905 | 247 |
| 3324.0977 | 698 | 8364 | 8.6 | 2475 | 535 | 192 | 992 | 339 | 762 | 1638 | 185 | 988 | 5157 | 907 | 5066 | 2674 | 1004 |
| 3324.0986 | 3886 | 21738 | 10587 | 7236 | 39494 | 346 | 8936 | 4244 | 4799 | 324 | 109 | 92 | 549 | 3087 | 106 | 6551 | 585 |
| 3324.0978 | 2104 | 29098 | 453 | 799 | 838 | 3705 | 26552 | 11155 | 368 | 583 | 5.3 | 4120 | 122 | 3322 | 2233 | 7868 | 9005 |
| 3324.0980 | 164 | 8722 | | 304 | 194 | 853 | 101 | 1406 | 12 | 400 | | 8.4 | | 1514 | 1394 | 703 | 6.9 |
| 3324.0974 | 364 | 7387 | 750 | 487 | 125 | 150 | 546 | 84 | 98 | 9.1 | 7.2 | 0.67 | 37 | 15 | 13 | 4280 | 3.5 |

TABLE 8-continued

HLA class II binding patterns of prevalently recognized epitope regions

| | | | | | | | | | | | | | | | | | |
|---|---|---|---|---|---|---|---|---|---|---|---|---|---|---|---|---|---|
| 3324.0975 | 113 | 8141 | 986 | 198 | 51 | 151 | 5043 | 1188 | 1056 | 323 | 177 | 24 | 273 | 83 | 76 | 32 | 379 |
| 3324.0971 | 2735 | 4750 | 56 | 3358 | 1265 | 219 | 666 | 1079 | 54 | 173 | 12 | 286 | 71 | 66 | 778 | 11410 | 509 |
| 3324.0004 | 2592 | 11232 | 13 | 9502 | 3892 | 1218 | 325 | 1451 | 198 | 85 | 63 | 820 | 7275 | 1500 | 493 | 38 | 1824 |
| 3324.0003 | 123 | 4170 | 1739 | 916 | 426 | 60 | 63 | 827 | 910 | 388 | 36 | 1879 | 1810 | 8114 | 54 | 1021 | 2570 |
| 3324.0007 | 13610 | 50000 | 557 | 31293 | 50000 | 6829 | 397 | 5806 | 8441 | 391 | 843 | 17488 | 18503 | 918 | 3.3 | 1042 | 50000 |
| 3324.0353 | 67 | 8672 | 1337 | 832 | 2035 | 3613 | 5095 | 8893 | 19 | 4094 | 7568 | 5614 | 6815 | 2700 | 336 | 5983 | 5918 |
| 3324.0352 | 3537 | 5376 | 642 | 32210 | 18603 | 871 | 1033 | 1170 | 6058 | 279 | 4651 | 12307 | 10528 | 1391 | 2.2 | 7590 | 12980 |
| 3324.0387 | 1075 | 12465 | 1060 | 8820 | 1240 | 5585 | 1272 | 3461 | 58 | 128 | 70 | 0.039 | 41 | 92 | 157 | 3767 | 3.3 |
| 3324.0386 | 1867 | 1491 | 121 | 6361 | 2791 | 1876 | 5835 | 650 | 19 | 1612 | 1352 | 5.1 | 5907 | 6715 | 1054 | 2923 | 178 |
| 3324.0517 | 3172 | 538 | 638 | 5593 | 27574 | 729 | 739 | 301 | 432 | 13 | 13 | 3.1 | 92 | 275 | 11 | 2884 | 83 |
| 3324.0523 | 10464 | 39726 | 31919 | 50000 | 30440 | 6387 | 9115 | 10733 | 2864 | 1618 | 5002 | 96 | 11533 | 16167 | 7505 | 525 | 4965 |
| 3324.0521 | 7924 | 8395 | 3764 | 10232 | 17866 | 3978 | 5872 | 2358 | 48 | 334 | 235 | 24 | 760 | 1461 | 599 | 3308 | 895 |
| 3324.0604 | 8265 | 36682 | 883 | 20699 | 28918 | 5797 | 50000 | 29047 | 3187 | 6935 | 1199 | 1602 | 1734 | 12055 | 2370 | 29 | 23870 |
| 3324.0607 | 684 | 918 | 710 | 827 | 1043 | 4578 | 4714 | 4899 | 262 | 692 | 819 | 7136 | 4187 | 1207 | 748 | 3578 | 13550 |
| 3324.0606 | 111 | 7541 | 1212 | 711 | 163 | 12904 | 2416 | 11286 | 8286 | 8235 | 7270 | 39613 | 13781 | 18705 | 14225 | 155 | 25475 |
| 3324.0615 | 2962 | 5556 | 7955 | 7270 | 6143 | 888 | 12985 | 1930 | 1344 | 676 | 1062 | 1170 | 1538 | 4707 | 1147 | 3563 | 9177 |
| 3324.0618 | 37377 | 24912 | 38760 | 50000 | 6739 | 25974 | 32436 | 35955 | 1863 | 806 | 304 | 50000 | 1594 | 75 | 179 | 6245 | 35360 |
| 3324.0624 | 50000 | 50000 | 3057 | 50000 | 27874 | 33698 | 20832 | 11703 | 14453 | 2364 | 18 | 7024 | 2078 | 991 | 3307 | 6585 | 25735 |
| 3324.0616 | 7308 | 28117 | 2356 | 30130 | 35059 | 3323 | 4140 | 4158 | 179 | 104 | 92 | 6026 | 561 | 3137 | 633 | 2140 | 10277 |
| 3324.1587 | 2114 | 6727 | 38 | 4693 | 3295 | 1321 | 636 | 1948 | 267 | 114 | 28 | 326 | 917 | 1062 | 341 | 3333 | 1167 |
| 3324.1585 | 12 | 310 | 1472 | 167 | 71 | 22 | 7.9 | 161 | 2603 | 17 | 36 | 30 | 52 | 92 | 80 | 2136 | 274 |
| 3324.1588 | 116 | 194 | 4575 | 3941 | 900 | 302 | 162 | 2639 | 864 | 141 | 171 | 2489 | 111 | 97 | 242 | 4441 | 3488 |
| 3324.1584 | 308 | 953 | 88 | 423 | 240 | 1252 | 5307 | 2036 | 183 | 21 | 46 | 133 | 51 | 73 | 31 | 40 | 1305 |

TABLE 8-continued

HLA class II binding patterns of prevalently recognized epitope regions

| | | | | | | | | | | | | | | | | | |
|---|---|---|---|---|---|---|---|---|---|---|---|---|---|---|---|---|---|
| 3324.0655 | 1131 | 3444 | 382 | 904 | 1191 | 629 | 2011 | 6210 | 330 | 1656 | 279 | 50000 | 5690 | 666 | 500 | 7748 | 12339 |
| 3324.0657 | 26713 | 7196 | 2419 | 9020 | 6027 | 30986 | 739 | 50000 | 130 | 557 | 672 | 3068 | 2847 | 641 | 144 | 8095 | 6268 |
| 3324.0658 | 1225 | 2121 | 6011 | 5470 | 2137 | 10389 | 3871 | 8965 | 258 | 1351 | 2426 | 18010 | 3779 | 799 | 717 | 31957 | 21638 |
| 3324.0663 | 4569 | 6212 | 9809 | 13492 | 3874 | 188 | 2016 | 981 | 12122 | 50000 | 50000 | 50000 | 23361 | 9581 | 1437 | 4557 | 50000 |
| 3324.1135 | 1405 | 5443 | 805 | 5850 | 1810 | 627 | 1316 | 667 | 114 | 103 | 2899 | 383 | 569 | 65 | 1052 | 13026 | |
| 3324.1138 | 4460 | 25959 | 5721 | 32683 | 5739 | 215 | 793 | 1597 | 9744 | 205 | 110 | 764 | 2058 | 849 | 0.25 | 1171 | 223 |
| 3337.0029 | 27269 | 26168 | 8997 | 50000 | 1829 | 50000 | 1441 | 903 | 50000 | 158 | 80 | 1407 | 53 | 786 | 51 | 18120 | 8.1 |
| 3324.1139 | 1068 | 530 | 698 | 39629 | 9885 | 50000 | 9236 | 50000 | 26620 | 18555 | 50000 | 1266 | 5209 | 50000 | 1295 | 7941 | |
| 3324.1140 | 4976 | 2241 | 33901 | 50000 | 39533 | 8398 | 38172 | 50000 | 9542 | 469 | 483 | 12300 | 19660 | 560 | 5375 | | |
| 3337.0030 | 646 | 148 | 20336 | 50000 | 622 | 50000 | 61 | 347 | 1987 | 4060 | 685 | 2929 | 50000 | 2212 | 24225 | 82 | |
| 3324.1142 | 19328 | 25717 | 26715 | 19079 | 10584 | 50000 | 50000 | 33924 | 28683 | 1420 | 11767 | 7261 | 11975 | 19 | 21639 | 23992 | |
| 3337.0031 | 4656 | 2441 | 48 | 50000 | 846 | 50000 | 2336 | 11264 | 3946 | 12984 | 6241 | 2618 | 26311 | 5538 | 18603 | 671 | |
| 3324.1141 | 1816 | 1696 | 10397 | 7083 | 1266 | 12367 | 17499 | 2899 | 6266 | 3859 | 5633 | 4342 | 30123 | 9031 | 16711 | 13196 | |
| 3324.1175 | 3075 | 50000 | 20 | 454 | 215 | 83 | 430 | 147 | 24 | 3337 | 251 | 339 | 41527 | 258 | 2418 | 4991 | |
| 3324.1167 | 707 | 1800 | 1118 | 543 | 125 | 50000 | 50000 | 50000 | 4717 | 7236 | 707 | 78 | 515 | 76 | 4399 | 597 | |
| 3324.1185 | 278 | 2248 | 132 | 854 | 40 | 6132 | 9812 | 4648 | 110 | 121 | 3168 | 469 | 1615 | 777 | 4125 | 4699 | |
| 3324.1165 | 943 | 5863 | 73 | 448 | 180 | 21294 | 50000 | 4637 | 962 | 79 | 69 | 2.5 | 86 | 6.9 | 4652 | 12 | |
| 3324.1184 | 1766 | 679 | 3.8 | 700 | 102 | 11352 | 7446 | 1738 | 224 | 5959 | 3491 | 81 | 21724 | 8768 | 12422 | 299 | 611 |
| 3324.1197 | 431 | 2314 | 4.2 | 277 | 138 | 16916 | 21605 | 6721 | 31 | 2717 | 5456 | 0.78 | 10255 | 44 | 0.70 | 2.1 | |
| 3324.1428 | 459 | 11971 | 1009 | 1243 | 2753 | 740 | 8618 | 50000 | 675 | 4818 | 119 | 8498 | 1760 | 1404 | 388 | 34437 | 50000 |
| 3324.1432 | 97 | 2038 | 2.5 | 2.3 | 230 | 610 | 24876 | 50000 | 70 | 7.9 | 7.4 | 275 | 8.0 | 3.0 | 20 | 29689 | 31 |
| 3324.1437 | 132 | 4668 | 75 | 189 | 151 | 4412 | 3107 | 181 | 23 | 872 | 5184 | 387 | 849 | 3350 | 4358 | 9.6 | 1139 |
| 3324.1441 | 237 | 1172 | 7.1 | 457 | 83 | 3079 | 982 | 86 | 25 | 675 | 181 | 0.84 | 3480 | 8061 | 103 | 1201 | 1.4 |

TABLE 8-continued

HLA class II binding patterns of prevalently recognized epitope regions

| | | | | | | | | | | | | | | | | | |
|---|---|---|---|---|---|---|---|---|---|---|---|---|---|---|---|---|---|
| 3324.1442 | 2630 | 1194 | 211 | 2614 | 1302 | 3407 | 966 | 2540 | 429 | 613 | 28 | 22 | 177 | 4312 | 141 | 444 | 97 |
| 3324.1433 | 515 | 163 | 81 | 72 | 36 | 191 | 70 | 358 | 846 | 51 | 113 | 15 | 76 | 92 | 306 | 7.2 | 1266 |
| 3324.1436 | 2114 | 2125 | 839 | 2370 | 640 | 9969 | 2647 | 1029 | 732 | 5958 | 272 | 38 | 1259 | 6874 | 22 | 285 | 1655 |
| 3324.1556 | 580 | 2173 | 143 | 4634 | 274 | 563 | 680 | 79 | 3426 | 2125 | 68 | 329 | 1331 | 5002 | 435 | 183 | 1038 |
| 3324.1580 | 9101 | 8072 | 1567 | 2884 | 785 | 1009 | 3189 | 5214 | 1291 | 787 | 160 | 595 | 1078 | 2614 | 15 | 69 | 2183 |
| 3324.1571 | 2268 | 9550 | 5.5 | 651 | 137 | 631 | 5410 | 663 | 34 | 5339 | 1467 | 67 | 20678 | 50000 | 436 | 2.6 | 295 |
| 3324.1575 | 3690 | 25684 | 1.9 | 1153 | 322 | 11872 | 6782 | 1380 | 793 | 24797 | 9228 | 39 | 28919 | 25866 | 2027 | 37 | 2935 |
| 3324.1570 | 1026 | 5123 | 628 | 197 | 24 | 2818 | 8000 | 910 | 3192 | 3256 | 2266 | 882 | 4846 | 20193 | 7.4 | 2772 | 3237 |
| 3324.1576 | 856 | 18825 | 844 | 11612 | 10345 | 1862 | 50000 | 10912 | 471 | 1518 | 1560 | 945 | 982 | 995 | 800 | 12 | 5142 |
| 3324.1578 | 1523 | 3198 | 32 | 2854 | 314 | 6808 | 50000 | 21644 | 144 | 675 | 1386 | 6.8 | 854 | 1593 | 297 | 297 | 13 |
| 3324.1583 | 7961 | 2754 | 938 | 7772 | 4639 | 6583 | 18032 | 5811 | 1029 | 566 | 941 | 3829 | 370 | 8774 | 1112 | 75 | 4830 |
| 3324.1579 | 1040 | 1496 | 407 | 183 | 44 | 5384 | 8336 | 5319 | 96 | 67 | 894 | 21 | 803 | 1132 | 496 | 485 | 352 |
| 3324.1564 | 1660 | 5850 | 38 | 1230 | 475 | 3581 | 10001 | 890 | 146 | 3569 | 1147 | 7.6 | 1071 | 5202 | 891 | 2003 | 84 |
| 3324.1590 | 734 | 3116 | 46 | 952 | 412 | 2582 | 6849 | 2356 | 1337 | 922 | 495 | 451 | 2043 | 2663 | 1311 | 1918 | 558 |
| 3324.1589 | 412 | 2977 | 1933 | 6628 | 2521 | 6188 | 19481 | 16501 | 1296 | 56 | 1782 | 438 | 568 | 1338 | 275 | 229 | 4884 |

REFERENCES

1. Locksley, R. M. 2010. Asthma and allergic inflammation. Cell 140:777-783.
2. Greiner, A. N., P. W. Hellings, G. Rotiroti, and G. K. Scadding. 2011. Allergic rhinitis. Lancet 378:2112-2122.
3. Oseroff, C., J. Sidney, M. F. Kotturi, R. Kolla, R. Alam, D. H. Broide, S. I. Wasserman, D. Weiskopf, D. M. McKinney, J. L. Chung, A. Petersen, H. Grey, B. Peters, and A. Sette. 2010. Molecular determinants of T cell epitope recognition to the common Timothy grass allergen. J Immunol 185:943-955.
4. Assarsson, E., J. A. Greenbaum, M. Sundstrom, L. Schaffer, J. A. Hammond, V. Pasquetto, C. Oseroff, R. C. Hendrickson, E. J. Lefkowitz, D. C. Tscharke, J. Sidney, H. M. Grey, S. R. Head, B. Peters, and A. Sette. 2008. Kinetic analysis of a complete poxvirus transcriptome reveals an immediate-early class of genes. Proc Natl Acad Sci USA 105:2140-2145.
5. Assarsson, E., J. Sidney, C. Oseroff, V. Pasquetto, H.-H. Bui, N. Frahm, C. Brander, B. Peters, H. Grey, and A. Sette. 2007. A Quantitative Analysis of the Variables Affecting the Repertoire of T Cell Specificities Recognized after Vaccinia Virus Infection. J Immunol 178:7890-7901.
6. Botten, J., J. Alexander, V. Pasquetto, J. Sidney, P. Barrowman, J. Ting, B. Peters, S. Southwood, B. Stewart, M. P. Rodriguez-Carreno, B. Mothe, J. L. Whitton, A. Sette, and M. J. Buchmeier. 2006. Identification of protective Lassa virus epitopes that are restricted by HLA-A2. J Virol 80:8351-8361.
7. Kotturi, M. F., J. Botten, J. Sidney, H.-H. Bui, L. Giancola, M. Maybeno, J. Babin, C. Oseroff, V. Pasquetto, J. A. Greenbaum, B. Peters, J. Ting, D. Do, L. Vang, J. Alexander, H. Grey, M. J. Buchmeier, and A. Sette. 2009. A Multivalent and Cross-Protective Vaccine Strategy against Arenaviruses Associated with Human Disease. PLoS Pathog 5:e1000695.
8. Mothe, B. R., B. S. Stewart, C. Oseroff, H.-H. Bui, S. Stogiera, Z. Garcia, C. Dow, M. P. Rodriguez-Carreno, M. Kotturi, V. Pasquetto, J. Botten, S. Crotty, E. Janssen, M. J. Buchmeier, and A. Sette. 2007. Chronic Lymphocytic Choriomeningitis Virus Infection Actively Down-Regulates CD4+ T Cell Responses Directed against a Broad Range of Epitopes. J Immunol 179:1058-1067.
9. Moutaftsi, M., H.-H. Bui, B. Peters, J. Sidney, S. Salek-Ardakani, C. Oseroff, V. Pasquetto, S. Crotty, M. Croft, E. J. Lefkowitz, H. Grey, and A. Sette. 2007. Vaccinia Virus-Specific CD4+ T Cell Responses Target a Set of Antigens Largely Distinct from Those Targeted by CD8+ T Cell Responses. J Immunol 178:6814-6820.
10. Moutaftsi, M., B. Peters, V. Pasquetto, D. C. Tscharke, J. Sidney, H. H. Bui, H. Grey, and A. Sette. 2006. A consensus epitope prediction approach identifies the breadth of murine T(CD8+)-cell responses to vaccinia virus. Nat Biotechnol 24:817-819.
11. Oseroff, C., F. Kos, H. H. Bui, B. Peters, V. Pasquetto, J. Glenn, T. Palmore, J. Sidney, D. C. Tscharke, J. R. Bennink, S. Southwood, H. M. Grey, J. W. Yewdell, and A. Sette. 2005. HLA class I-restricted responses to vaccinia recognize a broad array of proteins mainly involved in virulence and viral gene regulation. Proc Natl Acad Sci USA 102:13980-13985.
12. Oseroff, C., B. Peters, V. Pasquetto, M. Moutaftsi, J. Sidney, V. Panchanathan, D. C. Tscharke, B. Maillere, H. Grey, and A. Sette. 2008. Dissociation between Epitope Hierarchy and Immunoprevalence in CD8 Responses to Vaccinia Virus Western Reserve. J Immunol 180:7193-7202.
13. Assarsson, E., H.-H. Bui, J. Sidney, Q. Zhang, J. Glenn, C. Oseroff, I. N. Mbawuike, J. Alexander, M. J. Newman, H. Grey, and A. Sette. 2008. Immunomic Analysis of the Repertoire of T-Cell Specificities for Influenza A Virus in Humans. J. Virol. 82:12241-12251.
14. Bui, H. H., B. Peters, E. Assarsson, I. Mbawuike, and A. Sette. 2007. Ab and T cell epitopes of influenza A virus, knowledge and opportunities. Proc Natl Acad Sci USA 104:246-251.
15. Blythe, M., Q. Zhang, K. Vaughan, R. de Castro, N. Salimi, H.-H. Bui, D. Lewinsohn, J. Ernst, B. Peters, and A. Sette. 2007. An analysis of the epitope knowledge related to Mycobacteria. Immunome Research 3:10.
16. Vaughan, K., M. Blythe, J. Greenbaum, Q. Zhang, B. Peters, D. L. Doolan, and A. Sette. 2009. Meta-analysis of immune epitope data for all Plasmodia: overview and applications for malarial immunobiology and vaccine-related issues. Parasite Immunol 31:78-97.
17. Vaughan, K., J. Greenbaum, M. Blythe, B. Peters, and A. Sette. 2010. Meta-analysis of all immune epitope data in the Flavivirus genus: inventory of current immune epitope data status in the context of virus immunity and immunopathology. Viral Immunol 23:259-284.
18. Zarebski, L. M., K. Vaughan, J. Sidney, B. Peters, H. Grey, K. D. Janda, A. Casadevall, and A. Sette. 2008. Analysis of epitope information related to *Bacillus* anthracia and *Clostridium botulinum*. Expert Rev Vaccines 7:55-74.
19. Wang, P., J. Sidney, Y. Kim, A. Sette, O. Lund, M. Nielsen, and B. Peters. 2010. Peptide binding predictions for HLA DR, DP and DQ molecules. BMC Bioinformatics 11:568.
20. Sidney, J., S. Southwood, C. Oseroff, M. F. Del Guercio, A. Sette, and H. Grey. 1998. Measurement of MHC/Peptide Interactions by Gel Filtration. In Current Protocols in Immunology. John Wiley & Sons, Inc. 18.13.11-18.13.19.
21. Gulukota, K., J. Sidney, A. Sette, and C. DeLisi. 1997. Two complementary methods for predicting peptides binding major histocompatibility complex molecules. J Mol Biol 267:1258-1267.
22. Cheng, Y., and W. H. Prusoff. 1973. Relationship between the inhibition constant (K1) and the concentration of inhibitor which causes 50 percent inhibition (ISO) of an enzymatic reaction. Biochem Pharmacol 22:3099-3108.
23. Vita, R., L. Zarebski, J. A. Greenbaum, H. Emami, I. Hoof, N. Salimi, R. Damle, A. Sette, and B. Peters. 2009. The immune epitope database 2.0. Nucleic Acids Res 38:D854-862.
24. Sidney, J., A. Steen, C. Moore, S. Ngo, J. Chung, B. Peters, and A. Sette. 2010. Divergent motifs but overlapping binding repertoires of six HLA-DQ molecules frequently expressed in the worldwide human population. J Immunol 185:4189-4198.
25. Sidney, J., A. Steen, C. Moore, S. Ngo, J. Chung, B. Peters, and A. Sette. 2010. Five HLADP molecules frequently expressed in the worldwide human population share a common HLA supertypic binding specificity. J Immunol 184:2492-2503.
26. Greenbaum, J., J. Sidney, J. Chung, C. Brander, B. Peters, and A. Sette. 2011. Functional classification of class II human leukocyte antigen (HLA) molecules reveals seven different supertypes and a surprising degree of repertoire sharing across supertypes. Immunogenetics 63:325-335.
27. Vaughan, K., J. Greenbaum, Y. Kim, R. Vita, J. Chung, B. Peters, D. Broide, R. Goodman, H. Grey, and A. Sette. 2010. Towards defining molecular determinants recognized by adaptive immunity in allergic disease: an inventory of the available data. J Allergy (Cairo) 2010:628026.
28. Middleton, D., L. Menchaca, H. Rood, and R. Komerofsky. 2003. New allele frequency database: http://www.allelefrequencies.net. Tissue Antigens 61:403-407.
29. Meyer, D., R. Singe, S. Mack, A. Lancaster, M. Nelson, H. Erlich, M. Frenandez-Vina, and G. Thomson. 2007. Single Locus Polymorphism of Classical HLA Genes. Immunobiology of the Human MHC: Proceedings of the 13th International Histocompatibility Workshop and Conference; Seattle, Wash.: 653-704.

What is claimed is:

1. A pharmaceutical composition comprising a pharmaceutically acceptable carrier or excipient, an adjuvant, and an effective amount of a peptide, wherein the peptide consists of the amino acid sequence set forth in SEQ ID NO: 668.

2. The pharmaceutical composition of claim 1, wherein the composition
   i) elicits, stimulates, induces, promotes, increases or enhances an anti-allergen immune response; decreases, inhibits, suppresses or reduces an anti-allergen immune response;
   ii) decreases, inhibits, suppresses or reduces an anti-allergen immune response;
   iii) elicits, stimulates, induces, promotes, increases or enhances a T cell response to production of Ige Antibody;
   iv) decreases, inhibits, suppresses or reduces a T cell response or production of IgE Antibody;
   v) modulates a Th2 immune response;
   vi) modulates production of a lymphokine or cytokine by a cell;

vii) desensitizes, or improves, increases, or induces immunological tolerance of a subject to the allergen; or
viii) modulates production of IL-5 (interleukin-5), IL-4 (interleukin-4), IL-10 (interleukin-10), m IL-13 (interleukin 13), IL-17 (interleukin-17, or IFN (interferon-gamma).

3. The pharmaceutical composition of claim 1, wherein the peptide is immobilized on a substrate.

4. A kit, comprising a compartment and instructions, wherein the compartment comprises the pharmaceutical composition of claim 1, and wherein the instructions are for use in any of:
   i. modulating an immune response or activity of a cell against an allergen;
   ii. modulating an immune response against an allergen in a subject;
   iii. desensitizing, or inducing, eliciting, increasing or improving immunological tolerance to a protein or peptide allergen;
   iv. reducing risk or providing a subject protection against an allergic reaction, allergic response, allergic disorder or allergic disease;
   v. treating an allergic reaction, allergic response, allergic disorder or allergic disease; or
   vi. detecting an allergic response or diagnosing an allergy in a subject.

5. The pharmaceutical composition of claim 1, wherein the pharmaceutical composition is a powder.

6. The pharmaceutical composition of claim 5, wherein the powder is a freeze-dried powder.

\* \* \* \* \*